United States Patent
Wong

(10) Patent No.: US 12,269,854 B2
(45) Date of Patent: *Apr. 8, 2025

(54) MULTI-CHAIN CHIMERIC POLYPEPTIDES AND USES THEREOF

(71) Applicant: HCW Biologics, Inc., Miramar, FL (US)

(72) Inventor: Hing Wong, Miramar, FL (US)

(73) Assignee: ImmunityBio, Inc., San Diego, CA (US)

( * ) Notice: Subject to any disclaimer, the term of this patent is extended or adjusted under 35 U.S.C. 154(b) by 261 days.

This patent is subject to a terminal disclaimer.

(21) Appl. No.: 16/952,848

(22) Filed: Nov. 19, 2020

(65) Prior Publication Data

US 2021/0070825 A1    Mar. 11, 2021

Related U.S. Application Data

(63) Continuation of application No. 16/555,689, filed on Aug. 29, 2019, now Pat. No. 11,518,792.

(60) Provisional application No. 62/881,088, filed on Jul. 31, 2019, provisional application No. 62/817,230, filed on Mar. 12, 2019, provisional application No. 62/817,241, filed on Mar. 12, 2019, provisional application No. 62/816,683, filed on Mar. 11, 2019, provisional application No. 62/749,506, filed on Oct. 23, 2018, provisional application No. 62/749,007, filed on Oct. 22, 2018, provisional application No. 62/746,832, filed on Oct. 17, 2018, provisional application No. 62/724,969, filed on Aug. 30, 2018, provisional application No. 62/725,043, filed on Aug. 30, 2018, provisional application No. 62/725,010, filed on Aug. 30, 2018.

(51) Int. Cl.
| | |
|---|---|
| C07K 14/54 | (2006.01) |
| C07K 14/71 | (2006.01) |
| C07K 14/715 | (2006.01) |
| C07K 14/745 | (2006.01) |
| C07K 16/28 | (2006.01) |

(52) U.S. Cl.
CPC .......... C07K 14/5434 (2013.01); C07K 14/54 (2013.01); C07K 14/5418 (2013.01); C07K 14/71 (2013.01); C07K 14/7155 (2013.01); C07K 14/745 (2013.01); C07K 16/283 (2013.01); *C07K 2317/622* (2013.01); *C07K 2319/02* (2013.01); *C07K 2319/03* (2013.01); *C07K 2319/30* (2013.01)

(58) Field of Classification Search
CPC ................ C07K 14/5434; C07K 14/54; C07K 14/5418; C07K 14/7155; C07K 2319/03; C07K 2319/30; C07K 14/71; C07K 14/745; C07K 16/283; C07K 2317/622; C07K 2319/02
See application file for complete search history.

(56) References Cited

U.S. PATENT DOCUMENTS

| | | | |
|---|---|---|---|
| 6,117,980 A | 9/2000 | Gonzalez et al. | |
| 7,452,537 B2 | 11/2008 | Bauer et al. | |
| 7,482,436 B2 | 1/2009 | Sugimura et al. | |
| 7,488,802 B2 | 2/2009 | Collins et al. | |
| 7,521,051 B2 | 4/2009 | Collins et al. | |
| 7,612,181 B2 | 11/2009 | Wu et al. | |
| 7,691,380 B2 | 4/2010 | Thorpe et al. | |
| 7,723,482 B2 | 5/2010 | Soulillou et al. | |
| 7,968,094 B2 | 6/2011 | Jiao et al. | |
| 8,007,795 B2 | 8/2011 | Jiao et al. | |
| 8,133,485 B2 | 3/2012 | Levi-Schaffer et al. | |
| 8,217,149 B2 | 7/2012 | Irving et al. | |
| 8,258,268 B2 | 9/2012 | Wu et al. | |
| 8,475,792 B2 | 7/2013 | Dall'Acqua et al. | |
| 8,552,156 B2 | 10/2013 | Takayanagi et al. | |
| 8,586,714 B2 | 11/2013 | Ghayur et al. | |
| 8,716,450 B2 | 5/2014 | Ghayur et al. | |
| 8,722,855 B2 | 5/2014 | Ghayur et al. | |
| 8,735,546 B2 | 5/2014 | Ghayur et al. | |
| 8,741,604 B2 | 6/2014 | Campbell et al. | |

(Continued)

FOREIGN PATENT DOCUMENTS

| | | |
|---|---|---|
| CN | 101653603 | 2/2010 |
| CN | 101965364 | 2/2011 |

(Continued)

OTHER PUBLICATIONS

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*

(Continued)

*Primary Examiner* — Vanessa L. Ford
*Assistant Examiner* — Danaya L Middleton
(74) *Attorney, Agent, or Firm* — Sheridan Ross P.C.

(57) ABSTRACT

Provided herein are multi-chain chimeric polypeptides that include:

(a) a first chimeric polypeptide including a first target-binding domain, a soluble tissue factor domain, and a first domain of a pair of affinity domains; and (b) a second chimeric polypeptide including a second domain of a pair of affinity domains and a second target-binding domain, where the first chimeric polypeptide and the second chimeric polypeptide associate through the binding of the first domain and the second domain of the pair of affinity domains. Also provided here are methods of using these multi-chain chimeric polypeptides and nucleic acids encoding these multi-chain chimeric polypeptides.

36 Claims, 95 Drawing Sheets
Specification includes a Sequence Listing.

(56) References Cited

U.S. PATENT DOCUMENTS

| | | | |
|---|---|---|---|
| 8,753,640 B2 | 6/2014 | Wu et al. | |
| 8,759,494 B2 | 6/2014 | Bachmann et al. | |
| 8,822,645 B2 | 9/2014 | Ghayur et al. | |
| 9,035,026 B2 | 5/2015 | Hoffmann et al. | |
| 9,067,997 B2 | 6/2015 | Romagne et al. | |
| 9,085,623 B2 | 7/2015 | Rother et al. | |
| 9,090,684 B2 | 7/2015 | Borras et al. | |
| 9,226,962 B2 | 1/2016 | Le Gall et al. | |
| 9,238,084 B2 | 1/2016 | Liu et al. | |
| 9,273,136 B2 | 3/2016 | Rader et al. | |
| 9,371,395 B2 | 6/2016 | Takahashi et al. | |
| 9,441,034 B2 | 9/2016 | Sivakumar et al. | |
| 9,505,843 B2 | 11/2016 | Kim et al. | |
| 9,617,345 B2 | 4/2017 | Berne et al. | |
| 9,701,758 B2 | 7/2017 | Cooper et al. | |
| 11,518,792 B2 | 12/2022 | Wong | |
| 11,672,826 B2 | 6/2023 | Wong | |
| 11,730,762 B2 | 8/2023 | Wong | |
| 11,738,052 B2 * | 8/2023 | Wong | C07K 16/00 424/93.71 |
| 2001/0044427 A1 | 11/2001 | Mazel et al. | |
| 2003/0124678 A1 | 7/2003 | Epstein et al. | |
| 2003/0219441 A1 | 11/2003 | Thorpe et al. | |
| 2005/0014224 A1 | 1/2005 | Collins et al. | |
| 2006/0159655 A1 | 7/2006 | Collins et al. | |
| 2007/0160579 A1 | 7/2007 | Schmitz et al. | |
| 2009/0148942 A1 | 6/2009 | McDonagh et al. | |
| 2012/0171197 A1 | 7/2012 | Eriksson et al. | |
| 2012/0264920 A1 | 10/2012 | Wang et al. | |
| 2013/0274446 A1 | 10/2013 | Kumagai et al. | |
| 2014/0242077 A1 | 8/2014 | Choi | |
| 2015/0218274 A1 | 8/2015 | Sabatos-Peyton et al. | |
| 2015/0259429 A1 | 9/2015 | Benaroch et al. | |
| 2016/0175397 A1 | 6/2016 | Umana et al. | |
| 2016/0340413 A1 | 11/2016 | Duerner et al. | |
| 2016/0367664 A1 | 12/2016 | Wang et al. | |
| 2017/0051063 A1 | 2/2017 | Baum et al. | |
| 2017/0198042 A1 | 7/2017 | Williams et al. | |
| 2017/0283499 A1 | 10/2017 | Delhem et al. | |
| 2018/0200366 A1 | 7/2018 | Wong | |
| 2019/0078082 A1 | 3/2019 | Amorese et al. | |
| 2019/0092846 A1 | 3/2019 | Ibebunjo et al. | |
| 2019/0177406 A1 | 6/2019 | Ledbetter et al. | |
| 2019/0315850 A1 | 10/2019 | Bedinger et al. | |
| 2020/0123607 A1 | 4/2020 | Serrano Marugan et al. | |
| 2020/0190174 A1 | 6/2020 | Wong | |
| 2020/0392221 A1 | 12/2020 | Van Snick et al. | |
| 2020/0399358 A1 | 12/2020 | Shapiro et al. | |
| 2021/0060064 A1 | 3/2021 | Wong | |
| 2021/0061897 A1 | 3/2021 | Ledbetter et al. | |
| 2021/0100840 A1 | 4/2021 | Wong et al. | |
| 2021/0137981 A1 | 5/2021 | Wong | |
| 2021/0268022 A1 | 9/2021 | Wong et al. | |
| 2021/0277054 A1 | 9/2021 | Wong et al. | |
| 2021/0338724 A1 | 11/2021 | Wong | |
| 2021/0355204 A1 | 11/2021 | Bedinger et al. | |
| 2021/0403545 A1 | 12/2021 | Van Snick et al. | |
| 2022/0073578 A1 | 3/2022 | Wong et al. | |
| 2023/0023389 A1 | 1/2023 | Wong | |
| 2023/0039157 A1 | 2/2023 | Wong | |
| 2023/0174666 A1 | 6/2023 | Wong et al. | |
| 2023/0372399 A1 | 11/2023 | Wong | |
| 2023/0372444 A1 | 11/2023 | Wong et al. | |
| 2023/0381238 A1 | 11/2023 | Wong | |
| 2023/0398151 A1 | 12/2023 | Wong | |

FOREIGN PATENT DOCUMENTS

| | | | |
|---|---|---|---|
| CN | 102153653 | 8/2011 | |
| CN | 109513003 | 3/2019 | |
| EP | 1245676 | 10/2002 | |
| EP | 1719528 | 11/2006 | |
| EP | 2537933 | 12/2012 | |
| EP | 3029069 | 6/2016 | |
| EP | 3348276 | 7/2018 | |
| JP | 2005-124568 | 5/2005 | |
| JP | 2008-536487 | 9/2008 | |
| JP | 2009-512433 | 3/2009 | |
| JP | 4361133 | 8/2009 | |
| KR | 2016/0127688 | 11/2016 | |
| KR | 101778439 | 9/2017 | |
| WO | WO 1995/015341 | 6/1995 | |
| WO | WO 1996/001653 | 1/1996 | |
| WO | WO 2001/083755 | 11/2001 | |
| WO | WO 2002/083152 | 10/2002 | |
| WO | WO 2003/037911 | 5/2003 | |
| WO | WO 2003/104425 | 12/2003 | |
| WO | WO 2004/076488 | 9/2004 | |
| WO | WO 2006/096828 | 9/2006 | |
| WO | WO 2006/097743 | 9/2006 | |
| WO | WO 2006/119897 | 11/2006 | |
| WO | WO 2008/096158 | 8/2008 | |
| WO | WO 2011/127324 | 10/2011 | |
| WO | WO 2012/040323 | 3/2012 | |
| WO | WO 2012/120125 | 9/2012 | |
| WO | WO 2012/170470 | 12/2012 | |
| WO | WO 2012/175222 | 12/2012 | |
| WO | WO 2012/175692 | 12/2012 | |
| WO | WO 2013/068946 | 5/2013 | |
| WO | WO 2014/007513 | 1/2014 | |
| WO | WO 2014/026054 | 2/2014 | |
| WO | WO 2014/095808 | 6/2014 | |
| WO | WO 2014/130635 | 8/2014 | |
| WO | WO 2014/159531 | 10/2014 | |
| WO | WO 2015/089881 | 6/2015 | |
| WO | WO 2016/106221 | 6/2016 | |
| WO | WO 2016/154585 | 9/2016 | |
| WO | WO 2016/166348 | 10/2016 | |
| WO | WO 2017/053748 | 3/2017 | |
| WO | WO 2017/083612 | 5/2017 | |
| WO | WO 2017/149538 | 9/2017 | |
| WO | WO 2017/189526 | 11/2017 | |
| WO | WO 2018/067825 | 4/2018 | |
| WO | WO 2018/075989 | 4/2018 | |
| WO | WO 2018/129007 | 7/2018 | |
| WO | WO 2018/158350 | 9/2018 | |
| WO | WO 2018/165208 | 9/2018 | |
| WO | WO-2018165208 A1 * | 9/2018 | ....... A61K 39/00114 |
| WO | WO 2018/183169 | 10/2018 | |
| WO | WO 2019/046313 | 3/2019 | |
| WO | WO 2020/047333 | 3/2020 | |
| WO | WO 2020/047462 | 3/2020 | |
| WO | WO 2020/047473 | 3/2020 | |
| WO | WO 2021/163369 | 8/2021 | |

OTHER PUBLICATIONS

Bowie et al. Deciphering the Message in Protein Sequences: Tolerance to Amino Acid Substitutions. Science, 1990, 247:1306-1310 (Year: 1990).*

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*

Greenspan et al. 1999 Defining epitopes: It's not as easy as it seems; Nature Biotechnology, 17:936-937 (Year: 1999).*

Bork. Powers and Pitfalls in Sequence Analysis: The 70% Hurdle. Genome Research, 2000, 10:398-400 (Year: 2000).*

PCT International Preliminary Report on Patentability in International Appln. No. PCT/US2020/038717, dated Dec. 30, 2021, 9 pages.

Bork, "Powers and Pitfalls in Sequence Analysis: The 70% Hurdle," Genome Research, 2000, 10:398-400.

Bowie et al., "Deciphering the Message in Protein Sequences: Tolerance to Amino Acid Substitutions," Science, 1990, 247:1306-1310.

Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue," J. Cell Biol., 1990, 111:2129-2138.

(56) References Cited

OTHER PUBLICATIONS

Greenspan et al., "Defining epitopes: Its not as easy as it seems," Nature Biotechnology, 1999, 17:936-937.
Lazar et al., "Transforming Growth Factor Alpha: Mutation of Aspartic Acid 47 and Leucine 48 Results in Different Biological Activities," Mol. Cell. Biol., 1988, 8(3):1247-1252.
PCT International Search Report and Written Opinion in International Appln. No. PCT/US2021/029920, dated Oct. 6, 2021, 21 pages.
PCT International Search Report and Written Opinion in International Appln. No. PCT/US2021/035285, dated Oct. 18, 2021, 14 pages.
Li et al., "Transforming Growth Factor-β Regulation of Immune Responses," Annu. Rev. Immunol., 2006, 24:99-146.
McCarron et al., "TGF-β prevents T follicular helper cell accumulation and B cell autoreactivity," J Clin Invest., 2014, 124(10):4375-4386.
Voelker et al., "Anti-TGF-β1 Antibody Therapy in Patients with Diabetic Nephropathy," J Am Soc Nephrol., 2017, 28:953-962.
Wallace et al., "B lymphocytes confer immune tolerance via cell surface GARP-TGF-β complex," JCI Insight., 2018, 3(7):e99863, 19 pages.
Abbott et al., "Genomic organization, exact localization, and tissue expression of the human CD26 (dipeptidyl peptidase IV) gene," Immunogentics, Sep. 1994, 40(5):331-338.
Abdul-Aziz et al., "Acute myeloid leukemia induces protumoral p16INK4a-driven senescence in the bone marrow microenvironment," Blood, Jan. 31, 2019, 133(5):446-456.
Aertgeerts et al., "Crystal structure of human dipeptidyl peptidase IV in complex with a decapeptide reveals details on substrate specificity and tetrahedral intermediate formation," Protein Science, Feb. 2004, 13(2):412-421.
Ali et al., "Regulatory T cells in skin," Immunology, Jul. 12, 2017, 152(3):372-381.
Angevin et al., "First-in-human phase 1 of YS110, a monoclonal antibody directed against CD26 in advanced CD26-expressing cancers," British Journal of Cancer, Mar. 14, 2017, 116(9):1126-1134.
Bennett et al., "Erratum: Killing the old: cell senescence in atherosclerosis," Nature Reviews Cardiology, Jan. 12, 2017, 14(3):132.
Bennett et al., "Killing the old: cell senescence in atherosclerosis," Nature Reviews Cardiology, Dec. 12, 2016, 14(1):8-9, 2 pages.
Bentebibel et al., "A First-in-Human Study and Biomarker Analysis of NKTR-214, a Novel IL2[beta] [gamma] Biased Cytokine, in Patients with Advanced or Metastatic Solid Tumors," Cancer Discovery, Jun. 2019, 9(6):711-721.
Bhat et al., "Astrocyte Senescence as a Component of Alzheimer's Disease," PLoS One, Sep. 12, 2012, 7(9):e45069, 10 pages.
Biran et al., "Senescent cells communicate via intercellular protein transfer," Genes & Development, Apr. 8, 2015, 29(8):791-802, 13 pages.
Borea et al., "Pharmacology of Adenosine Receptors: The State of the Art," Physiological Reviews, May 30, 2018, 98(3):1591-1625.
Boyman et al., "IL-7/Anti-IL-7 mAb Complexes Restore T Cell Development and Induce Homeostatic T Cell Expansion without Lymphopenia," The Journal of Immunology, Jun. 1, 2008, 180:7265-7275.
Boyman et al., "Selective Stimulation of T Cell Subsets with Antibody-Cytokine Immune Complexes," Science, Mar. 31, 2006, 311(5769):1924-1927.
Broxmeyer et al., "Modulation of Hematopoietic Chemokine Effects In Vitro and In Vivo by DPP-4/CD26," Stem Cells and Development, Mar. 4, 2016, 25(8):575-585.
Buhling et al., "Functional role of CD26 on human B lymphocytes," Immunology Letters, Feb. 1995, 45(1-2):47-51.
Bussian et al., "Clearance of senescent glial cells prevents tau-dependent pathology and cognitive decline," Nature, Sep. 19, 2018, 562(7728):578-582, 21 pages.

Carr et al., "NK Cell-Mediated Lysis of Autologous HCMV-Infected Skin Fibroblasts Is Highly Variable among NK Cell Clones and Polyclonal NK Cell Lines," Clinical Immunology, Nov. 2002, 105(2):126-140.
Catania et al., "The tumor-targeting immunocytokine F16-IL2 in combination with doxorubicin: dose escalation in patients with advanced solid tumors and expansion into patients with metastatic breast cancer," Cell Adhesion and Migration, Jan.-Apr. 2015, 9(1-2):14-21.
Cavinato et al., "Molecular mechanisms of UVB-induced senescence of dermal fibroblasts and its relevance for photoaging of the human skin," Experimental Gerontology. Aug. 2017, 94:78-82.
Chambers et al., "Can blocking inflammation enhance immunity during aging?," Journal of Allergy and Clinical Immunology, May 2020, 145(5):1323-1331.
Childs et al., "Senescent cells: an emerging target for diseases of ageing," Nature Reviews Drug Discovery, Jul. 21, 2017, 16(10):718-735, 18 pages.
Childs et al., "Senescent intimal foam cells are deleterious at all stages of atherosclerosis," Science, Oct. 28, 2016, 354(6311):472-477.
Chong et al., "CD36 initiates the secretory phenotype during the establishment of cellular senescence," EMBO Rep., May 18, 2018, 19(6):e45274, 13 pages.
Cifaldi et al., "Boosting Natural Killer Cell-Based Immunotherapy with Anticancer Drugs: a Perspective," Trends Molecular Medicine, Dec. 2017, 23(12):1156-1175, 20 pages.
Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.
Conarello et al., "Mice lacking dipeptidyl peptidase IV are protected against obesity and insulin resistance," Proc. Natl. Acad. Sci. U.S.A., May 27, 2003, 100(11):6825-6830.
Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl.):CT082, Jul. 1, 2019, 2 pages.
Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42): 36396-36403.
Crews et al., "Molecular mechanisms of neurodegeneration in Alzheimer's disease," Human Molecular Genetics, Apr. 22, 2010, 19(R1):R12-R20, 9 pages.
Da Silva et al., "Dipeptidylpeptidase 4 inhibition enhances lymphocyte trafficking, improving both naturally occurring tumor immunity and immunotherapy," Nature Immunology, Jun. 15, 2015, 16(8), 11 pages.
De Stefano et al., "Establishing pathological cut-offs of brain atrophy rates in multiple sclerosis," Journal of Neurology, Neurosurgery, and Psychiatry, Jan. 2016, 87(1):93-99.
Deacon, "Physiology and Pharmacology of DPP-4 in Glucose Homeostasis and the Treatment of Type 2 Diabetes," Frontiers in Endocrinology, Feb. 2019, 10:80, 14 pages.
Deaglio et al., "Adenosine generation catalyzed by CD39 and CD73 expressed on regulatory T cells mediates immune suppression," Journal of Experimental Medicine, May 14, 2007, 204(6):1257-1265.
Dikov et al., "New fluorescent method for the histochemical detection of tripeptidyl peptidase I using glycyl-1-prolyl-1-met-2-anthraquinonyl hydrazide as substrate," Cellular and Molecular Biology, Jan. 1, 2004, 50 Online Pub: OL565-568, 1 page (Abstract Only).
Dimri et al., "A biomarker that identifies senescent human cells in culture and in aging skin in vivo," Proceedings of the National Academy of Sciences, Sep. 29, 1995, 92(20):9363-9367.
Dong et al., "Characterization of adenosine deaminase binding to human CD26 on T cells and its biologic role in immune response," Journal of Immunology, Feb. 15, 1996, 156(4):1349-1355.
Dong et al., "Determination of adenosine deaminase binding domain on CD26 and its immunoregulatory effect on T cell activation," Journal of Immunology, Dec. 15, 1997, 159(12):6070-6076.

(56) References Cited

OTHER PUBLICATIONS

Dou et al., "Cytoplasmic chromatin triggers inflammation in senescence and cancer," Nature, Oct. 4, 2017, 550(7676):402-406, 21 pages.
Dubois et al., "Preassociation of IL-15 with IL-15Rα-IgG1-Fc Enhances Its Activity on Proliferation of NK and CD8+/CD44high T Cells and Its Antitumor Action," The Journal of Immunology, Feb. 15, 2008, 180:2099-2106.
Elpek et al., "Mature natural killer cells with phenotypic and functional alterations accumulate upon sustained stimulation with IL-15/IL-15Rα complexes," Proceedings of the National Academy of Science, Dec. 14, 2010, 107(50): 21647-21652.
Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.
Epardaud et al., "Interleukin-15/Interleukin-15RA Complexes Promote Destruction of Established Tumors by Reviving Tumor-Resident CD8+ T Cells," Cancer Research 68(8): Apr. 15, 2008, 2972-2983.
Fehniger et al., "A Phase 1 Trial of CNDO-109-Activated Natural Killer Cells in Patients with High-Risk Acute Myeloid Leukemia," Biology of Blood and Marrow Transplantation, Aug. 2018, 24(8):1581-1589.
Finkelman et al., "Anti-cytokine antibodies as carrier proteins. Prolongation of in vivo effects of exogenous cytokines by injection of cytokine-anti-cytokine antibody complexes," The Journal of Immunology, Aug. 1, 1993, 151(3):1235-1244.
Finkelstein et al., "Obesity and Severe Obesity Forecasts Through 2030," American Journal of Preventative Medicine, Jun. 2012, 42(6):563-570.
Frutoso et al., "Emergence of NK Cell Hyporesponsiveness after Two IL-15 Stimulation Cycles," Journal of Immunology, May 30, 2018, 201: 493-506.
Ganesh et al., "TGF-β Inhibition and Immunotherapy: Checkmate," Immunity, Apr. 17, 2018, 48(4):626-628.
Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.
Ghosh et al., "The Senescence-Associated Secretory Phenotype: Critical Effector in SkinCancer and Aging," Journal of Investigative Dermatology, Nov. 2016, 136(11):2133-2139.
Gorrell et al., "Expression of the rat CD26 Antigen (dipeptidyl peptidase IV) on subpopulations of rat lymphocytes," Cellular Immunology, Apr. 15, 1991, 134(1):205-215.
Grupp et al., "Chimeric Antigen Receptor-Modified T Cells for Acute Lymphoid Leukemia," The New England Journal of Medicine, Apr. 18, 2013, 368(16):1509-1518.
Gutschmidt et al., "A quantitative histochemical study of dipeptidyl peptidase IV (DPP IV)," Histochemistry, 1981, 73(2):285-304.
Hayflick et al., "The serial cultivation of human diploid cell strains," Experimental Cell Research, Dec. 1961, 25:585-621.
He et al., "Senescence in Health and Disease," Cell, Jun. 1, 2017, 169(6):1000-1011.
Hoare et al., "The Power Behind the Throne: Senescence and the Hallmarks of Cancer," Annual Review of Cancer Biology, 2018, 2:175-194.
Hoffmann et al., "Large-scale in vitro expansion of polyclonal human CD4+CD25high regulatory T Cells," Blood, Aug. 2004, 104(3):895-903.
Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.
Huell et al., "Interleukin-6 is present in early stages of plaque formation and is restricted to the brains of Alzheimer's disease patients," Acta Neuropathologica, Nov. 1995, 89(6):544-551.
Inzucchi et al., "New Drugs for the Treatment of Diabetes, Part II: Incretin-Based Therapy and Beyond," Circulation, Jan. 29, 2008, 117(4):574-584, 21 pages.
Jain et al., "Mitochondrial Reactive Oxygen Species Regulate Transforming Growth Factor-β Signaling," Journal of Biological Chemistry, Jan. 11, 2013, 288(2):770-777.
Justice et al., "Senolytics in idiopathic pulmonary fibrosis: Results from a first-in-human, open-label, pilot study," EBioMedicine, Feb. 2019, 40:554-563.
Karin et al., "Senescent cell turnover slows with age providing an explanation for the Gompertz law," Nature Communications, 10:5495, 9 pages.
Karkera et al., "The anti-interleukin-6 antibody siltuximab down-regulates genes implicated in tumorigenesis in prostate cancer patients from a phase I study," The Prostate, Feb. 14, 2011, 71(13):1455-1465.
Katsuumi et al., "Vascular Senescence in Cardiovascular and Metabolic Diseases," Frontiers in Cardiovascular Medicine, 5:18, 13 pages.
Kim et al., "Identification of senescent cell surface targetable protein DPP4," Genes & Development, 2017, 31(15):1529-1534.
Kim et al., "SCAMP4 enhances the senescent cell secretome," Genes & Development, 2018, 32(13-14):909-914.
Kirkland et al., "Cellular Senescence: A Translational Perspective," EBioMedicine, Jul. 2017, 21:21-28.
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, 2017 6(3):e1277306, 15 pages.
Klemann et al., "Cut to the chase: a review of CD26/dipeptidyl peptidase-4's (DPP4) entanglement in the immune system," Clinical and Experimental Immunology, Feb. 25, 2016, 185(1):1-21.
Kritsilis et al., "Ageing, Cellular Senescence and Neurodegenerative Disease," International Journal of Molecular Sciences, Sep. 27, 2018, 19(10):2937, 37 pages.
Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.
Lansigan et al., "DI-Leu16-IL2, an Anti-CD20-Interleukin-2 Immunocytokine, Is Safe and Active in Patients with Relapsed and Refractory B-Cell Lymphoma: A Report of Maximum Tolerated Dose, Optimal Biologic Dose, and Recommended Phase 2 Dose," Blood, Dec. 2, 2016, 128(22):620, 3 pages (Abstract Only).
Li et al., "A Novel I L2-based Irrmunotherapeutic Protein Prevents the Development of Atherosclerosis in ApoE-/- mice and LDLR-/- mice," Journal of Immunology, May 1, 2020, 204(1):Supplement (Abstract Only), 2 pages.
Li et al., "Adoptive transfer of natural killer cells in combination with chemotherapy improves outcomes of patients with locally advanced colon carcinoma," Cytotherapy, Jan. 2018, 20(1):134-148, 15 pages.
Li et al., "The cGAS-cGAMP-STING pathway connects DNA damage to inflammation, senescence, and cancer," Journal of Experimental Medicine, Apr. 5, 2018, 215(5):1287-1299.
Liton et al., "Cellular senescence in the glaucomatous outflow pathway," Experimental Gerontology, Aug.-Sep. 2005, 40(8-9):745-748.
Liu et al., "Evaluation of the biological activities of the IL-15 superagonist complex, ALT-803, following intravenous versus subcutaneous administration in murine models," Cytokine, Jul. 2018, 107: 105-112, 8 pages.
Loster et al., "The Cysteine-Rich Region of Dipeptidyl Peptidase IV (CD 26) Is the Collagen Binding Site," Biochemical and Biophysical Research Communications, Dec. 5, 1995, 217(1):341-348.
Lu et al., "Molecular basis of binding between novel human coronavirus MERS-CoV and its receptor CD26," Nature, Jul. 7, 2013, 500(7461):227-231.
Lujambio et al., "Non-Cell-Autonomous Tumor Suppression by p53," Cell, Apr. 11, 2013, 153(2):449-460.
Marguet et al., "Enhanced insulin secretion and improved glucose tolerance in mice lacking CD26," Proc. Natl. Acad. Sci. U.S.A., Jun. 6, 2000, 97(12):6874-6879.

(56) References Cited

OTHER PUBLICATIONS

Mehta et al., "Why do trials for Alzheimer's disease drugs keep failing? A discontinued drug perspective for 2010-2015," Expert Opinion on Investigational Drugs, May 2017, 26(6):735-739.
Mentlein, "Dipeptidyl-peptidase IV (CD26)-role in the inactivation of regulatory peptides," Regulatory Peptides, Nov. 30, 1999, 85(1):9-24.
Michelet et al., "Metabolic reprogramming of natural killer cells in obesity limits antitumor responses," Nature Immunology, Nov. 12, 2018, 19(12):1330-1340.
Milanovic et al., "Senescence-associated reprogramming promotes cancer stemness," Nature, Dec. 20, 2017, 553(7686):96-100.
Milanovic et al., "The Senescence-Stemness Alliance—A Cancer-Hijacked Regeneration Principle," Trends in Cellular Biology, Dec. 2018, 28(12):1049-1061, 13 pages.
Miller et al., "Successful adoptive transfer and in vivo expansion of human haploidentical NK cells in patients with cancer," Blood, Apr. 15, 2005, 105(8):3051-3057.
Minamino et al., "A crucial role for adipose tissue p53 in the regulation of insulin resistance," Nature Medicine, Aug. 30, 2009, 15(9):1082-1087.
Mitterberger et al., "Adipogenic Differentiation Is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.
Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.
Moiseeva et al., "Metformin inhibits the senescence-associated secretory phenotype by interfering with IKK/NF- κB activation," Aging Cell, Mar. 23, 2013, 12(3):489-498.
Moreno et al., "Molecular Evidence of Adenosine Deaminase Linking Adenosine A2A Receptor and CD26 Proteins," Frontiers in Pharmacology, Feb. 15, 2018, 9:106, 18 pages.
Mulvihill et al., "Pharmacology, Physiology, and Mechanisms of Action of Dipeptidyl Peptidase-4 Inhibitors," Endocrine Reviews, Dec. 1, 2014, 35(6):992-1019.
Musi et al., "Tau protein aggregation is associated with cellular senescence in the brain," Aging Cell, Aug. 20, 2018, 17(6):e12840, 13 pages.
Must et al., "The Disease Burden Associated with Overweight and Obesity," Endotext, Feingold et al. (eds.), South Dartmouth, MA, 2000, 35 pages.
Myung et al., "Evidence of DNA damage in Alzheimer disease: phosphorylation of histone H2AX in astrocytes," Age, Apr. 23, 2008, 30(4):209-215.
Nelson et al., "A senescent cell bystander effect: senescence-induced senescence," Aging Cell, Feb. 9, 2012, 11(2):345-349.
Nishida et al., "CD26 is a potential therapeutic target by humanized monoclonal antibody for the treatment of multiple myeloma," Blood Cancer Journal, Oct. 22, 2018, 8(11):99, 17 pages.
Ogrodnik et al., "Cellular senescence drives age-dependent hepatic steatosis," Nat Commun. Jun. 13, 2017;8:15691, 12 pages.
Ogrodnik et al., "Obesity-Induced Cellular Senescence Drives Anxiety and Impairs Neurogenesis," Cell Metabolism, May 2019, 29(5):1061-1077, 25 pages.
Ohnuma et al., "Blockade of CD26-mediated T cell costimulation with soluble caveolin-1-Ig fusion protein induces anergy in CD4+T cells," Biochemical and Biophysics Research Communications, Jun. 10, 2009, 386(2):327-332.
Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.
Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.
Ohnuma et al., "Role of CD26/dipeptidyl peptidase IV in human T cell activation and function," Frontiers in Bioscience, Jan. 1, 2008, 13:2299-2310.
Ohnuma et al., "Soluble CD26/Dipeptidyl Peptidase IV Induces T Cell Proliferation Through CD86 Up-Regulation on APCs," Journal of Immunology, Dec. 15, 2001, 167(12):6745-6755.
Padutsch et al., "Superior Treg-Expanding Properties of a Novel Dual-Acting Cytokine Fusion Protein," Frontiers in Pharmacology, Dec. 18, 2019, 10:1490, 10 pages.
Palmer et al., "Cellular Senescence in Type 2 Diabetes: A Therapeutic Opportunity," Diabetes, Jul. 2015, 64(7):2289-2298.
PCT International Preliminary Report on Patentability in International Appln. No. PCT/US2019/048881, dated Mar. 11, 2021, 7 pages.
PCT International Preliminary Report on Patentability in International Appln. No. PCT/US2019/048930, dated Mar. 11, 2021, 9 pages.
PCT International Preliminary Report on Patentability in International Appln. No. PCT/US2019/049142, dated Mar. 11, 2021, 11 pages.
PCT International Preliminary Report on Patentability in International Appln. No. PCT/US2019/049158, dated Mar. 11, 2021, 8 pages.
PCT International Search Report and Written Opinion in International Appln. No. PCT/US2020/035598, dated Feb. 18, 2021, 12 pages.
PCT International Search Report and Written Opinion in International Appln. No. PCT/US2021/017620, dated Aug. 6, 2021, 22 pages.
PCT International Search Report and Written Opinion in International Appln. No. PCT/US2021/017621, dated Jun. 9, 2021, 15 pages.
PCT International Search Report and Written Opinion in International Appln. No. PCT/US2021/017714, dated Aug. 27, 2021, 22 pages.
Pittayapruek et al., "Role of Matrix Metalloproteinases in Photoaging and Photocarcinogenesis," International Journal of Molecular Sciences, 2016, 17(6):868, 20 pages.
Purohit et al., "Smad3-dependent regulation of type I collagen in human dermal fibroblasts: Impact on human skin connective tissue aging," Journal of Dermatological Science, Jul. 2016, 83(1):80-83, 4 pages.
Rafei et al., "Off-the-shelf virus specific T-cells for therapy of adenovirus disease in immunosuppressed patients," Journal of Clinical Oncology, May 26, 2019, 37(15 Suppl.):7008, 2 pages.
Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.
Rao et al., "Purification and characterization of rabbit tissue factor," Thrombosis Research, Oct. 1, 1989, 56(1):109-118.
Rasmussen et al., "Crystal structure of human dipeptidyl peptidase IV/CD26 in complex with a substrate analog," Nature Structural and Molecular Biology, 2003, 10(1):19-25.
Raz et al., "Efficacy and safety of the dipeptidyl peptidase-4 inhibitor sitagliptin as monotherapy in patients with type 2 diabetes mellitus," Diabetologia, Sep. 26, 2006, 49(11):2564-2571.
Resta et al., "Ecto-enzyme and signaling functions of lymphocyte CD 7 3," Immunological Reviews, 1998, 161:95-109.
Rittie et al., "Natural and Sun-Induced Aging of Human Skin," Cold Spring Harbor Perspective in Medicine, 2015, 5(1):a015370, 15 pages.
Rodier et al., "Persistent DNA damage signaling triggers senescence-associated inflammatory cytokine secretion," Nature Cell Biology, Jul. 13, 2009, 11(8): 973-979, 15 pages.
Romano et al., "Past, Present, and Future of Regulatory T Cell Therapy in Transplantation and Autoimmunity," Frontiers in Immunology, Jan. 31, 2019, 10:43, 14 pages.
Romee et al., "Cytokine activation induces human memory-like NK cells," Blood, Dec. 6, 2012, 120(24):4751-4760.
Rubinstein et al., "Converting IL-15 to a superagonist by binding to soluble IL-15Rα," Proceedings of the National Academy of Sciences U.S.A., Jun. 13, 2006, 103(24):9166-9171.

(56) References Cited

OTHER PUBLICATIONS

Ruscetti et al., "NK cell-mediated cytotoxicity contributes to tumor control by a cytostatic drug combination," Science, Dec. 21, 2018, 362(6421):1416-1422, 8 pages.

Sakamoto et al., "Phase I clinical trial of autologous NK cell therapy using novel expansion method in patients with advanced digestive cancer," Journal of Translational Medicine, Aug. 25, 2015, 13:277, 13 pages.

Salminen et al., "Emerging role of NF-κB signaling in the induction of senescence-associated secretory phenotype (SASP)," Cellular Signaling, Apr. 2012, 24(4):835-845.

Sato et al., "Recombinant soluble murine IL-4 receptor can inhibit or enhance IgE responses in vivo," The Journal of Immunology, Apr. 1, 1993, 150(7):2717-2723.

Schafer et al., "Cellular senescence mediates fibrotic pulmonary disease," Nat Commun., Feb. 2017, 8:14532, 11 pages.

Schwoppe et al., "Tissue-factor fusion proteins induce occlusion of tumor vessels," Thrombosis Research, Apr. 1, 2010, 125:S143-S150.

Seo et al., "Positive Feedback Loop between Plasminogen Activator Inhibitor-1 and Transforming Growth Factor-Beta1 during Renal Fibrosis in Diabetes," American Journal of Nephrology, Sep. 25, 2009, 30:481-490.

Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," Journal of Clinical Oncology, Jun. 1, 2018, 36(No. 15 Suppl.):e15155, 2 pages.

Sondel et al., "Combination Therapy with Interleukin-2 and Anti-tumor Monoclonal Antibodies," Cancer Journal from Scientific American, Jan. 1, 1997, 3(Suppl. 1):S121-S127.

Sone et al., "Pancreatic beta cell senescence contributes to the pathogenesis of type 2 diabetes in high-fat diet-induced diabetic mice," Diabetologia, 2005, 48(1):58-67.

Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.

Stoklasek et al., "Combined IL-15/IL-15Rα Immunotherapy Maximizes IL-15 Activity In Vivo," The Journal of Immunology, Nov. 1, 2006, 177(9):6072-6080.

Stryer, Biochemistry Fourth Edition, W. H. Freeman and Company, New York, 1995, pp. 18-23, 8 pages.

Takahashi et al., "Downregulation of cytoplasmic DNases is implicated in cytoplasmic DNA accumulation and SASP in senescent cells," Nature Communications, Mar. 28, 2018, 9:1249, 12 pages.

Takeda et al., "Phase I study of YS110, a recombinant humanized monoclonal antibody to CD26, in Japanese patients with advanced malignant pleural mesothelioma," Lung Cancer, Nov. 2019, 137:64-70.

Tanaka et al., "Cloning and functional expression of the T cell activation antigen CD26," Journal of Immunology, Jul. 15, 1992, 149(2):481-486.

Teng et al., "Structural assessment of the effects of amino acid substitutions on protein stability and protein-protein interaction," International journal of computational biology and drug design, Feb. 7, 2011, 3(4):334-349.

Tobin et al., "NK cells in childhood obesity are activated, metabolically stressed, and functionally deficient," JCI Insight, Dec. 21, 2017, 2(24):e94939, 9 pages.

Tomala et al., "In Vivo Expansion of Activated Naive CD8+ T Cells and NK Cells Driven by Complexes of IL-2 and Anti-IL-2 Monoclonal Antibody As Novel Approach of Cancer Immunotherapy," The Journal of Immunology, Oct. 15, 2009, 183:4904-4912.

Tominaga et al., "TGF-β Signaling in Cellular Senescence and Aging-Related Pathology," International Journal of Molecular Sciences, Oct. 10, 2019, 20(20):5002, 18 pages.

Tse et al., "ABT-263: A Potent and Orally Bioavailable Bcl-2 Family Inhibitor," Cancer Research, May 2008, 68(9):3421-3428.

Uryga et al., "Ageing induced vascular smooth muscle cell senescence in atherosclerosis," Journal of Physiology, Apr. 15, 2016, 594(8):2115-2124.

Vaishampayan et al., "A phase I trial of ALKS 4230, an engineered cytokine activator of NK and effector T cells, in patients with advanced solid tumors," Journal of Clinical Oncology, 2017, 35(15 Suppl.):TPS3111, 4 pages (Abstract Only).

Vankadari et al., "Emerging COVID-19 coronavirus: glycan shield and structure prediction of spike glycoprotein and its interaction with human CD26," Emerging Microbes and Infection, Mar. 17, 2020, 9(1):601-604.

Von Kobbe, "Cellular senescence: a view throughout organismal life," Cellular and Molecular Life Sciences, Jul. 20, 2018, 75:3553-3567, 15 pages.

Waaijer et al., "Do senescence markers correlate in vitro and in situ within individual human donors?," Aging Feb. 2018, 10(2):278-289.

Wang et al., "Biomarkers of Cellular Senescence and Skin Aging," Frontiers in Genetics, Aug. 23, 2018, 9:247, 14 pages.

Wang et al., "Loss of lamin B1 is a biomarker to quantify cellular senescence in photoaged skin," Scientific Reports, Nov. 15, 2017, 7(1):15678, 8 pages.

Weihermann et al., "Elastin structure and its involvement in skin photoageing," International Journal of Cosmetic Science, Jun. 2017, 39(3):241-247.

Weihofen et al., "Crystal Structure of CD26/Dipeptidyl-peptidase IV in Complex with Adenosine Deaminase Reveals a Highly Amphiphilic Interface," Journal of Biological Chemistry, Oct. 2004, 279(41):43330-43335.

Wiemann et al., "Hepatocyte telomere shortening and senescence are general markers of human liver cirrhosis," The FASEB Journal, Jul. 2002, 16(9):935-942.

Wiley et al., "Mitochondrial Dysfunction Induces Senescence with a Distinct Secretory Phenotype," Cell Metabolism, Feb. 9, 2016, 23(2):303-314.

Xu et al., "JAK inhibition alleviates the cellular senescence-associated secretory phenotype and frailty in old age," Proceedings of the National Academy of Sciences U.S.A., Nov. 2, 2015, 112(46):E6301-6310, 10 pages.

Yamazaki et al., "Vascular Cell Senescence Contributes to Blood-Brain Barrier Breakdown," Stroke, Feb. 16, 2016, 47(4):1068-1077, 15 pages.

Yan et al., "Obesity- and aging-induced excess of central transforming growth factor-β potentiates diabetic development via an RNA stress response," Nature Medicine, Aug. 3, 2014, 20:1001-1008, 9 pages.

Yanai et al., "Cellular senescence-like features of lung fibroblasts derived from idiopathic pulmonary fibrosis patients," Aging (Albany NY), Sep. 2015, 7(9):664-672.

Yousefzadeh et al., "An aged immune system drives senescence and ageing of solid organs," Nature, May 12, 2021, 594:100-105, 34 pages.

Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.

Yu et al., "The dipeptidyl peptidase IV family in cancer and cell biology," FEBS Journal, Feb. 5, 2010, 277(5):1126-1144.

Zhong et al., "A Potential Role for Dendritic Cell/Macrophage-Expressing DPP4 in Obesity-Induced Visceral Inflammation," Diabetes, Jan. 2013, 62(1):149-157.

Zhou et al., "A novel chimeric antigen receptor redirecting T-cell specificity towards CD26cancer cells," Leukemia, Apr. 2020, 35(1):119-129, 11 pages.

Zhu et al., "New agents that target senescent cells: the flavone, fisetin, and the BCL-XL inhibitors, A1331852 and A1155463," Aging (Albany NY), Mar. 2017, 9(3):955-963.

Zhu et al., "Novel Human Interleukin-15 Agonists," The Journal of Immunology, Sep. 15, 2009, 183(6):3598-3607.

Mikayama et al., "Molecular cloning and functional expression of a cDNA encoding glycosylation-inhibiting factor," Proc. Natl. Acad. Sci. USA, Nov. 1, 1993, 90(21):10056-10060.

Voet et al., Biochemistry, John Wiley & Sons, Inc., 1990, pp. 126-128 and 228-234, 12 pages.

(56) References Cited

OTHER PUBLICATIONS

Chandrudu et al., "Chemical methods for peptide and protein production," Molecules, 2013, 18(4):4373-4388.
Tam et al., "Methods and strategies of peptide ligation," Peptide Science: Original Research on Biomolecules, 2001, 60(3):194-205.
Ait-Oufella el al., "Natural regulatory T cells control the development of atherosclerosis in mice," Nature Medicine, Feb. 5, 2006, 12(2):178-180.
Brunstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.
Brunstein et al., "Umbilical cord blood-derived T regulatory cells to prevent GVHD:kinetics, toxicity profile, and clinical effect," Blood, Feb. 25, 2016, 127(8):1044-1051.
Cao, "Self-regulation and cross-regulation of pattern-recognition receptor signalling in health and disease," Nature Reviews Immunology, Dec. 29, 2015, 16(1):35-50.
Chen et al., "Sterile inflammation: sensing and reacting to damage," Nature Reviews Immunology, Nov. 19, 2010, 10(12):826-837.
Collado et al., "Senescence in tumours: evidence from mice and humans," Nature Reviews Cancer, Jan. 2010, 10(1):51-57.
Dall'Era et al., "Adoptive Regulatory T Cell Therapy in a Patient with Systemic Lupus Erythematosus," Arthritis Rheumatology, Mar. 2019, 71(3): 19 pages.
Demaria et al., "An Essential Role for Senescent Cellsin Optimal Wound Healingthrough Secretion of PDGF-AA," Developmental Cell, Dec. 22, 2014, 31(6):722-733.
Di Ianni et al., "Tregs prevent GVHD and promote immune reconstitution inHLA-haploidentical transplantation," Blood, Apr. 7, 2011, 117(14):3921-3928.
Dietel et al., "Decreased numbers of regulatory T cells are associated with human atherosclerotic lesion vulnerability and inversely correlate with infiltrated mature dendritic cells," Atherosclerosis, Jul. 2013, 230:92-99.
Dinarello, "Interleukin 1 and interleukin 18 as mediators of inflammation and the aging process," The American Journal of Clinical Nutrition, Feb. 1, 2006, 83(2):447S-455S.
Eisenhut et al., "Ion Channels in Inflammation," Pflugers Archive, Jan. 29, 2011, 461(4):401-421.
Esensten et al., "Regulatory T-cell therapy for autoimmune and autoinflammatory diseases: The next frontier," The Journal of Allergy and Clinical Immunology, Dec. 1, 2018, 142(6):1710-1718.
Feng et al., "The yin and yang functions of extracellular ATP and adenosine in tumor immunity," Cancer Cell International, Apr. 7, 2020, 20:110, 11 pages.
Ferreira et al., "Next-generation regulatory T cell therapy," Nature Reviews Drug Discovery, Sep. 20, 2019, 18(10):749-769, 21 pages.
Ferrucci et al., "The origins of age-related proinflammatory state," Blood, Mar. 15, 2005, 105(6):2294-2299.
Ford et al., "TREM and TREM-like receptors in inflammation and disease," Current Opinion in Immunology, Feb. 21, 2009, 21(1):38-46.
Franceschi et al., "Inflamm-aging. An evolutionary perspective on immunosenescence," Annals of the New York Academy of Sciences, Jun. 2000, 908:244-254.
Gong et al., "DAMP-sensing receptors in sterile inflammation and inflammatory diseases," Nature Reviews Immunology, Sep. 26, 2019, 20(2):95-112.
Gu et al., "Human CD39hi regulatory T cells present stronger stability and function under inflammatory conditions," Cellular and Molecular Immunology, Jul. 4, 2016, 14(6):521-528.
Heneka et al., "Inflammasome signalling in brain function and neurodegenerative disease," Nature Reviews Neuroscience, Sep. 11, 2018, 19(10):610-621.
Heneka et al., "NLRP3 is activated in Alzheimer's disease and contributes to pathology in APP/PS1 mice," Nature, Jan. 31, 2013, 493(7434):674-678, 8 pages.
Heng et al., "G Protein-Coupled Receptors Revisited: Therapeutic Applications Inspired by Synthetic Biology," Annual Review of Pharmacology and Toxicology, Jan. 2014, 54:227-249.

Highfill et al., "Overcoming Challenges in Process Development of Cellular Therapies," Current Hematologic Malignancy Reports, Jul. 6, 2019, 14(4):269-277, 9 pages.
Hudson et al., "Targeting RAGE Signaling in Inflammatory Disease," Annual Review of Medicine, Jan. 2018, 69:24.1-24.16, 16 pages.
Hynes et al., "In vitro analysis of cell metabolism using a long-decay pH-sensitive lanthanide probe and extracellular acidification assay," Analytical biochemistry,Apr. 18, 2009, 390(1):21-28.
Iihoshi et al., "Aclarubicin, an anthracycline anti-cancer drug, fluorescently contrasts mitochondria and reduces the oxygen consumption rate in living human cells," Toxicology Letters, Aug. 5, 2017, 277:109-114.
Janeway, "Approacing the Asymptote? Evolution and Revolution in Immunology," Cold Spring Harbor Symposia on Quantitative Biology, 1989, 54 Pt 1:1-13.
Jin et al., "Novel Insights Into the NLRP3 Inflammasome in Atherosclerosis," Journal of the American Heart Association, Jun. 11, 2019, 8(12):e012219, 12 pages.
Klingenberg et al., "Depletion of FOXP3+ regulatory T cells promotes hypercholesterolemia and atherosclerosis," The Journal of Clinical Investigation, Feb. 15, 2013, 123:1323-1334.
Kumagai et al., "Monitoring of glutamate-induced excitotoxicity by mitochondrial oxygen consumption," Synapse, Jan. 2019, 73(1):e22067, 24 Pages.
Lamkanfi et al., "Mechanisms and Functions of Inflammasomes," Cell, May 22, 2014, 157(5):1013-1022.
Latz et al., "Activation and regulation of the inflammasomes," Nature Reviews Immunology, May 24, 2013, 13(6):397-411.
Latz et al., "NLRP3 inflammasome activation in inflammaging," Seminars in Immunology, Dec. 2018, 40:61-73, 13 pages.
Lau et al., "RNA-associated autoantigens activate B cells by combined B cell antigen receptor/Toll-like receptor 7 engagement," The Journal of Experimental Medicine, Oct. 31, 2005, 202(9):1171-1177.
Maganto-García et al., "Dynamic Changes in Regulatory T Cells Are Linked to Levels of Diet-Induced Hypercholesterolemia," Circulation, Jun. 20, 2011, 124:185-195.
Martelli et al., "HLA-haploidentical transplantation with regulatory and conventionalT-cell adoptive immunotherapy prevents acute leukemia relapse," Blood, Jul. 24, 2014, 124(4):638-644.
McHugh et al., "Senescence and aging: Causes, consequences, and therapeutic avenues," Journal of Cellular Biology, Nov. 7, 2017, 217(1):65-77.
Moesta et al., "Targeting CD39 in cancer," Nature Reviews Immunology, Jul. 29, 2020, 20(12):739-755, 17 pages.
Mookerjee et al., "Measurement and Analysis of Extracellular Acid Production to Determine Glycolytic Rate," Journal of Visualized Experiments : Jove, Dec. 2015, (106):e53464, 9 Pages.
Moore et al., "Macrophages in atherosclerosis: a dynamic balance," Nature Reviews Immunology, Sep. 2, 2013, 13:709-721, 13 pages.
Munoz-Espin et al., "Cellular senescence: from physiology to pathology," Nature Reviews Molecular Cellular Biology, Jun. 23, 2014, 15(7):482-496.
Munoz-Espin et al., "Programmed Cell Senesceneduring Mammalian Embryonic Development," Cell, Nov. 21, 2013, 155(5):1104-1118.
Nayyar et al., "Overcoming Resistance to Natural Killer Cell Based Immunotherapies for Solid Tumors," Frontiers in Oncology, 2019, 9: DOI:10.3389/fonc.2019.00051.
Oberle et al., "Rapid Suppression of Cytokine Transcription in Human CD4+CD25-T Cells by CD4+Foxp3+ Regulatory T Cells: Independence of IL-2 Consumption, TGF-β, and Various Inhibitors of TCR Signaling," The Journal of Immunology, Sep. 15, 2007, 179(6):3578-3587.
Owicki et al., "Biosensors based on the energy metabolism of living cells: the physical chemistry and cell biology of extracellular acidification," Biosensors and Bioelectronics, Jan. 1, 1992, 7(4):255-272.
PCT International Search Report and Written Opinion in International Appln. No. PCTUS2020/038717, dated Oct. 16, 2020, 17 pages.

(56) References Cited

OTHER PUBLICATIONS

Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.
Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.
Roh et al., "Damage-Associated Molecular Patterns in Inflammatory Diseases," Immune Network, Aug. 2018, 18(4):e27, 14 pages.
Sakaguchi et al., "Regulatory T Cells and Human Disease," Annual Review of Immunology, Apr. 26, 2020, 38:541-566.
Sakaguchi et al., "Regulatory T Cells and Immune Tolerance," Cell, May 30, 2008, 133(5):775-787.
Sakaguchi et al., "Regulatory T cells: how do they suppress immune responses?" International Immunology, Sep. 7, 2009, 21(10):1105-1111.
Sakamuri et al., "Measurement of respiratory function in isolated cardiac mitochondria using Seahorse XFe24 Analyzer: applications for aging research," Geroscience, Jun. 2, 2018, 40(3):347-356.
Sharma et al., "Regulatory T Cells License Macrophage Pro Resolving Functions During Atherosclerosis Regression," Circulation Research, Apr. 27, 2020, 127:335-353.
Storer et al., "Senescence Is a Developmental Mechanism that Contributes to Embryonic Growth and Patterning," Cell, Nov. 21, 2013, 155(5):1119-1130.
Swanson et al., "The NLRP3 inflammasome: molecular activation and regulation to therapeutics," Nature Reviews Immunology, Apr. 29, 2019, 19(8):477-489, 13 pages.
Takahashi et al., "Simple and inexpensive technique for measuring oxygen consumption rate in adherent cultured cells," The Journal of Physiological Sciences, Nov. 2017, 67(6):731-737.
Tang et al., "The Foxp3+ regulatory T cell: a jack of all trades, master of regulation," Nature Immunology, Feb. 19, 2008, 9(3):239-244.
Teissier et al., "The receptor for advanced glycation end-products (RAGE) is an important pattern recognition receptor (PRR) for inflammaging," Biogerontology, Apr. 9, 2019, 20(3):279-301, 23 pages.
Theil et al., "Adoptive transfer of allogeneic regulatory T cells into patients with chronic graft-versus-host disease," Cytotherapy, Apr. 2015, 0: 1-14, 14 pages.
Thonhoff et al., "Expanded autologous regulatory T-lymphocyte infusions in ALS," Neurology Neuroimmunology Neuroinflammation, May 18, 2018, 5(4):e465, 8 pages.
Trevani et al., "Extracellular acidification induces human neutrophil activation," The Journal of Immunology, Apr. 15, 1999, 162(8):4849-4857.
Van Deursen, "The role of senescent cells in ageing," Nature, May 2014, 509(7501):439-446.
Vidarsson et al., "IgG subclasses and allotypes: from structure to effector functions," Frontiers in immunology, Oct. 20, 2014, 5:520, 17 Pages.
Walsh et al., "Inflammasomes in the CNS," Nature Reviews Neuroscience, Jan. 8, 2014, 15(2):84-97, 14 pages.
Weiss et al., "Formyl-Peptide Receptors in Infection, Inflammation, and Cancer," Trends in Immunology, Oct. 2018, 39(10):815-829, 15 pages.
Xu et al., "Senolytics improve physical function and increase lifespan in old age," Nature Medicine, Jul. 2018, 24(8): 15 Pages.
Xu, "Senolytics Improve Physical Function and Increase Lifespan in Old Age," Nature Medicine, Jul. 9, 2018, 24(8):1246-1256, 15 pages.
Yamamoto et al., "Measurement of glucose uptake in cultured cells," Curr Protoc Pharmacol, Dec. 2011, Chapter 12:Unit 12.14. 1-22.
Yun et al., "Recurrent turnover of senescent cells during regeneration of a complex structure," Elife, May 5, 2015, 4:e05505, 16 pages.
Zhang et al., "AAED1 modulates proliferation and glycolysis in gastric cancer," Oncology Reports, Aug. 1, 2018, 40(2):1156-1164.
Zhang et al., "The bone anabolic effects of irisin are through preferential stimulation of aerobic glycolysis," Bone, Sep. 1, 2018, 114:150-160.
Zhao et al., "Histone Deacetylase-3 Modification of MicroRNA-31 Promotes Cell Proliferation and Aerobic Glycolysis in Breast Cancer and Is Predictive of Poor Prognosis," Journal of breast cancer, Jun. 1, 2018, 21(2):112-123.
Zheng et al., "Acquisition of Suppressive Function by Activated Human CD4+CD25-T Cells Is Associated with the Expression of CTLA-4 Not FoxP3," The Journal of Immunology, Aug. 1, 2008, 181(3):1683-1691.
Zou et al., "2-NBDG as a fluorescent indicator for direct glucose uptake measurement," Journal of biochemical and biophysical methods, Sep. 30, 2005, 64(3):207-215.
International Preliminary Report on Patentability in International Appln. No. PCT/US2020/035598, mailed Dec. 15, 2022, 7 pages.
International Preliminary Report on Patentability in International Appln. No. PCT/US2021/035285, mailed Dec. 15, 2022, 7 pages.
Huang et al., "Targeting the vasculature of colorectal carcinoma with a fused protein of (RGD) 3-tTF" The Scientific World Journal, 2013(637086):1-11, 2013.
PCT International Preliminary Report on Patentability in International Appln. No. PCT/US2021/029920, dated Nov. 10, 2022, 11 pages.
Baker et al., "Chronic treatment with the beta(2)-adrenoceptor agonist prodrug BRL-47672 impairs rat skeletal muscle function by inducing a comprehensive shift to a faster muscle phenotype," J Pharmacol Exp Ther., Oct. 2006, 319(1):439-446.
Baker et al., "Effects of conjugated linoleic acid (CLA) on tissue composition parameters in a murine cachexia model," The FASEB Journal, Mar. 2006, 20(4), 2 pages (Abstract Only).
Berry et al., "Cancer Anorexia and Cachexia: Screening in an Ambulatory Infusion Service and Nutrition Consultation," Clin J Oncol Nurs., 2018, 22(1):63-68.
Chang et al., "Association Between Sarcopenia and Cognitive Impairment: A Systematic Review and Meta-Analysis," J Am Med Dir Assoc., Dec. 1, 2016, 17(12):1164e7-1164e15, 9 pages.
Chen et al., "Circulating levels of resistin and risk of type 2 diabetes in men and women: results from two prospective cohorts," Diabetes Care, Feb. 2009, 32(2):329-334.
Cosgrove et al., "Usher protein functions in hair cells and photoreceptors," Int J Biochem Cell Biol., Jan. 2014, 46:80-89.
Helman et al., "Effects of ageing and senescence on pancreatic β-cell function," Diabetes Obes Metab., Sep. 2016, 18(Suppl. 1):58-62.
Jeon et al., "Local clearance of senescent cells attenuates the development of post-traumatic osteoarthritis and creates a pro-regenerative environment," Nat Med., Jun. 2017, 23(6):775-781.
Kim et al., "Insulin resistance, inflammation, and nonalcoholic fatty liver disease in non-obese adults without metabolic syndrome components," Hepatol Int., Jun. 2013, 7(2):586-591.
Kuyinu et al., "Animal models of osteoarthritis: classification, update, and measurement of outcomes," J Orthop Surg Res., Feb. 2, 2016, 11:19, 27 pages.
Melk et al., "Expression of p16INK4a and other cell cycle regulator and senescence associated genes in aging human kidney," Kidney Int., Feb. 2004, 65(2):510-520.
Melk, "Senescence of renal cells: molecular basis and clinical implications," Nephrology Dialysis Transplantation, Dec. 2003, 18(12):2474-2478.
Price et al., "Comparison of collagenase-cleaved articular cartilage collagen in mice in the naturally occurring STR/ort model of osteoarthritis and in collagen-induced arthritis," Osteoarthritis and Cartilage, Mar. 2002, 10(3): 172-179.
Sousa-Victor et al., "Geroconversion of aged muscle stem cells under regenerative pressure," Cell Cycle, Oct. 15, 2014, 13(20):3183-3190.
Xu et al., "Celecoxib attenuates cachectic events in mice by modulating the expression of vascular endothelial growth factor," Mol Med Rep., Jan. 2015, 11(1):289-294.

(56) References Cited

OTHER PUBLICATIONS

PCT International Preliminary Report on Patentability in International Appln. No. PCT/US2021/017620, dated Aug. 25, 2022, 12 pages.
PCT International Preliminary Report on Patentability in International Appln. No. PCT/US2021/017621, dated Aug. 25, 2022, 8 pages.
PCT International Preliminary Report on Patentability in International Appln. No. PCT/US2021/017714, dated Aug. 25, 2022, 12 pages.
[No Author Listed], "CN Br-activated Sepharose 4 Fast Flow," 1999, Affinity Chromatography, 4 pages.
Brämer et al., "Membrane adsorber for the fast purification of a monoclonal antibody using protein a chromatography," Membranes, Nov. 27, 2019, 9(12):159, 15 pages.
Chabannon et al., "Manufacturing natural killer cells as medicinal products," Frontiers in Immunology, Nov. 15, 2016, 7(504): 1-9.
Chan et al., "Molecular mechanisms of natural killer cell activation in response to cellular stress," Cell Death & Differentiation, Jan. 2014, 21(1):5-14.
Chang et al., "The dock and lock method: a novel platform technology for building multivalent, multifunctional structures of defined composition with retained bioactivity," Clinical cancer research, Sep. 15, 2007, 13(18):5586s-5591s.
Guha et al., "Affinity purification of human tissue factor: interaction of factor VII and tissue factor in detergent micelles," Proceedings of the National Academy of Sciences, Jan. 1986, 83(2):299-302.
Hélie et al., "Application of the Protein Maker as a platform purification system for therapeutic antibody research and development," Computational and Structural Biotechnology Journal, Jan. 1, 2016, 14:238-244.
Hui et al., "Butyrate inhibit collagen-induced arthritis via Treg/IL-10/Th17 axis," International immunopharmacology, Mar. 1, 2019, 68: Abstract 1 page.
info.gbiosciences.com [Online], "G-Biosciences, The Basics of Affinity Purification/Affinity Chromatography," Jul. 31, 2018, retrieved on Apr. 18, 2023, retrieved from URL<https://info.gbiosciences.com/blog/the-basics-of-affinity-purification/affinity-chromatography?utm_campaign=G-Bio+Search+Ads&utm_term=&utm_source=adwords&utm_medium=ppc&hsa_src=g&hsa_ver=3&hsa_cam=737902488&hsa_kw=&hsa_ad=621736020174&hsa_tgt-dsa-460355902483&hsa_mt=&hsa_acc-6752996364&hsa_grp=92226101427&hsa_net-adwords&gclid-CjwKCAjw_ihBhADEiwAXEazJvXifVFgeRGV_W99XbY72eRROhWnHtd d695ydPgyh8qdvTwd9ikGIRoCdecQAvD_BwE>, 5 pages.
Klingemann et al., "Natural killer cells for immunotherapy—advantages of the NK-92 cell line over blood NK cells," Frontiers in immunology, Mar. 14, 2016, 7(91): 1-7.
Kozlowska et al., "Adoptive transfer of osteoclast-expanded natural killer cells for immunotherapy targeting cancer stem-like cells in humanized mice," Cancer Immunology, Immunotherapy, Jul. 2016, 65:835-845.
Li et al., "Lipid metabolism fuels cancer's spread," Cell metabolism, Feb. 7, 2017, 25(2):228-230.
Putnam et al., "Clinical grade manufacturing of human alloantigen-reactive regulatory T cells for use in transplantation," American journal of transplantation, Nov. 1, 2013, 13(11):3010-3020.
ThermoFisher.com [Online], "Covalent Immobilization of Affinity Ligands," 2018, retrieved on Apr. 18, 2023, retrieved from <URLhttps://www.thermofisher.com/us/en/home/life-science/protein-biology/protein-biology-learning-center/protein-biology-resource-library/pierce-protein-methods/covalent-immobilization-affinity-ligands.html>, 13 pages.
Uppendahl et al., "Natural killer cell-based immunotherapy in gynecologic malignancy: a review," Frontiers in immunology, Jan. 5, 2018, 8(1825): 1-15.
Urh et al., "Affinity chromatography: general methods," Methods in enzymology, Jan. 1, 2009, 463: 23 pages.
Veluchamy et al., "The rise of allogeneic natural killer cells as a platform for cancer immunotherapy: recent innovations and future developments," Frontiers in immunology, May 31, 2017, 8(631): 1-20.
Wilchek et al., "Essentials of biorecognition: The (strept) avidin-biotin system as a model for protein-protein and protein-ligand interaction," Immunology letters, Feb. 28, 2006, 103(1): Abstract 2 pages.
Zhang et al., "Depletion of NK cells improves cognitive function in the Alzheimer disease mouse model," The Journal of Immunology, Jul. 15, 2020, 205(2): 10pages.
Zhou, "Emerging mechanisms and applications of low-dose IL-2 therapy in autoimmunity," Cytokine & Growth Factor Reviews, Jun. 30, 2022, 67: 80-88.
Bartscht et al., "Dasatinib blocks transcriptional and promigratory responses to transforming growth factor-beta in pancreatic adenocarcinoma cells through inhibition of Smad signalling: implications for in vivo mode of action," Molecular Cancer, Dec. 2015, 14(199):1-12.
Bird et al., "TGFβ inhibition restores a regenerative response in acute liver injury by suppressing paracrine senescence," Science Translational Medicine, Aug. 15, 2018, 10(454):eaan 1230, 15 pages.
Cai et al., "Quercetin inhibits transforming growth factor β1-induced epithelial-mesenchymal transition in human retinal pigment epithelial cells via the Smad pathway," Drug Design, Development and Therapy, Dec. 6, 2018, 12:4149-4161.
Chen et al., "A novel idea for establishing Parkinson's disease mouse model by intranasal administration of paraquat," Neurological Research, 2021, 43(4):267-277.
Fernando et al., "Targeting tumor endothelial marker 8 in the tumor vasculature of colorectal carcinomas in mice," Cancer Research, Jun. 15, 2009, 69(12):5126-5132.
Igarashi et al., "VEGF-C and TGF-β reciprocally regulate mesenchymal stem cell commitment to differentiation into lymphatic endothelial or osteoblastic phenotypes," International Journal of Molecular Medicine, Apr. 1, 2016, 37(4):1005-1013.
Infante-Duarte et al., "New developments in understanding and treating neuroinflammation," Journal of Molecular Medicine, Sep. 2008, 86:975-985.
International Search Report and Written Opinion in International Appln. No. PCT/US2023/065745, mailed on Jun. 26, 2023, 14 pages.
Janeway et al., "The interaction of the antibody molecule with specific antigen" In Immunobiology: The Immune System in Health and Disease, 5th edition, 5 pages, 2001.
Matsuura et al., "Pole test is a useful method for evaluating the mouse movement disorder caused by striatal dopamine depletion," Journal of Neuroscience Methods, 73(1):45-48, 1997.
Mortier et al., "Soluble interleukin-15 receptor α (IL-15Rα)-sushi as a selective and potent agonist of IL-15 action through IL-15Rβ/γ: hyperagonist IL-15 · IL-15Rα fusion proteins," Journal of Biological Chemistry, Jan. 20, 2006, 281(3):1612-1619.
Reddy et al., "Linkers in the structural biology of protein-protein interactions," Protein Science, 2013, 22(2):153-167.
Ross et al., "Signaling and function of interleukin-2 in T lymphocytes" Annual Review of Immunology, 2018, 36:411-433.
Van Bockstaele et al., "The development of nanobodies for therapeutic applications" Current Opinion in Investigational Drugs, 2009, 10(11):1212-1224.
Wong et al., "Interleukin-15: Interleukin-15 receptor α scaffold for creation of multivalent targeted immune molecules," Protein Engineering, Design & Selection, Apr. 1, 2011, 24(4):373-383.
Akbari, et al., "Design, expression and evaluation of a novel humanized single chain antibody against epidermal growth factor receptor (EGFR)," Protein Expr. Purif., 2016, 127:8-15 Bachelet et al., "Mast Cell Costimulation by CD226/CD112 (DNAM-1/Nectin-2) A Novel Interface in the Allergic Process," Journal of Biological Chemistry, Sep. 15, 2006, 281(37):27190-6.
Bachelet et al., "Mast cell Costimulation by CD226/CD112 (DNAM-Nectin-2) A Novel Interface in the Allergic Process," Journal of Biological Chenistry, Sep. 15, 2006, 281(37):27190-6.

(56) References Cited

OTHER PUBLICATIONS

Baker, et al., "Clearance of p16Ink4a-positive senescent cells delays ageing-associated disorders," Nature, 2011, 479(7372): 232-236.
Borgerding et al., "B-lymphoma cells escape rituximab-triggered elimination by NK cells through increased HLA class I expression," Experimental Hematology, Mar. 1, 2010, 38(3):213-21.
Bourgeois et al., "Regulation of cellular senescence via the FOXO4-p53 axis," FEBS Lett., 2018, 592(12): 2083-2097.
Brennan et al., "Structural determination of lipid antigens captured at the CD1d-T-cell receptor interface," PNAS, 2017, 114(31):8348-8353.
Brighton et al., "Clearance of senescent decidual cells by uterine natural killer cells in cycling human endometrium," Elife, Dec. 11, 2017, 6:e31274, 23 pages.
Brooks et al., "Combined inhibition of PD1 and CD96 checkpoints improves survival in a resectable murine model of pancreatic cancer," European Journal of Cancer, Jul. 1, 2016, 61:S189, 1 page.
Cai et al., "Chibby suppresses aerobic glycolysis and proliferation of nasopharyngeal carcinoma via the Wnt/*catenin-Lin28/let7-PDK1 cascade," Journal of Experimental & Clinical Cancer Research, Dec. 1, 2018, 37(1):104.
Cao et al., "Expression and characterization of recombinant humanized anti-HER2 single-chain antibody in Pichia pastoris for targeted cancer therapy," Biotechnology Letters, Jul. 1, 2015, 37(7):1347-54.
Chalan et al., "Expression of Lectin-Like Transcript 1, the Ligand for CD161, in Rheumatoid Arthritis," PLoS One, 2015, 10(7):e0132436.
Chance et al., "A simple and rapid assay of oxidative phosphorylation," Nature, Jun. 1955, 175(4469):1120-1121.
Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.
Chichili et al., "Linkers in the structural biology of protein-protein interactions," Protein Science, Feb. 2013, 22(2):153-67.
Chinta, et al., "Cellular senescence is induced by the environmental neurotoxin paraquat and contributes to neuropathology linked to Parkinson's Disease," Cell Rep., 2018, 22(4): 930-940.
Ciaglia, et al., "Recognition by natural killer cells of N6-isopentenyladensoine-treated human glioma cell lines," Int. J. Cancer, 2018 142(1): 176-190.
Cichocki et al., "GSK3 inhibition drives maturation of NK cells and enhances their antitumor activity," Cancer Research, Oct. 15, 2017, 77(20):5664-75.
Clayton et al., "Soluble T Cell Immunoglobulin Mucin Domain 3 Is Shed from CD8 T Cells by the Sheddase ADAMO, Is Increased in Plasma during Untreated HIV Infection, and Correlates with HIV Disease Progression," J Viral., 2015, 89(7):3723-3736.
Cosman et al., "ULBPs, novel MHC class I-related molecules, bind to CMV glycoprotein UL16 and stimulate NK cytotoxicity through the NKG2D receptor," Immunity, Feb. 1, 2001, 14(2):123-33.
Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.
Cromie et al., "Nanobodies and their use in GPCR drug discovery," Current Topics in Medicinal Chemistry, Dec. 1, 2015, 15(24):2543-57.
Czaja et al., "A comprehensive analysis of the binding of anti-KIR antibodies to activating KIRs," Genes and Immunity, Jan. 2014, 15(1), 15 pages.
De Crescenzo et al., "Engineering TGF-β Traps: Artificially Dimerized Receptor Ectodomains as High-affinity Blockers of TGF-β Action," Transforming Growth Factor-β in Cancer Therapy, vol. II, 2008, Humana Press, 671-84.
De Genst et al., "Antibody repertoire development in camelids," Developmental & Comparative Immunology, Jan. 1, 2006, 30(1-2):187-98.
De Meyer et al., "Nanobody-based products as research and diagnostic tools," Trends in Biotechnology, May 1, 2014, 32(5):263-70.

Deyev et al., "Design of multivalent complexes using the barnase. barstar module," Nature Biotechnology, Dec. 2003, 21(12):1486-92.
DiGiammarino et al., "Design and generation of DVD-Ig™ molecules for dual-specific targeting," Therapeutic Proteins: Methods and Protocols, Methods in Molecular Biology, 2012, Humana Press, Totowa, NJ., 899:145-516.
Docagne et al., "A soluble transforming growth factor-β (TGF-) type I receptor mimics TGF-β responses," Journal of Biological Chemistry, Dec. 7, 2001, 276(49):46243-50.
Dong et al., "Loss of methylation at the IFNG promoter and CNS-1 is associated with the development of functional IFN-y memory in human CD4+T lymphocytes," European Journal of immunology, 2013, 43(3), 793-804.
Drees, et al., "Soluble production of a biologically active single-chain antibody against murine PD-LI in *Escherichia coli*," Protein Express. Purif., 2014, 94:60-66.
Edwardraja et al., "Redesigning of anti-c-met single chain Fv antibody for the cytoplasmic folding and its structural analysis," Biotechnology and Bioengineering, Jun. 15, 2010, 106(3):367-75.
Elgueta et al., "Molecular mechanism and function of CD40/CD40L engagement in the immune system," Immunological Reviews, 2009, 229(1):152-172 doi.org/10.1111/j.1600-065X.2009.00782.x.
Farr, et al., "Targeting cellular senescence prevents age-related bone loss in mice," Nat. Med., 2017, 23(9): 1072-1079.
Garber, "Bispecific antibodies rise again," Nat. Rev. Drug Discov., 2014, 13:799-801.
Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.
Gejima et al., "Human single-chain Fv (scFv) antibody specific to human IL-6 with the inhibitory activity on TIL-6-signaling," Human Antibodies, Jan. 1, 2002, 11(4):121-9.
Geng et al., "A novel anti-TNF scFv constructed with human antibody frameworks and antagonistic peptides," Immunol. Res. 62(3):377-385, 2015.
Gibbs et al., "Identification of the factor VIIa binding site on tissue factor by homologous loop swap and alanine scanning mutagenesis," Biochemistry, Nov. 1, 1994, 33(47):14003-10.
Guo et al., "Immunobiology of the IL-15-IL-15R complex as an antitumor and antiviral agent," 2017, Cytokine & Growth Factor Reviews, 38:10-21.
Haile et al., "Soluble CD80 Restores T Cell Activation and Overcomes Tumor Cell Programmed Death Ligand I-Mediated Immune Suppression," J. Immunol., 2013, 191(5):2829-2836.
Hebbar et al., "Detection of circulating soluble CD28 in patients with systemic lupus erythematosus, primary Sjogren's syndrome and systemic sclerosis," Clinical & Experimental Immunology, May 2004, 136(2):388-92.
Helfrich et al., "A rapid and versatile method for harnessing scFv antibody fragments with various biological effector functions," Journal of Immunological methods, 2000, 237(1-2):131-145 DOI:1O. 1O16/S0022-I759(99)OO220-3.
Heng et al., Sophea, et al. "Multiple soluble TGF-β receptors in addition to soluble endoglin are elevated in preeclamptic serum and they synergistically inhibit TGF-β signaling." Placenta, 2017 57:320 (1 page).
Hombach et al., "Generation of the single chain antibody fragment conserves the idiotypic profile of the anti-CD30 monoclonal antibody HRS3," Scandinavian Journal of Immunology, Nov. 1998, 48(5):497-501.
Hu et al., "Discovery of a novel IL-15 based protein with improved developability and efficacy for cancer immunotherapy," Scientific Reports, 2018, 8:7675, 11 pages.
Huang et al., "Substrate recognition by tissue factor-factor VIIa Evidence for interaction of residues Lys165 and Lys166 of tissue factor with the 4-carboxyglutamate-rich domain of factor X," Journal of Biological Chemistry, Sep. 6, 1996, 271(36):21752-7.
Hudak et al., "Glycocalyx engineering reveals a Siglec-based mechanism for NK cell immunoevasion," Nature Chemical Biology, Jan. 2014, 10(1), 20 pages.

(56) References Cited

OTHER PUBLICATIONS

Hughes, et al., "Transfer of a TCR gene derived from a patient with a marked antitumor response conveys highly active T-cell effector functions," Hum. Gene Ther., 2005, 16:457-72.
Iannello et al., "p53-dependent chemokine production by senescent tumor cells supports NKG2D-dependent tumor elimination by natural killer cells," Journal of Experimental Medicine, Sep. 23, 2013, 210(10):2057-69.
Jakob et al., Structure reveals function of the dual variable domain immunoglobulin (DVD-Ig™) molecule, Mabs, May 1, 2013, Taylor & Francis, 5(3):358-63.
Jeannin et al., "Soluble CD86 Is a Costimulatory Molecule for Human T Lymphocytes," Immunity, 2000, 13(3):303-312.
Kain et al., "The identification of the endogenous ligands of natural killer T cells reveals the presence of mammalian a-linked glycosylceramides," Immunity, Oct. 16, 2014, 41(4):543-54.
Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.
Kijanka et al., "Nanobody-based cancer therapy of solid tumors,"10(1):161-74.
Kim et al., "Experimental malaria infection triggers early expansion of natural killer cells," Infection and Immunity, Dec. 1, 2008, 76(12):5873-82.
Kirchhofer et al., "The tissue factor region that interacts with substrates factor IX and factor X," Biochemistry, Jun. 27, 2000, 39(25):7380-7.
Klein et al., "Design and characterization of structured protein linkers with differing flexibilities," Protein Engineering, Design & Selection, 2014, 27(10):325-30.
Kondo et al., "Requirements for the functional expression of OX40 ligand on human activated CD4+ and CDS+ T cells," Human Immunology, 2007, 68(7):563-571.
Kovaleva et al., "Shark variable new antigen receptor biologics-a novel technology platform for therapeutic drug development," Expert Opinion on Biological Therapy, Oct. 1, 2014, 14(10):1527-39.
Krah et al., "Single-domain antibodies for biomedical applications," Immunopharmacology and Immunotoxicology, Jan. 2, 2016, 38(1):21-8.
Krizhanovsky et al., "Senescence of activated stellate cells limits liver fibrosis," Cell, Aug. 22, 2008, 134(4):657-67.
Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.
Maeda et al., "Original Ligand for LTβR Is LIGHT: Insight into Evolution of the LT/LTβR System," J Immunol., 2018, 201(1):202-214.
Mandelboim et al., "Recognition of haemagglutinins on virus-infected cells by NKp46 activates lysis bv human NK cells," Nature, Feb. 2001, 409(6823):1055.
Masoumi et al., "The role of hypoxia as the driving force for non-erythroid production of globin chains in preeclamptic placentas," Placenta, 2017;57:320.
Menshawy et al., "CD58; leucocyte function adhesion-3 (LFA-3) could be used as a differentiating marker between immune and non-immune thyroid disorders," Comparative Clinical Pathology, 2018, 27(3), 721-727, doi.org/10.1007/s00580-018-2657-x.
Miah et al., "KIR2DL4 differentially signals downstream functions in human NK cells through distinct structural modules," The Journal of Immunology, Mar. 1, 2008, 180(5):2922-32.
Miller et al., "Soluble CD70: a novel immunotherapeutic agent for experimental glioblastoma," J Neurosurg., 2010, 113(2):280-285.
Molema et al., "The use of bispecific antibodies in tumor cell and tumor vasculature directed immunotherapy," Journal of Controlled Release, 2000, 64(1-3):229-239.
Molgora et al., "Regulatory role of IL-1R8 in immunity and disease," Frontiers in Immunology, Apr. 20, 2016, 7:149.
Moretta et al., "CD69-mediated pathway of lymphocyte activation: anti-CD69 monoclonal antibodies trigger the cytolytic activity of different lymphoid effector cells with the exception of cytolytic T lymphocytes expressing T cell receptor alpha/beta," Journal of Experimental Medicine, Dec. 1, 1991, 174(6):1393-8.
Mujic-Delic et al., "GPCR-targeting nanobodies: attractive research tools, diagnostics, and therapeutics," Trends in Pharmacological Sciences, May 1, 2014, 35(5):247-55.
Muller et al., "Antibody fusions with immunomodulatory proteins for cancer therapy," Pharmacology and Therapeutics, 2015, 154:57-66.
Muyldermans et al., "Recognition of antigens by single-domain antibody fragments: the superfluous luxury of paired domains," Trends in Biochemical Sciences, Apr. 1, 2001, 26(4):230-5.
Muyldermans, "Nanobodies: natural single-domain antibodies," Annual Review of Biochemistry, Jun. 2, 2013, 82:775-97.
Muyldermans, "Single domain camel antibodies: current status," Reviews in Molecular Biotechnology, Jun. 1, 2001, 74(4):277-302.
Nag et al., "Soluble MHC II-peptide complexes induce antigen-specific apoptosis in T cells," Cellular Immunology, May 25, 1996, 170(1):25-33.
Nilsson et al., "Targeted delivery of tissue factor to the ED-B domain of fibronectin, a marker of angiogenesis, mediates the infarction of solid tumors in mice," Cancer Research, American Association for Cancer Research, Proceedings: AACR 107th Annual Meeting, 2016, Apr. 16-20, 2016, New Orleans, LA 61(2):711-716.
O'Sullivan et al., "Natural Killer Cell Memory," Immunity, Oct. 20, 2015, 43(4):634-645.
Ovadya et al., "Strategies targeting cellular senescence," The Journal of Clinical Investigation, Apr. 2, 2018, 128(4):1247-54.
Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.
Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.
Priyanka et al., "Linkers in the structural biology of protein-protein interactions," Protein Sci., 2013, 22(2):153-167.
Rahbarizadeh et al., "Nanobody; an old concept and new vehicle for immunotargeting," Immunological Investigations, Jan. 1, 2011, 40(3):299-338 (Uploaded in 2 Parts).
Ranganathan et al., "Pinpointing the putative heparin/sialic acid-binding residues in the 'sushi' domain 7 of factor H: a molecular modeling study," Biocomputing 2000, 5:155-67.
Rhein et al., "Characterization of Human and Murine T-Cell Immunoglobulin Mucin Domain 4 (TIM-4) IgV Domain Residues Critical for Ebola Virus Entry," J Viral., 2016, 90(13):6097-6111.
Rippmann et al., "Fusion of the Tissue Factor Extracellular Domain to a Tumor Stroma Specific Single-Chain Fragment Variable Antibody Results in an Antigen-Specific Coagulation-Promoting Molecule," Biochemical Journal, 2000, 349(3):805-812.
Rogge et al., "Antibodies to the IL-12 receptor B2 chain mark human Th1 but not Th2 cells in vitro and in vivo," The Journal of Immunology, Apr. 1, 1999, 162(7):3926-32.
Rossi et al., "Complex and defined biostructures with the dock-and-lock method," Trends in Pharmacological Sciences, Sep. 1, 2012, 33(9):474-81.
Rossi et al., "Stably tethered multifunctional structures of defined composition made by the dock and lock method for use in cancer targeting," Proceedings of the National Academy of Sciences, May 2, 2006, 103(18):6841-6.
Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.
Ruf et al., "Tissue factor residues 157-167 are required for efficient proteolytic activation of factor X and factor VII," Journal of Biological Chemistry, Nov. 5, 1992, 267(31):22206-10.
Sagiv et al., "Granule exocytosis mediates immune surveillance of senescent cells," Oncogene, 2013, 32(15):1971-1977.

(56) References Cited

OTHER PUBLICATIONS

Sandusky et al., "Regulation of 2B4 (CD244)-mediated NK cell activation by ligand-induced receptor modulation," European Journal of Immunology, Dec. 2006, 36(12):3268-76.
Schullek et al., "Key ligand interface residues in tissue factor contribute independently to factor VIIa binding," Journal of Biological Chemistry, Jul. 29, 1994, 269(30):19399-403.
Sharkey et al., "Improved Therapeutic Results by Pretargeted Radioimmunotherapy of Non- Hodgkin's Lymphoma with a New Recombinant, Trivalent, Anti-CD20, Bispecific Antibody," Cancer Research, Jul. 1, 2008, 68(13):5282-90.
Smith et al., "Antigen Nature and Complexity Influence Human Antibody Light Chain Usage and Specificity," Vaccine, 2016, 34(25): 2813-2820.
Smith et al., "Development and evaluation of an optimal human single-chain variable fragment- derived BCMA-targeted CAR T cell vector," Molecular Therapy, Jun. 6, 2018, 26(6):1447-56.
Soriani et al., "ATM-ATR-dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.
Spiess et al., "Alternative molecular formats and therapeutic applications for bispecific antibodies," Molecular Immunology, Oct. 1, 2015, 67(2):95-106.
Szalay et al., "Cutting edge: anti-CD1 monoclonal antibody treatment reverses the production patterns of TGF-B2 and Th1 cytokines and ameliorates listeriosis in mice," The Journal of Immunology, Jun. 15, 1999, 162(12):6955-8.
Tahara-Hanaoka et al., "Functional characterization of DNAM-1 (CD226) interaction with its ligands Pvr (CD155) and nectin-2 (PRR-2/CD112)," International Immunology, Apr. 1, 2004, 16(4):533-8.
Van Audenhove et al., "Nanobodies as versatile tools to understand, diagnose, visualize and treat cancer," EBioMedicine, Jun. 1, 2016, 8:40-8.
Van den Bergh et al., "IL-15 receptor alpha as the magic wand to boost the success of IL-15 antitumor therapies: The upswing of IL-15 transpresentation," Pharmacology and Therapeutics, 2017, 170:73-79.
Vincke et al., "Introduction to heavy chain antibodies and derived Nanobodies," Single Domain Antibodies, Humana Press, Totowa, NJ, 2012, pp. 15-26.
Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565, DOI: 10.1093/jb/mvh065.
Wang et al., "Recombinant human CD137L for cancer immunotherapy: effects of different fusions and linkers on its activity," Cancer Immunol Immunother., 2012, 61(4):489-495.
Washburn et al., "A potential role for shed soluble major histocompatibility class I molecules as modulators of neurite outgrowth," PLoOS One, Mar. 31, 2011, 6(3):e18439.
Weber et al., "Specific low-affinity recognition of major histocompatibility complex plus peptide by soluble T-cell receptor," Nature, Apr. 1992, 356(6372):793.
Weiner et al., "Antibody-based immunotherapy of cancer," Cell, Mar. 16, 2012, 148(6):1081-4.
Wesolowski et al., "Single domain antibodies: promising experimental and therapeutic tools in infection and immunity," Medical Microbiology and Immunology. Aug. 1, 2009, 198(3):157-74.
Witkowsa et al., "Soluble intercellular adhesion molecule-1 (sICAM-1): an overview," Eur Cytokine Netw. 2004, 15(2):91-98.
Xiong et al., "Maternal uterine NK cell-activating receptor KIR2DS1 enhances placentation," The Journal of Clinical Investigation, Oct. 1, 2013, 123(10):4264-72.
Xu et al., "Transplanted senescent cells induce an osteoarthritis-like condition in mice," The Journals of Gerontology: Series A, Jun. 1, 2017, 72(6):780-5.
Yigit et al., "A combination of an anti-SLAMF6 antibody and ibrutinib efficiently abrogates expansion of chronic lymphocytic leukemia cells," Oncotarget, May 3, 2016, 7(18):26346.
Yung et al., "A selective transforming growth factor-ligand trap attenuates pulmonary hypertension," American Journal of Respiratory and Critical Care Medicine, Nov. 1, 2016, 194(9):1140-51.
Zwaagstra et al., "Engineering and therapeutic application of single-chain bivalent TGF-β family traps," Molecular Cancer Therapeutics, Jul. 1, 2012, 11(7):1477-87.
PCT International Search Report and Written Opinion in International Appln. No. PCT/US2019/048881, dated Nov. 19, 2019, 12 pages.
PCT International Search Report and Written Opinion in International Appin. No. PCT/US2019/048930, dated Nov. 20, 2019, 14 pages.
IPCT International Search Report and Written Opinion in International Appln. No. PCT/US2019/049158, dated Jan. 20, 2020, 13 pages.
PCT International Search Report and Written Opinion in International Appln No. PCT/US2019/049142, dated Jun. 23, 2020, 17 pages.

\* cited by examiner

MULTI-CHAIN CHIMERIC POLYPEPTIDES AND USES THEREOF

CROSS-REFERENCE TO RELATED APPLICATIONS

This application is a continuation of U.S. patent application Ser. No. 16/555,689, filed Aug. 29, 2019, now U.S. Pat. No. 11,518,792, which claims priority to: U.S. Patent Application Ser. No. 62/724,969, filed Aug. 30, 2018; U.S. Patent Application Ser. No. 62/817,230, filed Mar. 12, 2019; U.S. Patent Application Ser. No. 62/725,043, filed Aug. 30, 2018; U.S. Patent Application Ser. No. 62/725,010, filed Aug. 30, 2018; U.S. Patent Application Ser. No. 62/749,007, filed Oct. 22, 2018; U.S. Patent Application Ser. No. 62/746,832, filed Oct. 17, 2018; U.S. Patent Application Ser. No. 62/749,506, filed Oct. 23, 2018; U.S. Patent Application Ser. No. 62/817,241, filed Mar. 12, 2019; U.S. Patent Application Ser. No. 62/816,683, filed Mar. 11, 2019; and U.S. Patent Application Ser. No. 62/881,088, filed Jul. 31, 2019, each of which is herein incorporated by reference in its entirety.

SEQUENCE LISTING

This application contains a Sequence Listing that has been submitted electronically as an ASCII text file named "SEQ.txt". The ASCII text file, created on Nov. 17, 2020, is 524,307 bytes in size. The material in the ASCII text file is hereby incorporated by reference in its entirety.

TECHNICAL FIELD

The present disclosure relates to the field of biotechnology, and more specifically, to antigen-binding molecules.

BACKGROUND

Tissue factor (TF), a 263 amino acid integral membrane glycoprotein with a molecular weight of ~46 kDa and the trigger protein of the extrinsic blood coagulation pathway, is the primary initiator of coagulation in vivo. Tissue factor, normally not in contact with circulating blood, initiates the coagulation cascade upon exposure to the circulating coagulation serine protease factors. Vascular damage exposes sub-endothelial cells expressing tissue factor, resulting in the formation of a calcium-dependent, high-affinity complex with pre-existing plasma factor VIIa (FVIIa). Binding of the serine protease FVIIa to tissue factor promotes rapid cleavage of FX to FXa and FIX to FIXa. The proteolytic activity of the resulting FXa and an active membrane surface then inefficiently converts a small amount of prothrombin to thrombin. The thrombin generated by FXa initiates platelet activation and activates minute amounts of the pro-cofactors factor V (FV) and factor VIII (FVIII) to become active cofactors, factor Va (FVa) and factor VIIIa (FVIIIa). FIXa complexes with FVIIIa on the platelet surface forming the intrinsic tenase complex, which results in rapid generation of FXa. FXa complexes with FVa to form the pro-thrombinase complex on the activated platelet surface which results in rapid cleavage of prothrombin to thrombin.

In addition to the tissue factor-FVIIa complex, a recent study showed that the tissue factor-FVIIa-FXa complex can activate FVIII, which would provide additional levels of FVIIIa during the initiation phase. The extrinsic pathway is paramount in initiating coagulation via the activation of limited amounts of thrombin, whereas the intrinsic pathway maintains coagulation by dramatic amplification of the initial signal.

Much of the tissue factor expressed on a cell surface is "encrypted," which must be "decrypted" for full participation in coagulation. The mechanism of "decryption" of cell-surface tissue factor is still unclear at this time, however, exposure of anionic phospholipids plays a major role in this process. Healthy cells actively sequester anionic phospholipids such as phosphatidyl serine (PS) to the inner leaflet of the plasma membrane. Following cellular damage, activation, or increased levels of cytosolic $Ca^{2+}$, this bilayer asymmetry is lost, resulting in increased PS exposure on the outer leaflet, which increases the specific activity of cell-surface tissue factor-FVIIa complexes. PS exposure is known to decrease the apparent Km for activation of FIX and FX by tissue factor-FVIIa complexes, but additional mechanisms could include conformational rearrangement of tissue factor or tissue factor-FVIIa and subsequent exposure of substrate binding sites.

SUMMARY

The present invention is based on the discovery that soluble tissue factor can be used as a scaffold for chimeric polypeptides including an antigen-binding domain. Based on this discovery provided herein are multi-chain chimeric polypeptides that include: (a) a first chimeric polypeptide including: (i) a first target-binding domain; (ii) a soluble tissue factor domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains. Also provided herein are compositions that include any of the multi-chain chimeric polypeptides described herein, nucleic acids that encode any of the multi-chain chimeric polypeptides described herein, and cells that include any of the nucleic acids that encode any of the multi-chain chimeric polypeptides described herein. Also provided herein are methods of stimulating an immune cell and methods of treating a subject in need thereof that include the use of any of the multi-chain chimeric polypeptides described herein. Also provided herein are methods of producing any of the multi-chain chimeric polypeptides described herein.

Accordingly, provided herein is a multi-chain chimeric polypeptide comprising:
 (a) a first chimeric polypeptide comprising:
  (i) a first target-binding domain;
  (ii) a soluble tissue factor domain; and
  (iii) a first domain of a pair of affinity domains;
 (b) a second chimeric polypeptide comprising:
  (i) a second domain of a pair of affinity domains; and
  (ii) a second target-binding domain,
 wherein the first chimeric polypeptide and the second chimeric polypeptide associate through the binding of the first domain and the second domain of the pair of affinity domains. In some embodiments, the first target-binding domain and the soluble tissue factor domain directly abut each other in the first chimeric polypeptide. In some embodiments, the first chimeric polypeptide further comprises a linker sequence between the first target-binding domain and the soluble tissue factor domain in the first chimeric polypeptide. In some embodiments, the soluble tissue factor domain and the first domain of the pair of affinity domains directly abut each other in the first chimeric polypeptide. In some embodiments, the first chimeric polypeptide further comprises a linker sequence between the soluble tissue factor domain and the first domain of the pair of affinity domains in the first chimeric polypeptide. In some embodiments, the second domain of the pair of affinity domains and the second target-binding domain directly abut each other in the second chimeric polypeptide. In some embodiments, the second chimeric polypeptide further comprises a linker sequence between the second domain of the pair of affinity domains and the second target-binding domain in the second chimeric polypeptide. In some embodiments, the first target-binding domain and the second target-binding domain bind specifically to the same antigen. In some embodiments, the first target-binding domain and the second target-binding domain bind specifically to the same epitope. In some embodiments, the first target-binding domain and the second target-binding domain comprise the same amino acid sequence. In some embodiments, the first target-binding domain and the second target-binding domain bind specifically to different antigens. In some embodiments, one or both of the first target-binding domain and the second target-binding domain is an antigen-binding domain. In some embodiments, the first target-binding domain and the second target-binding domain are each antigen-binding domains. In some embodiments, the antigen-binding domain comprises a scFv or a single domain antibody. In some embodiments, one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or both of the first target-binding domain and the second target-binding domain is a soluble interleukin, a soluble cytokine protein, or a ligand protein. In some embodiments, the soluble interleukin, soluble cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L. In some embodiments, one or both of the first target-binding domain and the second target-binding domain is a soluble interleukin, a cytokine receptor, or a soluble cell surface receptor. In some embodiments, the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28. In some embodiments, the first chimeric polypeptide further comprises one or more additional target-binding domain(s), where at least one of the one or more additional antigen-binding domain(s) is positioned between the soluble tissue factor domain and the first domain of the pair of affinity domains. In some embodiments, the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains. In some embodiments, the first chimeric polypeptide further comprises one or more additional target-binding domains at the N-terminal and/or C-terminal end of the first chimeric polypeptide. In some embodiments, at least one of the one or more additional target-binding domains directly abuts the first domain of the pair of affinity domains in the first chimeric polypeptide. In some embodiments, the first chimeric polypeptide further comprises a linker sequence between the at least one of the one or more additional target-binding domains and the first domain of the pair of affinity domains. In some embodiments, the at least one of the one or more additional target-binding domains directly abuts the first target-binding domain in the first chimeric polypeptide. In some embodiments, the first chimeric polypeptide further comprises a linker sequence between the at least one of the one or more additional target-binding domains and the first target-binding domain. In some embodiments, at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide. In some embodiments, the at least one additional target-binding domain of the one or more additional target-binding domains disposed at the N-terminus directly abuts the first target-binding domain or the first domain of the pair of affinity domains in the first chimeric polypeptide. In some embodiments, the first chimeric polypeptide further comprises a linker sequence disposed between the at least one additional target-binding domain and the first target-binding domain or the first domain of the pair of affinity domains in the first chimeric polypeptide. In some embodiments, the at least one additional target-binding domain of the one or more additional target-binding domains disposed at the C-terminus directly abuts the first target-binding domain or the first domain of the pair of affinity domains in the first chimeric polypeptide. In some embodiments, the first chimeric polypeptide further comprises a linker sequence disposed between the at least one additional target-binding domain and the first target-binding domain or the first domain of the pair of affinity domains in the first chimeric polypeptide. In some embodiments, the at least one of the one or more additional target-binding domains positioned between the soluble tissue factor domain and the first domain of the pair of affinity domains, directly abuts the soluble tissue factor domain and/or the first domain of the pair of affinity domains. In some embodiments, the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains. In some embodiments, the second chimeric polypeptide further comprises one or more additional target-binding domains at the N-terminal end or the C-terminal end of the second chimeric polypeptide. In some embodiments, at least one of the one or more additional target-binding domains directly abuts the second domain of the pair of affinity domains in the second chimeric polypeptide. In some embodiments, the second chimeric polypeptide further comprises a linker sequence between at least one of the one or more additional target-binding domains and the second domain of the pair of affinity domains in the second chimeric polypeptide. In some embodiments, at least one of the one or more additional target-binding domains directly abuts the second target-binding domain in the second chimeric polypeptide. In some embodiments, the second chimeric polypeptide further comprises a linker sequence between at least one of the one or more additional target-binding domains and the second target-binding domain in the second chimeric polypeptide. In some embodiments, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each comprise the same amino acid sequence. In some embodiments, the first target-binding domain, the second target-binding domain, and the one or more additional target-binding domains bind specifically to different antigens. In some embodiments, one or more of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain. In some embodiments, antigen-binding domain comprises a scFv. In some embodiments, one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28. In some embodiments, one or more of the first target-binding domain, the second target-binding domain, and the one or more additional target-binding domains is a soluble interleukin, a soluble cytokine protein, or a ligand protein. In some embodiments, the soluble interleukin, soluble cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L. In some embodiments, one or more of the first target-binding domain, the second target-binding domain, and the one or more additional target-binding domains is a soluble interleukin or cytokine receptor. In some embodiments, the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28. In some embodiments, the first chimeric polypeptide further comprises a peptide tag at the N-terminal end or the C-terminal end of the first chimeric polypeptide. In some embodiments, the second chimeric polypeptide further comprises a peptide tag at the N-terminal end or the C-terminal end of the second chimeric polypeptide. In some embodiments, the soluble tissue factor domain is a soluble human tissue factor domain. In some embodiments, the soluble human tissue factor domain comprises a sequence that is at least 80% identical to SEQ ID NO: 1. In some embodiments, the soluble human tissue factor domain comprises a sequence that is at least 90% identical to SEQ ID NO: 1. In some embodiments, the soluble human tissue factor domain comprises a sequence that is at least 95% identical to SEQ ID NO: 1. In some embodiments, the soluble human tissue factor domain does not comprise one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding to Factor VIIa. In some embodiments, the soluble tissue factor domain does not convert inactive Factor X into Factor Xa. In some embodiments, the multi-chain chimeric polypeptide does not stimulate blood coagulation in a mammal. In some embodiments of any of the single-chain chimeric polypeptides provided herein, the human soluble tissue factor domain does not initiate blood coagulation. In some embodiments of any of the single-chain chimeric polypeptides provided herein, the soluble tissue factor domain comprises or consists of a soluble wildtype human tissue factor.

In some embodiments, the pair of affinity domains is a sushi domain from an alpha chain of human IL-15 receptor (IL15Rα) and a soluble IL-15. In some embodiments, the soluble IL15 has a D8N or D8A amino acid substitution. In some embodiments, the human IL15Rα is a mature full-length IL15Rα. In some embodiments, the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments, the first chimeric polypeptide and/or the second chimeric polypeptide further comprises a signal sequence at its N-terminal end.

In some embodiments, the multi-chain chimeric polypeptide comprises a composition. In some embodiments, the composition is a pharmaceutical composition. In some embodiments, the composition comprises at least one dose of the multi-chain chimeric polypeptide. In some embodiments, a kit comprises at least one dose of the composition.

In some embodiments, provided herein is a method of stimulating an immune cell, the method comprising: contacting an immune cell with an effective amount of any of the multi-chain chimeric polypeptides or compositions described above. In some embodiments, the method comprises contacting the immune cell in vitro. In some embodiments, the method comprises obtaining the immune cell from a subject. In some embodiments, the method comprises obtaining the immune cell from the subject prior to the contacting step. In some embodiments, the method comprises contacting the immune cell in vivo. In some embodiments, the method comprises selecting the immune cell from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8$^+$ T cell, a CD4$^+$ T cell, a natural killer T cell, a mast cell, a macrophage, a neutrophil, a dendritic cell, a basophil, an eosinophil, and a natural killer cell. In some embodiments, the method comprises genetically modifying the immune cell to express a chimeric antigen receptor or a recombinant T-cell receptor. In some embodiments, the method comprises introducing into the immune cell a nucleic acid encoding a chimeric antigen-receptor or a recombinant T-cell receptor after the contacting step. In some embodiments, the method comprises administering the immune cell to a subject in need thereof. In some embodiments, the method comprises identifying or diagnosing the subject as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is a method of inducing or increasing proliferation of an immune cell, the method comprising: contacting an immune cell with an effective amount of any of the multi-chain chimeric polypeptides or compositions described above. In some embodiments, the method comprises contacting the immune cell in vitro. In some embodiments, the method comprises obtaining the immune cell from a subject. In some embodiments, the method comprises obtaining the immune cell from the subject prior to the contacting step. In some embodiments, the method comprises contacting the immune cell in vivo. In some embodiments, the method comprises selecting the immune cell from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8$^+$ T cell, a CD4$^+$ T cell, a natural killer T cell, a mast cell, a macrophage, a neutrophil, a dendritic cell, a basophil, an eosinophil, and a natural killer cell. In some embodiments, the method comprises modifying the immune cell to express a chimeric antigen receptor or a recombinant T-cell receptor. In some embodiments, the method further comprises introducing into the immune cell a nucleic acid encoding a chimeric antigen-receptor or a recombinant T-cell receptor after the contacting step. In some embodiments, the method further comprises administering the immune cell to a subject in need thereof. In some embodiments, the method comprises identifying or diagnosing the subject as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is a method of inducing differentiation of an immune cell into a memory or memory-like immune cell, the method comprising: contacting an immune cell with an effective amount of any of the multi-chain chimeric polypeptides or compositions discussed above. In some embodiments, the method comprises contacting the immune cell in vitro. In some embodiments, the method comprises obtaining the immune cell from a subject. In some embodiments, the method further comprises obtaining the immune cell from the subject prior to the contacting step. In some embodiments, the method comprises contacting the immune cell in vivo. In some embodiments, the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments, the immune cell has previously been genetically modified to express a chimeric antigen receptor or a recombinant T-cell receptor. In some embodiments, the method further comprises introducing into the immune cell a nucleic acid encoding a chimeric antigen-receptor or a recombinant T-cell receptor after the contacting step. In some embodiments, the method further comprises administering the immune cell to a subject in need thereof. In some embodiments, the method comprises identifying or diagnosing the subject as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is a method of killing a cancer cell, an infected cell, or a senescent cell in a subject in need thereof, the method comprising administering to the subject a therapeutically effective amount of any of the multi-chain chimeric polypeptides or compositions discussed above. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises identifying or diagnosing the subject as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises administering to the subject a therapeutically effective amount of any of the multi-chain chimeric polypeptides or compositions discussed above. In some embodiments, the method comprises identifying or diagnosing the subject as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the method comprises identifying or diagnosing the subject as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the method comprises diagnosing or identifying the subject as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is a nucleic acid encoding any of the multi-chain chimeric polypeptides discussed above. Some embodiments comprise vector containing any of the nucleic acids discussed above. In some embodiments, the vector is an expression vector. Some embodiments comprise a cell containing any of the nucleic acids discussed above.

Also provided herein is a method of producing a multi-chain chimeric polypeptide, the method comprising: culturing the cell discussed above in a culture medium under conditions sufficient to result in the production of the multi-chain chimeric polypeptide; and recovering the multi-chain chimeric polypeptide from the cell and/or the culture medium. In some embodiments, the method comprises producing a multi-chain chimeric polypeptide by the methods discussed above.

In some embodiments, the mutant soluble human tissue factor domain comprises a sequence that is at least 80% identical to SEQ ID NO: 3. In some embodiments, the soluble human tissue factor domain comprises a sequence that is at least 90% identical to SEQ ID NO: 3. In some embodiments, the soluble human tissue factor domain comprises a sequence that is at least 95% identical to SEQ ID NO: 3. In some embodiments, the soluble human tissue factor domain comprises a sequence that is 100% identical to SEQ ID NO: 3. In some embodiments, the soluble human tissue factor domain comprises a sequence that is at least 80% identical to SEQ ID NO: 4. In some embodiments, the soluble human tissue factor domain comprises a sequence that is at least 90% identical to SEQ ID NO: 4. In some embodiments, the soluble human tissue factor domain comprises a sequence that is at least 95% identical to SEQ ID NO:4. In some embodiments, the soluble human tissue factor domain comprises a sequence that is 100% identical to SEQ ID NO: 4.

As used herein, the term "chimeric" refers to a polypeptide that includes amino acid sequences (e.g., domains) originally derived from two different sources (e.g., two different naturally-occurring proteins, e.g., from the same or different species). For example, a chimeric polypeptide can include domains from at least two different naturally occurring human proteins. In some examples, a chimeric polypeptide can include a domain that is a synthetic sequence (e.g., an scFv) and a domain that is derived from a naturally-occurring protein (e.g., a naturally-occurring human protein). In some embodiments, a chimeric polypeptide can include at least two different domains that are synthetic sequences (e.g., two different scFvs).

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

A "soluble tissue factor domain" refers to a polypeptide having at least 70% identity (e.g., at least 75% identity, at least 80% identity, at least 85% identity, at least 90% identity, at least 95% identity, at least 99% identity, or 100% identical) to a segment of a wildtype mammalian tissue factor protein (e.g., a wildtype human tissue factor protein) that lacks the transmembrane domain and the intracellular domain. Non-limiting examples of soluble tissue factor domains are described herein.

The term "soluble interleukin protein" is used herein to refer to a mature and secreted interleukin protein or a biologically active fragment thereof. In some examples, a soluble interleukin protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble interleukin proteins are described herein.

The term "soluble cytokine protein" is used herein to refer to a mature and secreted cytokine protein or a biologically active fragment thereof. In some examples, a soluble cytokine protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble cytokine proteins are described herein.

The term "soluble interleukin receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble interleukin receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype interleukin receptor and retains its ability to specifically bind to one or more of its natural ligands, but lacks its transmembrane domain (and optionally, further lacks its intracellular domain). Non-limiting examples of soluble interleukin receptors are described herein.

The term "soluble cytokine receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble cytokine receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype cytokine receptor and retains its ability to specifically bind to one or more of its natural ligands, but lacks its transmembrane domain (and optionally, further lacks its intracellular domain). Non-limiting examples of soluble cytokine receptors are described herein.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

A "multi-chain polypeptide" as used herein to refers to a polypeptide comprising two or more (e.g., three, four, five, six, seven, eight, nine, or ten) protein chains (e.g., at least a first chimeric polypeptide and a second polypeptide), where the two or more proteins chains associate through non-covalent bonds to form a quaternary structure.

The term "pair of affinity domains" is two different protein domain(s) that bind specifically to each other with a $K_D$ of less than of less than $1 \times 10^{-7}$ M (e.g., less than $1 \times 10^{-8}$ M, less than $1 \times 10^{-9}$ M, less than $1 \times 10^{-10}$ M, or less than $1 \times 10^{-11}$ M). In some examples, a pair of affinity domains can be a pair of naturally-occurring proteins. In some embodiments, a pair of affinity domains can be a pair of synthetic proteins. Non-limiting examples of pairs of affinity domains are described herein.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

An "immune effector cell" refers to a cell of the immune system of a mammal that is capable, directly or indirectly, of recognizing and/or causing cytostasis or cell death of a pathogenic cell (e.g., a cancer cell) in the mammal. Non-limiting examples of immune effector cells include macrophages, T-lymphocytes (e.g., cytotoxic T-lymphocytes and T-helper cells), natural killer cells, neutrophils, monocytes, and eosinophils. Additional examples of immune effector cells are known in the art.

The term "treatment" means to ameliorate at least one symptom of a disorder. In some examples, the disorder being treated is cancer and to ameliorate at least one symptom of cancer includes reducing aberrant proliferation, gene expression, signaling, translation, and/or secretion of factors. Generally, the methods of treatment include administering a therapeutically effective amount of composition that reduces at least one symptom of a disorder to a subject who is in need of, or who has been determined to be in need of such treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 1 shows exemplary diagrams for a multi-chain chimeric polypeptide: (i) a first chimeric polypeptide including a first target-binding domain (A), a soluble tissue factor domain, a first domain of an affinity pair of domains (soluble interleukin IL-15), and an additional target-binding domain (B); and (ii) second chimeric polypeptide including a second domain of an affinity pair of domains (IL-15 receptor alpha sushi domain), a second target-binding domain (C), and an additional antigen-binding domain (D). The top cartoon diagram depicts the association of the first and the second chimeric polypeptides through the pair of affinity domains. The bottom schematic diagrams show the order of the domains in the first and second chimeric polypeptides.

FIG. 2 shows exemplary diagrams for a multi-chain chimeric polypeptide: (i) a first chimeric polypeptide including a first target-binding domain (A), a soluble tissue factor domain including five amino acid substitutions in order to remove binding of the soluble tissue factor domain to FVIIa, a first domain of an affinity pair of domains (soluble interleukin IL-15 including a D8N or D8A amino acid substitution), and an additional target-binding domain (B); and (ii) second chimeric polypeptide including a second domain of an affinity pair of domains (IL-15 receptor alpha sushi domain), a second target-binding domain (C), and an additional antigen-binding domain (D). The top cartoon diagram depicts the association of the first and the second chimeric polypeptides through the pair of affinity domains. The bottom schematic diagrams show the order of the domains in the first and second chimeric polypeptides. In other embodiments of any of the multi-chain chimeric polypeptides described herein the soluble tissue factor domain can comprise or consists of a soluble wildtype human tissue factor domain (comprising or consisting of a contiguous sequence within wildtype human tissue factor).

FIG. 67A shows binding affinity of TGFRt15-16S21 with CHO cells expressing human CD16b. FIG. 67B shows binding affinity of 7t15-21s with CHO cells expressing human CD16b.

FIG. 85A shows spleen weight in mice treated with TGFRt15-TGFRs as compared to PBS control. FIG. 85B shows the percentage of CD4$^+$ T cells, CD8$^+$ T cells, and NK cells in mice treated with TGFRt15-TGFRs as compared to PBS control.

FIG. 86A shows spleen weight of mice treated with TGFRt15-TGFRs at 16, 24, 48, 72, and 92 hours after treatment. FIG. 86B shows the percentages of immune cells in mice treated with TGFRt15-TGFRs at 16, 24, 48, 72, and 92 hours after treatment.

FIG. 96A shows detection of IL15 in 7t15-21s137L (short version) with ELISA. FIG. 96B shows detection of IL21 in 7t15-21s137L (short version) with ELISA. FIG. 96C shows detection of IL7 in 7t15-21s137L (short version) with ELISA.

FIG. 107A shows spleen weight in mice treated with 7t15-TGFRs at various dosages, as compared to PBS control. FIG. 107B shows the percentage of CD4$^+$ T cells, CD8$^+$ T cells, and NK cells in mice treated with 7t15-TGFRs at various dosages, as compared to PBS control.

FIG. 122 shows a schematic of the TGFRt15-TGFRs16 construct.

FIG. 123 shows an additional schematic of the TGFRt15-TGFRs16 construct.

FIG. 124 shows a schematic of the TGFRt15-TGFRs137L construct.

FIG. 125 shows an additional schematic of the TGFRt15-TGFRs137L construct.

FIG. 126 shows changes in the surface phenotype of lymphocyte populations after stimulation with 18t15-12s, 18t15-12s16, and 7t15-21s.

FIG. 127 shows an increase in phospho-STAT4 and phospho-STAT5 levels in NK cells after stimulation with 18t15-12s.

FIGS. 128A-128C show in vivo stimulation of Tregs, NK cells, and CD8$^+$ T cells in ApoE$^{-/-}$ mice fed with a Western diet and treated with TGFRt15-TGFRs.

FIGS. 129A-129C show immunostimulation in C57BL/6 mice following treatment with TGFRt15-TGFRs.

FIGS. 130A and 130B show in vivo induction of proliferation of NK cells and CD8$^+$ T cells in ApoE$^{-/-}$ mice fed with a Western diet and treated with TGFRt15-TGFRs.

FIGS. 131A and 131B show enhancement of cytotoxicity of NK cells following treatment of NK cells with TGFRt15-TGFRs.

FIGS. 132A and 132B show enhancement of ADCC activity of NK cells following treatment of NK cells with TGFRt15-TGFRs.

FIGS. 133A-133H show antitumor activity of TGFRt15-TGFRs plus anti-TRP1 antibody (TA99) in combination with chemotherapy in a melanoma mouse model.

Figure 134A:
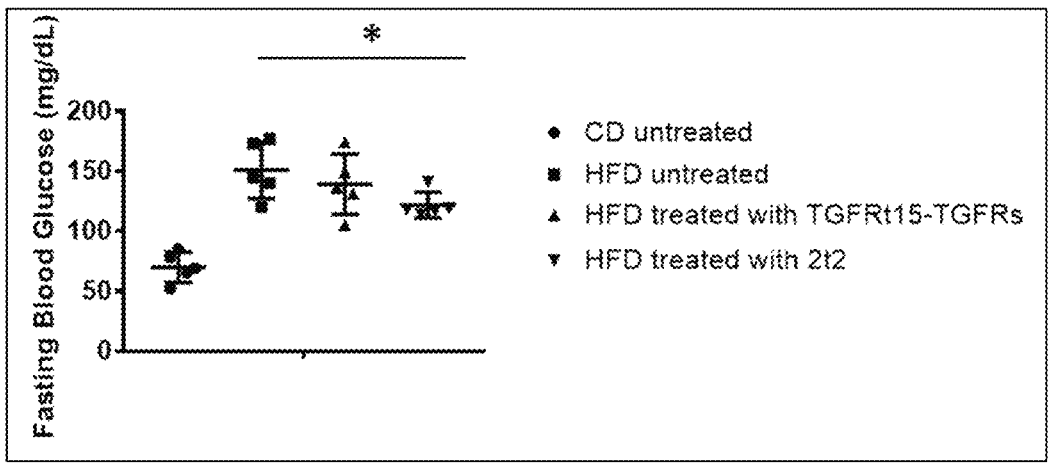
Figure 134B:
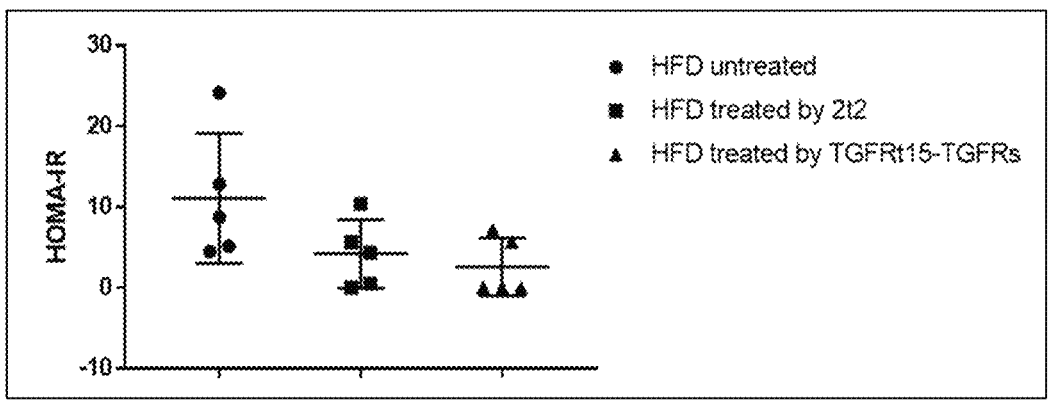
Figure 134C:
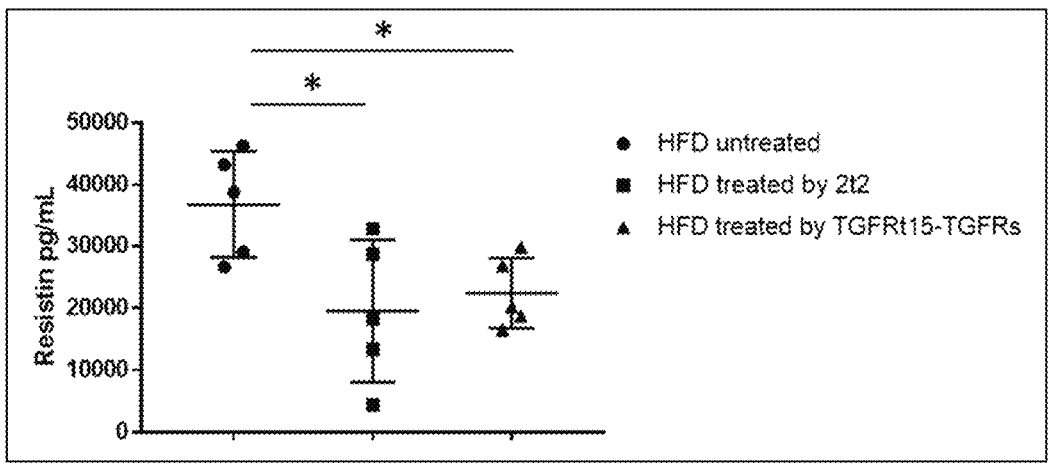

FIGS. 134A-134C show amelioration of the Western diet-induced hyperglycemia in ApoE$^{-/-}$ mice by TGFRt15-TGFRs.

Figure 135:
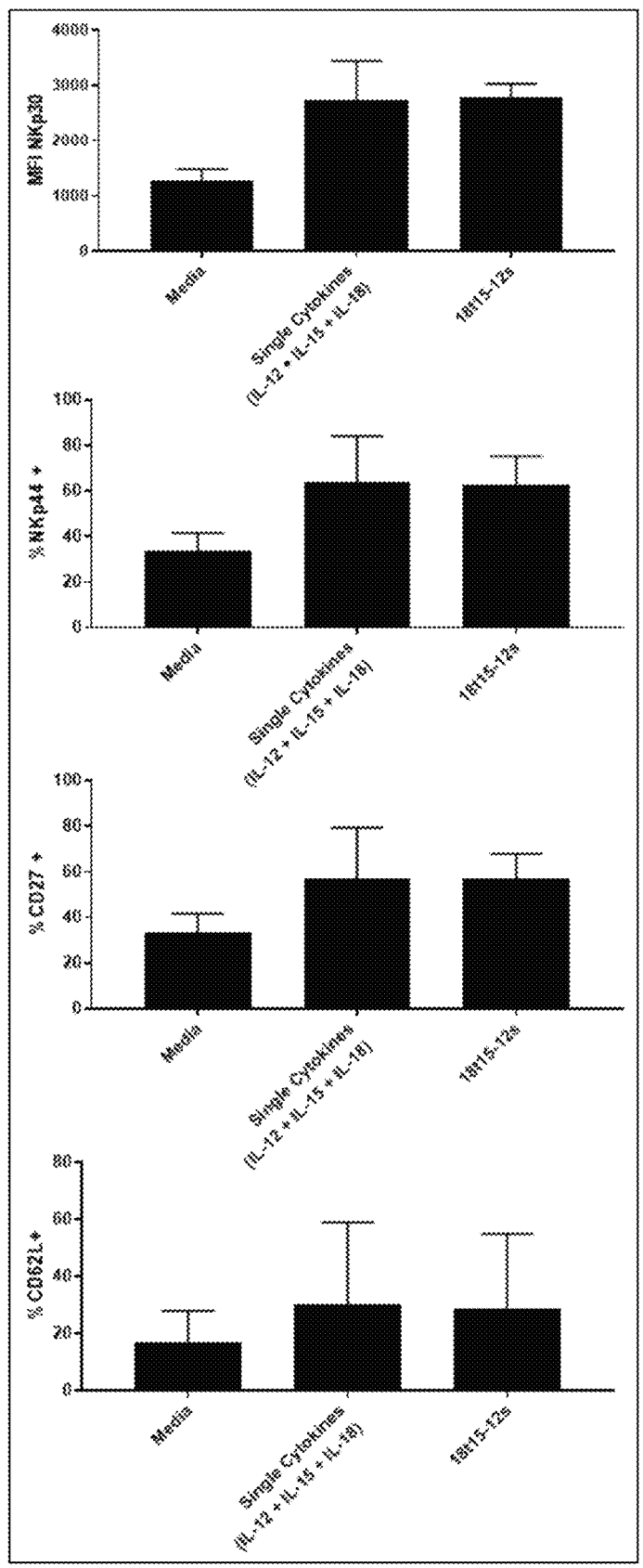

FIG. 135 shows cell surface staining summarizing the differentiation of NK cells into cytokine-induced memory like NK Cells (CIML-NK Cells) after stimulation with 18t15-12s and cultured in rhIL15.

Figure 136:
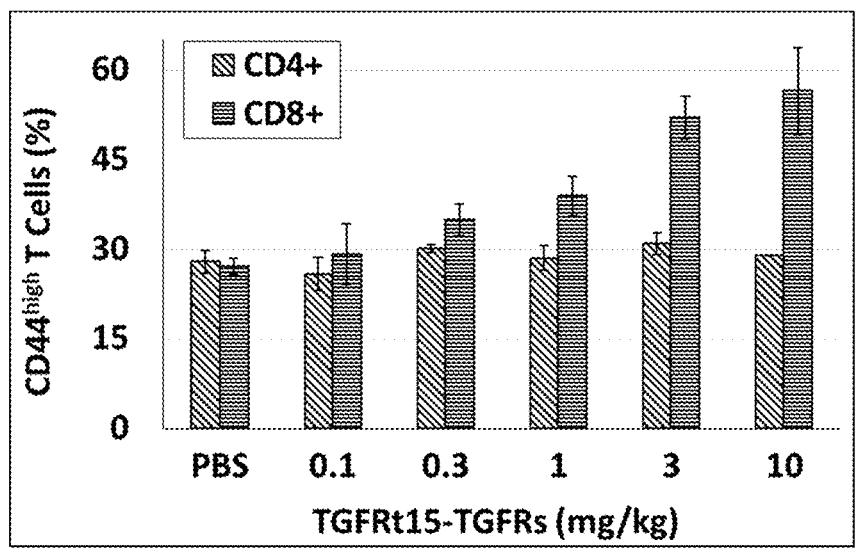

FIG. 136 shows upregulation shows upregulation of CD44hi memory T cells upon treatment with TGFRt15-TGFRs.

Figure 137:
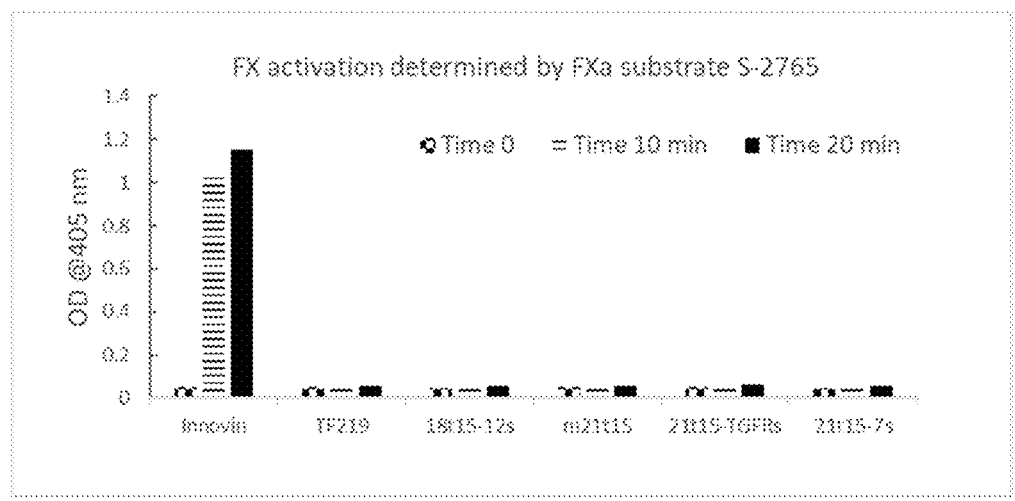

FIG. 137 shows a graph of Factor X (FX) activation following treatment with single-chain or multi-chain chimeric polypeptides.

Figure 138:
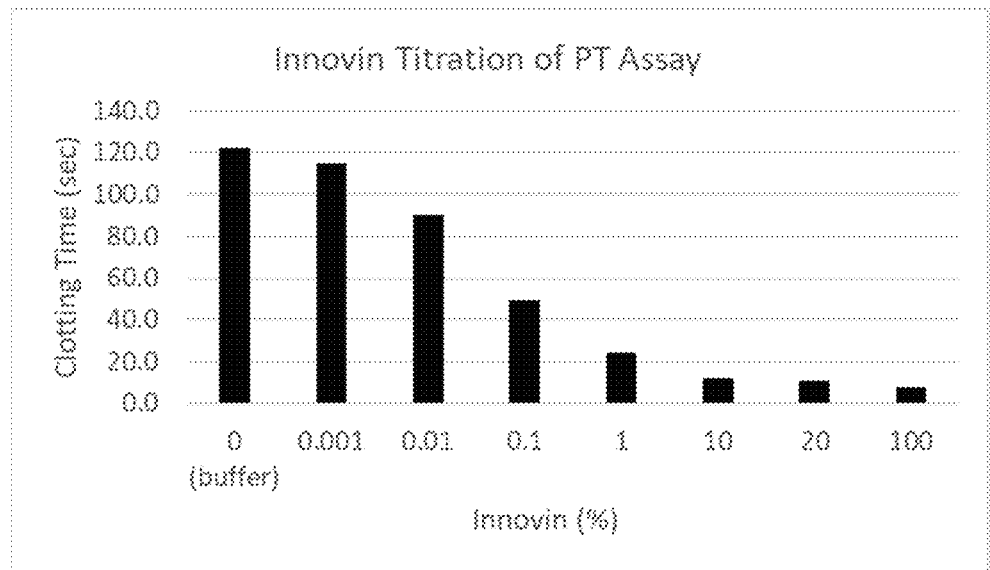

FIG. 138 shows clotting time for a buffer with varying concentrations of Innovin in a prothrombin time (PT) test.

Figure 139:
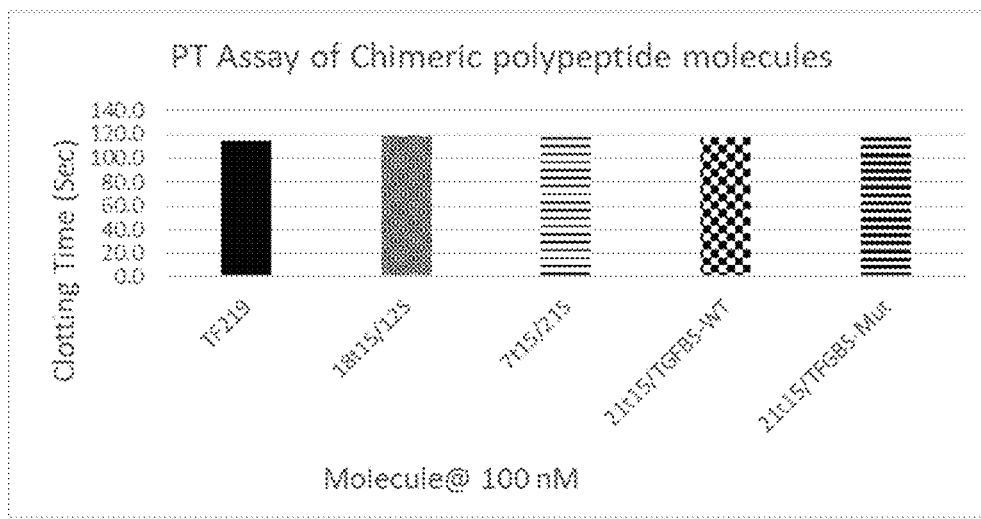

FIG. 139 shows clotting time for multi-chain chimeric polypeptides in a PT Assay.

Figure 140:
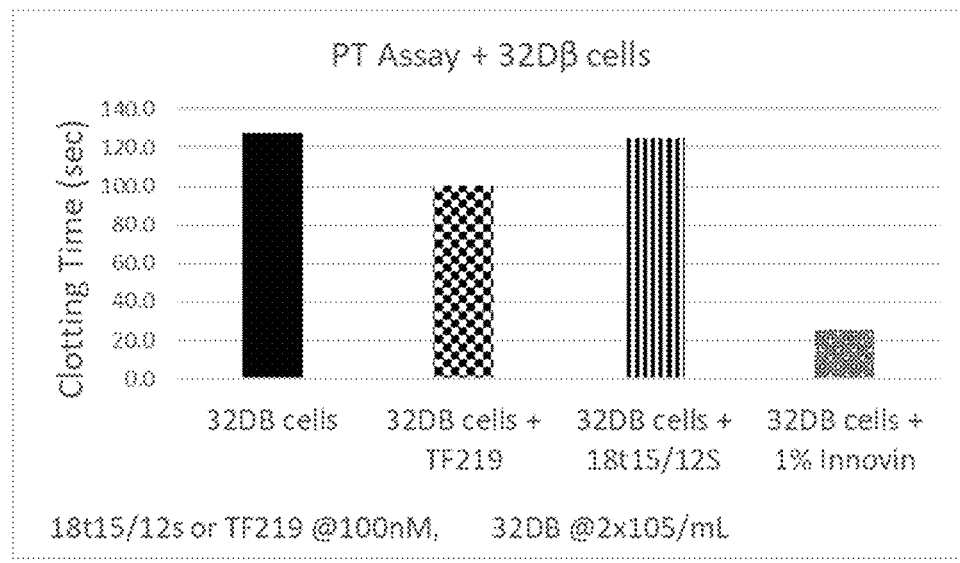

FIG. 140 shows clotting time of the multi-chain chimeric polypeptides in a PT assay when mixed with 32DB cells.

Figure 141:
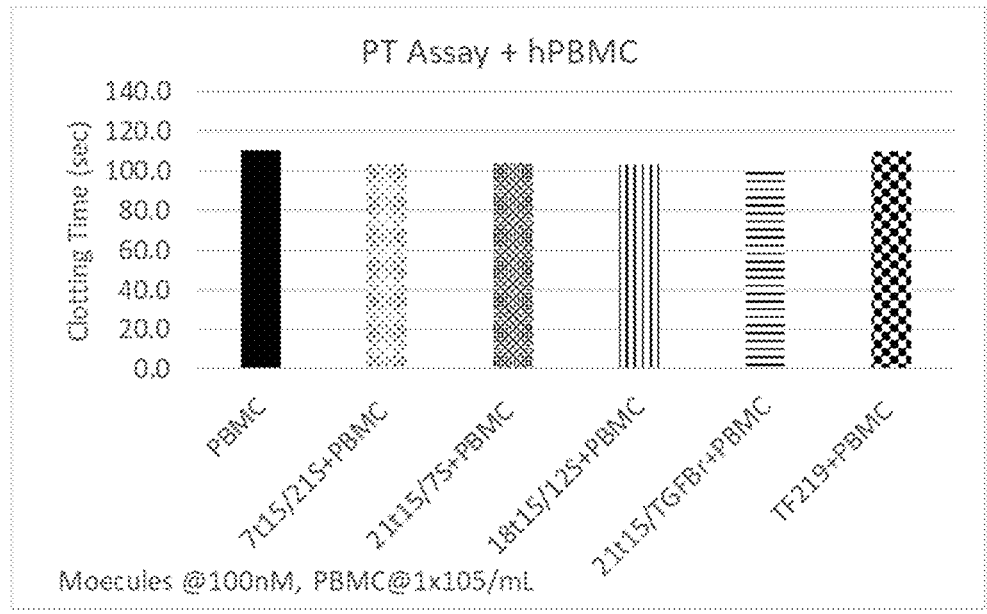

FIG. 141 shows clotting time of multi-chain chimeric polypeptides in a PT assay when mixed with human PBMC.

Figure 142:
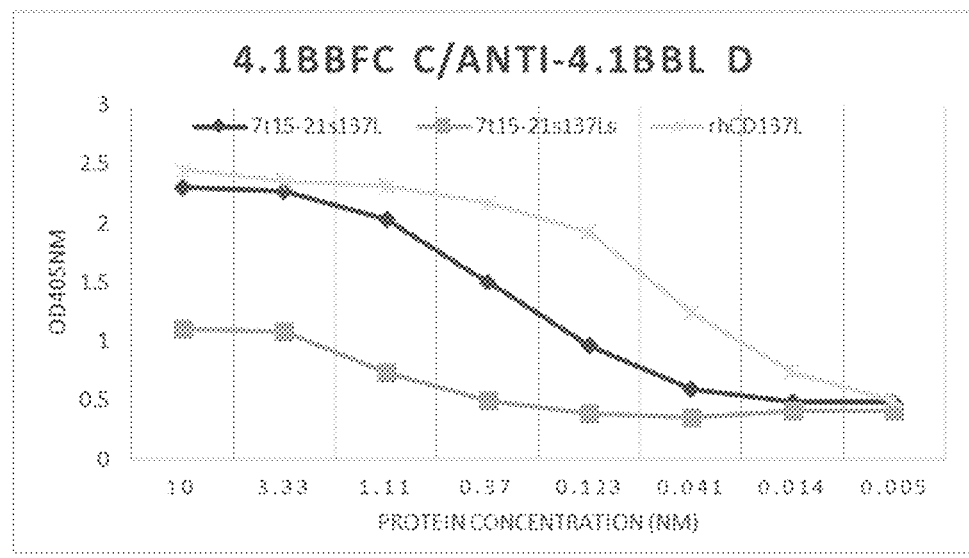
Figure 143A:
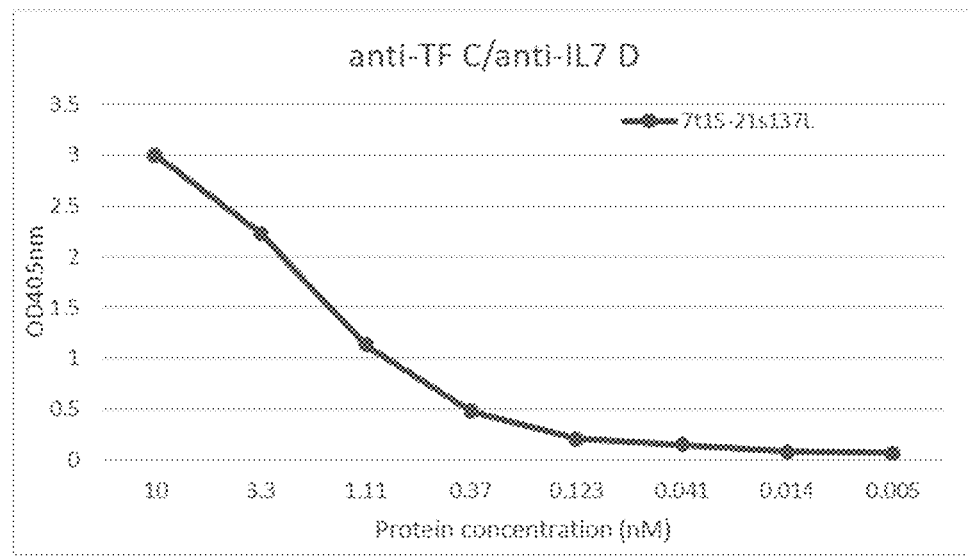
Figure 143B:
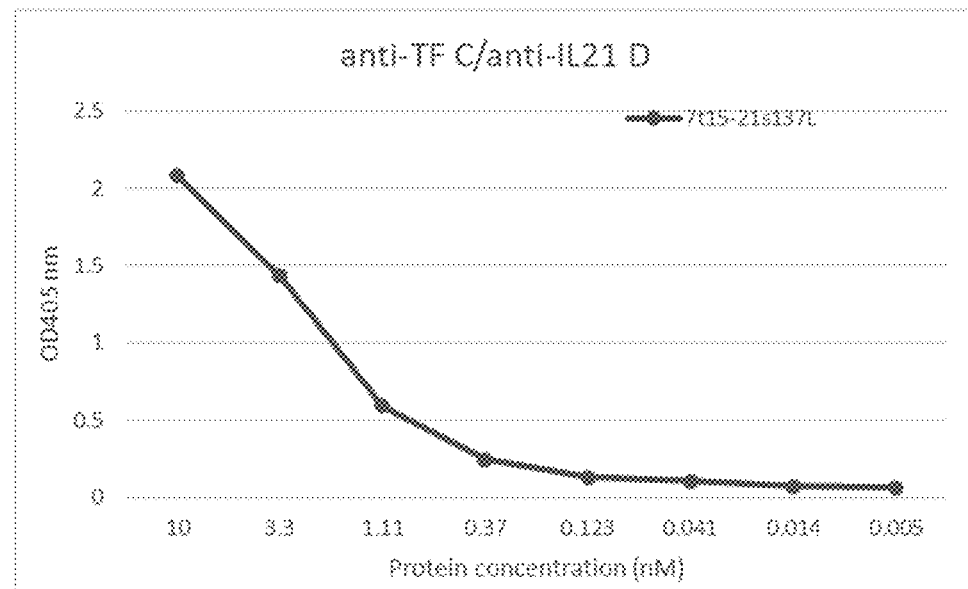
Figure 143C:
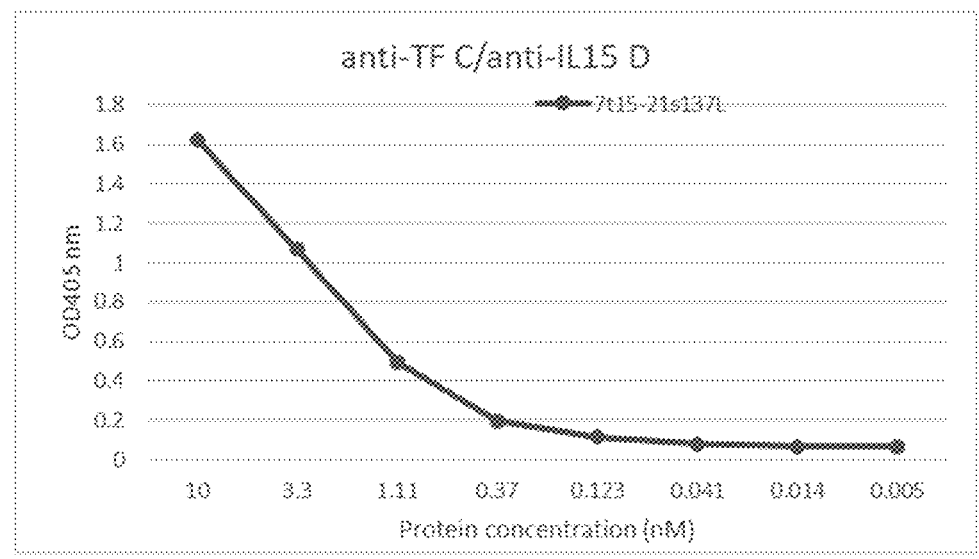
Figure 143D:
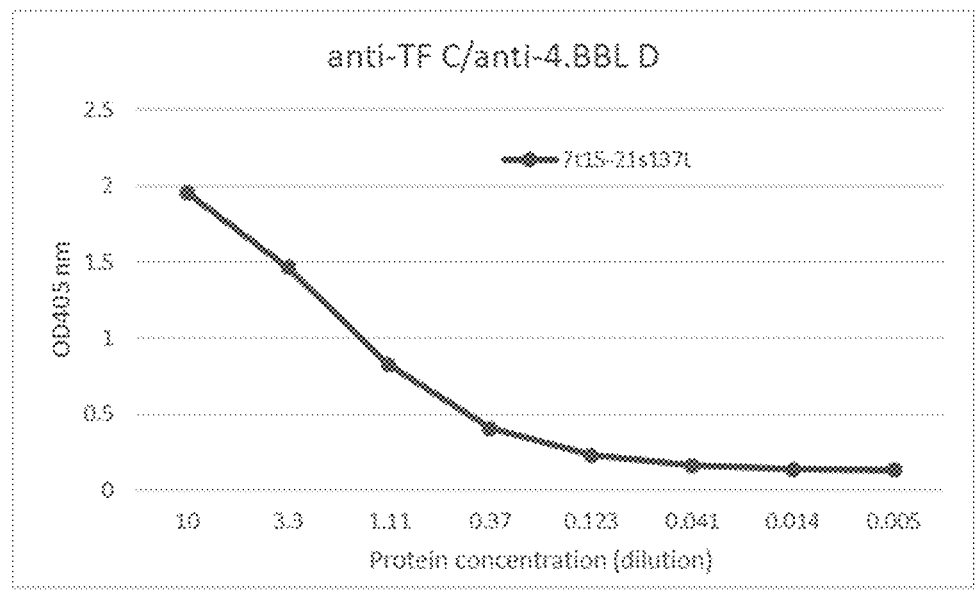

FIG. 142 shows binding of 7t15-21s137L (long version) and 7t15-21s137L (short version) to CD137 (4.1BB).

FIG. 143A-143D show detection of IL7, IL21, IL15, and 4.1BBL in 7t15-21s137L (long version) by the respective antibodies using ELISA.

Figure 144:
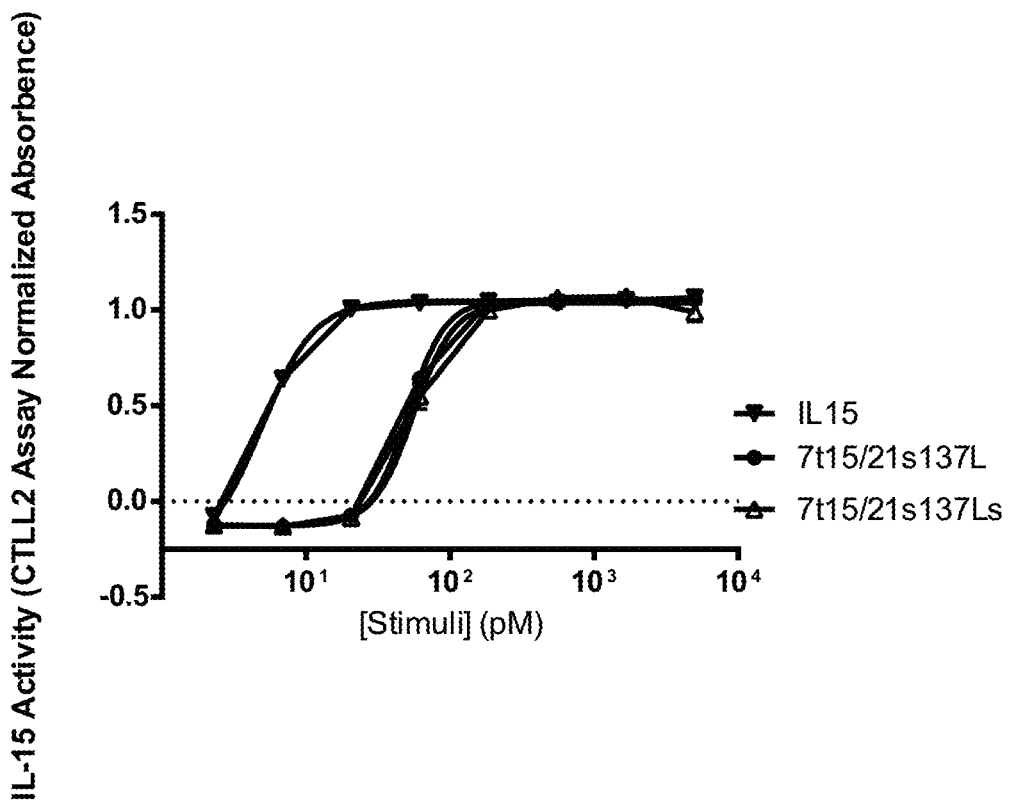

FIG. 144 shows IL-15 activity of 7t15-21s137L (long version) and 7t15-21s137L (short version) as evaluated by a IL2Rαβγ-containing CTLL2 cell proliferation assay.

DETAILED DESCRIPTION

Provided herein are multi-chain chimeric polypeptides that include: (a) a first chimeric polypeptide including: (i) a first target-binding domain; (ii) a soluble tissue factor domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains. Also provided herein are compositions that include any of the multi-chain chimeric polypeptides described herein, nucleic acids that encode any of the multi-chain chimeric polypeptides described herein, and cells that include any of the nucleic acids that encode any of the multi-chain chimeric polypeptides described herein. Also provided herein are methods of stimulating an immune cell and methods of treating a subject in need thereof that include the use of any of the multi-chain chimeric polypeptides described herein. Also provided herein are methods of producing any of the multi-chain chimeric polypeptides described herein.

Figures 1, 2:
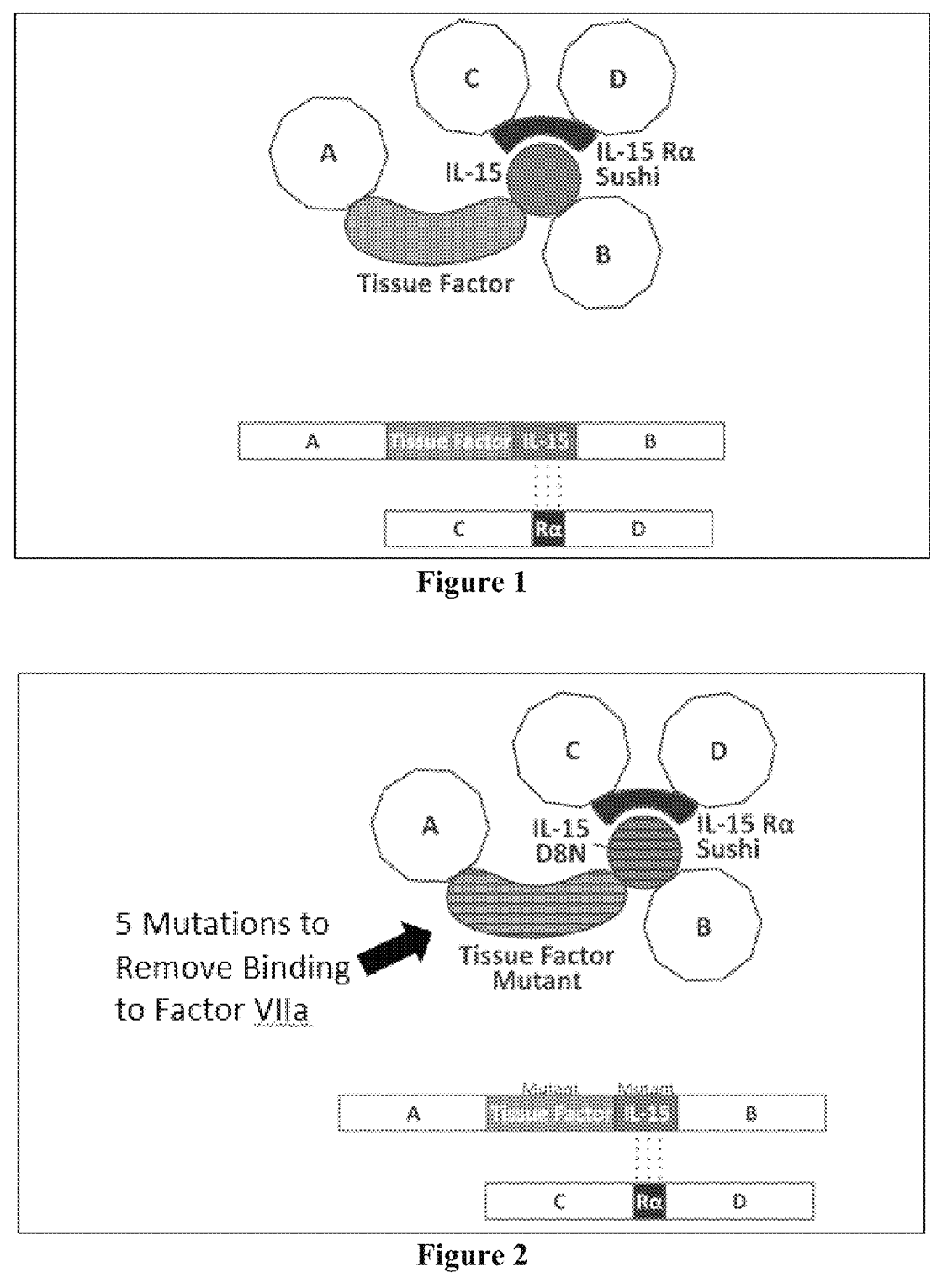

In some examples of any of the multi-chain chimeric polypeptides described herein the total length of first chimeric polypeptide and/or the second chimeric polypeptide can each independently be about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids. Diagrams of exemplary multi-chain chimeric polypeptides provided herein are depicted in FIGS. 1 and 2.

In some embodiments of any of the multi-chain chimeric polypeptides described herein, the first target-binding domain (e.g., any of the first target-binding domains described herein) and the soluble tissue factor domain (e.g., any of the exemplary soluble tissue factor domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the first target-binding domain (e.g., any of the exemplary first target-binding domains described herein) and the soluble tissue factor domain (e.g., any of the exemplary soluble tissue factor domains described herein) in the first chimeric polypeptide.

In some embodiments of any of the multi-chain chimeric polypeptides described herein, the soluble tissue factor domain (e.g., any of the exemplary soluble tissue factor domains described herein) and the first domain of the pair of affinity domains (e.g., any of the exemplary first domains of any of the exemplary pairs of affinity domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the soluble tissue factor domain (e.g., any of the exemplary soluble tissue factor domains described herein) and the first domain of the pair of affinity domains (e.g., any of the exemplary first domains of any of the exemplary pairs of affinity domains described herein) in the first chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the second chimeric polypeptide.

In some embodiments of any of the multi-chain chimeric polypeptides described herein, the second chimeric polypeptide further comprises a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the second chimeric polypeptide.

Non-limiting aspects of these chimeric polypeptides, nucleic acids, vectors, cells, and methods are described below, and can be used in any combination without limitation. Additional aspects of these chimeric polypeptides, nucleic acids, vectors, cells, and methods are known in the art.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at Ser253 and Ser258, and one S-palmitoylation site at Cys245. Deletion or mutation of the cytoplasmic domain was not found to affect tissue factor coagulation activity. Tissue factor has one S-palmitoylation site in the intracellular domain of the protein at Cys245. The Cys245 is located at the amino acid terminus of the intracellular domain and close to the membrane surface. The tissue factor transmembrane domain is composed of a single-spanning α-helix.

The extracellular domain of tissue factor, composed of two fibronectin type III domains, is connected to the transmembrane domain through a six-amino acid linker. This linker provides conformational flexibility to decouple the tissue factor extracellular domain from its transmembrane and cytoplasmic domains. Each tissue factor fibronectin type III module is composed of two overlapping β sheets with the top sheet domain containing three antiparallel β-strands and the bottom sheet containing four β-strands. The β-strands are connected by β-loops between strand βA and βB, βC and βD, and βE and βF, all of which are conserved in conformation in the two modules. There are three short α-helix segments connecting the β-strands. A unique feature of tissue factor is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue factor and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue factor-FVIIa complex on phospholipid bilayer (i.e., upon exposure of phosphatidyl-L-serine on membrane surfaces) increases the rate of FIX or FX activation, in a $Ca^{2+}$-dependent manner, an additional 1,000-fold. The roughly million-fold overall increase in FX activation by tissue factor-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the $Ile$-$^{154}$-$Arg^{152}$ bond in the short linker region between the EGF2 and the protease domain. This cleavage results in the light and heavy chains being held together by a single disulfide bond of $Cys^{135}$ and $Cys^{262}$. FVIIa binds phospholipid membrane in a $Ca^{2+}$-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of $His^{193}$, $Asp^{242}$, and $Ser^{344}$, and binding of a single $Ca^{2+}$ ion within the FVIIa protease domain is critical for its catalytic activity. Proteolytic activation of FVII to FVIIa frees the newly formed amino terminus at $Ile^{153}$ to fold back and be inserted into the activation pocket forming a salt bridge with the carboxylate of $Asp^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80 Å above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., *Biochemistry* 33(47): 14003-14010, 1994; Schullek et al., *J Biol Chem* 269(30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues $Arg^{135}$ and $Phe^{140}$ located on the protruding B-C loop provide an independent contact with FVIIa. $Leu^{133}$ is located at the base of the fingerlike structure and packed into the cleft between the two modules. This provides continuity to a major cluster of important binding residues consisting of $Lys^{20}$, $Thr^{60}$, $Asp^{58}$, and $Ile^{22}$. $Thr^{60}$ is only partially solvent-exposed and may play a local structural role rather than making a significant contact with ligand. The binding site extends onto the concave side of the intermodule angle involving $Glu^{24}$ and $Gln^{110}$, and potentially the more distant residue Val'". The binding region extends from Asp58 onto a convex surface area formed by $Lys^{48}$, $Lys^{46}$, $Gln^{37}$, $Asp^{44}$, and $Trp^{45}$. $Trp^{45}$ and $Asp^{44}$ do not interact independently with FVIIa, indicating that the mutational effect at the $Trp^{45}$ position may reflect a structural importance of this side chain for the local packing of the adjacent $Asp^{44}$ and $Gln^{37}$ side chain. The interactive area further includes two surface-exposed aromatic residues, $Phe^{76}$ and $Tyr^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., *J Biol Chem* 267(31): 22206-22210, 1992; Ruf et al., *J Biol Chem* 267(9): 6375-6381, 1992; Huang et al., *J Biol Chem* 271(36): 21752-21757, 1996; Kirchhofer et al., *Biochemistry* 39(25): 7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues $Lys^{165}$ and $Lys^{166}$ have also been demonstrated to be important for substrate recognition and binding. Mutation of either of these residues to alanine results in a significant decrease in the tissue factor co-factor function. $Lys^{165}$ and $Lys^{166}$ face away from each other, with $Lys^{165}$ pointing towards FVIIa in most tissue factor-FVIIa structures, and $Lys^{166}$ pointing into the substrate binding exosite region in the crystal structure. Putative salt bridge formation between $Lys^{165}$ of and $Gla^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Soluble Tissue Factor Domain

In some embodiments of any of the polypeptides, compositions, or methods described herein, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

```
Exemplary Soluble Human Tissue Factor Domain
                                          (SEQ ID NO: 1)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE

Exemplary Nucleic Acid Encoding Soluble Human
Tissue Factor Domain
                                          (SEQ ID NO: 2)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG

Exemplary Mutant Soluble Human Tissue Factor
Domain
                                          (SEQ ID NO: 3)
SGTTNTVAAYNLTWKSTNFATALEWEPKPVNQVYTVQISTKSGDWKSKCF

YTTDTECALTDEIVKDVKQTYLARVFSYPAGNVESTGSAGEPLYENSPEF

TPYLETNLGQPTIQSFEQVGTKVNVTVEDERTLVARNNTALSLRDVFGKD

LIYTLYYWKSSSSGKKTAKTNTNEFLIDVDKGENYCFSVQAVIPSRTVNR

KSTDSPVECMGQEKGEFRE

Exemplary Mutant Soluble Human Tissue Factor
Domain
                                          (SEQ ID NO: 4)
SGTTNTVAAYNLTWKSTNFATALEWEPKPVNQVYTVQISTKSGDAKSKCF

YTTDTECALTDEIVKDVKQTYLARVFSYPAGNVESTGSAGEPLAENSPEF

TPYLETNLGQPTIQSFEQVGTKVNVTVEDERTLVARNNTALSLRDVFGKD

LIYTLYYWKSSSSGKKTAKTNTNEFLIDVDKGENYCFSVQAVIPSRTVNR

KSTDSPVECMGQEKGEFRE

Exemplary Soluble Mouse Tissue Factor Domain
                                          (SEQ ID NO: 5)
agipekafnltwistdfktilewqpkptnytytvqisdrsrnwknkcfst tdtecdltdeivkdvtwayeakvlsvprrnsvhgdgdqlvihgeeppftn apkflpyrdtnlgqpviqqfeqdgrklnvvvkdsltlvrkngtfltlrqv fgkdlgyiityrkgsstgkktnitntnefsidveegvsycffvqamifsr ktnqnspgsstvcteqwksflge Exemplary Soluble Rat Tissue Factor Domain
                                          (SEQ ID NO: 6)
agtppgkafnltwistdfktilewqpkptnytytvqisdrsrnwkykctg ttdtecdltdeivkdvnwtyearvlsvpwrnsthgketlfgthgeeppft narkflpyrdtkigqpviqkyeqggtklkvtvkdsftlvrkngtfltlrq vfgndlgyiltyrkdsstgrktntthtneflidvekgvsycffaqavifs rktnhkspesitkcteqwksvlge
```

In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 1, 3, 4, 5, or 6. In some embodiments, a soluble tissue factor domain can include a sequence of SEQ ID NO: 1, 3, 4, 5, or 6, with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As can be appreciated in the art, one skilled in the art would understand that mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples of any of the multi-chain chimeric polypeptides described herein, the soluble tissue factor domain is not capable of binding to Factor VIIa. In some examples of any of the multi-chain chimeric polypeptides described herein, the soluble tissue factor domain does not convert inactive Factor X into Factor Xa. In some embodiments of any of the multi-chain chimeric polypeptides described herein, the multi-chain chimeric polypeptide does not stimulate blood coagulation in a mammal.

In some examples, the soluble tissue factor domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six, or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the mutant soluble tissue factor possesses the amino acid sequence of SEQ ID NO: 3 or SEQ ID NO: 4.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 2.

In some embodiments, the soluble tissue factor domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

Linker Sequences

In some embodiments, the linker sequence can be a flexible linker sequence. Non-limiting examples of linker sequences that can be used are described in Klein et al., *Protein Engineering, Design & Selection* 27(10):325-330, 2014; Priyanka et al., *Protein Sci.* 22(2):153-167, 2013. In some examples, the linker sequence is a synthetic linker sequence.

In some embodiments of any of the multi-chain chimeric polypeptides described herein, the first chimeric polypeptide can include one, two, three, four, five, six, seven, eight, nine, or ten linker sequence(s) (e.g., the same or different linker sequences, e.g., any of the exemplary linker sequences described herein or known in the art). In some embodiments of any of the multi-chain chimeric polypeptides described herein, the second chimeric polypeptide can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 90 amino acids, about 2 amino acids to about 80 amino acids, about 2 amino acids to about 70 amino acids, about 2 amino acids to about 60 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 90 amino acids, about 4 amino acids to about 80 amino acids, about 4 amino acids to about 70 amino acids, about 4 amino acids to about 60 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 90 amino acids, about 6 amino acids to about 80 amino acids, about 6 amino acids to about 70 amino acids, about 6 amino acids to about 60 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 90 amino acids, about 8 amino acids to about 80 amino acids, about 8 amino acids to about 70 amino acids, about 8 amino acids to about 60 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 24 amino acids, about 18 amino acids to about 22 amino acids, about 18 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 24 amino acids, about 20 amino acids to about 22 amino acids, about 22 amino acids to about 100 amino acids, about 22 amino acids to about 90 amino acids, about 22 amino acids to about 80 amino acids, about 22 amino acids to about 70 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 22 amino acids to about 24 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 100 amino acids, about 60 amino acids to about 90 amino acids, about 60 amino acids to about 80 amino acids, about 60 amino acids to about 70 amino acids, about 70 amino acids to about 100 amino acids, about 70 amino acids to about 90 amino acids, about 70 amino acids to about 80 amino acids, about 80 amino acids to about 100 amino acids, about 80 amino acids to about 90 amino acids, or about 90 amino acids to about 100 amino acids.

In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) sequences, e.g., 1, 2, 3, 4, 5, 6, 7, 8, 9, or 10 or more GGGS sequences. In some embodiments, the linker has one or more Gly-Gly-Gly-Gly-Ser (GGGGS) sequences, e.g., 1, 2, 3, 4, 5, 6, 7, 8, 9, or 10 or more GGGGS sequences. In some embodiments, the linker has one or more Gly-Gly-Ser-Gly (GGSG) sequences, e.g., 1, 2, 3, 4, 5, 6, 7, 8, 9, or 10 or more GGSG sequences.

In some embodiments, the linker sequence can comprise or consist of GGGGSGGGGSGGGGS (SEQ ID NO: 7). In some embodiments, the linker sequence can be encoded by a nucleic acid comprising or consisting of: GGCGGTGGAGGATCCGGAGGAGGTGGCTCCGGCGGCGGAGGATCT (SEQ ID NO: 8). In some embodiments, the linker sequence can comprise or consist of: GGGSGGGS (SEQ ID NO: 9).

Target-Binding Domains

In some embodiments of any of the multi-chain chimeric polypeptides described herein, the first target-binding domain, the second target-binding domain, and/or the additional one or more target-binding domains can be an antigen-binding domain (e.g., any of the exemplary antigen-binding domains described herein or known in the art), a soluble interleukin or cytokine protein (e.g., any of the exemplary soluble interleukin proteins or soluble cytokine proteins described herein), and a soluble interleukin or cytokine receptor (e.g., any of the exemplary soluble interleukin receptors or soluble cytokine receptors described herein).

In some embodiments of any of the multi-chain chimeric polypeptides described herein, one or more of the first target-binding domain (e.g., any of the exemplary first target binding domains described herein or known in the art), the second target-binding domain (e.g., any of the exemplary second target binding domains described herein or known in the art), and the one or more additional target binding domains can each, independently, bind specifically to a target selected from the group of: bind specifically to a target selected from the group consisting of: CD16a, CD28, CD3 (e.g., one or more of CD3α, CD3β, CD3δ, CD3ε, and CD3γ), CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein (e.g., ULBP1, ULBP2, ULBP3, ULBP4, ULBP5, and ULBP6), HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the multi-chain chimeric polypeptides described herein, the first target-binding domain, the second target-binding domain, and/or the one or more additional target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 1000 amino acids, about 10 amino acids to about 950 amino acids, about 10 amino acids to about 900 amino acids, about 10 amino acids to about 850 amino acids, about 10 amino acids to about 800 amino acids, about 10 amino acids to about 750 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 280 amino acids, about 10 amino acids to about 260 amino acids, about 10 amino acids to about 240 amino acids, about 10 amino acids to about 220 amino acids, about 10 amino acids to about 200 amino acids, about 10 amino acids to about 195 amino acids, about 10 amino acids to about 190 amino acids, about 10 amino acids to about 185 amino acids, about 10 amino acids to about 180 amino acids, about 10 amino acids to about 175 amino acids, about 10 amino acids to about 170 amino acids, about 10 amino acids to about 165 amino acids, about 10 amino acids to about 160 amino acids, about 10 amino acids to about 155 amino acids, about 10 amino acids to about 150 amino acids, about 10 amino acids to about 145 amino acids, about 10 amino acids to about 140 amino acids, about 10 amino acids to about 135 amino acids, about 10 amino acids to about 130 amino acids, about 10 amino acids to about 125 amino acids, about 10 amino acids to about 120 amino acids, about 10 amino acids to about 115 amino acids, about 10 amino acids to about 110 amino acids, about 10 amino acids to about 105 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 1000 amino acids, about 15 amino acids to about 950 amino acids, about 15 amino acids to about 900 amino acids, about 15 amino acids to about 850 amino acids, about 15 amino acids to about 800 amino acids, about 15 amino acids to about 750 amino acids, about 15 amino acids to about 700 amino acids, about 15 amino acids to about 650 amino acids, about 15 amino acids to about 600 amino acids, about 15 amino acids to about 550 amino acids, about 15 amino acids to about 500 amino acids, about 15 amino acids to about 450 amino acids, about 15 amino acids to about 400 amino acids, about 15 amino acids to about 350 amino acids, about 15 amino acids to about 300 amino acids, about 15 amino acids to about 280 amino acids, about 15 amino acids to about 260 amino acids, about 15 amino acids to about 240 amino acids, about 15 amino acids to about 220 amino acids, about 15 amino acids to about 200 amino acids, about 15 amino acids to about 195 amino acids, about 15 amino acids to about 190 amino acids, about 15 amino acids to about 185 amino acids, about 15 amino acids to about 180 amino acids, about 15 amino acids to about 175 amino acids, about 15 amino acids to about 170 amino acids, about 15 amino acids to about 165 amino acids, about 15 amino acids to about 160 amino acids, about 15 amino acids to about 155 amino acids, about 15 amino acids to about 150 amino acids, about 15 amino acids to about 145 amino acids, about 15 amino acids to about 140 amino acids, about 15 amino acids to about 135 amino acids, about 15 amino acids to about 130 amino acids, about 15 amino acids to about 125 amino acids, about 15 amino acids to about 120 amino acids, about 15 amino acids to about 115 amino acids, about 15 amino acids to about 110 amino acids, about 15 amino acids to about 105 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 280 amino acids, about 20 amino acids to about 260 amino acids, about 20 amino acids to about 240 amino acids, about 20 amino acids to about 220 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 280 amino acids, about 25 amino acids to about 260 amino acids, about 25 amino acids to about 240 amino acids, about 25 amino acids to about 220 amino acids, about 25 amino acids to about 200 amino acids, about 25 amino acids to about 195 amino acids, about 25 amino acids to about 190 amino acids, about 25 amino acids to about 185 amino acids, about 25 amino acids to about 180 amino acids, about 25 amino acids to about 175 amino acids, about 25 amino acids to about 170 amino acids, about 25 amino acids to about 165 amino acids, about 25 amino acids to about 160 amino acids, about 25 amino acids to about 155 amino acids, about 25 amino acids to about 150 amino acids, about 25 amino acids to about 145 amino acids, about 25 amino acids to about 140 amino acids, about 25 amino acids to about 135 amino acids, about 25 amino acids to about 130 amino acids, about 25 amino acids to about 125 amino acids, about 25 amino acids to about 120 amino acids, about 25 amino acids to about 115 amino acids, about 25 amino acids to about 110 amino acids, about 25 amino acids to about 105 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 280 amino acids, about 30 amino acids to about 260 amino acids, about 30 amino acids to about 240 amino acids, about 30 amino acids to about 220 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 280 amino acids, about 35 amino acids to about 260 amino acids, about 35 amino acids to about 240 amino acids, about 35 amino acids to about 220 amino acids, about 35 amino acids to about 200 amino acids, about 35 amino acids to about 195 amino acids, about 35 amino acids to about 190 amino acids, about 35 amino acids to about 185 amino acids, about 35 amino acids to about 180 amino acids, about 35 amino acids to about 175 amino acids, about 35 amino acids to about 170 amino acids, about 35 amino acids to about 165 amino acids, about 35 amino acids to about 160 amino acids, about 35 amino acids to about 155 amino acids, about 35 amino acids to about 150 amino acids, about 35 amino acids to about 145 amino acids, about 35 amino acids to about 140 amino acids, about 35 amino acids to about 135 amino acids, about 35 amino acids to about 130 amino acids, about 35 amino acids to about 125 amino acids, about 35 amino acids to about 120 amino acids, about 35 amino acids to about 115 amino acids, about 35 amino acids to about 110 amino acids, about 35 amino acids to about 105 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 280 amino acids, about 40 amino acids to about 260 amino acids, about 40 amino acids to about 240 amino acids, about 40 amino acids to about 220 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 280 amino acids, about 45 amino acids to about 260 amino acids, about 45 amino acids to about 240 amino acids, about 45 amino acids to about 220 amino acids, about 45 amino acids to about 200 amino acids, about 45 amino acids to about 195 amino acids, about 45 amino acids to about 190 amino acids, about 45 amino acids to about 185 amino acids, about 45 amino acids to about 180 amino acids, about 45 amino acids to about 175 amino acids, about 45 amino acids to about 170 amino acids, about 45 amino acids to about 165 amino acids, about 45 amino acids to about 160 amino acids, about 45 amino acids to about 155 amino acids, about 45 amino acids to about 150 amino acids, about 45 amino acids to about 145 amino acids, about 45 amino acids to about 140 amino acids, about 45 amino acids to about 135 amino acids, about 45 amino acids to about 130 amino acids, about 45 amino acids to about 125 amino acids, about 45 amino acids to about 120 amino acids, about 45 amino acids to about 115 amino acids, about 45 amino acids to about 110 amino acids, about 45 amino acids to about 105 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 1000 amino acids, about 55 amino acids to about 950 amino acids, about 55 amino acids to about 900 amino acids, about 55 amino acids to about 850 amino acids, about 55 amino acids to about 800 amino acids, about 55 amino acids to about 750 amino acids, about 55 amino acids to about 700 amino acids, about 55 amino acids to about 650 amino acids, about 55 amino acids to about 600 amino acids, about 55 amino acids to about 550 amino acids, about 55 amino acids to about 500 amino acids, about 55 amino acids to about 450 amino acids, about 55 amino acids to about 400 amino acids, about 55 amino acids to about 350 amino acids, about 55 amino acids to about 300 amino acids, about 55 amino acids to about 280 amino acids, about 55 amino acids to about 260 amino acids, about 55 amino acids to about 240 amino acids, about 55 amino acids to about 220 amino acids, about 55 amino acids to about 200 amino acids, about 55 amino acids to about 195 amino acids, about 55 amino acids to about 190 amino acids, about 55 amino acids to about 185 amino acids, about 55 amino acids to about 180 amino acids, about 55 amino acids to about 175 amino acids, about 55 amino acids to about 170 amino acids, about 55 amino acids to about 165 amino acids, about 55 amino acids to about 160 amino acids, about 55 amino acids to about 155 amino acids, about 55 amino acids to about 150 amino acids, about 55 amino acids to about 145 amino acids, about 55 amino acids to about 140 amino acids, about 55 amino acids to about 135 amino acids, about 55 amino acids to about 130 amino acids, about 55 amino acids to about 125 amino acids, about 55 amino acids to about 120 amino acids, about 55 amino acids to about 115 amino acids, about 55 amino acids to about 110 amino acids, about 55 amino acids to about 105 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 280 amino acids, about 60 amino acids to about 260 amino acids, about 60 amino acids to about 240 amino acids, about 60 amino acids to about 220 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 1000 amino acids, about 65 amino acids to about 950 amino acids, about 65 amino acids to about 900 amino acids, about 65 amino acids to about 850 amino acids, about 65 amino acids to about 800 amino acids, about 65 amino acids to about 750 amino acids, about 65 amino acids to about 700 amino acids, about 65 amino acids to about 650 amino acids, about 65 amino acids to about 600 amino acids, about 65 amino acids to about 550 amino acids, about 65 amino acids to about 500 amino acids, about 65 amino acids to about 450 amino acids, about 65 amino acids to about 400 amino acids, about 65 amino acids to about 350 amino acids, about 65 amino acids to about 300 amino acids, about 65 amino acids to about 280 amino acids, about 65 amino acids to about 260 amino acids, about 65 amino acids to about 240 amino acids, about 65 amino acids to about 220 amino acids, about 65 amino acids to about 200 amino acids, about 65 amino acids to about 195 amino acids, about 65 amino acids to about 190 amino acids, about 65 amino acids to about 185 amino acids, about 65 amino acids to about 180 amino acids, about 65 amino acids to about 175 amino acids, about 65 amino acids to about 170 amino acids, about 65 amino acids to about 165 amino acids, about 65 amino acids to about 160 amino acids, about 65 amino acids to about 155 amino acids, about 65 amino acids to about 150 amino acids, about 65 amino acids to about 145 amino acids, about 65 amino acids to about 140 amino acids, about 65 amino acids to about 135 amino acids, about 65 amino acids to about 130 amino acids, about 65 amino acids to about 125 amino acids, about 65 amino acids to about 120 amino acids, about 65 amino acids to about 115 amino acids, about 65 amino acids to about 110 amino acids, about 65 amino acids to about 105 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 280 amino acids, about 70 amino acids to about 260 amino acids, about 70 amino acids to about 240 amino acids, about 70 amino acids to about 220 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 1000 amino acids, about 75 amino acids to about 950 amino acids, about 75 amino acids to about 900 amino acids, about 75 amino acids to about 850 amino acids, about 75 amino acids to about 800 amino acids, about 75 amino acids to about 750 amino acids, about 75 amino acids to about 700 amino acids, about 75 amino acids to about 650 amino acids, about 75 amino acids to about 600 amino acids, about 75 amino acids to about 550 amino acids, about 75 amino acids to about 500 amino acids, about 75 amino acids to about 450 amino acids, about 75 amino acids to about 400 amino acids, about 75 amino acids to about 350 amino acids, about 75 amino acids to about 300 amino acids, about 75 amino acids to about 280 amino acids, about 75 amino acids to about 260 amino acids, about 75 amino acids to about 240 amino acids, about 75 amino acids to about 220 amino acids, about 75 amino acids to about 200 amino acids, about 75 amino acids to about 195 amino acids, about 75 amino acids to about 190 amino acids, about 75 amino acids to about 185 amino acids, about 75 amino acids to about 180 amino acids, about 75 amino acids to about 175 amino acids, about 75 amino acids to about 170 amino acids, about 75 amino acids to about 165 amino acids, about 75 amino acids to about 160 amino acids, about 75 amino acids to about 155 amino acids, about 75 amino acids to about 150 amino acids, about 75 amino acids to about 145 amino acids, about 75 amino acids to about 140 amino acids, about 75 amino acids to about 135 amino acids, about 75 amino acids to about 130 amino acids, about 75 amino acids to about 125 amino acids, about 75 amino acids to about 120 amino acids, about 75 amino acids to about 115 amino acids, about 75 amino acids to about 110 amino acids, about 75 amino acids to about 105 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 280 amino acids, about 80 amino acids to about 260 amino acids, about 80 amino acids to about 240 amino acids, about 80 amino acids to about 220 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 80 amino acids to about 85 amino acids, about 85 amino acids to about 1000 amino acids, about 85 amino acids to about 950 amino acids, about 85 amino acids to about 900 amino acids, about 85 amino acids to about 850 amino acids, about 85 amino acids to about 800 amino acids, about 85 amino acids to about 750 amino acids, about 85 amino acids to about 700 amino acids, about 85 amino acids to about 650 amino acids, about 85 amino acids to about 600 amino acids, about 85 amino acids to about 550 amino acids, about 85 amino acids to about 500 amino acids, about 85 amino acids to about 450 amino acids, about 85 amino acids to about 400 amino acids, about 85 amino acids to about 350 amino acids, about 85 amino acids to about 300 amino acids, about 85 amino acids to about 280 amino acids, about 85 amino acids to about 260 amino acids, about 85 amino acids to about 240 amino acids, about 85 amino acids to about 220 amino acids, about 85 amino acids to about 200 amino acids, about 85 amino acids to about 195 amino acids, about 85 amino acids to about 190 amino acids, about 85 amino acids to about 185 amino acids, about 85 amino acids to about 180 amino acids, about 85 amino acids to about 175 amino acids, about 85 amino acids to about 170 amino acids, about 85 amino acids to about 165 amino acids, about 85 amino acids to about 160 amino acids, about 85 amino acids to about 155 amino acids, about 85 amino acids to about 150 amino acids, about 85 amino acids to about 145 amino acids, about 85 amino acids to about 140 amino acids, about 85 amino acids to about 135 amino acids, about 85 amino acids to about 130 amino acids, about 85 amino acids to about 125 amino acids, about 85 amino acids to about 120 amino acids, about 85 amino acids to about 115 amino acids, about 85 amino acids to about 110 amino acids, about 85 amino acids to about 105 amino acids, about 85 amino acids to about 100 amino acids, about 85 amino acids to about 95 amino acids, about 85 amino acids to about 90 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 280 amino acids, about 90 amino acids to about 260 amino acids, about 90 amino acids to about 240 amino acids, about 90 amino acids to about 220 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 90 amino acids to about 95 amino acids, about 95 amino acids to about 1000 amino acids, about 95 amino acids to about 950 amino acids, about 95 amino acids to about 900 amino acids, about 95 amino acids to about 850 amino acids, about 95 amino acids to about 800 amino acids, about 95 amino acids to about 750 amino acids, about 95 amino acids to about 700 amino acids, about 95 amino acids to about 650 amino acids, about 95 amino acids to about 600 amino acids, about 95 amino acids to about 550 amino acids, about 95 amino acids to about 500 amino acids, about 95 amino acids to about 450 amino acids, about 95 amino acids to about 400 amino acids, about 95 amino acids to about 350 amino acids, about 95 amino acids to about 300 amino acids, about 95 amino acids to about 280 amino acids, about 95 amino acids to about 260 amino acids, about 95 amino acids to about 240 amino acids, about 95 amino acids to about 220 amino acids, about 95 amino acids to about 200 amino acids, about 95 amino acids to about 195 amino acids, about 95 amino acids to about 190 amino acids, about 95 amino acids to about 185 amino acids, about 95 amino acids to about 180 amino acids, about 95 amino acids to about 175 amino acids, about 95 amino acids to about 170 amino acids, about 95 amino acids to about 165 amino acids, about 95 amino acids to about 160 amino acids, about 95 amino acids to about 155 amino acids, about 95 amino acids to about 150 amino acids, about 95 amino acids to about 145 amino acids, about 95 amino acids to about 140 amino acids, about 95 amino acids to about 135 amino acids, about 95 amino acids to about 130 amino acids, about 95 amino acids to about 125 amino acids, about 95 amino acids to about 120 amino acids, about 95 amino acids to about 115 amino acids, about 95 amino acids to about 110 amino acids, about 95 amino acids to about 105 amino acids, about 95 amino acids to about 100 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 100 amino acids to about 105 amino acids, about 105 amino acids to about 1000 amino acids, about 105 amino acids to about 950 amino acids, about 105 amino acids to about 900 amino acids, about 105 amino acids to about 850 amino acids, about 105 amino acids to about 800 amino acids, about 105 amino acids to about 750 amino acids, about 105 amino acids to about 700 amino acids, about 105 amino acids to about 650 amino acids, about 105 amino acids to about 600 amino acids, about 105 amino acids to about 550 amino acids, about 105 amino acids to about 500 amino acids, about 105 amino acids to about 450 amino acids, about 105 amino acids to about 400 amino acids, about 105 amino acids to about 350 amino acids, about 105 amino acids to about 300 amino acids, about 105 amino acids to about 280 amino acids, about 105 amino acids to about 260 amino acids, about 105 amino acids to about 240 amino acids, about 105 amino acids to about 220 amino acids, about 105 amino acids to about 200 amino acids, about 105 amino acids to about 195 amino acids, about 105 amino acids to about 190 amino acids, about 105 amino acids to about 185 amino acids, about 105 amino acids to about 180 amino acids, about 105 amino acids to about 175 amino acids, about 105 amino acids to about 170 amino acids, about 105 amino acids to about 165 amino acids, about 105 amino acids to about 160 amino acids, about 105 amino acids to about 155 amino acids, about 105 amino acids to about 150 amino acids, about 105 amino acids to about 145 amino acids, about 105 amino acids to about 140 amino acids, about 105 amino acids to about 135 amino acids, about 105 amino acids to about 130 amino acids, about 105 amino acids to about 125 amino acids, about 105 amino acids to about 120 amino acids, about 105 amino acids to about 115 amino acids, about 105 amino acids to about 110 amino acids, about 110 amino acids to about 1000 amino acids, about 110 amino acids to about 950 amino acids, about 110 amino acids to about 900 amino acids, about 110 amino acids to about 850 amino acids, about 110 amino acids to about 800 amino acids, about 110 amino acids to about 750 amino acids, about 110 amino acids to about 700 amino acids, about 110 amino acids to about 650 amino acids, about 110 amino acids to about 600 amino acids, about 110 amino acids to about 550 amino acids, about 110 amino acids to about 500 amino acids, about 110 amino acids to about 450 amino acids, about 110 amino acids to about 400 amino acids, about 110 amino acids to about 350 amino acids, about 110 amino acids to about 300 amino acids, about 110 amino acids to about 280 amino acids, about 110 amino acids to about 260 amino acids, about 110 amino acids to about 240 amino acids, about 110 amino acids to about 220 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 1000 amino acids, about 115 amino acids to about 950 amino acids, about 115 amino acids to about 900 amino acids, about 115 amino acids to about 850 amino acids, about 115 amino acids to about 800 amino acids, about 115 amino acids to about 750 amino acids, about 115 amino acids to about 700 amino acids, about 115 amino acids to about 650 amino acids, about 115 amino acids to about 600 amino acids, about 115 amino acids to about 550 amino acids, about 115 amino acids to about 500 amino acids, about 115 amino acids to about 450 amino acids, about 115 amino acids to about 400 amino acids, about 115 amino acids to about 350 amino acids, about 115 amino acids to about 300 amino acids, about 115 amino acids to about 280 amino acids, about 115 amino acids to about 260 amino acids, about 115 amino acids to about 240 amino acids, about 115 amino acids to about 220 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 1000 amino acids, about 120 amino acids to about 950 amino acids, about 120 amino acids to about 900 amino acids, about 120 amino acids to about 850 amino acids, about 120 amino acids to about 800 amino acids, about 120 amino acids to about 750 amino acids, about 120 amino acids to about 700 amino acids, about 120 amino acids to about 650 amino acids, about 120 amino acids to about 600 amino acids, about 120 amino acids to about 550 amino acids, about 120 amino acids to about 500 amino acids, about 120 amino acids to about 450 amino acids, about 120 amino acids to about 400 amino acids, about 120 amino acids to about 350 amino acids, about 120 amino acids to about 300 amino acids, about 120 amino acids to about 280 amino acids, about 120 amino acids to about 260 amino acids, about 120 amino acids to about 240 amino acids, about 120 amino acids to about 220 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 1000 amino acids, about 125 amino acids to about 950 amino acids, about 125 amino acids to about 900 amino acids, about 125 amino acids to about 850 amino acids, about 125 amino acids to about 800 amino acids, about 125 amino acids to about 750 amino acids, about 125 amino acids to about 700 amino acids, about 125 amino acids to about 650 amino acids, about 125 amino acids to about 600 amino acids, about 125 amino acids to about 550 amino acids, about 125 amino acids to about 500 amino acids, about 125 amino acids to about 450 amino acids, about 125 amino acids to about 400 amino acids, about 125 amino acids to about 350 amino acids, about 125 amino acids to about 300 amino acids, about 125 amino acids to about 280 amino acids, about 125 amino acids to about 260 amino acids, about 125 amino acids to about 240 amino acids, about 125 amino acids to about 220 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 1000 amino acids, about 130 amino acids to about 950 amino acids, about 130 amino acids to about 900 amino acids, about 130 amino acids to about 850 amino acids, about 130 amino acids to about 800 amino acids, about 130 amino acids to about 750 amino acids, about 130 amino acids to about 700 amino acids, about 130 amino acids to about 650 amino acids, about 130 amino acids to about 600 amino acids, about 130 amino acids to about 550 amino acids, about 130 amino acids to about 500 amino acids, about 130 amino acids to about 450 amino acids, about 130 amino acids to about 400 amino acids, about 130 amino acids to about 350 amino acids, about 130 amino acids to about 300 amino acids, about 130 amino acids to about 280 amino acids, about 130 amino acids to about 260 amino acids, about 130 amino acids to about 240 amino acids, about 130 amino acids to about 220 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 1000 amino acids, about 135 amino acids to about 950 amino acids, about 135 amino acids to about 900 amino acids, about 135 amino acids to about 850 amino acids, about 135 amino acids to about 800 amino acids, about 135 amino acids to about 750 amino acids, about 135 amino acids to about 700 amino acids, about 135 amino acids to about 650 amino acids, about 135 amino acids to about 600 amino acids, about 135 amino acids to about 550 amino acids, about 135 amino acids to about 500 amino acids, about 135 amino acids to about 450 amino acids, about 135 amino acids to about 400 amino acids, about 135 amino acids to about 350 amino acids, about 135 amino acids to about 300 amino acids, about 135 amino acids to about 280 amino acids, about 135 amino acids to about 260 amino acids, about 135 amino acids to about 240 amino acids, about 135 amino acids to about 220 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 1000 amino acids, about 140 amino acids to about 950 amino acids, about 140 amino acids to about 900 amino acids, about 140 amino acids to about 850 amino acids, about 140 amino acids to about 800 amino acids, about 140 amino acids to about 750 amino acids, about 140 amino acids to about 700 amino acids, about 140 amino acids to about 650 amino acids, about 140 amino acids to about 600 amino acids, about 140 amino acids to about 550 amino acids, about 140 amino acids to about 500 amino acids, about 140 amino acids to about 450 amino acids, about 140 amino acids to about 400 amino acids, about 140 amino acids to about 350 amino acids, about 140 amino acids to about 300 amino acids, about 140 amino acids to about 280 amino acids, about 140 amino acids to about 260 amino acids, about 140 amino acids to about 240 amino acids, about 140 amino acids to about 220 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 1000 amino acids, about 145 amino acids to about 950 amino acids, about 145 amino acids to about 900 amino acids, about 145 amino acids to about 850 amino acids, about 145 amino acids to about 800 amino acids, about 145 amino acids to about 750 amino acids, about 145 amino acids to about 700 amino acids, about 145 amino acids to about 650 amino acids, about 145 amino acids to about 600 amino acids, about 145 amino acids to about 550 amino acids, about 145 amino acids to about 500 amino acids, about 145 amino acids to about 450 amino acids, about 145 amino acids to about 400 amino acids, about 145 amino acids to about 350 amino acids, about 145 amino acids to about 300 amino acids, about 145 amino acids to about 280 amino acids, about 145 amino acids to about 260 amino acids, about 145 amino acids to about 240 amino acids, about 145 amino acids to about 220 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 1000 amino acids, about 155 amino acids to about 950 amino acids, about 155 amino acids to about 900 amino acids, about 155 amino acids to about 850 amino acids, about 155 amino acids to about 800 amino acids, about 155 amino acids to about 750 amino acids, about 155 amino acids to about 700 amino acids, about 155 amino acids to about 650 amino acids, about 155 amino acids to about 600 amino acids, about 155 amino acids to about 550 amino acids, about 155 amino acids to about 500 amino acids, about 155 amino acids to about 450 amino acids, about 155 amino acids to about 400 amino acids, about 155 amino acids to about 350 amino acids, about 155 amino acids to about 300 amino acids, about 155 amino acids to about 280 amino acids, about 155 amino acids to about 260 amino acids, about 155 amino acids to about 240 amino acids, about 155 amino acids to about 220 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 1000 amino acids, about 160 amino acids to about 950 amino acids, about 160 amino acids to about 900 amino acids, about 160 amino acids to about 850 amino acids, about 160 amino acids to about 800 amino acids, about 160 amino acids to about 750 amino acids, about 160 amino acids to about 700 amino acids, about 160 amino acids to about 650 amino acids, about 160 amino acids to about 600 amino acids, about 160 amino acids to about 550 amino acids, about 160 amino acids to about 500 amino acids, about 160 amino acids to about 450 amino acids, about 160 amino acids to about 400 amino acids, about 160 amino acids to about 350 amino acids, about 160 amino acids to about 300 amino acids, about 160 amino acids to about 280 amino acids, about 160 amino acids to about 260 amino acids, about 160 amino acids to about 240 amino acids, about 160 amino acids to about 220 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 1000 amino acids, about 165 amino acids to about 950 amino acids, about 165 amino acids to about 900 amino acids, about 165 amino acids to about 850 amino acids, about 165 amino acids to about 800 amino acids, about 165 amino acids to about 750 amino acids, about 165 amino acids to about 700 amino acids, about 165 amino acids to about 650 amino acids, about 165 amino acids to about 600 amino acids, about 165 amino acids to about 550 amino acids, about 165 amino acids to about 500 amino acids, about 165 amino acids to about 450 amino acids, about 165 amino acids to about 400 amino acids, about 165 amino acids to about 350 amino acids, about 165 amino acids to about 300 amino acids, about 165 amino acids to about 280 amino acids, about 165 amino acids to about 260 amino acids, about 165 amino acids to about 240 amino acids, about 165 amino acids to about 220 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 1000 amino acids, about 170 amino acids to about 950 amino acids, about 170 amino acids to about 900 amino acids, about 170 amino acids to about 850 amino acids, about 170 amino acids to about 800 amino acids, about 170 amino acids to about 750 amino acids, about 170 amino acids to about 700 amino acids, about 170 amino acids to about 650 amino acids, about 170 amino acids to about 600 amino acids, about 170 amino acids to about 550 amino acids, about 170 amino acids to about 500 amino acids, about 170 amino acids to about 450 amino acids, about 170 amino acids to about 400 amino acids, about 170 amino acids to about 350 amino acids, about 170 amino acids to about 300 amino acids, about 170 amino acids to about 280 amino acids, about 170 amino acids to about 260 amino acids, about 170 amino acids to about 240 amino acids, about 170 amino acids to about 220 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 1000 amino acids, about 175 amino acids to about 950 amino acids, about 175 amino acids to about 900 amino acids, about 175 amino acids to about 850 amino acids, about 175 amino acids to about 800 amino acids, about 175 amino acids to about 750 amino acids, about 175 amino acids to about 700 amino acids, about 175 amino acids to about 650 amino acids, about 175 amino acids to about 600 amino acids, about 175 amino acids to about 550 amino acids, about 175 amino acids to about 500 amino acids, about 175 amino acids to about 450 amino acids, about 175 amino acids to about 400 amino acids, about 175 amino acids to about 350 amino acids, about 175 amino acids to about 300 amino acids, about 175 amino acids to about 280 amino acids, about 175 amino acids to about 260 amino acids, about 175 amino acids to about 240 amino acids, about 175 amino acids to about 220 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 1000 amino acids, about 180 amino acids to about 950 amino acids, about 180 amino acids to about 900 amino acids, about 180 amino acids to about 850 amino acids, about 180 amino acids to about 800 amino acids, about 180 amino acids to about 750 amino acids, about 180 amino acids to about 700 amino acids, about 180 amino acids to about 650 amino acids, about 180 amino acids to about 600 amino acids, about 180 amino acids to about 550 amino acids, about 180 amino acids to about 500 amino acids, about 180 amino acids to about 450 amino acids, about 180 amino acids to about 400 amino acids, about 180 amino acids to about 350 amino acids, about 180 amino acids to about 300 amino acids, about 180 amino acids to about 280 amino acids, about 180 amino acids to about 260 amino acids, about 180 amino acids to about 240 amino acids, about 180 amino acids to about 220 amino acids, about 180 amino acids to about 200 amino acids, about 180 amino acids to about 195 amino acids, about 180 amino acids to about 190 amino acids, about 180 amino acids to about 185 amino acids, about 185 amino acids to about 1000 amino acids, about 185 amino acids to about 950 amino acids, about 185 amino acids to about 900 amino acids, about 185 amino acids to about 850 amino acids, about 185 amino acids to about 800 amino acids, about 185 amino acids to about 750 amino acids, about 185 amino acids to about 700 amino acids, about 185 amino acids to about 650 amino acids, about 185 amino acids to about 600 amino acids, about 185 amino acids to about 550 amino acids, about 185 amino acids to about 500 amino acids, about 185 amino acids to about 450 amino acids, about 185 amino acids to about 400 amino acids, about 185 amino acids to about 350 amino acids, about 185 amino acids to about 300 amino acids, about 185 amino acids to about 280 amino acids, about 185 amino acids to about 260 amino acids, about 185 amino acids to about 240 amino acids, about 185 amino acids to about 220 amino acids, about 185 amino acids to about 200 amino acids, about 185 amino acids to about 195 amino acids, about 185 amino acids to about 190 amino acids, about 190 amino acids to about 1000 amino acids, about 190 amino acids to about 950 amino acids, about 190 amino acids to about 900 amino acids, about 190 amino acids to about 850 amino acids, about 190 amino acids to about 800 amino acids, about 190 amino acids to about 750 amino acids, about 190 amino acids to about 700 amino acids, about 190 amino acids to about 650 amino acids, about 190 amino acids to about 600 amino acids, about 190 amino acids to about 550 amino acids, about 190 amino acids to about 500 amino acids, about 190 amino acids to about 450 amino acids, about 190 amino acids to about 400 amino acids, about 190 amino acids to about 350 amino acids, about 190 amino acids to about 300 amino acids, about 190 amino acids to about 280 amino acids, about 190 amino acids to about 260 amino acids, about 190 amino acids to about 240 amino acids, about 190 amino acids to about 220 amino acids, about 190 amino acids to about 200 amino acids, about 190 amino acids to about 195 amino acids, about 195 amino acids to about 1000 amino acids, about 195 amino acids to about 950 amino acids, about 195 amino acids to about 900 amino acids, about 195 amino acids to about 850 amino acids, about 195 amino acids to about 800 amino acids, about 195 amino acids to about 750 amino acids, about 195 amino acids to about 700 amino acids, about 195 amino acids to about 650 amino acids, about 195 amino acids to about 600 amino acids, about 195 amino acids to about 550 amino acids, about 195 amino acids to about 500 amino acids, about 195 amino acids to about 450 amino acids, about 195 amino acids to about 400 amino acids, about 195 amino acids to about 350 amino acids, about 195 amino acids to about 300 amino acids, about 195 amino acids to about 280 amino acids, about 195 amino acids to about 260 amino acids, about 195 amino acids to about 240 amino acids, about 195 amino acids to about 220 amino acids, about 195 amino acids to about 200 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 450 amino acids, about 220 amino acids to about 400 amino acids, about 220 amino acids to about 350 amino acids, about 220 amino acids to about 300 amino acids, about 220 amino acids to about 280 amino acids, about 220 amino acids to about 260 amino acids, about 220 amino acids to about 240 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 450 amino acids, about 240 amino acids to about 400 amino acids, about 240 amino acids to about 350 amino acids, about 240 amino acids to about 300 amino acids, about 240 amino acids to about 280 amino acids, about 240 amino acids to about 260 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 450 amino acids, about 260 amino acids to about 400 amino acids, about 260 amino acids to about 350 amino acids, about 260 amino acids to about 300 amino acids, about 260 amino acids to about 280 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 450 amino acids, about 280 amino acids to about 400 amino acids, about 280 amino acids to about 350 amino acids, about 280 amino acids to about 300 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1000 amino acids, about 850 amino acids to about 950 amino acids, about 850 amino acids to about 900 amino acids, about 900 amino acids to about 1000 amino acids, about 900 amino acids to about 950 amino acids, or about 950 amino acids to about 1000 amino acids.

Any of the target-binding domains described herein can bind to its target with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the antigen-binding protein construct provided herein can bind to an identifying antigen with a $K_D$ of about $1\times10^{-3}$ M to about $1\times10^{-5}$ M, about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, or about $1\times10^{-9}$ M to about $1\times10^{-11}$ M (inclusive).

Any of the target-binding domains described herein can bind to its target with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 30 nM, about 15 pM to about 25 nM, about 15 pM to about 20 nM, about 15 pM to about 15 nM, about 15 pM to about 10 nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about 15 pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about 15 pM to about 50 pM, about 15 pM to about 40 pM, about 15 pM to about 30 pM, about 15 pM to about 20 pM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about 20 pM to about 60 pM, about 20 pM to about 50 pM, about 20 pM to about 40 pM, about 20 pM to about 30 pM, about 30 pM to about 30 nM, about 30 pM to about 25 nM, about 30 pM to about 30 nM, about 30 pM to about 15 nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about 90 pM, about 30 pM to about 80 pM, about 30 pM to about 70 pM, about 30 pM to about 60 pM, about 30 pM to about 50 pM, about 30 pM to about 40 pM, about 40 pM to about 30 nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about 40 pM to about 50 pM, about 50 pM to about 30 nM, about 50 pM to about 25 nM, about 50 pM to about 30 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about 30 nM, about 60 pM to about 25 nM, about 60 pM to about 30 nM, about 60 pM to about 15 nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about 30 nM, about 70 pM to about 25 nM, about 70 pM to about 30 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 30 nM, about 80 pM to about 25 nM, about 80 pM to about 30 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about 30 nM, about 90 pM to about 25 nM, about 90 pM to about 30 nM, about 90 pM to about 15 nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 30 nM, about 400 pM to about 25 nM, about 400 pM to about 30 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 30 nM, about 500 pM to about 25 nM, about 500 pM to about 30 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 30 nM, about 600 pM to about 25 nM, about 600 pM to about 30 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 30 nM, about 700 pM to about 25 nM, about 700 pM to about 30 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 30 nM, about 800 pM to about 25 nM, about 800 pM to about 30 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 30 nM, about 900 pM to about 25 nM, about 900 pM to about 30 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 30 nM, about 5 nM to about 25 nM, about 5 nM to about 20 nM, about 5 nM to about 15 nM, about 5 nM to about 10 nM, about 10 nM to about 30 nM, about 10 nM to about 25 nM, about 10 nM to about 20 nM, about 10 nM to about 15 nM, about 15 nM to about 30 nM, about 15 nM to about 25 nM, about 15 nM to about 20 nM, about 20 nM to about 30 nM, and about 20 nM to about 25 nM).

Any of the target-binding domains described herein can bind to its target with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the antigen-binding protein constructs described herein (e.g., an electrophoretic mobility shift assay, a filter binding assay, surface plasmon resonance, and a biomolecular binding kinetics assay, etc.).

Antigen-Binding Domains

In some embodiments of any of the multi-chain chimeric polypeptides described herein, the first target-binding domain and the second target-binding domain bind specifically to the same antigen. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of any of the multi-chain chimeric polypeptides described herein, the first target-binding domain and the second target-binding domain bind specifically to different antigens.

In some embodiments of any of the multi-chain chimeric polypeptides described herein, one or both of the first target-binding domain and the second target-binding domain is an antigen-binding domain. In some embodiments of any of the multi-chain chimeric polypeptides described herein, the first target-binding domain and the second target-binding domain are each antigen-binding domains.

In some embodiments of any of the multi-chain chimeric polypeptides described herein, the antigen-binding domain includes or is a scFv or a single domain antibody (e.g., a VHH or a VNAR domain).

In some examples, an antigen-binding domain (e.g., any of the antigen-binding domains described herein) can bind specifically to any one of CD16a (see, e.g., those described in U.S. Pat. No. 9,035,026), CD28 (see, e.g., those described in U.S. Pat. No. 7,723,482), CD3 (see, e.g., those described in U.S. Pat. No. 9,226,962), CD33 (see, e.g., those described in U.S. Pat. No. 8,759,494), CD20 (see, e.g., those described in WO 2014/026054), CD19 (see, e.g., those described in U.S. Pat. No. 9,701,758), CD22 (see, e.g., those described in WO 2003/104425), CD123 (see, e.g., those described in WO 2014/130635), IL-1R (see, e.g., those described in U.S. Pat. No. 8,741,604), IL-1 (see, e.g., those described in WO 2014/095808), VEGF (see, e.g., those described in U.S. Pat. No. 9,090,684), IL-6R (see, e.g., those described in U.S. Pat. No. 7,482,436), IL-4 (see, e.g., those described in U.S. Patent Application Publication No. 2012/0171197), IL-10 (see, e.g., those described in U.S. Patent Application Publication No. 2016/0340413), PDL-1 (see, e.g., those described in Drees et al., *Protein Express. Purif.* 94:60-66, 2014), TIGIT (see, e.g., those described in U.S. Patent Application Publication No. 2017/0198042), PD-1 (see, e.g., those described in U.S. Pat. No. 7,488,802), TIM3 (see, e.g., those described in U.S. Pat. No. 8,552,156), CTLA4 (see, e.g., those described in WO 2012/120125), MICA (see, e.g., those described in WO 2016/154585), MICB (see, e.g., those described in U.S. Pat. No. 8,753,640), IL-6 (see, e.g., those described in Gejima et al., *Human Antibodies* 11(4):121-129, 2002), IL-8 (see, e.g., those described in U.S. Pat. No. 6,117,980), TNFα (see, e.g., those described in Geng et al., *Immunol. Res.* 62(3):377-385, 2015), CD26a (see, e.g., those described in WO 2017/189526), CD36 (see, e.g., those described in U.S. Patent Application Publication No. 2015/0259429), ULBP2 (see, e.g., those described in U.S. Pat. No. 9,273,136), CD30 (see, e.g., those described in Homach et al., *Scand. J. Immunol.* 48(5):497-501, 1998), CD200 (see, e.g., those described in U.S. Pat. No. 9,085,623), IGF-1R (see, e.g., those described in U.S. Patent Application Publication No. 2017/0051063), MUC4AC (see, e.g., those described in WO 2012/170470), MUCSAC (see, e.g., those described in U.S. Pat. No. 9,238,084), Trop-2 (see, e.g., those described in WO 2013/068946), CMET (see, e.g., those described in Edwardraja et al., *Biotechnol. Bioeng.* 106(3):367-375, 2010), EGFR (see, e.g., those described in Akbari et al., *Protein Expr. Purif.* 127:8-15, 2016), HER1 (see, e.g., those described in U.S. Patent Application Publication No. 2013/0274446), HER2 (see, e.g., those described in Cao et al., *Biotechnol. Lett.* 37(7):1347-1354, 2015), HER3 (see, e.g., those described in U.S. Pat. No. 9,505,843), PSMA (see, e.g., those described in Parker et al., *Protein Expr. Purif.* 89(2):136-145, 2013), CEA (see, e.g., those described in WO 1995/015341), B7H3 (see, e.g., those described in U.S. Pat. No. 9,371,395), EPCAM (see, e.g., those described in WO 2014/159531), BCMA (see, e.g., those described in Smith et al., *Mol. Ther.* 26(6):1447-1456, 2018), P-cadherin (see, e.g., those described in U.S. Pat. No. 7,452,537), CEACAM5 (see, e.g., those described in U.S. Pat. No. 9,617,345), a UL16-binding protein (see, e.g., those described in WO 2017/083612), HLA-DR (see, e.g., Pistillo et al., *Exp. Clin. Immunogenet.* 14(2):123-130, 1997), DLL4 (see, e.g., those described in WO 2014/007513), TYRO3 (see, e.g., those described in WO 2016/166348), AXL (see, e.g., those described in WO 2012/175692), MER (see, e.g., those described in WO 2016/106221), CD122 (see, e.g., those described in U.S. Patent Application Publication No. 2016/0367664), CD155 (see, e.g., those described in WO 2017/149538), or PDGF-DD (see, e.g., those described in U.S. Pat. No. 9,441,034).

The antigen-binding domains present in any of the multi-chain chimeric polypeptides described herein are each independently selected from the group consisting of: a VHH domain, a VNAR domain, and a scFv. In some embodiments, any of the antigen-binding domains described herein is a BiTe, a $(scFv)_2$, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the multi-chain chimeric polypeptide are known in the art.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr. Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments, each of the antigen-binding domains in the multi-chain chimeric polypeptides described herein are both VHH domains, or at least one antigen-binding domain is a VHH domain. In some embodiments, each of the antigen-binding domains in the multi-chain chimeric polypeptides described herein are both VNAR domains, or at least one antigen-binding domain is a VNAR domain. In some embodiments, each of the antigen-binding domains in the multi-chain chimeric polypeptides described herein are both scFv domains, or at least one antigen-binding domain is a scFv domain.

In some embodiments, two or more of polypeptides present in the multi-chain chimeric polypeptide can assemble (e.g., non-covalently assemble) to form any of the antigen-binding domains described herein, e.g., an antigen-binding fragment of an antibody (e.g., any of the antigen-binding fragments of an antibody described herein), a VHH-scAb, a VHH-Fab, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, an Intrabody, a dock and lock, a 1 mmTAC, an IgG-IgG conjugate, a Cov-X-Body, and a scFv1-PEG-scFv2. See, e.g., Spiess et al., *Mol. Immunol.* 67:95-106, 2015, incorporated in its entirety herewith, for a description of these elements. Non-limiting examples of an antigen-binding fragment of an antibody include an Fv fragment, a Fab fragment, a F(ab')$_2$ fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG; e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

An "Fv" fragment includes a non-covalently-linked dimer of one heavy chain variable domain and one light chain variable domain.

A "Fab" fragment includes, the constant domain of the light chain and the first constant domain ($C_{H1}$) of the heavy chain, in addition to the heavy and light chain variable domains of the Fv fragment.

A "F(ab')$_2$" fragment includes two Fab fragments joined, near the hinge region, by disulfide bonds.

A "dual variable domain immunoglobulin" or "DVD-Ig" refers to multivalent and multispecific binding proteins as described, e.g., in DiGiammarino et al., *Methods Mol. Biol.* 899:145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

DARTs are described in, e.g., Garber, Nature Reviews Drug Discovery 13:799-801, 2014.

In some embodiments of any of the antigen-binding domains described herein can bind to an antigen selected from the group consisting of: a protein, a carbohydrate, a lipid, and a combination thereof.

Additional examples and aspects of antigen-binding domains are known in the art.

Soluble Interleukin or Cytokine Protein

In some embodiments of any of the multi-chain chimeric polypeptides described herein, one or both of the first target-binding domain and the second target-binding domain can be a soluble interleukin protein or soluble cytokine protein. In some embodiments, the soluble interleukin or soluble cytokine protein is selected from the group of: IL-2, IL-3, IL-7, IL-8, IL-10, IL-12, IL-15, IL-17, IL-18, IL-21, PDGF-DD, SCF, and FLT3L. Non-limiting examples of soluble IL-2, IL-3, IL-7, IL-8, IL-10, IL-15, IL-17, IL-18, IL-21, PDGF-DD, SCF, and FLT3Lare provided below.

```
Human Soluble IL-2
                                          (SEQ ID NO: 9)
aptssstkkt qlqlehllld lqmilnginn yknpkltrml tfkfympkka telkhlqcle eelkpleevl nlaqsknfhl rprdlisnin vivlelkgse ttfmceyade tativeflnr witfcqsiis tlt Human Soluble IL-3
                                          (SEQ ID NO: 10)
apmtqttplkt swvncsnmid eiithlkqpp lplldfnnln gedqdilmen nlrrpnleaf nravkslqna saiesilknl lpclplataa ptrhpihikd gdwnefrrkl tfylktlena qaqqttlsla if Human Soluble IL-7
                                          (SEQ ID NO: 11)
dcdiegkdgkqyesv lmvsidqlld smkeigsncl nnefnffkrh icdankegmf lfraarklrq flkmnstgdf dlhllkvseg ttillnctgq vkgrkpaalg eaqptkslee nkslkeqkkl ndlcflkrll qeiktcwnki lmgtkeh Human Soluble IL-8
                                          (SEQ ID NO: 12)
egavlprsak elrcqcikty skpfhpkfik elrviesgph canteiivkl sdgrelcldp kenwvqrvve kflkraens
```

-continued

Human Soluble IL-10
(SEQ ID NO: 13)
spgqgtqsensc thfpgnlpnm lrdlrdafsr vktffqmkdq ldnlllkesl ledfkgylgc qalsemiqfy leevmpqaen qdpdikahvn slgenlktlr lrlrrchrfl pcenkskave qvknafnklq ekgiykamse fdifinyiea ymtmkirn Human Soluble IL-15
(SEQ ID NO: 14)
Nwvnvisdlkki edliqsmhid atlytesdvh psckvtamkc fllelqvisl esgdasihdt venliilann slssngnvte sgckeceele eknikeflqs fvhivqmfin ts Human Soluble IL-17
(SEQ ID NO: 15)
gitiprn pgcpnsedkn fprtvmvnln ihnrntntnp krssdyynrs tspwnlhrne dperypsviw eakcrhlgci nadgnvdyhm nsvpiqqeil vlrrepphcp nsfrlekilv svgctcvtpi vhhva Human Soluble IL-18
(SEQ ID NO: 16)
yfgklesklsvirn lndqvlfidq gnrplfedmt dsdcrdnapr tifiismykd sqprgmavti svkcekistl scenkiisfk emnppdnikd tksdiiffqr svpghdnkmq fesssyegyf lacekerdlf klilkkedel gdrsimftvq ned Human Soluble PDGF-DD
(SEQ ID NO: 17)
rdtsatpqsasi kalrnanlrr desnhltdly rrdetiqvkg ngyvqsprfp nsyprnlllt wrlhsqentr iqlvfdnqfg leeaendicr ydfvevedis etstiirgrw cghkevppri ksrtnqikit fksddyfvak pgfkiyysll edfqpaaase tnwesvtssi sgvsynspsv tdptliadal dkkiaefdtv edllkyfnpe swqedlenmy ldtpryrgrs yhdrkskvdl drlnddakry sctprnysvn ireelklanv vffprcllvq rcggncgcgt vnwrsctcns gktvkkyhev lqfepghikr rgraktmalv diqldhherc dcicssrppr Human Soluble SCF
(SEQ ID NO: 18)
egicrnrvtnnvkdv tklvanlpkd ymitlkyvpg mdvlpshcwi semvvqlsds ltdlldkfsn iseglsnysi idklvnivdd lvecvkenss kdlkksfksp eprlftpeef frifnrsida fkdfvvaset sdcvvsstls pekdsrvsvt kpfmlppvaa sslrndssss nrkaknppgd sslhwaamal palfsliigf afgalywkkr qpsltraven iqineednei smlqekeref qev Human Soluble FLT3L
(SEQ ID NO: 19)
tqdcsfqhspissd favkirelsd yllqdypvtv asnlqdeelc gglwrlvlaq rwmerlktva gskmqgller vnteihfvtk cafqpppscl rfvqtnisrl lqetseqlva lkpwitrqnf srclelqcqp dsstlpppws prpleatapt apqppllll llpvgllla aawclhwqrt rrrtprpgeq vppvpspqdl llveh Non-limiting examples of soluble MICA, MICB, ULBP1, ULBP2, ULBP3, ULBP4, ULBP5, and ULBP6 are provided below.

```
Human Soluble MICA
                                             (SEQ ID NO: 20)
ephslry nltvlswdgs vqsgfltevh ldgqpflrcd rqkcrakpqg qwaedvlgnk twdretrdlt gngkdlrmtl ahikdqkegl hslqeirvce ihednstrss qhfyydgelf lsqnletkew tmpqssraqt lamnvrnflk edamktkthy hamhadclqe lrrylksgvv lrrtvppmvn vtrseasegn itvtcrasgf ypwnitlswr qdgvslshdt qqwgdvlpdg ngtyqtwvat ricqgeeqrf tcymehsgnh sthpvpsgkv lvlqshwqtf hvsavaaaai fviiifyvrc ckkktsaaeg pelvslqvld qhpvgtsdhr datqlgfqpl msdlgstgst ega Human Soluble MICB
                                             (SEQ ID NO: 21)
aephslry nlmvlsqdes vqsgflaegh ldgqpflryd rqkrrakpqg qwaedvlgak twdtetedlt engqdlrrtl thikdqkggl hslqeirvce ihedsstrgs rhfyydgelf lsqnletqes tvpqssraqt lamnvtnfwk edamktkthy ramqadclqk lqrylksgva irrtvppmvn vtcsevsegn itvtcrassf yprnitltwr qdgvslshnt qqwgdvlpdg ngtyqtwvat rirqgeeqrf tcymehsgnh gthpvpsgkv lvlqsqrtdf pyvsaampcf viiiilcvpc ckkktsaaeg pelvslqvld qhpvgtgdhr daaqlgfqpl msatgstgst ega Human Soluble ULBP1
                                             (SEQ ID NO: 22)
wvdthclcydfiit pksrpepqwc evqglvderp flhydcvnhk akafaslgkk vnvtktweeq tetlrdvvdf lkgqlldiqv enlipieplt lqarmscehe ahghgrgswq flfngqkfll fdsnnrkwta lhpgakkmte kweknrdvtm ffqkislgdc kmwleeflmy weqmldptkp pslapg Human Soluble ULBP2
                                             (SEQ ID NO: 23)
gradphslcyditvi pkfrpgprwc avqgqvdekt flhydcgnkt vtpvsplgkk lnvttawkaq npvlrevvdi lteqlrdiql enytpkeplt lqarmsceqk aeghssgswq fsfdgqifll fdsekrmwtt vhpgarkmke kwendkvvam sfhyfsmgdc igwledflmg mdstlepsag aplams Human Soluble ULBP3
                                             (SEQ ID NO: 24)
dahslwynfti ihlprhgqqw cevqsqvdqk nflsydcgsd kvlsmghlee qlyatdawgk qlemlrevgq rlrleladte ledftpsgpl tlqvrmscec eadgyirgsw qfsfdgrkfl lfdsnnrkwt vvhagarrmk ekwekdsglt tffkmvsmrd ckswlrdflm hrkkrlepta pptmapg Human Soluble ULBP4
                                             (SEQ ID NO: 25)
hslcfnftik slsrpgqpwc eaqvflnknl flqynsdnnm vkplgllgkk vyatstwgel tqtlgevgrd lrmllcdikp qiktsdpstl qvemfcqrea erctgaswqf atngeksllf damnmtwtvi nheaskiket wkkdrgleky
```

-continued

```
frklskgdcd hwlreflghw eampeptvsp vnasdihwss sslpdrwiil gafillvlmg ivlicvwwqn gewqaglwpl rts Human Soluble ULBP5
                                                    (SEQ ID NO: 26)
gladp hslcyditvi pkfrpgprwc avqgqvdekt flhydcgskt vtpvsplgkk lnvttawkaq npvlrevvdi lteqlldiql enyipkeplt lqarmsceqk aeghgsgswq lsfdgqifll fdsenrmwtt vhpgarkmke kwendkdmtm sfhyismgdc tgwledflmg mdstlepsag apptmssg Human Soluble ULBP6
                                                    (SEQ ID NO: 27)
rrddp hslcyditvi pkfrpgprwc avqgqvdekt flhydcgnkt vtpvsplgkk lnvtmawkaq npvlrevvdi lteqlldiql enytpkeplt lqarmsceqk aeghssgswq fsidgqtfll fdsekrmwtt vhpgarkmke kwendkdvam sfhyismgdc igwledflmg mdstlepsag aplamssg
```

Additional examples of soluble interleukin proteins and soluble cytokine proteins are known in the art.

Soluble Receptor

In some embodiments of any of the multi-chain chimeric polypeptides described herein, one or both of the first target-binding domain and the second target-binding domain is a soluble interleukin receptor, a soluble cytokine receptor or a ligand receptor. In some embodiments, the soluble receptor is a soluble TGF-β receptor II (TGF-β RII) (see, e.g., those described in Yung et al., *Am. J. Resp. Crit. Care Med.* 194(9):1140-1151, 2016), a soluble TGF-βRIII (see, e.g., those described in Heng et al., *Placenta* 57:320, 2017), a soluble NKG2D (see, e.g., Cosman et al., *Immunity* 14(2):123-133, 2001; Costa et al., *Front. Immunol.*, Vol. 9, Article 1150, May 29, 2018; doi: 10.3389/fimmu.2018.01150), a soluble NKp30 (see, e.g., Costa et al., *Front. Immunol.*, Vol. 9, Article 1150, May 29, 2018; doi: 10.3389/fimmu.2018.01150), a soluble NKp44 (see, e.g., those described in Costa et al., *Front. Immunol.*, Vol. 9, Article 1150, May 29, 2018; doi: 10.3389/fimmu.2018.01150), a soluble NKp46 (see, e.g., Mandelboim et al., *Nature* 409:1055-1060, 2001; Costa et al., *Front. Immunol.*, Vol. 9, Article 1150, May 29, 2018; doi: 10.3389/fimmu.2018.01150), a soluble DNAM-1 (see, e.g., those described in Costa et al., *Front. Immunol.*, Vol. 9, Article 1150, May 29, 2018; doi: 10.3389/fimmu.2018.01150), a scMHCI (see, e.g., those described in Washburn et al., *PLoS One* 6(3):e18439, 2011), a scMHCII (see, e.g., those described in Bishwajit et al., *Cellular Immunol.* 170(1):25-33, 1996), a scTCR (see, e.g., those described in Weber et al., *Nature* 356(6372):793-796, 1992), a soluble CD155 (see, e.g., those described in Tahara-Hanaoka et al., *Int. Immunol.* 16(4):533-538, 2004), or a soluble CD28 (see, e.g., Hebbar et al., *Clin. Exp. Immunol.* 136:388-392, 2004).

Additional examples of soluble interleukin receptors and soluble cytokine receptors are known in the art.

Additional Antigen-Binding Domains

In some embodiments of any of the multi-chain chimeric polypeptides, the first chimeric polypeptide further includes one or more (e.g., two, three, four, five, six, seven, eight, nine, or ten) additional target-binding domain(s) (e.g., any of the exemplary target-binding domains described herein or known in the art), where at least one of the one or more additional antigen-binding domain(s) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein). In some embodiments, the first chimeric polypeptide can further include a linker sequence (e.g., any of the exemplary linker sequences described herein or known in the art) between the soluble tissue factor domain (e.g., any of the exemplary soluble tissue factor domains described herein) and the at least one of the one or more additional target-binding domain(s) (e.g., any of the exemplary target-binding domains described herein or known in the art), and/or a linker sequence (e.g., any of the exemplary linker sequences described herein or known in the art) between the at least one of the one or more additional target-binding domain(s) (e.g., any of the exemplary target-binding domains described herein or known in the art) and the first domain of the pair of affinity domains (e.g., any of the exemplary first domains described herein of any of the exemplary pairs of affinity domains described herein).

In some embodiments of any of the multi-chain chimeric polypeptides described herein, the first chimeric polypeptide further includes one or more (e.g., two, three, four, five, six, seven, eight, nine, or ten) additional target-binding domains at the N-terminal and/or C-terminal end of the first chimeric polypeptide. In some embodiments, at least one of the one or more additional target-binding domains (e.g., any of the exemplary target-binding domains described herein or known in the art) directly abuts the first domain of the pair of affinity domains (e.g., any of the exemplary first domains described herein of any of the exemplary pairs of affinity domains described herein) in the first chimeric polypeptide. In some embodiments, the first chimeric polypeptide further includes a linker sequence (e.g., any of the exemplary linker sequences described herein or known in the art) between the at least one of the one or more additional target-binding domains (e.g., any of the exemplary target-binding domains described herein or known in the art) and the first domain of the pair of affinity domains (e.g., any of the exemplary first domains described herein of any of the exemplary pairs of affinity domains described herein). In some embodiments, the at least one of the one or more additional target-binding domains (e.g., any of the exemplary target-binding domains described herein or known in the art) directly abuts the first target-binding domain (e.g., any of the exemplary target-binding domains described herein or known in the art) in the first chimeric polypeptide. In some embodiments, the first chimeric polypeptide further comprises a linker sequence (e.g., any of the exemplary linker sequences described herein or known in the art) between the at least one of the one or more additional target-binding domains (e.g., any of the exemplary target-binding domains described herein or known in the art) and the first target-binding domain (e.g., any of the exemplary target-binding domains described herein or known in the art).

In some embodiments of any of the multi-chain chimeric polypeptides described herein, at least one of the one or more additional target-binding domains (e.g., any of the exemplary target-binding domains described herein or known in the art) is disposed at the N- and/or C-terminus of the first chimeric polypeptide, and at least one of the one or more additional target-binding domains (e.g., any of the exemplary target-binding domains described herein or known in the art) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the N-terminus directly abuts the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the first chimeric polypeptide further comprises a linker sequence (e.g., any of the linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the C-terminus directly abuts the first target-binding domain (e.g., any of the exemplary target-binding domains described herein or known in the art) or the first domain of the pair of affinity domains (e.g., any of the exemplary first domains of any of the exemplary pairs of affinity domains described herein) in the first chimeric polypeptide. In some embodiments, the first chimeric polypeptide further includes a linker sequence (e.g., any of the exemplary linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the first domains described herein or any of the exemplary pairs of affinity domains described herein), directly abuts the soluble tissue factor domain and/or the first domain of the pair of affinity domains. In some embodiments, the first chimeric polypeptide further comprises a linker sequence (e.g., any of the exemplary linker sequences described herein or known in the art) disposed (i) between the soluble tissue factor domain (e.g., any of the exemplary soluble tissue factor domains described herein) and the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the exemplary first domains of any of the exemplary pairs of affinity domains described herein), and/or (ii) between the first domain of the pair of affinity domains and the at least one of the one or more additional target-binding domains positioned between the soluble tissue factor domain and the first domain of the pair of affinity domains.

In some embodiments of any of the multi-chain chimeric polypeptides described herein, the second chimeric polypeptide further includes one or more (e.g., two, three, four, five, six, seven, eight, nine, or ten) additional target-binding domains (e.g., any of the exemplary target-binding domains described herein or known in the art) at the N-terminal end and/or the C-terminal end of the second chimeric polypeptide. In some embodiments, at least one of the one or more additional target-binding domains (e.g., any of the exemplary target-binding domains described herein or known in the art) directly abuts the second domain of the pair of affinity domains (e.g., any of the exemplary second domains of any of the exemplary pairs of affinity domains described herein) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target-binding domains described herein or known in the art) and the second domain of the pair of affinity domains (e.g., any of the second domains described herein of any of the exemplary pairs of affinity domains described herein) in the second chimeric polypeptide. In some embodiments, at least one of the one or more additional target-binding domains (e.g., any of the exemplary target-binding domains described herein or known in the art) directly abuts the second target-binding domain (e.g., any of the target-binding domains described herein or known in the art) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target binding domains described herein or known in the art) and the second target-binding domain (e.g., any of the exemplary target binding domains described herein or known in the art) in the second chimeric polypeptide.

In some embodiments of any of the multi-chain chimeric polypeptides described herein, two or more (e.g., three or more, four or more, five or more, six or more, seven or more, eight or more, nine or more, or ten or more) of the first target-binding domain, the second target-binding domain, and the one or more additional target-binding domains bind specifically to the same antigen. In some embodiments, two or more (e.g., three or more, four or more, five or more, six or more, seven or more, eight or more, nine or more, or ten or more) of the first target-binding domain, the second target-binding domain, and the one or more additional target-binding domains bind specifically to the same epitope. In some embodiments, two or more (e.g., three or more, four or more, five or more, six or more, seven or more, eight or more, nine or more, or ten or more) of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence.

In some embodiments of any of the multi-chain chimeric polypeptides described herein, the first target-binding domain, the second target-binding domain, and the one or more additional target-binding domains bind specifically to different antigens. In some embodiments of any of the multi-chain chimeric polypeptides described herein, one or more (e.g., two or more, three or more, four or more, five or more, six or more, seven or more, eight or more, nine or more, or ten or more) of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain (e.g., a scFv or a single-domain antibody).

Pairs of Affinity Domains

In some embodiments, a multi-chain chimeric polypeptide includes: 1) a first chimeric polypeptide that includes a first domain of a pair of affinity domains, and 2) a second chimeric polypeptide that includes a second domain of a pair of affinity domains such that the first chimeric polypeptide and the second chimeric polypeptide associate through the binding of the first domain and the second domain of the pair of affinity domains. In some embodiments, the pair of affinity domains is a sushi domain from an alpha chain of human IL-15 receptor (IL15Rα) and a soluble IL-15. A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and β2-glycoprotein. A typical Sushi domain has approximately 60 amino acid residues and contains four cysteines (Ranganathan, Pac. Symp Biocomput. 2000:155-67). The first cysteine can form a disulfide bond with the third cysteine, and the second cysteine can form a disulfide bridge with the fourth cysteine. In some embodiments in which one member of the pair of affinity domains is a soluble IL-15, the soluble IL15 has a D8N or D8A amino acid substitution. In some embodiments in which one member of the pair of affinity domains is an alpha chain of human IL-15 receptor (IL15Rα), the human IL15Rα is a mature full-length IL15Rα. In some embodiments, the pair of affinity domains is barnase and barnstar. In some embodiments, the pair of affinity domains is a PKA and an AKAP. In some embodiments, the pair of affinity domains is an adapter/docking tag module based on mutated RNase I fragments (Rossi, *Proc Natl Acad Sci USA*. 103: 6841-6846, 2006; Sharkey et al., *Cancer Res*. 68:5282-5290, 2008; Rossi et al., *Trends Pharmacol Sci*. 33:474-481, 2012) or SNARE modules based on interactions of the proteins syntaxin, synaptotagmin, synaptobrevin, and SNAP25 (Deyev et al., *Nat Biotechnol*. 1486-1492, 2003).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains and the second domain of the pair of affinity domains bind to each other with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the first domain of the pair of affinity domains and the second domain of the pair of affinity domains bind to each other with a $K_D$ of about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, about $1\times10^{-9}$ M to about $1\times10^{-11}$ M, about $1\times10^{-10}$ M to about $1\times10^{-12}$ M, about $1\times10^{-11}$ M to about $1\times10^{-13}$ M, about $1\times10^{-4}$ M to about $1\times10^{-5}$ M, about $1\times10^{-5}$ M to about $1\times10^{-6}$ M, about $1\times10^{-6}$ M to about $1\times10^{-7}$ M, about $1\times10^{-7}$ M to about $1\times10^{-8}$ M, about $1\times10^{-8}$ M to about $1\times10^{-9}$ M, about $1\times10^{-9}$ M to about $1\times10^{-10}$ M, about $1\times10^{-10}$ M to about $1\times10^{-11}$ M, about $1\times10^{-11}$ M to about $1\times10^{-12}$ M, or about $1\times10^{-12}$ M to about $1\times10^{-13}$ M (inclusive). Any of a variety of different methods known in the art can be used to determine the $K_D$ value of the binding of the first domain of the pair of affinity domains and the second domain of the pair of affinity domains (e.g., an electrophoretic mobility shift assay, a filter binding assay, surface plasmon resonance, and a biomolecular binding kinetics assay, etc.).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains, the second domain of the pair of affinity domains, or both is about 10 to 100 amino acids in length. For example, a first domain of a pair of affinity domains, a second domain of a pair of affinity domains, or both can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a first domain of a pair of affinity domains, a second domain of a pair of affinity domains, or both is about 10, 15, 20, 25, 30, 35, 40, 45, 50, 55, 60, 65, 70, 75, 80, 85, 90, 95, or 100 amino acids in length.

In some embodiments, any of the first and/or second domains of a pair of affinity domains disclosed herein can include one or more additional amino acids (e.g., 1, 2, 3, 5, 6, 7, 8, 9, 10, or more amino acids) at its N-terminus and/or C-terminus, so long as the function of the first and/or second domains of a pair of affinity domains remains intact. For example, a sushi domain from an alpha chain of human IL-15 receptor (IL15Rα) can include one or more additional amino acids at the N-terminus and/or the C-terminus, while still retaining the ability to bind to a soluble IL-15. Additionally or alternatively, a soluble IL-15 can include one or more additional amino acids at the N-terminus and/or the C-terminus, while still retaining the ability to bind to a sushi domain from an alpha chain of human IL-15 receptor (IL15Rα).

A non-limiting example of a sushi domain from an alpha chain of IL-15 receptor alpha (IL15Rα) can include a sequence that is at least 70% identical, at least 75% identical, at least 80% identical, at least 85% identical, at least 90% identical, at least 95% identical, at least 99% identical, or 100% identical to ITCPPPMSVEHADIWVKSYSLYSR-ERYICNSGFKRKAGTSSLTECVLNKATNVAH WTTPSLKCIR (SEQ ID NO: 28). In some embodiments, a sushi domain from an alpha chain of IL15Rα can be encoded by a nucleic acid including (SEQ ID NO: 29)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG.

In some embodiments, a soluble IL-15 can include a sequence that is at least 70% identical, at least 75% identical, at least 80% identical, at least 85% identical, at least 90% identical, at least 95% identical, at least 99% identical, or 100% identical to NWVNVISDLKKIEDLIQSMHIDAT-LYTESDVHPSCKVTAMKCFLLELQVISLESGD ASIHDTVENLIILANNSLSSNGNVTESGCKE-CEELEEKNIKEFLQSFVHIVQMFINT S (SEQ ID NO: 14). In some embodiments, a soluble IL-15 can be encoded by a nucleic acid including the sequence of (SEQ ID NO: 30)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC.

Signal Sequence

In some embodiments, a multi-chain chimeric polypeptide includes a first chimeric polypeptide that includes a signal sequence at its N-terminal end. In some embodiments, a multi-chain chimeric polypeptide includes a second chimeric polypeptide that includes a signal sequence at its N-terminal end. In some embodiments, both the first chimeric polypeptide of a multi-chain chimeric polypeptide and a second chimeric polypeptide of the multi-chain chimeric polypeptide include a signal sequence. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a first chimeric polypeptide of a multi-chain chimeric polypeptide, a second chimeric polypeptide of the multi-chain chimeric polypeptide, or both includes a signal sequence having an amino acid sequence MKWVTFISLLFLFSSAYS (SEQ ID NO: 31). In some embodiments, a first chimeric polypeptide of a multi-chain chimeric polypeptide, a second chimeric polypeptide of the multi-chain chimeric polypeptide, or both includes a signal sequence encoded by the nucleic acid sequence (SEQ ID NO: 32)
ATGAAATGGGTGACCTTTATTTCTTTACTGTTCCTCTTTAGCAGCGCCTA

CTCC, (SEQ ID NO: 33)
ATGAAGTGGGTCACATTTATCTCTTTACTGTTCCTCTTCTCCAGCGCCTA

CAGC,
or (SEQ ID NO: 34)
ATGAAATGGGTGACCTTTATTTCTTTACTGTTCCTCTTTAGCAGCGCCTA

CTCC.

In some embodiments, a first chimeric polypeptide of a multi-chain chimeric polypeptide, a second chimeric polypeptide of the multi-chain chimeric polypeptide, or both includes a signal sequence having an amino acid sequence MKCLLYLAFLFLGVNC (SEQ ID NO: 35). In some embodiments, a first chimeric polypeptide of a multi-chain chimeric polypeptide, a second chimeric polypeptide of the multi-chain chimeric polypeptide, or both includes a signal sequence having an amino acid sequence MGQIVTIVIFE-ALPHIIDEVINMIVLIIITSIKAVYNFATCGILALVSFL-FLAGRSCG (SEQ ID NO: 36). In some embodiments, a first chimeric polypeptide of a multi-chain chimeric polypeptide, a second chimeric polypeptide of the multi-chain chimeric polypeptide, or both includes a signal sequence having an amino acid sequence MPNHQSGSPTGSSDLLLSGKKQRPHLALRRKRRRE-MRKINRKVRRMNLAPIKEK TAWQHLQALISE-AEEVLKTSQTPQNSLTLFLALLSVLGPPVTG (SEQ ID NO: 37). In some embodiments, a first chimeric polypeptide of a multi-chain chimeric polypeptide, a second chimeric polypeptide of the multi-chain chimeric polypeptide, or both includes a signal sequence having an amino acid sequence MDSKGSSQKGSRLLLLLVVSNLLLCQGVVS (SEQ ID NO: 38). Those of ordinary skill in the art will be aware of other appropriate signal sequences for use in a first chimeric polypeptide and/or a second chimeric polypeptide of multi-chain chimeric polypeptides described herein.

In some embodiments, a first chimeric polypeptide of a multi-chain chimeric polypeptide, a second chimeric polypeptide of the multi-chain chimeric polypeptide, or both includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKCLLY-LAFLFLGVNC (SEQ ID NO: 35) can include one or more additional amino acids at the N-terminus or C-terminus, while still retaining the ability to direct a first chimeric polypeptide of a multi-chain chimeric polypeptide, a second chimeric polypeptide of the multi-chain chimeric polypeptide, or both to the secretory pathway.

In some embodiments, a first chimeric polypeptide of a multi-chain chimeric polypeptide, a second chimeric polypeptide of the multi-chain chimeric polypeptide, or both includes a signal sequence that directs the multi-chain chimeric polypeptide into the extracellular space. Such embodiments are useful in producing multi-chain chimeric polypeptides that are relatively easy to be isolated and/or purified.

Peptide Tags

In some embodiments, a multi-chain chimeric polypeptide includes a first chimeric polypeptide that includes a peptide tag (e.g., at the N-terminal end or the C-terminal end of the first chimeric polypeptide). In some embodiments, a multi-chain chimeric polypeptide includes a second chimeric polypeptide that includes a peptide tag (e.g., at the N-terminal end or the C-terminal end of the second chimeric polypeptide). In some embodiments, both the first chimeric polypeptide of a multi-chain chimeric polypeptide and a second chimeric polypeptide of the multi-chain chimeric polypeptide include a peptide tag. In some embodiments, a first chimeric polypeptide of a multi-chain chimeric polypeptide, a second chimeric polypeptide of the multi-chain chimeric polypeptide, or both include two or more peptide tags.

Exemplary peptide tags that can be included in a first chimeric polypeptide of a multi-chain chimeric polypeptide, a second chimeric polypeptide of the multi-chain chimeric polypeptide, or both include, without limitation, AviTag (GLNDIFEAQKIEWHE; SEQ ID NO: 39), a calmodulin-tag (KRRWKKNFIAVSAANRFKKISSSGAL; SEQ ID NO: 40), a polyglutamate tag (EEEEEE; SEQ ID NO: 41), an E-tag (GAPVPYPDPLEPR; SEQ ID NO: 42), a FLAG-tag (DYKDDDDK; SEQ ID NO: 43), an HA-tag, a peptide from hemagglutinin (YPYDVPDYA; SEQ ID NO: 44), a his-tag (HHHHH (SEQ ID NO: 45); HHHHHH (SEQ ID NO: 46); HHHHHHH (SEQ ID NO: 47); HHHHHHHH (SEQ ID NO: 48); HHHHHHHHH (SEQ ID NO: 49); or HHHHHHHHHH (SEQ ID NO: 50)), a myc-tag (EQKLISEEDL; SEQ ID NO: 51), NE-tag (TKENPRSNQEESYDDNES; SEQ ID NO: 52), S-tag, (KETAAAKFERQHMDS; SEQ ID NO: 53), SBP-tag (MDEKTTGWRGGHVVEGLAGELEQLRAR-LEHHPQGQREP; SEQ ID NO: 54), Softag 1 (SLAEL-LNAGLGGS; SEQ ID NO: 55), Softag 3 (TQDPSRVG; SEQ ID NO: 56), Spot-tag (PDRVRAVSHWSS; SEQ ID NO: 57), Strep-tag (WSHPQFEK; SEQ ID NO: 58), TC tag (CCPGCC; SEQ ID NO: 59), Ty tag (EVHTNQDPLD; SEQ ID NO: 60), V5 tag (GKPIPNPLLGLDST; SEQ ID NO: 61), VSV-tag (YTDIEMNRLGK; SEQ ID NO: 62), and Xpress tag (DLYDDDDK; SEQ ID NO: 63). In some embodiments, tissue factor protein is a peptide tag.

Peptide tags that can be included in a first chimeric polypeptide of a multi-chain chimeric polypeptide, a second chimeric polypeptide of the multi-chain chimeric polypeptide, or both can be used in any of a variety of applications related to the multi-chain chimeric polypeptide. For example, a peptide tag can be used in the purification of a multi-chain chimeric polypeptide. As one non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a myc tag; the multi-chain chimeric polypeptide that includes the myc-tagged first chimeric polypeptide, the myc-tagged second chimeric polypeptide, or both can be purified using an antibody that recognizes the myc tag(s). One non-limiting example of an antibody that recognizes a myc tag is 9E10, available from the non-commercial Developmental Studies Hybridoma Bank. As another non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a histidine tag; the multi-chain chimeric polypeptide that includes the histidine-tagged first chimeric polypeptide, the histidine-tagged second chimeric polypeptide, or both can be purified using a nickel or cobalt chelate. Those of ordinary skill in the art will be aware of other suitable tags and agent that bind those tags for use in purifying multi-chain chimeric polypeptide. In some embodiments, a peptide tag is removed from the first chimeric polypeptide and/or the second chimeric polypeptide of the multi-chain chimeric polypeptide after purification. In some embodiments, a peptide tag is not removed from the first chimeric polypeptide and/or the second chimeric polypeptide of the multi-chain chimeric polypeptide after purification.

Peptide tags that can be included in a first chimeric polypeptide of a multi-chain chimeric polypeptide, a second chimeric polypeptide of the multi-chain chimeric polypeptide, or both can be used, for example, in immunoprecipitation of the multi-chain chimeric polypeptide, imaging of the multi-chain chimeric polypeptide (e.g., via Western blotting, ELISA, flow cytometry, and/or immunocytochemistry), and/or solubilization of the multi-chain chimeric polypeptide.

In some embodiments, a first chimeric polypeptide of a multi-chain chimeric polypeptide, a second chimeric polypeptide of the multi-chain chimeric polypeptide, or both includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a first chimeric polypeptide of a multi-chain chimeric polypeptide, a second chimeric polypeptide of the multi-chain chimeric polypeptide, or both can be of any suitable length. For example, peptide tags can be 5, 6, 7, 8, 9, 10, 11, 12, 13, 14, 15, 16, 17, 18, 19, 20, or more amino acids in length. In embodiments in which a multi-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 64) can include one or more additional amino acids (e.g., at the N-terminus and/or the C-terminus of the peptide tag), while still retaining the ability to be bound by an antibody (e.g., 9E10).

Exemplary Multi-Chain Chimeric Polypeptides—Type A

In some embodiments of any of the multi-chain chimeric polypeptides described herein, the first target-binding domain and the second targeting-binding domain each independently bind specifically to a receptor of IL-18 or a receptor of IL-12. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is an agonistic antigen-binding domain. In some embodiments of these multi-chain chimeric polypeptides, the first target-binding domain and the second target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 16)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNED.

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 65)
TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA

CCGACTCCGATTGCCGGGACAATGCCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGAT.

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-12β (p40) and a sequence of soluble human IL-12α (p35). In some embodiments of these multi-chain chimeric polypeptides, the soluble IL-15 human IL-15 further includes a linker sequence (e.g., any of the exemplary linker sequences described herein) between the sequence of soluble IL-12β (p40) and the sequence of soluble human IL-12α (p35). In some examples of these multi-chain chimeric polypeptides, the linker sequence comprises GGGGSGGGGSGGGGS (SEQ ID NO: 7).

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 66)
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS.

In some embodiments of these multi-chain chimeric polypeptides, the soluble human IL-12β (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 67)
ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA

AAGACCCTCACAATCCAAGTTAAGGAGTTCGGAGACGCTGGCCAATACAC

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC

GCTACCCTCAGCGCTGAGAGGGTTCGTGGCGATAACAAGGAATACGAGTA

CAGCGTGGAGTGCCAAGAAGATAGCGCTTGTCCCGCTGCCGAAGAATCTT

TACCCATTGAGGTGATGGTGGACGCCGTGCACAAACTCAAGTACGAGAAC

TACACCTCCTCCTTCTTTATCCGGGACATCATTAAGCCCGATCCTCCTAA

GAATTTACAGCTGAAGCCTCTCAAAAATAGCCGGCAAGTTGAGGTCTCTT

GGGAATATCCCGACACTTGGAGCACACCCCACAGCTACTTCTCTTTAACC

TTTTGTGTGCAAGTTCAAGGTAAAAGCAAGCGGGAGAAGAAAGACCGGGT

GTTTACCGACAAAACCAGCGCCACCGTCATCTGTCGGAAGAACGCCTCCA

TCAGCGTGAGGGCTCAAGATCGTTATTACTCCAGCAGCTGGTCCGAGTGG

GCCAGCGTGCCTTGTTCC.

In some embodiments of these multi-chain chimeric polypeptides, the soluble human IL-12α (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 68)
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

-continued

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS.

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 69)
CGTAACCTCCCCGTGGCTACCCCCGATCCCGGAATGTTCCCTTGTTTACA

CCACAGCCAGAATTTACTGAGGGCCGTGAGCAACATGCTGCAGAAAGCTA

GGCAGACTTTAGAATTTTACCCTTGCACCAGCGAGGAGATCGACCATGAA

GATATCACCAAGGACAAGACATCCACCGTGGAGGCTTGTTTACCTCTGGA

GCTGACAAAGAACGAGTCTTGTCTCAACTCTCGTGAAACCAGCTTCATCA

CAAATGGCTCTTGTTTAGCTTCCCGGAAGACCTCCTTTATGATGGCTTTA

TGCCTCAGCTCCATCTACGAGGATTTAAAGATGTACCAAGTGGAGTTCAA

GACCATGAACGCCAAGCTGCTCATGGACCCTAAACGGCAGATCTTTTTAG

ACCAGAACATGCTGGCTGTGATTGATGAGCTGATGCAAGCTTTAAACTTC

AACTCCGAGACCGTCCCTCAGAAGTCCTCCCTCGAGGAGCCCGATTTTTA

CAAGACAAAGATCAAACTGTGCATTTTACTCCACGCCTTTAGGATCCGGG

CCGTGACCATTGACCGGGTCATGAGCTATTTAAACGCCAGC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 70)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNEDSGTTNTVAAYNLTWKSTNFKTILEWEPKPVNQVYTVQISTKSG

DWKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLSL

RDVFGKDLIYTLYYWKSSSSGKKTAKTNTNEFLIDVDKGENYCFSVQAVI

PSRTVNRKSTDSPVECMGQEKGEFRENWVNVISDLKKIEDLIQSMHIDAT

LYTESDVHPSCKVTAMKCFLLELQVISLESGDASIHDTVENLIILANNSL

SSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 71)
TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA

CCGACTCCGATTGCCGGGACAATGCCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGATAGCGGCACAACCAACACAGTCGCTGCCTA

TAACCTCACTTGGAAGAGCACCAACTTCAAAACCATCCTCGAATGGGAAC

CCAAACCCGTTAACCAAGTTTACACCGTGCAGATCAGCACCAAGTCCGGC

GACTGGAAGTCCAAATGTTTCTATACCACCGACACCGAGTGCGATCTCAC

CGATGAGATCGTGAAAGATGTGAAACAGACCTACCTCGCCCGGGTGTTTA

GCTACCCCGCCGGCAATGTGGAGAGCACTGGTTCCGCTGGCGAGCCTTTA

TACGAGAACAGCCCCGAATTTACCCCTTACCTCGAGACCAATTTAGGACA

GCCCACCATCCAAAGCTTTGAGCAAGTTGGCACAAAGGTGAATGTGACAG

TGGAGGACGAGCGGACTTTAGTGCGGCGGAACAACACCTTTCTCAGCCTC

CGGGATGTGTTCGGCAAAGATTTAATCTACACACTGTATTACTGGAAGTC

CTCTTCCTCCGGCAAGAAGACAGCTAAAACCAACACAAACGAGTTTTTAA

TCGACGTGGATAAAGGCGAAAACTACTGTTTCAGCGTGCAAGCTGTGATC

CCCTCCCGGACCGTGAATAGGAAAAGCACCGATAGCCCCGTTGAGTGCAT

GGGCCAAGAAAAGGGCGAGTTCCGGGAGAACTGGGTGAACGTCATCAGCG

ATTTAAAGAAGATCGAAGATTTAATTCAGTCCATGCATATCGACGCCACT

TTATACACAGAATCCGACGTGCACCCCTCTTGTAAGGTGACCGCCATGAA

ATGTTTTTTACTGGAGCTGCAAGTTATCTCTTTAGAGAGCGGAGACGCTA

GCATCCACGACACCGTGGAGAATTTAATCATTTTAGCCAATAACTCTTTA

TCCAGCAACGGCAACGTGACAGAGTCCGGCTGCAAGGAGTGCGAAGAGCT

GGAGGAGAAGAACATCAAGGAGTTTCTGCAATCCTTTGTGCACATTGTCC

AGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 72)
MKWVTFISLLFLFSSAYSYFGKLESKLSVIRNLNDQVLFIDQGNRPLFED

MTDSDCRDNAPRTIFIISMYKDSQPRGMAVTISVKCEKISTLSCENKIIS

FKEMNPPDNIKDTKSDIIFFQRSVPGHDNKMQFESSSYEGYFLACEKERD

LFKLILKKEDELGDRSIMFTVQNEDSGTTNTVAAYNLTWKSTNFKTILEW

EPKPVNQVYTVQISTKSGDWKSKCFYTTDTECDLTDEIVKDVKQTYLARV

FSYPAGNVESTGSAGEPLYENSPEFTPYLETNLGQPTIQSFEQVGTKVNV

TVEDERTLVRRNNTFLSLRDVFGKDLIYTLYYWKSSSSGKKTAKTNTNEF

LIDVDKGENYCFSVQAVIPSRTVNRKSTDSPVECMGQEKGEFRENWVNVI

SDLKKIEDLIQSMHIDATLYTESDVHPSCKVTAMKCFLLELQVISLESGD

ASIHDTVENLIILANNSLSSNGNVTESGCKECEELEEKNIKEFLQSFVHI

VQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 73)
ATGAAGTGGGTCACATTTATCTCTTTACTGTTCCTCTTCTCCAGCGCCTA

CAGCTACTTCGGCAAACTGGAATCCAAGCTGAGCGTGATCCGGAATTTAA

ACGACCAAGTTCTGTTTATCGATCAAGGTAACCGGCCTCTGTTCGAGGAC

ATGACCGACTCCGATTGCCGGGACAATGCCCCCCGGACCATCTTCATTAT

CTCCATGTACAAGGACAGCCAGCCCCGGGGCATGGCTGTGACAATTAGCG

TGAAGTGTGAGAAAATCAGCACTTTATCTTGTGAGAACAAGATCATCTCC

TTTAAGGAAATGAACCCCCCCGATAACATCAAGGACACCAAGTCCGATAT

CATCTTCTTCCAGCGGTCCGTGCCCGGTCACGATAACAAGATGCAGTTCG

AATCCTCCTCCTACGAGGGCTACTTTTTAGCTTGTGAAAAGGAGAGGGAT

TTATTCAAGCTGATCCTCAAGAAGGAGGACGAGCTGGGCGATCGTTCCAT

CATGTTCACCGTCCAAAACGAGGATAGCGGCACAACCAACACAGTCGCTG

CCTATAACCTCACTTGGAAGAGCACCAACTTCAAAACCATCCTCGAATGG

GAACCCAAACCCGTTAACCAAGTTTACACCGTGCAGATCAGCACCAAGTC

CGGCGACTGGAAGTCCAAATGTTTCTATACCACCGACACCGAGTGCGATC

TCACCGATGAGATCGTGAAAGATGTGAAACAGACCTACCTCGCCCGGGTG

TTTAGCTACCCCGCCGGCAATGTGGAGAGCACTGGTTCCGCTGGCGAGCC

TTTATACGAGAACAGCCCCGAATTTACCCCTTACCTCGAGACCAATTTAG

GACAGCCCACCATCCAAAGCTTTGAGCAAGTTGGCACAAAGGTGAATGTG

ACAGTGGAGGACGAGCGGACTTTAGTGCGGCGGAACAACACCTTTCTCAG

CCTCCGGGATGTGTTCGGCAAAGATTTAATCTACACACTGTATTACTGGA

AGTCCTCTTCCTCCGGCAAGAAGACAGCTAAAACCAACACAAACGAGTTT

TTAATCGACGTGGATAAAGGCGAAAACTACTGTTTCAGCGTGCAAGCTGT

GATCCCCTCCCGGACCGTGAATAGGAAAAGCACCGATAGCCCCGTTGAGT

GCATGGGCCAAGAAAAGGGCGAGTTCCGGGAGAACTGGGTGAACGTCATC

AGCGATTTAAAGAAGATCGAAGATTTAATTCAGTCCATGCATATCGACGC

CACTTTATACACAGAATCCGACGTGCACCCCTCTTGTAAGGTGACCGCCA

TGAAATGTTTTTTACTGGAGCTGCAAGTTATCTCTTTAGAGAGCGGAGAC

GCTAGCATCCACGACACCGTGGAGAATTTAATCATTTTAGCCAATAACTC

TTTATCCAGCAACGGCAACGTGACAGAGTCCGGCTGCAAGGAGTGCGAAG

AGCTGGAGGAGAAGAACATCAAGGAGTTTCTGCAATCCTTTGTGCACATT

GTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 74)
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCSGGGGSGGGGSGGGGSRNLPVATPDPGMFPCLHHSQNLLRAVSNM

LQKARQTLEFYPCTSEEIDHEDITKDKTSTVEACLPLELTKNESCLNSRE

TSFITNGSCLASRKTSFMMALCLSSIYEDLKMYQVEFKTMNAKLLMDPKR

QIFLDQNMLAVIDELMQALNFNSETVPQKSSLEEPDFYKTKIKLCILLHA

FRIRAVTIDRVMSYLNASITCPPPMSVEHADIWVKSYSLYSRERYICNSG

FKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 75)
ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA

AAGACCCTCACAATCCAAGTTAAGGAGTTCGGAGACGCTGGCCAATACAC

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC

GCTACCCTCAGCGCTGAGAGGGTTCGTGGCGATAACAAGGAATACGAGTA

CAGCGTGGAGTGCCAAGAAGATAGCGCTTGTCCCGCTGCCGAAGAATCTT

TACCCATTGAGGTGATGGTGGACGCCGTGCACAAACTCAAGTACGAGAAC

TACACCTCCTCCTTCTTTATCCGGGACATCATTAAGCCCGATCCTCCTAA

GAATTTACAGCTGAAGCCTCTCAAAAATAGCCGGCAAGTTGAGGTCTCTT

GGGAATATCCCGACACTTGGAGCACACCCCACAGCTACTTCTCTTTAACC

TTTTGTGTGCAAGTTCAAGGTAAAAGCAAGCGGGAGAAGAAAGACCGGGT

GTTTACCGACAAAACCAGCGCCACCGTCATCTGTCGGAAGAACGCCTCCA

TCAGCGTGAGGGCTCAAGATCGTTATTACTCCAGCAGCTGGTCCGAGTGG

GCCAGCGTGCCTTGTTCCGGCGGTGGAGGATCCGGAGGAGGTGGCTCCGG

CGGCGGAGGATCTCGTAACCTCCCCGTGGCTACCCCCGATCCCGGAATGT

TCCCTTGTTTACACCACAGCCAGAATTTACTGAGGGCCGTGAGCAACATG

CTGCAGAAAGCTAGGCAGACTTTAGAATTTTACCCTTGCACCAGCGAGGA

GATCGACCATGAAGATATCACCAAGGACAAGACATCCACCGTGGAGGCTT

GTTTACCTCTGGAGCTGACAAAGAACGAGTCTTGTCTCAACTCTCGTGAA

ACCAGCTTCATCACAAATGGCTCTTGTTTAGCTTCCCGGAAGACCTCCTT

TATGATGGCTTTATGCCTCAGCTCCATCTACGAGGATTTAAAGATGTACC

AAGTGGAGTTCAAGACCATGAACGCCAAGCTGCTCATGGACCCTAAACGG

CAGATCTTTTTAGACCAGAACATGCTGGCTGTGATTGATGAGCTGATGCA

AGCTTTAAACTTCAACTCCGAGACCGTCCCTCAGAAGTCCTCCCTCGAGG

AGCCCGATTTTTACAAGACAAAGATCAAACTGTGCATTTTACTCCACGCC

TTTAGGATCCGGGCCGTGACCATTGACCGGGTCATGAGCTATTTAAACGC

CAGCATTACATGCCCCCCTCCCATGAGCGTGGAGCACGCCGACATCTGGG

TGAAGAGCTATAGCCTCTACAGCCGGGAGAGGTATATCTGTAACAGCGGC

TTCAAGAGGAAGGCCGGCACCAGCAGCCTCACCGAGTGCGTGCTGAATAA

GGCTACCAACGTGGCTCACTGGACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 76)
MKWVTFISLLFLFSSAYSIWELKKDVYVVELDWYPDAPGEMVVLTCDTPE

EDGITWTLDQSSEVLGSGKTLTIQVKEFGDAGQYTCHKGGEVLSHSLLLL

HKKEDGIWSTDILKDQKEPKNKTFLRCEAKNYSGRFTCWWLTTISTDLTF

SVKSSRGSSDPQGVTCGAATLSAERVRGDNKEYEYSVECQEDSACPAAEE

SLPIEVMVDAVHKLKYENYTSSFFIRDIIKPDPPKNLQLKPLKNSRQVEV

SWEYPDTWSTPHSYFSLTFCVQVQGKSKREKKDRVFTDKTSATVICRKNA

SISVRAQDRYYSSSWSEWASVPCSGGGSGGGGSGGGGSRNLPVATPDPG

MFPCLHHSQNLLRAVSNMLQKARQTLEFYPCTSEEIDHEDITKDKTSTVE

ACLPLELTKNESCLNSRETSFITNGSCLASRKTSFMMALCLSSIYEDLKM

YQVEFKTMNAKLLMDPKRQIFLDQNMLAVIDELMQALNFNSETVPQKSSL

EEPDFYKTKIKLCILLHAFRIRAVTIDRVMSYLNASITCPPPMSVEHADI

WVKSYSLYSRERYICNSGFKRKAGTSSLTECVLNKATNVAHWTTPSLKCI

R.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 77)
ATGAAATGGGTGACCTTTATTTCTTTACTGTTCCTCTTTAGCAGCGCCTA

CTCCATTTGGGAACTGAAGAAGGACGTCTACGTGGTCGAACTGGACTGGT

ATCCCGATGCTCCCGGCGAAATGGTGGTGCTCACTTGTGACACCCCCGAA

GAAGACGGCATCACTTGGACCCTCGATCAGAGCAGCGAGGTGCTGGGCTC

CGGAAAGACCCTCACAATCCAAGTTAAGGAGTTCGGAGACGCTGGCCAAT

ACACATGCCACAAGGGAGGCGAGGTGCTCAGCCATTCCTTATTATTATTA

CACAAGAAGGAAGACGGAATCTGGTCCACCGACATTTTAAAAGATCAGAA

GGAGCCCAAGAATAAGACCTTTTTAAGGTGTGAGGCCAAAAACTACAGCG

GTCGTTTCACTTGTTGGTGGCTGACCACCATTTCCACCGATTTAACCTTC

TCCGTGAAAAGCAGCCGGGGAAGCTCCGACCCTCAAGGTGTGACATGTGG

AGCCGCTACCCTCAGCGCTGAGAGGGTTCGTGGCGATAACAAGGAATACG

AGTACAGCGTGGAGTGCCAAGAAGATAGCGCTTGTCCCGCTGCCGAAGAA

TCTTTACCCATTGAGGTGATGGTGGACGCCGTGCACAAACTCAAGTACGA

GAACTACACCTCCTCCTTCTTTATCCGGGACATCATTAAGCCCGATCCTC

CTAAGAATTTACAGCTGAAGCCTCTCAAAAATAGCCGGCAAGTTGAGGTC

TCTTGGGAATATCCCGACACTTGGAGCACACCCCACAGCTACTTCTCTTT

AACCTTTTGTGTGCAAGTTCAAGGTAAAAGCAAGCGGGAGAAGAAAGACC

GGGTGTTTACCGACAAAACCAGCGCCACCGTCATCTGTCGGAAGAACGCC

TCCATCAGCGTGAGGGCTCAAGATCGTTATTACTCCAGCAGCTGGTCCGA

GTGGGCCAGCGTGCCTTGTTCCGGCGGTGGAGGATCCGGAGGAGGTGGCT

CCGGCGGCGGAGGATCTCGTAACCTCCCCGTGGCTACCCCCGATCCCGGA

ATGTTCCCTTGTTTACACCACAGCCAGAATTTACTGAGGGCCGTGAGCAA

CATGCTGCAGAAAGCTAGGCAGACTTTAGAATTTTACCCTTGCACCAGCG

AGGAGATCGACCATGAAGATATCACCAAGGACAAGACATCCACCGTGGAG

GCTTGTTTACCTCTGGAGCTGACAAAGAACGAGTCTTGTCTCAACTCTCG

TGAAACCAGCTTCATCACAAATGGCTCTTGTTTAGCTTCCCGGAAGACCT

CCTTTATGATGGCTTTATGCCTCAGCTCCATCTACGAGGATTTAAAGATG

TACCAAGTGGAGTTCAAGACCATGAACGCCAAGCTGCTCATGGACCCTAA

ACGGCAGATCTTTTTAGACCAGAACATGCTGGCTGTGATTGATGAGCTGA

TGCAAGCTTTAAACTTCAACTCCGAGACCGTCCCTCAGAAGTCCTCCCTC

GAGGAGCCCGATTTTTACAAGACAAAGATCAAACTGTGCATTTTACTCCA

CGCCTTTAGGATCCGGGCCGTGACCATTGACCGGGTCATGAGCTATTTAA

-continued

```
ACGCCAGCATTACATGCCCCCCTCCCATGAGCGTGGAGCACGCCGACATC

TGGGTGAAGAGCTATAGCCTCTACAGCCGGGAGAGGTATATCTGTAACAG

CGGCTTCAAGAGGAAGGCCGGCACCAGCAGCCTCACCGAGTGCGTGCTGA

ATAAGGCTACCAACGTGGCTCACTGGACAACACCCTCTTTAAAGTGCATC

CGG.
```

Exemplary Multi-Chain Chimeric Polypeptides—Type B

In some embodiments of any of the multi-chain chimeric polypeptides described herein, the first target-binding domain and the second targeting-binding domain each independently bind specifically to a receptor of IL-21 or to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble TGF-β receptor (e.g., a soluble TGFRβRII receptor). In some embodiments of these multi-chain chimeric polypeptides, the first target-binding domain and the second target-binding domain are each independently a soluble IL-21 or a soluble TGF-β receptor (e.g., a soluble TGFRβRII receptor). In some embodiments of these multi-chain chimeric polypeptides, the first target-binding domain and the second target-binding domain both bind specifically to a receptor of IL-21 or to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to TGF-β. In some embodiments of these multi-chain chimeric polypeptides, the first target-binding domain binds specifically to TGF-β, and the second target-binding domain bind specifically to a receptor for IL-21.

In some embodiments of these multi-chain chimeric polypeptides, the first target-binding domain includes a soluble IL-21 (e.g., a soluble human IL-21). In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 78)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 79)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC.
```

In some embodiments of these multi-chain chimeric polypeptides, the second target-binding domain includes a soluble TGF-β receptor (e.g., a soluble TGFRβRII receptor (e.g., a soluble human TGFRβRII receptor)). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 80)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCACGATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCACAATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCACGATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCACA

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.

In some embodiments of these multi-chain chimeric polypeptides, the human TGFβRII receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 86)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDSSGTTNTVAAYNLTWKST

NFKTILEWEPKPVNQVYTVQISTKSGDWKSKCFYTTDTECDLTDEIVKDV

KQTYLARVFSYPAGNVESTGSAGEPLYENSPEFTPYLETNLGQPTIQSFE

QVGTKVNVTVEDERTLVRRNNTFLSLRDVFGKDLIYTLYYWKSSSSGKKT

AKTNTNEFLIDVDKGENYCFSVQAVIPSRTVNRKSTDSPVECMGQEKGEF

RENWVNVISDLKKIEDLIQSMHIDATLYTESDVHPSCKVTAMKCFLLELQ

VISLESGDASIHDTVENLIILANNSLSSNGNVTESGCKECEELEEKNIKE

FLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 87)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCGAGGACTCCT

CCGGCACCACCAATACCGTGGCCGCTTATAACCTCACATGGAAGAGCACC

AACTTCAAGACAATTCTGGAATGGGAACCCAAGCCCGTCAATCAAGTTTA

CACCGTGCAGATCTCCACCAAATCCGGAGACTGGAAGAGCAAGTGCTTCT

ACACAACAGACACCGAGTGTGATTTAACCGACGAAATCGTCAAGGACGTC

AAGCAAACCTATCTGGCTCGGGTCTTTTCCTACCCCGCTGGCAATGTCGA

GTCCACCGGCTCCGCTGGCGAGCCTCTCTACGAGAATTCCCCCGAATTCA

CCCCTTATTTAGAGACCAATTTAGGCCAGCCTACCATCCAGAGCTTCGAG

CAAGTTGGCACCAAGGTGAACGTCACCGTCGAGGATGAAAGGACTTTAGT

GCGGCGGAATAACACATTTTTATCCCTCCGGGATGTGTTCGGCAAAGACC

TCATCTACACACTGTACTATTGGAAGTCCAGCTCCTCCGGCAAAAAGACC

GCTAAGACCAACACCAACGAGTTTTTAATTGACGTGGACAAAGGCGAGAA

CTACTGCTTCAGCGTGCAAGCCGTGATCCCTTCTCGTACCGTCAACCGGA

AGAGCACAGATTCCCCCGTTGAGTGCATGGGCCAAGAAAAGGGCGAGTTC

CGGGAGAACTGGGTGAACGTCATCAGCGATTTAAAGAAGATCGAAGATTT

AATTCAGTCCATGCATATCGACGCCACTTTATACACAGAATCCGACGTGC

ACCCCTCTTGTAAGGTGACCGCCATGAAATGTTTTTACTGGAGCTGCAA

GTTATCTCTTTAGAGAGCGGAGACGCTAGCATCCACGACACCGTGGAGAA

TTTAATCATTTTAGCCAATAACTCTTTATCCAGCAACGGCAACGTGACAG

AGTCCGGCTGCAAGGAGTGCGAAGAGCTGGAGGAGAAGAACATCAAGGAG

TTTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 88)
MKWVTFISLLFLFSSAYSQGQDRHMIRMRQLIDIVDQLKNYVNDLVPEFL

PAPEDVETNCEWSAFSCFQKAQLKSANTGNNERIINVSIKKLKRKPPSTN

AGRRQKHRLTCPSCDSYEKKPPKEFLERFKSLLQKMIHQHLSSRTHGSED

SSGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSPE

FTPYLETNLGQPTIQSFEQVGTKVNVTVEDERTLVRRNNTFLSLRDVFGK

DLIYTLYYWKSSSSGKKTAKTNTNEFLIDVDKGENYCFSVQAVIPSRTVN

RKSTDSPVECMGQEKGEFRENWVNVISDLKKIEDLIQSMHIDATLYTESD

VHPSCKVTAMKCFLLELQVISLESGDASIHDTVENLIILANNSLSSNGNV

TESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 89)
ATGAAGTGGGTGACCTTCATCAGCCTGCTGTTCCTGTTCTCCAGCGCCTA

CTCCCAGGGCCAGGACAGGCACATGATCCGGATGAGGCAGCTCATCGACA

TCGTCGACCAGCTGAAGAACTACGTGAACGACCTGGTGCCCGAGTTTCTG

CCTGCCCCCGAGGACGTGGAGACCAACTGCGAGTGGTCCGCCTTCTCCTG

CTTTCAGAAGGCCCAGCTGAAGTCCGCCAACACCGGCAACAACGAGCGGA

-continued

```
TCATCAACGTGAGCATCAAGAAGCTGAAGCGGAAGCCTCCCTCCACAAAC
GCCGGCAGGAGGCAGAAGCACAGGCTGACCTGCCCCAGCTGTGACTCCTA
CGAGAAGAAGCCCCCAAGGAGTTCCTGGAGAGGTTCAAGTCCCTGCTGC
AGAAGATGATCCATCAGCACCTGTCCTCCAGGACCCACGGCTCCGAGGAC
TCCTCCGGCACCACCAATACCGTGGCCGCTTATAACCTCACATGGAAGAG
CACCAACTTCAAGACAATTCTGGAATGGGAACCCAAGCCCGTCAATCAAG
TTTACACCGTGCAGATCTCCACCAAATCCGGAGACTGGAAGAGCAAGTGC
TTCTACACAACAGACACCGAGTGTGATTTAACCGACGAAATCGTCAAGGA
CGTCAAGCAAACCTATCTGGCTCGGGTCTTTTCCTACCCCGCTGGCAATG
TCGAGTCCACCGGCTCCGCTGGCGAGCCTCTCTACGAGAATTCCCCCGAA
TTCACCCCTTATTTAGAGACCAATTTAGGCCAGCCTACCATCCAGAGCTT
CGAGCAAGTTGGCACCAAGGTGAACGTCACCGTCGAGGATGAAAGGACTT
TAGTGCGGCGGAATAACACATTTTTATCCCTCCGGGATGTGTTCGGCAAA
GACCTCATCTACACACTGTACTATTGGAAGTCCAGCTCCTCCGGCAAAAA
GACCGCTAAGACCAACACCAACGAGTTTTTAATTGACGTGGACAAAGGCG
AGAACTACTGCTTCAGCGTGCAAGCCGTGATCCCTTCTCGTACCGTCAAC
CGGAAGAGCACAGATTCCCCCGTTGAGTGCATGGGCCAAGAAAAGGGCGA
GTTCCGGGAGAACTGGGTGAACGTCATCAGCGATTTAAAGAAGATCGAAG
ATTTAATTCAGTCCATGCATATCGACGCCACTTTATACACAGAATCCGAC
GTGCACCCCTCTTGTAAGGTGACCGCCATGAAATGTTTTTTACTGGAGCT
GCAAGTTATCTCTTTAGAGAGCGGAGACGCTAGCATCCACGACACCGTGG
AGAATTTAATCATTTTAGCCAATAACTCTTTATCCAGCAACGGCAACGTG
ACAGAGTCCGGCTGCAAGGAGTGCGAAGAGCTGGAGGAGAAGAACATCAA
GGAGTTTCTGCAATCCTTTGTGCACATTGTCCAGATGTTCATCAATACCT
CC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 90)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPDGGGGSGGGGSGGGG
SIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSSDECNDNIIFSEEYNTSNPDITCPPPMSVEHAD
IWVKSYSLYSRERYICNSGFKRKAGTSSLTECVLNKATNVAHWTTPSLKC
IR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 91)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCACGATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCACA
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGACATCACGTGTCCTCCTCCTATGTCCGTGGAACACGCAGAC
ATCTGGGTCAAGAGCTACAGCTTGTACTCCAGGGAGCGGTACATTTGTAA
CTCTGGTTTCAAGCGTAAAGCCGGCACGTCCAGCCTGACGGAGTGCGTGT
TGAACAAGGCCACGAATGTCGCCCACTGGACAACCCCCAGTCTCAAATGT
ATTAGA.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 92)
MKWVTFISLLFLFSSAYSIPPHVQKSVNNDMIVTDNNGAVKFPQLCKFCD
VRFSTCDNQKSCMSNCSITSICEKPQEVCVAVWRKNDENITLETVCHDPK
LPYHDFILEDAASPKCIMKEKKKPGETFFMCSCSSDECNDNIIFSEEYNT
SNPDGGGGSGGGGSGGGGSIPPHVQKSVNNDMIVTDNNGAVKFPQLCKFC
DVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYN
TSNPDITCPPPMSVEHADIWVKSYSLYSRERYICNSGFKRKAGTSSLTEC
VLNKATNVAHWTTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 93)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAC

GATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CACAATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACATCACGTGTCCTCCTCCTATGTCCGTGGAACACGC

AGACATCTGGGTCAAGAGCTACAGCTTGTACTCCAGGGAGCGGTACATTT

GTAACTCTGGTTTCAAGCGTAAAGCCGGCACGTCCAGCCTGACGGAGTGC

GTGTTGAACAAGGCCACGAATGTCGCCCACTGGACAACCCCCAGTCTCAA

ATGTATTAGA.

Exemplary Multi-Chain Chimeric Polypeptides—Type C

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the first target-binding domain includes a soluble IL-21 (e.g., a soluble human IL-21).

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 94)
CAAGGTCAAGATCGCCACATGATTAGAATGCGTCAACTTATAGATATTGT

TGATCAGCTGAAAAATTATGTGAATGACTTGGTCCCTGAATTTCTGCCAG

CTCCAGAAGATGTAGAGACAAACTGTGAGTGGTCAGCTTTTTCCTGTTTT

CAGAAGGCCCAACTAAAGTCAGCAAATACAGGAAACAATGAAAGGATAAT

CAATGTATCAATTAAAAAGCTGAAGAGGAAACCACCTTCCACAAATGCAG

GGAGAAGACAGAAACACAGACTAACATGCCCTTCATGTGATTCTTATGAG

AAAAAACCACCCAAAGAATTCCTAGAAAGATTCAAATCACTTCTCCAAAA

GATGATTCATCAGCATCTGTCCTCTAGAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC.

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 11)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 95)
GATTGTGATATTGAAGGTAAAGATGGCAAACAATATGAGAGTGTTCTAAT

GGTCAGCATCGATCAATTATTGGACAGCATGAAAGAAATTGGTAGCAATT

GCCTGAATAATGAATTTAACTTTTTTAAAAGACATATCTGTGATGCTAAT

AAGGAAGGTATGTTTTTATTCCGTGCTGCTCGCAAGTTGAGGCAATTTCT

TAAAATGAATAGCACTGGTGATTTTGATCTCCACTTATTAAAAGTTTCAG

AAGGCACAACAATACTGTTGAACTGCACTGGCCAGGTTAAAGGAAGAAAA

CCAGCTGCCCTGGGTGAAGCCCAACCAACAAAGAGTTTGGAAGAAAATAA

ATCTTTAAAGGAACAGAAAAAACTGAATGACTTGTGTTTCCTAAAGAGAC

TATTACAAGAGATAAAAACTTGTTGGAATAAAATTTTGATGGGCACTAAA

GAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 96)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDSSGTTNTVAAYNLTWKST

NFKTILEWEPKPVNQVYTVQISTKSGDWKSKCFYTTDTECDLTDEIVKDV

KQTYLARVFSYPAGNVESTGSAGEPLYENSPEFTPYLETNLGQPTIQSFE

QVGTKVNVTVEDERTLVRRNNTFLSLRDVFGKDLIYTLYYWKSSSSGKKT

AKTNTNEFLIDVDKGENYCFSVQAVIPSRTVNRKSTDSPVECMGQEKGEF

RENWVNVISDLKKIEDLIQSMHIDATLYTESDVHPSCKVTAMKCFLLELQ

VISLESGDASIHDTVENLIILANNSLSSNGNVTESGCKECEELEEKNIKE

FLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 97)
CAAGGTCAAGATCGCCACATGATTAGAATGCGTCAACTTATAGATATTGT

TGATCAGCTGAAAAATTATGTGAATGACTTGGTCCCTGAATTTCTGCCAG

CTCCAGAAGATGTAGAGACAAACTGTGAGTGGTCAGCTTTTTCCTGTTTT

CAGAAGGCCCAACTAAAGTCAGCAAATACAGGAAACAATGAAAGGATAAT

CAATGTATCAATTAAAAAGCTGAAGAGGAAACCACCTTCCACAAATGCAG

GGAGAAGACAGAAACACAGACTAACATGCCCTTCATGTGATTCTTATGAG

AAAAAACCACCCAAAGAATTCCTAGAAAGATTCAAATCACTTCTCCAAAA

GATGATTCATCAGCATCTGTCCTCTAGAACACACGGAAGTGAAGATTCCT

CAGGCACTACAAATACTGTGGCAGCATATAATTTAACTTGGAAATCAACT

AATTTCAAGACAATTTTGGAGTGGGAACCCAAACCCGTCAATCAAGTCTA

-continued

CACTGTTCAAATAAGCACTAAGTCAGGAGATTGGAAAAGCAAATGCTTTT

ACACAACAGACACAGAGTGTGACCTCACCGACGAGATTGTGAAGGATGTG

AAGCAGACGTACTTGGCACGGGTCTTCTCCTACCCGGCAGGGAATGTGGA

GAGCACCGGTTCTGCTGGGGAGCCTCTGTATGAGAACTCCCCAGAGTTCA

CACCTTACCTGGAGACAAACCTCGGACAGCCAACAATTCAGAGTTTTGAA

CAGGTGGGAACAAAAGTGAATGTGACCGTAGAAGATGAACGGACTTTAGT

CAGAAGGAACAACACTTTCCTAAGCCTCCGGGATGTTTTTGGCAAGGACT

TAATTTATACACTTTATTATTGGAAATCTTCAAGTTCAGGAAAGAAAACA

GCCAAAACAAACACTAATGAGTTTTTGATTGATGTGGATAAAGGAGAAAA

CTACTGTTTCAGTGTTCAAGCAGTGATTCCCTCCCGAACAGTTAACCGGA

AGAGTACAGACAGCCCGGTAGAGTGTATGGGCCAGGAGAAAGGGGAATTC

AGAGAAAACTGGGTGAACGTCATCAGCGATTTAAAGAAGATCGAAGATTT

AATTCAGTCCATGCATATCGACGCCACTTTATACACAGAATCCGACGTGC

ACCCCTCTTGTAAGGTGACCGCCATGAAATGTTTTTTACTGGAGCTGCAA

GTTATCTCTTTAGAGAGCGGAGACGCTAGCATCCACGACACCGTGGAGAA

TTTAATCATTTTAGCCAATAACTCTTTATCCAGCAACGGCAACGTGACAG

AGTCCGGCTGCAAGGAGTGCGAAGAGCTGGAGGAGAAGAACATCAAGGAG

TTTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 98)
MGVKVLFALICIAVAEAQGQDRHMIRMRQLIDIVDQLKNYVNDLVPEFLP

APEDVETNCEWSAFSCFQKAQLKSANTGNNERIINVSIKKLKRKPPSTNA

GRRQKHRLTCPSCDSYEKKPPKEFLERFKSLLQKMIHQHLSSRTHGSEDS

SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRENWVNVISDLKKIEDLIQSMHIDATLYTESDV

HPSCKVTAMKCFLLELQVISLESGDASIHDTVENLIILANNSLSSNGNVT

ESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 99)
ATGGGAGTGAAAGTTCTTTTTGCCCTTATTTGTATTGCTGTGGCCGAGGC

CCAAGGTCAAGATCGCCACATGATTAGAATGCGTCAACTTATAGATATTG

TTGATCAGCTGAAAAATTATGTGAATGACTTGGTCCCTGAATTTCTGCCA

GCTCCAGAAGATGTAGAGACAAACTGTGAGTGGTCAGCTTTTTCCTGTTT

TCAGAAGGCCCAACTAAAGTCAGCAAATACAGGAAACAATGAAAGGATAA

TCAATGTATCAATTAAAAAGCTGAAGAGGAAACCACCTTCCACAAATGCA

GGGAGAAGACAGAAACACAGACTAACATGCCCTTCATGTGATTCTTATGA

GAAAAAACCACCCAAAGAATTCCTAGAAAGATTCAAATCACTTCTCCAAA

AGATGATTCATCAGCATCTGTCCTCTAGAACACACGGAAGTGAAGATTCC

TCAGGCACTACAAATACTGTGGCAGCATATAATTTAACTTGGAAATCAAC

TAATTTCAAGACAATTTTGGAGTGGGAACCCAAACCCGTCAATCAAGTCT

ACACTGTTCAAATAAGCACTAAGTCAGGAGATTGGAAAAGCAAATGCTTT

TACACAACAGACACAGAGTGTGACCTCACCGACGAGATTGTGAAGGATGT

GAAGCAGACGTACTTGGCACGGGTCTTCTCCTACCCGGCAGGGAATGTGG

AGAGCACCGGTTCTGCTGGGGAGCCTCTGTATGAGAACTCCCCAGAGTTC

ACACCTTACCTGGAGACAAACCTCGGACAGCCAACAATTCAGAGTTTTGA

ACAGGTGGGAACAAAAGTGAATGTGACCGTAGAAGATGAACGGACTTTAG

TCAGAAGGAACAACACTTTCCTAAGCCTCCGGGATGTTTTTGGCAAGGAC

TTAATTTATACACTTTATTATTGGAAATCTTCAAGTTCAGGAAAGAAAAC

AGCCAAAACAAACACTAATGAGTTTTTGATTGATGTGGATAAAGGAGAAA

ACTACTGTTTCAGTGTTCAAGCAGTGATTCCCTCCCGAACAGTTAACCGG

AAGAGTACAGACAGCCCGGTAGAGTGTATGGGCCAGGAGAAAGGGGAATT

CAGAGAAAACTGGGTGAACGTCATCAGCGATTTAAAGAAGATCGAAGATT

TAATTCAGTCCATGCATATCGACGCCACTTTATACACAGAATCCGACGTG

CACCCCTCTTGTAAGGTGACCGCCATGAAATGTTTTTTACTGGAGCTGCA

AGTTATCTCTTTAGAGAGCGGAGACGCTAGCATCCACGACACCGTGGAGA

ATTTAATCATTTTAGCCAATAACTCTTTATCCAGCAACGGCAACGTGACA

GAGTCCGGCTGCAAGGAGTGCGAAGAGCTGGAGGAGAAGAACATCAAGGA

GTTTCTGCAATCCTTTGTGCACATTGTCCAGATGTTCATCAATACCTCC

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 100)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EHITCPPPMSVEHADIWVKSYSLYSRERYICNSGFKRKAGTSSLTECVLN

KATNVAHWTTPSLKCIR

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 101)
GATTGTGATATTGAAGGTAAAGATGGCAAACAATATGAGAGTGTTCTAAT

GGTCAGCATCGATCAATTATTGGACAGCATGAAAGAAATTGGTAGCAATT

GCCTGAATAATGAATTTAACTTTTTTAAAAGACATATCTGTGATGCTAAT

AAGGAAGGTATGTTTTTATTCCGTGCTGCTCGCAAGTTGAGGCAATTTCT

TAAAATGAATAGCACTGGTGATTTTGATCTCCACTTATTAAAAGTTTCAG

AAGGCACAACAATACTGTTGAACTGCACTGGCCAGGTTAAAGGAAGAAAA

CCAGCTGCCCTGGGTGAAGCCCAACCAACAAAGAGTTTGGAAGAAAATAA

ATCTTTAAAGGAACAGAAAAAACTGAATGACTTGTGTTTCCTAAAGAGAC

TATTACAAGAGATAAAAACTTGTTGGAATAAAATTTTGATGGGCACTAAA

GAACACATCACGTGCCCTCCCCCCATGTCCGTGGAACACGCAGACATCTG

GGTCAAGAGCTACAGCTTGTACTCCAGGGAGCGGTACATTTGTAACTCTG

GTTTCAAGCGTAAAGCCGGCACGTCCAGCCTGACGGAGTGCGTGTTGAAC

AAGGCCACGAATGTCGCCCACTGGACAACCCCCAGTCTCAAATGCATTAG

A.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 102)
MGVKVLFALICIAVAEADCDIEGKDGKQYESVLMVSIDQLLDSMKEIGSN

CLNNEFNFFKRHICDANKEGMFLFRAARKLRQFLKMNSTGDFDLHLLKVS

EGTTILLNCTGQVKGRKPAALGEAQPTKSLEENKSLKEQKKLNDLCFLKR

LLQEIKTCWNKILMGTKEHITCPPPMSVEHADIWVKSYSLYSRERYICNS

GFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 103)
ATGGGAGTGAAAGTTCTTTTTGCCCTTATTTGTATTGCTGTGGCCGAGGC

CGATTGTGATATTGAAGGTAAAGATGGCAAACAATATGAGAGTGTTCTAA

TGGTCAGCATCGATCAATTATTGGACAGCATGAAAGAAATTGGTAGCAAT

TGCCTGAATAATGAATTTAACTTTTTTAAAAGACATATCTGTGATGCTAA

TAAGGAAGGTATGTTTTTATTCCGTGCTGCTCGCAAGTTGAGGCAATTTC

TTAAAATGAATAGCACTGGTGATTTTGATCTCCACTTATTAAAAGTTTCA

GAAGGCACAACAATACTGTTGAACTGCACTGGCCAGGTTAAAGGAAGAAA

ACCAGCTGCCCTGGGTGAAGCCCAACCAACAAAGAGTTTGGAAGAAATA

AATCTTTAAAGGAACAGAAAAAACTGAATGACTTGTGTTTCCTAAAGAGA

CTATTACAAGAGATAAAAACTTGTTGGAATAAAATTTTGATGGGCACTAA

AGAACACATCACGTGCCCTCCCCCCATGTCCGTGGAACACGCAGACATCT

GGGTCAAGAGCTACAGCTTGTACTCCAGGGAGCGGTACATTTGTAACTCT

GGTTTCAAGCGTAAAGCCGGCACGTCCAGCCTGACGGAGTGCGTGTTGAA

CAAGGCCACGAATGTCGCCCACTGGACAACCCCCAGTCTCAAATGCATTA

GA.

Exemplary Multi-Chain Chimeric Polypeptides—Type D

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 94)
CAAGGTCAAGATCGCCACATGATTAGAATGCGTCAACTTATAGATATTGT

TGATCAGCTGAAAAATTATGTGAATGACTTGGTCCCTGAATTTCTGCCAG

CTCCAGAAGATGTAGAGACAAACTGTGAGTGGTCAGCTTTTTCCTGTTTT

CAGAAGGCCCAACTAAAGTCAGCAAATACAGGAAACAATGAAAGGATAAT

CAATGTATCAATTAAAAAGCTGAAGAGGAAACCACCTTCCACAAATGCAG

GGAGAAGACAGAAACACAGACTAACATGCCCTTCATGTGATTCTTATGAG

AAAAAACCACCCAAAGAATTCCTAGAAAGATTCAAATCACTTCTCCAAAA

GATGATTCATCAGCATCTGTCCTCTAGAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC.

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 11)
DCDIEGKDGKQYESVLMVSIDQLLDSMKEIGSNCLNNEFNFFKRHICDAN

KEGMFLFRAARKLRQFLKMNSTGDFDLHLLKVSEGTTILLLNCTGQVKGRK

PAALGEAQPTKSLEENKSLKEQKKLNDLCFLKRLLQEIKTCWNKILMGTK

EH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 95)
GATTGTGATATTGAAGGTAAAGATGGCAAACAATATGAGAGTGTTCTAAT

GGTCAGCATCGATCAATTATTGGACAGCATGAAAGAAATTGGTAGCAATT

GCCTGAATAATGAATTTAACTTTTTTAAAAGACATATCTGTGATGCTAAT

AAGGAAGGTATGTTTTTATTCCGTGCTGCTCGCAAGTTGAGGCAATTTCT

TAAAATGAATAGCACTGGTGATTTTGATCTCCACTTATTAAAAGTTTCAG

AAGGCACAACAATACTGTTGAACTGCACTGGCCAGGTTAAAGGAAGAAAA

CCAGCTGCCCTGGGTGAAGCCCAACCAACAAAGAGTTTGGAAGAAAATAA

ATCTTTAAAGGAACAGAAAAAACTGAATGACTTGTGTTTCCTAAAGAGAC

TATTACAAGAGATAAAAACTTGTTGGAATAAAATTTTGATGGGCACTAAA

GAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 104)
DCDIEGKDGKQYESVLMVSIDQLLDSMKEIGSNCLNNEFNFFKRHICDAN

KEGMFLFRAARKLRQFLKMNSTGDFDLHLLKVSEGTTILLLNCTGQVKGRK

PAALGEAQPTKSLEENKSLKEQKKLNDLCFLKRLLQEIKTCWNKILMGTK

EHSGTTNTVAAYNLTWKSTNFKTILEWEPKPVNQVYTVQISTKSGDWKSK

CFYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVFG

KDLIYTLYYWKSSSSGKKTAKTNTNEFLIDVDKGENYCFSVQAVIPSRTV

NRKSTDSPVECMGQEKGEFRENWVNVISDLKKIEDLIQSMHIDATLYTES

DVHPSCKVTAMKCFLLELQVISLESGDASIHDTVENLIILANNSLSSNGN

VTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 105)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCATAGCGGCACAACCAACACAGTCGCTGCCTATAACCTCACTTGGAA

GAGCACCAACTTCAAAACCATCCTCGAATGGGAACCCAAACCCGTTAACC

AAGTTTACACCGTGCAGATCAGCACCAAGTCCGGCGACTGGAAGTCCAAA

TGTTTCTATACCACCGACACCGAGTGCGATCTCACCGATGAGATCGTGAA

AGATGTGAAACAGACCTACCTCGCCCGGGTGTTTAGCTACCCCGCCGGCA

ATGTGGAGAGCACTGGTTCCGCTGGCGAGCCTTTATACGAGAACAGCCCC

GAATTTACCCCTTACCTCGAGACCAATTTAGGACAGCCCACCATCCAAAG

CTTTGAGCAAGTTGGCACAAAGGTGAATGTGACAGTGGAGGACGAGCGGA

CTTTAGTGCGGCGGAACAACACCTTTCTCAGCCTCCGGGATGTGTTCGGC

AAAGATTTAATCTACACACTGTATTACTGGAAGTCCTCTTCCTCCGGCAA

GAAGACAGCTAAAACCAACACAAACGAGTTTTTAATCGACGTGGATAAAG

GCGAAAACTACTGTTTCAGCGTGCAAGCTGTGATCCCCTCCGGACCCGTG

AATAGGAAAAGCACCGATAGCCCCGTTGAGTGCATGGGCCAAGAAAAGGG

CGAGTTCCGGGAGAACTGGGTGAACGTCATCAGCGATTTAAAGAAGATCG

AAGATTTAATTCAGTCCATGCATATCGACGCCACTTTATACACAGAATCC

GACGTGCACCCCTCTTGTAAGGTGACCGCCATGAAATGTTTTTTACTGGA

GCTGCAAGTTATCTCTTTAGAGAGCGGAGACGCTAGCATCCACGACACCG

TGGAGAATTTAATCATTTTAGCCAATAACTCTTTATCCAGCAACGGCAAC

GTGACAGAGTCCGGCTGCAAGGAGTGCGAAGAGCTGGAGGAGAAGAACAT

CAAGGAGTTTCTGCAATCCTTTGTGCACATTGTCCAGATGTTCATCAATA

CCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 106)
MKWVTFISLLFLFSSAYSDCDIEGKDGKQYESVLMVSIDQLLDSMKEIGS

NCLNNEFNFFKRHICDANKEGMFLFRAARKLRQFLKMNSTGDFDLHLLKV

SEGTTILLLNCTGQVKGRKPAALGEAQPTKSLEENKSLKEQKKLNDLCFLK

RLLQEIKTCWNKILMGTKEHSGTTNTVAAYNLTWKSTNFKTILEWEPKPV

NQVYTVQISTKSGDWKSKCFYTTDTECDLTDEIVKDVKQTYLARVFSYPA

GNVESTGSAGEPLYENSPEFTPYLETNLGQPTIQSFEQVGTKVNVTVEDE

RTLVRRNNTFLSLRDVFGKDLIYTLYYWKSSSSGKKTAKTNTNEFLIDVD

KGENYCFSVQAVIPSRTVNRKSTDSPVECMGQEKGEFRENWVNVISDLKK

IEDLIQSMHIDATLYTESDVHPSCKVTAMKCFLLELQVISLESGDASIHD

TVENLIILANNSLSSNGNVTESGCKECEELEEKNIKEFLQSFVHIVQMFI

NTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 107)
ATGAAGTGGGTGACCTTCATCAGCCTGCTGTTCCTGTTCTCCAGCGCCTA

CTCCGATTGCGACATCGAGGGCAAGGACGGCAAGCAGTACGAGAGCGTGC

TGATGGTGTCCATCGACCAGCTGCTGGACAGCATGAAGGAGATCGGCTCC

AACTGCCTCAACAACGAGTTCAACTTCTTCAAGCGGCACATCTGCGACGC

CAACAAGGAGGGCATGTTCCTGTTCAGGGCCGCCAGGAAACTGCGGCAGT

TCCTGAAGATGAACTCCACCGGCGACTTCGACCTGCACCTGCTGAAGGTG

TCCGAGGGCACCACCATCCTGCTGAACTGCACCGGACAGGTGAAGGGCCG

GAAACCTGCTGCTCTGGGAGAGGCCCAACCCACCAAGAGCCTGGAGGAGA

ACAAGTCCCTGAAGGAGCAGAAGAAGCTGAACGACCTGTGCTTCCTGAAG

AGGCTGCTGCAGGAGATCAAGACCTGCTGGAACAAGATCCTGATGGGCAC

CAAGGAGCATAGCGGCACAACCAACACAGTCGCTGCCTATAACCTCACTT

GGAAGAGCACCAACTTCAAAACCATCCTCGAATGGGAACCCAAACCCGTT

AACCAAGTTTACACCGTGCAGATCAGCACCAAGTCCGGCGACTGGAAGTC

CAAATGTTTCTATACCACCGACACCGAGTGCGATCTCACCGATGAGATCG

TGAAAGATGTGAAACAGACCTACCTCGCCCGGGTGTTTAGCTACCCCGCC

GGCAATGTGGAGAGCACTGGTTCCGCTGGCGAGCCTTTATACGAGAACAG

CCCCGAATTTACCCCTTACCTCGAGACCAATTTAGGACAGCCCACCATCC

AAAGCTTTGAGCAAGTTGGCACAAAGGTGAATGTGACAGTGGAGGACGAG

CGGACTTTAGTGCGGCGGAACAACACCTTTCTCAGCCTCCGGGATGTGTT

CGGCAAAGATTTAATCTACACACTGTATTACTGGAAGTCCTCTTCCTCCG

GCAAGAAGACAGCTAAAACCAACACAAACGAGTTTTTAATCGACGTGGAT

AAAGGCGAAAACTACTGTTTCAGCGTGCAAGCTGTGATCCCCTCCCGGAC

CGTGAATAGGAAAAGCACCGATAGCCCCGTTGAGTGCATGGGCCAAGAAA

AGGGCGAGTTCCGGGAGAACTGGGTGAACGTCATCAGCGATTTAAAGAAG

ATCGAAGATTTAATTCAGTCCATGCATATCGACGCCACTTTATACACAGA

ATCCGACGTGCACCCCTCTTGTAAGGTGACCGCCATGAAATGTTTTTAC

TGGAGCTGCAAGTTATCTCTTTAGAGAGCGGAGACGCTAGCATCCACGAC

ACCGTGGAGAATTTAATCATTTTAGCCAATAACTCTTTATCCAGCAACGG

CAACGTGACAGAGTCCGGCTGCAAGGAGTGCGAAGAGCTGGAGGAGAAGA

ACATCAAGGAGTTTCTGCAATCCTTTGTGCACATTGTCCAGATGTTCATC

AATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 108)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQLSSRTHGSEDSITCPPPMSVEHADIWVK

SYSLYSRERYICNSGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 109)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCCA

TTACATGCCCCCCTCCCATGAGCGTGGAGCACGCCGACATCTGGGTGAAG

AGCTATAGCCTCTACAGCCGGGAGAGGTATATCTGTAACAGCGGCTTCAA

GAGGAAGGCCGGCACCAGCAGCCTCACCGAGTGCGTGCTGAATAAGGCTA

CCAACGTGGCTCACTGGACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 110)
MKWVTFISLLFLFSSAYSQGQDRHMIRMRQLIDIVDQLKNYVNDLVPEFL

PAPEDVETNCEWSAFSCFQKAQLKSANTGNNERIINVSIKKLKRKPPSTN

AGRRQKHRLTCPSCDSYEKKPPKEFLERFKSLLQKMIHQLSSRTHGSED

SITCPPPMSVEHADIWVKSYSLYSRERYICNSGFKRKAGTSSLTECVLNK

ATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 111)
ATGAAGTGGGTGACCTTCATCAGCCTGCTGTTCCTGTTCTCCAGCGCCTA

CTCCCAGGGCCAGGACAGGCACATGATCCGGATGAGGCAGCTCATCGACA

TCGTCGACCAGCTGAAGAACTACGTGAACGACCTGGTGCCCGAGTTTCTG

CCTGCCCCCGAGGACGTGGAGACCAACTGCGAGTGGTCCGCCTTCTCCTG

CTTTCAGAAGGCCCAGCTGAAGTCCGCCAACACCGGCAACAACGAGCGGA

TCATCAACGTGAGCATCAAGAAGCTGAAGCGGAAGCCTCCCTCCACAAAC

GCCGGCAGGAGGCAGAAGCACAGGCTGACCTGCCCCAGCTGTGACTCCTA

CGAGAAGAAGCCCCCCAAGGAGTTCCTGGAGAGGTTCAAGTCCCTGCTGC

AGAAGATGATCCATCAGCACCTGTCCTCCAGGACCCACGGCTCCGAGGAC

TCCATTACATGCCCCCCTCCCATGAGCGTGGAGCACGCCGACATCTGGGT

GAAGAGCTATAGCCTCTACAGCCGGGAGAGGTATATCTGTAACAGCGGCT

TCAAGAGGAAGGCCGGCACCAGCAGCCTCACCGAGTGCGTGCTGAATAAG

GCTACCAACGTGGCTCACTGGACAACACCCTCTTTAAAGTGCATCCGG.

Exemplary Multi-Chain Chimeric Polypeptides—Type E

In some embodiments of any of the multi-chain chimeric polypeptides described herein, the first target-binding domain and the second targeting-binding domain each independently bind specifically to a receptor for IL-18 (e.g., a soluble human IL-18), a receptor for IL-12 (e.g., a soluble human IL-12), or CD16 (e.g., an anti-CD16 scFv). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-12.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12. In some embodiments of these multi-chain chimeric polypeptides, the first target-binding domain binds specifically to CD16, and the second target-binding domain binds specifically to a receptor for IL-18. In some embodiments of these multi-chain chimeric polypeptides, the first target-binding domain binds specifically to a receptor for IL-18, and the second target-binding domain bind specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 16)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

-continued

FFQRSVPGHDNKMQFESSSYEGYFLACEKERDLFKLILKKEDELGDRSIM

FTVQNED.

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 65)
TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA

CCGACTCCGATTGCCGGGACAATGCCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGAT.

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-12β (p40) and a sequence of soluble human IL-12α (p35). In some embodiments of these multi-chain chimeric polypeptides, the soluble IL-15 (e.g., soluble human IL-15) further includes a linker sequence (e.g., any of the exemplary linker sequences described herein) between the sequence of soluble IL-12β (p40) and the sequence of soluble human IL-12α (p35). In some examples of these multi-chain chimeric polypeptides, the linker sequence comprises GGGGSGGGGSGGGGS (SEQ ID NO: 7).

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 66)
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS.

In some embodiments of these multi-chain chimeric polypeptides, the soluble human IL-12β (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 67)
ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA

AAGACCCTCACAATCCAAGTTAAGGAGTTCGGAGACGCTGGCCAATACAC

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC

GCTACCCTCAGCGCTGAGAGGGTTCGTGGCGATAACAAGGAATACGAGTA

CAGCGTGGAGTGCCAAGAAGATAGCGCTTGTCCCGCTGCCGAAGAATCTT

TACCCATTGAGGTGATGGTGGACGCCGTGCACAAACTCAAGTACGAGAAC

TACACCTCCTCCTTCTTTATCCGGGACATCATTAAGCCCGATCCTCCTAA

GAATTTACAGCTGAAGCCTCTCAAAAATAGCCGGCAAGTTGAGGTCTCTT

GGGAATATCCCGACACTTGGAGCACACCCCACAGCTACTTCTCTTTAACC

TTTTGTGTGCAAGTTCAAGGTAAAAGCAAGCGGGAGAAGAAAGACCGGGT

GTTTACCGACAAAACCAGCGCCACCGTCATCTGTCGGAAGAACGCCTCCA

TCAGCGTGAGGGCTCAAGATCGTTATTACTCCAGCAGCTGGTCCGAGTGG

GCCAGCGTGCCTTGTTCC.

In some embodiments of these multi-chain chimeric polypeptides, the soluble human IL-12α (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 68)
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS.

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 69)
CGTAACCTCCCCGTGGCTACCCCCGATCCCGGAATGTTCCCTTGTTTACA

CCACAGCCAGAATTTACTGAGGGCCGTGAGCAACATGCTGCAGAAAGCTA

GGCAGACTTTAGAATTTTACCCTTGCACCAGCGAGGAGATCGACCATGAA

GATATCACCAAGGACAAGACATCCACCGTGGAGGCTTGTTTACCTCTGGA

GCTGACAAAGAACGAGTCTTGTCTCAACTCTCGTGAAACCAGCTTCATCA

CAAATGGCTCTTGTTTAGCTTCCCGGAAGACCTCCTTTATGATGGCTTTA

TGCCTCAGCTCCATCTACGAGGATTTAAAGATGTACCAAGTGGAGTTCAA

GACCATGAACGCCAAGCTGCTCATGGACCCTAAACGGCAGATCTTTTTAG

ACCAGAACATGCTGGCTGTGATTGATGAGCTGATGCAAGCTTTAAACTTC

AACTCCGAGACCGTCCCTCAGAAGTCCTCCCTCGAGGAGCCCGATTTTTA

CAAGACAAAGATCAAACTGTGCATTTTACTCCACGCCTTTAGGATCCGGG

CCGTGACCATTGACCGGGTCATGAGCTATTTAAACGCCAGC.

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 112)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 113)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 114)
EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 115)
GAGGTGCAGCTGGTGGAGTCCGGAGGAGGAGTGGTGAGGCCTGGAGGCTC

CCTGAGGCTGAGCTGTGCTGCCTCCGGCTTCACCTTCGACGACTACGGCA

TGTCCTGGGTGAGGCAGGCTCCTGGAAAGGGCCTGGAGTGGGTGTCCGGC

ATCAACTGGAACGGCGGATCCACCGGCTACGCCGATTCCGTGAAGGGCAG

GTTCACCATCAGCAGGGACAACGCCAAGAACTCCCTGTACCTGCAGATGA

ACTCCCTGAGGGCCGAGGACACCGCCGTGTACTACTGCGCCAGGGGCAGG

TCCCTGCTGTTCGACTACTGGGGACAGGGCACCCTGGTGACCGTGTCCAG

G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 116)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNEDSGTTNTVAAYNLTWKSTNFKTILEWEPKPVNQVYTVQISTKSG

DWKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLSL

RDVFGKDLIYTLYYWKSSSSGKKTAKTNTNEFLIDVDKGENYCFSVQAVI

PSRTVNRKSTDSPVECMGQEKGEFRENWVNVISDLKKIEDLIQSMHIDAT

LYTESDVHPSCKVTAMKCFLLELQVISLESGDASIHDTVENLIILANNSL

SSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 117)
TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA

CCGACTCCGATTGCCGGGACAATGCCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGATAGCGGCACAACCAACACAGTCGCTGCCTA

TAACCTCACTTGGAAGAGCACCAACTTCAAAACCATCCTCGAATGGGAAC

CCAAACCCGTTAACCAAGTTTACACCGTGCAGATCAGCACCAAGTCCGGC

GACTGGAAGTCCAAATGTTTCTATACCACCGACACCGAGTGCGATCTCAC

CGATGAGATCGTGAAAGATGTGAAACAGACCTACCTCGCCCGGGTGTTTA

GCTACCCCGCCGGCAATGTGGAGAGCACTGGTTCCGCTGGCGAGCCTTTA

TACGAGAACAGCCCCGAATTTACCCCTTACCTCGAGACCAATTTAGGACA

GCCCACCATCCAAAGCTTTGAGCAAGTTGGCACAAAGGTGAATGTGACAG

TGGAGGACGAGCGGACTTTAGTGCGGCGGAACAACACCTTTCTCAGCCTC

CGGGATGTGTTCGGCAAAGATTTAATCTACACACTGTATTACTGGAAGTC

CTCTTCCTCCGGCAAGAAGACAGCTAAAACCAACACAAACGAGTTTTTAA

TCGACGTGGATAAAGGCGAAAACTACTGTTTCAGCGTGCAAGCTGTGATC

CCCTCCCGGACCGTGAATAGGAAAAGCACCGATAGCCCCGTTGAGTGCAT

GGGCCAAGAAAAGGGCGAGTTCCGGGAGAACTGGGTGAACGTCATCAGCG

ATTTAAAGAAGATCGAAGATTTAATTCAGTCCATGCATATCGACGCCACT

TTATACACAGAATCCGACGTGCACCCCTCTTGTAAGGTGACCGCCATGAA

ATGTTTTTTACTGGAGCTGCAAGTTATCTCTTTAGAGAGCGGAGACGCTA

GCATCCACGACACCGTGGAGAATTTAATCATTTTAGCCAATAACTCTTTA

TCCAGCAACGGCAACGTGACAGAGTCCGGCTGCAAGGAGTGCGAAGAGCT

GGAGGAGAAGAACATCAAGGAGTTTCTGCAATCCTTTGTGCACATTGTCC

AGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 118)
MKWVTFISLLFLFSSAYSYFGKLESKLSVIRNLNDQVLFIDQGNRPLFED

MTDSDCRDNAPRTIFIISMYKDSQPRGMAVTISVKCEKISTLSCENKIIS

FKEMNPPDNIKDTKSDIIFFQRSVPGHDNKMQFESSSYEGYFLACEKERD

LFKLILKKEDELGDRSIMFTVQNEDSGTTNTVAAYNLTWKSTNFKTILEW

EPKPVNQVYTVQISTKSGDWKSKCFYTTDTECDLTDEIVKDVKQTYLARV

FSYPAGNVESTGSAGEPLYENSPEFTPYLETNLGQPTIQSFEQVGTKVNV

TVEDERTLVRRNNTFLSLRDVFGKDLIYTLYYWKSSSSGKKTAKTNTNEF

LIDVDKGENYCFSVQAVIPSRTVNRKSTDSPVECMGQEKGEFRENWVNVI

SDLKKIEDLIQSMHIDATLYTESDVHPSCKVTAMKCFLLELQVISLESGD

ASIHDTVENLIILANNSLSSNGNVTESGCKECEELEEKNIKEFLQSFVHI

VQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 119)
ATGAAGTGGGTCACATTTATCTCTTTACTGTTCCTCTTCTCCAGCGCCTA

CAGCTACTTCGGCAAACTGGAATCCAAGCTGAGCGTGATCCGGAATTTAA

ACGACCAAGTTCTGTTTATCGATCAAGGTAACCGGCCTCTGTTCGAGGAC

ATGACCGACTCCGATTGCCGGGACAATGCCCCCCGGACCATCTTCATTAT

CTCCATGTACAAGGACAGCCAGCCCCGGGGCATGGCTGTGACAATTAGCG

TGAAGTGTGAGAAAATCAGCACTTTATCTTGTGAGAACAAGATCATCTCC

TTTAAGGAAATGAACCCCCCCGATAACATCAAGGACACCAAGTCCGATAT

CATCTTCTTCCAGCGGTCCGTGCCCGGTCACGATAACAAGATGCAGTTCG

AATCCTCCTCCTACGAGGGCTACTTTTTAGCTTGTGAAAAGGAGAGGGAT

TTATTCAAGCTGATCCTCAAGAAGGAGGACGAGCTGGGCGATCGTTCCAT

CATGTTCACCGTCCAAAACGAGGATAGCGGCACAACCAACACAGTCGCTG

CCTATAACCTCACTTGGAAGAGCACCAACTTCAAAACCATCCTCGAATGG

GAACCCAAACCCGTTAACCAAGTTTACACCGTGCAGATCAGCACCAAGTC

CGGCGACTGGAAGTCCAAATGTTTCTATACCACCGACACCGAGTGCGATC

TCACCGATGAGATCGTGAAAGATGTGAAACAGACCTACCTCGCCCGGGTG

TTTAGCTACCCCGCCGGCAATGTGGAGAGCACTGGTTCCGCTGGCGAGCC

TTTATACGAGAACAGCCCCGAATTTACCCCTTACCTCGAGACCAATTTAG

GACAGCCCACCATCCAAAGCTTTGAGCAAGTTGGCACAAAGGTGAATGTG

ACAGTGGAGGACGAGCGGACTTTAGTGCGGCGGAACAACACCTTTCTCAG

CCTCCGGGATGTGTTCGGCAAAGATTTAATCTACACACTGTATTACTGGA

AGTCCTCTTCCTCCGGCAAGAAGACAGCTAAAACCAACACAAACGAGTTT

TTAATCGACGTGGATAAAGGCGAAAACTACTGTTTCAGCGTGCAAGCTGT

GATCCCCTCCCGGACCGTGAATAGGAAAAGCACCGATAGCCCCGTTGAGT

GCATGGGCCAAGAAAAGGGCGAGTTCCGGGAGAACTGGGTGAACGTCATC

```
AGCGATTTAAAGAAGATCGAAGATTTAATTCAGTCCATGCATATCGACGC
CACTTTATACACAGAATCCGACGTGCACCCCTCTTGTAAGGTGACCGCCA
TGAAATGTTTTTTACTGGAGCTGCAAGTTATCTCTTTAGAGAGCGGAGAC
GCTAGCATCCACGACACCGTGGAGAATTTAATCATTTTAGCCAATAACTC
TTTATCCAGCAACGGCAACGTGACAGAGTCCGGCTGCAAGGAGTGCGAAG
AGCTGGAGGAGAAGAACATCAAGGAGTTTCTGCAATCCTTTGTGCACATT
GTCCAGATGTTCATCAATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                     (SEQ ID NO: 120)
IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQGKSKREKKDRVFTDKTSATVICRKNASISVRAQDRYYSSSWSEW
ASVPCSGGGGSGGGGSGGGGSRNLPVATPDPGMFPCLHHSQNLLRAVSNM
LQKARQTLEFYPCTSEEIDHEDITKDKTSTVEACLPLELTKNESCLNSRE
TSFITNGSCLASRKTSFMMALCLSSIYEDLKMYQVEFKTMNAKLLMDPKR
QIFLDQNMLAVIDELMQALNFNSETVPQKSSLEEPDFYKTKIKLCILLHA
FRIRAVTIDRVMSYLNASITCPPPMSVEHADIWVKSYSLYSRERYICNSG
FKRKAGTSSLTECVLNKATNVAHWTTPSLKCIRSELTQDPAVSVALGQTV
RITCQGDSLRSYYASWYQQKPGQAPVLVIYGKNNRPSGIPDRFSGSSSGN
TASLTITGAQAEDEADYYCNSRDSSGNHVVFGGGTKLTVGHGGGSGGGG
SGGGGSEVQLVESGGGVVRPGGSLRLSCAASGFTFDDYGMSWVRQAPGKG
LEWVSGINWNGGSTGYADSVKGRFTISRDNAKNSLYLQMNSLRAEDTAVY
YCARGRSLLFDYWGQGTLVTVSR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                     (SEQ ID NO: 121)
ATTTGGGAACTGAAGAAGGACGTCTACGTGGTCGAACTGGACTGGTATCC
CGATGCTCCCGGCGAAATGGTGGTGCTCACTTGTGACACCCCCGAAGAAG
ACGGCATCACTTGGACCCTCGATCAGAGCAGCGAGGTGCTGGGCTCCGGA
AAGACCCTCACAATCCAAGTTAAGGAGTTCGGAGACGCTGGCCAATACAC
ATGCCACAAGGGAGGCGAGGTGCTCAGCCATTCCTTATTATTATTACACA
AGAAGGAAGACGGAATCTGGTCCACCGACATTTTAAAAGATCAGAAGGAG
CCCAAGAATAAGACCTTTTTAAGGTGTGAGGCCAAAAACTACAGCGGTCG
TTTCACTTGTTGGTGGCTGACCACCATTTCCACCGATTTAACCTTCTCCG
TGAAAAGCAGCCGGGGAAGCTCCGACCCTCAAGGTGTGACATGTGGAGCC
GCTACCCTCAGCGCTGAGAGGGTTCGTGGCGATAACAAGGAATACGAGTA
CAGCGTGGAGTGCCAAGAAGATAGCGCTTGTCCCGCTGCCGAAGAATCTT
TACCCATTGAGGTGATGGTGGACGCCGTGCACAAACTCAAGTACGAGAAC
TACACCTCCTCCTTCTTTATCCGGGACATCATTAAGCCCGATCCTCCTAA
GAATTTACAGCTGAAGCCTCTCAAAAATAGCCGGCAAGTTGAGGTCTCTT
GGGAATATCCCGACACTTGGAGCACACCCCACAGCTACTTCTCTTTAACC
TTTTGTGTGCAAGTTCAAGGTAAAAGCAAGCGGGAGAAGAAAGACCGGGT
GTTTACCGACAAAACCAGCGCCACCGTCATCTGTCGGAAGAACGCCTCCA
TCAGCGTGAGGGCTCAAGATCGTTATTACTCCAGCAGCTGGTCCGAGTGG
GCCAGCGTGCCTTGTTCCGGCGGTGGAGGATCCGGAGGAGGTGGCTCCGG
CGGCGGAGGATCTCGTAACCTCCCCGTGGCTACCCCCGATCCCGGAATGT
TCCCTTGTTTACACCACAGCCAGAATTTACTGAGGGCCGTGAGCAACATG
CTGCAGAAAGCTAGGCAGACTTTAGAATTTTACCCTTGCACCAGCGAGGA
GATCGACCATGAAGATATCACCAAGGACAAGACATCCACCGTGGAGGCTT
GTTTACCTCTGGAGCTGACAAAGAACGAGTCTTGTCTCAACTCTCGTGAA
ACCAGCTTCATCACAAATGGCTCTTGTTTAGCTTCCCGGAAGACCTCCTT
TATGATGGCTTTATGCCTCAGCTCCATCTACGAGGATTTAAAGATGTACC
AAGTGGAGTTCAAGACCATGAACGCCAAGCTGCTCATGGACCCTAAACGG
CAGATCTTTTTAGACCAGAACATGCTGGCTGTGATTGATGAGCTGATGCA
AGCTTTAAACTTCAACTCCGAGACCGTCCCTCAGAAGTCCTCCCTCGAGG
AGCCCGATTTTTACAAGACAAAGATCAAACTGTGCATTTTACTCCACGCC
TTTAGGATCCGGGCCGTGACCATTGACCGGGTCATGAGCTATTTAAACGC
CAGCATTACATGCCCCCCTCCCATGAGCGTGGAGCACGCCGACATCTGGG
TGAAGAGCTATAGCCTCTACAGCCGGGAGAGGTATATCTGTAACAGCGGC
TTCAAGAGGAAGGCCGGCACCAGCAGCCTCACCGAGTGCGTGCTGAATAA
GGCTACCAACGTGGCTCACTGGACAACACCCTCTTTAAAGTGCATCCGGT
CCGAGCTGACCCAGGACCCTGCTGTGTCCGTGGCTCTGGGCCAGACCGTG
AGGATCACCTGCCAGGGCGACTCCCTGAGGTCCTACTACGCCTCCTGGTA
CCAGCAGAAGCCCGGCCAGGCTCCTGTGCTGGTGATCTACGGCAAGAACA
ACAGGCCCTCCGGCATCCCTGACAGGTTCTCCGGATCCTCCTCCGGCAAC
ACCGCCTCCCTGACCATCACAGGCGCTCAGGCCGAGGACGAGGCTGACTA
CTACTGCAACTCCAGGGACTCCTCCGGCAACCATGTGGTGTTCGGCGGCG
GCACCAAGCTGACCGTGGGCCATGGCGGCGGCGGCTCCGGAGGCGGCGGC
AGCGGCGGAGGAGGATCCGAGGTGCAGCTGGTGGAGTCCGGAGGAGGAGT
GGTGAGGCCTGGAGGCTCCCTGAGGCTGAGCTGTGCTGCCTCCGGCTTCA
CCTTCGACGACTACGGCATGTCCTGGGTGAGGCAGGCTCCTGGAAAGGGC
```

CTGGAGTGGGTGTCCGGCATCAACTGGAACGGCGGATCCACCGGCTACGC

CGATTCCGTGAAGGGCAGGTTCACCATCAGCAGGGACAACGCCAAGAACT

CCCTGTACCTGCAGATGAACTCCCTGAGGGCCGAGGACACCGCCGTGTAC

TACTGCGCCAGGGGCAGGTCCCTGCTGTTCGACTACTGGGGACAGGGCAC

CCTGGTGACCGTGTCCAGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 122)
MKWVTFISLLFLFSSAYSIWELKKDVYVVELDWYPDAPGEMVVLTCDTPE

EDGITWTLDQSSEVLGSGKTLTIQVKEFGDAGQYTCHKGGEVLSHSLLLL

HKKEDGIWSTDILKDQKEPKNKTFLRCEAKNYSGRFTCWWLTTISTDLTF

SVKSSRGSSDPQGVTCGAATLSAERVRGDNKEYEYSVECQEDSACPAAEE

SLPIEVMVDAVHKLKYENYTSSFFIRDIIKPDPPKNLQLKPLKNSRQVEV

SWEYPDTWSTPHSYFSLTFCVQVQGKSKREKKDRVFTDKTSATVICRKNA

SISVRAQDRYYSSSWSEWASVPCSGGGGSGGGGSGGGGSRNLPVATPDPG

MFPCLHHSQNLLRAVSNMLQKARQTLEFYPCTSEEIDHEDITKDKTSTVE

ACLPLELTKNESCLNSRETSFITNGSCLASRKTSFMMALCLSSIYEDLKM

YQVEFKTMNAKLLMDPKRQIFLDQNMLAVIDELMQALNFNSETVPQKSSL

EEPDFYKTKIKLCILLHAFRIRAVTIDRVMSYLNASITCPPPMSVEHADI

WVKSYSLYSRERYICNSGFKRKAGTSSLTECVLNKATNVAHWTTPSLKCI

RSELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVFG

GGTKLTVGHGGGGSGGGGSGGGGSEVQLVESGGGVVRPGGSLRLSCAASG

FTFDDYGMSWVRQAPGKGLEWVSGINWNGGSTGYADSVKGRFTISRDNAK

NSLYLQMNSLRAEDTAVYYCARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 123)
ATGAAATGGGTGACCTTTATTTCTTTACTGTTCCTCTTTAGCAGCGCCTA

CTCCATTTGGGAACTGAAGAAGGACGTCTACGTGGTCGAACTGGACTGGT

ATCCCGATGCTCCCGGCGAAATGGTGGTGCTCACTTGTGACACCCCCGAA

GAAGACGGCATCACTTGGACCCTCGATCAGAGCAGCGAGGTGCTGGGCTC

CGGAAAGACCCTCACAATCCAAGTTAAGGAGTTCGGAGACGCTGGCCAAT

ACACATGCCACAAGGGAGGCGAGGTGCTCAGCCATTCCTTATTATTATTA

CACAAGAAGGAAGACGGAATCTGGTCCACCGACATTTTAAAAGATCAGAA

GGAGCCCAAGAATAAGACCTTTTTAAGGTGTGAGGCCAAAAACTACAGCG

GTCGTTTCACTTGTTGGTGGCTGACCACCATTTCCACCGATTTAACCTTC

TCCGTGAAAAGCAGCCGGGGAAGCTCCGACCCTCAAGGTGTGACATGTGG

AGCCGCTACCCTCAGCGCTGAGAGGGTTCGTGGCGATAACAAGGAATACG

AGTACAGCGTGGAGTGCCAAGAAGATAGCGCTTGTCCCGCTGCCGAAGAA

TCTTTACCCATTGAGGTGATGGTGGACGCCGTGCACAAACTCAAGTACGA

GAACTACACCTCCTCCTTCTTTATCCGGGACATCATTAAGCCCGATCCTC

CTAAGAATTTACAGCTGAAGCCTCTCAAAAATAGCCGGCAAGTTGAGGTC

TCTTGGGAATATCCCGACACTTGGAGCACACCCCACAGCTACTTCTCTTT

AACCTTTTGTGTGCAAGTTCAAGGTAAAAGCAAGCGGGAGAAGAAAGACC

GGGTGTTTACCGACAAAACCAGCGCCACCGTCATCTGTCGGAAGAACGCC

TCCATCAGCGTGAGGGCTCAAGATCGTTATTACTCCAGCAGCTGGTCCGA

GTGGGCCAGCGTGCCTTGTTCCGGCGGTGGAGGATCCGGAGGAGGTGGCT

CCGGCGGCGGAGGATCTCGTAACCTCCCCGTGGCTACCCCCGATCCCGGA

ATGTTCCCTTGTTTACACCACAGCCAGAATTTACTGAGGGCCGTGAGCAA

CATGCTGCAGAAAGCTAGGCAGACTTTAGAATTTTTACCCTTGCACCAGCG

AGGAGATCGACCATGAAGATATCACCAAGGACAAGACATCCACCGTGGAG

GCTTGTTTACCTCTGGAGCTGACAAAGAACGAGTCTTGTCTCAACTCTCG

TGAAACCAGCTTCATCACAAATGGCTCTTGTTTAGCTTCCCGGAAGACCT

CCTTTATGATGGCTTTATGCCTCAGCTCCATCTACGAGGATTTAAAGATG

TACCAAGTGGAGTTCAAGACCATGAACGCCAAGCTGCTCATGGACCCTAA

ACGGCAGATCTTTTTAGACCAGAACATGCTGGCTGTGATTGATGAGCTGA

TGCAAGCTTTAAACTTCAACTCCGAGACCGTCCCTCAGAAGTCCTCCCTC

GAGGAGCCCGATTTTTACAAGACAAAGATCAAACTGTGCATTTTACTCCA

CGCCTTTAGGATCCGGGCCGTGACCATTGACCGGGTCATGAGCTATTTAA

ACGCCAGCATTACATGCCCCCCTCCCATGAGCGTGGAGCACGCCGACATC

TGGGTGAAGAGCTATAGCCTCTACAGCCGGGAGAGGTATATCTGTAACAG

CGGCTTCAAGAGGAAGGCCGGCACCAGCAGCCTCACCGAGTGCGTGCTGA

ATAAGGCTACCAACGTGGCTCACTGGACAACACCCTCTTTAAAGTGCATC

CGGTCCGAGCTGACCCAGGACCCTGCTGTGTCCGTGGCTCTGGGCCAGAC

CGTGAGGATCACCTGCCAGGGCGACTCCCTGAGGTCCTACTACGCCTCCT

GGTACCAGCAGAAGCCCGGCCAGGCTCCTGTGCTGGTGATCTACGGCAAG

AACAACAGGCCCTCCGGCATCCCTGACAGGTTCTCCGGATCCTCCTCCGG

CAACACCGCCTCCCTGACCATCACAGGCGCTCAGGCCGAGGACGAGGCTG

ACTACTACTGCAACTCCAGGGACTCCTCCGGCAACCATGTGGTGTTCGGC

GGCGGCACCAAGCTGACCGTGGGCCATGGCGGCGGCGGCTCCGGAGGCGG

CGGCAGCGGCGGAGGAGGATCCGAGGTGCAGCTGGTGGAGTCCGGAGGAG

GAGTGGTGAGGCCTGGAGGCTCCCTGAGGCTGAGCTGTGCTGCCTCCGGC

TTCACCTTCGACGACTACGGCATGTCCTGGGTGAGGCAGGCTCCTGGAAA

GGGCCTGGAGTGGGTGTCCGGCATCAACTGGAACGGCGGATCCACCGGCT

```
-continued
ACGCCGATTCCGTGAAGGGCAGGTTCACCATCAGCAGGGACAACGCCAAG

AACTCCCTGTACCTGCAGATGAACTCCCTGAGGGCCGAGGACACCGCCGT

GTACTACTGCGCCAGGGGCAGGTCCCTGCTGTTCGACTACTGGGGACAGG

GCACCCTGGTGACCGTGTCCAGG.
```

Exemplary Multi-Chain Chimeric Polypeptides—Type F

In some embodiments of any of the multi-chain chimeric polypeptides described herein, the first target-binding domain and the second targeting-binding domain each independently bind specifically to a receptor for IL-7 (e.g., a soluble human IL-7), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain binds specifically to a receptor IL-7 and the second target-binding domain binds specifically to CD16 or a receptor for IL-21. In some embodiments of any of the multi-chain chimeric polypeptides described herein, the first target-binding domain includes a soluble IL-7 protein. In some embodiments of any of the multi-chain chimeric polypeptides described herein, the soluble IL-7 protein is a soluble human IL-7. In some embodiments of any of the multi-chain chimeric polypeptides described herein, the second antigen-binding domain includes a target-binding domain that binds specifically to CD16. In some embodiments of any of the multi-chain chimeric polypeptides described herein, the second target-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-7 (e.g., a soluble human IL-7).

In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 11)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 95)
GATTGTGATATTGAAGGTAAAGATGGCAAACAATATGAGAGTGTTCTAAT

GGTCAGCATCGATCAATTATTGGACAGCATGAAAGAAATTGGTAGCAATT

GCCTGAATAATGAATTTAACTTTTTTAAAAGACATATCTGTGATGCTAAT

AAGGAAGGTATGTTTTTATTCCGTGCTGCTCGCAAGTTGAGGCAATTTCT

TAAAATGAATAGCACTGGTGATTTTGATCTCCACTTATTAAAAGTTTCAG

AAGGCACAACAATACTGTTGAACTGCACTGGCCAGGTTAAAGGAAGAAAA

CCAGCTGCCCTGGGTGAAGCCCAACCAACAAAGAGTTTGGAAGAAAATAA

ATCTTTAAAGGAACAGAAAAAACTGAATGACTTGTGTTTCCTAAAGAGAC

TATTACAAGAGATAAAAACTTGTTGGAATAAAATTTTGATGGGCACTAAA

GAACAC.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT.

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 94)
CAAGGTCAAGATCGCCACATGATTAGAATGCGTCAACTTATAGATATTGT

TGATCAGCTGAAAAATTATGTGAATGACTTGGTCCCTGAATTTCTGCCAG

CTCCAGAAGATGTAGAGACAAACTGTGAGTGGTCAGCTTTTTCCTGTTTT

CAGAAGGCCCAACTAAAGTCAGCAAATACAGGAAACAATGAAAGGATAAT

CAATGTATCAATTAAAAAGCTGAAGAGGAAACCACCTTCCACAAATGCAG

GGAGAAGACAGAAACACAGACTAACATGCCCTTCATGTGATTCTTATGAG

AAAAAACCACCCAAAGAATTCCTAGAAAGATTCAAATCACTTCTCCAAAA

GATGATTCATCAGCATCTGTCCTCTAGAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

```
CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCGAGGACTCC
```

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 112)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGH.
```

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 113)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCAT.
```

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical or 100% identical) to:

```
                                        (SEQ ID NO: 114)
EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSR.
```

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 115)
GAGGTGCAGCTGGTGGAGTCCGGAGGAGGAGTGGTGAGGCCTGGAGGCTC

CCTGAGGCTGAGCTGTGCTGCCTCCGGCTTCACCTTCGACGACTACGGCA

TGTCCTGGGTGAGGCAGGCTCCTGGAAAGGGCCTGGAGTGGGTGTCCGGC

ATCAACTGGAACGGCGGATCCACCGGCTACGCCGATTCCGTGAAGGGCAG

GTTCACCATCAGCAGGGACAACGCCAAGAACTCCCTGTACCTGCAGATGA

ACTCCCTGAGGGCCGAGGACACCGCCGTGTACTACTGCGCCAGGGGCAGG

TCCCTGCTGTTCGACTACTGGGGACAGGGCACCCTGGTGACCGTGTCCAG

G.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 125)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EHSGTTNTVAAYNLTWKSTNFKTILEWEPKPVNQVYTVQISTKSGDWKSK

CFYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVFG

KDLIYTLYYWKSSSSGKKTAKTNTNEFLIDVDKGENYCFSVQAVIPSRTV

NRKSTDSPVECMGQEKGEFRENWVNVISDLKKIEDLIQSMHIDATLYTES

DVHPSCKVTAMKCFLLELQVISLESGDASIHDTVENLIILANNSLSSNGN

VTESGCKECEELEEKNIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 126)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG
```

-continued
```
AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCATAGCGGCACAACCAACACAGTCGCTGCCTATAACCTCACTTGGAA

GAGCACCAACTTCAAAACCATCCTCGAATGGGAACCCAAACCCGTTAACC

AAGTTTACACCGTGCAGATCAGCACCAAGTCCGGCGACTGGAAGTCCAAA

TGTTTCTATACCACCGACACCGAGTGCGATCTCACCGATGAGATCGTGAA

AGATGTGAAACAGACCTACCTCGCCCGGGTGTTTAGCTACCCCGCCGGCA

ATGTGGAGAGCACTGGTTCCGCTGGCGAGCCTTTATACGAGAACAGCCCC

GAATTTACCCCTTACCTCGAGACCAATTTAGGACAGCCCACCATCCAAAG

CTTTGAGCAAGTTGGCACAAAGGTGAATGTGACAGTGGAGGACGAGCGGA

CTTTAGTGCGGCGGAACAACACCTTTCTCAGCCTCCGGGATGTGTTCGGC

AAAGATTTAATCTACACACTGTATTACTGGAAGTCCTCTTCCTCCGGCAA

GAAGACAGCTAAAACCAACACAAACGAGTTTTTAATCGACGTGGATAAAG

GCGAAAACTACTGTTTCAGCGTGCAAGCTGTGATCCCCTCCCGGACCGTG

AATAGGAAAAGCACCGATAGCCCCGTTGAGTGCATGGGCCAAGAAAAGGG

CGAGTTCCGGGAGAACTGGGTGAACGTCATCAGCGATTTAAAGAAGATCG

AAGATTTAATTCAGTCCATGCATATCGACGCCACTTTATACACAGAATCC

GACGTGCACCCCTCTTGTAAGGTGACCGCCATGAAATGTTTTTTACTGGA

GCTGCAAGTTATCTCTTTAGAGAGCGGAGACGCTAGCATCCACGACACCG

TGGAGAATTTAATCATTTTAGCCAATAACTCTTTATCCAGCAACGGCAAC

GTGACAGAGTCCGGCTGCAAGGAGTGCGAAGAGCTGGAGGAGAAGAACAT

CAAGGAGTTTCTGCAATCCTTTGTGCACATTGTCCAGATGTTCATCAATA

CCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 127)
```
MKWVTFISLLFLFSSAYSDCDIEGKDGKQYESVLMVSIDQLLDSMKEIGS

NCLNNEFNFFKRHICDANKEGMFLFRAARKLRQFLKMNSTGDFDLHLLKV

SEGTTILLNCTGQVKGRKPAALGEAQPTKSLEENKSLKEQKKLNDLCFLK

RLLQEIKTCWNKILMGTKEHSGTTNTVAAYNLTWKSTNFKTILEWEPKPV

NQVYTVQISTKSGDWKSKCFYTTDTECDLTDEIVKDVKQTYLARVFSYPA

GNVESTGSAGEPLYENSPEFTPYLETNLGQPTIQSFEQVGTKVNVTVEDE

RTLVRRNNTFLSLRDVFGKDLIYTLYYWKSSSSGKKTAKTNTNEFLIDVD

KGENYCFSVQAVIPSRTVNRKSTDSPVECMGQEKGEFRENWVNVISDLKK

IEDLIQSMHIDATLYTESDVHPSCKVTAMKCFLLELQVISLESGDASIHD
```

-continued
```
TVENLIILANNSLSSNGNVTESGCKECEELEEKNIKEFLQSFVHIVQMFI

NTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 128)
```
ATGAAGTGGGTGACCTTCATCAGCCTGCTGTTCCTGTTCTCCAGCGCCTA

CTCCGATTGCGACATCGAGGGCAAGGACGGCAAGCAGTACGAGAGCGTGC

TGATGGTGTCCATCGACCAGCTGCTGGACAGCATGAAGGAGATCGGCTCC

AACTGCCTCAACAACGAGTTCAACTTCTTCAAGCGGCACATCTGCGACGC

CAACAAGGAGGGCATGTTCCTGTTCAGGGCCGCCAGGAAACTGCGGCAGT

TCCTGAAGATGAACTCCACCGGCGACTTCGACCTGCACCTGCTGAAGGTG

TCCGAGGGCACCACCATCCTGCTGAACTGCACCGGACAGGTGAAGGGCCG

GAAACCTGCTGCTCTGGGAGAGGCCCAACCCACCAAGAGCCTGGAGGAGA

ACAAGTCCCTGAAGGAGCAGAAGAAGCTGAACGACCTGTGCTTCCTGAAG

AGGCTGCTGCAGGAGATCAAGACCTGCTGGAACAAGATCCTGATGGGCAC

CAAGGAGCATAGCGGCACAACCAACACAGTCGCTGCCTATAACCTCACTT

GGAAGAGCACCAACTTCAAAACCATCCTCGAATGGGAACCCAAACCCGTT

AACCAAGTTTACACCGTGCAGATCAGCACCAAGTCCGGCGACTGGAAGTC

CAAATGTTTCTATACCACCGACACCGAGTGCGATCTCACCGATGAGATCG

TGAAAGATGTGAAACAGACCTACCTCGCCCGGGTGTTTAGCTACCCCGCC

GGCAATGTGGAGAGCACTGGTTCCGCTGGCGAGCCTTTATACGAGAACAG

CCCCGAATTTACCCCTTACCTCGAGACCAATTTAGGACAGCCCACCATCC

AAAGCTTTGAGCAAGTTGGCACAAAGGTGAATGTGACAGTGGAGGACGAG

CGGACTTTAGTGCGGCGGAACAACACCTTTCTCAGCCTCCGGGATGTGTT

CGGCAAAGATTTAATCTACACACTGTATTACTGGAAGTCCTCTTCCTCCG

GCAAGAAGACAGCTAAAACCAACACAAACGAGTTTTTAATCGACGTGGAT

AAAGGCGAAAACTACTGTTTCAGCGTGCAAGCTGTGATCCCCTCCCGGAC

CGTGAATAGGAAAAGCACCGATAGCCCCGTTGAGTGCATGGGCCAAGAAA

AGGGCGAGTTCCGGGAGAACTGGGTGAACGTCATCAGCGATTTAAAGAAG

ATCGAAGATTTAATTCAGTCCATGCATATCGACGCCACTTTATACACAGA

ATCCGACGTGCACCCCTCTTGTAAGGTGACCGCCATGAAATGTTTTTTAC

TGGAGCTGCAAGTTATCTCTTTAGAGAGCGGAGACGCTAGCATCCACGAC

ACCGTGGAGAATTTAATCATTTTAGCCAATAACTCTTTATCCAGCAACGG

CAACGTGACAGAGTCCGGCTGCAAGGAGTGCGAAGAGCTGGAGGAGAAGA

ACATCAAGGAGTTTCTGCAATCCTTTGTGCACATTGTCCAGATGTTCATC

AATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 129)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGHGGGGSGGGGSGGGGSEVQLVESGGGVVRPGGSLRLSCAASGF

TFDDYGMSWVRQAPGKGLEWVSGINWNGGSTGYADSVKGRFTISRDNAKN

SLYLQMNSLRAEDTAVYYCARGRSLLFDYWGQGTLVTVSRITCPPPMSVE

HADIWVKSYSLYSRERYICNSGFKRKAGTSSLTECVLNKATNVAHWTTPS

LKCIRQGQDRHMIRMRQLIDIVDQLKNYVNDLVPEFLPAPEDVETNCEWS

AFSCFQKAQLKSANTGNNERIINVSIKKLKRKPPSTNAGRRQKHRLTCPS

CDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 130)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCATGGCGGCGGCGGCTCCGGAGGCGGCGG

CAGCGGCGGAGGAGGATCCGAGGTGCAGCTGGTGGAGTCCGGAGGAGGAG

TGGTGAGGCCTGGAGGCTCCCTGAGGCTGAGCTGTGCTGCCTCCGGCTTC

ACCTTCGACGACTACGGCATGTCCTGGGTGAGGCAGGCTCCTGGAAAGGG

CCTGGAGTGGGTGTCCGGCATCAACTGGAACGGCGGATCCACCGGCTACG

CCGATTCCGTGAAGGGCAGGTTCACCATCAGCAGGGACAACGCCAAGAAC

TCCCTGTACCTGCAGATGAACTCCCTGAGGGCCGAGGACACCGCCGTGTA

CTACTGCGCCAGGGGCAGGTCCCTGCTGTTCGACTACTGGGGACAGGGCA

CCCTGGTGACCGTGTCCAGGATTACATGCCCCCCTCCCATGAGCGTGGAG

CACGCCGACATCTGGGTGAAGAGCTATAGCCTCTACAGCCGGGAGAGGTA

TATCTGTAACAGCGGCTTCAAGAGGAAGGCCGGCACCAGCAGCCTCACCG

AGTGCGTGCTGAATAAGGCTACCAACGTGGCTCACTGGACAACACCCTCT

TTAAAGTGCATCCGGCAGGGCCAGGACAGGCACATGATCCGGATGAGGCA

GCTCATCGACATCGTCGACCAGCTGAAGAACTACGTGAACGACCTGGTGC

CCGAGTTTCTGCCTGCCCCCGAGGACGTGGAGACCAACTGCGAGTGGTCC

GCCTTCTCCTGCTTTCAGAAGGCCCAGCTGAAGTCCGCCAACACCGGCAA

CAACGAGCGGATCATCAACGTGAGCATCAAGAAGCTGAAGCGGAAGCCTC

CCTCCACAAACGCCGGCAGGAGGCAGAAGCACAGGCTGACCTGCCCCAGC

TGTGACTCCTACGAGAAGAAGCCCCCCAAGGAGTTCCTGGAGAGGTTCAA

GTCCCTGCTGCAGAAGATGATCCATCAGCACCTGTCCTCCAGGACCCACG

GCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 131)
MKWVTFISLLFLFSSAYSSELTQDPAVSVALGQTVRITCQGDSLRSYYAS

WYQQKPGQAPVLVIYGKNNRPSGIPDRFSGSSSGNTASLTITGAQAEDEA

DYYCNSRDSSGNHVVFGGGTKLTVGHGGGGSGGGGSGGGGSEVQLVESGG

GVVRPGGSLRLSCAASGFTFDDYGMSWVRQAPGKGLEWVSGINWNGGSTG

YADSVKGRFTISRDNAKNSLYLQMNSLRAEDTAVYYCARGRSLLFDYWGQ

GTLVTVSRITCPPPMSVEHADIWVKSYSLYSRERYICNSGFKRKAGTSSL

TECVLNKATNVAHWTTPSLKCIRQGQDRHMIRMRQLIDIVDQLKNYVNDL

VPEFLPAPEDVETNCEWSAFSCFQKAQLKSANTGNNERIINVSIKKLKRK

PPSTNAGRRQKHRLTCPSCDSYEKKPPKEFLERFKSLLQKMIHQHLSSRT

HGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 132)
ATGAAGTGGGTGACCTTCATCAGCCTGCTGTTCCTGTTCTCCAGCGCCTA

CTCCTCCGAGCTGACCCAGGACCCTGCTGTGTCCGTGGCTCTGGGCCAGA

CCGTGAGGATCACCTGCCAGGGCGACTCCCTGAGGTCCTACTACGCCTCC

TGGTACCAGCAGAAGCCCGGCCAGGCTCCTGTGCTGGTGATCTACGGCAA

GAACAACAGGCCCTCCGGCATCCCTGACAGGTTCTCCGGATCCTCCTCCG

GCAACACCGCCTCCCTGACCATCACAGGCGCTCAGGCCGAGGACGAGGCT

GACTACTACTGCAACTCCAGGGACTCCTCCGGCAACCATGTGGTGTTCGG

CGGCGGCACCAAGCTGACCGTGGGCCATGGCGGCGGCGGCTCCGGAGGCG

GCGGCAGCGGCGGAGGAGGATCCGAGGTGCAGCTGGTGGAGTCCGGAGGA

GGAGTGGTGAGGCCTGGAGGCTCCCTGAGGCTGAGCTGTGCTGCCTCCGG

CTTCACCTTCGACGACTACGGCATGTCCTGGGTGAGGCAGGCTCCTGGAA

AGGGCCTGGAGTGGGTGTCCGGCATCAACTGGAACGGCGGATCCACCGGC

TACGCCGATTCCGTGAAGGGCAGGTTCACCATCAGCAGGGACAACGCCAA

GAACTCCCTGTACCTGCAGATGAACTCCCTGAGGGCCGAGGACACCGCCG

```
-continued
TGTACTACTGCGCCAGGGGCAGGTCCCTGCTGTTCGACTACTGGGGACAG

GGCACCCTGGTGACCGTGTCCAGGATTACATGCCCCCCTCCCATGAGCGT

GGAGCACGCCGACATCTGGGTGAAGAGCTATAGCCTCTACAGCCGGGAGA

GGTATATCTGTAACAGCGGCTTCAAGAGGAAGGCCGGCACCAGCAGCCTC

ACCGAGTGCGTGCTGAATAAGGCTACCAACGTGGCTCACTGGACAACACC

CTCTTTAAAGTGCATCCGGCAGGGCCAGGACAGGCACATGATCCGGATGA

GGCAGCTCATCGACATCGTCGACCAGCTGAAGAACTACGTGAACGACCTG

GTGCCCGAGTTTCTGCCTGCCCCCGAGGACGTGGAGACCAACTGCGAGTG

GTCCGCCTTCTCCTGCTTTCAGAAGGCCCAGCTGAAGTCCGCCAACACCG

GCAACAACGAGCGGATCATCAACGTGAGCATCAAGAAGCTGAAGCGGAAG

CCTCCCTCCACAAACGCCGGCAGGAGGCAGAAGCACAGGCTGACCTGCCC

CAGCTGTGACTCCTACGAGAAGAAGCCCCCCAAGGAGTTCCTGGAGAGGT

TCAAGTCCCTGCTGCAGAAGATGATCCATCAGCACCTGTCCTCCAGGACC

CACGGCTCCGAGGACTCC.
```

Exemplary Multi-Chain Chimeric Polypeptides—Type G

In some embodiments of any of the multi-chain chimeric polypeptides described herein, the first target-binding domain and the second targeting-binding domain each independently bind specifically to TGFβ (e.g., a human TGFβRII receptor), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain and the second targeting-binding domain each independently bind specifically to TGF-β, CD16, or a receptor for IL-21. In some embodiments of any of the multi-chain chimeric polypeptides described herein, the first target-binding domain binds specifically to a TGF-β and the second target-binding domain binds specifically to CD16 or a receptor of IL-21. In some embodiments of any of the multi-chain chimeric polypeptides described herein, the first target-binding domain is a soluble TGF-β receptor. In some embodiments of any of the multi-chain chimeric polypeptides described herein, soluble TGF-β receptor is a soluble TGFβRII receptor. In some embodiments of any of the multi-chain chimeric polypeptides described herein, the second target-binding domain binds specifically to CD16. In some embodiments of any of the multi-chain chimeric polypeptides described herein, the second antigen-binding domain includes an antigen-binding domain that binds specifically to CD16. In some embodiments of any of the multi-chain chimeric polypeptides described herein, the second antigen-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the second target-binding domain includes a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a TGFβRII receptor (e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 80)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments of these multi-chain chimeric polypeptides, the soluble human TGFβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 94)
CAAGGTCAAGATCGCCACATGATTAGAATGCGTCAACTTATAGATATTGT

TGATCAGCTGAAAAATTATGTGAATGACTTGGTCCCTGAATTTCTGCCAG

CTCCAGAAGATGTAGAGACAAACTGTGAGTGGTCAGCTTTTTCCTGTTTT

CAGAAGGCCCAACTAAAGTCAGCAAATACAGGAAACAATGAAAGGATAAT

CAATGTATCAATTAAAAAGCTGAAGAGGAAACCACCTTCCACAAATGCAG

GGAGAAGACAGAAACACAGACTAACATGCCCTTCATGTGATTCTTATGAG

AAAAAACCACCCAAAGAATTCCTAGAAAGATTCAAATCACTTCTCCAAAA

GATGATTCATCAGCATCTGTCCTCTAGAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC.

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 112)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 113)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 114)
EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 115)
GAGGTGCAGCTGGTGGAGTCCGGAGGAGGAGTGGTGAGGCCTGGAGGCTC

CCTGAGGCTGAGCTGTGCTGCCTCCGGCTTCACCTTCGACGACTACGGCA

TGTCCTGGGTGAGGCAGGCTCCTGGAAAGGGCCTGGAGTGGGTGTCCGGC

ATCAACTGGAACGGCGGATCCACCGGCTACGCCGATTCCGTGAAGGGCAG

GTTCACCATCAGCAGGGACAACGCCAAGAACTCCCTGTACCTGCAGATGA

ACTCCCTGAGGGCCGAGGACACCGCCGTGTACTACTGCGCCAGGGGCAGG

TCCCTGCTGTTCGACTACTGGGGACAGGGCACCCTGGTGACCGTGTCCAG

G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 133)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 134)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACAGCGGCACAACCAACACAGTCGCTGCCTATAACCTCACT

TGGAAGAGCACCAACTTCAAAACCATCCTCGAATGGGAACCCAAACCCGT

TAACCAAGTTTACACCGTGCAGATCAGCACCAAGTCCGGCGACTGGAAGT

CCAAATGTTTCTATACCACCGACACCGAGTGCGATCTCACCGATGAGATC

GTGAAAGATGTGAAACAGACCTACCTCGCCCGGGTGTTTAGCTACCCCGC

CGGCAATGTGGAGAGCACTGGTTCCGCTGGCGAGCCTTTATACGAGAACA

```
GCCCCGAATTTACCCCTTACCTCGAGACCAATTTAGGACAGCCCACCATC

CAAAGCTTTGAGCAAGTTGGCACAAAGGTGAATGTGACAGTGGAGGACGA

GCGGACTTTAGTGCGGCGGAACAACACCTTTCTCAGCCTCCGGGATGTGT

TCGGCAAAGATTTAATCTACACACTGTATTACTGGAAGTCCTCTTCCTCC

GGCAAGAAGACAGCTAAAACCAACACAAACGAGTTTTTAATCGACGTGGA

TAAAGGCGAAAACTACTGTTTCAGCGTGCAAGCTGTGATCCCCTCCCGGA

CCGTGAATAGGAAAAGCACCGATAGCCCCGTTGAGTGCATGGGCCAAGAA

AAGGGCGAGTTCCGGGAGAACTGGGTGAACGTCATCAGCGATTTAAAGAA

GATCGAAGATTTAATTCAGTCCATGCATATCGACGCCACTTTATACACAG

AATCCGACGTGCACCCCTCTTGTAAGGTGACCGCCATGAAATGTTTTTA

CTGGAGCTGCAAGTTATCTCTTTAGAGAGCGGAGACGCTAGCATCCACGA

CACCGTGGAGAATTTAATCATTTTAGCCAATAACTCTTTATCCAGCAACG

GCAACGTGACAGAGTCCGGCTGCAAGGAGTGCGAAGAGCTGGAGGAGAAG

AACATCAAGGAGTTTCTGCAATCCTTTGTGCACATTGTCCAGATGTTCAT

CAATACCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 135)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDSGTTNTVAAYNLTWKSTNFKTILEWEPKPVNQVYTVQISTKSGDW

KSKCFYTTDTECDLTDEIVKDVKQTYLARVFSYPAGNVESTGSAGEPLYE

NSPEFTPYLETNLGQPTIQSFEQVGTKVNVTVEDERTLVRRNNTFLSLRD

VFGKDLIYTLYYWKSSSSGKKTAKTNTNEFLIDVDKGENYCFSVQAVIPS

RTVNRKSTDSPVECMGQEKGEFRENWVNVISDLKKIEDLIQSMHIDATLY

TESDVHPSCKVTAMKCFLLELQVISLESGDASIHDTVENLIILANNSLSS

NGNVTESGCKECEELEEKNIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 136)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACAGCGGCACAACCAACACAGTCGCTGCCTATAACCT

CACTTGGAAGAGCACCAACTTCAAAACCATCCTCGAATGGGAACCCAAAC

CCGTTAACCAAGTTTACACCGTGCAGATCAGCACCAAGTCCGGCGACTGG

AAGTCCAAATGTTTCTATACCACCGACACCGAGTGCGATCTCACCGATGA

GATCGTGAAAGATGTGAAACAGACCTACCTCGCCCGGGTGTTTAGCTACC

CCGCCGGCAATGTGGAGAGCACTGGTTCCGCTGGCGAGCCTTTATACGAG

AACAGCCCCGAATTTACCCCTTACCTCGAGACCAATTTAGGACAGCCCAC

CATCCAAAGCTTTGAGCAAGTTGGCACAAAGGTGAATGTGACAGTGGAGG

ACGAGCGGACTTTAGTGCGGCGGAACAACACCTTTCTCAGCCTCCGGGAT

GTGTTCGGCAAAGATTTAATCTACACACTGTATTACTGGAAGTCCTCTTC

CTCCGGCAAGAAGACAGCTAAAACCAACACAAACGAGTTTTTAATCGACG

TGGATAAAGGCGAAAACTACTGTTTCAGCGTGCAAGCTGTGATCCCCTCC

CGGACCGTGAATAGGAAAAGCACCGATAGCCCCGTTGAGTGCATGGGCCA

AGAAAAGGGCGAGTTCCGGGAGAACTGGGTGAACGTCATCAGCGATTTAA

AGAAGATCGAAGATTTAATTCAGTCCATGCATATCGACGCCACTTTATAC

ACAGAATCCGACGTGCACCCCTCTTGTAAGGTGACCGCCATGAAATGTTT

TTTACTGGAGCTGCAAGTTATCTCTTTAGAGAGCGGAGACGCTAGCATCC

ACGACACCGTGGAGAATTTAATCATTTTAGCCAATAACTCTTTATCCAGC

AACGGCAACGTGACAGAGTCCGGCTGCAAGGAGTGCGAAGAGCTGGAGGA

GAAGAACATCAAGGAGTTTCTGCAATCCTTTGTGCACATTGTCCAGATGT

TCATCAATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 137)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGHGGGGSGGGGSGGGGSEVQLVESGGGVVRPGGSLRLSCAASGF

TFDDYGMSWVRQAPGKGLEWVSGINWNGGSTGYADSVKGRFTISRDNAKN

SLYLQMNSLRAEDTAVYYCARGRSLLFDYWGQGTLVTVSRITCPPPMSVE

HADIWVKSYSLYSRERYICNSGFKRKAGTSSLTECVLNKATNVAHWTTPS

LKCIRQGQDRHMIRMRQLIDIVDQLKNYVNDLVPEFLPAPEDVETNCEWS

AFSCFQKAQLKSANTGNNERIINVSIKKLKRKPPSTNAGRRQKHRLTCPS

CDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 138)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCATGGCGGCGGCGGCTCCGGAGGCGGCGG

CAGCGGCGGAGGAGGATCCGAGGTGCAGCTGGTGGAGTCCGGAGGAGGAG

TGGTGAGGCCTGGAGGCTCCCTGAGGCTGAGCTGTGCTGCCTCCGGCTTC

ACCTTCGACGACTACGGCATGTCCTGGGTGAGGCAGGCTCCTGGAAAGGG

CCTGGAGTGGGTGTCCGGCATCAACTGGAACGGCGGATCCACCGGCTACG

CCGATTCCGTGAAGGGCAGGTTCACCATCAGCAGGGACAACGCCAAGAAC

TCCCTGTACCTGCAGATGAACTCCCTGAGGGCCGAGGACACCGCCGTGTA

CTACTGCGCCAGGGGCAGGTCCCTGCTGTTCGACTACGGGGACAGGGCA

CCCTGGTGACCGTGTCCAGGATTACATGCCCCCCTCCCATGAGCGTGGAG

CACGCCGACATCTGGGTGAAGAGCTATAGCCTCTACAGCCGGGAGAGGTA

TATCTGTAACAGCGGCTTCAAGAGGAAGGCCGGCACCAGCAGCCTCACCG

AGTGCGTGCTGAATAAGGCTACCAACGTGGCTCACTGGACAACACCCTCT

TTAAAGTGCATCCGGCAGGGCCAGGACAGGCACATGATCCGGATGAGGCA

GCTCATCGACATCGTCGACCAGCTGAAGAACTACGTGAACGACCTGGTGC

CCGAGTTTCTGCCTGCCCCCGAGGACGTGGAGACCAACTGCGAGTGGTCC

GCCTTCTCCTGCTTTCAGAAGGCCCAGCTGAAGTCCGCCAACACCGGCAA

-continued
CAACGAGCGGATCATCAACGTGAGCATCAAGAAGCTGAAGCGGAAGCCTC

CCTCCACAAACGCCGGCAGGAGGCAGAAGCACAGGCTGACCTGCCCCAGC

TGTGACTCCTACGAGAAGAAGCCCCCCAAGGAGTTCCTGGAGAGGTTCAA

GTCCCTGCTGCAGAAGATGATCCATCAGCACCTGTCCTCCAGGACCCACG

GCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 139)
MKWVTFISLLFLFSSAYSSELTQDPAVSVALGQTVRITCQGDSLRSYYAS

WYQQKPGQAPVLVIYGKNNRPSGIPDRFSGSSSGNTASLTITGAQAEDEA

DYYCNSRDSSGNHVVFGGGTKLTVGHGGGGSGGGGSGGGGSEVQLVESGG

GVVRPGGSLRLSCAASGFTFDDYGMSWVRQAPGKGLEWVSGINWNGGSTG

YADSVKGRFTISRDNAKNSLYLQMNSLRAEDTAVYYCARGRSLLFDYWGQ

GTLVTVSRITCPPPMSVEHADIWVKSYSLYSRERYICNSGFKRKAGTSSL

TECVLNKATNVAHWTTPSLKCIRQGQDRHMIRMRQLIDIVDQLKNYVNDL

VPEFLPAPEDVETNCEWSAFSCFQKAQLKSANTGNNERIINVSIKKLKRK

PPSTNAGRRQKHRLTCPSCDSYEKKPPKEFLERFKSLLQKMIHQHLSSRT

HGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 140)
ATGAAGTGGGTGACCTTCATCAGCCTGCTGTTCCTGTTCTCCAGCGCCTA

CTCCTCCGAGCTGACCCAGGACCCTGCTGTGTCCGTGGCTCTGGGCCAGA

CCGTGAGGATCACCTGCCAGGGCGACTCCCTGAGGTCCTACTACGCCTCC

TGGTACCAGCAGAAGCCCGGCCAGGCTCCTGTGCTGGTGATCTACGGCAA

GAACAACAGGCCCTCCGGCATCCCTGACAGGTTCTCCGGATCCTCCTCCG

GCAACACCGCCTCCCTGACCATCACAGGCGCTCAGGCCGAGGACGAGGCT

GACTACTACTGCAACTCCAGGGACTCCTCCGGCAACCATGTGGTGTTCGG

CGGCGGCACCAAGCTGACCGTGGGCCATGGCGGCGGCGGCTCCGGAGGCG

GCGGCAGCGGCGGAGGAGGATCCGAGGTGCAGCTGGTGGAGTCCGGAGGA

GGAGTGGTGAGGCCTGGAGGCTCCCTGAGGCTGAGCTGTGCTGCCTCCGG

CTTCACCTTCGACGACTACGGCATGTCCTGGGTGAGGCAGGCTCCTGGAA

AGGGCCTGGAGTGGGTGTCCGGCATCAACTGGAACGGCGGATCCACCGGC

TACGCCGATTCCGTGAAGGGCAGGTTCACCATCAGCAGGGACAACGCCAA

GAACTCCCTGTACCTGCAGATGAACTCCCTGAGGGCCGAGGACACCGCCG

-continued

```
TGTACTACTGCGCCAGGGGCAGGTCCCTGCTGTTCGACTACTGGGGACAG

GGCACCCTGGTGACCGTGTCCAGGATTACATGCCCCCCTCCCATGAGCGT

GGAGCACGCCGACATCTGGGTGAAGAGCTATAGCCTCTACAGCCGGGAGA

GGTATATCTGTAACAGCGGCTTCAAGAGGAAGGCCGGCACCAGCAGCCTC

ACCGAGTGCGTGCTGAATAAGGCTACCAACGTGGCTCACTGGACAACACC

CTCTTTAAAGTGCATCCGGCAGGGCCAGGACAGGCACATGATCCGGATGA

GGCAGCTCATCGACATCGTCGACCAGCTGAAGAACTACGTGAACGACCTG

GTGCCCGAGTTTCTGCCTGCCCCCGAGGACGTGGAGACCAACTGCGAGTG

GTCCGCCTTCTCCTGCTTTCAGAAGGCCCAGCTGAAGTCCGCCAACACCG

GCAACAACGAGCGGATCATCAACGTGAGCATCAAGAAGCTGAAGCGGAAG

CCTCCCTCCACAAACGCCGGCAGGAGGCAGAAGCACAGGCTGACCTGCCC

CAGCTGTGACTCCTACGAGAAGAAGCCCCCCAAGGAGTTCCTGGAGAGGT

TCAAGTCCCTGCTGCAGAAGATGATCCATCAGCACCTGTCCTCCAGGACC

CACGGCTCCGAGGACTCC.
```

Exemplary Multi-Chain Chimeric Polypeptides—Type H

In some embodiments of any of the multi-chain chimeric polypeptides described herein, the first target-binding domain and the second targeting-binding domain each independently bind specifically to a receptor of IL-7. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to a receptor for IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain include a soluble IL-7 (e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 11)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 95)
```
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EHSGTTNTVAAYNLTWKSTNFKTILEWEPKPVNQVYTVQISTKSGDWKSK

CFYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVFG

KDLIYTLYYWKSSSSGKKTAKTNTNEFLIDVDKGENYCFSVQAVIPSRTV

NRKSTDSPVECMGQEKGEFRENWVNVISDLKKIEDLIQSMHIDATLYTES

DVHPSCKVTAMKCFLLELQVISLESGDASIHDTVENLIILANNSLSSNGN

VTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCATAGCGGCACAACCAACACAGTCGCTGCCTATAACCTCACTTGGAA

GAGCACCAACTTCAAAACCATCCTCGAATGGGAACCCAAACCCGTTAACC

AAGTTTACACCGTGCAGATCAGCACCAAGTCCGGCGACTGGAAGTCCAAA

TGTTTCTATACCACCGACACCGAGTGCGATCTCACCGATGAGATCGTGAA

AGATGTGAAACAGACCTACCTCGCCCGGGTGTTTAGCTACCCCGCCGGCA

ATGTGGAGAGCACTGGTTCCGCTGGCGAGCCTTTATACGAGAACAGCCCC

GAATTTACCCCTTACCTCGAGACCAATTTAGGACAGCCCACCATCCAAAG

CTTTGAGCAAGTTGGCACAAAGGTGAATGTGACAGTGGAGGACGAGCGGA

CTTTAGTGCGGCGGAACAACACCTTTCTCAGCCTCCGGGATGTGTTCGGC

AAAGATTTAATCTACACACTGTATTACTGGAAGTCCTCTTCCTCCGGCAA

GAAGACAGCTAAAACCAACACAAACGAGTTTTTAATCGACGTGGATAAAG

GCGAAAACTACTGTTTCAGCGTGCAAGCTGTGATCCCCTCCCGGACCGTG

AATAGGAAAAGCACCGATAGCCCCGTTGAGTGCATGGGCCAAGAAAAGGG

CGAGTTCCGGGAGAACTGGGTGAACGTCATCAGCGATTTAAAGAAGATCG

AAGATTTAATTCAGTCCATGCATATCGACGCCACTTTATACACAGAATCC

GACGTGCACCCCTCTTGTAAGGTGACCGCCATGAAATGTTTTTTACTGGA

GCTGCAAGTTATCTCTTTAGAGAGCGGAGACGCTAGCATCCACGACACCG

TGGAGAATTTAATCATTTTAGCCAATAACTCTTTATCCAGCAACGGCAAC

GTGACAGAGTCCGGCTGCAAGGAGTGCGAAGAGCTGGAGGAGAAGAACAT

CAAGGAGTTTCTGCAATCCTTTGTGCACATTGTCCAGATGTTCATCAATA

CCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 143)
MKWVTFISLLFLFSSAYSDCDIEGKDGKQYESVLMVSIDQLLDSMKEIGS

NCLNNEFNFFKRHICDANKEGMFLFRAARKLRQFLKMNSTGDFDLHLLKV

SEGTTILLNCTGQVKGRKPAALGEAQPTKSLEENKSLKEQKKLNDLCFLK

RLLQEIKTCWNKILMGTKEHSGTTNTVAAYNLTWKSTNFKTILEWEPKPV

NQVYTVQISTKSGDWKSKCFYTTDTECDLTDEIVKDVKQTYLARVFSYPA

GNVESTGSAGEPLYENSPEFTPYLETNLGQPTIQSFEQVGTKVNVTVEDE

RTLVRRNNTFLSLRDVFGKDLIYTLYYWKSSSSGKKTAKTNTNEFLIDVD

KGENYCFSVQAVIPSRTVNRKSTDSPVECMGQEKGEFRENWVNVISDLKK

IEDLIQSMHIDATLYTESDVHPSCKVTAMKCFLLELQVISLESGDASIHD

TVENLIILANNSLSSNGNVTESGCKECEELEEKNIKEFLQSFVHIVQMFI

NTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 144)
ATGAAGTGGGTGACCTTCATCAGCCTGCTGTTCCTGTTCTCCAGCGCCTA

CTCCGATTGCGACATCGAGGGCAAGGACGGCAAGCAGTACGAGAGCGTGC

TGATGGTGTCCATCGACCAGCTGCTGGACAGCATGAAGGAGATCGGCTCC

AACTGCCTCAACAACGAGTTCAACTTCTTCAAGCGGCACATCTGCGACGC

CAACAAGGAGGGCATGTTCCTGTTCAGGGCCGCCAGGAAACTGCGGCAGT

TCCTGAAGATGAACTCCACCGGCGACTTCGACCTGCACCTGCTGAAGGTG

TCCGAGGGCACCACCATCCTGCTGAACTGCACCGGACAGGTGAAGGGCCG

GAAACCTGCTGCTCTGGGAGAGGCCCAACCCACCAAGAGCCTGGAGGAGA

ACAAGTCCCTGAAGGAGCAGAAGAAGCTGAACGACCTGTGCTTCCTGAAG

AGGCTGCTGCAGGAGATCAAGACCTGCTGGAACAAGATCCTGATGGGCAC

CAAGGAGCATAGCGGCACAACCAACACAGTCGCTGCCTATAACCTCACTT

GGAAGAGCACCAACTTCAAAACCATCCTCGAATGGGAACCCAAACCCGTT

AACCAAGTTTACACCGTGCAGATCAGCACCAAGTCCGGCGACTGGAAGTC

CAAATGTTTCTATACCACCGACACCGAGTGCGATCTCACCGATGAGATCG

```
TGAAAGATGTGAAACAGACCTACCTCGCCCGGGTGTTTAGCTACCCCGCC

GGCAATGTGGAGAGCACTGGTTCCGCTGGCGAGCCTTTATACGAGAACAG

CCCCGAATTTACCCCTTACCTCGAGACCAATTTAGGACAGCCCACCATCC

AAAGCTTTGAGCAAGTTGGCACAAAGGTGAATGTGACAGTGGAGGACGAG

CGGACTTTAGTGCGGCGGAACAACACCTTTCTCAGCCTCCGGGATGTGTT

CGGCAAAGATTTAATCTACACACTGTATTACTGGAAGTCCTCTTCCTCCG

GCAAGAAGACAGCTAAAACCAACACAAACGAGTTTTTAATCGACGTGGAT

AAAGGCGAAAACTACTGTTTCAGCGTGCAAGCTGTGATCCCCTCCCGGAC

CGTGAATAGGAAAAGCACCGATAGCCCCGTTGAGTGCATGGGCCAAGAAA

AGGGCGAGTTCCGGGAGAACTGGGTGAACGTCATCAGCGATTTAAAGAAG

ATCGAAGATTTAATTCAGTCCATGCATATCGACGCCACTTTATACACAGA

ATCCGACGTGCACCCCTCTTGTAAGGTGACCGCCATGAAATGTTTTTAC

TGGAGCTGCAAGTTATCTCTTTAGAGAGCGGAGACGCTAGCATCCACGAC

ACCGTGGAGAATTTAATCATTTTAGCCAATAACTCTTTATCCAGCAACGG

CAACGTGACAGAGTCCGGCTGCAAGGAGTGCGAAGAGCTGGAGGAGAAGA

ACATCAAGGAGTTTCTGCAATCCTTTGTGCACATTGTCCAGATGTTCATC

AATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 145)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EHITCPPPMSVEHADIWVKSYSLYSRERYICNSGFKRKAGTSSLTECVLN

KATNVAHWTTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 146)
GATTGTGATATTGAAGGTAAAGATGGCAAACAATATGAGAGTGTTCTAAT

GGTCAGCATCGATCAATTATTGGACAGCATGAAAGAAATTGGTAGCAATT

GCCTGAATAATGAATTTAACTTTTTTAAAAGACATATCTGTGATGCTAAT

AAGGAAGGTATGTTTTTATTCCGTGCTGCTCGCAAGTTGAGGCAATTTCT

TAAAATGAATAGCACTGGTGATTTTGATCTCCACTTATTAAAAGTTTCAG

AAGGCACAACAATACTGTTGAACTGCACTGGCCAGGTTAAAGGAAGAAAA

CCAGCTGCCCTGGGTGAAGCCCAACCAACAAAGAGTTTGGAAGAAAATAA

ATCTTTAAAGGAACAGAAAAAACTGAATGACTTGTGTTTCCTAAAGAGAC

TATTACAAGAGATAAAAACTTGTTGGAATAAAATTTTGATGGGCACTAAA

GAACACATCACGTGCCCTCCCCCCATGTCCGTGGAACACGCAGACATCTG

GGTCAAGAGCTACAGCTTGTACTCCAGGGAGCGGTACATTTGTAACTCTG

GTTTCAAGCGTAAAGCCGGCACGTCCAGCCTGACGGAGTGCGTGTTGAAC

AAGGCCACGAATGTCGCCCACTGGACAACCCCCAGTCTCAAATGCATTAG
A.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 147)
MKWVTFISLLFLFSSAYSDCDIEGKDGKQYESVLMVSIDQLLDSMKEIGS

NCLNNEFNFFKRHICDANKEGMFLFRAARKLRQFLKMNSTGDFDLHLLKV

SEGTTILLNCTGQVKGRKPAALGEAQPTKSLEENKSLKEQKKLNDLCFLK

RLLQEIKTCWNKILMGTKEHITCPPPMSVEHADIWVKSYSLYSRERYICN

SGFKRKAGTSSLTECVLNKATNVAHWTTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 148)
ATGAAGTGGGTGACCTTCATCAGCCTGCTGTTCCTGTTCTCCAGCGCCTA

CTCCGATTGCGACATCGAGGGCAAGGACGGCAAGCAGTACGAGAGCGTGC

TGATGGTGTCCATCGACCAGCTGCTGGACAGCATGAAGGAGATCGGCTCC

AACTGCCTCAACAACGAGTTCAACTTCTTCAAGCGGCACATCTGCGACGC

CAACAAGGAGGGCATGTTCCTGTTCAGGGCCGCCAGGAAACTGCGGCAGT

TCCTGAAGATGAACTCCACCGGCGACTTCGACCTGCACCTGCTGAAGGTG

TCCGAGGGCACCACCATCCTGCTGAACTGCACCGGACAGGTGAAGGGCCG

GAAACCTGCTGCTCTGGGAGAGGCCCAACCCACCAAGAGCCTGGAGGAGA

ACAAGTCCCTGAAGGAGCAGAAGAAGCTGAACGACCTGTGCTTCCTGAAG

AGGCTGCTGCAGGAGATCAAGACCTGCTGGAACAAGATCCTGATGGGCAC

CAAGGAGCATATTACATGCCCCCCTCCCATGAGCGTGGAGCACGCCGACA

TCTGGGTGAAGAGCTATAGCCTCTACAGCCGGGAGAGGTATATCTGTAAC

AGCGGCTTCAAGAGGAAGGCCGGCACCAGCAGCCTCACCGAGTGCGTGCT

GAATAAGGCTACCAACGTGGCTCACTGGACAACACCCTCTTTAAAGTGCA

TCCGG.
```

Exemplary Multi-Chain Chimeric Polypeptides—Type I

In some embodiments of any of the multi-chain chimeric polypeptides described herein, the first target-binding domain and the second targeting-binding domain each independently bind specifically to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain is a soluble TGF-β receptor (e.g., a soluble TGFβRII receptor, e.g., a soluble human TGFβRII). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 80)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to: c (SEQ ID NO: 81).

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.
```

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG
```

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 149)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 150)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACAGCGGCACAACCAACACAGTCGCTGCCTATAACCTCACT

-continued

```
TGGAAGAGCACCAACTTCAAAACCATCCTCGAATGGGAACCCAAACCCGT

TAACCAAGTTTACACCGTGCAGATCAGCACCAAGTCCGGCGACTGGAAGT

CCAAATGTTTCTATACCACCGACACCGAGTGCGATCTCACCGATGAGATC

GTGAAAGATGTGAAACAGACCTACCTCGCCCGGGTGTTTAGCTACCCCGC

CGGCAATGTGGAGAGCACTGGTTCCGCTGGCGAGCCTTTATACGAGAACA

GCCCCGAATTTACCCCTTACCTCGAGACCAATTTAGGACAGCCCACCATC

CAAAGCTTTGAGCAAGTTGGCACAAAGGTGAATGTGACAGTGGAGGACGA

GCGGACTTTAGTGCGGCGGAACAACACCTTTCTCAGCCTCCGGGATGTGT

TCGGCAAAGATTTAATCTACACACTGTATTACTGGAAGTCCTCTTCCTCC

GGCAAGAAGACAGCTAAAACCAACACAAACGAGTTTTTAATCGACGTGGA

TAAAGGCGAAAACTACTGTTTCAGCGTGCAAGCTGTGATCCCCTCCCGGA

CCGTGAATAGGAAAAGCACCGATAGCCCCGTTGAGTGCATGGGCCAAGAA

AAGGGCGAGTTCCGGGAGAACTGGGTGAACGTCATCAGCGATTTAAAGAA

GATCGAAGATTTAATTCAGTCCATGCATATCGACGCCACTTTATACACAG

AATCCGACGTGCACCCCTCTTGTAAGGTGACCGCCATGAAATGTTTTTA

CTGGAGCTGCAAGTTATCTCTTTAGAGAGCGGAGACGCTAGCATCCACGA

CACCGTGGAGAATTTAATCATTTTAGCCAATAACTCTTTATCCAGCAACG

GCAACGTGACAGAGTCCGGCTGCAAGGAGTGCGAAGAGCTGGAGGAGAAG

AACATCAAGGAGTTTCTGCAATCCTTTGTGCACATTGTCCAGATGTTCAT

CAATACCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 151)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDSGTTNTVAAYNLTWKSTNFKTILEWEPKPVNQVYTVQISTKSGDW

KSKCFYTTDTECDLTDEIVKDVKQTYLARVFSYPAGNVESTGSAGEPLYE

NSPEFTPYLETNLGQPTIQSFEQVGTKVNVTVEDERTLVRRNNTFLSLRD

VFGKDLIYTLYYWKSSSSGKKTAKTNTNEFLIDVDKGENYCFSVQAVIPS

RTVNRKSTDSPVECMGQEKGEFRENWVNVISDLKKIEDLIQSMHIDATLY

TESDVHPSCKVTAMKCFLLELQVISLESGDASIHDTVENLIILANNSLSS

NGNVTESGCKECEELEEKNIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 152)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACAGCGGCACAACCAACACAGTCGCTGCCTATAACCT

CACTTGGAAGAGCACCAACTTCAAAACCATCCTCGAATGGGAACCCAAAC

CCGTTAACCAAGTTTACACCGTGCAGATCAGCACCAAGTCCGGCGACTGG

AAGTCCAAATGTTTCTATACCACCGACACCGAGTGCGATCTCACCGATGA

GATCGTGAAAGATGTGAAACAGACCTACCTCGCCCGGGTGTTTAGCTACC

CCGCCGGCAATGTGGAGAGCACTGGTTCCGCTGGCGAGCCTTTATACGAG

AACAGCCCCGAATTTACCCCTTACCTCGAGACCAATTTAGGACAGCCCAC

CATCCAAAGCTTTGAGCAAGTTGGCACAAAGGTGAATGTGACAGTGGAGG

ACGAGCGGACTTTAGTGCGGCGGAACAACACCTTTCTCAGCCTCCGGGAT

GTGTTCGGCAAAGATTTAATCTACACACTGTATTACTGGAAGTCCTCTTC

CTCCGGCAAGAAGACAGCTAAAACCAACACAAACGAGTTTTTAATCGACG

TGGATAAAGGCGAAAACTACTGTTTCAGCGTGCAAGCTGTGATCCCCTCC

CGGACCGTGAATAGGAAAAGCACCGATAGCCCCGTTGAGTGCATGGGCCA

AGAAAAGGGCGAGTTCCGGGAGAACTGGGTGAACGTCATCAGCGATTTAA

AGAAGATCGAAGATTTAATTCAGTCCATGCATATCGACGCCACTTTATAC

ACAGAATCCGACGTGCACCCCTCTTGTAAGGTGACCGCCATGAAATGTTT

TTTACTGGAGCTGCAAGTTATCTCTTTAGAGAGCGGAGACGCTAGCATCC

ACGACACCGTGGAGAATTTAATCATTTTAGCCAATAACTCTTTATCCAGC

AACGGCAACGTGACAGAGTCCGGCTGCAAGGAGTGCGAAGAGCTGGAGGA
```

```
GAAGAACATCAAGGAGTTTCTGCAATCCTTTGTGCACATTGTCCAGATGT

TCATCAATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 153)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDITCPPPMSVEHAD

IWVKSYSLYSRERYICNSGFKRKAGTSSLTECVLNKATNVAHWTTPSLKC

IR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 154)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACATTACATGCCCCCCTCCCATGAGCGTGGAGCACGCCGAC

ATCTGGGTGAAGAGCTATAGCCTCTACAGCCGGGAGAGGTATATCTGTAA
```

```
CAGCGGCTTCAAGAGGAAGGCCGGCACCAGCAGCCTCACCGAGTGCGTGC

TGAATAAGGCTACCAACGTGGCTCACTGGACAACACCCTCTTTAAAGTGC

ATCCGG.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 155)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDITCPPPMSVEHADIWVKSYSLYSRERYICNSGFKRKAGTSSLTEC

VLNKATNVAHWTTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 156)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT
```

```
-continued
GCAGCAGCGACGAATGCAACGACAATATCATCTTTAGCGAGGAATACAAT

ACCAGCAACCCCGACATTACATGCCCCCCTCCCATGAGCGTGGAGCACGC

CGACATCTGGGTGAAGAGCTATAGCCTCTACAGCCGGGAGAGGTATATCT

GTAACAGCGGCTTCAAGAGGAAGGCCGGCACCAGCAGCCTCACCGAGTGC

GTGCTGAATAAGGCTACCAACGTGGCTCACTGGACAACACCCTCTTTAAA

GTGCATCCGG.
```

Exemplary Multi-Chain Chimeric Polypeptides—Type J

In some embodiments of any of the multi-chain chimeric polypeptides described herein, the first target-binding domain and the second targeting-binding domain each independently bind specifically to a receptor of IL-7, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments, the second chimeric polypeptide can include an additional target-binding domain. In some embodiments, the additional target-binding domain and the In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to a receptor for IL-7, and the second target-binding domain binds specifically to a receptor for IL-21 or a receptor for CD137L. In some embodiments, the additional target-binding domain binds specifically to a receptor for IL-21 or a receptor for CD137L.

In some embodiments of these multi-chain chimeric polypeptides, the first target-binding domain is a soluble IL-7 (e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                           (SEQ ID NO: 11)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH.
```

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT.

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain is a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.

In some embodiments of these multi-chain chimeric polypeptides, a soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCGAGGACTCC.

In some embodiments of these multi-chain chimeric polypeptides, the second target-binding domain binds specifically to a receptor for CD137L. In some embodiments of these multi-chain chimeric polypeptides, the second chimeric polypeptide further comprises an additional target-binding domain that binds specifically to a receptor for CD137L. In some embodiments of these multi-chain chimeric polypeptides, the second target-binding domain and/or the additional target-binding domain is a soluble CD137L (e.g., a soluble human CD137L).

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 157)
REGPELSPDDPAGLLDLRQGMFAQLVAQNVLLIDGPLSWYSDPGLAGVSL

TGGLSYKEDTKELVVAKAGVYYVFFQLELRRVVAGEGSGSVSLALHLQPL

RSAAGAAALALTVDLPPASSEARNSAFGFQGRLLHLSAGQRLGVHLHTEA

RARHAWQLTQGATVLGLFRVTPEIPAGLPSPRSE.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 158)
CGCGAGGGTCCCGAGCTTTCGCCCGACGATCCCGCCGGCCTCTTGGACCT

GCGGCAGGGCATGTTTGCGCAGCTGGTGGCCCAAAATGTTCTGCTGATCG

ATGGGCCCCTGAGCTGGTACAGTGACCCAGGCCTGGCAGGCGTGTCCCTG

ACGGGGGGCCTGAGCTACAAAGAGGACACGAAGGAGCTGGTGGTGGCCAA

GGCTGGAGTCTACTATGTCTTCTTTCAACTAGAGCTGCGGCGCGTGGTGG

CCGGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCACC

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTCGG

AA.

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 159)
DPAGLLDLRQGMFAQLVAQNVLLIDGPLSWYSDPGLAGVSLTGGLSYKED

TKELVVAKAGVYYVFFQLELRRVVAGEGSGSVSLALHLQPLRSAAGAAAL

ALTVDLPPASSEARNSAFGFQGRLLHLSAGQRLGVHLHTEARARHAWQLT

QGATVLGLFRVTPEI.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 160)
GATCCCGCCGGCCTCTTGGACCTGCGGCAGGGCATGTTTGCGCAGCTGGT

GGCCCAAAATGTTCTGCTGATCGATGGGCCCCTGAGCTGGTACAGTGACC

CAGGCCTGGCAGGCGTGTCCCTGACGGGGGGCCTGAGCTACAAAGAGGAC

ACGAAGGAGCTGGTGGTGGCCAAGGCTGGAGTCTACTATGTCTTCTTTCA

ACTAGAGCTGCGGCGCGTGGTGGCCGGCGAGGGCTCAGGCTCCGTTTCAC

TTGCGCTGCACCTGCAGCCACTGCGCTCTGCTGCTGGGGCCGCCGCCCTG

GCTTTGACCGTGGACCTGCCACCCGCCTCCTCCGAGGCTCGGAACTCGGC

CTTCGGTTTCCAGGGCCGCTTGCTGCACCTGAGTGCCGGCCAGCGCCTGG

GCGTCCATCTTCACACTGAGGCCAGGGCACGCCATGCCTGGCAGCTTACC

CAGGGCGCCACAGTCTTGGGACTCTTCCGGGTGACCCCCGAAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)
DCDIEGKDGKQYESVLMVSIDQLLDSMKEIGSNCLNNEFNFFKRHICDAN

KEGMPLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EHSGTTNTVAAYNLTWKSTNFKTILEWEPKPVNQVYTVQISTKSGDWKSK

CFYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVFG

KDLIYTLYYWKSSSSGKKTAKTNTNEFLIDVDKGENYCFSVQAVIPSRTV

NRKSTDSPVECMGQEKGEFRENWVNVISDLKKIEDLIQSMHIDATLYTES

DVHPSCKVTAMKCFLLELQVISLESGDASIHDTVENLIILANNSLSSNGN

VTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCATAGCGGCACAACCAACACAGTCGCTGCCTATAACCTCACTTGGAA

GAGCACCAACTTCAAAACCATCCTCGAATGGGAACCCAAACCCGTTAACC

AAGTTTACACCGTGCAGATCAGCACCAAGTCCGGCGACTGGAAGTCCAAA

TGTTTCTATACCACCGACACCGAGTGCGATCTCACCGATGAGATCGTGAA

AGATGTGAAACAGACCTACCTCGCCCGGGTGTTTAGCTACCCCGCCGGCA

ATGTGGAGAGCACTGGTTCCGCTGGCGAGCCTTTATACGAGAACAGCCCC

GAATTTACCCCTTACCTCGAGACCAATTTAGGACAGCCCACCATCCAAAG

CTTTGAGCAAGTTGGCACAAAGGTGAATGTGACAGTGGAGGACGAGCGGA

CTTTAGTGCGGCGGAACAACACCTTTCTCAGCCTCCGGGATGTGTTCGGC

AAAGATTTAATCTACACACTGTATTACTGGAAGTCCTCTTCCTCCGGCAA

GAAGACAGCTAAAACCAACACAAACGAGTTTTTAATCGACGTGGATAAAG

GCGAAAACTACTGTTTCAGCGTGCAAGCTGTGATCCCCTCCCGGACCGTG

AATAGGAAAAGCACCGATAGCCCCGTTGAGTGCATGGGCCAAGAAAAGGG

CGAGTTCCGGGAGAACTGGGTGAACGTCATCAGCGATTTAAAGAAGATCG

AAGATTTAATTCAGTCCATGCATATCGACGCCACTTTATACACAGAATCC

GACGTGCACCCCTCTTGTAAGGTGACCGCCATGAAATGTTTTTTACTGGA

GCTGCAAGTTATCTCTTTAGAGAGCGGAGACGCTAGCATCCACGACACCG

TGGAGAATTTAATCATTTTAGCCAATAACTCTTTATCCAGCAACGGCAAC

GTGACAGAGTCCGGCTGCAAGGAGTGCGAAGAGCTGGAGGAGAAGAACAT

CAAGGAGTTTCTGCAATCCTTTGTGCACATTGTCCAGATGTTCATCAATA

CCTCC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)
MKWVTFISLLFLFSSAYSDCDIEGKDGKQYESVLMVSIDQLLDSMKEIGS

NCLNNEFNFFKRHICDANKEGMPLFRAARKLRQFLKMNSTGDFDLHLLKV

SEGTTILLNCTGQVKGRKPAALGEAQPTKSLEENKSLKEQKKLNDLCFLK

RLLQEIKTCWNKILMGTKEHSGTTNTVAAYNLTWKSTNFKTILEWEPKPV

NQVYTVQISTKSGDWKSKCFYTTDTECDLTDEIVKDVKQTYLARVFSYPA

GNVESTGSAGEPLYENSPEFTPYLETNLGQPTIQSFEQVGTKVNVTVEDE

RTLVRRNNTFLSLRDVFGKDLIYTLYYWKSSSSGKKTAKTNTNEFLIDVD

KGENYCFSVQAVIPSRTVNRKSTDSPVECMGQEKGEFRENWVNVISDLKK

IEDLIQSMHIDATLYTESDVHPSCKVTAMKCFLLELQVISLESGDASIHD

TVENLIILANNSLSSNGNVTESGCKECEELEEKNIKEFLQSFVHIVQMFI

NTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)
ATGAAGTGGGTGACCTTCATCAGCCTGCTGTTCCTGTTCTCCAGCGCCTA

CTCCGATTGCGACATCGAGGGCAAGGACGGCAAGCAGTACGAGAGCGTGC

TGATGGTGTCCATCGACCAGCTGCTGGACAGCATGAAGGAGATCGGCTCC

AACTGCCTCAACAACGAGTTCAACTTCTTCAAGCGGCACATCTGCGACGC

CAACAAGGAGGGCATGTTCCTGTTCAGGGCCGCCAGGAAACTGCGGCAGT

TCCTGAAGATGAACTCCACCGGCGACTTCGACCTGCACCTGCTGAAGGTG

TCCGAGGGCACCACCATCCTGCTGAACTGCACCGGACAGGTGAAGGGCCG

GAAACCTGCTGCTCTGGGAGAGGCCCAACCCACCAAGAGCCTGGAGGAGA

ACAAGTCCCTGAAGGAGCAGAAGAAGCTGAACGACCTGTGCTTCCTGAAG

AGGCTGCTGCAGGAGATCAAGACCTGCTGGAACAAGATCCTGATGGGCAC

CAAGGAGCATAGCGGCACAACCAACACAGTCGCTGCCTATAACCTCACTT

GGAAGAGCACCAACTTCAAAACCATCCTCGAATGGGAACCCAAACCCGTT

AACCAAGTTTACACCGTGCAGATCAGCACCAAGTCCGGCGACTGGAAGTC

CAAATGTTTCTATACCACCGACACCGAGTGCGATCTCACCGATGAGATCG

TGAAAGATGTGAAACAGACCTACCTCGCCCGGGTGTTTAGCTACCCCGCC

GGCAATGTGGAGAGCACTGGTTCCGCTGGCGAGCCTTTATACGAGAACAG

CCCCGAATTTACCCCTTACCTCGAGACCAATTTAGGACAGCCCACCATCC

AAAGCTTTGAGCAAGTTGGCACAAAGGTGAATGTGACAGTGGAGGACGAG

CGGACTTTAGTGCGGCGGAACAACACCTTTCTCAGCCTCCGGGATGTGTT

CGGCAAAGATTTAATCTACACACTGTATTACTGGAAGTCCTCTTCCTCCG

GCAAGAAGACAGCTAAAACCAACACAAACGAGTTTTTAATCGACGTGGAT

AAAGGCGAAAACTACTGTTTCAGCGTGCAAGCTGTGATCCCCTCCCGGAC

CGTGAATAGGAAAAGCACCGATAGCCCCGTTGAGTGCATGGGCCAAGAAA

AGGGCGAGTTCCGGGAGAACTGGGTGAACGTCATCAGCGATTTAAAGAAG

ATCGAAGATTTAATTCAGTCCATGCATATCGACGCCACTTTATACACAGA

ATCCGACGTGCACCCCTCTTGTAAGGTGACCGCCATGAAATGTTTTTTAC

TGGAGCTGCAAGTTATCTCTTTAGAGAGCGGAGACGCTAGCATCCACGAC

ACCGTGGAGAATTTAATCATTTTAGCCAATAACTCTTTATCCAGCAACGG

CAACGTGACAGAGTCCGGCTGCAAGGAGTGCGAAGAGCTGGAGGAGAAGA

ACATCAAGGAGTTTCTGCAATCCTTTGTGCACATTGTCCAGATGTTCATC

AATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 165)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDSITCPPPMSVEHADIWVK

SYSLYSRERYICNSGFKRKAGTSSLTECVLNKATNVAHWTTPSLKCIRGG

GGSGGGGSGGGGSREGPELSPDDPAGLLDLRQGMFAQLVAQNVLLIDGPL

SWYSDPGLAGVSLTGGLSYKEDTKELVVAKAGVYYVFFQLELRRVVAGEG

SGSVSLALHLQPLRSAAGAAALALTVDLPPASSEARNSAFGFQGRLLHLS

AGQRLGVHLHTEARARHAWQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 166)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCCA

TTACATGCCCCCCTCCCATGAGCGTGGAGCACGCCGACATCTGGGTGAAG

AGCTATAGCCTCTACAGCCGGGAGAGGTATATCTGTAACAGCGGCTTCAA

GAGGAAGGCCGGCACCAGCAGCCTCACCGAGTGCGTGCTGAATAAGGCTA

CCAACGTGGCTCACTGGACAACACCCTCTTTAAAGTGCATCCGGGGCGGT

GGAGGATCCGGAGGAGGTGGCTCCGGCGGCGGAGGATCTCGCGAGGGTCC

CGAGCTTTCGCCCGACGATCCCGCCGGCCTCTTGGACCTGCGGCAGGGCA

TGTTTGCGCAGCTGGTGGCCCAAAATGTTCTGCTGATCGATGGGCCCCTG

AGCTGGTACAGTGACCCAGGCCTGGCAGGCGTGTCCCTGACGGGGGCCT

GAGCTACAAAGAGGACACGAAGGAGCTGGTGGTGGCCAAGGCTGGAGTCT

ACTATGTCTTCTTTCAACTAGAGCTGCGGCGCGTGGTGGCCGGCGAGGGC

TCAGGCTCCGTTTCACTTGCGCTGCACCTGCAGCCACTGCGCTCTGCTGC

TGGGGCCGCCGCCCTGGCTTTGACCGTGGACCTGCCACCCGCCTCCTCCG

AGGCTCGGAACTCGGCCTTCGGTTTCCAGGGCCGCTTGCTGCACCTGAGT

GCCGGCCAGCGCCTGGGCGTCCATCTTCACACTGAGGCCAGGGCACGCCA

TGCCTGGCAGCTTACCCAGGGCGCCACAGTCTTGGGACTCTTCCGGGTGA

CCCCCGAAATCCCAGCCGGACTCCCTTCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 167)
MKWVTFISLLFLFSSAYSQGQDRHMIRMRQLIDIVDQLKNYVNDLVPEFL

PAPEDVETNCEWSAFSCFQKAQLKSANTGNNERIINVSIKKLKRKPPSTN

AGRRQKHRLTCPSCDSYEKKPPKEFLERFKSLLQKMIHQHLSSRTHGSED

SITCPPPMSVEHADIWVKSYSLYSRERYICNSGFKRKAGTSSLTECVLNK

ATNVAHWTTPSLKCIRGGGGSGGGGSGGGGSREGPELSPDDPAGLLDLRQ

GMFAQLVAQNVLLIDGPLSWYSDPGLAGVSLTGGLSYKEDTKELVVAKAG

VYYVFFQLELRRVVAGEGSGSVSLALHLQPLRSAAGAAALALTVDLPPAS

SEARNSAFGFQGRLLHLSAGQRLGVHLHTEARARHAWQLTQGATVLGLFR

VTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 168)
ATGAAGTGGGTGACCTTCATCAGCCTGCTGTTCCTGTTCTCCAGCGCCTA

CTCCCAGGGCCAGGACAGGCACATGATCCGGATGAGGCAGCTCATCGACA

TCGTCGACCAGCTGAAGAACTACGTGAACGACCTGGTGCCCGAGTTTCTG

CCTGCCCCCGAGGACGTGGAGACCAACTGCGAGTGGTCCGCCTTCTCCTG

CTTTCAGAAGGCCCAGCTGAAGTCCGCCAACACCGGCAACAACGAGCGGA

TCATCAACGTGAGCATCAAGAAGCTGAAGCGGAAGCCTCCCTCCACAAAC

GCCGGCAGGAGGCAGAAGCACAGGCTGACCTGCCCCAGCTGTGACTCCTA

CGAGAAGAAGCCCCCAAGGAGTTCCTGGAGAGGTTCAAGTCCCTGCTGC

AGAAGATGATCCATCAGCACCTGTCCTCCAGGACCCACGGCTCCGAGGAC

TCCATTACATGCCCCCCTCCCATGAGCGTGGAGCACGCCGACATCTGGGT

GAAGAGCTATAGCCTCTACAGCCGGGAGAGGTATATCTGTAACAGCGGCT

TCAAGAGGAAGGCCGGCACCAGCAGCCTCACCGAGTGCGTGCTGAATAAG

GCTACCAACGTGGCTCACTGGACAACACCCTCTTTAAAGTGCATCCGGGG

CGGTGGAGGATCCGGAGGAGGTGGCTCCGGCGGCGGAGGATCTCGCGAGG

GTCCCGAGCTTTCGCCCGACGATCCCGCCGGCCTCTTGGACCTGCGGCAG

GGCATGTTTGCGCAGCTGGTGGCCCAAAATGTTCTGCTGATCGATGGGCC

CCTGAGCTGGTACAGTGACCCAGGCCTGGCAGGCGTGTCCCTGACGGGGG

GCCTGAGCTACAAGAGGACACGAAGGAGCTGGTGGTGGCCAAGGCTGGA

GTCTACTATGTCTTCTTTCAACTAGAGCTGCGGCGCGTGGTGGCCGGCGA

GGGCTCAGGCTCCGTTTCACTTGCGCTGCACCTGCAGCCACTGCGCTCTG

CTGCTGGGGCCGCCGCCCTGGCTTTGACCGTGGACCTGCCACCCGCCTCC

TCCGAGGCTCGGAACTCGGCCTTCGGTTTCCAGGGCCGCTTGCTGCACCT

GAGTGCCGGCCAGCGCCTGGGCGTCCATCTTCACACTGAGGCCAGGGCAC

GCCATGCCTGGCAGCTTACCCAGGGCGCCACAGTCTTGGGACTCTTCCGG

GTGACCCCCGAAATCCCAGCCGGACTCCCTTCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 169)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDSITCPPPMSVEHADIWVK

SYSLYSRERYICNSGFKRKAGTSSLTECVLNKATNVAHWTTPSLKCIRGG

GGSGGGGSGGGGSDPAGLLDLRQGMFAQLVAQNVLLIDGPLSWYSDPGLA

GVSLTGGLSYKEDTKELVVAKAGVYYVFFQLELRRVVAGEGSGSVSLALH

LQPLRSAAGAAALALTVDLPPASSEARNSAFGFQGRLLHLSAGQRLGVHL

HTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 170)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCGAGGACTCCA

TTACATGCCCCCCTCCCATGAGCGTGGAGCACGCCGACATCTGGGTGAAG

AGCTATAGCCTCTACAGCCGGGAGAGGTATATCTGTAACAGCGGCTTCAA

GAGGAAGGCCGGCACCAGCAGCCTCACCGAGTGCGTGCTGAATAAGGCTA

CCAACGTGGCTCACTGGACAACACCCTCTTTAAAGTGCATCCGGGGCGGT

```
GGAGGATCCGGAGGAGGTGGCTCCGGCGGCGGAGGATCTGATCCCGCCGG

CCTCTTGGACCTGCGGCAGGGCATGTTTGCGCAGCTGGTGGCCCAAATG

TTCTGCTGATCGATGGGCCCCTGAGCTGGTACAGTGACCCAGGCCTGGCA

GGCGTGTCCCTGACGGGGGGCCTGAGCTACAAAGAGGACACGAAGGAGCT

GGTGGTGGCCAAGGCTGGAGTCTACTATGTCTTCTTTCAACTAGAGCTGC

GGCGCGTGGTGGCCGGCGAGGGCTCAGGCTCCGTTTCACTTGCGCTGCAC

CTGCAGCCACTGCGCTCTGCTGCTGGGGCCGCCGCCCTGGCTTTGACCGT

GGACCTGCCACCCGCCTCCTCCGAGGCTCGGAACTCGGCCTTCGGTTTCC

AGGGCCGCTTGCTGCACCTGAGTGCCGGCCAGCGCCTGGGCGTCCATCTT

CACACTGAGGCCAGGGCACGCCATGCCTGGCAGCTTACCCAGGGCGCCAC

AGTCTTGGGACTCTTCCGGGTGACCCCCGAAATC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 171)
MKWVTFISLLFLFSSAYSQGQDRHMIRMRQLIDIVDQLKNYVNDLVPEFL

PAPEDVETNCEWSAFSCFQKAQLKSANTGNNERIINVSIKKLKRKPPSTN

AGRRQKHRLTCPSCDSYEKKPPKEFLERFKSLLQKMIHQHLSSRTHGSED

SITCPPPMSVEHADIWVKSYSLYSRERYICNSGFKRKAGTSSLTECVLNK

ATNVAHWTTPSLKCIRGGGGSGGGGSGGGGSDPAGLLDLRQGMFAQLVAQ

NVLLIDGPLSWYSDPGLAGVSLTGGLSYKEDTKELVVAKAGVYYVFFQLE

LRRVVAGEGSGSVSLALHLQPLRSAAGAAALALTVDLPPASSEARNSAFG

FQGRLLHLSAGQRLGVHLHTEARARHAWQLTQGATVLGLFRVTPEI.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 172)
ATGAAGTGGGTGACCTTCATCAGCCTGCTGTTCCTGTTCTCCAGCGCCTA

CTCCCAGGGCCAGGACAGGCACATGATCCGGATGAGGCAGCTCATCGACA

TCGTCGACCAGCTGAAGAACTACGTGAACGACCTGGTGCCCGAGTTTCTG

CCTGCCCCCGAGGACGTGGAGACCAACTGCGAGTGGTCCGCCTTCTCCTG

CTTTCAGAAGGCCCAGCTGAAGTCCGCCAACACCGGCAACAACGAGCGGA

TCATCAACGTGAGCATCAAGAAGCTGAAGCGGAAGCCTCCCTCCACAAAC

GCCGGCAGGAGGCAGAAGCACAGGCTGACCTGCCCCAGCTGTGACTCCTA

CGAGAAGAAGCCCCCCAAGGAGTTCCTGGAGAGGTTCAAGTCCCTGCTGC

AGAAGATGATCCATCAGCACCTGTCCTCCAGGACCCACGGCTCCGAGGAC

TCCATTACATGCCCCCCTCCCATGAGCGTGGAGCACGCCGACATCTGGGT

GAAGAGCTATAGCCTCTACAGCCGGGAGAGGTATATCTGTAACAGCGGCT

TCAAGAGGAAGGCCGGCACCAGCAGCCTCACCGAGTGCGTGCTGAATAAG

GCTACCAACGTGGCTCACTGGACAACACCCTCTTTAAAGTGCATCCGGGG

CGGTGGAGGATCCGGAGGAGGTGGCTCCGGCGGCGGAGGATCTGATCCCG

CCGGCCTCTTGGACCTGCGGCAGGGCATGTTTGCGCAGCTGGTGGCCCAA

AATGTTCTGCTGATCGATGGGCCCCTGAGCTGGTACAGTGACCCAGGCCT

GGCAGGCGTGTCCCTGACGGGGGGCCTGAGCTACAAAGAGGACACGAAGG

AGCTGGTGGTGGCCAAGGCTGGAGTCTACTATGTCTTCTTTCAACTAGAG

CTGCGGCGCGTGGTGGCCGGCGAGGGCTCAGGCTCCGTTTCACTTGCGCT

GCACCTGCAGCCACTGCGCTCTGCTGCTGGGGCCGCCGCCCTGGCTTTGA

CCGTGGACCTGCCACCCGCCTCCTCCGAGGCTCGGAACTCGGCCTTCGGT

TTCCAGGGCCGCTTGCTGCACCTGAGTGCCGGCCAGCGCCTGGGCGTCCA

TCTTCACACTGAGGCCAGGGCACGCCATGCCTGGCAGCTTACCCAGGGCG

CCACAGTCTTGGGACTCTTCCGGGTGACCCCCGAAATC.
```

Exemplary Multi-Chain Chimeric Polypeptides—Type K

In some embodiments of any of the multi-chain chimeric polypeptides described herein, the first target-binding domain and the second targeting-binding domain each independently bind specifically to a receptor of IL-7 or TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to a receptor for IL-7, and the second target-binding domain binds specifically to TGF-β. In some embodiments of these multi-chain chimeric polypeptides, the first target-binding domain binds specifically to TGF-β, and the second target-binding domain binds specifically to a receptor for IL-7.

In some embodiments of these multi-chain chimeric polypeptides, the first target-binding domain includes a soluble IL-7 protein (e.g., a soluble human IL-7 protein). In some embodiments of these multi-chain chimeric polypeptides, the soluble human IL-7 protein includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 11)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMG

TKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT.

In some embodiments of these multi-chain chimeric polypeptides, the second target-binding domain comprises a target-binding domain that binds specifically to TGF-β. In some embodiments of these multi-chain chimeric polypeptides, the second target-binding domain is a soluble TGF-β receptor (e.g., a soluble TGFβRII receptor, e.g., a soluble human TGFβRII receptor). In some embodiments of these multi-chain chimeric polypeptides, the soluble human TGFβRII includes a first sequence of soluble human TGFβRII and a second sequence of soluble human TGFβRII. In some embodiments of these multi-chain chimeric polypeptides, the soluble human TGFβRII includes a linker disposed between the first sequence of soluble human TGFβRII and the second sequence of soluble human TGFβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 80)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

```
GGTTTTCCACCTGCGACAACCAGAAGTCCTGTATGAGCAACTGCTCCATC
ACCTCCATCTGTGAGAAGCCTCAGGAGGTGTGCGTGGCTGTCTGGCGGAA
GAATGACGAGAATATCACCCTGGAAACCGTCTGCCACGATCCCAAGCTGC
CCTACCACGATTTCATCCTGGAAGACGCCGCCAGCCCTAAGTGCATCATG
AAAGAGAAAAAGAAGCCTGGCGAGACCTTTTTCATGTGCTCCTGCAGCAG
CGACGAATGCAACGACAATATCATCTTTAGCGAGGAATACAATACCAGCA
ACCCCGAC.
```

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 85)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPDGGGGSGGGGSGGGG
SIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSSDECNDNIIFSEEYNTSNPD.
```

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 84)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGAC.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 173)
DCDIEGKDGKQYESVLMVSIDQLLDSMKEIGSNCLNNEFNFFKRHICDAN
KEGMFLFRAARKLRQFLKMNSTGDFDLHLLKVSEGTTILLNCTGQVKGRK
PAALGEAQPTKSLEENKSLKEQKKLNDLCFLKRLLQEIKTCWNKILMGTK
EHSGTTNTVAAYNLTWKSTNFKTILEWEPKPVNQVYTVQISTKSGDWKSK
CFYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVFG
KDLIYTLYYWKSSSSGKKTAKTNTNEFLIDVDKGENYCFSVQAVIPSRTV
NRKSTDSPVECMGQEKGEFRENWVNVISDLKKIEDLIQSMHIDATLYTES
DVHPSCKVTAMKCFLLELQVISLESGDASIHDTVENLIILANNSLSSNGN
VTESGCKECEELEEKNIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 174)
GATTGCGACATCGAGGGCAAGGACGGCAAGCAGTACGAGAGCGTGCTGAT
GGTGTCCATCGACCAGCTGCTGGACAGCATGAAGGAGATCGGCTCCAACT
GCCTCAACAACGAGTTCAACTTCTTCAAGCGGCACATCTGCGACGCCAAC
AAGGAGGGCATGTTCCTGTTCAGGGCCGCCAGGAAACTGCGGCAGTTCCT
GAAGATGAACTCCACCGGCGACTTCGACCTGCACCTGCTGAAGGTGTCCG
AGGGCACCACCATCCTGCTGAACTGCACCGGACAGGTGAAGGGCCGGAAA
CCTGCTGCTCTGGGAGAGGCCCAACCCACCAAGAGCCTGGAGGAGAACAA
GTCCCTGAAGGAGCAGAAGAAGCTGAACGACCTGTGCTTCCTGAAGAGGC
TGCTGCAGGAGATCAAGACCTGCTGGAACAAGATCCTGATGGGCACCAAG
GAGCATAGCGGCACAACCAACACAGTCGCTGCCTATAACCTCACTTGGAA
GAGCACCAACTTCAAAACCATCCTCGAATGGGAACCCAAACCCGTTAACC
AAGTTTACACCGTGCAGATCAGCACCAAGTCCGGCGACTGGAAGTCCAAA
TGTTTCTATACCACCGACACCGAGTGCGATCTCACCGATGAGATCGTGAA
```

```
AGATGTGAAACAGACCTACCTCGCCCGGGTGTTTAGCTACCCCGCCGGCA

ATGTGGAGAGCACTGGTTCCGCTGGCGAGCCTTTATACGAGAACAGCCCC

GAATTTACCCCTTACCTCGAGACCAATTTAGGACAGCCCACCATCCAAAG

CTTTGAGCAAGTTGGCACAAAGGTGAATGTGACAGTGGAGGACGAGCGGA

CTTTAGTGCGGCGGAACAACACCTTTCTCAGCCTCCGGGATGTGTTCGGC

AAAGATTTAATCTACACACTGTATTACTGGAAGTCCTCTTCCTCCGGCAA

GAAGACAGCTAAAACCAACACAAACGAGTTTTTAATCGACGTGGATAAAG

GCGAAAACTACTGTTTCAGCGTGCAAGCTGTGATCCCCTCCCGGACCGTG

AATAGGAAAAGCACCGATAGCCCCGTTGAGTGCATGGGCCAAGAAAAGGG

CGAGTTCCGGGAGAACTGGGTGAACGTCATCAGCGATTTAAAGAAGATCG

AAGATTTAATTCAGTCCATGCATATCGACGCCACTTTATACACAGAATCC

GACGTGCACCCCTCTTGTAAGGTGACCGCCATGAAATGTTTTTTACTGGA

GCTGCAAGTTATCTCTTTAGAGAGCGGAGACGCTAGCATCCACGACACCG

TGGAGAATTTAATCATTTTAGCCAATAACTCTTTATCCAGCAACGGCAAC

GTGACAGAGTCCGGCTGCAAGGAGTGCGAAGAGCTGGAGGAGAAGAACAT

CAAGGAGTTTCTGCAATCCTTTGTGCACATTGTCCAGATGTTCATCAATA

CCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 175)
MKWVTFISLLFLFSSAYSDCDIEGKDGKQYESVLMVSIDQLLDSMKEIGS

NCLNNEFNFFKRHICDANKEGMFLFRAARKLRQFLKMNSTGDFDLHLLKV

SEGTTILLNCTGQVKGRKPAALGEAQPTKSLEENKSLKEQKKLNDLCFLK

RLLQEIKTCWNKILMGTKEHSGTTNTVAAYNLTWKSTNFKTILEWEPKPV

NQVYTVQISTKSGDWKSKCFYTTDTECDLTDEIVKDVKQTYLARVFSYPA

GNVESTGSAGEPLYENSPEFTPYLETNLGQPTIQSFEQVGTKVNVTVEDE

RTLVRRNNTFLSLRDVFGKDLIYTLYYWKSSSSGKKTAKTNTNEFLIDVD

KGENYCFSVQAVIPSRTVNRKSTDSPVECMGQEKGEFRENWVNVISDLKK

IEDLIQSMHIDATLYTESDVHPSCKVTAMKCFLLELQVISLESGDASIHD

TVENLIILANNSLSSNGNVTESGCKECEELEEKNIKEFLQSFVHIVQMFI

NTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 176)
ATGAAGTGGGTGACCTTCATCAGCCTGCTGTTCCTGTTCTCCAGCGCCTA

CTCCGATTGCGACATCGAGGGCAAGGACGGCAAGCAGTACGAGAGCGTGC

TGATGGTGTCCATCGACCAGCTGCTGGACAGCATGAAGGAGATCGGCTCC

AACTGCCTCAACAACGAGTTCAACTTCTTCAAGCGGCACATCTGCGACGC

CAACAAGGAGGGCATGTTCCTGTTCAGGGCCGCCAGGAAACTGCGGCAGT

TCCTGAAGATGAACTCCACCGGCGACTTCGACCTGCACCTGCTGAAGGTG

TCCGAGGGCACCACCATCCTGCTGAACTGCACCGGACAGGTGAAGGGCCG

GAAACCTGCTGCTCTGGGAGAGGCCCAACCCACCAAGAGCCTGGAGGAGA

ACAAGTCCCTGAAGGAGCAGAAGAAGCTGAACGACCTGTGCTTCCTGAAG

AGGCTGCTGCAGGAGATCAAGACCTGCTGGAACAAGATCCTGATGGGCAC

CAAGGAGCATAGCGGCACAACCAACACAGTCGCTGCCTATAACCTCACTT

GGAAGAGCACCAACTTCAAAACCATCCTCGAATGGGAACCCAAACCCGTT

AACCAAGTTTACACCGTGCAGATCAGCACCAAGTCCGGCGACTGGAAGTC

CAAATGTTTCTATACCACCGACACCGAGTGCGATCTCACCGATGAGATCG

TGAAAGATGTGAAACAGACCTACCTCGCCCGGGTGTTTAGCTACCCCGCC

GGCAATGTGGAGAGCACTGGTTCCGCTGGCGAGCCTTTATACGAGAACAG

CCCCGAATTTACCCCTTACCTCGAGACCAATTTAGGACAGCCCACCATCC

AAAGCTTTGAGCAAGTTGGCACAAAGGTGAATGTGACAGTGGAGGACGAG

CGGACTTTAGTGCGGCGGAACAACACCTTTCTCAGCCTCCGGGATGTGTT

CGGCAAAGATTTAATCTACACACTGTATTACTGGAAGTCCTCTTCCTCCG

GCAAGAAGACAGCTAAAACCAACACAAACGAGTTTTTAATCGACGTGGAT

AAAGGCGAAAACTACTGTTTCAGCGTGCAAGCTGTGATCCCCTCCCGGAC

CGTGAATAGGAAAAGCACCGATAGCCCCGTTGAGTGCATGGGCCAAGAAA

AGGGCGAGTTCCGGGAGAACTGGGTGAACGTCATCAGCGATTTAAAGAAG

ATCGAAGATTTAATTCAGTCCATGCATATCGACGCCACTTTATACACAGA

ATCCGACGTGCACCCCTCTTGTAAGGTGACCGCCATGAAATGTTTTTTAC

TGGAGCTGCAAGTTATCTCTTTAGAGAGCGGAGACGCTAGCATCCACGAC

ACCGTGGAGAATTTAATCATTTTAGCCAATAACTCTTTATCCAGCAACGG

CAACGTGACAGAGTCCGGCTGCAAGGAGTGCGAAGAGCTGGAGGAGAAGA

ACATCAAGGAGTTTCTGCAATCCTTTGTGCACATTGTCCAGATGTTCATC

AATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 177)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS
```

-continued

ITSICEKPQEVCVAVWRKNDENITLETVCHDPKLPYHDFILEDAASPKCI

MKEKKKPGETFFMCSCSSDECNDNIIFSEEYNTSNPDITCPPPMSVEHAD

IWVKSYSLYSRERYICNSGFKRKAGTSSLTECVLNKATNVAHWTTPSL

KCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 178)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACATTACATGCCCCCCTCCCATGAGCGTGGAGCACGCCGAC

ATCTGGGTGAAGAGCTATAGCCTCTACAGCCGGGAGAGGTATATCTGTAA

CAGCGGCTTCAAGAGGAAGGCCGGCACCAGCAGCCTCACCGAGTGCGTGC

TGAATAAGGCTACCAACGTGGCTCACTGGACAACACCCTCTTTAAAGTGC

ATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 179)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDITCPPPMSVEHADIWVKSYSLYSRERYICNSGFKRKAGTSSLTEC

VLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 180)
ATGAAGTGGGTGACCTTCATCAGCCTGCTGTTCCTGTTCTCCAGCGCCTA

CTCCATCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACATTACATGCCCCCCTCCCATGAGCGTGGAGCACGC

CGACATCTGGGTGAAGAGCTATAGCCTCTACAGCCGGGAGAGGTATATCT

GTAACAGCGGCTTCAAGAGGAAGGCCGGCACCAGCAGCCTCACCGAGTGC

GTGCTGAATAAGGCTACCAACGTGGCTCACTGGACAACACCCTCTTTAAA

GTGCATCCGG.

Exemplary Multi-Chain Chimeric Polypeptides—Type L

In some embodiments of any of the multi-chain chimeric polypeptides described herein, the first target-binding domain and the second targeting-binding domain each independently bind specifically to TGF-β, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to TGF-β and the second target-binding domain binds specifically to a receptor for IL-21 or a receptor for CD137L.

In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 80)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 81)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA
```

```
                                                  (SEQ ID NO: 84)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.
```

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain includes a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                                  (SEQ ID NO: 78)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                                  (SEQ ID NO: 79)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT
```

---

(column 193)

```
GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT
```

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                                  (SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.
```

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                                  (SEQ ID NO: 85)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.
```

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCGAGGACTCC.
```

In some embodiments of these multi-chain chimeric polypeptides, the second target-binding domain or the additional target-binding domain binds specifically to a receptor for CD137L. In some embodiments of these multi-chain chimeric polypeptides, the second target-binding domain and/or the additional target-binding domain includes a soluble CD137L (e.g., a soluble human CD137L).

In some embodiments of these multi-chain chimeric polypeptides, a soluble CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 157)
REGPELSPDDPAGLLDLRQGMFAQLVAQNVLLIDGPLSWYSDPGLAGVSL

TGGLSYKEDTKELVVAKAGVYYVFFQLELRRVVAGEGSGSVSLALHLQPL

RSAAGAAALALTVDLPPASSEARNSAFGFQGRLLHLSAGQRLGVHLHTEA

RARHAWQLTQGATVLGLFRVTPEIPAGLPSPRSE.
```

In some embodiments of these multi-chain chimeric polypeptides, a soluble CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 158)
CGCGAGGGTCCCGAGCTTTCGCCCGACGATCCCGCCGGCCTCTTGGACCT

GCGGCAGGGCATGTTTGCGCAGCTGGTGGCCCAAAATGTTCTGCTGATCG

ATGGGCCCTGAGCTGGTACAGTGACCCAGGCCTGGCAGGCGTGTCCCTG

ACGGGGGGCCTGAGCTACAAAGAGGACACGAAGGAGCTGGTGGTGGCCAA

GGCTGGAGTCTACTATGTCTTCTTTCAACTAGAGCTGCGGCGCGTGGTGG

CCGGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCACC

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTCGG

AA.
```

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

```
                                        (SEQ ID NO: 159)
DPAGLLDLRQGMFAQLVAQNVLLIDGPLSWYSDPGLAGVSLTGGLSYKED

TKELVVAKAGVYYVFFQLELRRVVAGEGSGSVSLALHLQPLRSAAGAAAL

ALTVDLPPASSEARNSAFGFQGRLLHLSAGQRLGVHLHTEARARHAWQLT

QGATVLGLFRVTPEI.
```

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

```
                                        (SEQ ID NO: 160)
GATCCCGCCGGCCTCTTGGACCTGCGGCAGGGCATGTTTGCGCAGCTGGT

GGCCCAAAATGTTCTGCTGATCGATGGGCCCCTGAGCTGGTACAGTGACC

CAGGCCTGGCAGGCGTGTCCCTGACGGGGGGCCTGAGCTACAAAGAGGAC

ACGAAGGAGCTGGTGGTGGCCAAGGCTGGAGTCTACTATGTCTTCTTTCA

ACTAGAGCTGCGGCGCGTGGTGGCCGGCGAGGGCTCAGGCTCCGTTTCAC

TTGCGCTGCACCTGCAGCCACTGCGCTCTGCTGCTGGGGCCGCCGCCCTG

GCTTTGACCGTGGACCTGCCACCCGCCTCCTCCGAGGCTCGGAACTCGGC

CTTCGGTTTCCAGGGCCGCTTGCTGCACCTGAGTGCCGGCCAGCGCCTGG

GCGTCCATCTTCACACTGAGGCCAGGGCACGCCATGCCTGGCAGCTTACC

CAGGGCGCCACAGTCTTGGGACTCTTCCGGGTGACCCCCGAAATC.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 181)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGACAGCGGCACAACCAACACAGTCGCTGCCTATAACCTCACT
TGGAAGAGCACCAACTTCAAAACCATCCTCGAATGGGAACCCAAACCCGT
TAACCAAGTTTACACCGTGCAGATCAGCACCAAGTCCGGCGACTGGAAGT
CCAAATGTTTCTATACCACCGACACCGAGTGCGATCTCACCGATGAGATC
GTGAAAGATGTGAAACAGACCTACCTCGCCCGGGTGTTTAGCTACCCCGC
CGGCAATGTGGAGAGCACTGGTTCCGCTGGCGAGCCTTTATACGAGAACA
GCCCCGAATTTACCCCTTACCTCGAGACCAATTTAGGACAGCCCACCATC
CAAAGCTTTGAGCAAGTTGGCACAAAGGTGAATGTGACAGTGGAGGACGA
GCGGACTTTAGTGCGGCGGAACAACACCTTTCTCAGCCTCCGGGATGTGT
TCGGCAAAGATTTAATCTACACACTGTATTACTGGAAGTCCTCTTCCTCC
GGCAAGAAGACAGCTAAAACCAACACAAACGAGTTTTTAATCGACGTGGA
TAAAGGCGAAAACTACTGTTTCAGCGTGCAAGCTGTGATCCCCTCCCGGA
CCGTGAATAGGAAAAGCACCGATAGCCCCGTTGAGTGCATGGGCCAAGAA
AAGGGCGAGTTCCGGGAGAACTGGGTGAACGTCATCAGCGATTTAAAGAA
GATCGAAGATTTAATTCAGTCCATGCATATCGACGCCACTTTATACACAG
AATCCGACGTGCACCCCTCTTGTAAGGTGACCGCCATGAAATGTTTTTTA
CTGGAGCTGCAAGTTATCTCTTTAGAGAGCGGAGACGCTAGCATCCACGA
CACCGTGGAGAATTTAATCATTTTAGCCAATAACTCTTTATCCAGCAACG
GCAACGTGACAGAGTCCGGCTGCAAGGAGTGCGAAGAGCTGGAGGAGAAG
AACATCAAGGAGTTTCTGCAATCCTTTGTGCACATTGTCCAGATGTTCAT
CAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
MKWVTFISLLFLFSSAYSIPPHVQKSVNNDMIVTDNNGAVKFPQLCKFCD
VRFSTCDNQKSCMSNCSITSICEKPQEVCVAVWRKNDENITLETVCHDPK
LPYHDFILEDAASPKCIMKEKKKPGETFFMCSCSSDECNDNIIFSEEYNT
SNPDGGGGSGGGGSGGGGSIPPHVQKSVNNDMIVTDNNGAVKFPQLCKFC
DVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYN
TSNPDSGTTNTVAAYNLTWKSTNFKTILEWEPKPVNQVYTVQISTKSGDW
KSKCFYTTDTECDLTDEIVKDVKQTYLARVFSYPAGNVESTGSAGEPLYE
NSPEFTPYLETNLGQPTIQSFEQVGTKVNVTVEDERTLVRRNNTFLSLRD
VFGKDLIYTLYYWKSSSSGKKTAKTNTNEFLIDVDKGENYCFSVQAVIPS
RTVNRKSTDSPVECMGQEKGEFRENWVNVISDLKKIEDLIQSMHIDATLY
TESDVHPSCKVTAMKCFLLELQVISLESGDASIHDTVENLIILANNSLSS
NGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
ATGAAGTGGGTGACCTTCATCAGCCTGCTGTTCCTGTTCTCCAGCGCCTA
CTCCATCCCCCCCCATGTGCAAAAGAGCGTGAACAACGATATGATCGTGA
CCGACAACAACGGCGCCGTGAAGTTTCCCCAGCTCTGCAAGTTCTGCGAT
GTCAGGTTCAGCACCTGCGATAATCAGAAGTCCTGCATGTCCAACTGCAG
CATCACCTCCATCTGCGAGAAGCCCCAAGAAGTGTGCGTGGCCGTGTGGC
GGAAAAATGACGAGAACATCACCCTGGAGACCGTGTGTCACGACCCCAAG
CTCCCTTATCACGACTTCATTCTGGAGGACGCTGCCTCCCCCAAATGCAT
CATGAAGGAGAAGAAGAAGCCCGGAGAGACCTTCTTTATGTGTTCCTGTA
GCAGCGACGAGTGTAACGACAACATCATCTTCAGCGAAGAGTACAACACC
AGCAACCCTGATGGAGGTGGCGGATCCGGAGGTGGAGGTTCTGGTGGAGG
TGGGAGTATTCCTCCCCACGTGCAGAAGAGCGTGAATAATGACATGATCG
TGACCGATAACAATGGCGCCGTGAAATTTCCCCAGCTGTGCAAATTCTGC
GATGTGAGGTTTTCCACCTGCGACAACCAGAAGTCCTGTATGAGCAACTG
CTCCATCACCTCCATCTGTGAGAAGCCTCAGGAGGTGTGCGTGGCTGTCT
GGCGGAAGAATGACGAGAATATCACCCTGGAAACCGTCTGCCACGATCCC
AAGCTGCCCTACCACGATTTCATCCTGGAAGACGCCGCCAGCCCTAAGTG

-continued
```
CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACAGCGGCACAACCAACACAGTCGCTGCCTATAACCT

CACTTGGAAGAGCACCAACTTCAAAACCATCCTCGAATGGGAACCCAAAC

CCGTTAACCAAGTTTACACCGTGCAGATCAGCACCAAGTCCGGCGACTGG

AAGTCCAAATGTTTCTATACCACCGACACCGAGTGCGATCTCACCGATGA

GATCGTGAAAGATGTGAAACAGACCTACCTCGCCCGGGTGTTTAGCTACC

CCGCCGGCAATGTGGAGAGCACTGGTTCCGCTGGCGAGCCTTTATACGAG

AACAGCCCCGAATTTACCCCTTACCTCGAGACCAATTTAGGACAGCCCAC

CATCCAAAGCTTTGAGCAAGTTGGCACAAAGGTGAATGTGACAGTGGAGG

ACGAGCGGACTTTAGTGCGGCGGAACAACACCTTTCTCAGCCTCCGGGAT

GTGTTCGGCAAAGATTTAATCTACACACTGTATTACTGGAAGTCCTCTTC

CTCCGGCAAGAAGACAGCTAAAACCAACACAAACGAGTTTTTAATCGACG

TGGATAAAGGCGAAAACTACTGTTTCAGCGTGCAAGCTGTGATCCCCTCC

CGGACCGTGAATAGGAAAAGCACCGATAGCCCCGTTGAGTGCATGGGCCA

AGAAAAGGGCGAGTTCCGGGAGAACTGGGTGAACGTCATCAGCGATTTAA

AGAAGATCGAAGATTTAATTCAGTCCATGCATATCGACGCCACTTTATAC

ACAGAATCCGACGTGCACCCCTCTTGTAAGGTGACCGCCATGAAATGTTT

TTTACTGGAGCTGCAAGTTATCTCTTTAGAGAGCGGAGACGCTAGCATCC

ACGACACCGTGGAGAATTTAATCATTTTAGCCAATAACTCTTTATCCAGC

AACGGCAACGTGACAGAGTCCGGCTGCAAGGAGTGCGAAGAGCTGGAGGA

GAAGAACATCAAGGAGTTTCTGCAATCCTTTGTGCACATTGTCCAGATGT

TCATCAATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 185)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDSITCPPPMSVEHADIWVK

SYSLYSRERYICNSGFKRKAGTSSLTECVLNKATNVAHWTTPSLKCIRGG

GGSGGGGSGGGGSREGPELSPDDPAGLLDLRQGMFAQLVAQNVLLIDGPL

SWYSDPGLAGVSLTGGLSYKEDTKELVVAKAGVYYVFFQLELRRVVAGEG

SGSVSLALHLQPLRSAAGAAALALTVDLPPASSEARNSAFGFQGRLLHLS

AGQRLGVHLHTEARARHAWQLTQGATVLGLFRVTPEIPAGLPSPRSE.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 186)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCCA

TTACATGCCCCCCTCCCATGAGCGTGGAGCACGCCGACATCTGGGTGAAG

AGCTATAGCCTCTACAGCCGGGAGAGGTATATCTGTAACAGCGGCTTCAA

GAGGAAGGCCGGCACCAGCAGCCTCACCGAGTGCGTGCTGAATAAGGCTA

CCAACGTGGCTCACTGGACAACACCCTCTTTAAAGTGCATCCGGGGCGGT

GGAGGATCCGGAGGAGGTGGCTCCGGCGGCGGAGGATCTCGCGAGGGTCC

CGAGCTTTCGCCCGACGATCCCGCCGGCCTCTTGGACCTGCGGCAGGGCA

TGTTTGCGCAGCTGGTGGCCCAAAATGTTCTGCTGATCGATGGGCCCCTG

AGCTGGTACAGTGACCCAGGCCTGGCAGGCGTGTCCCTGACGGGGGGCCT

GAGCTACAAAGAGGACACGAAGGAGCTGGTGGTGGCCAAGGCTGGAGTCT

ACTATGTCTTCTTTCAACTAGAGCTGCGGCGCGTGGTGGCCGGCGAGGGC

TCAGGCTCCGTTTCACTTGCGCTGCACCTGCAGCCACTGCGCTCTGCTGC

TGGGGCCGCCGCCCTGGCTTTGACCGTGGACCTGCCACCCGCCTCCTCCG

AGGCTCGGAACTCGGCCTTCGGTTTCCAGGGCCGCTTGCTGCACCTGAGT

GCCGGCCAGCGCCTGGGCGTCCATCTTCACACTGAGGCCAGGGCACGCCA

TGCCTGGCAGCTTACCCAGGGCGCCACAGTCTTGGGACTCTTCCGGGTGA

CCCCCGAAATCCCAGCCGGACTCCCTTCACCGAGGTCGGAA.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 187)
MKWVTFISLLFLFSSAYSQGQDRHMIRMRQLIDIVDQLKNYVNDLVPEFL

PAPEDVETNCEWSAFSCFQKAQLKSANTGNNERIINVSIKKLKRKPPSTN

AGRRQKHRLTCPSCDSYEKKPPKEFLERFKSLLQKMIHQHLSSRTHGSED

SITCPPPMSVEHADIWVKSYSLYSRERYICNSGFKRKAGTSSLTECVLNK

ATNVAHWTTPSLKCIRGGGGSGGGGSGGGGSREGPELSPDDPAGLLDLRQ

GMFAQLVAQNVLLIDGPLSWYSDPGLAGVSLTGGLSYKEDTKELVVAKAG

VYYVFFQLELRRVVAGEGSGSVSLALHLQPLRSAAGAAALALTVDLPPAS

SEARNSAFGFQGRLLHLSAGQRLGVHLHTEARARHAWQLTQGATVLGLFR

VTPEIPAGLPSPRSE.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
ATGAAGTGGGTGACCTTCATCAGCCTGCTGTTCCTGTTCTCCAGCGCCTA
CTCCCAGGGCCAGGACAGGCACATGATCCGGATGAGGCAGCTCATCGACA
TCGTCGACCAGCTGAAGAACTACGTGAACGACCTGGTGCCCGAGTTTCTG
CCTGCCCCCGAGGACGTGGAGACCAACTGCGAGTGGTCCGCCTTCTCCTG
CTTTCAGAAGGCCCAGCTGAAGTCCGCCAACACCGGCAACAACGAGCGGA
TCATCAACGTGAGCATCAAGAAGCTGAAGCGGAAGCCTCCCTCCACAAAC
GCCGGCAGGAGGCAGAAGCACAGGCTGACCTGCCCCAGCTGTGACTCCTA
CGAGAAGAAGCCCCCCAAGGAGTTCCTGGAGAGGTTCAAGTCCCTGCTGC
AGAAGATGATCCATCAGCACCTGTCCTCCAGGACCCACGGCTCCGAGGAC
TCCATTACATGCCCCCCTCCCATGAGCGTGGAGCACGCCGACATCTGGGT
GAAGAGCTATAGCCTCTACAGCCGGGAGAGGTATATCTGTAACAGCGGCT
TCAAGAGGAAGGCCGGCACCAGCAGCCTCACCGAGTGCGTGCTGAATAAG
GCTACCAACGTGGCTCACTGGACAACACCCTCTTTAAAGTGCATCCGGGG
CGGTGGAGGATCCGGAGGAGGTGGCTCCGGCGGCGGAGGATCTCGCGAGG
GTCCCGAGCTTTCGCCCGACGATCCCGCCGGCCTCTTGGACCTGCGGCAG
GGCATGTTTGCGCAGCTGGTGGCCCAAAATGTTCTGCTGATCGATGGGCC
CCTGAGCTGGTACAGTGACCCAGGCCTGGCAGGCGTGTCCCTGACGGGGG
GCCTGAGCTACAAAGAGGACACGAAGGAGCTGGTGGTGGCCAAGGCTGGA
GTCTACTATGTCTTCTTTCAACTAGAGCTGCGGCGCGTGGTGGCCGGCGA
GGGCTCAGGCTCCGTTTCACTTGCGCTGCACCTGCAGCCACTGCGCTCTG
CTGCTGGGGCCGCCGCCCTGGCTTTGACCGTGGACCTGCCACCCGCCTCC
TCCGAGGCTCGGAACTCGGCCTTCGGTTTCCAGGGCCGCTTGCTGCACCT
GAGTGCCGGCCAGCGCCTGGGCGTCCATCTTCACACTGAGGCCAGGGCAC
GCCATGCCTGGCAGCTTACCCAGGGCGCCACAGTCTTGGGACTCTTCCGG
GTGACCCCCGAAATCCCAGCCGGACTCCCTTCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 189)
QGQDRHMIRMRQLIDIVDQLKNYVNDLVPEFLPAPEDVETNCEWSAFSCF
QKAQLKSANTGNNERIINVSIKKLKRKPPSTNAGRRQKHRLTCPSCDSYE
KKPPKEFLERFKSLLQKMIHQHLSSRTHGSEDSITCPPPMSVEHADIWVK
SYSLYSRERYICNSGFKRKAGTSSLTECVLNKATNVAHWTTPSLKCIRGG
GGSGGGGSGGGGSDPAGLLDLRQGMFAQLVAQNVLLIDGPLSWYSDPGLA
GVSLTGGLSYKEDTKELVVAKAGVYYVFFQLELRRVVAGEGSGSVSLALH

-continued
LQPLRSAAGAAALALTVDLPPASSEARNSAFGFQGRLLHLSAGQRLGVHL
HTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 190)
CAGGGCCAGGACAGGCACATGATCCGGATGAGGCAGCTCATCGACATCGT
CGACCAGCTGAAGAACTACGTGAACGACCTGGTGCCCGAGTTTCTGCCTG
CCCCCGAGGACGTGGAGACCAACTGCGAGTGGTCCGCCTTCTCCTGCTTT
CAGAAGGCCCAGCTGAAGTCCGCCAACACCGGCAACAACGAGCGGATCAT
CAACGTGAGCATCAAGAAGCTGAAGCGGAAGCCTCCCTCCACAAACGCCG
GCAGGAGGCAGAAGCACAGGCTGACCTGCCCCAGCTGTGACTCCTACGAG
AAGAAGCCCCCAAGGAGTTCCTGGAGAGGTTCAAGTCCCTGCTGCAGAA
GATGATCCATCAGCACCTGTCCTCCAGGACCCACGGCTCCGAGGACTCCA
TTACATGCCCCCCTCCCATGAGCGTGGAGCACGCCGACATCTGGGTGAAG
AGCTATAGCCTCTACAGCCGGGAGAGGTATATCTGTAACAGCGGCTTCAA
GAGGAAGGCCGGCACCAGCAGCCTCACCGAGTGCGTGCTGAATAAGGCTA
CCAACGTGGCTCACTGGACAACACCCTCTTTAAAGTGCATCCGGGGCGGT
GGAGGATCCGGAGGAGGTGGCTCCGGCGGCGGAGGATCTGATCCCGCCGG
CCTCTTGGACCTGCGGCAGGGCATGTTTGCGCAGCTGGTGGCCCAAAATG
TTCTGCTGATCGATGGGCCCCTGAGCTGGTACAGTGACCCAGGCCTGGCA
GGCGTGTCCCTGACGGGGGCCTGAGCTACAAAGAGGACACGAAGGAGCT
GGTGGTGGCCAAGGCTGGAGTCTACTATGTCTTCTTTCAACTAGAGCTGC
GGCGCGTGGTGGCCGGCGAGGGCTCAGGCTCCGTTTCACTTGCGCTGCAC
CTGCAGCCACTGCGCTCTGCTGCTGGGGCCGCCGCCCTGGCTTTGACCGT
GGACCTGCCACCCGCCTCCTCCGAGGCTCGGAACTCGGCCTTCGGTTTCC
AGGGCCGCTTGCTGCACCTGAGTGCCGGCCAGCGCCTGGGCGTCCATCTT
CACACTGAGGCCAGGGCACGCCATGCCTGGCAGCTTACCCAGGGCGCCAC
AGTCTTGGGACTCTTCCGGGTGACCCCCGAAATC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 191)
MKWVTFISLLFLFSSAYSQGQDRHMIRMRQLIDIVDQLKNYVNDLVPEFL
PAPEDVETNCEWSAFSCFQKAQLKSANTGNNERIINVSIKKLKRKPPSTN
AGRRQKHRLTCPSCDSYEKKPPKEFLERFKSLLQKMIHQHLSSRTHGSED
SITCPPPMSVEHADIWVKSYSLYSRERYICNSGFKRKAGTSSLTECVLNK

-continued

ATNVAHWTTPSLKCIRGGGGSGGGGSGGGGSDPAGLLDLRQGMFAQLVAQ

NVLLIDGPLSWYSDPGLAGVSLTGGLSYKEDTKELVVAKAGVYYVFFQLE

LRRVVAGEGSGSVSLALHLQPLRSAAGAAALALTVDLPPASSEARNSAFG

FQGRLLHLSAGQRLGVHLHTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 192)
ATGAAGTGGGTGACCTTCATCAGCCTGCTGTTCCTGTTCTCCAGCGCCTA

CTCCCAGGGCCAGGACAGGCACATGATCCGGATGAGGCAGCTCATCGACA

TCGTCGACCAGCTGAAGAACTACGTGAACGACCTGGTGCCCGAGTTTCTG

CCTGCCCCCGAGGACGTGGAGACCAACTGCGAGTGGTCCGCCTTCTCCTG

CTTTCAGAAGGCCCAGCTGAAGTCCGCCAACACCGGCAACAACGAGCGGA

TCATCAACGTGAGCATCAAGAAGCTGAAGCGGAAGCCTCCCTCCACAAAC

GCCGGCAGGAGGCAGAAGCACAGGCTGACCTGCCCCAGCTGTGACTCCTA

CGAGAAGAAGCCCCCCAAGGAGTTCCTGGAGAGGTTCAAGTCCCTGCTGC

AGAAGATGATCCATCAGCACCTGTCCTCCAGGACCCACGGCTCCGAGGAC

TCCATTACATGCCCCCCTCCCATGAGCGTGGAGCACGCCGACATCTGGGT

GAAGAGCTATAGCCTCTACAGCCGGGAGAGGTATATCTGTAACAGCGGCT

TCAAGAGGAAGGCCGGCACCAGCAGCCTCACCGAGTGCGTGCTGAATAAG

GCTACCAACGTGGCTCACTGGACAACACCCTCTTTAAAGTGCATCCGGGG

CGGTGGAGGATCCGGAGGAGGTGGCTCCGGCGGCGGAGGATCTGATCCCG

CCGGCCTCTTGGACCTGCGGCAGGGCATGTTTGCGCAGCTGGTGGCCCAA

AATGTTCTGCTGATCGATGGGCCCCTGAGCTGGTACAGTGACCCAGGCCT

GGCAGGCGTGTCCCTGACGGGGGGCCTGAGCTACAAAGAGGACACGAAGG

AGCTGGTGGTGGCCAAGGCTGGAGTCTACTATGTCTTCTTTCAACTAGAG

CTGCGGCGCGTGGTGGCCGGCGAGGGCTCAGGCTCCGTTTCACTTGCGCT

GCACCTGCAGCCACTGCGCTCTGCTGCTGGGGCCGCCGCCCTGGCTTTGA

CCGTGGACCTGCCACCCGCCTCCTCCGAGGCTCGGAACTCGGCCTTCGGT

TTCCAGGGCCGCTTGCTGCACCTGAGTGCCGGCCAGCGCCTGGGCGTCCA

TCTTCACACTGAGGCCAGGGCACGCCATGCCTGGCAGCTTACCCAGGGCG

CCACAGTCTTGGGACTCTTCCGGGTGACCCCCGAAATC.

Exemplary Multi-Chain Chimeric Polypeptides—Type M

In some embodiments of any of the multi-chain chimeric polypeptides described herein, the first target-binding domain and the second targeting-binding domain each independently bind specifically to TGF-β or a receptor of IL-21. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or a receptor for IL-21. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 80)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

-continued
```
CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.
```

In some embodiments of these multi-chain chimeric polypeptides, the second target-binding domain binds specifically to a receptor for IL-21. In some embodiments of these multi-chain chimeric polypeptides, the second target-binding domain includes a soluble IL-21 (e.g., a human soluble IL-21). In some embodiments of these multi-chain chimeric polypeptides, the soluble IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 78)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.
```

In some embodiments of these multi-chain chimeric polypeptides, the soluble IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                       (SEQ ID NO: 79)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCGAGGACTCC.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 193)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                      (SEQ ID NO: 194)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACAGCGGCACAACCAACACAGTCGCTGCCTATAACCTCACT
```

-continued
```
TGGAAGAGCACCAACTTCAAAACCATCCTCGAATGGGAACCCAAACCCGT
TAACCAAGTTTACACCGTGCAGATCAGCACCAAGTCCGGCGACTGGAAGT
CCAAATGTTTCTATACCACCGACACCGAGTGCGATCTCACCGATGAGATC
GTGAAAGATGTGAAACAGACCTACCTCGCCCGGGTGTTTAGCTACCCCGC
CGGCAATGTGGAGAGCACTGGTTCCGCTGGCGAGCCTTTATACGAGAACA
GCCCCGAATTTACCCCTTACCTCGAGACCAATTTAGGACAGCCCACCATC
CAAAGCTTTGAGCAAGTTGGCACAAAGGTGAATGTGACAGTGGAGGACGA
GCGGACTTTAGTGCGGCGGAACAACACCTTTCTCAGCCTCCGGGATGTGT
TCGGCAAAGATTTAATCTACACACTGTATTACTGGAAGTCCTCTTCCTCC
GGCAAGAAGACAGCTAAAACCAACACAAACGAGTTTTTAATCGACGTGGA
TAAAGGCGAAAACTACTGTTTCAGCGTGCAAGCTGTGATCCCCTCCCGGA
CCGTGAATAGGAAAAGCACCGATAGCCCCGTTGAGTGCATGGGCCAAGAA
AAGGGCGAGTTCCGGGAGAACTGGGTGAACGTCATCAGCGATTTAAAGAA
GATCGAAGATTTAATTCAGTCCATGCATATCGACGCCACTTTATACACAG
AATCCGACGTGCACCCCTCTTGTAAGGTGACCGCCATGAAATGTTTTTTA
CTGGAGCTGCAAGTTATCTCTTTAGAGAGCGGAGACGCTAGCATCCACGA
CACCGTGGAGAATTTAATCATTTTAGCCAATAACTCTTTATCCAGCAACG
GCAACGTGACAGAGTCCGGCTGCAAGGAGTGCGAAGAGCTGGAGGAGAAG
AACATCAAGGAGTTTCTGCAATCCTTTGTGCACATTGTCCAGATGTTCAT
CAATACCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 195)
MKWVTFISLLFLFSSAYSIPPHVQKSVNNDMIVTDNNGAVKFPQLCKFCD
VRFSTCDNQKSCMSNCSITSICEKPQEVCVAVWRKNDENITLETVCHDPK
LPYHDFILEDAASPKCIMKEKKKPGETFFMCSCSSDECNDNIIFSEEYNT
SNPDGGGGSGGGGSGGGGSIPPHVQKSVNNDMIVTDNNGAVKFPQLCKFC
DVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYN
TSNPDSGTTNTVAAYNLTWKSTNFKTILEWEPKPVNQVYTVQISTKSGDW
KSKCFYTTDTECDLTDEIVKDVKQTYLARVFSYPAGNVESTGSAGEPLYE
NSPEFTPYLETNLGQPTIQSFEQVGTKVNVTVEDERTLVRRNNTFLSLRD
VFGKDLIYTLYYWKSSSSGKKTAKTNTNEFLIDVDKGENYCFSVQAVIPS
RTVNRKSTDSPVECMGQEKGEFRENWVNVISDLKKIEDLIQSMHIDATLY
TESDVHPSCKVTAMKCFLLELQVISLESGDASIHDTVENLIILANNSLSS
NGNVTESGCKECEELEEKNIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 196)
ATGAAGTGGGTGACCTTCATCAGCCTGCTGTTCCTGTTCTCCAGCGCCTA
CTCCATCCCCCCCCATGTGCAAAAGAGCGTGAACAACGATATGATCGTGA
CCGACAACAACGGCGCCGTGAAGTTTCCCCAGCTCTGCAAGTTCTGCGAT
GTCAGGTTCAGCACCTGCGATAATCAGAAGTCCTGCATGTCCAACTGCAG
CATCACCTCCATCTGCGAGAAGCCCCAAGAAGTGTGCGTGGCCGTGTGGC
GGAAAAATGACGAGAACATCACCCTGGAGACCGTGTGTCACGACCCCAAG
CTCCCTTATCACGACTTCATTCTGGAGGACGCTGCCTCCCCAAATGCAT
CATGAAGGAGAAGAAGAAGCCCGGAGAGACCTTCTTTATGTGTTCCTGTA
GCAGCGACGAGTGTAACGACAACATCATCTTCAGCGAAGAGTACAACACC
AGCAACCCTGATGGAGGTGGCGGATCCGGAGGTGGAGGTTCTGGTGGAGG
TGGGAGTATTCCTCCCCACGTGCAGAAGAGCGTGAATAATGACATGATCG
TGACCGATAACAATGGCGCCGTGAAATTTCCCCAGCTGTGCAAATTCTGC
GATGTGAGGTTTTCCACCTGCGACAACCAGAAGTCCTGTATGAGCAACTG
CTCCATCACCTCCATCTGTGAGAAGCCTCAGGAGGTGTGCGTGGCTGTCT
GGCGGAAGAATGACGAGAATATCACCCTGGAAACCGTCTGCCACGATCCC
AAGCTGCCCTACCACGATTTCATCCTGGAAGACGCCGCCAGCCCTAAGTG
CATCATGAAAGAGAAAAAGAAGCCTGGCGAGACCTTTTTCATGTGCTCCT
GCAGCAGCGACGAATGCAACGACAATATCATCTTTAGCGAGGAATACAAT
ACCAGCAACCCCGACAGCGGCACAACCAACACAGTCGCTGCCTATAACCT
CACTTGGAAGAGCACCAACTTCAAAACCATCCTCGAATGGGAACCCAAAC
CCGTTAACCAAGTTTACACCGTGCAGATCAGCACCAAGTCCGGCGACTGG
AAGTCCAAATGTTTCTATACCACCGACACCGAGTGCGATCTCACCGATGA
GATCGTGAAAGATGTGAAACAGACCTACCTCGCCCGGGTGTTTAGCTACC
CCGCCGGCAATGTGGAGAGCACTGGTTCCGCTGGCGAGCCTTTATACGAG
AACAGCCCCGAATTTACCCCTTACCTCGAGACCAATTTAGGACAGCCCAC
CATCCAAAGCTTTGAGCAAGTTGGCACAAAGGTGAATGTGACAGTGGAGG
ACGAGCGGACTTTAGTGCGGCGGAACAACACCTTTCTCAGCCTCCGGGAT
GTGTTCGGCAAAGATTTAATCTACACACTGTATTACTGGAAGTCCTCTTC
CTCCGGCAAGAAGACAGCTAAAACCAACACAAACGAGTTTTTAATCGACG
TGGATAAAGGCGAAAACTACTGTTTCAGCGTGCAAGCTGTGATCCCCTCC
CGGACCGTGAATAGGAAAAGCACCGATAGCCCCGTTGAGTGCATGGGCCA
AGAAAAGGGCGAGTTCCGGGAGAACTGGGTGAACGTCATCAGCGATTTAA
AGAAGATCGAAGATTTAATTCAGTCCATGCATATCGACGCCACTTTATAC
ACAGAATCCGACGTGCACCCCTCTTGTAAGGTGACCGCCATGAAATGTTT
TTTACTGGAGCTGCAAGTTATCTCTTTAGAGAGCGGAGACGCTAGCATCC
ACGACACCGTGGAGAATTTAATCATTTTAGCCAATAACTCTTTATCCAGC
AACGGCAACGTGACAGAGTCCGGCTGCAAGGAGTGCGAAGAGCTGGAGGA
```

GAAGAACATCAAGGAGTTTCTGCAATCCTTTGTGCACATTGTCCAGATGT

TCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDITCPPPMSVEHAD

IWVKSYSLYSRERYICNSGFKRKAGTSSLTECVLNKATNVAHWTTPSLKC

IRQGQDRHMIRMRQLIDIVDQLKNYVNDLVPEFLPAPEDVETNCEWSAFS

CFQKAQLKSANTGNNERIINVSIKKLKRKPPSTNAGRRQKHRLTCPSCDS

YEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACATTACATGCCCCCCTCCCATGAGCGTGGAGCACGCCGAC

ATCTGGGTGAAGAGCTATAGCCTCTACAGCCGGGAGAGGTATATCTGTAA

CAGCGGCTTCAAGAGGAAGGCCGGCACCAGCAGCCTCACCGAGTGCGTGC

TGAATAAGGCTACCAACGTGGCTCACTGGACAACACCCTCTTTAAAGTGC

ATCCGGCAGGGCCAGGACAGGCACATGATCCGGATGAGGCAGCTCATCGA

CATCGTCGACCAGCTGAAGAACTACGTGAACGACCTGGTGCCCGAGTTTC

TGCCTGCCCCCGAGGACGTGGAGACCAACTGCGAGTGGTCCGCCTTCTCC

TGCTTTCAGAAGGCCCAGCTGAAGTCCGCCAACACCGGCAACAACGAGCG

GATCATCAACGTGAGCATCAAGAAGCTGAAGCGGAAGCCTCCCTCCACAA

ACGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGCT

GCAGAAGATGATCCATCAGCACCTGTCCTCCAGGACCCACGGCTCCGAGG

ACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 199)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDITCPPPMSVEHADIWVKSYSLYSRERYICNSGFKRKAGTSSLTEC

VLNKATNVAHWTTPSLKCIRQGQDRHMIRMRQLIDIVDQLKNYVNDLVPE

FLPAPEDVETNCEWSAFSCFQKAQLKSANTGNNERIINVSIKKLKRKPPS

TNAGRRQKHRLTCPSCDSYEKKPPKEFLERFKSLLQKMIHQHLSSRTHGS

EDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 200)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

-continued

```
GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACATTACATGCCCCCCTCCCATGAGCGTGGAGCACGC

CGACATCTGGGTGAAGAGCTATAGCCTCTACAGCCGGGAGAGGTATATCT

GTAACAGCGGCTTCAAGAGGAAGGCCGGCACCAGCAGCCTCACCGAGTGC

GTGCTGAATAAGGCTACCAACGTGGCTCACTGGACAACACCCTCTTTAAA

GTGCATCCGGCAGGGCCAGGACAGGCACATGATCCGGATGAGGCAGCTCA

TCGACATCGTCGACCAGCTGAAGAACTACGTGAACGACCTGGTGCCCGAG

TTTCTGCCTGCCCCCGAGGACGTGGAGACCAACTGCGAGTGGTCCGCCTT

CTCCTGCTTTCAGAAGGCCCAGCTGAAGTCCGCCAACACCGGCAACAACG

AGCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTGA

CTCCTACGAGAAGAAGCCCCCCAAGGAGTTCCTGGAGAGGTTCAAGTCCC

TGCTGCAGAAGATGATCCATCAGCACCTGTCCTCCAGGACCCACGGCTCC

GAGGACTCC.
```

Exemplary Multi-Chain Chimeric Polypeptides—Type N

In some embodiments of any of the multi-chain chimeric polypeptides described herein, the first target-binding domain and the second targeting-binding domain each independently bind specifically to TGF-β or CD16. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 (e.g., an anti-CD16 scFv) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or CD16. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 80)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

-continued
TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.

In some embodiments of these multi-chain chimeric polypeptides, the second target-binding domain binds specifically to CD16. In some embodiments of these multi-chain chimeric polypeptides, the second target-binding domain includes an anti-CD16 scFv. In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 112)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 113)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 114)
EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 115)
GAGGTGCAGCTGGTGGAGTCCGGAGGAGGAGTGGTGAGGCCTGGAGGCTC

CCTGAGGCTGAGCTGTGCTGCCTCCGGCTTCACCTTCGACGACTACGGCA

TGTCCTGGGTGAGGCAGGCTCCTGGAAAGGGCCTGGAGTGGGTGTCCGGC

ATCAACTGGAACGGCGGATCCACCGGCTACGCCGATTCCGTGAAGGGCAG

GTTCACCATCAGCAGGGACAACGCCAAGAACTCCCTGTACCTGCAGATGA

ACTCCCTGAGGGCCGAGGACACCGCCGTGTACTACTGCGCCAGGGGCAGG

TCCCTGCTGTTCGACTACTGGGGACAGGGCACCCTGGTGACCGTGTCCAG

G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 201)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 202)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

```
ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACAGCGGCACAACCAACACAGTCGCTGCCTATAACCTCACT

TGGAAGAGCACCAACTTCAAAACCATCCTCGAATGGGAACCCAAACCCGT

TAACCAAGTTTACACCGTGCAGATCAGCACCAAGTCCGGCGACTGGAAGT

CCAAATGTTTCTATACCACCGACACCGAGTGCGATCTCACCGATGAGATC

GTGAAAGATGTGAAACAGACCTACCTCGCCCGGGTGTTTAGCTACCCCGC

CGGCAATGTGGAGAGCACTGGTTCCGCTGGCGAGCCTTTATACGAGAACA

GCCCCGAATTTACCCCTTACCTCGAGACCAATTTAGGACAGCCCACCATC

CAAAGCTTTGAGCAAGTTGGCACAAAGGTGAATGTGACAGTGGAGGACGA

GCGGACTTTAGTGCGGCGGAACAACACCTTTCTCAGCCTCCGGGATGTGT

TCGGCAAAGATTTAATCTACACACTGTATTACTGGAAGTCCTCTTCCTCC

GGCAAGAAGACAGCTAAAACCAACACAAACGAGTTTTTAATCGACGTGGA

TAAAGGCGAAAACTACTGTTTCAGCGTGCAAGCTGTGATCCCCTCCCGGA

CCGTGAATAGGAAAAGCACCGATAGCCCCGTTGAGTGCATGGGCCAAGAA

AAGGGCGAGTTCCGGGAGAACTGGGTGAACGTCATCAGCGATTTAAAGAA

GATCGAAGATTTAATTCAGTCCATGCATATCGACGCCACTTTATACACAG

AATCCGACGTGCACCCCTCTTGTAAGGTGACCGCCATGAAATGTTTTTTA

CTGGAGCTGCAAGTTATCTCTTTAGAGAGCGGAGACGCTAGCATCCACGA

CACCGTGGAGAATTTAATCATTTTAGCCAATAACTCTTTATCCAGCAACG

GCAACGTGACAGAGTCCGGCTGCAAGGAGTGCGAAGAGCTGGAGGAGAAG

AACATCAAGGAGTTTCTGCAATCCTTTGTGCACATTGTCCAGATGTTCAT

CAATACCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 203)
MKWVTFISLLFLFSSAYSIPPHVQKSVNNDMIVTDNNGAVKFPQLCKFCD
VRFSTCDNQKSCMSNCSITSICEKPQEVCVAVWRKNDENITLETVCHDPK
LPYHDFILEDAASPKCIMKEKKKPGETFFMCSCSSDECNDNIIFSEEYNT
SNPDGGGGSGGGGSGGGGSIPPHVQKSVNNDMIVTDNNGAVKFPQLCKFC
DVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYN
TSNPDSGTTNTVAAYNLTWKSTNFKTILEWEPKPVNQVYTVQISTKSGDW
KSKCFYTTDTECDLTDEIVKDVKQTYLARVFSYPAGNVESTGSAGEPLYE
NSPEFTPYLETNLGQPTIQSFEQVGTKVNVTVEDERTLVRRNNTFLSLRD
VFGKDLIYTLYYWKSSSSGKKTAKTNTNEFLIDVDKGENYCFSVQAVIPS
RTVNRKSTDSPVECMGQEKGEFRENWVNVISDLKKIEDLIQSMHIDATLY
TESDVHPSCKVTAMKCFLLELQVISLESGDASIHDTVENLIILANNSLSS
NGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 204)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACAGCGGCACAACCAACACAGTCGCTGCCTATAACCT

CACTTGGAAGAGCACCAACTTCAAAACCATCCTCGAATGGGAACCCAAAC

CCGTTAACCAAGTTTACACCGTGCAGATCAGCACCAAGTCCGGCGACTGG
```

-continued

```
AAGTCCAAATGTTTCTATACCACCGACACCGAGTGCGATCTCACCGATGA

GATCGTGAAAGATGTGAAACAGACCTACCTCGCCCGGGTGTTTAGCTACC

CCGCCGGCAATGTGGAGAGCACTGGTTCCGCTGGCGAGCCTTTATACGAG

AACAGCCCCGAATTTACCCCTTACCTCGAGACCAATTTAGGACAGCCCAC

CATCCAAAGCTTTGAGCAAGTTGGCACAAAGGTGAATGTGACAGTGGAGG

ACGAGCGGACTTTAGTGCGGCGGAACAACACCTTTCTCAGCCTCCGGGAT

GTGTTCGGCAAAGATTTAATCTACACACTGTATTACTGGAAGTCCTCTTC

CTCCGGCAAGAAGACAGCTAAAACCAACACAAACGAGTTTTTAATCGACG

TGGATAAAGGCGAAAACTACTGTTTCAGCGTGCAAGCTGTGATCCCCTCC

CGGACCGTGAATAGGAAAAGCACCGATAGCCCCGTTGAGTGCATGGGCCA

AGAAAAGGGCGAGTTCCGGGAGAACTGGGTGAACGTCATCAGCGATTTAA

AGAAGATCGAAGATTTAATTCAGTCCATGCATATCGACGCCACTTTATAC

ACAGAATCCGACGTGCACCCCTCTTGTAAGGTGACCGCCATGAAATGTTT

TTTACTGGAGCTGCAAGTTATCTCTTTAGAGAGCGGAGACGCTAGCATCC

ACGACACCGTGGAGAATTTAATCATTTTAGCCAATAACTCTTTATCCAGC

AACGGCAACGTGACAGAGTCCGGCTGCAAGGAGTGCGAAGAGCTGGAGGA

GAAGAACATCAAGGAGTTTCTGCAATCCTTTGTGCACATTGTCCAGATGT

TCATCAATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 205)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDITCPPPMSVEHAD

IWVKSYSLYSRERYICNSGFKRKAGTSSLTECVLNKATNVAHWTTPSLKC

IRSELTQDPAVSVALGQTVRITCQGDSLRSYYASWYQQKPGQAPVLVIYG

KNNRPSGIPDRFSGSSSGNTASLTITGAQAEDEADYYCNSRDSSGNHVVF

GGGTKLTVGHGGGGSGGGGSGGGGSEVQLVESGGGVVRPGGSLRLSCAAS

GFTFDDYGMSWVRQAPGKGLEWVSGINWNGGSTGYADSVKGRFTISRDNA

KNSLYLQMNSLRAEDTAVYYCARGRSLLFDYWGQGTLVTVSR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 206)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACATTACATGCCCCCCTCCCATGAGCGTGGAGCACGCCGAC

ATCTGGGTGAAGAGCTATAGCCTCTACAGCCGGGAGAGGTATATCTGTAA

CAGCGGCTTCAAGAGGAAGGCCGGCACCAGCAGCCTCACCGAGTGCGTGC

TGAATAAGGCTACCAACGTGGCTCACTGGACAACACCCTCTTTAAAGTGC

ATCCGGTCCGAGCTGACCCAGGACCCTGCTGTGTCCGTGGCTCTGGGCCA

GACCGTGAGGATCACCTGCCAGGGCGACTCCCTGAGGTCCTACTACGCCT

CCTGGTACCAGCAGAAGCCCGGCCAGGCTCCTGTGCTGGTGATCTACGGC

AAGAACAACAGGCCCTCCGGCATCCCTGACAGGTTCTCCGGATCCTCCTC

CGGCAACACCGCCTCCCTGACCATCACAGGCGCTCAGGCCGAGGACGAGG

CTGACTACTACTGCAACTCCAGGGACTCCTCCGGCAACCATGTGGTGTTC

GGCGGCGGCACCAAGCTGACCGTGGGCCATGGCGGCGGCGGCTCCGGAGG

CGGCGGCAGCGGCGGAGGAGGATCCGAGGTGCAGCTGGTGGAGTCCGGAG

GAGGAGTGGTGAGGCCTGGAGGCTCCCTGAGGCTGAGCTGTGCTGCCTCC

GGCTTCACCTTCGACGACTACGGCATGTCCTGGGTGAGGCAGGCTCCTGG

AAAGGGCCTGGAGTGGGTGTCCGGCATCAACTGGAACGGCGGATCCACCG

GCTACGCCGATTCCGTGAAGGGCAGGTTCACCATCAGCAGGGACAACGCC

AAGAACTCCCTGTACCTGCAGATGAACTCCCTGAGGGCCGAGGACACCGC

CGTGTACTACTGCGCCAGGGGCAGGTCCCTGCTGTTCGACTACTGGGGAC

AGGGCACCCTGGTGACCGTGTCCAGG.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)
MKWVTFISLLFLFSSAYSIPPHVQKSVNNDMIVTDNNGAVKFPQLCKFCD
VRFSTCDNQKSCMSNCSITSICEKPQEVCVAVWRKNDENITLETVCHDPK
LPYHDFILEDAASPKCIMKEKKKPGETFFMCSCSSDECNDNIIFSEEYNT
SNPDGGGGSGGGGSGGGGSIPPHVQKSVNNDMIVTDNNGAVKFPQLCKFC
DVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYN
TSNPDITCPPPMSVEHADIWVKSYSLYSRERYICNSGFKRKAGTSSLTEC
VLNKATNVAHWTTPSLKCIRSELTQDPAVSVALGQTVRITCQGDSLRSYY
ASWYQQKPGQAPVLVIYGKNNRPSGIPDRFSGSSSGNTASLTITGAQAED
EADYYCNSRDSSGNHVVFGGGTKLTVGHGGGGSGGGGSGGGGSEVQLVES
GGGVVRPGGSLRLSCAASGFTFDDYGMSWVRQAPGKGLEWVSGINWNGGS
TGYADSVKGRFTISRDNAKNSLYLQMNSLRAEDTAVYYCARGRSLLFDYW
GQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)
ATGAAGTGGGTGACCTTCATCAGCCTGCTGTTCCTGTTCTCCAGCGCCTA
CTCCATCCCCCCCCATGTGCAAAAGAGCGTGAACAACGATATGATCGTGA
CCGACAACAACGGCGCCGTGAAGTTTCCCCAGCTCTGCAAGTTCTGCGAT
GTCAGGTTCAGCACCTGCGATAATCAGAAGTCCTGCATGTCCAACTGCAG
CATCACCTCCATCTGCGAGAAGCCCCAAGAAGTGTGCGTGGCCGTGTGGC
GGAAAAATGACGAGAACATCACCCTGGAGACCGTGTGTCACGACCCCAAG
CTCCCTTATCACGACTTCATTCTGGAGGACGCTGCCTCCCCCAAATGCAT
CATGAAGGAGAAGAAGAAGCCCGGAGAGACCTTCTTTATGTGTTCCTGTA
GCAGCGACGAGTGTAACGACAACATCATCTTCAGCGAAGAGTACAACACC
AGCAACCCTGATGGAGGTGGCGGATCCGGAGGTGGAGGTTCTGGTGGAGG
TGGGAGTATTCCTCCCCACGTGCAGAAGAGCGTGAATAATGACATGATCG
TGACCGATAACAATGGCGCCGTGAAATTTCCCCAGCTGTGCAAATTCTGC
GATGTGAGGTTTTCCACCTGCGACAACCAGAAGTCCTGTATGAGCAACTG
CTCCATCACCTCCATCTGTGAGAAGCCTCAGGAGGTGTGCGTGGCTGTCT
GGCGGAAGAATGACGAGAATATCACCCTGGAAACCGTCTGCCACGATCCC
AAGCTGCCCTACCACGATTTCATCCTGGAAGACGCCGCCAGCCCTAAGTG
CATCATGAAAGAGAAAAAGAAGCCTGGCGAGACCTTTTTCATGTGCTCCT
GCAGCAGCGACGAATGCAACGACAATATCATCTTTAGCGAGGAATACAAT
ACCAGCAACCCCGACATTACATGCCCCCCTCCCATGAGCGTGGAGCACGC
CGACATCTGGGTGAAGAGCTATAGCCTCTACAGCCGGGAGAGGTATATCT
GTAACAGCGGCTTCAAGAGGAAGGCCGGCACCAGCAGCCTCACCGAGTGC

GTGCTGAATAAGGCTACCAACGTGGCTCACTGGACAACACCCTCTTTAAA
GTGCATCCGGTCCGAGCTGACCCAGGACCCTGCTGTGTCCGTGGCTCTGG
GCCAGACCGTGAGGATCACCTGCCAGGGCGACTCCCTGAGGTCCTACTAC
GCCTCCTGGTACCAGCAGAAGCCCGGCCAGGCTCCTGTGCTGGTGATCTA
CGGCAAGAACAACAGGCCCTCCGGCATCCCTGACAGGTTCTCCGGATCCT
CCTCCGGCAACACCGCCTCCCTGACCATCACAGGCGCTCAGGCCGAGGAC
GAGGCTGACTACTACTGCAACTCCAGGGACTCCTCCGGCAACCATGTGGT
GTTCGGCGGCGGCACCAAGCTGACCGTGGGCCATGGCGGCGGCGGCTCCG
GAGGCGGCGGCAGCGGCGGAGGAGGATCCGAGGTGCAGCTGGTGGAGTCC
GGAGGAGGAGTGGTGAGGCCTGGAGGCTCCCTGAGGCTGAGCTGTGCTGC
CTCCGGCTTCACCTTCGACGACTACGGCATGTCCTGGGTGAGGCAGGCTC
CTGGAAAGGGCCTGGAGTGGGTGTCCGGCATCAACTGGAACGGCGGATCC
ACCGGCTACGCCGATTCCGTGAAGGGCAGGTTCACCATCAGCAGGGACAA
CGCCAAGAACTCCCTGTACCTGCAGATGAACTCCCTGAGGGCCGAGGACA
CCGCCGTGTACTACTGCGCCAGGGGCAGGTCCCTGCTGTTCGACTACTGG
GGACAGGGCACCCTGGTGACCGTGTCCAGG.

Exemplary Multi-Chain Chimeric Polypeptides—Type O

In some embodiments of any of the multi-chain chimeric polypeptides described herein, the first target-binding domain and the second targeting-binding domain each independently bind specifically to TGF-β or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor to TGF-β (e.g., a soluble TGF-β receptor, e.g., a soluble TGFβRII receptor) or CD137L.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein)

between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to CD137L. In some embodiments of these multi-chain chimeric polypeptides, the first target-binding domain or the additional target-binding domain is a soluble TGF-β receptor (e.g., a soluble TGFβRII receptor, e.g., a soluble human TGFβRII receptor).

In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 80)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 81)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 82)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.
```

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 83)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.
```

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 85)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPDGGGGSGGGGSGGGG
SIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 84)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGAC.

In some embodiments of these multi-chain chimeric polypeptides, the second target-binding domain includes a soluble CD137L protein (e.g., a soluble human CD137L protein). In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 157)
REGPELSPDDPAGLLDLRQGMFAQLVAQNVLLIDGPLSWYSDPGLAGVSL
TGGLSYKEDTKELVVAKAGVYYVFFQLELRRVVAGEGSGSVSLALHLQPL
RSAAGAAALALTVDLPPASSEARNSAFGFQGRLLHLSAGQRLGVHLHTEA
RARHAWQLTQGATVLGLFRVTPEIPAGLPSPRSE.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 158)
CGCGAGGGTCCCGAGCTTTCGCCCGACGATCCCGCCGGCCTCTTGGACCT
GCGGCAGGGCATGTTTGCGCAGCTGGTGGCCCAAAATGTTCTGCTGATCG
ATGGGCCCCTGAGCTGGTACAGTGACCCAGGCCTGGCAGGCGTGTCCCTG
ACGGGGGCCTGAGCTACAAAGAGGACACGAAGGAGCTGGTGGTGGCCAA
GGCTGGAGTCTACTATGTCTTCTTTCAACTAGAGCTGCGGCGCGTGGTGG
CCGGCGAGGGCTCAGGCTCCGTTTCACTTGCGCTGCACCTGCAGCCACTG
CGCTCTGCTGCTGGGGCCGCCGCCCTGGCTTTGACCGTGGACCTGCCACC
CGCCTCCTCCGAGGCTCGGAACTCGGCCTTCGGTTTCCAGGGCCGCTTGC
TGCACCTGAGTGCCGGCCAGCGCCTGGGCGTCCATCTTCACACTGAGGCC
AGGGCACGCCATGCCTGGCAGCTTACCCAGGGCGCCACAGTCTTGGGACT
CTTCCGGGTGACCCCCGAAATCCCAGCCGGACTCCCTTCACCGAGGTCGG
AA.

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 159)
DPAGLLDLRQGMFAQLVAQNVLLIDGPLSWYSDPGLAGVSLTGGLSYKED
TKELVVAKAGVYYVFFQLELRRVVAGEGSGSVSLALHLQPLRSAAGAAAL
ALTVDLPPASSEARNSAFGFQGRLLHLSAGQRLGVHLHTEARARHAWQLT
QGATVLGLFRVTPEI.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 160)
GATCCCGCCGGCCTCTTGGACCTGCGGCAGGGCATGTTTGCGCAGCTGGT
GGCCCAAAATGTTCTGCTGATCGATGGGCCCCTGAGCTGGTACAGTGACC
CAGGCCTGGCAGGCGTGTCCCTGACGGGGGCCTGAGCTACAAAGAGGAC
ACGAAGGAGCTGGTGGTGGCCAAGGCTGGAGTCTACTATGTCTTCTTTCA
ACTAGAGCTGCGGCGCGTGGTGGCCGGCGAGGGCTCAGGCTCCGTTTCAC
TTGCGCTGCACCTGCAGCCACTGCGCTCTGCTGCTGGGGCCGCCGCCCTG

```
GCTTTGACCGTGGACCTGCCACCCGCCTCCTCCGAGGCTCGGAACTCGGC

CTTCGGTTTCCAGGGCCGCTTGCTGCACCTGAGTGCCGGCCAGCGCCTGG

GCGTCCATCTTCACACTGAGGCCAGGGCACGCCATGCCTGGCAGCTTACC

CAGGGCGCCACAGTCTTGGGACTCTTCCGGGTGACCCCCGAAATC.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 209)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 210)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACAGCGGCACAACCAACACAGTCGCTGCCTATAACCTCACT

TGGAAGAGCACCAACTTCAAAACCATCCTCGAATGGGAACCCAAACCCGT

TAACCAAGTTTACACCGTGCAGATCAGCACCAAGTCCGGCGACTGGAAGT

CCAAATGTTTCTATACCACCGACACCGAGTGCGATCTCACCGATGAGATC

GTGAAAGATGTGAAACAGACCTACCTCGCCCGGGTGTTTAGCTACCCCGC

CGGCAATGTGGAGAGCACTGGTTCCGCTGGCGAGCCTTTATACGAGAACA

GCCCCGAATTTACCCCTTACCTCGAGACCAATTTAGGACAGCCCACCATC

CAAAGCTTTGAGCAAGTTGGCACAAAGGTGAATGTGACAGTGGAGGACGA

GCGGACTTTAGTGCGGCGGAACAACACCTTTCTCAGCCTCCGGGATGTGT

TCGGCAAAGATTTAATCTACACACTGTATTACTGGAAGTCCTCTTCCTCC

GGCAAGAAGACAGCTAAAACCAACACAAACGAGTTTTTAATCGACGTGGA

TAAAGGCGAAAACTACTGTTTCAGCGTGCAAGCTGTGATCCCCTCCCGGA

CCGTGAATAGGAAAAGCACCGATAGCCCCGTTGAGTGCATGGGCCAAGAA

AAGGGCGAGTTCCGGGAGAACTGGGTGAACGTCATCAGCGATTTAAAGAA

GATCGAAGATTTAATTCAGTCCATGCATATCGACGCCACTTTATACACAG

AATCCGACGTGCACCCCTCTTGTAAGGTGACCGCCATGAAATGTTTTTTA

CTGGAGCTGCAAGTTATCTCTTTAGAGAGCGGAGACGCTAGCATCCACGA

CACCGTGGAGAATTTAATCATTTTAGCCAATAACTCTTTATCCAGCAACG

GCAACGTGACAGAGTCCGGCTGCAAGGAGTGCGAAGAGCTGGAGGAGAAG

AACATCAAGGAGTTTCTGCAATCCTTTGTGCACATTGTCCAGATGTTCAT

CAATACCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 211)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDSGTTNTVAAYNLTWKSTNFKTILEWEPKPVNQVYTVQISTKSGDW

KSKCFYTTDTECDLTDEIVKDVKQTYLARVFSYPAGNVESTGSAGEPLYE
```

NSPEFTPYLETNLGQPTIQSFEQVGTKVNVTVEDERTLVRRNNTFLSLRD

VFGKDLIYTLYYWKSSSSGKKTAKTNTNEFLIDVDKGENYCFSVQAVIPS

RTVNRKSTDSPVECMGQEKGEFRENWVNVISDLKKIEDLIQSMHIDATLY

TESDVHPSCKVTAMKCFLLELQVISLESGDASIHDTVENLIILANNSLSS

NGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 212)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACAGCGGCACAACCAACACAGTCGCTGCCTATAACCT

CACTTGGAAGAGCACCAACTTCAAAACCATCCTCGAATGGGAACCCAAAC

CCGTTAACCAAGTTTACACCGTGCAGATCAGCACCAAGTCCGGCGACTGG

AAGTCCAATGTTTCTATACCACCGACACCGAGTGCGATCTCACCGATGA

GATCGTGAAAGATGTGAAACAGACCTACCTCGCCCGGGTGTTTAGCTACC

CCGCCGGCAATGTGGAGAGCACTGGTTCCGCTGGCGAGCCTTTATACGAG

AACAGCCCCGAATTTACCCCTTACCTCGAGACCAATTTAGGACAGCCCAC

CATCCAAAGCTTTGAGCAAGTTGGCACAAAGGTGAATGTGACAGTGGAGG

ACGAGCGGACTTTAGTGCGGCGGAACAACACCTTTCTCAGCCTCCGGGAT

GTGTTCGGCAAAGATTTAATCTACACACTGTATTACTGGAAGTCCTCTTC

CTCCGGCAAGAAGACAGCTAAAACCAACACAAACGAGTTTTTAATCGACG

TGGATAAAGGCGAAAACTACTGTTTCAGCGTGCAAGCTGTGATCCCCTCC

CGGACCGTGAATAGGAAAAGCACCGATAGCCCCGTTGAGTGCATGGGCCA

AGAAAAGGGCGAGTTCCGGGAGAACTGGGTGAACGTCATCAGCGATTTAA

AGAAGATCGAAGATTTAATTCAGTCCATGCATATCGACGCCACTTTATAC

ACAGAATCCGACGTGCACCCCTCTTGTAAGGTGACCGCCATGAAATGTTT

TTTACTGGAGCTGCAAGTTATCTCTTTAGAGAGCGGAGACGCTAGCATCC

ACGACACCGTGGAGAATTTAATCATTTTAGCCAATAACTCTTTATCCAGC

AACGGCAACGTGACAGAGTCCGGCTGCAAGGAGTGCGAAGAGCTGGAGGA

GAAGAACATCAAGGAGTTTCTGCAATCCTTTGTGCACATTGTCCAGATGT

TCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 213)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDITCPPPMSVEHAD

IWVKSYSLYSRERYICNSGFKRKAGTSSLTECVLNKATNVAHWTTPSLKC

IRGGGGSGGGGSGGGGSREGPELSPDDPAGLLDLRQGMFAQLVAQNVLLI

DGPLSWYSDPGLAGVSLTGGLSYKEDTKELVVAKAGVYYVFFQLELRRVV

AGEGSGSVSLALHLQPLRSAAGAAALALTVDLPPASSEARNSAFGFQGRL

LHLSAGQRLGVHLHTEARARHAWQLTQGATVLGLFRVTPEIPAGLPSPRS

E.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 214)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACATTACATGCCCCCCTCCCATGAGCGTGGAGCACGCCGAC

ATCTGGGTGAAGAGCTATAGCCTCTACAGCCGGGAGAGGTATATCTGTAA

CAGCGGCTTCAAGAGGAAGGCCGGCACCAGCAGCCTCACCGAGTGCGTGC

TGAATAAGGCTACCAACGTGGCTCACTGGACAACACCCTCTTTAAAGTGC

ATCCGGGCGGTGGAGGATCCGGAGGAGGTGGCTCCGGCGGCGGAGGATC

TCGCGAGGGTCCCGAGCTTTCGCCCGACGATCCCGCCGGCCTCTTGGACC

TGCGGCAGGGCATGTTTGCGCAGCTGGTGGCCCAAAATGTTCTGCTGATC

GATGGGCCCCTGAGCTGGTACAGTGACCCAGGCCTGGCAGGCGTGTCCCT

GACGGGGGGCCTGAGCTACAAAGAGGACACGAAGGAGCTGGTGGTGGCCA

AGGCTGGAGTCTACTATGTCTTCTTTCAACTAGAGCTGCGGCGCGTGGTG

GCCGGCGAGGGCTCAGGCTCCGTTTCACTTGCGCTGCACCTGCAGCCACT

GCGCTCTGCTGCTGGGGCCGCCGCCCTGGCTTTGACCGTGGACCTGCCAC

CCGCCTCCTCCGAGGCTCGGAACTCGGCCTTCGGTTTCCAGGGCCGCTTG

CTGCACCTGAGTGCCGGCCAGCGCCTGGGCGTCCATCTTCACACTGAGGC

CAGGGCACGCCATGCCTGGCAGCTTACCCAGGGCGCCACAGTCTTGGGAC

TCTTCCGGGTGACCCCCGAAATCCCAGCCGGACTCCCTTCACCGAGGTCG

GAA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 215)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDITCPPPMSVEHADIWVKSYSLYSRERYICNSGFKRKAGTSSLTEC

VLNKATNVAHWTTPSLKCIRGGGGSGGGGSGGGGSREGPELSPDDPAGLL

DLRQGMFAQLVAQNVLLIDGPLSWYSDPGLAGVSLTGGLSYKEDTKELVV

AKAGVYYVFFQLELRRVVAGEGSGSVSLALHLQPLRSAAGAAALALTVDL

PPASSEARNSAFGFQGRLLHLSAGQRLGVHLHTEARARHAWQLTQGATVL

GLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 216)
ATGAAGTGGGTGACCTTCATCAGCCTGCTGTTCCTGTTCTCCAGCGCCTA

CTCCATCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACATTACATGCCCCCCTCCCATGAGCGTGGAGCACGC

CGACATCTGGGTGAAGAGCTATAGCCTCTACAGCCGGGAGAGGTATATCT

GTAACAGCGGCTTCAAGAGGAAGGCCGGCACCAGCAGCCTCACCGAGTGC

GTGCTGAATAAGGCTACCAACGTGGCTCACTGGACAACACCCTCTTTAAA

GTGCATCCGGGGCGGTGGAGGATCCGGAGGAGGTGGCTCCGGCGGCGGAG

GATCTCGCGAGGGTCCCGAGCTTTCGCCCGACGATCCCGCCGGCCTCTTG

GACCTGCGGCAGGGCATGTTTGCGCAGCTGGTGGCCCAAAATGTTCTGCT

GATCGATGGGCCCCTGAGCTGGTACAGTGACCCAGGCCTGGCAGGCGTGT

CCCTGACGGGGGGCCTGAGCTACAAAGAGGACACGAAGGAGCTGGTGGTG

GCCAAGGCTGGAGTCTACTATGTCTTCTTTCAACTAGAGCTGCGGCGCGT

GGTGGCCGGCGAGGGCTCAGGCTCCGTTTCACTTGCGCTGCACCTGCAGC

CACTGCGCTCTGCTGCTGGGGCCGCCGCCCTGGCTTTGACCGTGGACCTG

```
CCACCCGCCTCCTCCGAGGCTCGGAACTCGGCCTTCGGTTTCCAGGGCCG

CTTGCTGCACCTGAGTGCCGGCCAGCGCCTGGGCGTCCATCTTCACACTG

AGGCCAGGGCACGCCATGCCTGGCAGCTTACCCAGGGCGCCACAGTCTTG

GGACTCTTCCGGGTGACCCCCGAAATCCCAGCCGGACTCCCTTCACCGAG

GTCGGAA.
```

Compositions/Kits

Also provided herein are compositions (e.g., pharmaceutical compositions) that include at least one of any multi-chain chimeric polypeptides, any of the cells, or any of the nucleic acids described herein. In some embodiments, the compositions include at least one of any of the multi-chain chimeric polypeptides described herein. In some embodiments, the compositions include any of the immune cells (e.g., any of the immune cells described herein, e.g., any of the immune cells produced using any of the methods described herein).

In some embodiments, the pharmaceutical compositions are formulated for different routes of administration (e.g., intravenous, subcutaneous). In some embodiments, the pharmaceutical compositions can include a pharmaceutically acceptable carrier (e.g., phosphate buffered saline).

Single or multiple administrations of pharmaceutical compositions can be given to a subject in need thereof depending on for example: the dosage and frequency as required and tolerated by the subject. The formulation should provide a sufficient quantity of active agent to effectively treat, prevent or ameliorate conditions, diseases or symptoms.

Also provided herein are kits that include any of the multi-chain chimeric polypeptides, compositions, nucleic acids, or cells (e.g., immune cells) described herein. In some embodiments, the kits can include instructions for performing any of the methods described herein. In some embodiments, the kits can include at least one dose of any of the pharmaceutical compositions described herein.

Nucleic Acids/Vectors

Also provided herein are nucleic acids that encode any of the multi-chain chimeric polypeptides described herein. In some embodiments, a first nucleic acid can encode the first chimeric polypeptide and a second nucleic acid can encode the second chimeric polypeptide. In some embodiments, a single nucleic acid can encode both the first chimeric polypeptide and the second chimeric polypeptide.

Also provided herein are vectors that include any of the nucleic acids encoding any of the multi-chain chimeric polypeptides described herein. In some embodiments, a first vector can include a nucleic acid encoding the first chimeric polypeptide and a second vector can include a nucleic acid encoding the second chimeric polypeptide. In some embodiments, a single vector can include a first nucleic acid encoding the first chimeric polypeptide and a second nucleic acid encoding the second chimeric polypeptide.

Any of the vectors described herein can be an expression vector. For example, an expression vector can include a promoter sequence operably linked to the sequence encoding the first chimeric polypeptide and the second chimeric polypeptide.

Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, e.g., include sufficient cis-acting elements for expression; other elements for expression can be supplied by the host mammalian cell or in an in vitro expression system. Skilled practitioners will be capable of selecting suitable vectors and mammalian cells for making any of the multi-chain chimeric polypeptides described herein.

Cells

Also provided herein are cells (e.g., any of the exemplary cells described herein or known in the art) comprising any of the nucleic acids described herein that encode any of the multi-chain chimeric polypeptides described herein (e.g., encoding both the first and second chimeric polypeptides). Also provided herein are cells (e.g., any of the exemplary cells described herein or known in the art) comprising any of the nucleic acids described herein that encode any of the first chimeric polypeptides described herein. Also provided are cells (e.g., any of the exemplary cells described herein or known in the art) comprising any of the nucleic acids described herein that encode any of the second chimeric polypeptides described herein.

Also provided herein are cells (e.g., any of the exemplary cells described herein or known in the art) that include any of the vectors described herein that encode any of the multi-chain chimeric polypeptides described herein (e.g., encoding both the first and second chimeric polypeptides). Also provided herein are cells (e.g., any of the exemplary cells described herein or known in the art) that include any of the vectors described herein that encode any of the first chimeric polypeptides described herein. Also provided herein are cells (e.g., any of the exemplary cells described herein or known in the art) that include any of the vectors described herein that encode any of the second chimeric polypeptides described herein).

In some embodiments of any of the methods described herein, the cell can be a eukaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. Non-limiting examples of mammalian cells include Chinese hamster ovary cells and human embryonic kidney cells (e.g., HEK293 cells).

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral and lentiviral transduction), and nanoparticle transfection.

Methods of Producing Multi-Chain Chimeric Polypeptides

Also provided herein are methods of producing any of the multi-chain chimeric polypeptides described herein that include culturing any of the cells described herein in a culture medium under conditions sufficient to result in the production of the multi-chain chimeric polypeptide; and recovering the multi-chain chimeric polypeptide from the cell and/or the culture medium.

Also provided herein are method of producing any of the multi-chain chimeric polypeptides described herein that include: culturing any of cells described herein in a first culture medium under conditions sufficient to result in the production of the first chimeric polypeptide; recovering the first chimeric polypeptide from the cell and/or the first culture medium; culturing any of the cells described herein in a second culture medium under conditions sufficient to result in the production of the second chimeric polypeptide; recovering the second chimeric polypeptide from the cell and/or the second culture medium; and combining (e.g., mixing) the recovered first chimeric polypeptide and the recovered second chimeric polypeptide to form the multi-chain chimeric polypeptide (e.g., any of the multi-chain chimeric polypeptides described herein).

The recovery of the multi-chain chimeric polypeptide, the first chimeric polypeptide, or the second chimeric polypeptide from a cell (e.g., a eukaryotic cell) can be performed using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Methods of culturing cells are well known in the art. Cells can be maintained in vitro under conditions that favor proliferation, differentiation and growth. Briefly, cells can be cultured by contacting a cell (e.g., any cell) with a cell culture medium that includes the necessary growth factors and supplements to support cell viability and growth.

Also provided herein are multi-chain chimeric polypeptides (e.g., any of the multi-chain chimeric polypeptides described herein), first chimeric polypeptides (e.g., any of the first chimeric polypeptides), or second chimeric polypeptides (e.g., any of the second chimeric polypeptides described herein) produced by any of the methods described herein.

Methods of Stimulating an Immune Cell

Also provided herein are methods of stimulating an immune cell (e.g., any of the exemplary immune cells described herein or known in the art) that include contacting an immune cell with an effective amount of any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell).

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the multi-chain chimeric polypeptide is administered to a subject (e.g., a mammal, e.g., a human) in an amount sufficient to result in stimulation of an immune cell in the subject.

In some examples of any of the methods described herein, the immune cell can be an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8$^+$ T cell, a CD4$^+$ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Activation of an immune cell can be determined using methods known in the art. For example, activation of an immune cell can be determined by detecting the levels of cytokines and chemokines that are secreted or cytotoxicity granules and regulatory molecules that are upregulated upon activation of an immune cell. Non-limiting examples of cytokines, chemokines, cytotoxicity granules, and regulatory molecules that are secreted or upregulated upon activation of an immune cell include: IL-2, IFN-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, granzymes, perforin, TGFβ, STAT3, STAT4, STAT5, RORγT, FOXP3, STAT6, and GATA3. The detection of these cytokines, chemokines, cytotoxicity granules, or regulatory molecules can be performed using an immunoassay (e.g., an enzyme-linked immunosorbent assay) and quantitative PCR. For example, activation of an immune cell can result in an increase of about 1% to about 800% (e.g., about 1% to about 750%, about 1% to about 700%, about 1% to about 650%, about 1% to about 600%, about 1% to about 550%, about 1% to about 500%, about 1% to about 450%, about 1% to about 400%, about 1% to about 350%, about 1% to about 300%, about 1% to about 280%, about 1% to about 260%, about 1% to about 240%, about 1% to about 220%, about 1% to about 200%, about 1% to about 180%, about 1% to about 160%, about 1% to about 140%, about 1% to about 120%, about 1% to about 100%, about 1% to about 90%, about 1% to about 80%, about 1% to about 70%, about 1% to about 60%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 800%, about 5% to about 750%, about 5% to about 700%, about 5% to about 650%, about 5% to about 600%, about 5% to about 550%, about 5% to about 500%, about 5% to about 450%, about 5% to about 400%, about 5% to about 350%, about 5% to about 300%, about 5% to about 280%, about 5% to about 260%, about 5% to about 240%, about 5% to about 220%, about 5% to about 200%, about 5% to about 180%, about 5% to about 160%, about 5% to about 140%, about 5% to about 120%, about 5% to about 100%, about 5% to about 90%, about 5% to about 80%, about 5% to about 70%, about 5% to about 60%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 800%, about 10% to about 750%, about 10% to about 700%, about 10% to about 650%, about 10% to about 600%, about 10% to about 550%, about 10% to about 500%, about 10% to about 450%, about 10% to about 400%, about 10% to about 350%, about 10% to about 300%, about 10% to about 280%, about 10% to about 260%, about 10% to about 240%, about 10% to about 220%, about 10% to about 200%, about 10% to about 180%, about 10% to about 160%, about 10% to about 140%, about 10% to about 120%, about 10% to about 100%, about 10% to about 90%, about 10% to about 80%, about 10% to about 70%, about 10% to about 60%, about 10% to about 50%, about 10% to about 45%, about 10% to about 40%, about 10% to about 35%, about 10% to about 30%, about 10% to about 25%, about 10% to about 20%, about 10% to about 15%, about 15% to about 800%, about 15% to about 750%, about 15% to about 700%, about 15% to about 650%, about 15% to about 600%, about 15% to about 550%, about 15% to about 500%, about 15% to about 450%, about 15% to about 400%, about 15% to about 350%, about 15% to about 300%, about 15% to about 280%, about 15% to about 260%, about 15% to about 240%, about 15% to about 220%, about 15% to about 200%, about 15% to about 180%, about 15% to about 160%, about 15% to about 140%, about 15% to about 120%, about 15% to about 100%, about 15% to about 90%, about 15% to about 80%, about 15% to about 70%, about 15% to about 60%, about 15% to about 50%, about 15% to about 45%, about 15% to about 40%, about 15% to about 35%, about 15% to about 30%, about 15% to about 25%, about 15% to about 20%, about 20% to about 800%, about 20% to about 750%, about 20% to about 700%, about 20% to about 650%, about 20% to about 600%, about 20% to about 550%, about 20% to about 500%, about 20% to about 450%, about 20% to about 400%, about 20% to about 350%, about 20% to about 300%, about 20% to about 280%, about 20% to about 260%, about 20% to about 240%, about 20% to about 220%, about 20% to about 200%, about 20% to about 180%, about 20% to about 160%, about 20% to about 140%, about 20% to about 120%, about 20% to about 100%, about 20% to about 90%, about 20% to about 80%, about 20% to about 70%, about 20% to about 60%, about 20% to about 50%, about 20% to about 45%, about 20% to about 40%, about 20% to about 35%, about 20% to about 30%, about 20% to about 25%, about 25% to about 800%, about 25% to about 750%, about 25% to about 700%, about 25% to about 650%, about 25% to about 600%, about 25% to about 550%, about 25% to about 500%, about 25% to about 450%, about 25% to about 400%, about 25% to about 350%, about 25% to about 300%, about 25% to about 280%, about 25% to about 260%, about 25% to about 240%, about 25% to about 220%, about 25% to about 200%, about 25% to about 180%, about 25% to about 160%, about 25% to about 140%, about 25% to about 120%, about 25% to about 100%, about 25% to about 90%, about 25% to about 80%, about 25% to about 70%, about 25% to about 60%, about 25% to about 50%, about 25% to about 45%, about 25% to about 40%, about 25% to about 35%, about 35% to about 800%, about 35% to about 750%, about 35% to about 700%, about 35% to about 650%, about 35% to about 600%, about 35% to about 550%, about 35% to about 500%, about 35% to about 450%, about 35% to about 400%, about 35% to about 350%, about 35% to about 300%, about 35% to about 280%, about 35% to about 260%, about 35% to about 240%, about 35% to about 220%, about 35% to about 200%, about 35% to about 180%, about 35% to about 160%, about 35% to about 140%, about 35% to about 120%, about 35% to about 100%, about 35% to about 90%, about 35% to about 80%, about 35% to about 70%, about 35% to about 60%, about 35% to about 50%, about 35% to about 45%, about 35% to about 40%, about 40% to about 800%, about 40% to about 750%, about 40% to about 700%, about 40% to about 650%, about 40% to about 600%, about 40% to about 550%, about 40% to about 500%, about 40% to about 450%, about 40% to about 400%, about 40% to about 350%, about 40% to about 300%, about 40% to about 280%, about 40% to about 260%, about 40% to about 240%, about 40% to about 220%, about 40% to about 200%, about 40% to about 180%, about 40% to about 160%, about 40% to about 140%, about 40% to about 120%, about 40% to about 100%, about 40% to about 90%, about 40% to about 80%, about 40% to about 70%, about 40% to about 60%, about 40% to about 50%, about 40% to about 45%, about 45% to about 800%, about 45% to about 750%, about 45% to about 700%, about 45% to about 650%, about 45% to about 600%, about 45% to about 550%, about 45% to about 500%, about 45% to about 450%, about 45% to about 400%, about 45% to about 350%, about 45% to about 300%, about 45% to about 280%, about 45% to about 260%, about 45% to about 240%, about 45% to about 220%, about 45% to about 200%, about 45% to about 180%, about 45% to about 160%, about 45% to about 140%, about 45% to about 120%, about 45% to about 100%, about 45% to about 90%, about 45% to about 80%, about 45% to about 70%, about 45% to about 60%, about 45% to about 50%, about 50% to about 800%, about 50% to about 750%, about 50% to about 700%, about 50% to about 650%, about 50% to about 600%, about 50% to about 550%, about 50% to about 500%, about 50% to about 450%, about 50% to about 400%, about 50% to about 350%, about 50% to about 300%, about 50% to about 280%, about 50% to about 260%, about 50% to about 240%, about 50% to about 220%, about 50% to about 200%, about 50% to about 180%, about 50% to about 160%, about 50% to about 140%, about 50% to about 120%, about 50% to about 100%, about 50% to about 90%, about 50% to about 80%, about 50% to about 70%, about 50% to about 60%, about 60% to about 800%, about 60% to about 750%, about 60% to about 700%, about 60% to about 650%, about 60% to about 600%, about 60% to about 550%, about 60% to about 500%, about 60% to about 450%, about 60% to about 400%, about 60% to about 350%, about 60% to about 300%, about 60% to about 280%, about 60% to about 260%, about 60% to about 240%, about 60% to about 220%, about 60% to about 200%, about 60% to about 180%, about 60% to about 160%, about 60% to about 140%, about 60% to about 120%, about 60% to about 100%, about 60% to about 90%, about 60% to about 80%, about 60% to about 70%, about 70% to about 800%, about 70% to about 750%, about 70% to about 700%, about 70% to about 650%, about 70% to about 600%, about 70% to about 550%, about 70% to about 500%, about 70% to about 450%, about 70% to about 400%, about 70% to about 350%, about 70% to about 300%, about 70% to about 280%, about 70% to about 260%, about 70% to about 240%, about 70% to about 220%, about 70% to about 200%, about 70% to about 180%, about 70% to about 160%, about 70% to about 140%, about 70% to about 120%, about 70% to about 100%, about 70% to about 90%, about 70% to about 80%, about 80% to about 800%, about 80% to about 750%, about 80% to about 700%, about 80% to about 650%, about 80% to about 600%, about 80% to about 550%, about 80% to about 500%, about 80% to about 450%, about 80% to about 400%, about 80% to about 350%, about 80% to about 300%, about 80% to about 280%, about 80% to about 260%, about 80% to about 240%, about 80% to about 220%, about 80% to about 200%, about 80% to about 180%, about 80% to about 160%, about 80% to about 140%, about 80% to about 120%, about 80% to about 100%, about 80% to about 90%, about 90% to about 800%, about 90% to about 750%, about 90% to about 700%, about 90% to about 650%, about 90% to about 600%, about 90% to about 550%, about 90% to about 500%, about 90% to about 450%, about 90% to about 400%, about 90% to about 350%, about 90% to about 300%, about 90% to about 280%, about 90% to about 260%, about 90% to about 240%, about 90% to about 220%, about 90% to about 200%, about 90% to about 180%, about 90% to about 160%, about 90% to about 140%, about 90% to about 120%, about 90% to about 100%, about 100% to about 800%, about 100% to about 750%, about 100% to about 700%, about 100% to about 650%, about 100% to about 600%, about 100% to about 550%, about 100% to about 500%, about 100% to about 450%, about 100% to about 400%, about 100% to about 350%, about 100% to about 300%, about 100% to about 280%, about 100% to about 260%, about 100% to about 240%, about 100% to about 220%, about 100% to about 200%, about 100% to about 180%, about 100% to about 160%, about 100% to about 140%, about 100% to about 120%, about 120% to about 800%, about 120% to about 750%, about 120% to about 700%, about 120% to about 650%, about 120% to about 600%, about 120% to about 550%, about 120% to about 500%, about 120% to about 450%, about 120% to about 400%, about 120% to about 350%, about 120% to about 300%, about 120% to about 280%, about 120% to about 260%, about 120% to about 240%, about 120% to about 220%, about 120% to about 200%, about 120% to about 180%, about 120% to about 160%, about 120% to about 140%, about 140% to about 800%, about 140% to about 750%, about 140% to about 700%, about 140% to about 650%, about 140% to about 600%, about 140% to about 550%, about 140% to about 500%, about 140% to about 450%, about 140% to about 400%, about 140% to about 350%, about 140% to about 300%, about 140% to about 280%, about 140% to about 260%, about 140% to about 240%, about 140% to about 220%, about 140% to about 200%, about 140% to about 180%, about 140% to about 160%, about 160% to about 800%, about 160% to about 750%, about 160% to about 700%, about 160% to about 650%, about 160% to about 600%, about 160% to about 550%, about 160% to about 500%, about 160% to about 450%, about 160% to about 400%, about 160% to about 350%, about 160% to about 300%, about 160% to about 280%, about 160% to about 260%, about 160% to about 240%, about 160% to about 220%, about 160% to about 200%, about 160% to about 180%, about 180% to about 800%, about 180% to about 750%, about 180% to about 700%, about 180% to about 650%, about 180% to about 600%, about 180% to about 550%, about 180% to about 500%, about 180% to about 450%, about 180% to about 400%, about 180% to about 350%, about 180% to about 300%, about 180% to about 280%, about 180% to about 260%, about 180% to about 240%, about 180% to about 220%, about 180% to about 200%, about 200% to about 800%, about 200% to about 750%, about 200% to about 700%, about 200% to about 650%, about 200% to about 600%, about 200% to about 550%, about 200% to about 500%, about 200% to about 450%, about 200% to about 400%, about 200% to about 350%, about 200% to about 300%, about 200% to about 280%, about 200% to about 260%, about 200% to about 240%, about 200% to about 220%, about 220% to about 800%, about 220% to about 750%, about 220% to about 700%, about 220% to about 650%, about 220% to about 600%, about 220% to about 550%, about 220% to about 500%, about 220% to about 450%, about 220% to about 400%, about 220% to about 350%, about 220% to about 300%, about 220% to about 280%, about 220% to about 260%, about 220% to about 240%, about 240% to about 800%, about 240% to about 750%, about 240% to about 700%, about 240% to about 650%, about 240% to about 600%, about 240% to about 550%, about 240% to about 500%, about 240% to about 450%, about 240% to about 400%, about 240% to about 350%, about 240% to about 300%, about 240% to about 280%, about 260% to about 800%, about 260% to about 750%, about 260% to about 700%, about 260% to about 650%, about 260% to about 600%, about 260% to about 550%, about 260% to about 500%, about 260% to about 450%, about 260% to about 400%, about 260% to about 350%, about 260% to about 300%, about 260% to about 280%, about 280% to about 800%, about 280% to about 750%, about 280% to about 700%, about 280% to about 650%, about 280% to about 600%, about 280% to about 550%, about 280% to about 500%, about 280% to about 450%, about 280% to about 400%, about 280% to about 350%, about 280% to about 300%, about 300% to about 800%, about 300% to about 750%, about 300% to about 700%, about 300% to about 650%, about 300% to about 600%, about 300% to about 550%, about 300% to about 500%, about 300% to about 450%, about 300% to about 400%, about 300% to about 350%, about 350% to about 800%, about 350% to about 750%, about 350% to about 700%, about 350% to about 650%, about 350% to about 600%, about 350% to about 550%, about 350% to about 500%, about 350% to about 450%, about 350% to about 400%, about 400% to about 800%, about 400% to about 750%, about 400% to about 700%, about 400% to about 650%, about 400% to about 600%, about 400% to about 550%, about 400% to about 500%, about 400% to about 450%, about 450% to about 800%, about 450% to about 750%, about 450% to about 700%, about 450% to about 650%, about 450% to about 600%, about 450% to about 550%, about 450% to about 500%, about 500% to about 800%, about 500% to about 750%, about 500% to about 700%, about 500% to about 650%, about 500% to about 600%, about 500% to about 550%, about 550% to about 800%, about 550% to about 750%, about 550% to about 700%, about 550% to about 650%, about 550% to about 600%, about 600% to about 800%, about 600% to about 750%, about 600% to about 700%, about 650% to about 800%, about 650% to about 750%, about 650% to about 700%, about 700% to about 800%, about 700% to about 750%, or about 750% to about 800%) of one or more of any of the cytokines or chemokines or cytotoxicity granules or regulatory molecules described herein (e.g., one or more of any of IL-2, IFN-γ, IL-1, IL-4, IL-5, IL-6, IL-7, IL-9, IL-10, IL-12, IL-13, IL-15, IL-17, IL-18, IL-22, IL-33, leukotriene B4, CCLS, TNFα, granzymes, perforin, TGFβ, STAT3, STAT4, STAT5, RORγT, FOXP3, and GATA3) (e.g., as compared to the level of the one or more cytokines, chemokines, cytotoxicity granules, and regulatory molecules in a control not contacted with any of the multi-chain chimeric polypeptides described herein).

Methods of Inducing or Increasing Proliferation of an Immune Cell

Also provided herein are methods of inducing or increasing proliferation of an immune cell (e.g., any of the exemplary immune cells described herein or known in the art) that include contacting an immune cell with an effective amount of any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell).

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the multi-chain chimeric polypeptide is administered to a subject (e.g., a mammal, e.g., a human) in an amount sufficient to result in stimulation of an immune cell in the subject.

In some examples of any of the methods described herein, the immune cell can be an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Detection of the proliferation of an immune cell can be performed using methods known in the art, e.g., cytometry (e.g., fluorescence-assisted flow cytometry), microscopy, and immunofluorescence microscopy, e.g., by comparing the rate of increase in the concentration of the immune cell in a sample not contacted with a multi-chain chimeric polypeptide to the rate of increase in the concentration of the immune cell in a similar sample contacted with any of the multi-chain chimeric polypeptides described herein).

In other examples, the proliferation of an immune cell can be indirectly detected by detecting an increase in the level of one or more cytokines or chemokines or cytotoxicity granules or regulatory molecules secreted or upregulated by proliferating immune cells (e.g., one or more of IL-2, IFN-γ, IL-1, IL-4, IL-5, IL-6, IL-7, IL-9, IL-10, IL-12, IL-13, IL-15, IL-17, IL-18, IL-22, IL-33, leukotriene B4, CCLS, TNFα, granzymes, perforin, TGFβ, STAT3, STAT4, STAT5, RORγT, FOXP3, and GATA3) (e.g., as compared to the level of the one or more cytokines, chemokines, cytotoxicity granules, and regulatory molecules in a control not contacted with any of the multi-chain chimeric polypeptides described herein).

In some embodiments, the methods provided herein can result in an increase (e.g., about 1% to about 800% increase, or any of the subranges of this range described herein) in the rate of increase in the concentration of the immune cell in a sample contacted with any of the multi-chain chimeric polypeptides described herein as compared to the rate of increase in a similar control sample not contacted with any of the multi-chain chimeric polypeptides described herein.

Methods of Inducing Differentiation of an Immune Cell

Also provided herein are method of inducing differentiation of an immune cell (e.g., any of the exemplary immune cells described herein or known in the art) into a memory or memory-like immune cell that include contacting an immune cell with an effective amount of any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell).

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the multi-chain chimeric polypeptide is administered to a subject (e.g., a mammal, e.g., a human) in an amount sufficient to result in stimulation of an immune cell in the subject.

In some examples of any of the methods described herein, the immune cell can be an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

In some examples, an effective amount of any of the multi-chain chimeric polypeptides described herein or any of the compositions (e.g., pharmaceutical compositions) described herein is combined with an anti-TF IgG1 antibody to create a memory or memory like immune cell.

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

In some examples, the immune cell is a NK cell, and the detection of a memory NK cell can include, e.g., the detection of the level of one or more of IL-12, IL-18, IL-33, CD25, CD69, CD62L, STAT4, Zbtb32, DNAM-1, NKp30, NKp44, NKp46, BIM, Noxa, SOCS1, BNIP3, BNIP3L, IFN-γ, CXCL16, CXCR6, NKG2D, TRAIL, CD49, Ly49D, CD49b, and Ly79H. A description of NK memory cells and methods of detecting the same is described in O'Sullivan et al., *Immunity* 43:634-645, 2015.

In some examples, the immune cell is a T cell, and the detection of memory T cells can include, e.g., the detection of the level of expression of one or more of CD45RO, CCR7, L-selectin (CD62L), CD44, CD45RA, integrin αeβ7, CD43, CD27, CD28, IL-7Rα, CD95, IL-2Rβ, CXCR3, and LFA-1. In some examples, the immune cell is a B cell and the detection of memory B cells can include, e.g., the detection of the level of expression of CD27. Other types and markers of memory or memory-like immune cells are known in the art.

Methods of Treatment

Also provided herein are methods of treating a subject in need thereof (e.g., any of the exemplary subjects described herein or known in the art) that include administering to the subject a therapeutically effective amount of any of the multi-chain chimeric polypeptides described herein or any of the compositions (e.g., pharmaceutical compositions) described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, these methods can result in a reduction in the number, severity, or frequency of one or more symptoms of the cancer in the subject (e.g., as compared to the number, severity, or frequency of the one or more symptoms of the cancer in the subject prior to treatment). In some embodiments, these methods can result in a reduction (e.g., about 1% reduction to about 99% reduction, about 1% reduction to about 95% reduction, about 1% reduction to about 90% reduction, about 1% reduction to about 85% reduction, about 1% reduction to about 80% reduction, about 1% reduction to about 75% reduction, about 1% reduction to about 70% reduction, about 1% reduction to about 65% reduction, about 1% reduction to about 60% reduction, about 1% reduction to about 55% reduction, about 1% reduction to about 50% reduction, about 1% reduction to about 45% reduction, about 1% reduction to about 40% reduction, about 1% reduction to about 35% reduction, about 1% reduction to about 30% reduction, about 1% reduction to about 25% reduction, about 1% reduction to about 20% reduction, about 1% reduction to about 15% reduction, about 1% reduction to about 10% reduction, about 1% reduction to about 5% reduction, about 5% reduction to about 99% reduction, about 5% reduction to about 95% reduction, about 5% reduction to about 90% reduction, about 5% reduction to about 85% reduction, about 5% reduction to about 80% reduction, about 5% reduction to about 75% reduction, about 5% reduction to about 70% reduction, about 5% reduction to about 65% reduction, about 5% reduction to about 60% reduction, about 5% reduction to about 55% reduction, about 5% reduction to about 50% reduction, about 5% reduction to about 45% reduction, about 5% reduction to about 40% reduction, about 5% reduction to about 35% reduction, about 5% reduction to about 30% reduction, about 5% reduction to about 25% reduction, about 5% reduction to about 20% reduction, about 5% reduction to about 15% reduction, about 5% reduction to about 10% reduction, about 10% reduction to about 99% reduction, about 10% reduction to about 95% reduction, about 10% reduction to about 90% reduction, about 10% reduction to about 85% reduction, about 10% reduction to about 80% reduction, about 10% reduction to about 75% reduction, about 10% reduction to about 70% reduction, about 10% reduction to about 65% reduction, about 10% reduction to about 60% reduction, about 10% reduction to about 55% reduction, about 10% reduction to about 50% reduction, about 10% reduction to about 45% reduction, about 10% reduction to about 40% reduction, about 10% reduction to about 35% reduction, about 10% reduction to about 30% reduction, about 10% reduction to about 25% reduction, about 10% reduction to about 20% reduction, about 10% reduction to about 15% reduction, about 15% reduction to about 99% reduction, about 15% reduction to about 95% reduction, about 15% reduction to about 90% reduction, about 15% reduction to about 85% reduction, about 15% reduction to about 80% reduction, about 15% reduction to about 75% reduction, about 15% reduction to about 70% reduction, about 15% reduction to about 65% reduction, about 15% reduction to about 60% reduction, about 15% reduction to about 55% reduction, about 15% reduction to about 50% reduction, about 15% reduction to about 45% reduction, about 15% reduction to about 40% reduction, about 15% reduction to about 35% reduction, about 15% reduction to about 30% reduction, about 15% reduction to about 25% reduction, about 15% reduction to about 20% reduction, about 20% reduction to about 99% reduction, about 20% reduction to about 95% reduction, about 20% reduction to about 90% reduction, about 20% reduction to about 85% reduction, about 20% reduction to about 80% reduction, about 20% reduction to about 75% reduction, about 20% reduction to about 70% reduction, about 20% reduction to about 65% reduction, about 20% reduction to about 60% reduction, about 20% reduction to about 55% reduction, about 20% reduction to about 50% reduction, about 20% reduction to about 45% reduction, about 20% reduction to about 40% reduction, about 20% reduction to about 35% reduction, about 20% reduction to about 30% reduction, about 20% reduction to about 25% reduction, about 25% reduction to about 99% reduction, about 25% reduction to about 95% reduction, about 25% reduction to about 90% reduction, about 25% reduction to about 85% reduction, about 25% reduction to about 80% reduction, about 25% reduction to about 75% reduction, about 25% reduction to about 70% reduction, about 25% reduction to about 65% reduction, about 25% reduction to about 60% reduction, about 25% reduction to about 55% reduction, about 25% reduction to about 50% reduction, about 25% reduction to about 45% reduction, about 25% reduction to about 40% reduction, about 25% reduction to about 35% reduction, about 25% reduction to about 30% reduction, about 30% reduction to about 99% reduction, about 30% reduction to about 95% reduction, about 30% reduction to about 90% reduction, about 30% reduction to about 85% reduction, about 30% reduction to about 80% reduction, about 30% reduction to about 75% reduction, about 30% reduction to about 70% reduction, about 30% reduction to about 65% reduction, about 30% reduction to about 60% reduction, about 30% reduction to about 55% reduction, about 30% reduction to about 50% reduction, about 30% reduction to about 45% reduction, about 30% reduction to about 40% reduction, about 30% reduction to about 35% reduction, about 35% reduction to about 99% reduction, about 35% reduction to about 95% reduction, about 35% reduction to about 90% reduction, about 35% reduction to about 85% reduction, about 35% reduction to about 80% reduction, about 35% reduction to about 75% reduction, about 35% reduction to about 70% reduction, about 35% reduction to about 65% reduction, about 35% reduction to about 60% reduction, about 35% reduction to about 55% reduction, about 35% reduction to about 50% reduction, about 35% reduction to about 45% reduction, about 35% reduction to about 40% reduction, about 40% reduction to about 99% reduction, about 40% reduction to about 95% reduction, about 40% reduction to about 90% reduction, about 40% reduction to about 85% reduction, about 40% reduction to about 80% reduction, about 40% reduction to about 75% reduction, about 40% reduction to about 70% reduction, about 40% reduction to about 65% reduction, about 40% reduction to about 60% reduction, about 40% reduction to about 55% reduction, about 40% reduction to about 50% reduction, about 40% reduction to about 45% reduction, about 45% reduction to about 99% reduction, about 45% reduction to about 95% reduction, about 45% reduction to about 90% reduction, about 45% reduction to about 85% reduction, about 45% reduction to about 80% reduction, about 45% reduction to about 75% reduction, about 45% reduction to about 70% reduction, about 45% reduction to about 65% reduction, about 45% reduction to about 60% reduction, about 45% reduction to about 55% reduction, about 45% reduction to about 50% reduction, about 50% reduction to about 99% reduction, about 50% reduction to about 95% reduction, about 50% reduction to about 90% reduction, about 50% reduction to about 85% reduction, about 50% reduction to about 80% reduction, about 50% reduction to about 75% reduction, about 50% reduction to about 70% reduction, about 50% reduction to about 65% reduction, about 50% reduction to about 60% reduction, about 50% reduction to about 55% reduction, about 55% reduction to about 99% reduction, about 55% reduction to about 95% reduction, about 55% reduction to about 90% reduction, about 55% reduction to about 85% reduction, about 55% reduction to about 80% reduction, about 55% reduction to about 75% reduction, about 55% reduction to about 70% reduction, about 55% reduction to about 65% reduction, about 55% reduction to about 60% reduction, about 60% reduction to about 99% reduction, about 60% reduction to about 95% reduction, about 60% reduction to about 90% reduction, about 60% reduction to about 85% reduction, about 60% reduction to about 80% reduction, about 60% reduction to about 75% reduction, about 60% reduction to about 70% reduction, about 60% reduction to about 65% reduction, about 65% reduction to about 99% reduction, about 65% reduction to about 95% reduction, about 65% reduction to about 90% reduction, about 65% reduction to about 85% reduction, about 65% reduction to about 80% reduction, about 65% reduction to about 75% reduction, about 65% reduction to about 70% reduction, about 70% reduction to about 99% reduction, about 70% reduction to about 95% reduction, about 70% reduction to about 90% reduction, about 70% reduction to about 85% reduction, about 70% reduction to about 80% reduction, about 70% reduction to about 75% reduction, about 75% reduction to about 99% reduction, about 75% reduction to about 95% reduction, about 75% reduction to about 90% reduction, about 75% reduction to about 85% reduction, about 75% reduction to about 80% reduction, about 80% reduction to about 99% reduction, about 80% reduction to about 95% reduction, about 80% reduction to about 90% reduction, about 80% reduction to about 85% reduction, about 85% reduction to about 99% reduction, about 85% reduction to about 95% reduction, about 85% reduction to about 90% reduction, about 90% reduction to about 99% reduction, about 90% reduction to about 95% reduction, or about 95% reduction to about 99% reduction) in the volume of one or more solid tumors in the subject (e.g., as compared to the volume of the one or more solid tumors prior to treatment or at the start of treatment). In some embodiments, the these methods can reduce (e.g., about 1% reduction to about 99% reduction, or any of the subranges of this range described herein) the risk of developing a metastasis or developing one or more additional metastasis in a subject (e.g., as compared to the risk of developing a metastasis or developing one or more additional metastasis in a subject prior to treatment or in a similar subject or a population of subjects administered a different treatment).

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples, these methods can result in a reduction in the number, severity, or frequency of one or more symptoms of the aging-related disease or condition in the subject (e.g., as compared to the number, severity, or frequency of the one or more symptoms of the aging-related disease or condition in the subject prior to treatment). In some examples, the methods can result in a decrease (e.g., about 1% decrease to about 99% decrease, an about 1% decrease to about 95% decrease, about 1% decrease to about 90% decrease, about 1% decrease to about 85% decrease, about 1% decrease to about 80% decrease, about 1% decrease to about 75% decrease, about 1% to about 70% decrease, about 1% decrease to about 65% decrease, about 1% decrease to about 60% decrease, about 1% decrease to about 55% decrease, about 1% decrease to about 50% decrease, about 1% decrease to about 45% decrease, about 1% decrease to about 40% decrease, about 1% decrease to about 35% decrease, about 1% decrease to about 30% decrease, about 1% decrease to about 25% decrease, about 1% decrease to about 20% decrease, about 1% decrease to about 15% decrease, about 1% decrease to about 10% decrease, about 1% decrease to about 5% decrease, about 5% decrease to about 99% decrease, an about 5% decrease to about 95% decrease, about 5% decrease to about 90% decrease, about 5% decrease to about 85% decrease, about 5% decrease to about 80% decrease, about 5% decrease to about 75% decrease, about 5% to about 70% decrease, about 5% decrease to about 65% decrease, about 5% decrease to about 60% decrease, about 5% decrease to about 55% decrease, about 5% decrease to about 50% decrease, about 5% decrease to about 45% decrease, about 5% decrease to about 40% decrease, about 5% decrease to about 35% decrease, about 5% decrease to about 30% decrease, about 5% decrease to about 25% decrease, about 5% decrease to about 20% decrease, about 5% decrease to about 15% decrease, about 5% decrease to about 10% decrease, about 10% decrease to about 99% decrease, an about 10% decrease to about 95% decrease, about 10% decrease to about 90% decrease, about 10% decrease to about 85% decrease, about 10% decrease to about 80% decrease, about 10% decrease to about 75% decrease, about 10% to about 70% decrease, about 10% decrease to about 65% decrease, about 10% decrease to about 60% decrease, about 10% decrease to about 55% decrease, about 10% decrease to about 50% decrease, about 10% decrease to about 45% decrease, about 10% decrease to about 40% decrease, about 10% decrease to about 35% decrease, about 10% decrease to about 30% decrease, about 10% decrease to about 25% decrease, about 10% decrease to about 20% decrease, about 10% decrease to about 15% decrease, about 15% decrease to about 99% decrease, an about 15% decrease to about 95% decrease, about 15% decrease to about 90% decrease, about 15% decrease to about 85% decrease, about 15% decrease to about 80% decrease, about 15% decrease to about 75% decrease, about 15% to about 70% decrease, about 15% decrease to about 65% decrease, about 15% decrease to about 60% decrease, about 15% decrease to about 55% decrease, about 15% decrease to about 50% decrease, about 15% decrease to about 45% decrease, about 15% decrease to about 40% decrease, about 15% decrease to about 35% decrease, about 15% decrease to about 30% decrease, about 15% decrease to about 25% decrease, about 15% decrease to about 20% decrease, about 20% decrease to about 99% decrease, an about 20% decrease to about 95% decrease, about 20% decrease to about 90% decrease, about 20% decrease to about 85% decrease, about 20% decrease to about 80% decrease, about 20% decrease to about 75% decrease, about 20% to about 70% decrease, about 20% decrease to about 65% decrease, about 20% decrease to about 60% decrease, about 20% decrease to about 55% decrease, about 20% decrease to about 50% decrease, about 20% decrease to about 45% decrease, about 20% decrease to about 40% decrease, about 20% decrease to about 35% decrease, about 20% decrease to about 30% decrease, about 20% decrease to about 25% decrease, about 25% decrease to about 99% decrease, an about 25% decrease to about 95% decrease, about 25% decrease to about 90% decrease, about 25% decrease to about 85% decrease, about 25% decrease to about 80% decrease, about 25% decrease to about 75% decrease, about 25% to about 70% decrease, about 25% decrease to about 65% decrease, about 25% decrease to about 60% decrease, about 25% decrease to about 55% decrease, about 25% decrease to about 50% decrease, about 25% decrease to about 45% decrease, about 25% decrease to about 40% decrease, about 25% decrease to about 35% decrease, about 25% decrease to about 30% decrease, about 30% decrease to about 99% decrease, an about 30% decrease to about 95% decrease, about 30% decrease to about 90% decrease, about 30% decrease to about 85% decrease, about 30% decrease to about 80% decrease, about 30% decrease to about 75% decrease, about 30% to about 70% decrease, about 30% decrease to about 65% decrease, about 30% decrease to about 60% decrease, about 30% decrease to about 55% decrease, about 30% decrease to about 50% decrease, about 30% decrease to about 45% decrease, about 30% decrease to about 40% decrease, about 30% decrease to about 35% decrease, about 35% decrease to about 99% decrease, an about 35% decrease to about 95% decrease, about 35% decrease to about 90% decrease, about 35% decrease to about 85% decrease, about 35% decrease to about 80% decrease, about 35% decrease to about 75% decrease, about 35% to about 70% decrease, about 35% decrease to about 65% decrease, about 35% decrease to about 60% decrease, about 35% decrease to about 55% decrease, about 35% decrease to about 50% decrease, about 35% decrease to about 45% decrease, about 35% decrease to about 40% decrease, about 40% decrease to about 99% decrease, an about 40% decrease to about 95% decrease, about 40% decrease to about 90% decrease, about 40% decrease to about 85% decrease, about 40% decrease to about 80% decrease, about 40% decrease to about 75% decrease, about 40% to about 70% decrease, about 40% decrease to about 65% decrease, about 40% decrease to about 60% decrease, about 40% decrease to about 55% decrease, about 40% decrease to about 50% decrease, about 40% decrease to about 45% decrease, about 45% decrease to about 99% decrease, an about 45% decrease to about 95% decrease, about 45% decrease to about 90% decrease, about 45% decrease to about 85% decrease, about 45% decrease to about 80% decrease, about 45% decrease to about 75% decrease, about 45% to about 70% decrease, about 45% decrease to about 65% decrease, about 45% decrease to about 60% decrease, about 45% decrease to about 55% decrease, about 45% decrease to about 50% decrease, about 50% decrease to about 99% decrease, an about 50% decrease to about 95% decrease, about 50% decrease to about 90% decrease, about 50% decrease to about 85% decrease, about 50% decrease to about 80% decrease, about 50% decrease to about 75% decrease, about 50% to about 70% decrease, about 50% decrease to about 65% decrease, about 50% decrease to about 60% decrease, about 50% decrease to about 55% decrease, about 55% decrease to about 99% decrease, an about 55% decrease to about 95% decrease, about 55% decrease to about 90% decrease, about 55% decrease to about 85% decrease, about 55% decrease to about 80% decrease, about 55% decrease to about 75% decrease, about 55% to about 70% decrease, about 55% decrease to about 65% decrease, about 55% decrease to about 60% decrease, about 60% decrease to about 99% decrease, an about 60% decrease to about 95% decrease, about 60% decrease to about 90% decrease, about 60% decrease to about 85% decrease, about 60% decrease to about 80% decrease, about 60% decrease to about 75% decrease, about 60% to about 70% decrease, about 60% decrease to about 65% decrease, about 65% decrease to about 99% decrease, an about 65% decrease to about 95% decrease, about 65% decrease to about 90% decrease, about 65% decrease to about 85% decrease, about 65% decrease to about 80% decrease, about 65% decrease to about 75% decrease, about 65% to about 70% decrease, about 70% decrease to about 99% decrease, an about 70% decrease to about 95% decrease, about 70% decrease to about 90% decrease, about 70% decrease to about 85% decrease, about 70% decrease to about 80% decrease, about 70% decrease to about 75% decrease, about 75% decrease to about 99% decrease, an about 75% decrease to about 95% decrease, about 75% decrease to about 90% decrease, about 75% decrease to about 85% decrease, about 75% decrease to about 80% decrease, about 80% decrease to about 99% decrease, an about 80% decrease to about 95% decrease, about 80% decrease to about 90% decrease, about 80% decrease to about 85% decrease, about 85% decrease to about 99% decrease, an about 85% decrease to about 95% decrease, about 85% decrease to about 90% decrease, about 90% decrease to about 99% decrease, an about 90% decrease to about 95% decrease, or about 95% decrease to about 99% decrease) in the number of senescent cells in the subject (e.g., a decrease in the number of senescent cells in one or more specific tissues involved and/or implicated in the aging-related disease or disorder in the subject), e.g., as compared to the number of senescent cells in the subject prior to treatment.

In some examples of these methods, the subject has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus. In some embodiments, these methods can result in a decrease in the infectious titer (e.g., viral titer) in a subject (e.g., as compared to the infectious titer in the subject prior to treatment). In some embodiments, these methods can result in a reduction in the number, severity, or frequency of one or more symptoms of the infectious disease (e.g., viral infection) in the subject (e.g., as compared to the number, severity, or frequency of the one or more symptoms of the infectious disease in the subject prior to treatment).

The term "subject" refers to any mammal. In some embodiments, the subject or "subject in need of treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject or "subject in need of treatment" may be a non-human mammal, especially mammals that are conventionally used as models for demonstrating therapeutic efficacy in humans (e.g., murine, lapine, porcine, canine or primate animals) may be employed.

Methods of Killing a Cancer Cell, an Infected Cell, or a Senescent Cell

Also provided herein are methods of killing a cancer cell (e.g., any of the exemplary types of cancer described herein or known in the art), an infected cell (e.g., a cell infected with any of the exemplary viruses described herein or known in the art), or a senescent cell (e.g., a senescent cancer cell, a senescent fibroblast, or a senescent endothelial cell) in a subject in need thereof (e.g., any of the exemplary subjects described herein or known in the art) that include administering to the subject a therapeutically effective amount of any of the multi-chain chimeric polypeptides described herein or any of the compositions (e.g., pharmaceutical compositions) described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. Non-limiting examples of an infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Senescent Cells

Senescence is a form of irreversible growth arrest accompanied by phenotypic changes, resistance to apoptosis and activation of damage-sensing signaling pathways. Cellular senescence was first described in cultured human fibroblast cells that lost their ability to proliferate, reaching permanent arrest after about 50 population doublings (referred to as the Hayflick limit). Senescence is considered a stress response that can be induced by a wide range of intrinsic and extrinsic insults, including oxidative and genotoxic stress, DNA damage, telomere attrition, oncogenic activation, mitochondrial dysfunction, or chemotherapeutic agents.

Senescent cells remain metabolically active and can influence the tissue hemostasis, disease and aging through their secretory phenotype. Senescence is considered as a physiologic process and is important in promoting wound healing, tissue homeostasis, regeneration, and fibrosis regulation. For instance, transient induction of senescent cells is observed during would healing and contributes to wound resolution. Perhaps one of the most important roles of senescence is its role in tumor suppression. However, the accumulation of senescent cells also drives aging- and aging-related diseases and conditions. The senescent phenotype also can trigger chronic inflammatory responses and consequently augment chronic inflammatory conditions to promote tumor growth. The connection between senescence and aging was initially based on observations that senescent cells accumulate in aged tissue. The use of transgenic models has enabled the detection of senescent cells systematically in many age-related pathologies. Strategies to selectively eliminate senescent cells has demonstrated that senescent cells can indeed play a causal role in aging and related pathologies.

Senescent cells display important and unique properties which include changes in morphology, chromatin organization, gene expression, and metabolism. There are several biochemical and functional properties associated with cellular senescence, such as (i) increased expression of p16 and p21, inhibitors of cyclin-dependent kinases, (ii) presence of senescence-associated β-galactosidase, a marker of lysosomal activity, (iii) appearance of senescence-associated heterochromatin foci and downregulation of lamin B1 levels, (iv) resistance to apoptosis caused by an increased expression of anti-apoptotic BCL-family protein, and (v) upregulation of CD26 (DPP4), CD36 (Scavenger receptor), forkhead box 4 (FOXO4), and secretory carrier membrane protein 4 (SCAMP4). Senescent cells also express an inflammatory signature, the so-called senescence-associated secretory phenotype (SASP). Through SASP, the senescent cells produce a wide range of inflammatory cytokines (IL-6, IL-8), growth factors (TGF-β), chemokines (CCL-2), and matrix metalloproteinases (MMP-3, MMP-9) that operate in a cell-autonomous manner to reinforce senescence (autocrine effects) and communicate with and modify the microenvironment (paracrine effects). SASP factors can contribute to tumor suppression by triggering senescence surveillance, an immune-mediated clearance of senescent cells. However, chronic inflammation is also a known driver of tumorigenesis, and accumulating evidence indicates that chronic SASP can also boost cancer and aging-related diseases.

The secretion profile of senescent cells is context dependent. For instance, the mitochondrial dysfunction-associated senescence (MiDAS), induced by different mitochondrial dysfunction in human fibroblasts, led to the appearance of a SASP that was deficient in IL-1-dependent inflammatory factors. A decrease in the NAD+/NADH ratio activated AMPK signaling which induced MiDAS through the activation of p53. As a result, p53 inhibited NF-κB signaling which is a crucial inducer of pro-inflammatory SASP. In contrast, the cellular senescence caused by persistent DNA damage in human cells induced an inflammatory SASP, which was dependent on the activation of ataxia-telangiectasia mutated (ATM) kinase but not on that of p53. In particular, the expression and secretion levels of IL-6 and IL-8 were increased. It was also demonstrated that cellular senescence caused by the ectopic expression p16INK4a and p21CIP1 induced the senescent phenotype in human fibroblasts without an inflammatory SASP indicating that the growth arrest itself did not stimulate SASP.

One of the most defining characteristics of senescence is stable growth arrest. This is achieved by two important pathways, the p16/Rb and the p53/p21, both of which are central in tumor suppression. DNA damage results in: (1) high deposition of γH2Ax (histone coding gene) and 53BP1 (involved in DNA damage response) in chromatin: this leads to activation of a kinase cascade eventually resulting in p53 activation, and (2) activation of p16INK4a and ARF (both encoded by CDKN2A) and P15INK4b (encoded by CDKN2B): p53 induces transcription of cyclin-dependent kinase inhibitor (p21) and along with both p16INK4a and p15INK4b block genes for cell cycle progression (CDK4 and CDK6). This eventually leads to hypophosphorylation of Retinoblastoma protein (Rb) and cell cycle arrest at the G1 phase.

Selectively killing senescent cells has been shown to significantly improve the health span of mice in the context of normal aging and ameliorates the consequences of age-related disease or cancer therapy (Ovadya, J Clin Invest. 128(4):1247-1254, 2018). In nature, the senescent cells are normally removed by the innate immune cells. Induction of senescence not only prevents the potential proliferation and transformation of damaged/altered cells, but also favors tissue repair through the production of SASP factors that function as chemoattractants mainly for Natural Killer (NK) cells (such as IL-15 and CCL2) and macrophages (such as CFS-1 and CCL2). These innate immune cells mediate the immunosurveillance mechanism for eliminating stressed cells. Senescent cells usually up-regulate the NK-cell activating receptor NKG2D and DNAM-1 ligands, which belong to a family of stress-inducible ligands: an important component of the frontline immune defense against infectious diseases and malignancies. Upon receptor activation, NK cells can then specifically induce the death of senescent cells through their cytolytic machinery. A role for NK cells in the immune surveillance of senescent cells has been pointed out in liver fibrosis (Sagiv, Oncogene 32(15): 1971-1977, 2013), hepatocellular carcinoma (Iannello, J Exp Med 210(10): 2057-2069, 2013), multiple myeloma (Soriani, Blood 113(15): 3503-3511, 2009), and glioma cells stressed by dysfunction of the mevalonate pathway (Ciaglia, Int J Cancer 142(1): 176-190, 2018). Endometrial cells undergo acute cellular senescence and do not differentiate into decidual cells. The differentiated decidual cells secrete IL-15 and thereby recruit uterine NK cells to target and eliminate the undifferentiated senescent cells thus helping to re-model and rejuvenate the endometrium (Brighton, Elife 6: e31274, 2017). With a similar mechanism, during liver fibrosis, p53-expressing senescent liver satellite cells skewed the polarization of resident Kupfer macrophages and freshly infiltrated macrophages toward the pro-inflammatory M1 phenotype, which display senolytic activity. F4/80+ macrophages have been shown to play a key role in the clearance of mouse uterine senescent cells to maintain postpartum uterine function.

Senescent cells recruit NK cells by mainly upregulating ligands to NKG2D (expressed on NK cells), chemokines, and other SASP factors. In vivo models of liver fibrosis have shown effective clearance of senescent cells by activated NK cells (Krizhanovsky, Cell 134(4): 657-667, 2008). Studies have described various models to study senescence including liver fibrosis (Krizhanovsky, Cell 134(4): 657-667, 2008), osteoarthritis (Xu, J Gerontol A Biol Sci Med Sci 72(6): 780-785, 2017), and Parkinson's disease (Chinta, Cell Rep 22(4): 930-940, 2018). Animal models for studying senescent cells are described in: Krizhanovsky, Cell 134(4): 657-667, 2008; Baker, Nature 479(7372): 232-236, 2011; Farr, Nat Med 23(9): 1072-1079, 2017; Bourgeois, FEBS Lett 592(12): 2083-2097, 2018; Xu, Nat Med 24(8): 1246-1256, 2018).

Additional Therapeutic Agents

Some embodiments of any of the methods described herein can further include administering to a subject (e.g., any of the subjects described herein) a therapeutically effective amount of one or more additional therapeutic agents. The one or more additional therapeutic agents can be administered to the subject at substantially the same time as the multi-chain chimeric polypeptide (e.g., any of the multi-chain chimeric polypeptides described herein) or immune cell (e.g., administered as a single formulation or two or more formulations to the subject). In some embodiments, one or more additional therapeutic agents can be administered to the subject prior to administration of the multi-chain chimeric polypeptide (e.g., any of the multi-chain chimeric polypeptides described herein) or immune cell. In some embodiments, one or more additional therapeutic agents can be administered to the subject after administration of the multi-chain chimeric polypeptide (e.g., any of the multi-chain chimeric polypeptides described herein) or immune cell to the subject.

Non-limiting examples of additional therapeutic agents include: anti-cancer drugs, activating receptor agonists, immune checkpoint inhibitors, agents for blocking HLA-specific inhibitory receptors, Glucogen Synthase Kinase (GSK) 3 inhibitors, and antibodies.

Non-limiting examples of anticancer drugs include anti-metabolic drugs (e.g., 5-fluorouracil (5-FU), 6-mercaptopurine (6-MP), capecitabine, cytarabine, floxuridine, fludarabine, gemcitabine, hydroxycarbamide, methotrexate, 6-thioguanine, cladribine, nelarabine, pentostatin, or pemetrexed), plant alkaloids (e.g., vinblastine, vincristine, vindesine, camptothecin, 9-methoxycamptothecin, coronaridine, taxol, naucleaorals, diprenylated indole alkaloid, montamine, schischkiniin, protoberberine, berberine, sanguinarine, chelerythrine, chelidonine, liriodenine, clivorine, β-carboline, antofine, tylophorine, cryptolepine, neocryptolepine, corynoline, sampangine, carbazole, crinamine, montanine, ellipticine, paclitaxel, docetaxel, etoposide, tenisopide, irinotecan, topotecan, or acridone alkaloids), proteasome inhibitors (e.g., lactacystin, disulfiram, epigallocatechin-3-gallate, marizomib (salinosporamide A), oprozomib (ONX-0912), delanzomib (CEP-18770), epoxomicin, MG132, beta-hydroxy beta-methylbutyrate, bortezomib, carfilzomib, or ixazomib), antitumor antibiotics (e.g., doxorubicin, daunorubicin, epirubicin, mitoxantrone, idarubicin, actinomycin, plicamycin, mitomycin, or bleomycin), histone deacetylase inhibitors (e.g., vorinostat, panobinostat, belinostat, givinostat, abexinostat, depsipeptide, entinostat, phenyl butyrate, valproic acid, trichostatin A, dacinostat, mocetinostat, pracinostat, nicotinamide, cambinol, tenovin 1, tenovin 6, sirtinol, ricolinostat, tefinostat, kevetrin, quisinostat, resminostat, tacedinaline, chidamide, or selisistat), tyrosine kinase inhibitors (e.g., axitinib, dasatinib, encorafinib, erlotinib, imatinib, nilotinib, pazopanib, and sunitinib), and chemotherapeutic agents (e.g., all-trans retinoic acid, azacitidine, azathioprine, doxifluridine, epothilone, hydroxyurea, imatinib, teniposide, tioguanine, valrubicin, vemurafenib, and lenalidomide). Additional examples of chemotherapeutic agents include alkylating agents, e.g., mechlorethamine, cyclophosphamide, chlorambucil, melphalan, ifosfamide, thiotepa, hexamethylmelamine, busulfan, altretamine, procarbazine, dacarbazine, temozolomide, carmustine, lumustine, streptozocin, carboplatin, cisplatin, and oxaliplatin.

Non-limiting examples of activating receptor agonists include any agonists for activating receptors which activate and enhance the cytotoxicity of NK cells, including anti-CD16 antibodies (e.g., anti-CD16/CD30 bispecific monoclonal antibody (BiMAb)) and Fc-based fusion proteins. Non-limiting examples of checkpoint inhibitors include anti-PD-1 antibodies (e.g., MEDI0680), anti-PD-L1 antibodies (e.g., BCD-135, BGB-A333, CBT-502, CK-301, CS1001, FAZ053, KN035, MDX-1105, MSB2311, SHR-1316, anti-PD-L1/CTLA-4 bispecific antibody KN046, anti-PD-L1/TGFβRII fusion protein M7824, anti-PD-L1/TIM-3 bispecific antibody LY3415244, atezolizumab, or avelumab), anti-TIM3 antibodies (e.g., TSR-022, Sym023, or MBG453) and anti-CTLA-4 antibodies (e.g., AGEN1884, MK-1308, or an anti-CTLA-4/OX40 bispecific antibody ATOR-1015). Non-limiting examples of agents for blocking HLA-specific inhibitory receptors include monalizumab (e.g., an anti-HLA-E NKG2A inhibitory receptor monoclonal antibody). Non-limiting examples of GSK3 inhibitor include tideglusib or CHIR99021. Non-limiting examples of antibodies that can be used as additional therapeutic agents include anti-CD26 antibodies (e.g., YS110), anti-CD36 antibodies, and any other antibody or antibody construct that can bind to and activate an Fc receptor (e.g., CD16) on a NK cell. In some embodiments, an additional therapeutic agent can be insulin or metformin.

EXAMPLES

The invention is further described in the following examples, which do not limit the scope of the invention described in the claims.

Example 1. Construction of Exemplary Multi-Chain Chimeric Polypeptides and Evaluation of Properties Thereof Two multi-chain chimeric polypeptides were generated and their properties were evaluated. Each of the two multi-chain chimeric polypeptides includes a first chimeric polypeptide that includes a soluble tissue factor domain covalently linked a first target-binding domain and a first domain of an affinity pair of domains. The second chimeric polypeptide in each of the two multi-chain chimeric polypeptides includes a second domain of the affinity pair of domains, and a second target-binding domain.

Description of Logic Underlying Construction of Multi-Chain Chimeric Polypeptides Tissue Factor (TF) is a stable, transmembrane protein containing 236 amino acid residues. The truncated, recombinant 219-amino-acid extracellular domain of tissue factor is soluble and is known to be expressed at high levels in bacteria or mammalian cells. Without wishing to be bound to a particular theory, the applicants speculated that the 219-aa tissue factor could be used as a connector linker for creation of unique multi-chain chimeric polypeptides.

First chimeric polypeptides including soluble tissue factor domain were produced at high levels by CHO cells grown in fermentation broth. These first chimeric polypeptides were purified by an anti-tissue factor monoclonal antibody (mAb) coupled on a solid matrix. Notably, tissue factor contains binding sites for FVIIa and FX. The catalytic activity of the tissue factor-FVIIa complex for FX is approximately 1 million-fold lower when tissue factor is not anchored to a phospholipid bilayer. Thus, without wishing to be bound to a particular theory, applicants speculated that using the 219-aa extracellular domain of tissue factor without the transmembrane in construction of the first chimeric polypeptides may eliminate the pro-coagulation activity of tissue factor in the first chimeric polypeptides. In an effort to further reduce or eliminate the pro-coagulation activity of the 219-aa tissue factor, select mutations in tissue factor can be made, specifically at seven amino acid residues that are known to contribute to binding energy of the FVIIa binding site.

Characterization of Binding Interactions for Described Chimeric Polypeptides

To determine if the first and second chimeric polypeptides bind to each other to form multi-chain chimeric polypeptides, in vitro binding assays were performed. To determine if the first chimeric polypeptide comprising soluble tissue factor domain are recognized and bound by anti-TF mAb, in vitro binding assays were performed. Notably, the data indicated that the mutated tissue factor proteins are still recognized and selectively bound by the anti-TF mAb which is known to bind to the FX binding site on tissue factor. To determine if the first chimeric polypeptides comprising soluble tissue factor domain covalently linked to scFvs or cytokines (see FIG. 1 and FIG. 2) possess functional scFvs or cytokines, in vitro binding assays were performed. The data from the aforementioned assays were consistent with the purified first chimeric polypeptides having the expected biological activities (e.g. scFvs selectively bind expected target antigens or cytokines selectively bind expected receptors or binding proteins).

In addition, experiments performed using the two multi-chain chimeric polypeptides including a first and second chimeric polypeptide bound to each other demonstrate the expected target binding activity (e.g., the multi-chain chimeric polypeptide binds specifically to the target specifically recognized by the first target-binding domain and the target specifically recognized by the second target-binding domain).

Based on the aforementioned results, applicants concluded that the soluble tissue factor connecter linker provided or enabled appropriate display of the polypeptides encoding either scFvs, interleukins, cytokines, interleukin receptors, or cytokine receptors in three-dimensional space relative to soluble tissue factor domain and relative to one another such that each retained expected biological properties and activities.

When both the first and second chimeric polypeptides were co-expressed, the heterodimeric complexes were secreted into the fermentation broths at high levels. The complexes were captured and readily purified by anti-TF mAb conjugated to a solid matrix using affinity chromatography. The first and second target-binding domains of these multi-chain chimeric polypeptides retained their expected biological activities as assayed by in vitro binding assays. Thus, the assembly of the multi-chain chimeric polypeptides provides the appropriate spatial display and folding of the domains for biological activities. Importantly, the spatial arrangement of the multi-chain chimeric polypeptides does not interfere with the FX binding site on tissue factor which enables the use of anti-TF mAb for affinity purification.

Characterization of Stability for Described Chimeric Polypeptides

Both purified multi-chain chimeric polypeptides are stable. These multi-chain chimeric polypeptides are structurally intact and fully biologically active when they are incubated in human serum at 37° C. for 72 hours.

Characterization of Propensity of Described Chimeric Polypeptides to Aggregate

Both purified multi-chain chimeric polypeptides developed do not form aggregates when stored at 4° C. in PBS.

Characterization of Viscosity of Described Chimeric Polypeptides

There is no viscosity issue when the multi-chain chimeric polypeptides are formulated at a concentration as high as 50 mg/mL in PBS.

Additional Applications of the Multi-Chain Chimeric Polypeptide Platform

The data from these studies show that the platform technologies described herein can be utilized to create molecules that could be fused to target-binding domains derived from antibodies, in any of the formats as described herein including, without limitation, adhesion molecules, receptors, cytokines, ligands, and chemokines. With the appropriate target-binding domain, the resulting multi-chain chimeric polypeptides could promote conjugation of various immune effector cells and mediate destruction of target cells, including cancer cells, virally-infected cells, or senescent cells. Other domains in the multi-chain chimeric polypeptides stimulate, activate, and attract the immune system for enhancing cytotoxicity of effector cells for the targeted cells.

Example 2: Creation of an IL-12/IL-15RαSu DNA Construct

In a non-limiting example, an IL-12/IL-15RαSu DNA construct was created (FIG. 3). The human IL-12 subunit sequences, human IL-15RαSu sequence, human IL-15 sequence, human tissue factor 219 sequence, and human IL-18 sequence were obtained from the UniProt website and DNA for these sequences was synthesized by Genewiz. A DNA construct was made linking the IL-12 subunit beta (p40) to IL-12 subunit alpha (p35) with a GS (3) linker to generate a single chain version of IL-12 and then directly linking the IL-12 sequence to the IL-15RαSu sequence. The final IL-12/IL-15RαSu DNA construct sequence was synthesized by Genewiz.

The nucleic acid sequence of the IL12/IL-15RαSu construct (including signal peptide sequence) is as follows (SEQ ID NO: 77):

```
(Signal peptide)
ATGAAATGGGTGACCTTTATTTCTTTACTGTTCCTCTTTAGCAGCGCCT

ACTCC (Human IL-12 subunit beta (p40))
ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA

AAGACCCTCACAATCCAAGTTAAGGAGTTCGGAGACGCTGGCCAATACAC

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC

GCTACCCTCAGCGCTGAGAGGGTTCGTGGCGATAACAAGGAATACGAGTA

CAGCGTGGAGTGCCAAGAAGATAGCGCTTGTCCCGCTGCCGAAGAATCTT

TACCCATTGAGGTGATGGTGGACGCCGTGCACAAACTCAAGTACGAGAAC

TACACCTCCTCCTTCTTTATCCGGGACATCATTAAGCCCGATCCTCCTAA

GAATTTACAGCTGAAGCCTCTCAAAAATAGCCGGCAAGTTGAGGTCTCTT

GGGAATATCCCGACACTTGGAGCACACCCCACAGCTACTTCTCTTTAACC

TTTTGTGTGCAAGTTCAAGGTAAAAGCAAGCGGGAGAAGAAAGACCGGGT

GTTTACCGACAAAACCAGCGCCACCGTCATCTGTCGGAAGAACGCCTCCA

TCAGCGTGAGGGCTCAAGATCGTTATTACTCCAGCAGCTGGTCCGAGTGG

GCCAGCGTGCCTTGTTCC (Linker)
GGCGGTGGAGGATCCGGAGGAGGTGGCTCCGGCGGCGGAGGATCT (Human IL-12 subunit alpha (p35))
CGTAACCTCCCCGTGGCTACCCCCGATCCCGGAATGTTCCCTTGTTTACA

CCACAGCCAGAATTTACTGAGGGCCGTGAGCAACATGCTGCAGAAAGCTA

GGCAGACTTTAGAATTTTACCCTTGCACCAGCGAGGAGATCGACCATGAA

GATATCACCAAGGACAAGACATCCACCGTGGAGGCTTGTTTACCTCTGGA

GCTGACAAAGAACGAGTCTTGTCTCAACTCTCGTGAAACCAGCTTCATCA

CAAATGGCTCTTGTTTAGCTTCCCGGAAGACCTCCTTTATGATGGCTTTA

TGCCTCAGCTCCATCTACGAGGATTTAAAGATGTACCAAGTGGAGTTCAA

GACCATGAACGCCAAGCTGCTCATGGACCCTAAACGGCAGATCTTTTTAG

ACCAGAACATGCTGGCTGTGATTGATGAGCTGATGCAAGCTTTAAACTTC

AACTCCGAGACCGTCCCTCAGAAGTCCTCCCTCGAGGAGCCCGATTTTTA

CAAGACAAAGATCAAACTGTGCATTTTACTCCACGCCTTTAGGATCCGGG

CCGTGACCATTGACCGGGTCATGAGCTATTTAAACGCCAGC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG
```

Example 3: Creation of an IL-18/TF/IL-15 DNA Construct

Figure 3:
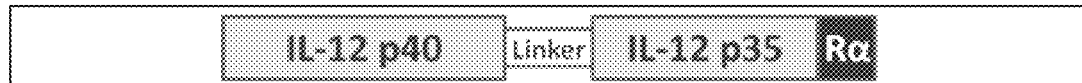
FIG. 3 shows a schematic diagram of an exemplary IL-12/IL-15RαSu DNA construct.
Figure 4:
FIG. 4 shows a schematic diagram of an exemplary IL-18/TF/IL-15 DNA construct.

In a non-limiting example, an IL-18/TF/IL-15 construct was made (FIG. 4) linking the IL-18 sequence to the N-terminus coding region of tissue factor 219, and further linking the IL-18/TF construct with the N-terminus coding region of IL-15. The nucleic acid sequence of the IL-18/TF/IL-15 construct (including leader sequence), synthesized by Genewiz, is as follows (SEQ ID NO: 73):

(Signal peptide)
ATGAAGTGGGTCACATTTATCTCTTTACTGTTCCTCTTCTCCAGCGCCT

ACAGC (Human IL-18)
TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA

CCGACTCCGATTGCCGGGACAATGCCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGAT (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

Example 4: Secretion of IL-12/IL-15RαSu and IL-18/TF/IL-15 Fusion Proteins

Figure 5:
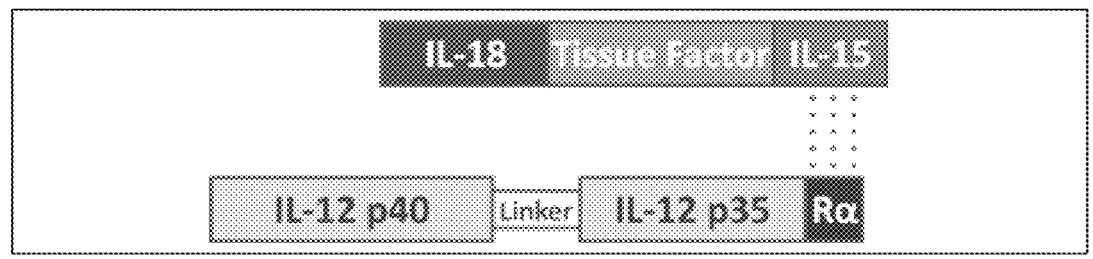
FIG. 5 shows a schematic diagram of the interaction between the exemplary IL-12/IL-15RαSu and IL-18/TF/IL-15 DNA constructs.
Figure 6:
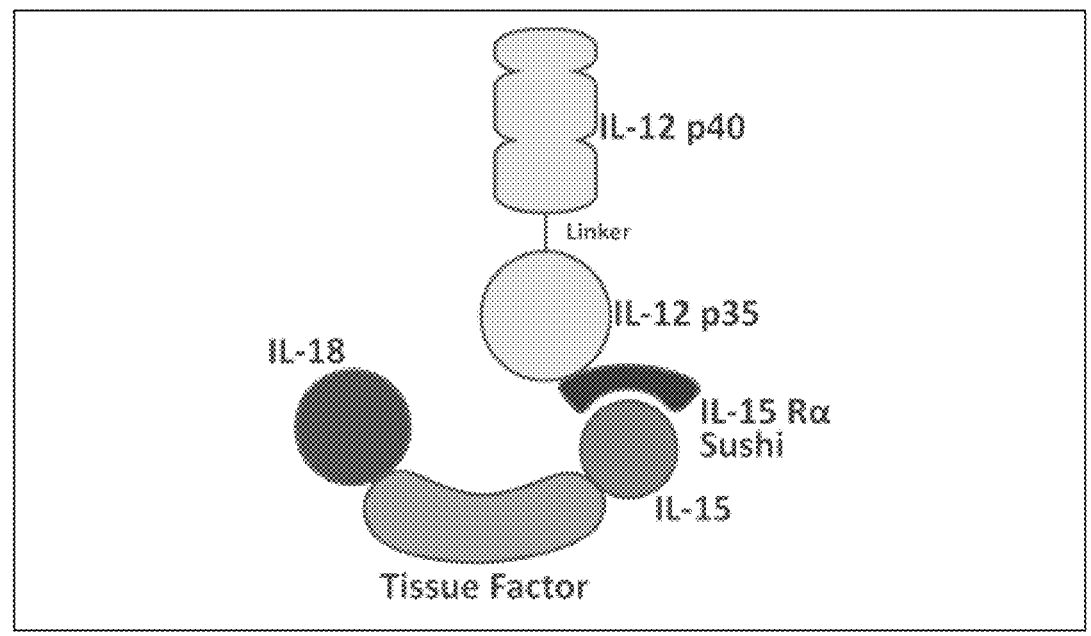
FIG. 6 shows a schematic diagram of the interaction between the exemplary IL-12/IL-15RαSu and IL-18/TF/IL-15 fusion proteins resulting in IL-18/TF/IL-15:IL-12/IL-15RαSu complex (18t15-12s).

The IL-12/IL-15RαSu and IL-18/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-18/TF/IL-15:IL-12/IL-15RαSu protein complex (referred to as 18t15-12s; FIG. 5 and FIG. 6). The 18t15-12s protein was purified from CHO-K1 cell culture supernatant using anti-TF antibody affinity chromatography and size exclusion chromatography resulting in soluble (non-aggregated) protein complexes consisting of IL-12/IL-15RαSu and IL-18/TF/IL-15 fusion proteins.

The amino acid sequence of the IL12/IL-15RαSu fusion protein (including signal peptide sequence) is as follows (SEQ ID NO: 76):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS (Human IL-15R α sushi domain)
ITCPPPMSVEHADIWVKSYSLYSRERYICNSGFKRKAGTSSLTECVLNKA

TNVAHWTTPSLKCIR

The amino acid sequence of the IL-18/TF/IL-15 fusion protein (including signal peptide sequence) is as follows (SEQ ID NO: 72):

(Signal peptide)
MKWVTFISLLFLFSSAYS (Human IL-18)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

```
                                    -continued
FFQRSVPGHDNKMQFESSSYEGYFLACEKERDLFKLILKKEDELGDRSIM

FTVQNED (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

In some cases, the leader (signal sequence) peptide is cleaved from the intact polypeptide to generate the mature form that may be soluble or secreted.

Example 5: Purification of 18t15-12s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Figure 7:
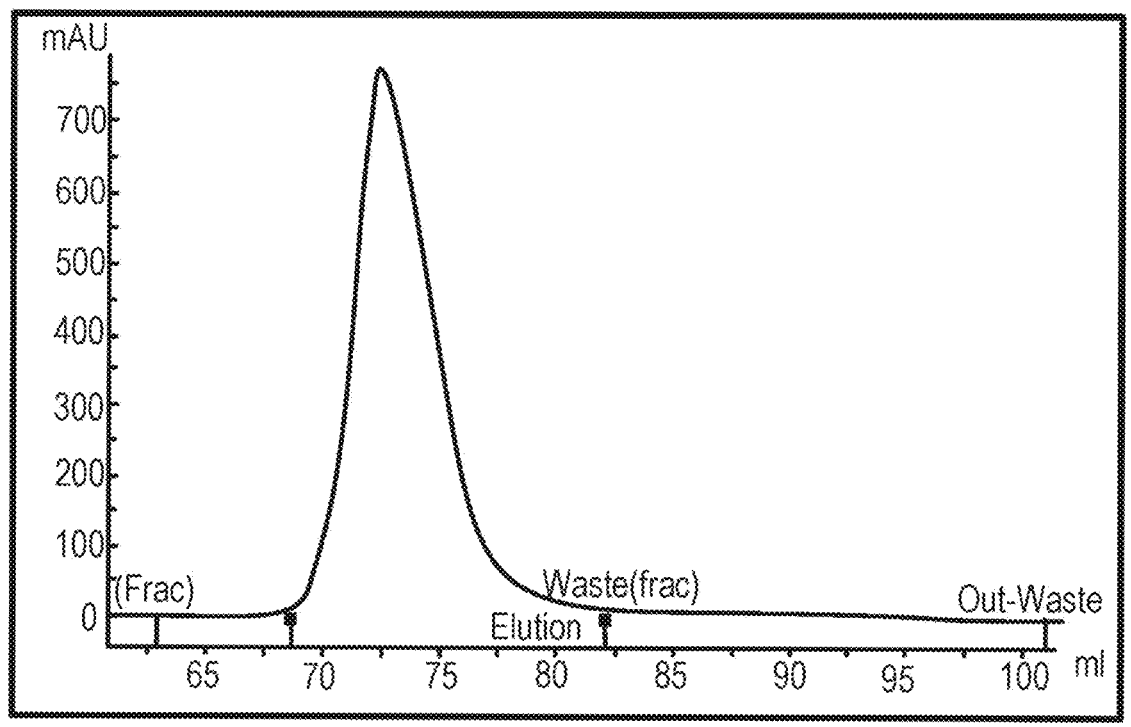
FIG. 7 shows a chromatograph of 18t15-12s purification elution from an anti-TF antibody affinity column.

Cell culture harvest of 18t15-12s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. FIG. 7 shows that the 18t15-12s complex binds the anti-TF antibody affinity column, wherein TF is an 18t15-12s binding partner. The buffer-exchanged protein sample is stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 6: Size Exclusion Chromatography of 18t15-12s

Figure 8:
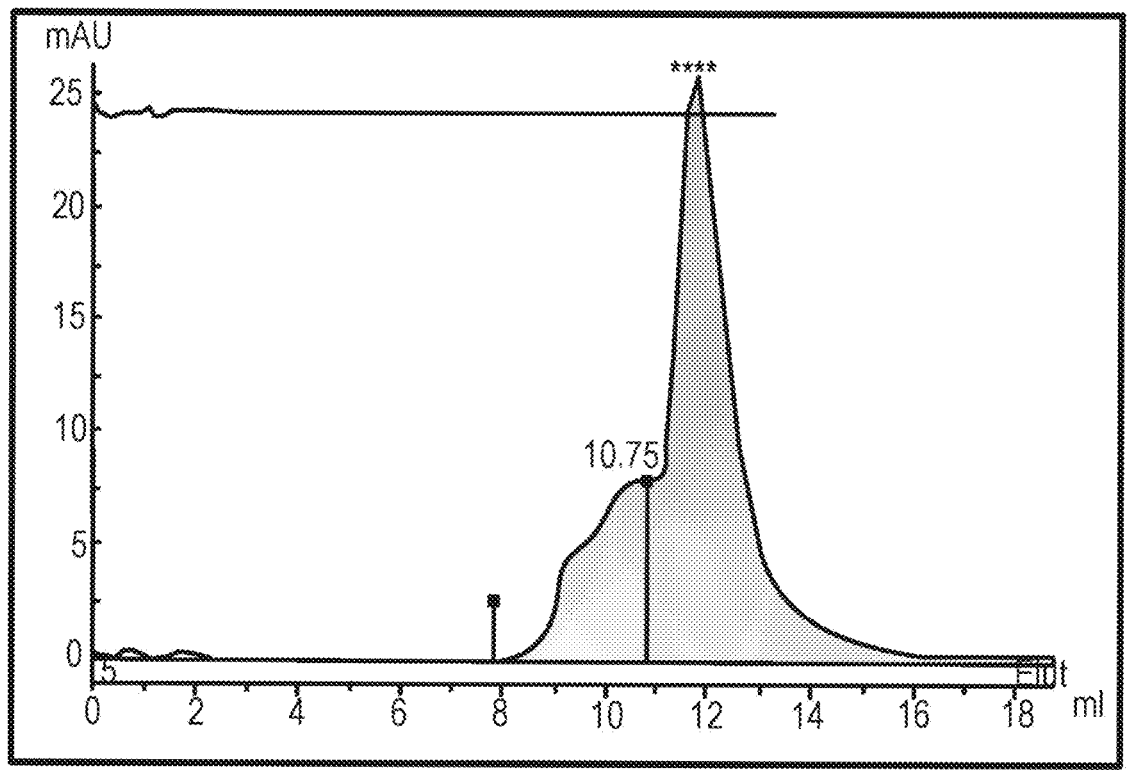
FIG. 8 shows an exemplary chromatographic profile of anti-TF Ab/SEC-purified 18t15-12s protein following elution on an analytical size exclusion column, demonstrating separation of monomeric multiprotein 18t15-12s complexes from protein aggregates.

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 200 µL of 1 mg/mL of 18t15-12s complex onto the column. The injection was chased with 1.25 column volumes of PBS. The SEC chromatograph is shown in FIG. 8. There is a main 18t15-12s protein peak with a minor high molecular weight peak, likely due to differing degrees of glycosylation of 18t15-12s dimers or aggregates.

Example 7: SDS-PAGE of 18t15-12s

Figure 9:
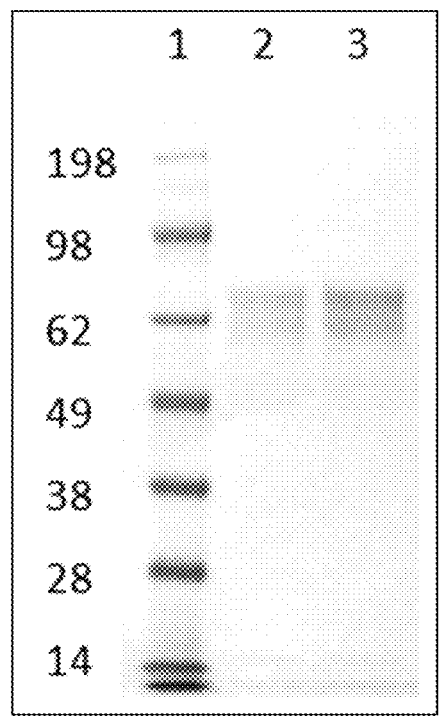
FIG. 9 shows an example of a 4-12% SDS-PAGE of the 18t15-12s complex following disulfide bond reduction. Lane 1: SeeBlue Plus2 marker; Lane 2: an anti-tissue factor antibody affinity column-purified 18t15-12s (0.5 µg); Lane 3: an anti-tissue factor antibody affinity column-purified 18t15-12s (1 µg).

To determine the purity and protein molecular weight, the purified 18t15-12s protein sample was analyzed using 4-12% NuPage Bis-Tris protein gel SDS-PAGE. The gel was stained with InstantBlue™ for about 30 min, followed by destaining overnight in purified water. FIG. 9 shows an example SDS gel of anti-TF antibody affinity purified 18t15-12s, with bands at the expected molecular weights (66 kDa and 56 kDa).

Example 8: Glycosylation of 18t15-12s in CHO-K1 Cells

Figure 10:
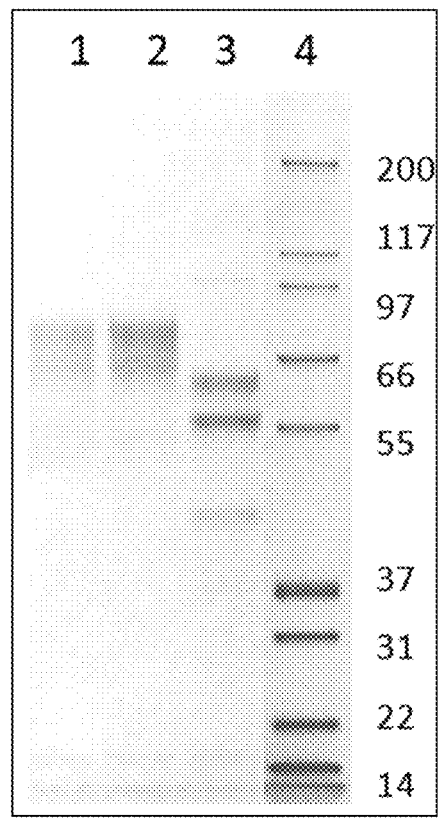
FIG. 10 shows SDS PAGE analysis of deglycosylated and non-deglycosylated 18t15-12s. Lane 1: an anti-tissue factor antibody affinity column-purified 18t15-12s (0.5 µg), non-deglycosylated; Lane 2: anti-TF Ab-purified 18t15-12s (1 µg), non-deglycosylated; Lane 3: 18t15-12s (1 µg), deglycosylated, Lane 4: Mark12 unstained maker.
Figure 11:
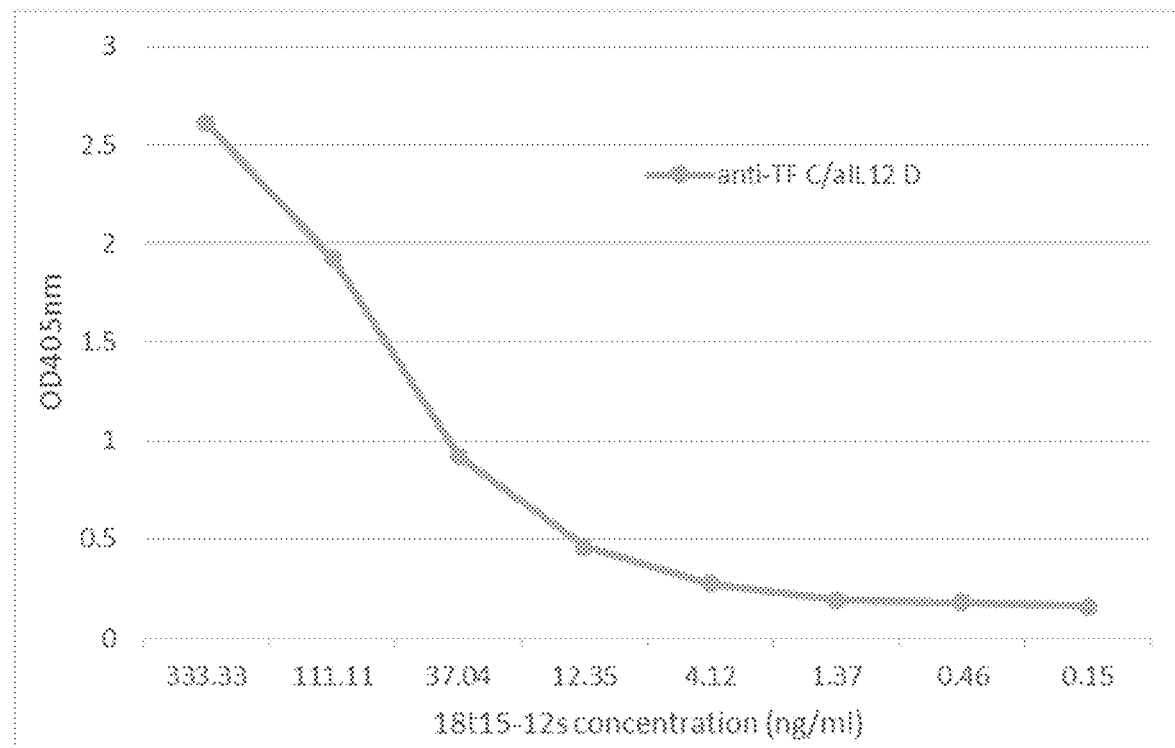
FIG. 11 shows a sandwich ELISA for the 18t15-12s complex, comprising an anti-human tissue factor capture antibody and a biotinylated anti-human IL-12 detection antibody (BAF 219).
Figure 12:
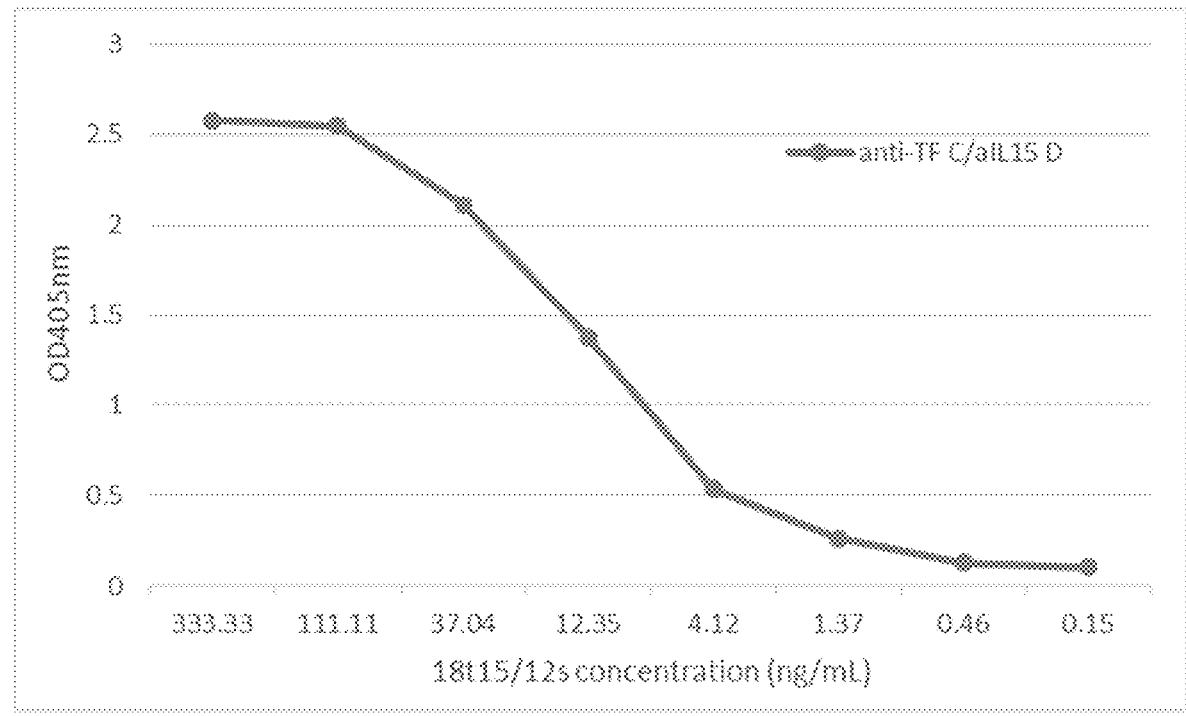
FIG. 12 shows a sandwich ELISA for the 18t15-12s complex, comprising an anti-human tissue factor capture antibody and a biotinylated anti-human IL-15 detection antibody (BAM 247).
Figure 13:
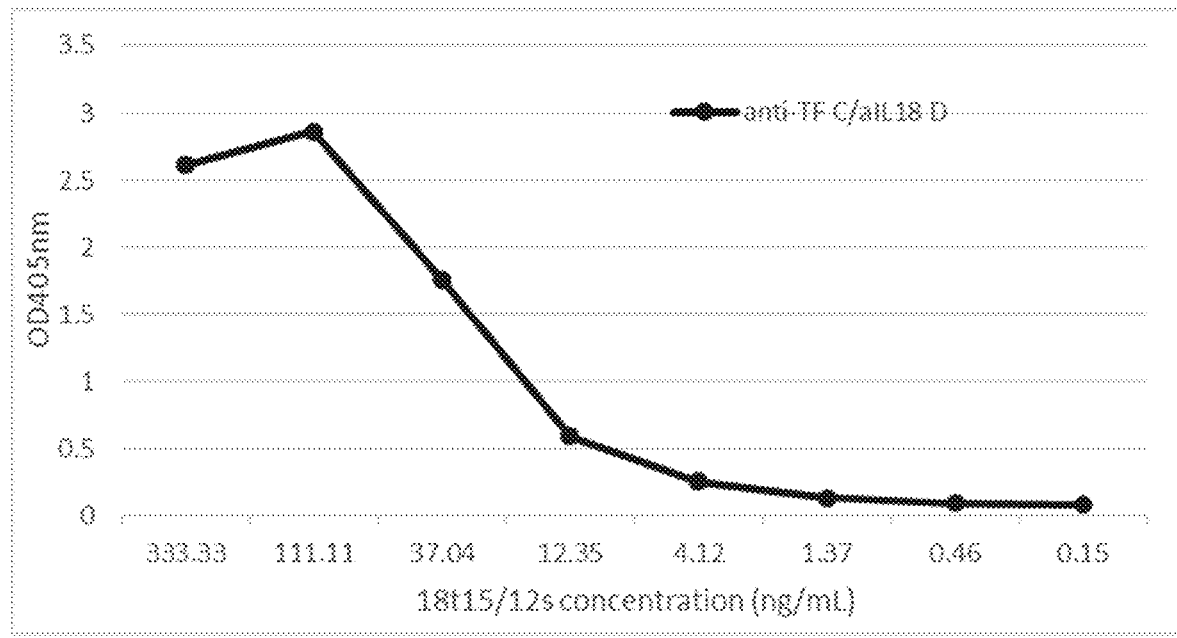
FIG. 13 shows a sandwich ELISA for the 18t15-12s complex, comprising an anti-human tissue factor capture antibody and a biotinylated anti-human IL-18 detection antibody (D045-6).
Figure 14:
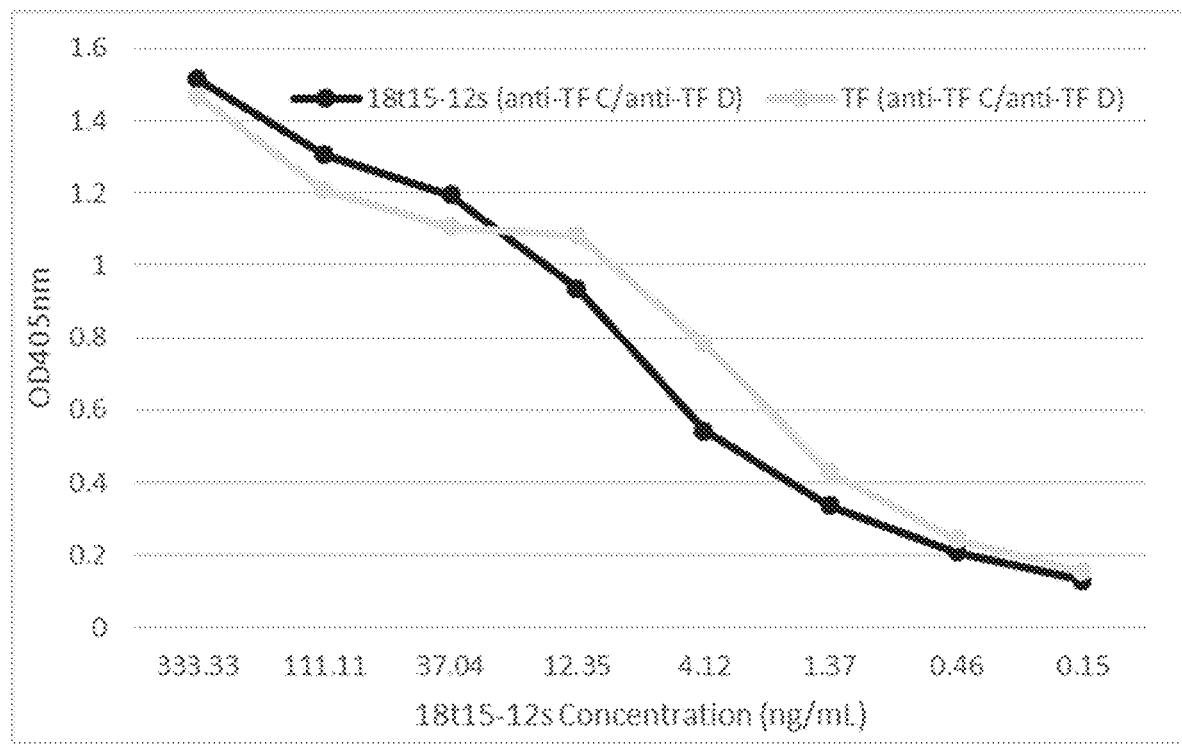
FIG. 14 shows a sandwich ELISA for the 18t15-12s complex, comprising an anti-human tissue factor (143) capture antibody and an anti-human tissue factor detection antibody.

Glycosylation of 18t15-12s in CHO-K1 cells was confirmed using the Protein Deglycosylation Mix II kit (New England Biolabs), according to the manufacturer's instructions. FIG. 10 shows an example SDS PAGE of deglycosylated and non-deglycosylated 18t15-12s. Deglycosylation reduces the molecular weight of 18t15-12s as seen in FIG. 10, lane 4.

Example 9: Recombinant Protein Quantitation of 18t15-12s Complexes

The 18t15-12s complex was detected and quantified using standard sandwich ELISA methods (FIGS. 11-14). Anti-human tissue factor antibody served as the capture antibody and biotinylated anti-human IL-12, IL-15, or IL-18 antibody (BAF 219, BAM 247, D045-6, all R&D Systems) served as the detection antibody. Tissue factor in purified 18t15-12s protein complexes was also detected using an anti-human tissue factor capture antibody (143), and anti-human tissue factor antibody detection antibody. The 143/anti-TF antibody ELISA was compared to purified tissue factor at similar concentrations.

Example 10: Immunostimulatory Capacity of the 18t15-12s Complex

Figure 15:
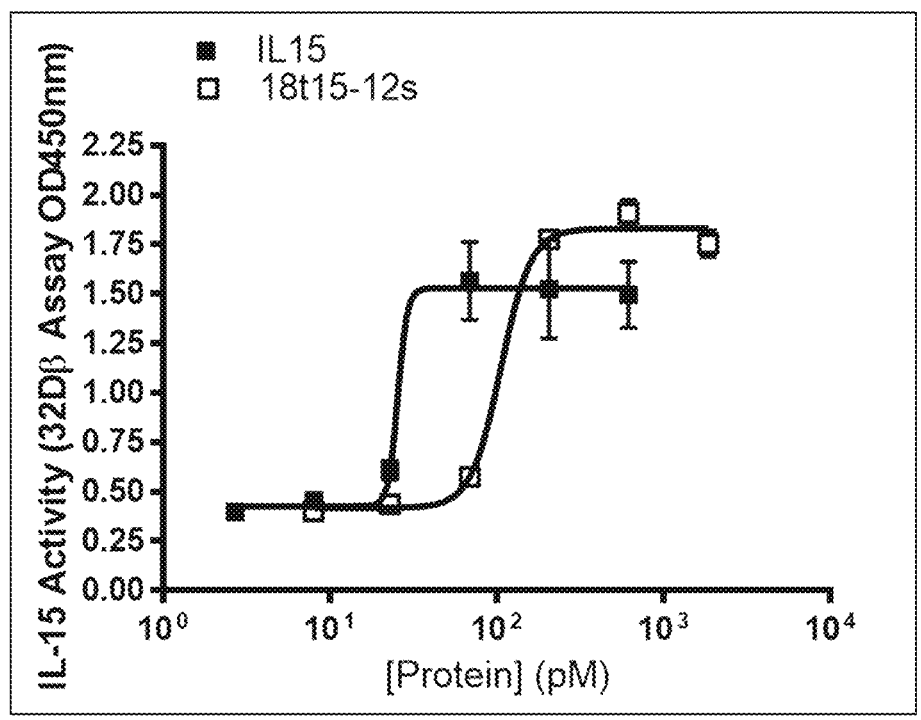
FIG. 15 shows proliferation of IL-15-dependent 32Dβ cells mediated by the 18t15-12s complex (open squares) and recombinant IL-15 (black squares).

To assess the IL-15 immunostimulatory activity of the 18t15-12s complex, increasing concentrations of 18t15-12s was added to 32Dβ cells (104 cell/well) in 200 IMDM:10% FBS media. The 32Dβ cells were incubated for 3 days at 37° C. On the fourth day, WST-1 proliferation reagent (10 µL/well) was added and after 4 hours, absorbance was measured at 450 nm to determine cell proliferation based on cleavage of WST-1 to a soluble formazan dye. Bioactivity of human recombinant IL-15 was assessed as a positive control. As shown in FIG. 15, 18t15-12s demonstrated IL-15-dependent cell proliferation of 32Dβ cells. The 18t15-12s complex demonstrated reduced activity compared to human recombinant IL-15, possibly due to the linkage of IL-18 and tissue factor to the IL-15 domain.

Figure 16:
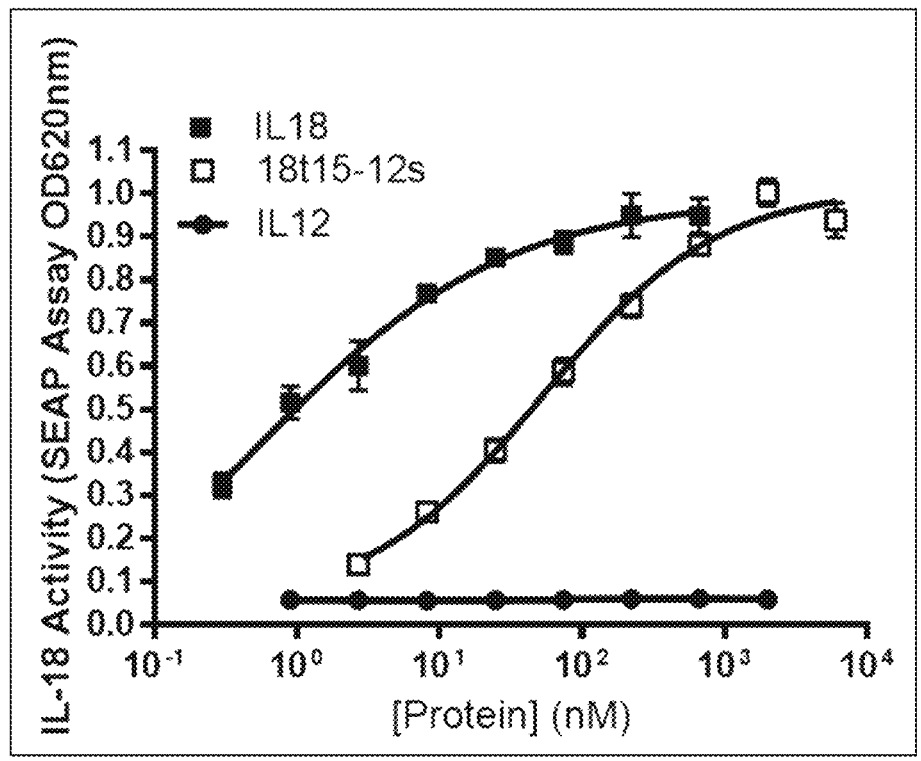
FIG. 16 shows biological activity of IL-18 within the 18t15-12s complex (open squares), where recombinant IL-18 (black squares) and recombinant IL-12 (black circles) serve as positive and negative controls, respectively.
Figure 17:
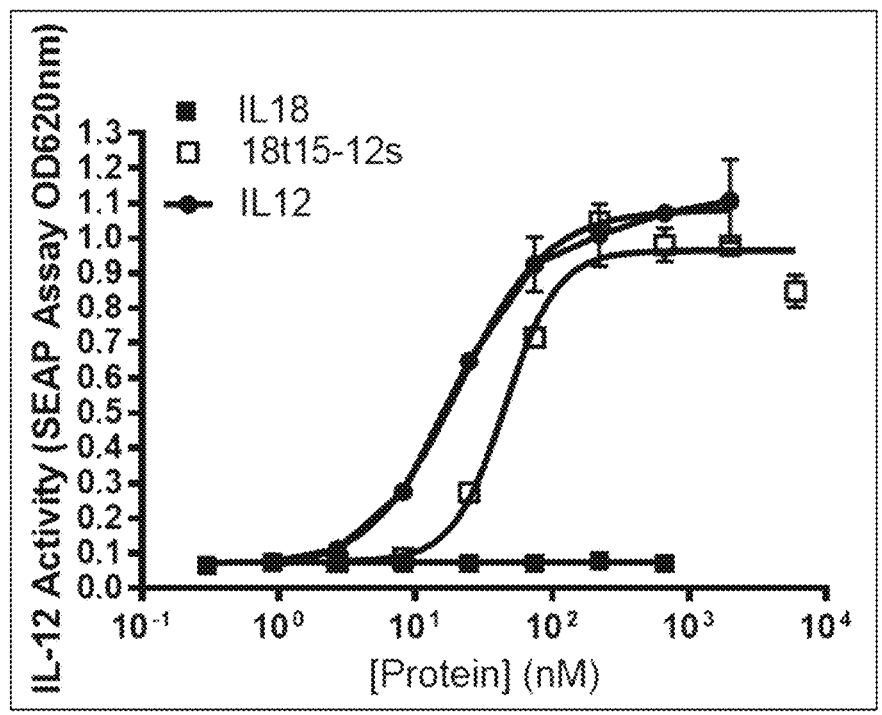
FIG. 17 shows biological activity of IL-12 within the 18t15-12s complex (open squares), where recombinant IL-12 (black circles) and recombinant IL-18 (open squares) serve as positive and negative controls, respectively.

In order to assess the individual activities of IL-12 and IL-18 in the 18t15-12s complex, 18t15-12s was added to HEK-Blue IL-12 and HEK-Blue IL-18 reporter cells (5×10⁴ cell/well; hkb-il12 and hkb-hmill8, InvivoGen) in 200 µL IMDM:10% heat-inactivated FBS media. Cells were incubated for overnight at 37° C. 20 µl of induced HEK-Blue IL-12 and HEK-Blue IL-18 reporter cell supernatant was added to 180 µl of QUANTI-Blue (InvivoGen), and incubated for 1-3 hours at 37° C. IL-12 or IL-18 activity was assessed by measuring absorbance at 620 nm. Human recombinant IL-12 or IL-18 was assessed as a positive or negative control. As shown in FIG. 16 and FIG. 17, each of the cytokine domains of the 18t15-12s complex retain specific biological activity. The activity of 18t15-12s was reduced compared to that of human recombinant IL-18 or

Example 11: Induction of Cytokine-Induced Memory-Like NK Cells by the 18t15-12s Complex Cytokine-induced memory-like NK cells can be induced ex vivo following overnight stimulation of purified NK cells with saturating amounts of IL-12 (10 ng/mL), IL-15 (50 ng/mL), and IL-18 (50 ng/mL). These memory-like properties have been measured through expression of IL-2 receptor α (IL-2Rα, CD25), CD69 (and other activation markers), and increased IFN-γ production. To evaluate the ability of 18t15-12s complexes to promote generation of cytokine-induced memory-like NK cells, purified human NK cells (>95% CD56+) were stimulated for 14-18 hours with 0.01 nM to 10000 nM of the 18t15-12s complex or a combination of individual cytokines (recombinant IL-12 (10 ng/mL), IL-18 (50 ng/mL), and IL-15 (50 ng/mL)). Cell-surface CD25 and CD 69 expression and intracellular IFN-γ levels were assessed by antibody-staining and flow cytometry.

Figure 18A:
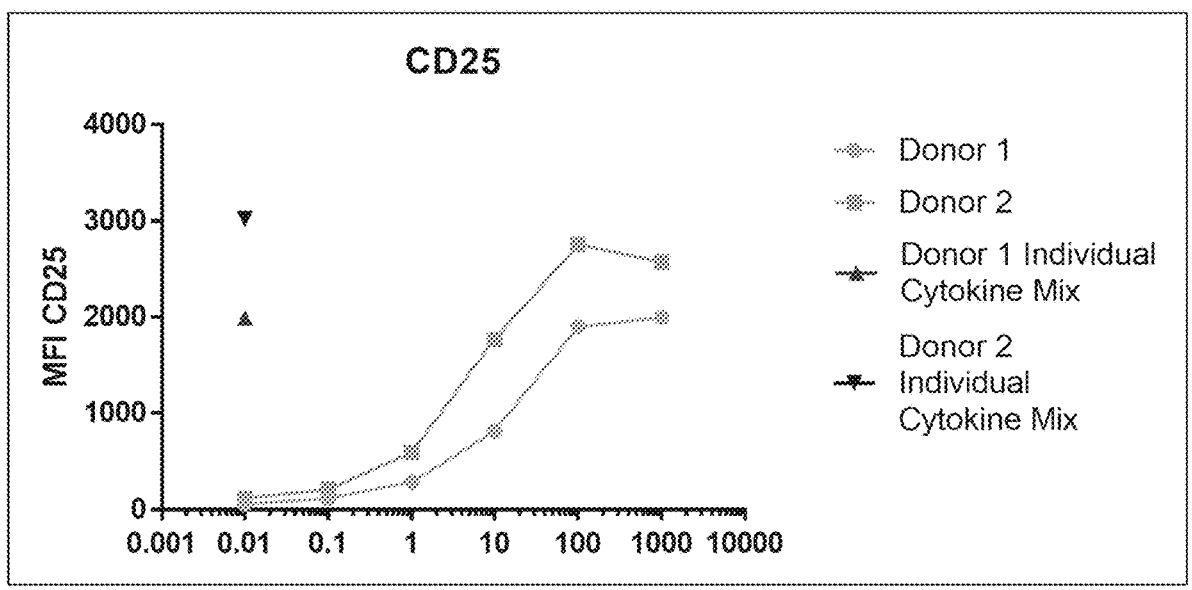
FIGS. 18A and 18B show cell-surface expression of CD25 on NK cells induced by the 18t15-12s complex and cell-surface CD69 expression of NK cells induced by the 18t15-12s complex.
Figure 18B:
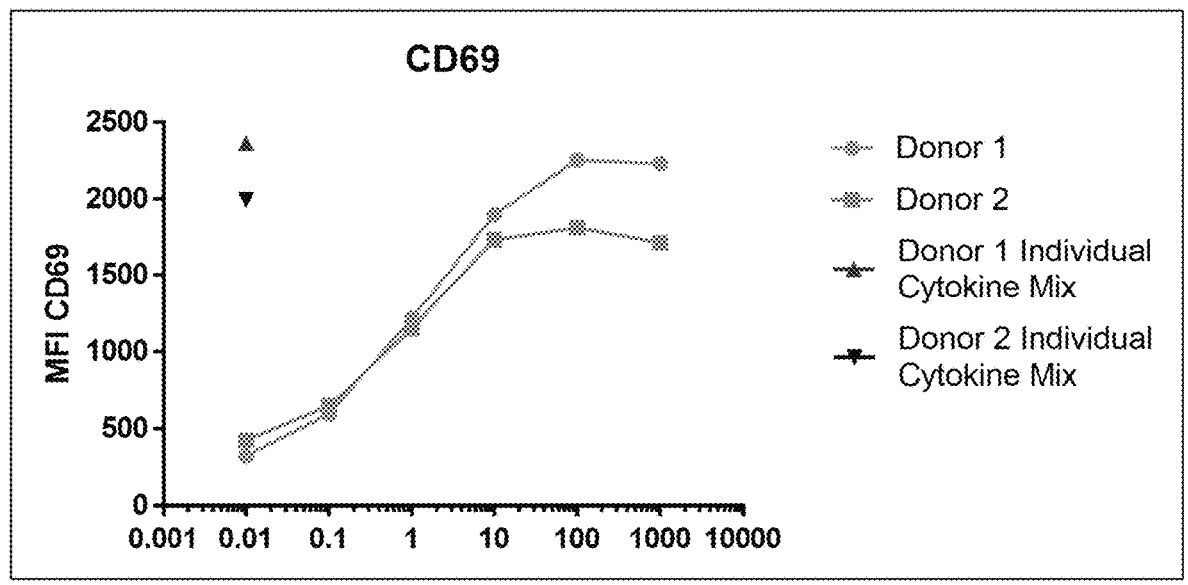

Fresh human leukocytes were obtained from a blood bank and CD56+NK cells were isolated with the RosetteSep/human NK cell reagent (StemCell Technologies). The purity of NK cells was >70% and confirmed by staining with antibodies specific to CD56-BV421, CD16-BV510, CD25-PE, CD69-APCFire750 (BioLegend). Cells were counted and resuspended in $0.2 \times 10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a mixture of cytokines hIL-12 (10 ng/mL) (Biolegend), hIL-18 (50 ng/mL) (R&D Systems) and hIL-15 (50 ng/mL) (NCI) or with 0.01 nM to 10000 nM of the 18t15-12s at 37° C., 5% $CO_2$ for 14-18 hrs. The cells were then harvested and surface stained with antibodies specific to CD56-BV421, CD16-BV510, CD25-PE, CD69-APCFire750 (BioLegend) for 30 minutes. After staining, cells were washed (1500 RPM for 5 minutes at room temperature) in FACS buffer (1×PBS (Hyclone), with 0.5% BSA (EMD Millipore) and 0.001% sodium azide (Sigma)). After two washes, cells were analyzed using a BD FACSCelesta™ flow cytometer (Plotted Data-Mean Fluorescence Intensity; FIG. 18A and FIG. 18B).

Figure 19:
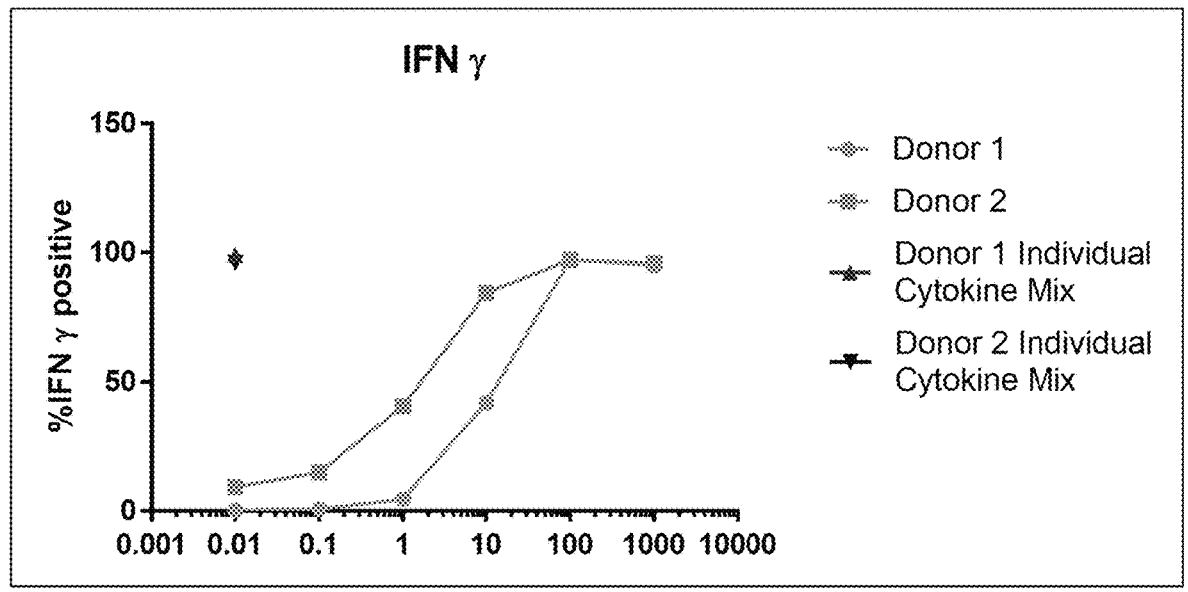
FIG. 19 shows a flow cytometry graph of intracellular interferon gamma expression of NK cells induced by the 18t15-12s complex.

Fresh human leukocytes were obtained from a blood bank and CD56+ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2 \times 10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a cytokine mix of hIL-12 (10 ng/mL) (Biolegend), hIL-18 (50 ng/mL) (R&D), and hIL-15 (50 ng/mL) (NCI), or 0.01 nM to 10000 nM of the 18t15-12s complex at 37° C., 5% CO2 for 14-18 hrs. The cells were then treated with 10 μg/mL of Brefeldin A (Sigma) and 1× of Monensin (eBioscience) for 4 hrs before harvesting and staining with antibodies specific to CD56-BV421, CD16-BV510, CD25-PE, CD69-APCFire750 for 30 minutes. After staining, cells were washed (1500 RPM for 5 minutes in room temperature) in FACS buffer (1×PBS (Hyclone), with 0.5% BSA (EMD Millipore) and 0.001% sodium azide (Sigma)) and fixed for 10 minutes at room temperature. After fixation, cells were washed (1500 RPM for 5 minutes in room temperature) in 1× permeabilized buffer (eBioscience) and stained with IFN-γ-PE Ab (Biolegend) for 30 minutes at room temperature. Cells were washed once again with 1× permeabilized buffer and then washed with FACS buffer. Cell pellets were resuspended in 300 μls of FACS buffer and analyzed using a BD FACSCelesta™ flow cytometer (Plotted % of IFN-γ Positive Cells; FIG. 19).

Example 12: In Vitro Cytotoxicity of NK Cells Against Human Tumor Cells

Figure 20:
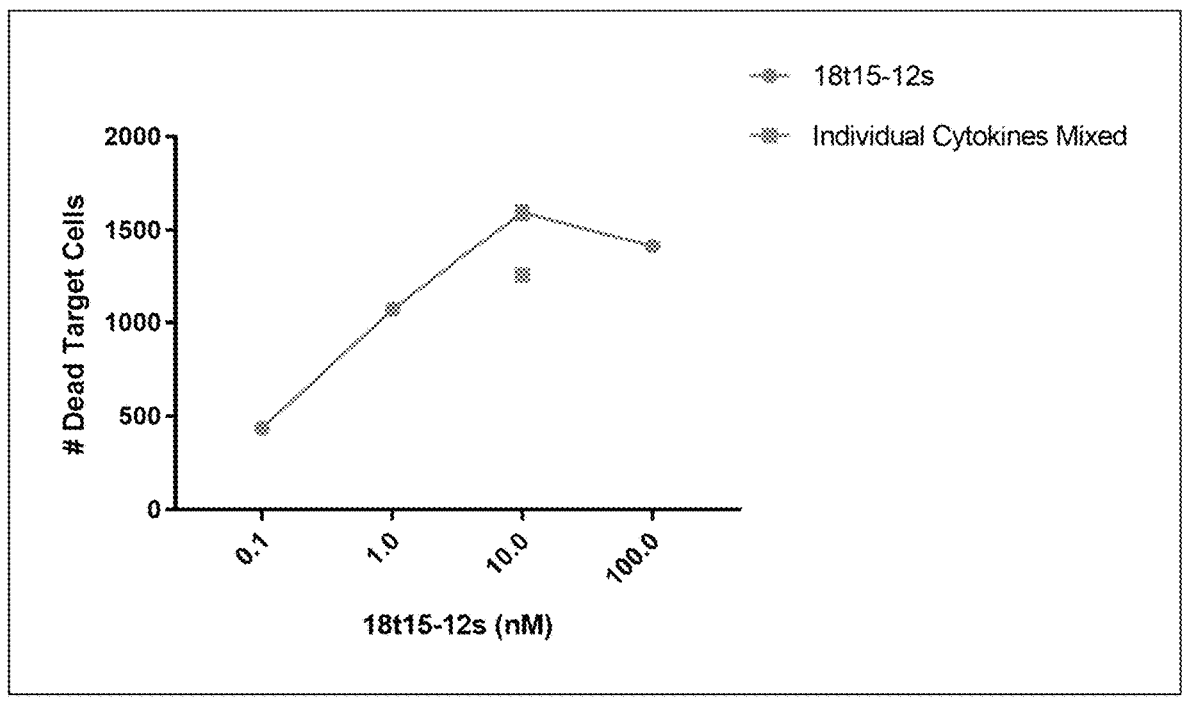
FIG. 20 shows cytotoxicity of 18t15-12s induced human NK cells against K562 cells.

Human myelogenous leukemia cells, K562 (CELL-TRACE®, violet dye, labelled), were incubated with purified human NK cells in the presence of increasing concentrations of the 18t15-12s complex or a mixture of cytokines as a control. After 20 hours, the cultures were harvested, stained with propidium iodide (PI), and assessed by flow cytometry. As shown in FIG. 20, the 18t15-12s complex induced human NK cytotoxicity against K562, at levels similar or greater than the cytokine mixture, wherein both the 18t15-12s complex and the cytokine mixture induced greater cytotoxicity than the medium control.

Figure 21:
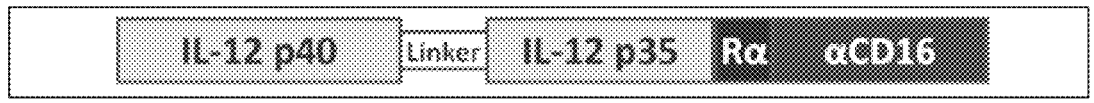
FIG. 21 shows a schematic diagram of an exemplary IL-12/IL-15RαSu/αCD16 DNA construct.
Figure 22:
FIG. 22 shows a schematic diagram of an exemplary IL-18/TF/IL-15 DNA construct.

Example 13: Creation of IL-12/IL-15RαSu/αCD16scFv and IL-18/TF/IL-15 DNA Constructs In a non-limiting example, IL-12/IL-15RαSu/αCD16scFv and IL-18/TF/IL-15 DNA constructs were created (FIG. 21 and FIG. 22). The human IL-12 subunit sequences, human IL-15RαSu sequence, human IL-15 sequence, human tissue factor 219 sequence, and human IL-18 sequence were synthesized by Genewiz. A DNA construct was made linking the IL-12 subunit beta (p40) to IL-12 subunit alpha (p35) with a GS (3) linker to generate a single chain version of IL-12, directly linking the IL-12 sequence to the IL-15RαSu sequence, and directly linking the IL-12/IL-15RαSu construct to the N-terminus coding region of αCD16scFv.

The nucleic acid sequence of the IL-12/IL-15RαSu/αCD16scFv construct is as follows (SEQ ID NO: 123):

```
(Signal peptide)
ATGAAATGGGTGACCTTTATTTCTTTACTGTTCCTCTTTAGCAGCGCCTA

CTCC (Human IL-12 subunit beta (p40))
ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA

AAGACCCTCACAATCCAAGTTAAGGAGTTCGGAGACGCTGGCCAATACAC

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC
```

-continued
```
GCTACCCTCAGCGCTGAGAGGGTTCGTGGCGATAACAAGGAATACGAGTA
CAGCGTGGAGTGCCAAGAAGATAGCGCTTGTCCCGCTGCCGAAGAATCTT
TACCCATTGAGGTGATGGTGGACGCCGTGCACAAACTCAAGTACGAGAAC
TACACCTCCTCCTTCTTTATCCGGGACATCATTAAGCCCGATCCTCCTAA
GAATTTACAGCTGAAGCCTCTCAAAAATAGCCGGCAAGTTGAGGTCTCTT
GGGAATATCCCGACACTTGGAGCACACCCCACAGCTACTTCTCTTTAACC
TTTTGTGTGCAAGTTCAAGGTAAAAGCAAGCGGGAGAAGAAAGACCGGGT
GTTTACCGACAAAACCAGCGCCACCGTCATCTGTCGGAAGAACGCCTCCA
TCAGCGTGAGGGCTCAAGATCGTTATTACTCCAGCAGCTGGTCCGAGTGG
GCCAGCGTGCCTTGTTCC
```

(Linker)
```
GGCGGTGGAGGATCCGGAGGAGGTGGCTCCGGCGGCGGAGGATCT
```

(Human IL-12 subunit alpha (p35))
```
CGTAACCTCCCCGTGGCTACCCCCGATCCCGGAATGTTCCCTTGTTTACA
CCACAGCCAGAATTTACTGAGGGCCGTGAGCAACATGCTGCAGAAAGCTA
GGCAGACTTTAGAATTTTACCCTTGCACCAGCGAGGAGATCGACCATGAA
GATATCACCAAGGACAAGACATCCACCGTGGAGGCTTGTTTACCTCTGGA
GCTGACAAAGAACGAGTCTTGTCTCAACTCTCGTGAAACCAGCTTCATCA
CAAATGGCTCTTGTTTAGCTTCCCGGAAGACCTCCTTTATGATGGCTTTA
TGCCTCAGCTCCATCTACGAGGATTTAAAGATGTACCAAGTGGAGTTCAA
GACCATGAACGCCAAGCTGCTCATGGACCCTAAACGGCAGATCTTTTTAG
ACCAGAACATGCTGGCTGTGATTGATGAGCTGATGCAAGCTTTAAACTTC
AACTCCGAGACCGTCCCTCAGAAGTCCTCCCTCGAGGAGCCCGATTTTTA
CAAGACAAAGATCAAACTGTGCATTTTACTCCACGCCTTTAGGATCCGGG
CCGTGACCATTGACCGGGTCATGAGCTATTTAAACGCCAGC
```

(Human IL-15R α sushi domain)
```
ATTACATGCCCCCCTCCCATGAGCGTGGAGCACGCCGACATCTGGGTGAA
GAGCTATAGCCTCTACAGCCGGGAGAGGTATATCTGTAACAGCGGCTTCA
AGAGGAAGGCCGGCACCAGCAGCCTCACCGAGTGCGTGCTGAATAAGGCT
ACCAACGTGGCTCACTGGACAACACCCTCTTTAAAGTGCATCCGG
```

(anti-Human CD16 light chain variable domain)
```
TCCGAGCTGACCCAGGACCCTGCTGTGTCCGTGGCTCTGGGCCAGACCGT
GAGGATCACCTGCCAGGGCGACTCCCTGAGGTCCTACTACGCCTCCTGGT
ACCAGCAGAAGCCCGGCCAGGCTCCTGTGCTGGTGATCTACGGCAAGAAC
AACAGGCCCTCCGGCATCCCTGACAGGTTCTCCGGATCCTCCTCCGGCAA
CACCGCCTCCCTGACCATCACAGGCGCTCAGGCCGAGGACGAGGCTGACT
ACTACTGCAACTCCAGGGACTCCTCCGGCAACCATGTGGTGTTCGGCGGC
GGCACCAAGCTGACCGTGGGCCAT
```

(Linker)
```
GGCGGCGGCGGCTCCGGAGGCGGCGGCAGCGGCGGAGGAGGATCC
```

(anti-Human CD16 heavy chain variable domain)
```
GAGGTGCAGCTGGTGGAGTCCGGAGGAGGAGTGGTGAGGCCTGGAGGCTC
CCTGAGGCTGAGCTGTGCTGCCTCCGGCTTCACCTTCGACGACTACGCA
TGTCCTGGGTGAGGCAGGCTCCTGGAAAGGGCCTGGAGTGGGTGTCCGGC
```

-continued
```
ATCAACTGGAACGGCGGATCCACCGGCTACGCCGATTCCGTGAAGGGCAG
GTTCACCATCAGCAGGGACAACGCCAAGAACTCCCTGTACCTGCAGATGA
ACTCCCTGAGGGCCGAGGACACCGCCGTGTACTACTGCGCCAGGGGCAGG
TCCCTGCTGTTCGACTACTGGGGACAGGGCACCCTGGTGACCGTGTCCAG
G
```

Constructs were also made linking the IL-18 sequence to the N-terminus coding region of tissue factor 219, and linking the IL-18/TF construct with the N-terminus coding region of IL-15 (FIG. 22). The nucleic acid sequence of the IL-18/TF/IL-15 construct (including leader sequence) is as follows (SEQ ID NO: 73):

(Signal peptide)
```
ATGAAGTGGGTCACATTTATCTCTTTACTGTTCCTCTTCTCCAGCGCCT
ACAGC
```

(Human IL-18)
```
TACTTCGGCAAACTGGAATCCAAGCTGAGCGTGATCCGGAATTTAAACGA
CCAAGTTCTGTTTATCGATCAAGGTAACCGGCCTCTGTTCGAGGACATGA
CCGACTCCGATTGCCGGGACAATGCCCCCCGGACCATCTTCATTATCTCC
ATGTACAAGGACAGCCAGCCCCGGGGCATGGCTGTGACAATTAGCGTGAA
GTGTGAGAAAATCAGCACTTTATCTTGTGAGAACAAGATCATCTCCTTTA
AGGAAATGAACCCCCCCGATAACATCAAGGACACCAAGTCCGATATCATC
TTCTTCCAGCGGTCCGTGCCCGGTCACGATAACAAGATGCAGTTCGAATC
CTCCTCCTACGAGGGCTACTTTTTAGCTTGTGAAAAGGAGAGGGATTTAT
TCAAGCTGATCCTCAAGAAGGAGGACGAGCTGGGCGATCGTTCCATCATG
TTCACCGTCCAAAACGAGGAT
```

(Human Tissue Factor 219)
```
AGCGGCACAACCAACACAGTCGCTGCCTATAACCTCACTTGGAAGAGCAC
CAACTTCAAAACCATCCTCGAATGGGAACCCAAACCCGTTAACCAAGTTT
ACACCGTGCAGATCAGCACCAAGTCCGGCGACTGGAAGTCCAAATGTTTC
TATACCACCGACACCGAGTGCGATCTCACCGATGAGATCGTGAAAGATGT
GAAACAGACCTACCTCGCCCGGGTGTTTAGCTACCCCGCCGGCAATGTGG
AGAGCACTGGTTCCGCTGGCGAGCCTTTATACGAGAACAGCCCCGAATTT
ACCCCTTACCTCGAGACCAATTTAGGACAGCCCACCATCCAAAGCTTTGA
GCAAGTTGGCACAAAGGTGAATGTGACAGTGGAGGACGAGCGGACTTTAG
TGCGGCGGAACAACACCTTTCTCAGCCTCCGGGATGTGTTCGGCAAAGAT
TTAATCTACACACTGTATTACTGGAAGTCCTCTTCCTCCGGCAAGAAGAC
AGCTAAAACCAACACAAACGAGTTTTTAATCGACGTGGATAAAGGCGAAA
ACTACTGTTTCAGCGTGCAAGCTGTGATCCCCTCCCGGACCGTGAATAGG
AAAAGCACCGATAGCCCCGTTGAGTGCATGGGCCAAGAAAAGGGCGAGTT
CCGGGAG
```

(Human IL-15)
```
AACTGGGTGAACGTCATCAGCGATTTAAAGAAGATCGAAGATTTAATTCA
GTCCATGCATATCGACGCCACTTTATACACAGAATCCGACGTGCACCCCT
```

-continued
CTTGTAAGGTGACCGCCATGAAATGTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

Figure 23:
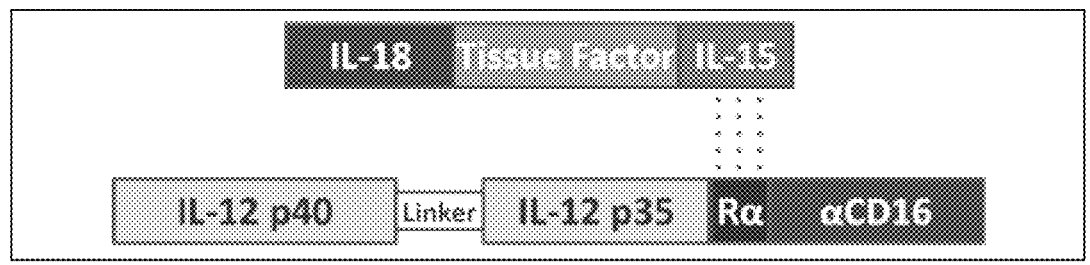
FIG. 23 shows a schematic diagram of the interaction between the exemplary IL-12/IL-15RαSu/αCD16scFv and IL-18/TF/IL-15 DNA constructs.
Figure 24:
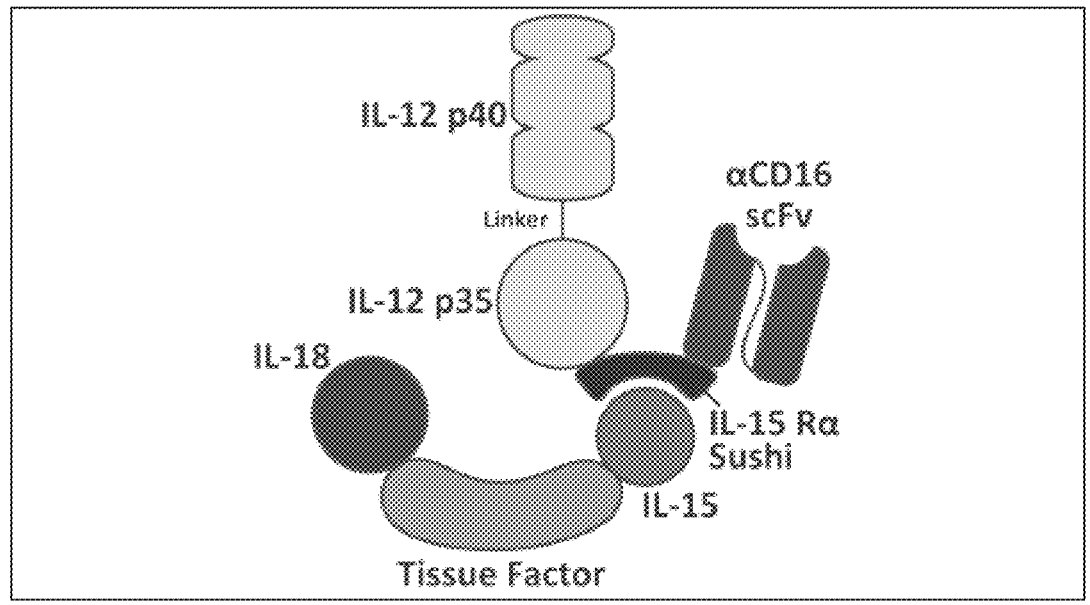
FIG. 24 shows a schematic diagram of an exemplary 18t15-12s/αCD16 protein complex.

Example 14: Secretion of
IL-12/IL-15RαSu/αCD16scFv and IL-18/TF/IL-15
Fusion Proteins The IL-12/IL-15RαSu/αCD16scFv and IL-18/TF/IL-15 constructs were cloned into a pMSGV-1 modified retrovirus expression vector (Hughes, *Hum Gene Ther* 16:457-72, 2005, herein incorporated by reference), and the expression vector was transfected into CHO-K1 cells. Co-expression of the two constructs in CHO-K1 cells resulted in secretion of a soluble IL-18/TF/IL-15:IL-12/IL-15RαSu/αCD16scFv protein complex (referred to as 18t15-12s/αCD16; FIGS. 23 and 24). Co-expression of the two constructs in CHO-K1 cells resulted in secretion of the soluble IL-18/TF/IL-15:IL-12/IL-15RαSu/αCD16scFv protein complex (referred to as 18t15-12s/αCD16; FIG. 23 and FIG. 24), which can be purified by anti-TF Ab affinity and other chromatography methods. In some cases, the signal peptide is cleaved from the intact polypeptide to generate the mature form.

The amino acid sequence of the IL-12/IL-15RαSu/αCD16scFv fusion protein (including signal peptide sequence) is as follows (SEQ ID NO: 122):

```
(Signal peptide)
MKWVTFISLLFLFSSAYS (Human IL-12 subunit beta (p40))
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS (Human IL-15R α sushi domain)
ITCPPPMSVEHADIWVKSYSLYSRERYICNSGFKRKAGTSSLTECVLNKA

TNVAHWTTPSLKCIR (anti-Human CD16 light chain variable domain)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGH (Linker)
GGGGSGGGGSGGGGS (anti-Human CD16 heavy chain variable domain)
EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSR
```

The amino acid sequence of the IL-18/TF/IL-15 fusion protein (including leader sequence) is as follows (SEQ ID NO: 72):

```
(Signal peptide)
MKWVTFISLLFLFSSAYS (Human IL-18)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNED (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

Example 15: Creation of IL-18/IL-15RαSu and IL-12/TF/IL-15 DNA Constructs

In a non-limiting example, IL-18/IL-15RαSu and IL-12/TF/IL-15 DNA constructs were created. The human IL-18 subunit sequences, human IL-15RαSu sequence, human IL-12 sequence, human tissue factor 219 sequence, and human IL-15 sequence were synthesized by Genewiz. A DNA construct was made linking IL-18 directly to IL-15RαSu. An additional construct was also made linking IL-12 sequence to the N-terminus coding region of human tissue factor 219 form, and further linking the IL-12/TF construct to the N-terminus coding region of IL-15. As described above, a single-chain version of IL-12 (p40-linker-p35) was used.

The nucleic acid sequence of the IL-18/IL-15RαSu construct (including signal peptide sequence) is as follows (SEQ ID NO: 217):

```
(Signal peptide)
ATGAAGTGGGTCACATTTATCTCTTTACTGTTCCTCTTCTCCAGCGCCTA

CAGC (Human IL-18)
TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA
```

CCGACTCCGATTGCCGGGACAATGCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGAT (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG

The nucleic acid sequence of the IL-12/TF/IL-15 construct (including leader sequence) is as follows (SEQ ID NO: 218):

(Signal peptide)
ATGGAAATGGGTGACCTTTATTTCTTTACTGTTCCTCTTTAGCAGCGCCTA

CTCC (Human IL-12 subunit beta (p40))
ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA

AAGACCCTCACAATCCAAGTTAAGGAGTTCGGAGACGCTGGCCAATACAC

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC

GCTACCCTCAGCGCTGAGAGGGTTCGTGGCGATAACAAGGAATACGAGTA

CAGCGTGGAGTGCCAAGAAGATAGCGCTTGTCCCGCTGCCGAAGAATCTT

TACCCATTGAGGTGATGGTGGACGCCGTGCACAAACTCAAGTACGAGAAC

TACACCTCCTCCTTCTTTATCCGGGACATCATTAAGCCCGATCCTCCTAA

GAATTTACAGCTGAAGCCTCTCAAAAATAGCCGGCAAGTTGAGGTCTCTT

GGGAATATCCCGACACTTGGAGCACACCCCACAGCTACTTCTCTTTAACC

TTTTGTGTGCAAGTTCAAGGTAAAAGCAAGCGGGAGAAGAAAGACCGGGT

GTTTACCGACAAAACCAGCGCCACCGTCATCTGTCGGAAGAACGCCTCCA

TCAGCGTGAGGGCTCAAGATCGTTATTACTCCAGCAGCTGGTCCGAGTGG

GCCAGCGTGCCTTGTTCC (Linker)
GGCGGTGGAGGATCCGGAGGAGGTGGCTCCGGCGGCGGAGGATCT (Human IL-12 subunit alpha (p35))
CGTAACCTCCCCGTGGCTACCCCCGATCCCGGAATGTTCCCTTGTTTACA

CCACAGCCAGAATTTACTGAGGGCCGTGAGCAACATGCTGCAGAAAGCTA

GGCAGACTTTAGAATTTTACCCTTGCACCAGCGAGGAGATCGACCATGAA

GATATCACCAAGGACAAGCATCCACCGTGGAGGCTTGTTTACCTCTGGA

GCTGACAAAGAACGAGTCTTGTCTCAACTCTCGTGAAACCAGCTTCATCA

CAAATGGCTCTTGTTTAGCTTCCCGGAAGACCTCCTTTATGATGGCTTTA

TGCCTCAGCTCCATCTACGAGGATTTAAAGATGTACCAAGTGGAGTTCAA

GACCATGAACGCCAAGCTGCTCATGGACCCTAAACGGCAGATCTTTTTAG

ACCAGAACATGCTGGCTGTGATTGATGAGCTGATGCAAGCTTTAAACTTC

AACTCCGAGACCGTCCCTCAGAAGTCCTCCCTCGAGGAGCCCGATTTTTA

CAAGACAAAGATCAAACTGTGCATTTTACTCCACGCCTTTAGGATCCGGG

CCGTGACCATTGACCGGGTCATGAGCTATTTAAACGCCAGC (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

Example 16: Secretion of IL-18/IL-15RαSu and IL-12/TF/IL-15 Fusion Proteins

The IL-18/IL-15RαSu and IL-12/TF/IL-15 constructs were cloned into a pMSGV-1 modified retrovirus expression vector (Hughes, *Hum Gene Ther* 16:457-72, 2005 herein incorporated by reference), and the expression vector was transfected into CHO-K1 cells. Co-expression of the two constructs in CHO-K1 cells resulted in secretion of a soluble IL-12/TF/IL-15:IL-18/IL-15RαSu protein complex (referred to as 12t15/518), which can be purified by anti-TF Ab affinity and other chromatography methods.

The amino acid sequence of the IL-18/IL-15RαSu fusion protein (including signal peptide sequence) is as follows (SEQ ID NO: 219):

(Signal peptide)
MKWVTFISLLFLFSSAYS (Human IL-18)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNED (Human IL-15R α sushi domain)
ITCPPPMSVEHADIWVKSYSLYSRERYICNSGFKRKAGTSSLTECVLNKA

TNVAHWTTPSLKCIR

The amino acid sequence of the IL-12/TF/IL-15 fusion protein (including leader sequence) is as follows (SEQ ID NO: 220):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

In some cases, the leader peptide is cleaved from the intact polypeptide to generate the mature form that may be soluble or secreted.

Example 17: Recombinant Protein Quantitation of the 18t15-12s16 Complex

Figure 25:
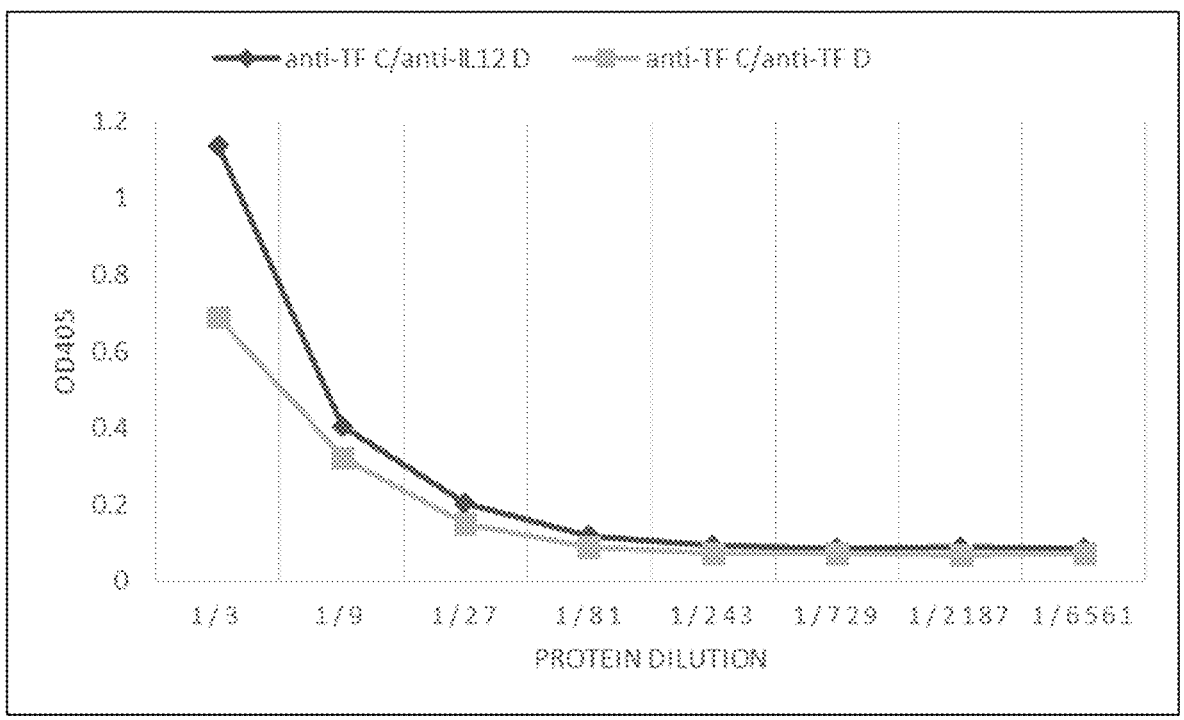
FIG. 25 shows a sandwich ELISA for the 18t15-12s16 complex, comprising an anti-human tissue factor capture antibody and a biotinylated anti-human IL-12 or IL-18 detection antibody.

The 18t15-12s16 complex (comprising IL-12/IL-15RαSu/αCD16scFv; IL-18/TF/IL-15) was detected and quantified using standard sandwich ELISA methods (FIG. 25). Anti-human tissue factor antibody/IL-2 or anti-TF Ab/IL-18 served as the capture antibody and biotinylated anti-human IL-12 or IL-18 antibody (BAF 219, D045-6, both R&D Systems) served as the detection antibody. Tissue factor was also detected using an anti-human tissue factor antibody (143), and anti-human tissue factor antibody detection antibody.

Example 18: Creation of TGFβRII/IL-15RαSu and IL-21/TF/IL-15 DNA Constructs

Figure 26:
FIG. 26 shows a schematic diagram of an exemplary TGFβRII-15RαSu DNA construct.

In a non-limiting example, a TGFβRII/IL-15RαSu DNA construct was created (FIG. 26). The human TGFβRII dimer and human IL-21 sequences were obtained from the UniProt website and DNA for these sequences was synthesized by Genewiz. A DNA construct was made linking the TGFβRII to another TGFβRII with a linker to generate a single chain version of TGFβRII and then directly linking the TGFβRII single chain dimer sequence to the N-terminal coding region of IL-15RαSu.

The nucleic acid sequences of the TGFβRII/IL-15RαSu construct (including signal sequence) is as follows (SEQ ID NO: 93):

(Signal peptide)
ATGAAGTGGGTGACCTTCATCAGCCTGCTGTTCCTGTTCTCCAGCGCCTA

CTCC (Human TGFβRII-1$^{st}$ fragment)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCACGATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT (Linker)
GGAGGTGGCGGATCCGGAGGTGGAGGTTCTGGTGGAGGTGGGAGT (Human TGFβRII-2$^{nd}$ fragment)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCACAATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

```
AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC (Human IL-15R α sushi domain)
ATCACGTGTCCTCCTCCTATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCCAGTCTCAAATGTATTAGA
```

Figure 27:
FIG. 27 shows a schematic diagram of an exemplary IL-21/TF/IL-15 construct.

Additionally, an IL-21/TF/IL-15 construct was made linking the IL-21 sequence to the N-terminus coding region of tissue factor 219, and further linking the IL-21/TF construct to the N-terminus coding region of IL-15 (FIG. 27). The nucleic acid sequence of the IL-21/TF/IL-15 construct (including leader sequence) is as follows (SEQ ID NO: 89):

```
(Signal peptide)
ATGAAGTGGGTGACCTTCATCAGCCTGCTGTTCCTGTTCTCCAGCGCCTA

CTCC (Human IL-21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCAGGACTCC (Human Tissue Factor 219)
TCCGGCACCACCAATACCGTGGCCGCTTATAACCTCACATGGAAGAGCAC

CAACTTCAAGACAATTCTGGAATGGGAACCCAAGCCCGTCAATCAAGTTT

ACACCGTGCAGATCTCCACCAAATCCGGAGACTGGAAGAGCAAGTGCTTC

TACACAACAGACACCGAGTGTGATTTAACCGACGAAATCGTCAAGGACGT

CAAGCAAACCTATCTGGCTCGGGTCTTTTCCTACCCCGCTGGCAATGTCG

AGTCCACCGGCTCCGCTGGCGAGCCTCTCTACGAGAATTCCCCCGAATTC

ACCCCTTATTTAGAGACCAATTTAGGCCAGCCTACCATCCAGAGCTTCGA

GCAAGTTGGCACCAAGGTGAACGTCACCGTCGAGGATGAAAGGACTTTAG

TGCGGCGGAATAACACATTTTTATCCCTCCGGGATGTGTTCGGCAAAGAC

CTCATCTACACACTGTACTATTGGAAGTCCAGCTCCTCCGGCAAAAAGAC

CGCTAAGACCAACACCAACGAGTTTTTAATTGACGTGGACAAAGGCGAGA

ACTACTGCTTCAGCGTGCAAGCCGTGATCCCTTCTCGTACCGTCAACCGG

AAGAGCACAGATTCCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT
```

```
CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

Example 19: Secretion of TGFβRII/IL-15RαSu and IL-21/TF/IL-15 Fusion Proteins

Figure 28:
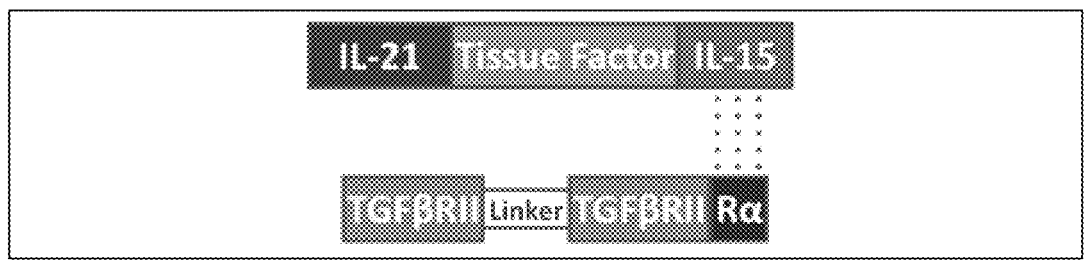
FIG. 28 shows a schematic diagram of the interaction between the exemplary IL-IL-21/TF/IL-15 and TGFβRII/IL-15RαSu constructs.
Figure 29:
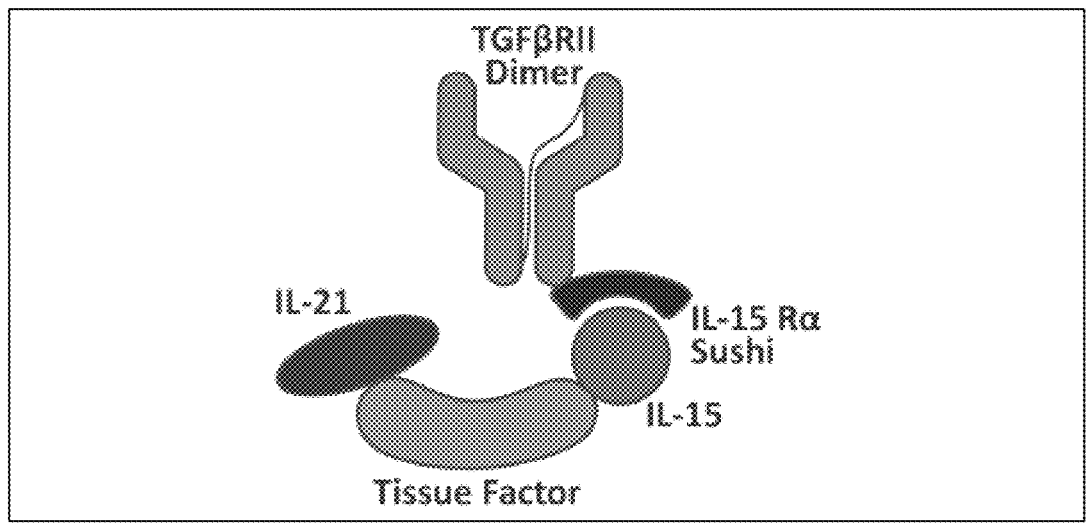
FIG. 29 shows a schematic diagram of the interaction between the exemplary TGFβRII/IL-15RαSu and IL-21/TF/IL-15 fusion proteins, resulting in an IL-21/TF/IL-15/TGFβRI/IL-15RαSu complex (21t15-TGFRs).

The TGFβRII/IL-15RαSu and IL-21/TF/IL-15 DNA constructs were cloned into a pMSGV-1 modified retrovirus expression vector (as described in Hughes et al., *Hum Gene Ther* 16:457-72, 2005, herein incorporated by reference), and the expression vector was transfected into CHO-K1 cells. Co-expression of the two constructs in CHO-K1 cells resulted in secretion of the soluble IL-21/TF/IL-15: TGFβRII/IL-15RαSu protein complex (referred to as 21t15-TGFRs; FIG. 28 and FIG. 29). The 21t15-TGFRs complex was purified from CHO-K1 cell culture supernatant using anti-TF antibody affinity chromatography and other chromatography methods.

The amino acid sequence of the TGFβRII/IL-15RαSu construct (including signal peptide sequence) is as follows (SEQ ID NO: 92):

```
(Signal peptide)
MKWVTFISLLFLFSSAYS (Human TGFβRII-1ˢᵗ fragment)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD (Linker)
GGGGSGGGGSGGGGS (Human TGFβRII-2ⁿᵈ fragment)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNKA

TNVAHWTTPSLKCIR
```

The amino acid sequence of the mature IL-21/TF/IL-15 fusion protein (including signal peptide sequence) is as follows (SEQ ID NO: 88):

```
(Signal peptide)
MKWVTFISLLFLFSSAYS (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS
```

-continued (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

In some cases, the leader peptide is cleaved from the intact polypeptide to generate a mature form that may be soluble or secreted.

Example 20: Purification of 21t15-TGFRs by Immunoaffinity Chromatography

An anti-TF antibody affinity column was connected to a GE Healthcare AKTA™ Avant protein purification system. The flow rate was 4 mL/min for all steps except the elution step, which was 2 mL/min.

Figure 30:
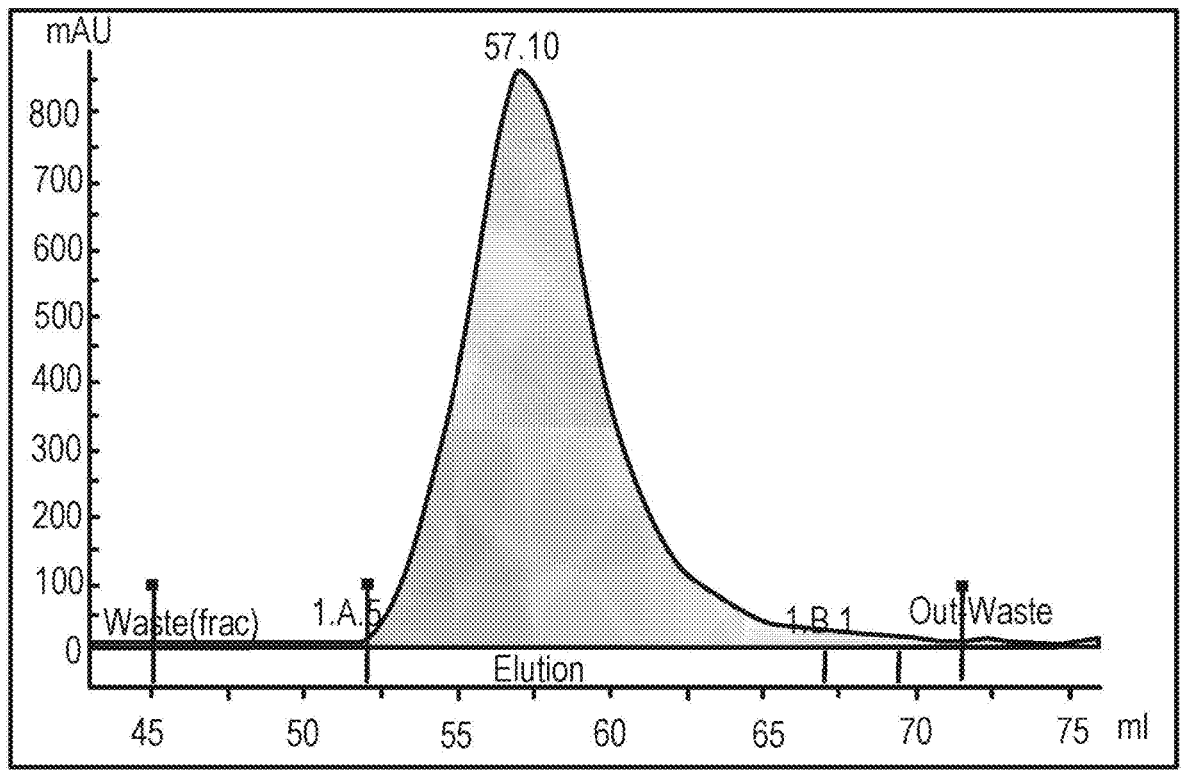
FIG. 30 shows a chromatograph of 21t15-TGFRs purification elution from an anti-TF antibody affinity column.

Cell culture harvest of 21t15-TGFRs was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was then neutralized to pH 7.5-8.0 by adding 1M Tris base. The neutralized sample was then buffer exchanged into PBS using Amicon® centrifugal filters with a 30 KDa molecular weight cutoff. FIG. 30 shows that the 21t15-TGFRs complex binds anti-TF antibody affinity column, wherein TF is a 21t15-TGFRs binding partner. The buffer-exchanged protein sample is stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide, and stored at 2-8° C.

Example 21: Size Exclusion Chromatography of 21t15-TGFRs

Figure 31:
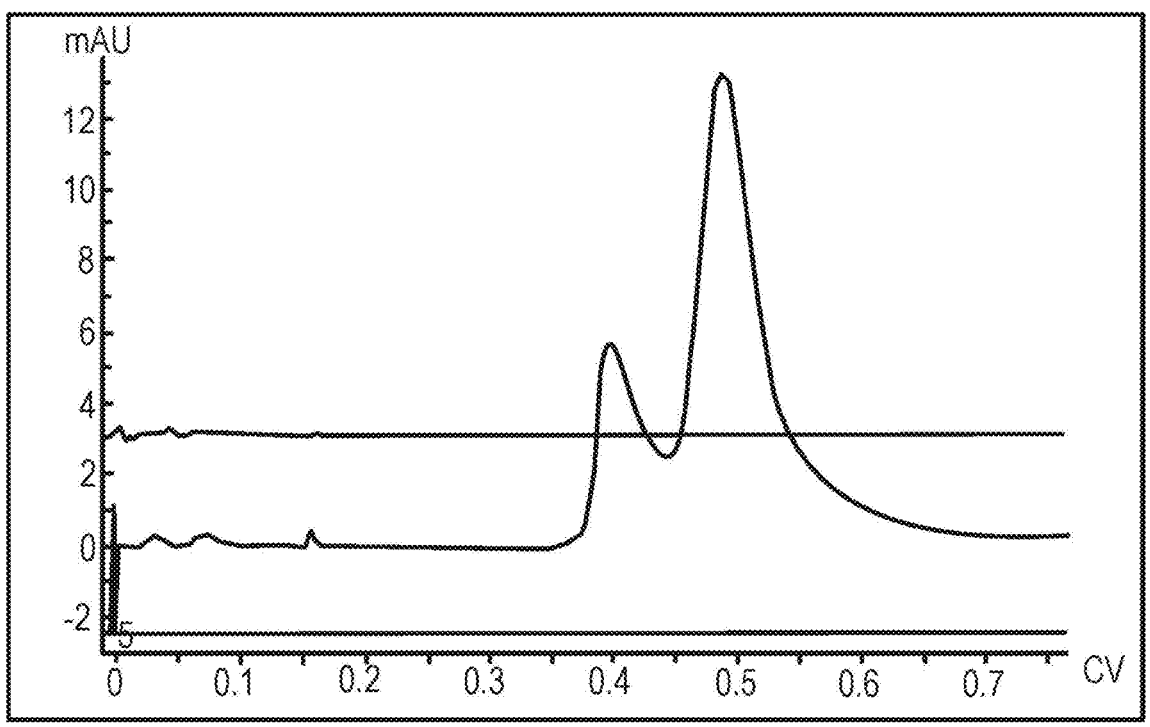
FIG. 31 shows an exemplary 21t15-TGFRs size exclusion chromatograph showing a main protein peak and a high molecular weight peak

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 200 µL of 1 mg/mL of 21t15-TGFRs complex onto the column. The injection was then chased with 1.25 column volumes of PBS. The SEC chromatograph was shown in FIG. 31. There were two protein peaks, likely representing a monomer and dimer forms of 21t15-TGFRs.

Example 22: SDS-PAGE of 21t15-TGFRs

Figure 32:
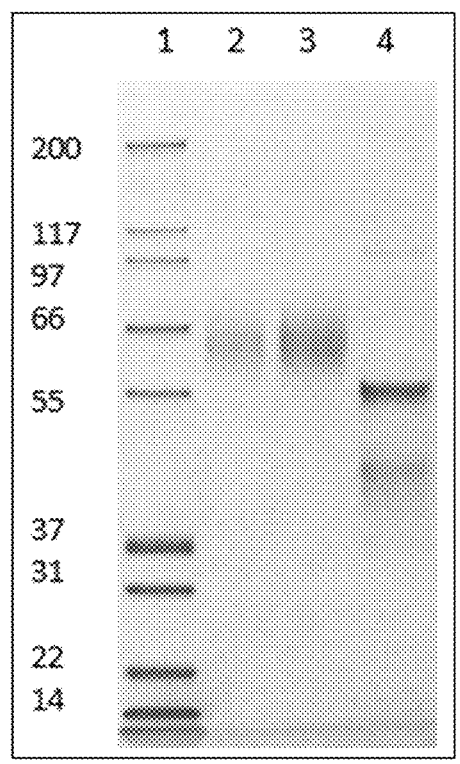
FIG. 32 shows an example of a 4-12% SDS-PAGE of the 21t15-TGFRs complex following disulfide bond reduction. Lane 1: Mark12 unstained marker (numbers on the left side indicate molecular weights in kDa); Lane 2: 21t15-TGFRs (0.5 µg); Lane 3: 21t15-TGFRs (1 µg); Lane 4: 21t15-TGFRs, deglycosylated (1 µg), wherein the MW was the expected size of 53 kDa and 39.08 kDa.
Figure 33:
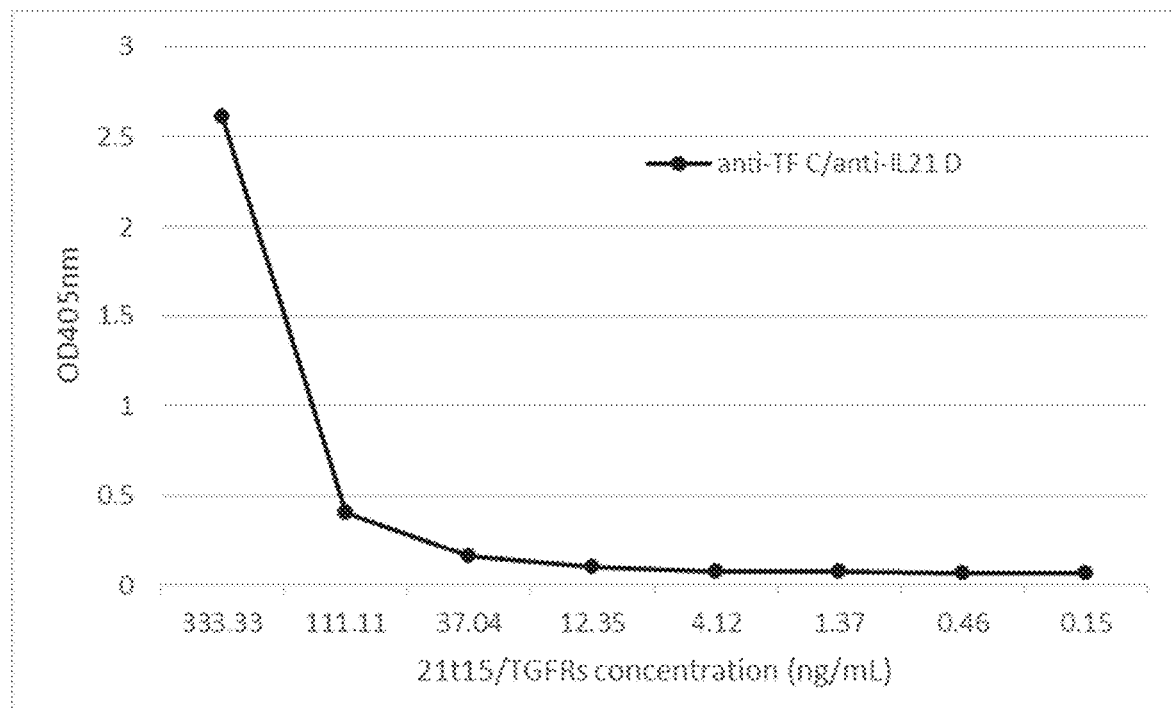
FIG. 33 shows a sandwich ELISA for the 21t15-TGFRs complex, comprising an anti-human tissue factor capture antibody and a biotinylated anti-human IL-21 detection antibody (13-7218-81, BioLegend).
Figure 34:
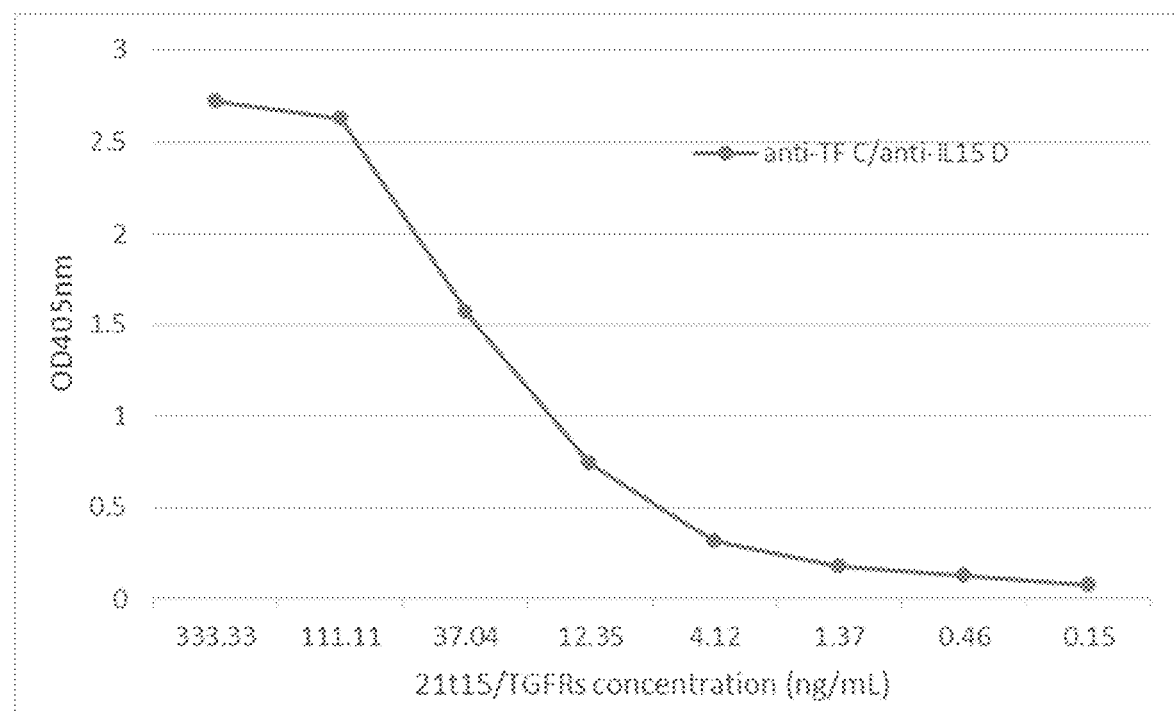
FIG. 34 shows a sandwich ELISA for the 21t15-TGFRs complex, comprising an anti-human tissue factor capture antibody and a biotinylated anti-human IL-15 detection antibody (BAM 247, R&D Systems).
Figure 35:
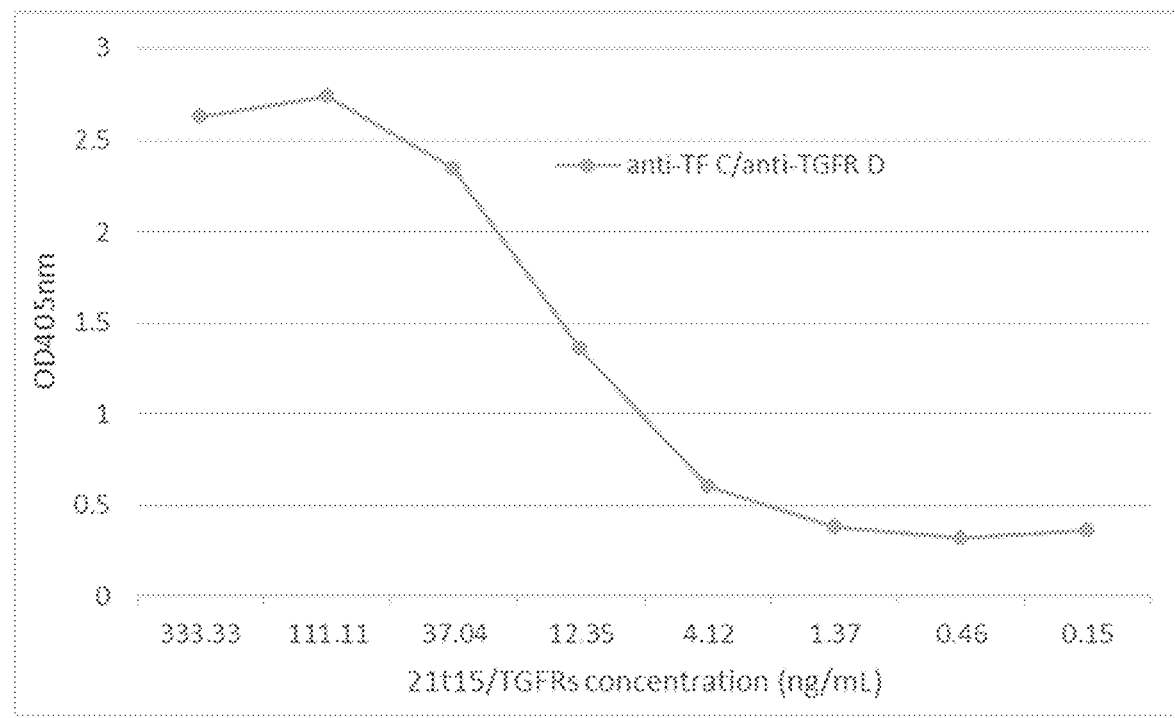
FIG. 35 shows a sandwich ELISA for the 21t15-TGFRs complex, comprising an anti-human tissue factor capture antibody and a biotinylated anti-human TGFβRII detection antibody (BAF241, R&D Systems).
Figure 36:
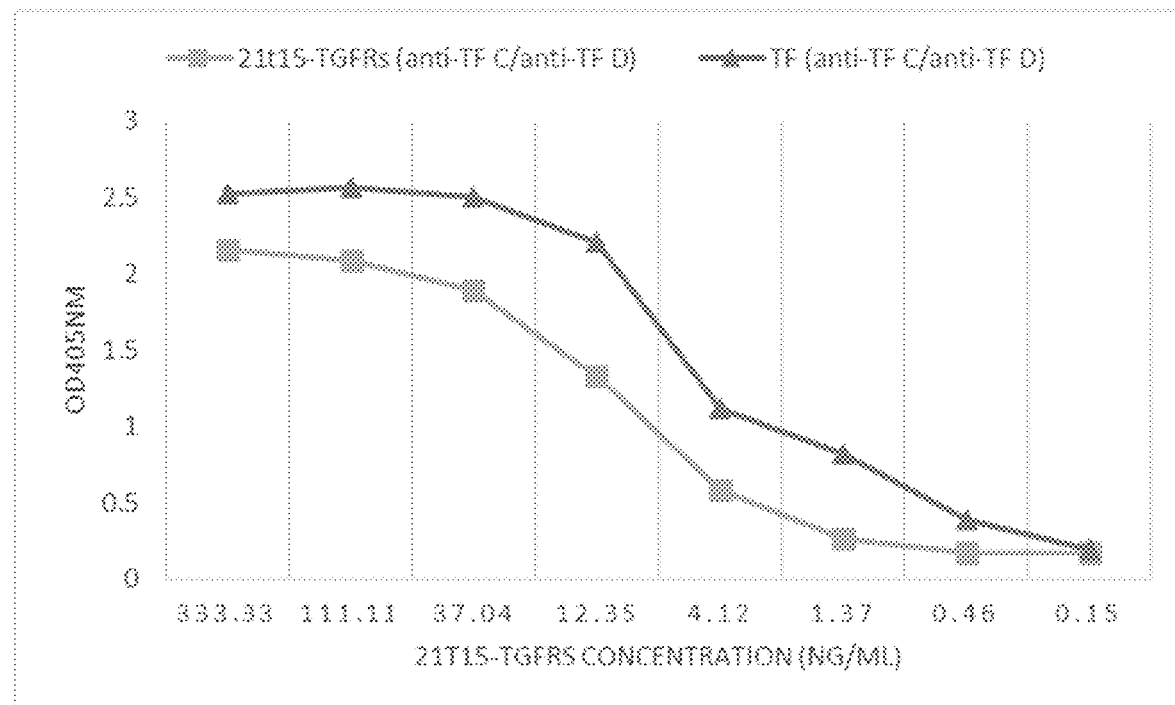
FIG. 36 shows a sandwich ELISA for the 21t15-TGFRs complex, comprising an anti-human tissue factor (143) capture antibody and an anti-human tissue factor detection antibody.

To determine the purity and protein molecular weight, the purified 21t15-TGFRs complex protein sample was analyzed using 4-12% NuPage Bis-Tris protein gel SDS-PAGE under reduced conditions. The gel was stained with InstantBlue™ for about 30 min, followed by destaining overnight in purified water. FIG. 32 shows an example SDS gel of anti-TF antibody affinity purified 21t15-TGFRs, with bands at 39.08 kDa and 53 kDa Glycosylation of 21t15-TGFRs in CHO cells was confirmed using the Protein Deglycosylation Mix II kit (New England Biolabs) and the manufacturer's instructions.

Deglycosylation reduces the molecular weight of 21t15-TGFRs, as seen in lane 4 of FIG. 32.

Example 23: Recombinant Protein Quantitation of 21t15-TGFRs Complexes

The 21t15-TGFRs complex was detected and quantified using standard sandwich ELISA methods (Figures. 33-37). Anti-human tissue factor antibody served as the capture antibody and biotinylated anti-human IL-21, IL-15, or TGFβRII served as the detection antibody. Tissue factor was also detected using an anti-human tissue factor capture antibody (143), and anti-human tissue factor antibody detection antibody. The I43/anti-TF antibody ELISA was compared to purified tissue factor at similar concentrations.

Example 24: Immunostimulatory Capacity of the 21t15-TGFRs Complex

Figure 37:
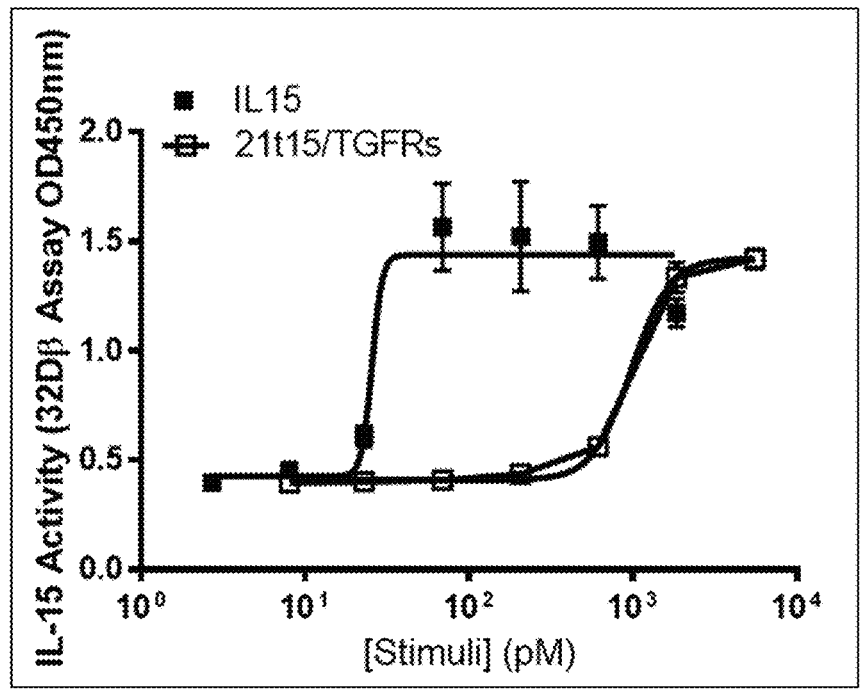
FIG. 37 shows IL-15-dependent proliferation of 32D13 cells mediated by the 21t15-TGFRs complex (open squares) compared to IL-15 (black squares).

To assess the IL-15 immunostimulatory activity of the 21t15-TGFRs complexes, increasing concentrations of 21t15-TGFRs was added to 32Dβ cells ($10^4$ cell/well) in 200 µL IMDM:10% FBS media and cells were incubated for 3 days at 37° C. On the fourth day, WST-1 proliferation reagent (10 µL/well) then was added and after 4 hours, absorbance was measured at 450 nm to determine cell proliferation based on cleavage of WST-1 to a soluble formazan dye. Bioactivity of the human recombinant IL-15 was assessed as a positive control. As shown in FIG. 37, 21t15-TGFRs demonstrated IL-15-dependent 32Dβ cell proliferation. The 21t15-TGFRs complex was reduced compared to that of human recombinant IL-15, possibly due to the linkage of IL-21 and tissue factor to the IL-15 domain.

Figure 38:
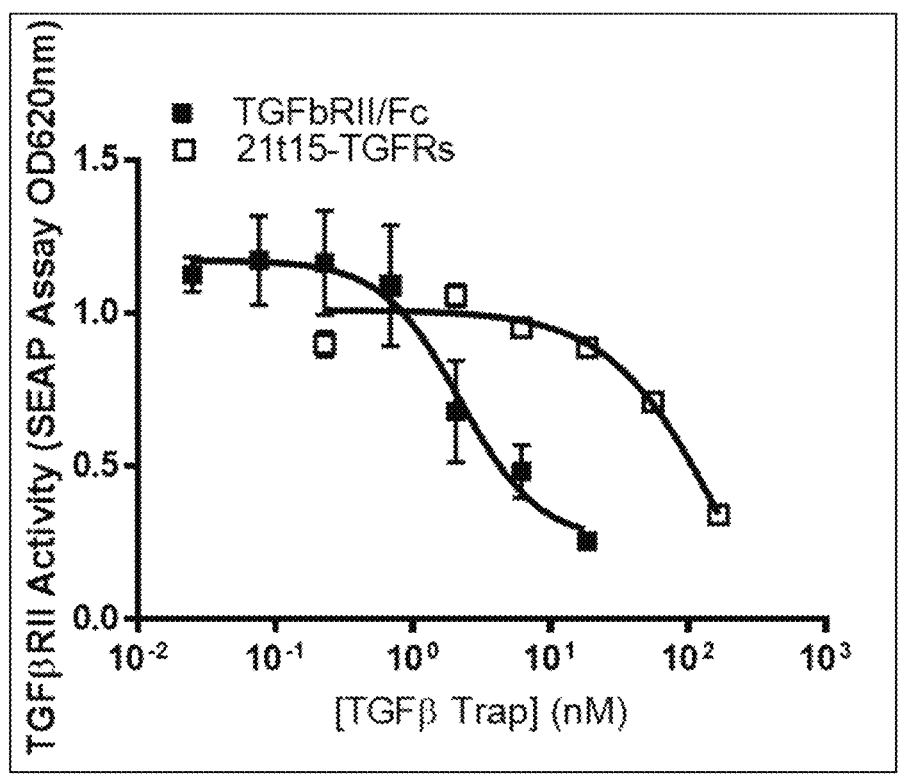
FIG. 38 shows biological activity of the TGFβRII domain within the 21t15-TGFRs complex (open squares). TGFβRII/Fc (black squares) served as a positive control.

Additionally, HEK-Blue TGFβ reporter cells (hkb-tgfb, InvivoGen) were used to measure the ability of 21t15-TGFRs to block TGFβ1 activity (FIG. 38). Increasing concentrations of 21t15-TGFRs were mixed with 0.1 nM of TGFβ1 and added to HEK-Blue TGFβ reporter cells (2.5× $10^4$ cell/well) in 200 µL IMDM:10% heat-inactivated FBS media. Cells were incubated overnight at 37° C. The next day, 20 µl of induced HEK-Blue TGFβ reporter cell supernatant was added to 180 µl of QUANTI-Blue (InvivoGen) and incubated for 1-3 hours at 37° C. 21t15-TGFRs activity was assessed by measuring absorbance at 620 nm. Human recombinant TGFβRII/Fc activity was assessed as a positive control.

These results demonstrate that TGFβRII domain of the 21t15-TGFRs complex retains its ability to trap TGFβ1. The ability of 21t15-TGFRs to block TGFβ1 activity was reduced compared to that of human recombinant TGFβRII/Fc, possibly due to the linkage of TGFβRII to the IL-15Rα sushi domain.

Example 25: Induction of Cytokine-Induced Memory-Like NK Cells by the 21t15-TGFRs Complex Cytokine-induced memory-like NK cells can be induced ex vivo following overnight stimulation of purified NK cells with saturating amounts of cytokines. These memory-like properties can be measured through expression of IL-2 receptor α (IL-2Rα, CD25), CD69 (and other activation markers), and increased IFN-γ production. To evaluate the ability of 21t15-TGFRs complexes to promote generation of cytokine-induced memory-like NK cells, purified human NK cells (>95% CD56+) were stimulated for 14-18 hours with 1 nM to 100 nM of the 21t15-TGFRs complex. Cell-surface CD25 and CD 69 expression and intracellular IFN-γ levels were assessed by antibody-staining and flow cytometry.

Figure 39:
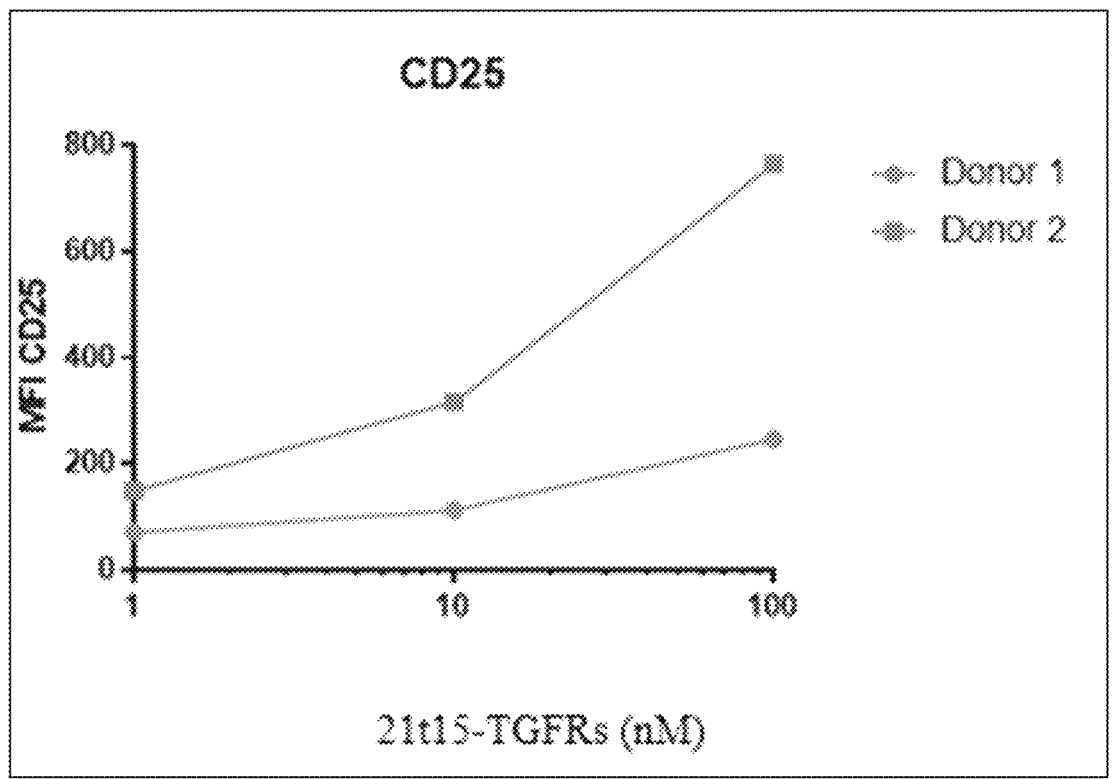
FIG. 39A shows a flow cytometry graph of cell-surface CD25 expression of NK cells induced by the 21t15-TGFRs complex.
Figure 40:
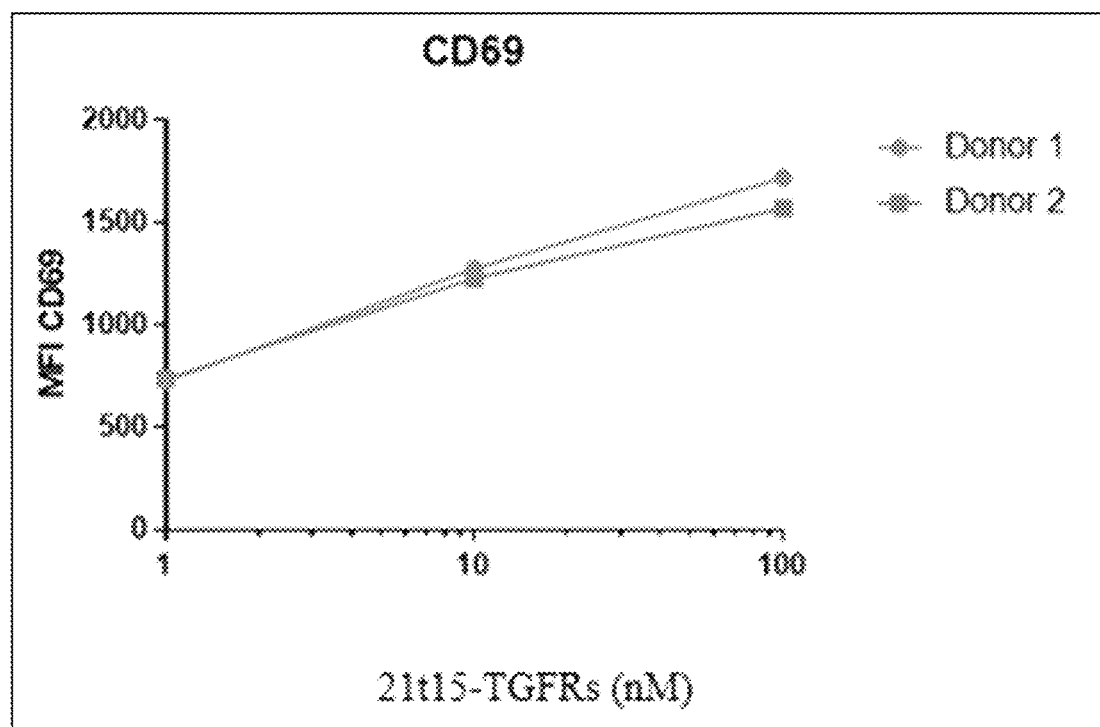
FIG. 40 shows a flow cytometry graph of cell-surface CD69 expression of NK cells induced by the 21t15-TGFRs complex.

Fresh human leukocytes were obtained from a blood bank and CD56+ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in 0.2×10⁶/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/mL) (Biolegend) and hIL-15 (50 ng/mL) (NCI) or with 1 nM, 10 nM, or 100 nM 21t15-TGFRs complex overnight at 37° C., 5% $CO_2$ for 14-18 hrs. The cells were then harvested and surface stained with CD56-BV421, CD16-BV510, CD25-PE, CD69-APCFire750 specific antibodies for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)). After two washes, cells were analyzed using a BD FACSCelesta™ flow cytometer. (Plotted Data-Mean Fluorescence Intensity; FIG. 39 and FIG. 40).

Figure 41:
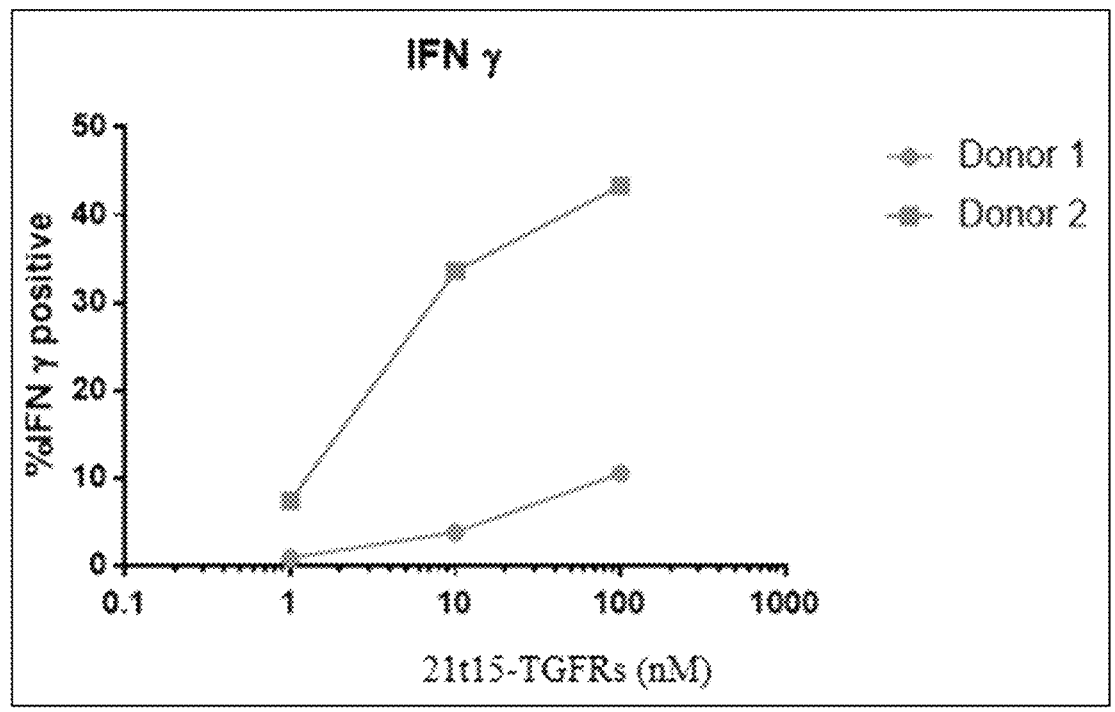
FIG. 41 shows a flow cytometry graph of intracellular interferon gamma expression of NK cells induced by the 21t15-TGFRs complex.

Fresh human leukocytes were obtained from a blood bank and CD56+ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in 0.2×106/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/mL) (Biolegend) and hIL-15 (50 ng/mL) (NCI) or with 1 nM, 10 nM, or 100 nM 21t15-TGFRs complex overnight at 37° C., 5% CO2 for 14-18 hrs. The cells were then treated with 10 µg/mL of Brefeldin A (Sigma) and 1× of Monensin (eBioscience) for 4 hrs. Cells were harvested and surface stained with CD56-BV421, CD16-BV510, CD25-PE, CD69-APCFire750 specific antibodies for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)) and fixed for 10 minutes at room temperature. After fixation, cells were washed (1500 RPM for 5 minutes at room temperature) with 1× permeabilized buffer (eBioscience) and stained for intracellular IFN-γ-PE Ab (Biolegend) for 30 minutes at room temperature. Cells were washed once again with 1× permeabilized buffer and then washed with FACS buffer. Cell pellets were resuspended in 300 µls of FACS Buffer and analyzed using a BD FACSCelesta™ flow cytometer. (Plotted % of IFN-γ Positive Cells; FIG. 41).

Example 26: In Vitro Cytotoxicity of NK Cells Against Human Tumor Cells

Figure 42:
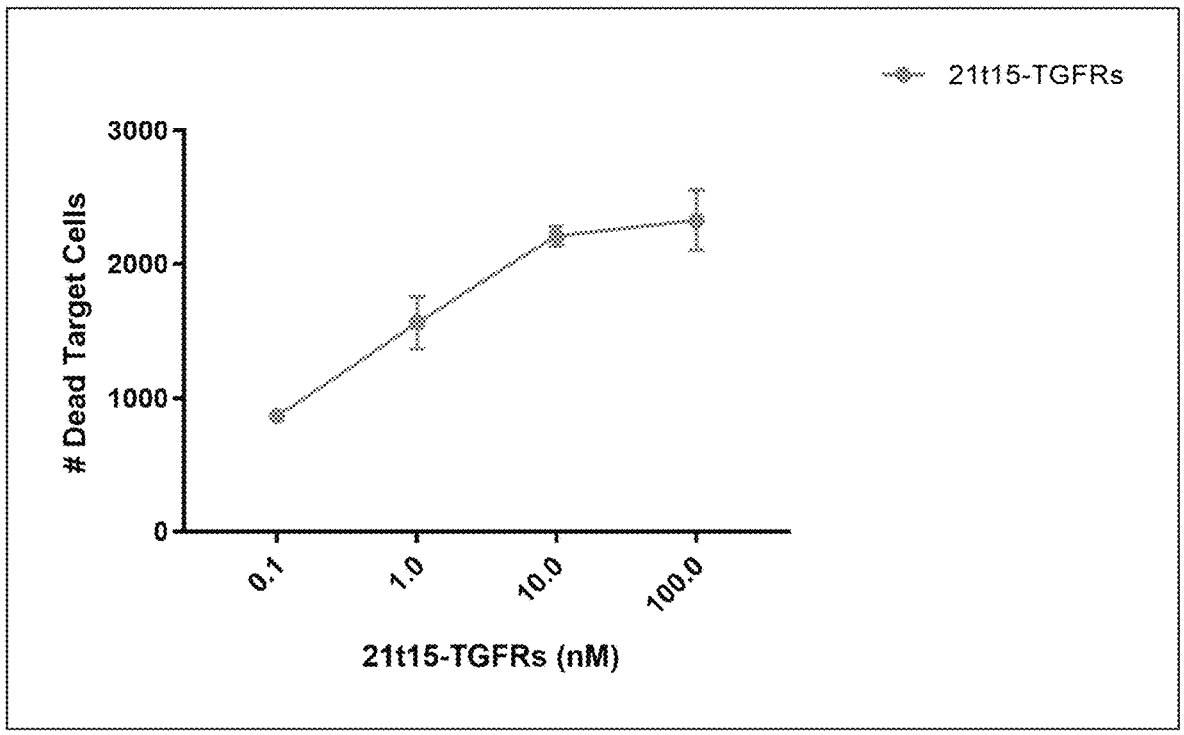
FIG. 42 shows cytotoxicity of 21t15-TGFRs-induced human NK cells against K562 cells.

K562 (CELLTRACE®, violet dye, labelled), human myelogenous leukemia cells, were incubated with purified human NK cells (using StemCell human NK cell purification kit (E:T ratio; 2:1)) in the presence of increasing concentrations of the 21t15-TGFRs complex. After 20 hours, the cultures were harvested, stained with propidium iodide (PI), and assessed by flow cytometry. As shown in FIG. 42, the 21t15-TGFRs complex induced human NK cytotoxicity against K562, as compared to control.

Example 27: Creation of an IL-21/TF Mutant/IL-15 DNA Construct and Resulting Fusion Protein Complex with TGFβRII/IL-15RαSu In a non-limiting example, an IL-21/TF mutant/IL-15 DNA construct was made by linking IL-21 directly to the N-terminus coding region of a tissue factor 219 mutant, and further linking the IL-21/TF mutant to the N-terminus coding region of IL-15.

The nucleic acid sequence of the IL-21/TF mutant/IL-15 construct (including signal peptide sequence) is as follows (SEQ ID NO: 221, shaded nucleotides are mutant and the mutant codons are underlined):

```
(Signal sequence)
ATGAAGTGGGTGACCTTCATCAGCCTGCTGTTCCTGTTCTCCAGCGCCTA

CTCC (Human IL-21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC (Human Tissue Factor 219 mutants)
TCCGGCACCACCAATACCGTGGCCGCTTATAACCTCACATGGAAGAGCAC

CAACTTCAAGACAATCTGGAATGGGAACCCAAGCCCGTCAATCAAGTTT

ACACCGTGCAGATCTCCACCAAATCCGGAGACTGGAAGAGCAAGTGCTTC

TACACAACAGACACCGAGTGTGATTTAACCGACGAAATCGTCAAGGACGTC

AAGCAAACCTATCTGGCTCGGGTCTTTTCCTACCCCGCTGGCAATGTCGA

GTCCACCGGCTCCGCTGGCGAGCCTCTCTACGAGAATTCCCCCGAATTCA

CCCCTTATTTAGAGACCAATTTAGGCCAGCCTACCATCCAGAGCTTCGAG

CAAGTTGGCACCAAGGTGAACGTCACCGTCGAGGATGAAAGGACTTTAGT

GGCGCGGAATAACACAGCTTTATCCCTCCGGGATGTGTTCGGCAAAGACC

TCATCTACACACTGTACTATTGGAAGTCCAGCTCCTCCGGCAAAAAGACC

GCTAAGACCAACACCAACGAGTTTTTAATTGACGTGGACAAAGGCGAGAA
```

```
-continued
CTACTGCTTCAGCGTGCAAGCCGTGATCCCTTCTCGTACCGTCAACCGGA

AGAGCACAGATTCCCCCGTTGAGTGCATGGGCCAAGAAAAGGGCGAGTTC

CGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

The amino acid sequence of the IL-21/TF mutant/IL-15 construct (including signal peptide sequence) is as follows (SEQ ID NO: 222, substituted residues are shaded):

```
(Signal peptide)
MKWVTFISLLFLFSSAYS (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS (Human Tissue Factor 219)
SGTTNTVAAYNLTWKSTNFATALEWEPKPVNQVYTVQISTKSGDWKSKCF

YTTDTECALTDEIVKDVKQTYLARVFSYPAGNVESTGSAGEPLYENSPEFT

PYLETNLGQPTIQSFEQVGTKVNVTVEDERTLVARNNTALSLRDVFGKDLI

YTLYYWKSSSSGKKTAKTNTNEFLIDVDKGENYCFSVQAVIPSRTVNRKS

TDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

In some cases, the leader peptide is cleaved from the intact polypeptide to generate a mature form that may be soluble or secreted.

In some embodiments, the IL-21/TF mutant/IL-15 DNA construct may be combined with an TGFβRII/IL-15RαSu DNA construct, transfected into cells using a retroviral vector as described above, and expressed as IL-21/TF mutant/IL-15 and TGFβRII/IL-15RαSu fusion proteins. The IL-15RαSu domain of the TGFβRII/IL-15RαSu fusion protein binds to the IL-15 domain of the IL-21/TF mutant/IL-15 fusion protein to create an IL-21/TF mutant/IL-15: TGFβRII/IL-15RαSu complex.

Example 28: Creation of IL-21/IL-15RαSu and TGFβRII/TF/IL-15 DNA Constructs and the Resulting Fusion Protein Complex In a non-limiting example, an IL-21/IL-15RαSu DNA construct was made by linking IL-21 directly to the IL-15RαSu subunit sequence. The nucleic acid sequence of the IL-21/IL-15RαSu construct (including signal sequence) is as follows (SEQ ID NO: 111):

```
(Signal sequence)
ATGAAGTGGGTGACCTTCATCAGCCTGCTGTTCCTGTTCTCCAGCGCCTA

CTCC (Human IL-21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG
```

The amino acid sequence of the IL-21/IL-15RαSu construct (including signal peptide sequence) is as follows (SEQ ID NO: 110):

```
(Signal peptide)
MKWVTFISLLFLFSSAYS (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLNKA

TNVAHWTTPSLKCIR
```

In some cases, the leader peptide is cleaved from the intact polypeptide to generate a mature form that may be soluble or secreted.

In some embodiments, the IL-21/IL-15RαSu DNA construct may be combined with a TGFβRII/TF/IL-15 DNA construct, transfected into a retroviral vector as described above, and expressed as IL-21/IL-15RαSu and TGFβRII/TF/IL-15 fusion proteins. The IL-15RαSu domain of the IL-21/IL-15RαSu fusion protein binds to the IL-15 domain of the TGFβRII/TF/IL-15 fusion protein to create a TGFβRII/TF/IL-15:IL-21/IL-15RαSu complex.

The TGFβRII/TF/IL-15 DNA construct was created by linking the TGFβRII sequence to the N-terminus coding region of human tissue factor 219 form, and then linking the TGFβRII/TF construct to the N-terminus coding region of IL-15. As described above, a single-chain version of TGFβRII (TGFβRII-linker-TGFβRII) was used. The nucleic acid sequence of the TGFβRII/TF/IL-15 construct (including leader sequence) is as follows (SEQ ID NO: 136):

(Signal peptide)
ATGAAGTGGGTGACCTTCATCAGCCTGCTGTTCCTGTTCTCCAGCGCCTA

CTCC (Human TGFβRII-1$^{st}$ fragment)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCACGATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT (Linker)
GGAGGTGGCGGATCCGGAGGTGGAGGTTCTGGTGGAGGTGGGAGT (Human TGFβRII-2$^{nd}$ fragment)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCACAATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC (Human Tissue Factor 219)
TCCGGCACCACCAATACCGTGGCCGCTTATAACCTCACATGGAAGAGCAC

CAACTTCAAGACAATTCTGGAATGGGAACCCAAGCCCGTCAATCAAGTTT

ACACCGTGCAGATCTCCACCAAATCCGGAGACTGGAAGAGCAAGTGCTTC

TACACAACAGACACCGAGTGTGATTTAACCGACGAAATCGTCAAGGACGT

CAAGCAAACCTATCTGGCTCGGGTCTTTTCCTACCCCGCTGGCAATGTCG

AGTCCACCGGCTCCGCTGGCGAGCCTCTCTACGAGAATTCCCCCGAATTC

ACCCCTTATTTAGAGACCAATTTAGGCCAGCCTACCATCCAGAGCTTCGA

GCAAGTTGGCACCAAGGTGAACGTCACCGTCGAGGATGAAAGGACTTTAG

TGCGGCGGAATAACACATTTTTATCCCTCCGGGATGTGTTCGGCAAAGAC

CTCATCTACACACTGTACTATTGGAAGTCCAGCTCCTCCGGCAAAAAGAC

CGCTAAGACCAACACCAACGAGTTTTTAATTGACGTGGACAAAGGCGAGA

ACTACTGCTTCAGCGTGCAAGCCGTGATCCCTTCTCGTACCGTCAACCGG

AAGAGCACAGATTCCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of the TGFβRII/TF/IL-15 fusion protein (including signal peptide) is as follows (SEQ ID NO: 135):

(Signal peptide)
MKWVTFISLLFLFSSAYS (Human TGFβRII-1$^{st}$ fragment)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD (Linker)
GGGGSGGGGSGGGGS (Human TGFβRII-2$^{nd}$ fragment)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Example 29: Creation of an IL-7/IL-15RαSu DNA Construct

Figure 43:
FIG. 43 shows a schematic diagram of an exemplary IL-7/IL-15RαSu DNA construct.

In a non-limiting example, an IL-7/IL-15RαSu DNA construct was created (see FIG. 43). The human IL-7 sequence, human IL-15RαSu sequence, human IL-15 sequence, and human tissue factor 219 sequence were obtained from the UniProt website and DNA for these sequences was synthesized by Genewiz. A DNA construct was made linking the IL-7 sequence to the IL-15RαSu sequence. The final IL-7/IL-15RαSu DNA construct sequence was synthesized by Genewiz.

The nucleic acid sequence encoding the second chimeric polypeptide of IL-7/IL-15RαSu construct (including signal peptide sequence) is as follows (SEQ ID NO: 103):

(Signal peptide)
ATGGGAGTGAAAGTTCTTTTTGCCCTTATTTGTATTGCTGTGGCCGAGGC

C (Human IL-7)
GATTGTGATATTGAAGGTAAAGATGGCAAACAATATGAGAGTGTTCTAAT

GGTCAGCATCGATCAATTATTGGACAGCATGAAAGAAATTGGTAGCAATT

GCCTGAATAATGAATTTAACTTTTTTAAAAGACATATCTGTGATGCTAAT

AAGGAAGGTATGTTTTTATTCCGTGCTGCTCGCAAGTTGAGGCAATTTCT

TAAAATGAATAGCACTGGTGATTTTGATCTCCACTTATTAAAAGTTTCAG

AAGGCACAACAATACTGTTGAACTGCACTGGCCAGGTTAAAGGAAGAAAA

CCAGCTGCCCTGGGTGAAGCCCAACCAACAAAGAGTTTGGAAGAAAATAA

ATCTTTAAAGGAACAGAAAAAACTGAATGACTTGTGTTTCCTAAAGAGAC

TATTACAAGAGATAAAAACTTGTTGGAATAAAATTTTGATGGGCACTAAA

GAACAC (Human IL-15R α sushi domain)
ATCACGTGCCCTCCCCCCATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCCAGTCTCAAATGCATTAGA

The second chimeric polypeptide of IL-7/IL-15RαSu construct (including signal peptide sequence) is as follows (SEQ ID NO: 102):

(Signal peptide)
MKWVTFISLLFLFSSAYS (Human IL-7)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Example 30: Creation of an IL-21/TF/IL-15 DNA Construct

Figure 44:
FIG. 44 shows a schematic diagram of an exemplary IL-21/TF/IL-15 DNA construct.

In a non-limiting example, an IL-21/TF/IL-15 construct was made (FIG. 44) by linking the IL-21 sequence to the N-terminus coding region of tissue factor 219, and further linking the IL-21/TF construct with the N-terminus coding region of IL-15.

The nucleic acid sequence encoding the first chimeric polypeptide of IL-21/TF/IL-15 construct (including leader sequence), synthesized by Genewiz, is as follows (SEQ ID NO: 89):

(Signal peptide)
ATGGGAGTGAAAGTTCTTTTTGCCCTTATTTGTATTGCTGTGGCCGAGG

CC (Human IL-21 fragment)
CAAGGTCAAGATCGCCACATGATTAGAATGCGTCAACTTATAGATATTGT

TGATCAGCTGAAAAATTATGTGAATGACTTGGTCCCTGAATTTCTGCCAG

CTCCAGAAGATGTAGAGACAAACTGTGAGTGGTCAGCTTTTTCCTGTTTT

CAGAAGGCCCAACTAAAGTCAGCAAATACAGGAAACAATGAAAGGATAAT

CAATGTATCAATTAAAAAGCTGAAGAGGAAACCACCTTCCACAAATGCAG

GGAGAAGACAGAAACACAGACTAACATGCCCTTCATGTGATTCTTATGAG

AAAAAACCACCCAAAGAATTCCTAGAAAGATTCAAATCACTTCTCCAAAA

GATGATTCATCAGCATCTGTCCTCTAGAACACACGGAAGTGAAGATTCC (Human Tissue Factor 219)
TCAGGCACTACAAATACTGTGGCAGCATATAATTTAACTTGGAAATCAAC

TAATTTCAAGACAATTTTGGAGTGGGAACCCAAACCCGTCAATCAAGTCT

ACACTGTTCAAATAAGCACTAAGTCAGGAGATTGGAAAAGCAAATGCTTT

TACACAACAGACACAGAGTGTGACCTCACCGACGAGATTGTGAAGGATGT

GAAGCAGACGTACTTGGCACGGGTCTTCTCCTACCCGGCAGGGAATGTGG

AGAGCACCGGTTCTGCTGGGGAGCCTCTGTATGAGAACTCCCCAGAGTTC

ACACCTTACCTGGAGACAAACCTCGGACAGCCAACAATTCAGAGTTTTGA

ACAGGTGGGAACAAAAGTGAATGTGACCGTAGAAGATGAACGGACTTTAG

TCAGAAGGAACAACACTTTCCTAAGCCTCCGGGATGTTTTTGGCAAGGAC

TTAATTTATACACTTTATTATTGGAAATCTTCAAGTTCAGGAAAGAAAAC

AGCCAAAACAAACACTAATGAGTTTTTGATTGATGTGGATAAAGGAGAAA

ACTACTGTTTCAGTGTTCAAGCAGTGATTCCCTCCCGAACAGTTAACCGG

AAGAGTACAGACAGCCCGGTAGAGTGTATGGGCCAGGAGAAAGGGGAATT

CAGAGAA (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The first chimeric polypeptide of IL-21/TF/IL-15 construct including leader sequence is SEQ ID NO: 88:

(Signal peptide) (SEQ ID NO: 223)
MGVKVLFALICIAVAEA (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS

-continued (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Example 31: Secretion of IL-7/IL-15RαSu and IL-21/TF/IL-15 Fusion Proteins

Figure 45:
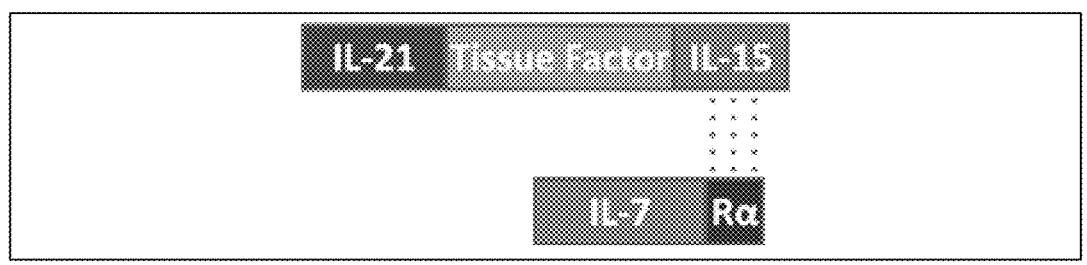
FIG. 45 shows a schematic diagram of the interaction between the exemplary IL-7/IL-15RαSu and IL-21/TF/IL-15 DNA constructs.
Figure 46:
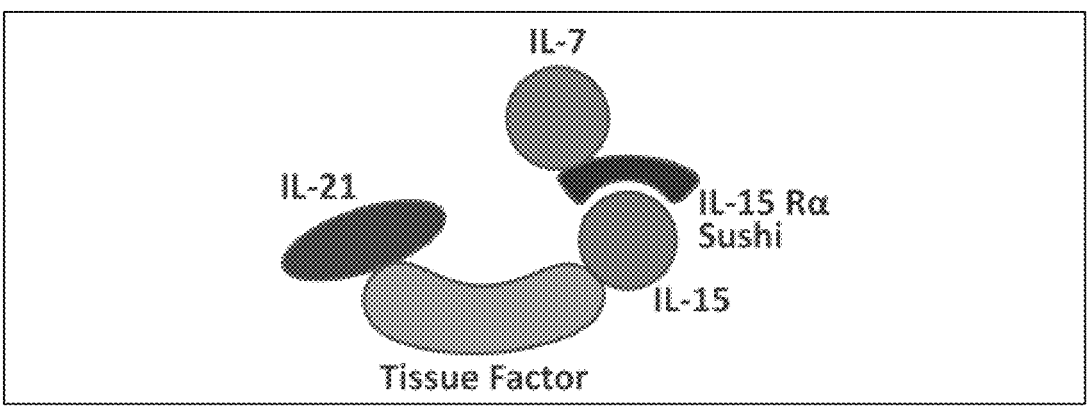
FIG. 46 shows a schematic diagram of the interaction between the exemplary IL-7/IL-15RαSu and IL-21/TF/IL-15 fusion proteins resulting in an IL-21/TF/IL-15:IL-7/IL-15RαSu complex (21t15-7s).

The IL-7/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:IL-7/IL-15RαSu protein complex (referred to as 21t15-7s; FIG. 45 and FIG. 46). The 21t15-7s protein was purified from CHO-K1 cell culture supernatant using anti-TF antibody affinity chromatography and size exclusion chromatography resulting in soluble (non-aggregated) protein complexes consisting of IL-7/IL-15RαSu and IL-21/TF/IL-15 fusion proteins.

In some cases, the leader (signal sequence) peptide is cleaved from the intact polypeptide to generate the mature form that may be soluble or secreted.

Example 32: Purification of 21t15-7s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Cell culture harvest of 21t15-7s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. The buffer-exchanged protein sample was stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 33: Size Exclusion Chromatography

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.7 mL/min. A capillary loop was used to inject 200 μL of 1 mg/mL of 7t15-21scomplex onto the column. The injection was chased with 1.25 column volumes of PBS.

Example 34: SDS-PAGE of 21t15-7s and 21t15-TGFRs

To determine the purity and protein molecular weight, the purified 21t15-7s or 21t15-TGFRs protein sample were analyzed using 4-12% NuPage Bis-Tris protein gel SDS-PAGE. The gel will be stained with InstantBlue™ for about 30 min, followed by destaining overnight in purified water.

Example 35: Glycosylation of 21t15-7s and 21t15-TGFRs in CHO-K1 Cells

Glycosylation of 21t15-7s in CHO-K1 cells or 21t15-TGFRs in CHO-K1 cells were confirmed using the Protein Deglycosylation Mix II kit (New England Biolabs), according to the manufacturer's instructions.

Example 36: Recombinant Protein Quantitation of 21t15-7s and 21t15-TGFRs Complexes The 21t15-7s complex or the 21t15-TGFRs complex were detected and quantified using standard sandwich ELISA methods. Anti-human tissue factor antibody (IgG1) served as the capture antibody and biotinylated anti-human IL-21, IL-15, or IL-7 antibody (21t15-7s) or biotinylated anti-human IL-21, IL-15, or TGF-βRII antibody (21t15-TGFRs) served as the detection antibody. Tissue factor in purified 21t15-7s or 21t15-TGFRs protein complexes was detected using an anti-human tissue factor capture antibody, and anti-human tissue factor antibody (IgG1) detection antibody. The anti-TF antibody ELISA will be compared to purified tissue factor at similar concentrations.

Figure 47:
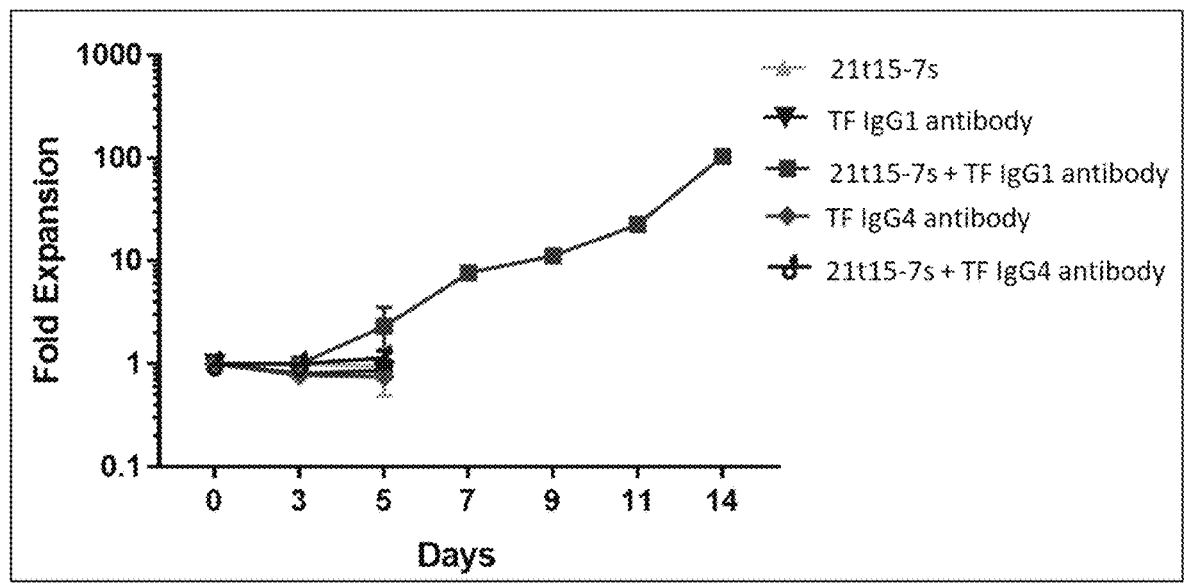
FIG. 47 shows the expansion of primary natural killer (NK) cells by stimulation with 21t15-7s+ anti-TF IgG1 antibody.
Figure 54:
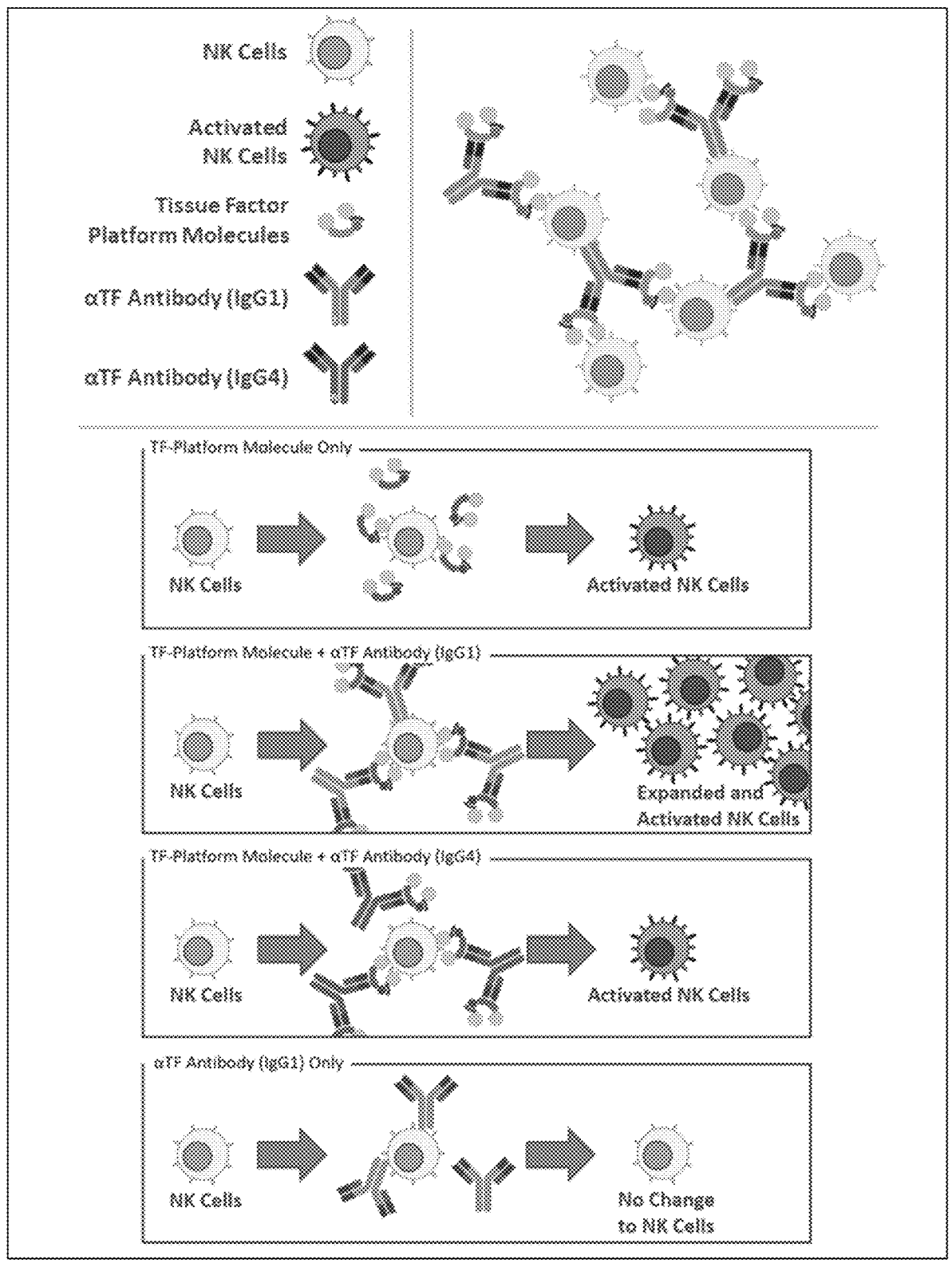
FIG. 54 shows in diagrammatic form the activation and expansion of primary natural killer (NK) cells by stimulation with 21t15-TGFRs+ anti-TF IgG1 antibody.

Example 37: Expansion Capacity of Primary Natural Killer (NK) Cells by 21t15-7s Complex+Anti-TF IgG1 Antibody or 21t15-TGFRs Complex+Anti-TF IgG1 Antibody To assess the 21t15-7s complex's ability to expand primary natural killer (NK) cells, 21t15-7s complex and 21t15-7s complex+anti-TF IgG1 antibody was added to NK cells obtained from samples of fresh human leukocytes. Cells were stimulated with 50 nM of 21t15-7s complex with or without 25 nM of anti-TF IgG1 or anti-TF IgG4 antibody at 37° C. and 5% $CO_2$. Cells were maintained at concentration at $0.5 \times 10^6$/mL not exceeding $2.0 \times 10^6$/mL by counting every 48-72 hours and media was replenished with fresh stimulator. Cells stimulated with 21t15-7s complex or anti-TF IgG1 antibody or anti-TF IgG4 antibody, or anti-TF IgG4+21t15-7s complex were maintained up to day 5. FIG. 47 shows expansion of primary NK cells upon incubation with 21t15-7s complex+anti-TF IgG1 antibody. FIG. 54 also shows a schematic of the results.

Figure 48:
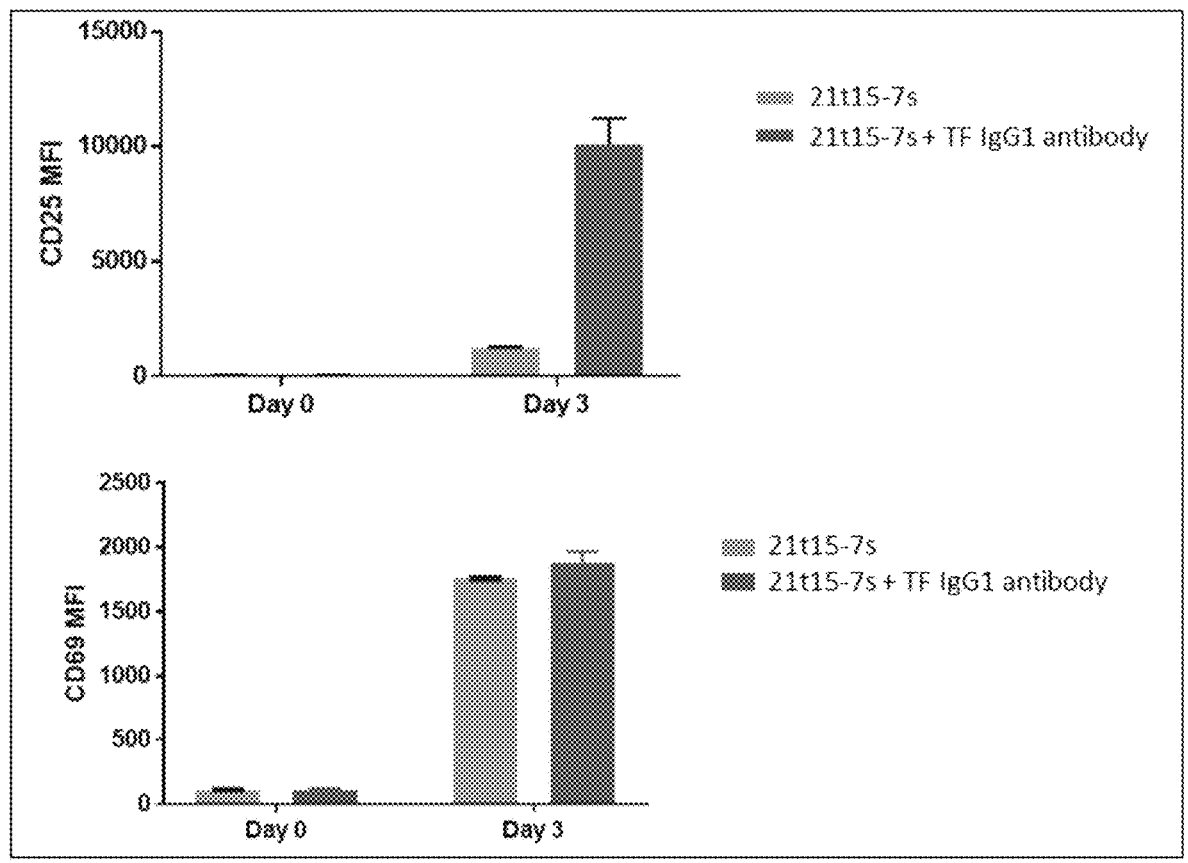
FIG. 48 shows activation of expanded primary NK cells, using CD25 MFI and CD69 MFI as markers of NK cell activation.

Example 38: Activation of Expanded NK Cells by the 21t15-7s Complex+Anti-TF IgG1 Antibody or the 21t15-TGFRs Complex+Anti-TF IgG1 Antibody Primary NK cells can be induced ex vivo following overnight stimulation of purified NK cells with 21t15-7s complex+anti-TF IgG1 antibody. Fresh human leukocytes were obtained from a blood bank and CD56+ NK cells were isolated with the RosetteSep/human NK cell reagent (Stem-Cell Technologies). The purity of NK cells was >80% and confirmed by staining with CD56-BV421 and CD16-BV510 specific antibodies (BioLegend). Cells were counted and resuspended in 1×10⁶/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells were stimulated with 50 nM of 21t15-7s with or without 25 nM of anti-TF IgG1 antibody at 37° C. and 5% $CO_2$. Cells were counted every 48-72 hours and maintained at a concentration of 0.5×10⁶/mL to 2.0×10⁶/mL until day 14. Media was periodically replenished with fresh stimulator. Cells were harvested and surface stained at day 3 with CD56-BV421, CD16-BV510, CD25-PE, CD69-APCFire750 specific antibodies (Biolegend and analyzed by Flow Cytometry-Celeste-BD Bioscience). FIG. 48 shows the activation markers CD25 MFI and CD69 MFI. The activation marker CD25 MFI increased with 21t15-7s complex+anti-TF IgG1 antibody stimulation, but not 21t15-7s complex stimulation. The activation marker CD69 MFI increased with both 21t15-7s complex+anti-TF IgG1 antibody and with 21t15-7s complex, alone.

Example 39: Cytotoxicity of NK Cells Against Human Tumor Cells

Figure 49:
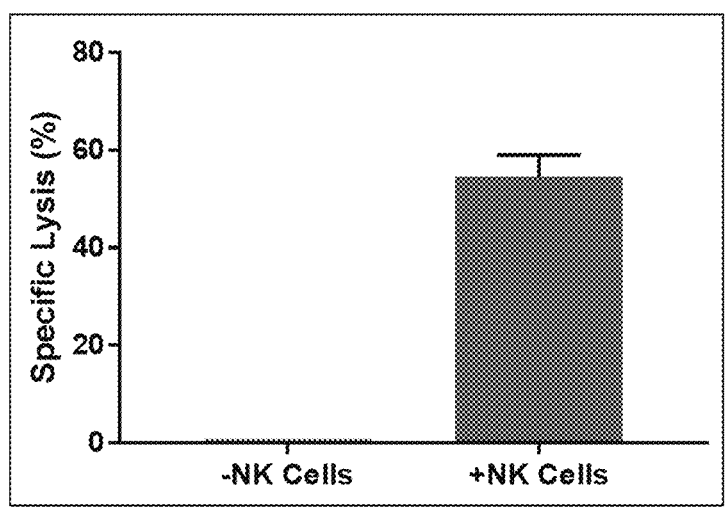
FIG. 49 shows cytotoxic activity of expanded NK cells against K562 human tumor cells, wherein NK cells stimulated with 21t15-7s+ anti-TF IgG1 antibody demonstrate greater specific lysis of K562 cells than NK cells not stimulated with 21t15-7s+ anti-TF IgG1 antibody.

Fresh human blood buffy coat was obtained from a blood bank. NK cells were isolated via negative selection using the RosetteSep/human NK cell reagent (StemCell Technologies). The NK cells were cultured in complete RPMI-1640 medium with 21t15-7s 100 nM and 50 nM of anti-TF IgG1 antibody for up to 11 days at 37° C. and 5% $CO_2$. The activated NK cells were mixed with CELLTRACE®, violet dye, labeled K562 cells at E:T ratio equal to 2:1 and incubated at 37° C. for 4 hours. The mixture was harvested and the percentage of dead K562 cells were determined by propidium iodide staining and flow cytometry. FIG. 49 shows increased specific lysis of K562 cells when incubated with expanded NK cells.

Example 40: Creation of an IL-21/IL-15RαSu DNA Construct

Figure 50:
FIG. 50 shows a schematic diagram of an exemplary IL-21/IL-15RαSu DNA construct.

In a non-limiting example, an IL-21/IL-15RαSu DNA construct was created. The human IL-21 sequence and human IL-15RαSu sequence were obtained from the UniProt website and DNA for these sequences was synthesized by Genewiz. A DNA construct was made linking the IL-21 sequence to the IL-15RαSu sequence. The final IL-21/IL-15RαSu DNA construct sequence was synthesized by Genewiz. See FIG. 50.

Example 41: Creation of an IL-7/TF/IL-15 DNA Construct

Figure 51:
FIG. 51 shows a schematic diagram of an exemplary IL-7/TF/IL-15 DNA construct.

In a non-limiting example, an IL-7/TF/IL-15 construct was made by linking the IL-7 sequence to the N-terminus coding region of tissue factor 219, and further linking the IL-7/TF construct with the N-terminus coding region of IL-15. See FIG. 51.

Example 42: Creation of an IL-21/IL-15Rα Sushi DNA Construct

In a non-limiting example, a second chimeric polypeptide of IL-21/IL-15RαSu was generated. The human IL-21 and human IL-15Rα sushi sequences were obtained from the UniProt website and DNA for these sequences was synthesized by Genewiz. A DNA construct was made linking the IL-21 sequence to the IL-15Rα sushi sequence. The final IL-21/IL-15RαSu DNA construct sequence was synthesized by Genewiz.

The nucleic acid sequence encoding the second chimeric polypeptide of IL-21/IL-15RαSu domain (including leader sequence), synthesized by Genewiz, is as follows (SEQ ID NO: 111):

```
(Signal peptide)
ATGAAGTGGGTGACCTTCATCAGCCTGCTGTTCCTGTTCTCCAGCGCCTA
CTCC (Human IL-21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG
```

The second chimeric polypeptide of IL-21/IL-15Rα sushi domain (including leader sequence) is as follows (SEQ ID NO: 110):

```
(Signal Sequence)
MKWVTFISLLFLFSSAYS (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLNKA

TNVAHWTTPSLKCIR
```

Example 43: Creation of an IL-7/TF/IL-15 DNA Construct

In a non-limiting example, an exemplary first chimeric polypeptide of IL-7/TF/IL-15 was made by linking the IL-7 sequence to the N-terminus coding region of tissue factor 219, and further linking the IL-7/TF construct with the N-terminus coding region of IL-15. The nucleic acid sequence encoding the first chimeric polypeptide of IL-7/TF/IL-15 (including leader sequence), synthesized by Genewiz, is as follows (SEQ ID NO: 107):

(Signal peptide)
ATGAAGTGGGTGACCTTCATCAGCCTGCTGTTCCTGTTCTCCAGCGCCTA

CTCC (Human IL-7 fragment)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The first chimeric polypeptide of IL-7/TF/IL-15 (including leader sequence), is as follows (SEQ ID NO: 106):

(Signal peptide)
MKWVTFISLLFLFSSAYS (Human IL-7)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Example 44: Secretion of IL-21/IL-15RαSu and IL-7/TF/IL-15 Fusion Proteins

Figure 52:
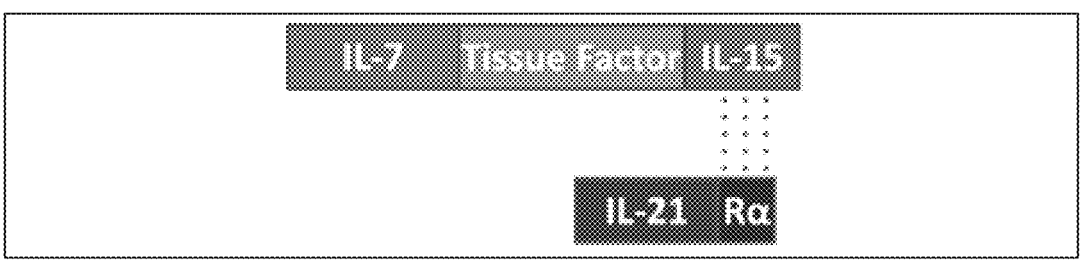
FIG. 52 shows a schematic diagram of the interaction between the exemplary IL-21/IL-15RαSu and IL-7/TF/IL-15 DNA constructs.
Figure 53:
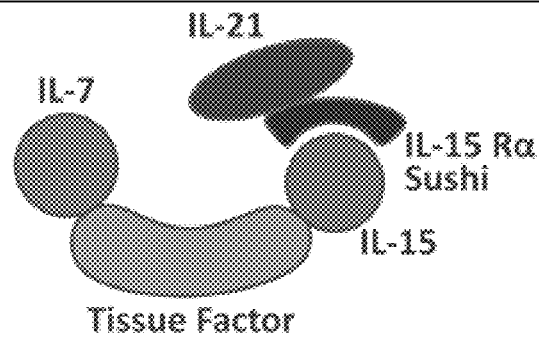
FIG. 53 shows a schematic diagram of the interaction between the exemplary IL-21/IL-15RαSu and IL-7/TF/IL-15 fusion proteins resulting in an IL-7/TF/IL-15:IL-21/IL-15RαSU complex (7t15-21s).

The IL-21/IL-15RαSu and IL-7/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-7/TF/IL-15:IL-21/IL-15RαSu protein complex (referred to as 7t15-21s). The 7t15-21s protein was purified from CHO-K1 cell culture supernatant using anti-TF antibody (IgG1) affinity chromatography and size exclusion chromatography resulting in soluble (non-aggregated) protein complexes consisting of IL-21/IL-15RαSu and IL-7/TF/IL-15 fusion proteins. See FIG. 52 and FIG. 53.

Figure 55:
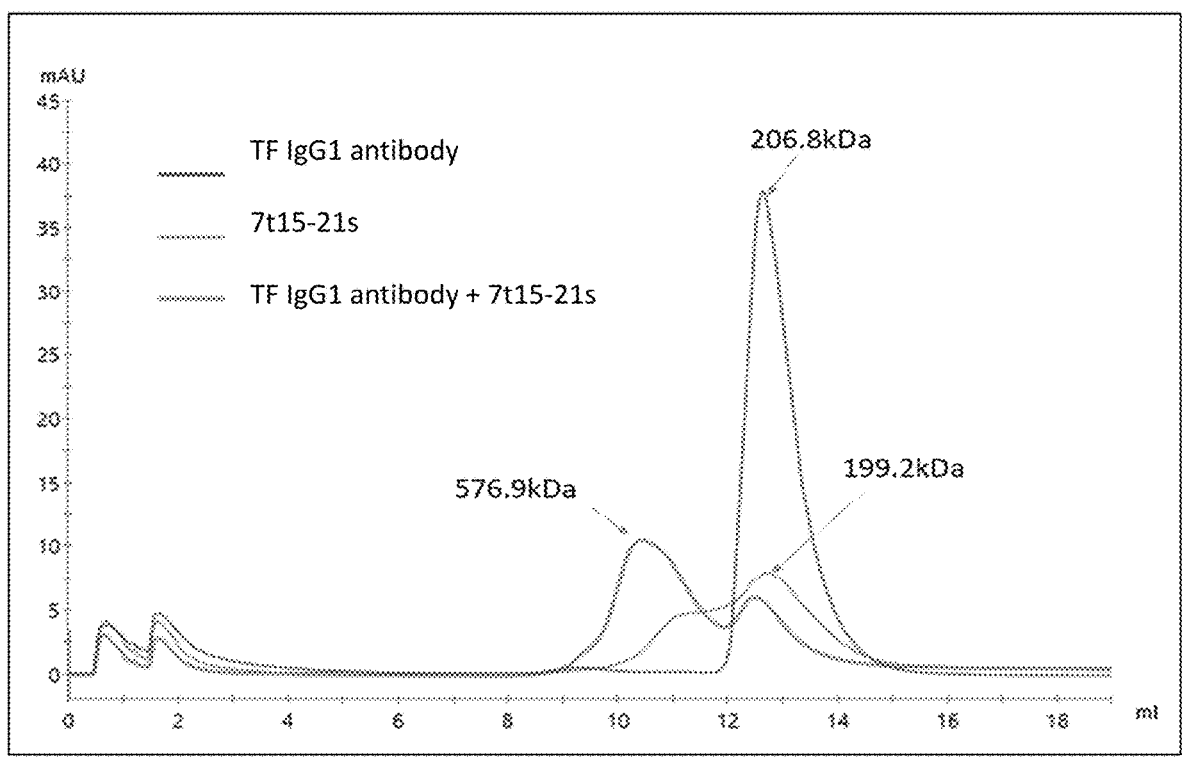
FIG. 55 shows size exclusion chromatography (SEC) profiles of anti-TF IgG1 antibody, 7t15-21s and the complex containing equal amounts of anti-TF IgG1 antibody and 7t15-21s.

Example 45: Analytical Size Exclusion Chromatography (SEC) Analysis of IL-21/IL-15RαSu and IL-7/TF/IL-15 Fusion Proteins To determine if anti-tissue factor monoclonal antibody and 7t15-21s can form an antibody-fusion-molecule complex, analytical size exclusion chromatography (SEC) was performed. A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. Samples of the anti-TF mAb (1 mg/mL), 7t15-21s (1 mg/mL), and a mixture of combined at a 1:1 ratio, so the final concentration of each protein is 0.5 mg/mL) were in PBS. Each sample was injected into the Superdex 200 column using a capillary loop, and analyzed by SEC. The SEC chromatograph of each sample was shown in FIG. 55. The SEC results indicated that there are two protein peaks for 7t15-21s, likely representing a dimer (with an apparent molecular weight of 199.2 kDa) and a higher oligomer of 7t15-21s, and there is one peak (with an apparent molecular weight of 206.8 kDa) for the anti-TF mAb. However, as expected, a new protein peak with a higher molecular weight (with an apparent molecular weight of 576.9 kDa) was formed in the mixture sample containing the anti-TF mAb and 7t15-21s, indicating that the anti-TF mAb and 7t15-21s form an antibody-antigen complex through the binding of anti-TF mAb to TF in the fusion protein complex.

Example 46: Expansion Capacity of Primary Natural Killer (NK) Cells by 7t15-21s Complex+Anti-TF IgG1 Antibody To assess the 7t15-21s complex's ability to expand primary natural killer (NK) cells, 7t15-21s complex and 7t15-21s complex+anti-TF IgG1 antibody are added to NK cells obtained from samples of fresh human leukocytes. Cells are stimulated with 50 nM of 7t15-21s complex with or without 25 nM of anti-TF IgG1 or anti-TF IgG4 antibody at 37° C. and 5% $CO_2$. Cells are maintained at concentration at $0.5 \times 10^6$/mL not exceeding $2.0 \times 10^6$/mL by counting every 48-72 hours and media is replenished with fresh stimulator. Cells stimulated with 7t15-21s complex or anti-TF IgG1 antibody or anti-TF IgG4 antibody or anti-TF IgG4+7t15-21s complex are maintained up to day 5. Expansion of primary NK cells upon incubation with 21t15-7s complex+ anti-TF IgG1 antibody is observed.

Example 47: Activation of Expanded NK Cells by the 7t15-21s Complex+Anti-TF IgG1 Antibody Primary NK cells are induced ex vivo following overnight stimulation of purified NK cells with 7t15-21s complex+ anti-TF IgG1 antibody. Fresh human leukocytes are obtained from a blood bank and CD56+NK cells are isolated with the RosetteSep/human NK cell reagent (StemCell Technologies). The purity of NK cells is >80% and is confirmed by staining with CD56-BV421 and CD16-BV510 specific antibodies (BioLegend). Cells are counted and resuspended in $1 \times 10^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells are stimulated with 50 nM of 7t15-21s with or without 25 nM of anti-TF IgG1 antibody at 37° C. and 5% $CO_2$. Cells are counted every 48-72 hours and maintained at a concentration of $0.5 \times 10^6$/ mL to $2.0 \times 10^6$/mL until day 14. Media is periodically replenished with fresh stimulator. Cells are harvested and surface stained at day 3 with CD56-BV421, CD16-BV510, CD25-PE, CD69-APCFire750 specific antibodies (Biolegend) and analyzed by Flow Cytometry-Celeste-BD Bioscience). The activation marker CD25 MFI are observed to increase with 7t15-21s complex+anti-TF IgG1 antibody stimulation, but not 7t15-21s complex stimulation. The activation marker CD69 MFI is observed to increase with both 7t15-21s complex+anti-TF IgG1 antibody and with 7t15-21s complex, alone.

Example 48: Increase in Glucose Metabolism in NK Cells Using 18t15-12s

A set of experiments was performed to determine the effect of the construct of 18t15-12s (FIG. 6) on oxygen consumption rate and extracellular acidification rate (ECAR) on NK cells purified from human blood.

In these experiments, fresh human leukocytes were obtained from the blood bank from two different human donors and NK cells were isolated via negative selection using the RosetteSep/human NK cell reagent (StemCell Technologies). The purity of NK cells was >80% and confirmed by staining with CD56-BV421 and CD16-BV510 specific Abs (BioLegend). The cells were counted and resuspended in $2 \times 10^6$/mL in 24-well, flat-bottom plates in 1 mL of complete media (RPMI 1640 (Gibco) supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies) and 10% FBS (Hyclone)). The cells were stimulated with either (1) media alone, (2) 100 nM 18t15-12s, or (3) mixture of single cytokines recombinant human IL-12 (0.25 µg), recombinant human IL-15 (1.25 µg), and recombinant human IL-18 (1.25 µg) overnight at 37° C. and 5% $CO_2$. On the next day, the cells were harvested and extracellular flux assays on expanded NK cells were performed using a XFp Analyzer (Seahorse Bioscience). The harvested cells washed and plated $2.0 \times 10^5$ cells/well in at least duplicate for extracellular flux analysis of OCR (Oxygen Consumption Rate) and ECAR (Extracellular Acidification Rate). The glycolysis stress tests were performed in Seahorse Media contain 2 mM of glutamine. The following were used during the assay: 10 mM glucose; 100 nM oligomycin; and 100 mM 2-deoxy-D-glycose (2DG).

Figure 56:
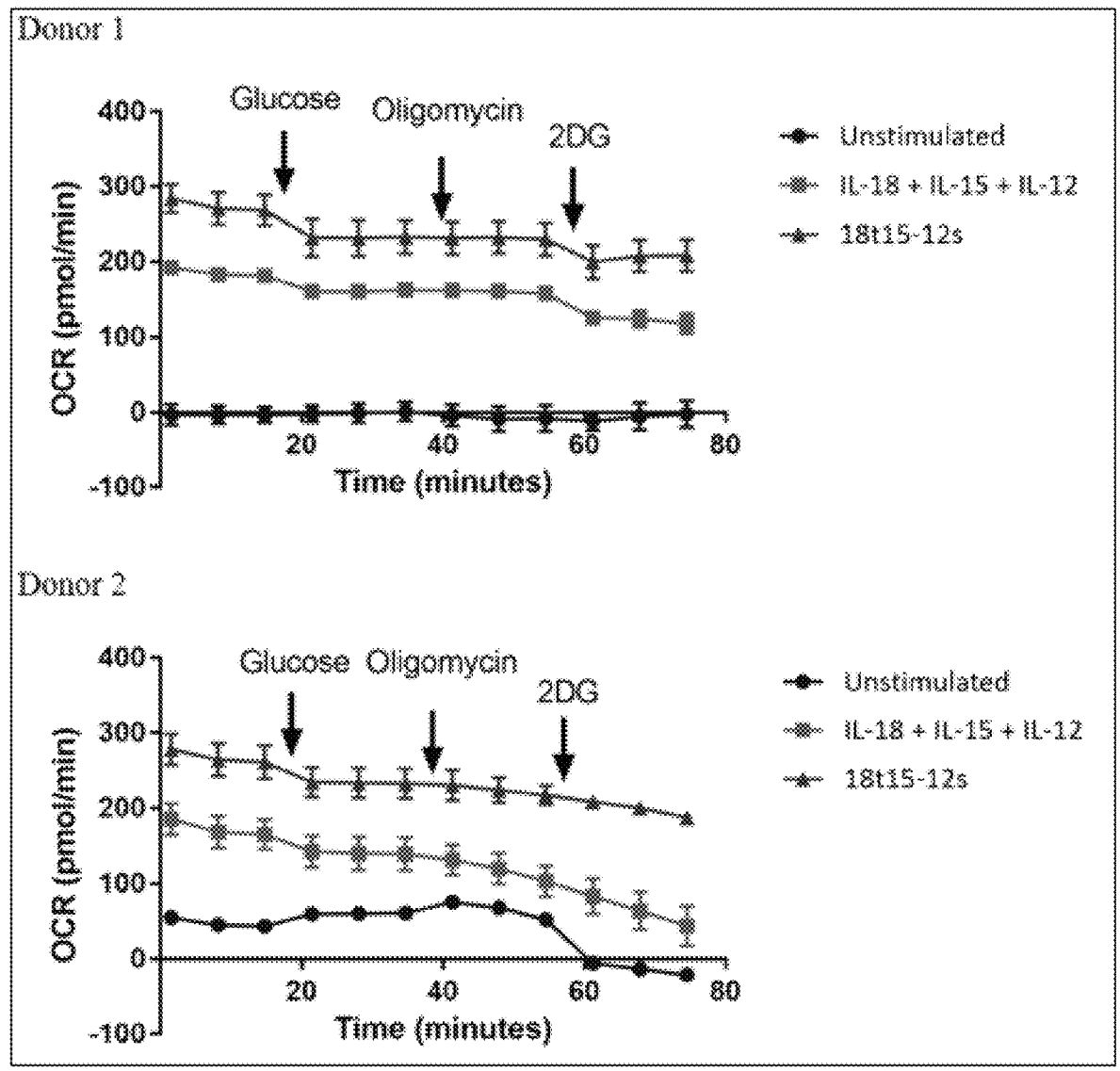
FIG. 56 shows the oxygen consumption rate (OCR) in pmoles/min for human NK cells isolated from blood ($2 \times 10^6$ cells/mL) of two different donors.
Figure 57:
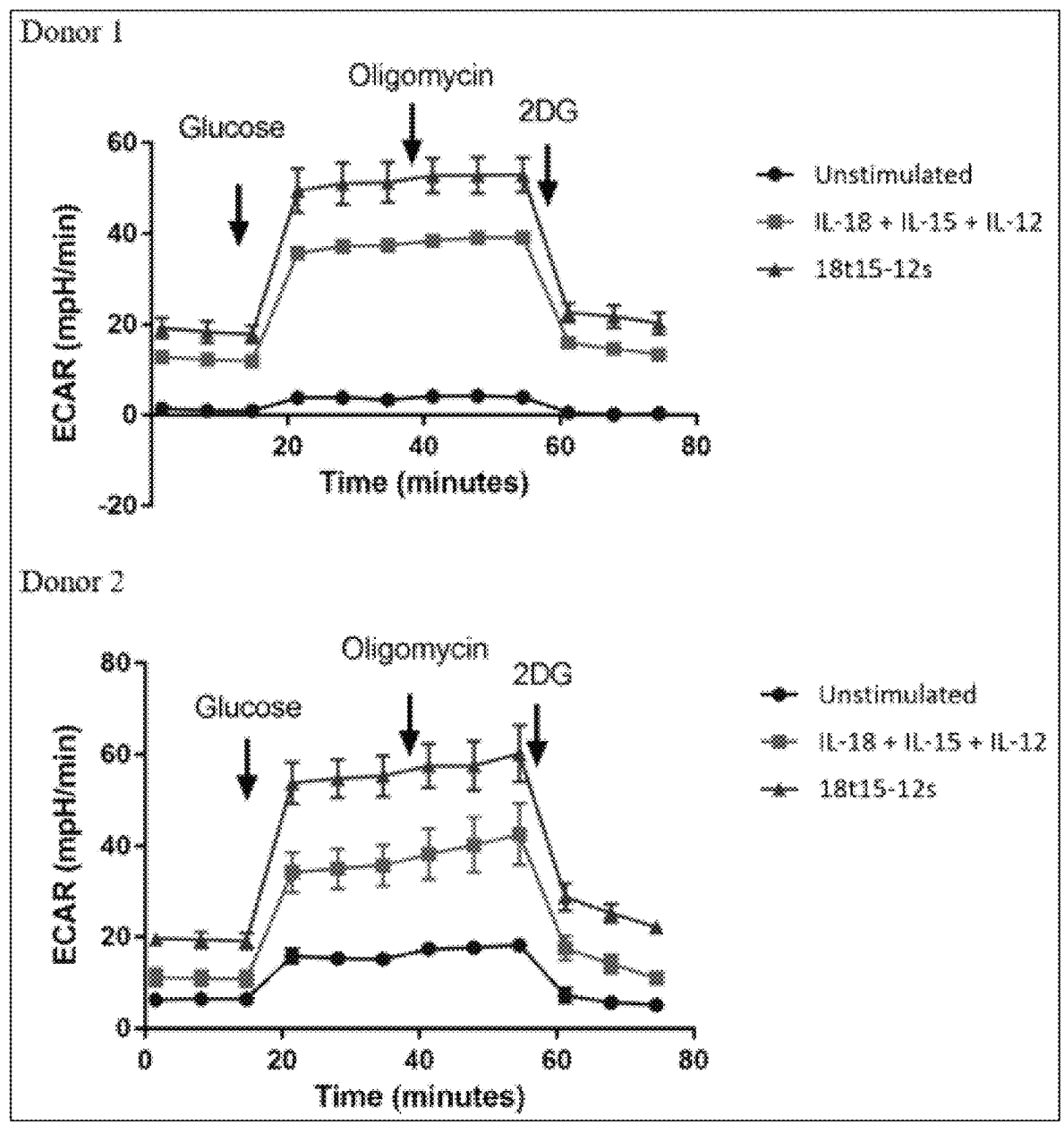
FIG. 57 shows the extracellular acidification rate (ECAR) in mPH/minute for human NK cells isolated from blood ($2 \times 10^6$ cells/mL) of two different donors.

The data show that the 18t15-12s results in significantly increased oxygen consumption rate (FIG. 56) and extracellular acidification rate (ECAR) as compared to the same cells activated with a combination of recombinant human IL-12, recombinant human IL-15, and recombinant human IL-18 (FIG. 57).

Example 49: 7t15-16s21 Fusion Protein Generation and Characterization

A fusion protein complex was generated comprising of anti-CD16scFv/IL-15RαSu/IL-21 and IL-7/TF/IL-15 fusion proteins. The human IL-7 and IL-21 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15.

The nucleic acid and protein sequences of a construct comprising IL-7 linked to the N-terminus of tissue factor 219 following with the N-terminus of IL-15 are shown below.

The nucleic acid sequence of the IL-7/TF/IL-15 construct (including signal peptide sequence) is as follows:

```
(Signal peptide)
ATGAAGTGGGTGACCTTCATCAGCCTGCTGTTCCTGTTCTCCAGCGCCTA

CTCC (Human IL-7)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC
```

```
TGCTGCAGGAGATCAAGACCTGCTGGAACAAGATCCTGATGGGCACCAAG

GAGCAT (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

The amino acid sequence of IL-7/TF/IL-15 fusion protein (including the leader sequence) is as follows:

```
(Signal peptide)
MKWVTFISLLFLFSSAYS (Human IL-7)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

Constructs were also made by linking the anti-CD16scFv sequence to the N-terminus coding region of IL-15RαSu chain followed by the N-terminus coding region of IL-21 which was synthesized by Genewiz. The nucleic acid and protein sequences of a construct comprising the anti-CD16scFv linked to the N-terminus of IL-15RαSu chain followed by the N-terminus coding region of IL-21 are shown below.

The nucleic acid sequence of the anti-CD16SscFv/IL-15 RαSu/IL-21 construct (including signal peptide sequence) is as follows:

```
(Signal peptide)
ATGAAGTGGGTGACCTTCATCAGCCTGCTGTTCCTGTTCTCCAGCGCCTA

CTCC ((Anti-human CD16scFv)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCATGGCGGCGGCGGCTCCGGAGGCGGCGG

CAGCGGCGGAGGAGGATCCGAGGTGCAGCTGGTGGAGTCCGGAGGAGGAG

TGGTGAGGCCTGGAGGCTCCCTGAGGCTGAGCTGTGCTGCCTCCGGCTTC

ACCTTCGACGACTACGGCATGTCCTGGGTGAGGCAGGCTCCTGGAAAGGG

CCTGGAGTGGGTGTCCGGCATCAACTGGAACGGCGGATCCACCGGCTACG

CCGATTCCGTGAAGGGCAGGTTCACCATCAGCAGGGACAACGCCAAGAAC

TCCCTGTACCTGCAGATGAACTCCCTGAGGGCCGAGGACACCGCCGTGTA

CTACTGCGCCAGGGGCAGGTCCCTGCTGTTCGACTACTGGGGACAGGGCA

CCCTGGTGACCGTGTCCAGG (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG (Human IL-21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG
```

-continued

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC

The amino acid sequence of the anti-CD16scFv/IL-15RαSu/IL-21 construct (including signal peptide sequence) is as follows:

(Signal peptide)
MKWVTFISLLFLFSSAYS (Anti-human CD16scFv)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGHGGGSGGGGSGGGGSEVQLVESGGGVVRPGGSLRLSCAASGF

TFDDYGMSWVRQAPGKGLEWVSGINWNGGSTGYADSVKGRFTISRDNAKN

SLYLQMNSLRAEDTAVYYCARGRSLLFDYWGQGTLVTVSR (Human IL-15R α sushi domain)
ITCPPPMSVEHADIWVKSYSLYSRERYICNSGFKRKAGTSSLTECVLNKA

TNVAHWTTPSLKCIR (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS

In some cases, the leader peptide is cleaved from the intact polypeptide to generate the mature form that may be soluble or secreted.

Figure 58:
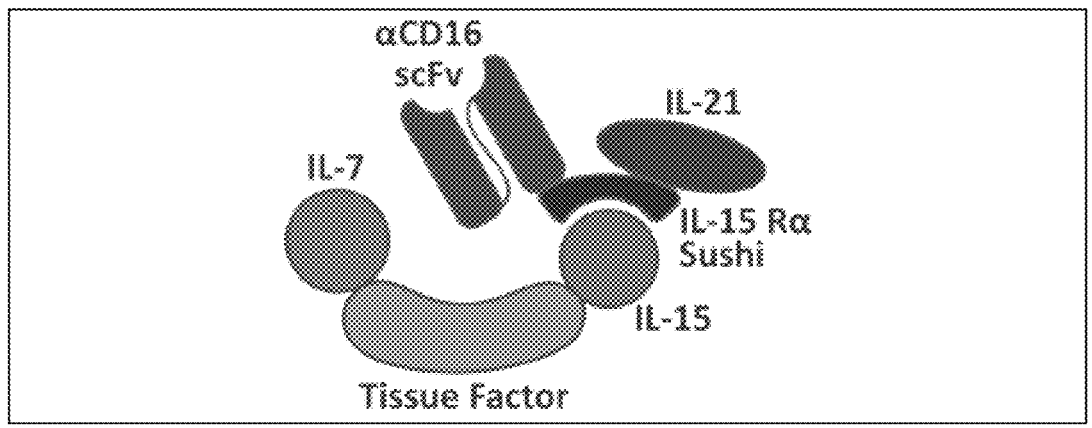
FIG. 58 shows a schematic of the 7t15-16s21 construct.
Figure 59:
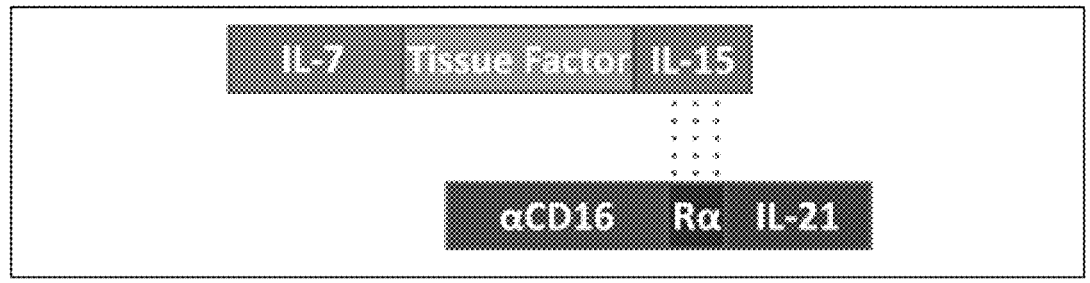
FIG. 59 shows an additional schematic of the 7t15-16s21 construct.

The anti-CD16scFv/IL-15RαSu/IL-21 and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15:anti-CD16scFv/IL-15RαSu/IL-21 protein complex (referred to as 7t15-16s21; FIG. 58 and FIG. 59), which can be purified by anti-TF IgG1-based affinity and other chromatography methods.

Binding of 7t15-16s21 to CHO Cells Expressing Human CD16b

Figure 60A:
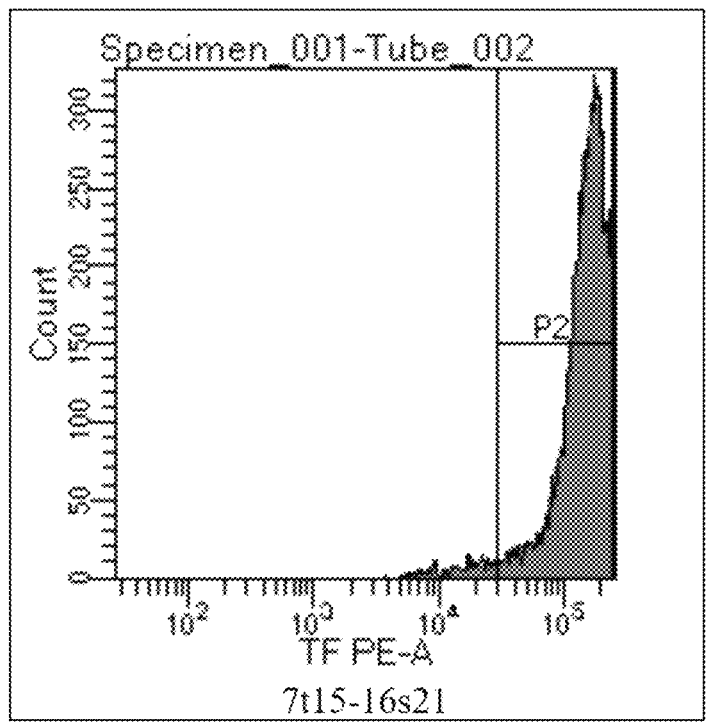
FIGS. 60A and 60B show binding of 7t15-16s21 to CHO cells expressing human CD16b as compared to a control protein.
Figure 60B:
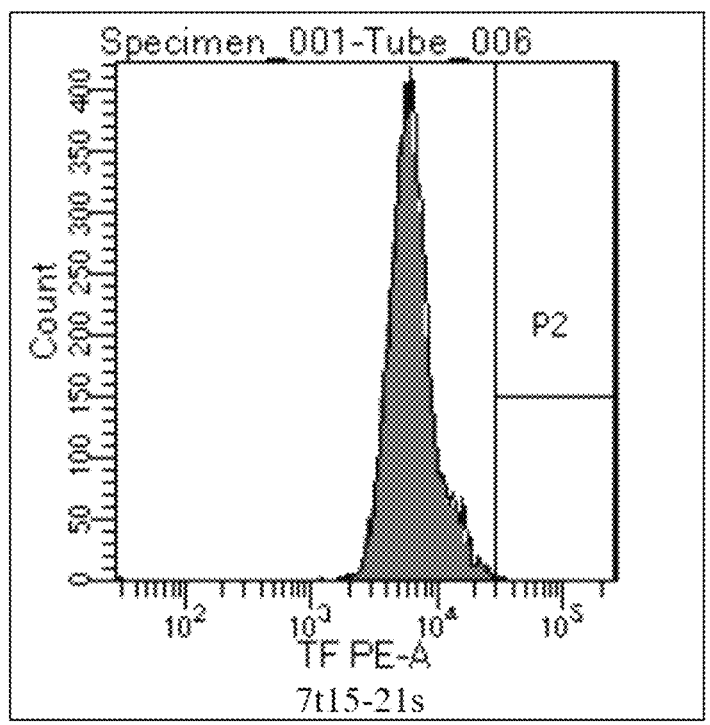

CHO cells were transfected with human CD16b in a pMC plasmid and selected with 10 μg/mL of blasticidin for 10 days. The CHO cells stably expressing CD16b were stained with 1.2 μg/mL of 7t15-16s21, containing anti-human CD16 scFv or 18t15-12s, which does not contain anti-human CD16 scFv, as a negative control, and then stained with biotinylated anti-human tissue factor Ab and PE conjugated streptavidin. Only anti-human CD16scFv containing 7t15-16s21 stained the cells as shown in FIG. 60A. 18t15-12s did not stain the CHO cells expressing human CD16b as showed in FIG. 60B.

Detection of IL-15, IL-21, and IL-7 in 7t15-16s21 Using ELISA

Figure 61A:
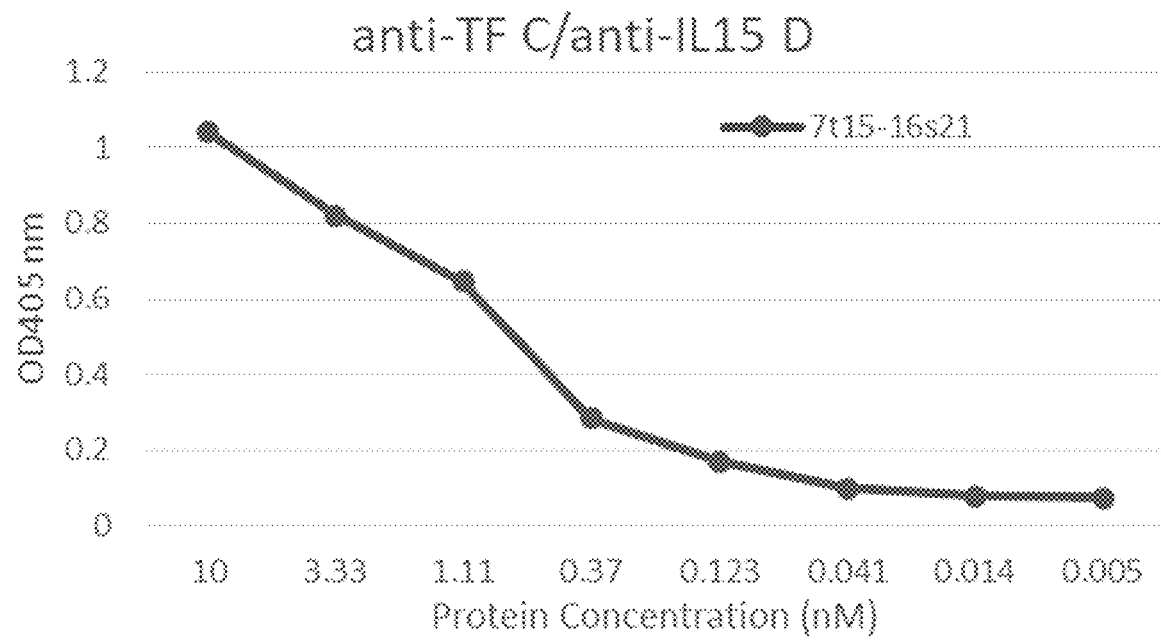
FIGS. 61A-61C are results from ELISA experiments using antibodies against IL-15, IL-21, and IL-7 in detecting 7t15-16s21.
Figure 61B:
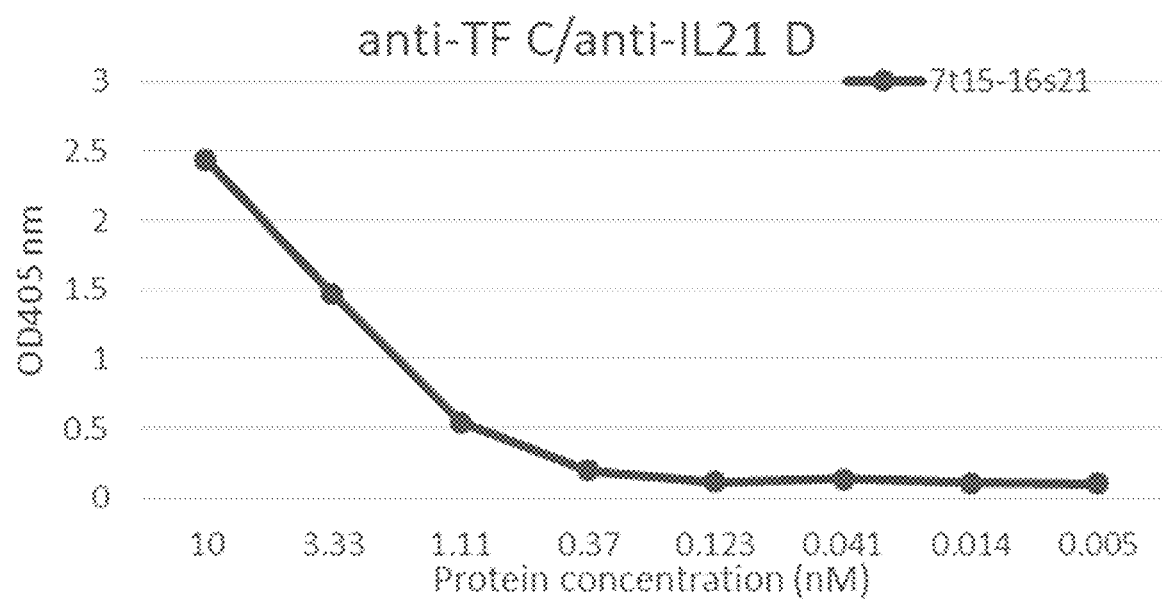
Figure 61C:
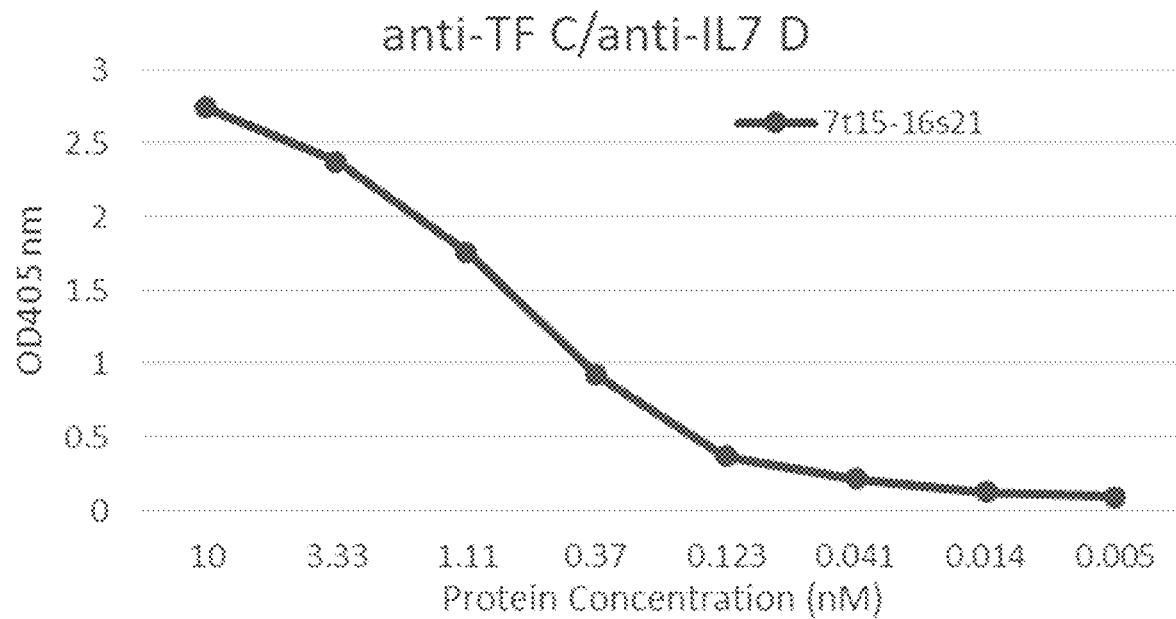

A 96-well plate was coated with 100 μL (8 μg/mL) of anti-TF IgG1 in R5 (coating buffer) and incubated at room temperature (RT) for 2 hrs. The plates were washed 3 times and blocked with 100 μL of 1% BSA in PBS. Serial dilution of 7t15-16s21 (at a 1:3 ratio) were added to the wells, and incubated at RT for 60 min. Following 3 washes, 50 ng/mL of biotinylated-anti-IL15 antibody (BAM247, R&D Systems), 500 ng/mL of biotinylated-anti-IL-21 antibody (13-7218-81, R&D Systems), or 500 ng/mL of biotinylated-anti-IL-7 antibody (506602, R&D Systems) was added to the wells and incubated at RT for 60 min. The plate was washed 3 times, and incubated with 0.25 μg/mL of HRP-SA (Jackson ImmunoResearch) at 100 μL per well for 30 min at RT, followed by 4 washes and incubation with 100 μl of ABTS for 2 mins at RT. Absorbance was read at 405 nm. As shown in FIGS. 61A-61C, the IL-15, IL-21, and IL-7 domains in 7t15-16s21 were detected by the individual antibodies.

Figure 62:
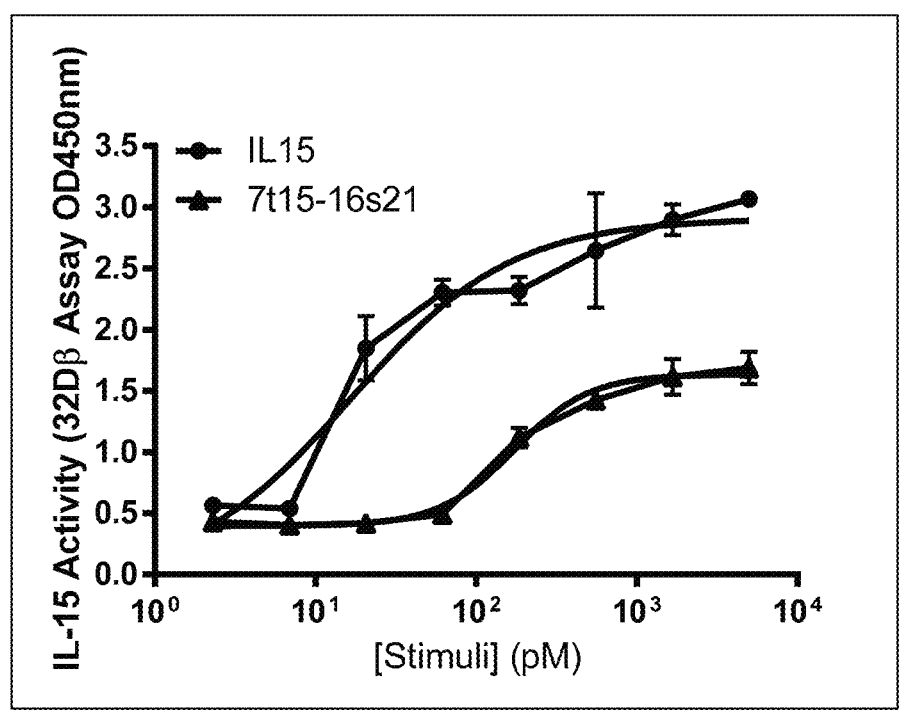
FIG. 62 shows results of the 32Dβ cell proliferation assay with 7t15-16s21 or recombinant IL-15.

The IL-15 in 7t15-16s21 Promotes IL-2R/3 and Common γ Chain Containing 32D/3 Cell Proliferation To analyze the activity of IL-15 in 7t15-16s21, the IL-15 activity of 7t15-16s21 was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted 7t15-16s21 or IL-15 were added to the cells (FIG. 62). Cells were incubated in a $CO_2$ incubator at 37° C. for 3 days. Cell proliferation was detected by adding 10 μl of WST1 to each well on day 3 and incubating for an additional 3 hours in a $CO_2$ incubator at 37° C. The absorbance at 450 nm was measured by analyzing the amount of formazan dye produced. As shown in FIG. 62, 7t15-16s21 and IL-15 promoted 32Dβ cell proliferation, with the $EC_{50}$ of 7t15-16s21 and IL-15 being 172.2 pM and 16.63 pM, respectively.

Figure 63:
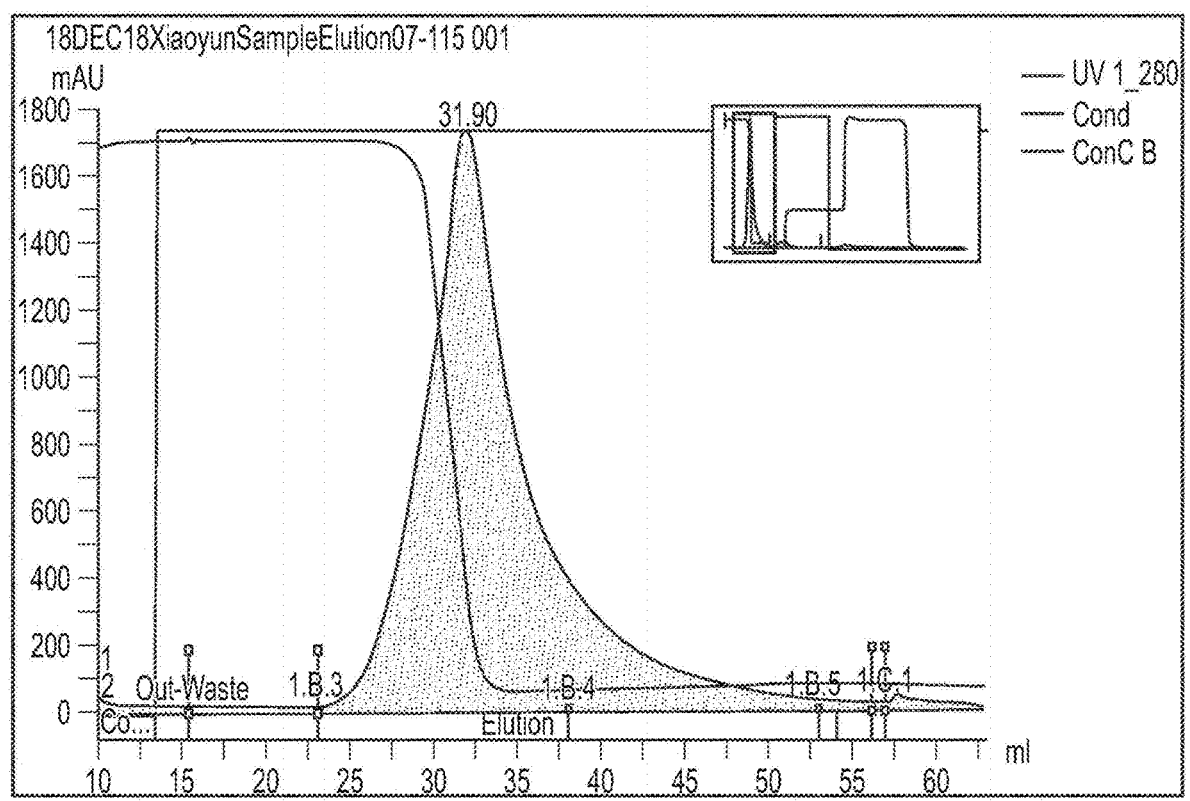
FIG. 63 shows the chromatographic profile of 7t15-16s21 protein containing cell culture supernatant following binding and elution on anti-TF antibody resin.

Purification Elution Chromatograph of 7t15-16s21 from Anti-TF Antibody Affinity Column 7t15-16s21 harvested from cell culture was loaded onto the anti-TF antibody affinity column equilibrated with 5 column volumes of PBS. The column was then washed with 5 column volumes of PBS, followed by elution with 6 column volumes of 0.1M acetic acid (pH 2.9). A280 elution peak was collected and neutralized to pH 7.5-8.0 with 1M Tris base. The neutralized sample was buffer exchanged into PBS using Amicon centrifugal filters with a 30 KDa molecular weight cutoff. FIG. 63 is a line graph showing the chromatographic profile of 7t15-16s21 protein containing cell culture supernatant following binding and elution on anti-TF antibody resin. As shown in FIG. 63, the anti-TF antibody affinity column bound 7t15-16s21 which contains TF. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of 7t15-16s21

Figure 64:
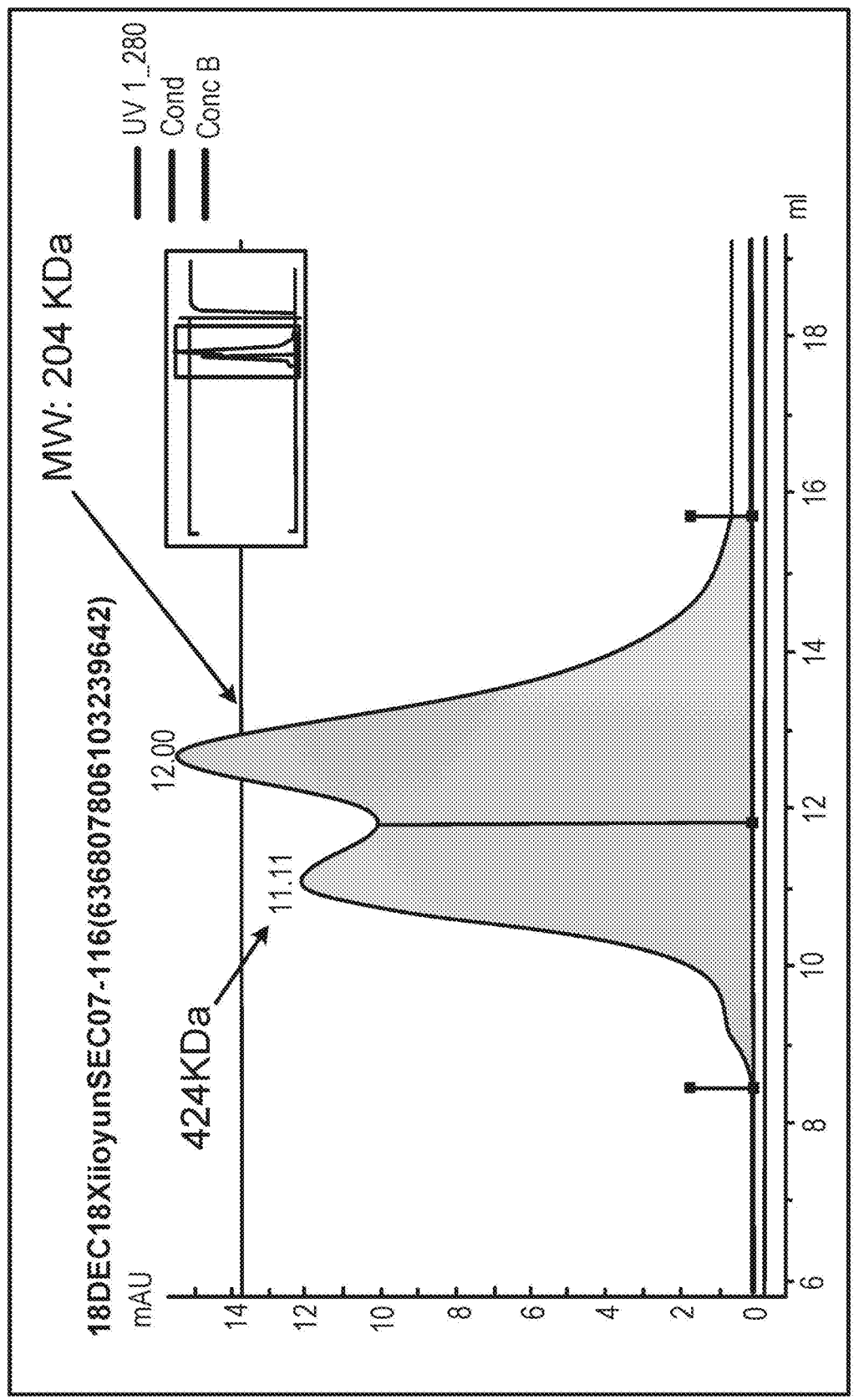
FIG. 64 shows the analytical SEC Profile of 7t15-16s21.

To perform size exclusion chromatography (SEC) analysis for 7t15-16s21, a Superdex 200 Increase 10/300 GL gel filtration column (GE Healthcare) connected to an AKTA Avant system (GE Healthcare) was used. The column was equilibrated with 2 column volumes of PBS. The flow rate was 0.7 mL/min. A sample containing 7t15-16s21 in PBS was injected into the Superdex 200 column using a capillary loop, and analyzed by SEC. As shown in FIG. 64, the SEC results showed two protein peaks for 7t15-16s21.

Example 50: TGFRt15-16s21 Fusion Protein Generation and Characterization

Figure 65:
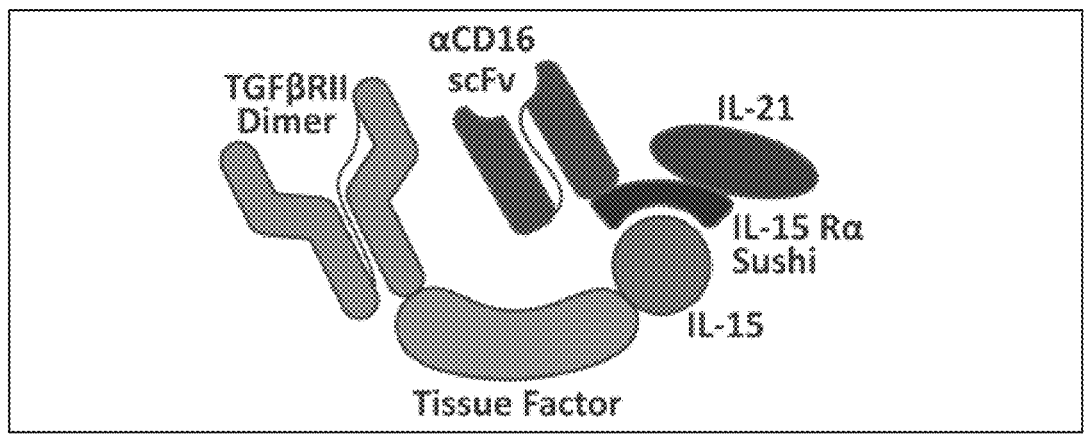
FIG. 65 shows a schematic of the TGFRt15-16s21 construct.
Figure 66:
FIG. 66 shows an additional schematic of the TGFRt15-16s21 construct.

A fusion protein complex was generated comprising anti-human CD16scFv/IL-15RαSu/IL21 and TGFβ Receptor II/TF/IL-15 fusion proteins (FIGS. 65 and 66). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G45(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

```
(Signal peptide)
ATGAAGTGGGTGACCTTCATCAGCCTGCTGTTCCTGTTCTCCAGCGCCTA

CTCC (Two Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

The amino acid sequence of TGFβ Receptor II/TF/IL-15 fusion protein (including the leader sequence) is as follows:

```
(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

Constructs were also made by attaching anti-human CD16scFv directly linking to the N-terminus coding region of IL-15RαSu chain followed by the N-terminus coding region of IL-21 which was synthesized by Genewiz. The nucleic acid and protein sequences of a construct comprising the anti-human CD16scFv linked to the N-terminus of IL-15RαSu followed by the N-terminus coding region of IL-21 are shown below.

The nucleic acid sequence of the anti-CD16scFv/IL-15 RαSu/IL-21 construct (including signal peptide sequence) is as follows:

(Signal peptide)
ATGAAGTGGGTGACCTTCATCAGCCTGCTGTTCCTGTTCTCCAGCGCCTA

CTCC (Anti-human CD16scFv)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCATGGCGGCGGCGGCTCCGGAGGCGGCGG

CAGCGGCGGAGGAGGATCCGAGGTGCAGCTGGTGGAGTCCGGAGGAGGAG

TGGTGAGGCCTGGAGGCTCCCTGAGGCTGAGCTGTGCTGCCTCCGGCTTC

ACCTTCGACGACTACGGCATGTCCTGGGTGAGGCAGGCTCCTGGAAAGGG

CCTGGAGTGGGTGTCCGGCATCAACTGGAACGGCGGATCCACCGGCTACG

CCGATTCCGTGAAGGGCAGGTTCACCATCAGCAGGGACAACGCCAAGAAC

TCCCTGTACCTGCAGATGAACTCCCTGAGGGCCGAGGACACCGCCGTGTA

CTACTGCGCCAGGGGCAGGTCCCTGCTGTTCGACTACTGGGGACAGGGCA

CCCTGGTGACCGTGTCCAGG (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG (Human IL-21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCGAGGACTCC

The amino acid sequence of the anti-CD16scFv/IL-15RαSu/IL-21 construct (including signal peptide sequence) is as follows:

(Signal peptide)
MKWVTFISLLFLFSSAYS (Anti-human CD16scFv)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGHGGGGSGGGGSGGGGSEVQLVESGGGVVRPGGSLRLSCAASGF

TFDDYGMSWVRQAPGKGLEWVSGINWNGGSTGYADSVKGRFTISRDNAKN

SLYLQMNSLRAEDTAVYYCARGRSLLFDYWGQGTLVTVSR (Human IL-15R α sushi domain)
ITCPPPMSVEHADIWVKSYSLYSRERYICNSGFKRKAGTSSLTECVLNKA

TNVAHWTTPSLKCIR (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS

In some cases, the leader peptide is cleaved from the intact polypeptide to generate the mature form that may be soluble or secreted.

The anti-CD16scFv/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:CD16scFv/IL-15RαSu/IL-21 protein complex (referred to as TGFRt15-16s21), which can be purified by anti-TF IgG1-based affinity and other chromatography methods.

Interaction Between TGFRt15-16s21 and CHO Cells Expressing Human CD16b

Figure 67A:
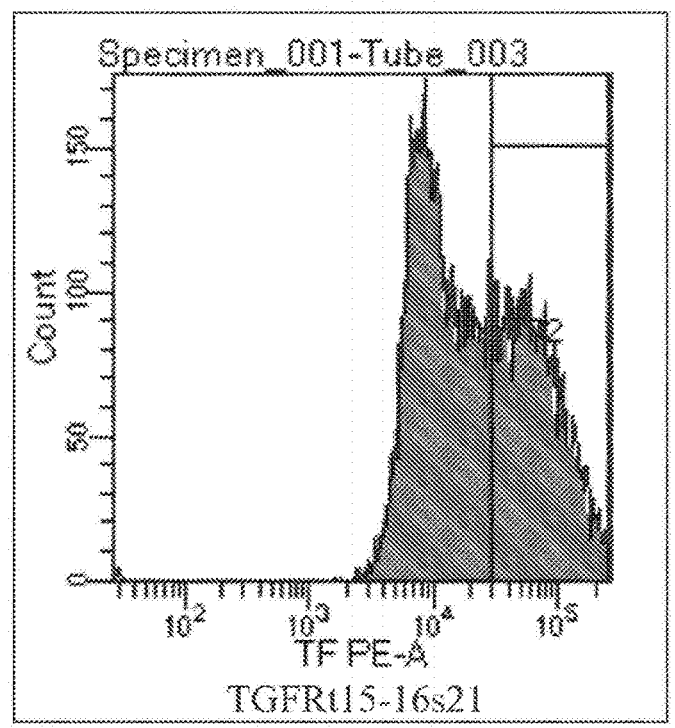
FIGS. 67A and 67B show binding affinity of TGFRt15-16521 and 7t15-21s with CHO cells expressing human CD16b.
Figure 67B:
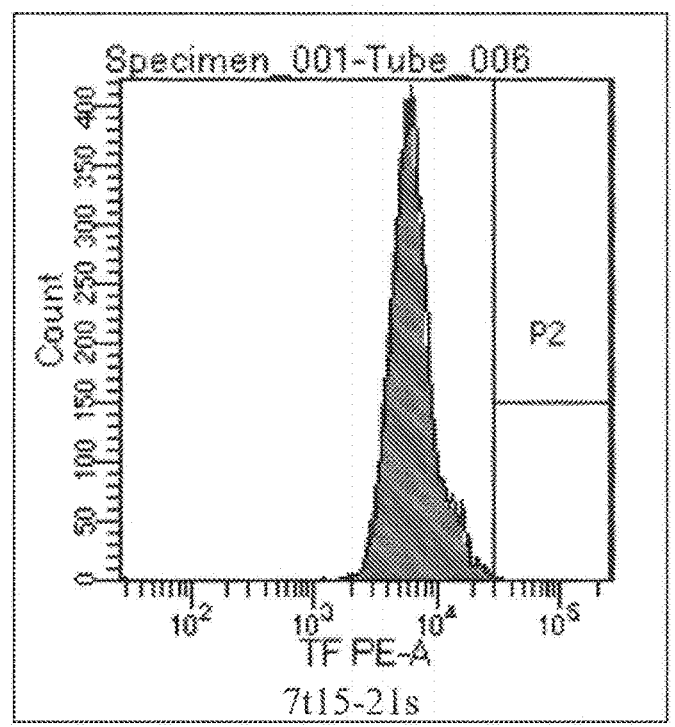

CHO cells were transfected with human CD16b in a pMC plasmid and selected with 10 μg/mL of blasticidin for 10 days. Cells stably expressing CD16b were stained with 1.2 μg/mL of TGFRt15-16s21, containing anti-human CD16 scFv, or 7t15-21s, not containing anti-human CD16 scFv, as a negative control, and with biotinylated anti-human tissue factor antibody and PE conjugated streptavidin. As shown in FIGS. 67A and 67B, TGFRt15-16s21, which contains anti-human CD16scFv, showed positive binding, while 7t15-21s did not show binding.

Effect of TGFRt15-16s21 on TGF/31 Activity in HEK-Blue TGFβ Cells

To evaluate the activity of TGFβRII in TGFRt15-16s21, the effect of TGFRt15-16s21 on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5 \times 10^5$ cells/mL. In a flat-bottom 96-well plate, 50 μl cells were added to each well ($2.5 \times 10^4$ cells/well) and followed with 50 μL 0.1 nM TGFβ1 (R&D systems). TGFRt15-16s21 or TGFR-Fc (R&D Systems) prepared at a 1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. The $IC_{50}$ of each protein sample was calculated with GraphPad Prism 7.04. The $IC_{50}$ of TGFRt15-16s21 and TGFR-Fc were 9127 pM and 460.6 pM respectively. These results showed that the TGFβRII domain in TGFRt15-16s21 was able to block the activity of TGFβ-1 in HEK-Blue TGFβ cells.

Figure 68:
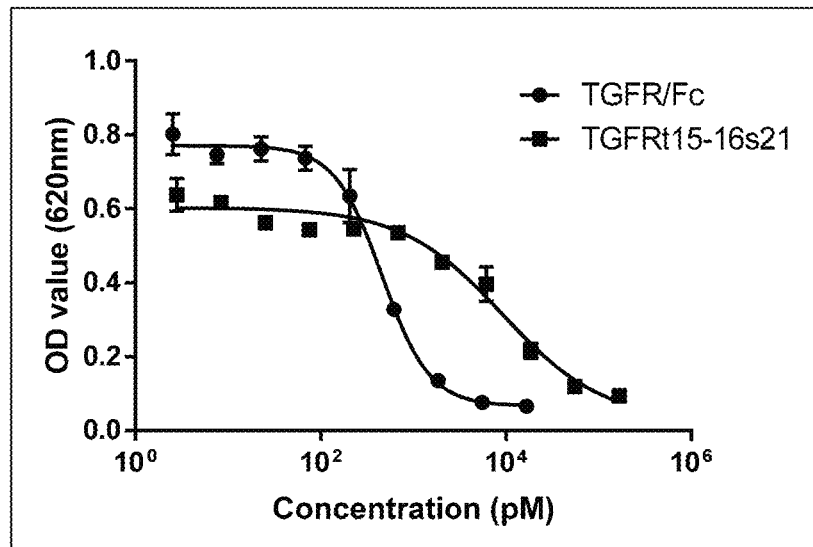
FIG. 68 shows results of TGFβ1 inhibition by TGFRt15-16s21 and TGFR-Fc.

The IL-15 in TGFRt15-16s21 Promotes IL-2Rβ and Common γ Chain Containing 32Dβ Cell Proliferation To analyze the activity of IL-15 in TGFRt15-16s21, the IL-15 activity of TGFRt15-16s21 was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-16s21 or IL-15 were added to the cells (FIG. 68). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The absorbance at 450 nm was measured by analyzing the amount of formazan dye produced. As shown in FIG. 68, TGFRt15-16s21 and IL-15 promoted 32Dβ cell proliferation, with the $EC_{50}$ of TGFRt15-46s21 and IL-15 being 51298 pM and 10.63 pM, respectively.

Detection of IL-15, IL-21, and TGFβRII in TGFRt15-16s21 Using ELISA

Figure 69:
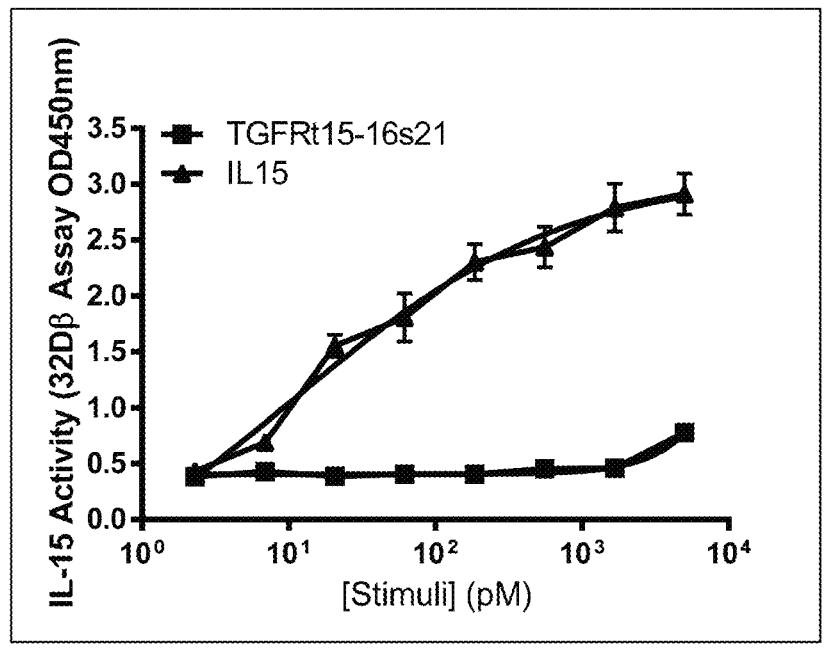
FIG. 69 shows results of 32Dβ cell proliferation assay with TGFRt15-16s21 or recombinant IL-15.
Figure 70A:
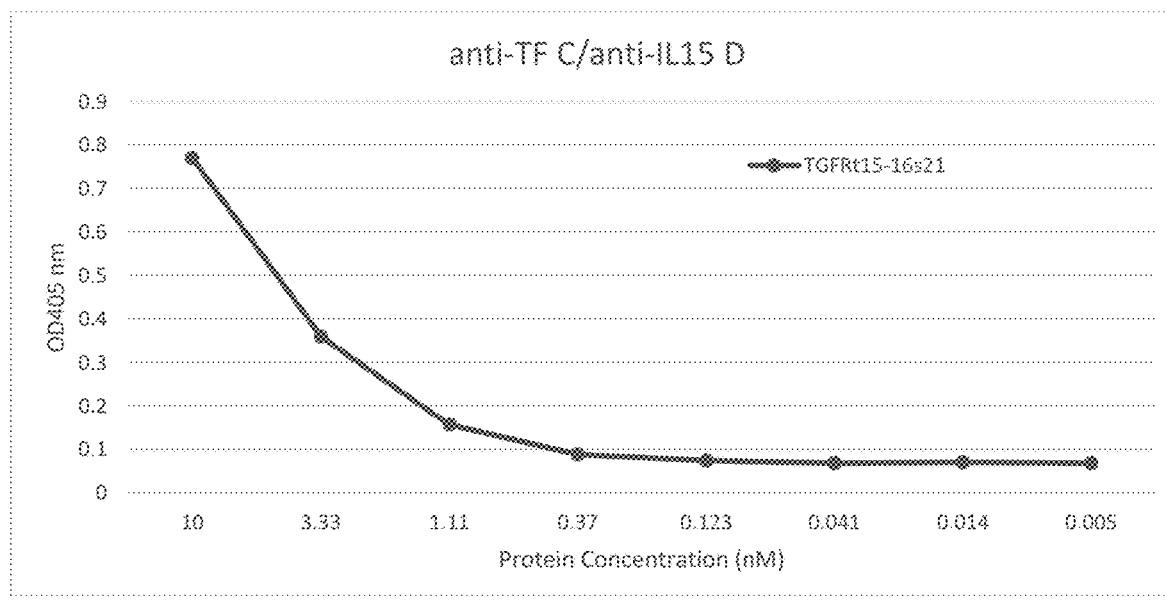
FIGS. 70A-70C show results of detecting IL-15, IL-21, and TGFβRII in TGFRt15-16s21 with corresponding antibodies using ELISA.
Figure 70B:
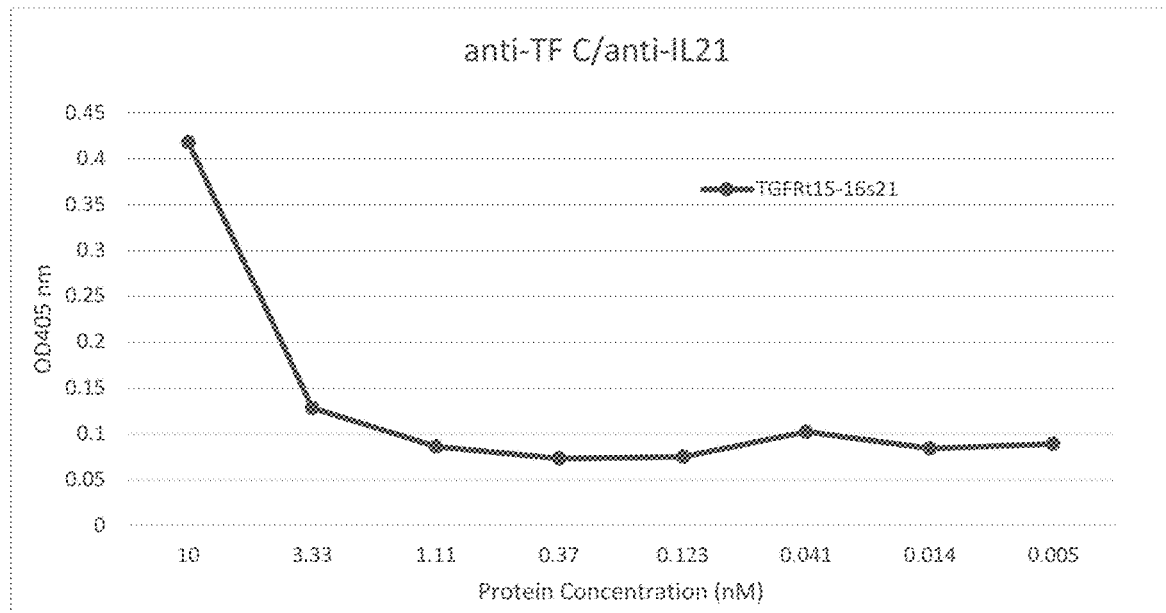
Figure 70C:
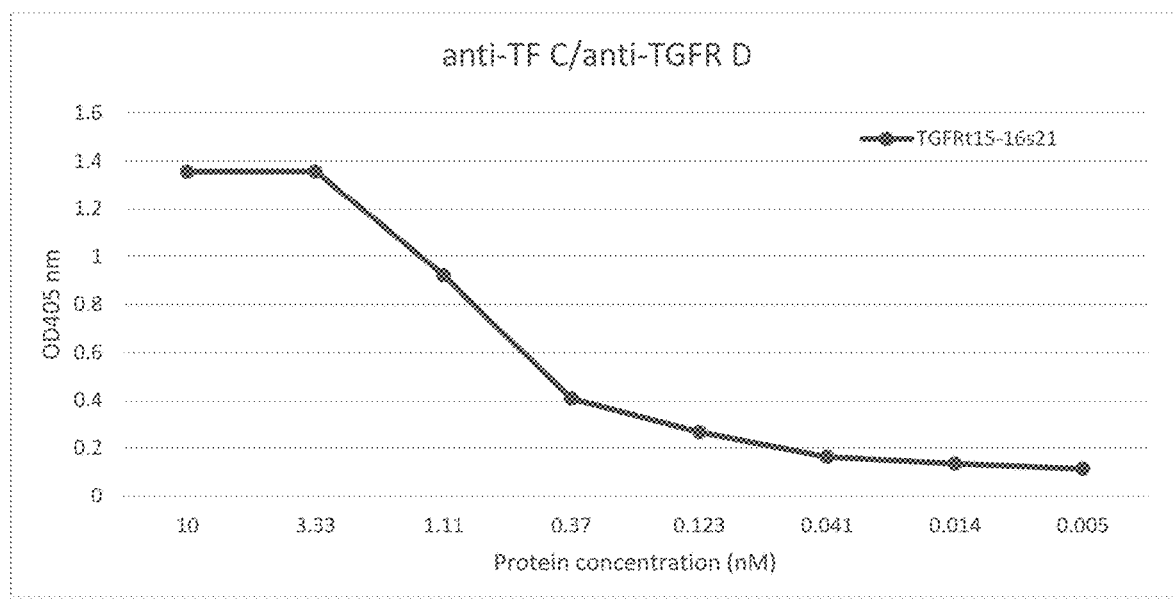

A 96-well plate was coated with 100 μL (8 μg/mL) of anti-TF IgG1 in R5 (coating buffer) and incubated at room temperature (RT) for 2 hrs. The plates were washed 3 times and blocked with 100 μL of 1% BSA in PBS. TGFRt15-16s21 serially diluted at a 1:3 ratio was added and incubated at RT for 60 min. Following three washes, 50 ng/mL of biotinylated-anti-IL-15 antibody (BAM247, R&D Systems), 500 ng/mL of biotinylated-anti-IL-21 antibody (13-7218-81, R&D Systems), or 200 ng/mL of biotinylated-anti-TGFβRII antibody (BAF241, R&D Systems) was applied per well, and incubated at RT for 60 min. Following three washes, incubation with 0.25 μg/mL of HRP-SA (Jackson ImmunoResearch at 100 μL per well for 30 min at RT was carried out, followed by 4 washes and incubation with 100 μL of ABTS for 2 mins at RT. Absorbance was read at 405 nm. The data are shown in FIG. 69. As shown in FIGS. 70A-70C, the IL-15, IL-21, and TGFβRII domains in TGFRt15-16s21 were detected by the respective antibodies.

Figure 71:
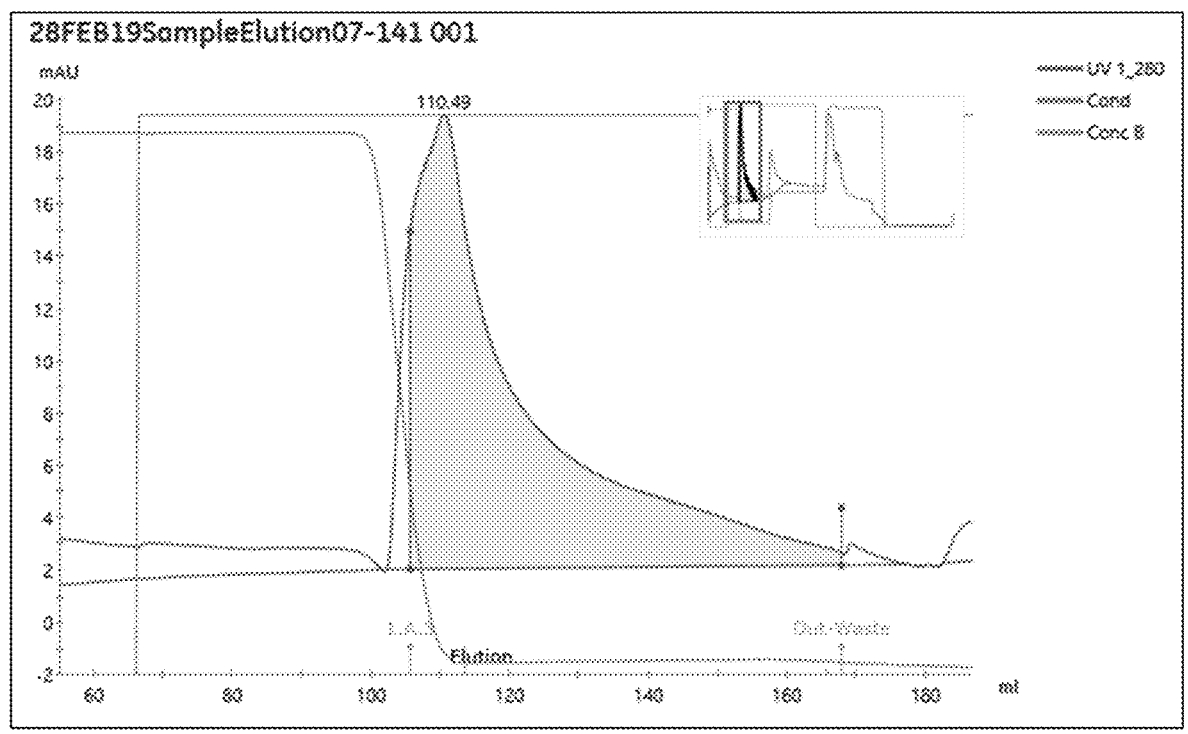
FIG. 71 shows the chromatographic profile of TGFRt15-16s21 protein containing cell culture supernatant following binding and elution on anti-TF antibody resin.

Purification Elution Chromatograph of TGFRt15-16s21 Using Anti-TF Antibody Affinity Column TGFRt15-16s21 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 71, the anti-TF antibody affinity column bound to TGFRt15-16s21, which contains tissue factor as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE of TGFRt15-16s21

To determine the purity and molecular weight of the TGFRt15-16s21 protein, protein sample purified with anti-TF antibody affinity column was analyzed by sodium dodecyl sulfate polyacrylamide gel (4-12% NuPage Bis-Tris gel) electrophoresis (SDS-PAGE) under reduced condition. After electrophoresis, the gel was stained with InstantBlue for about 30 min, followed by destaining overnight in purified water.

Figure 72:
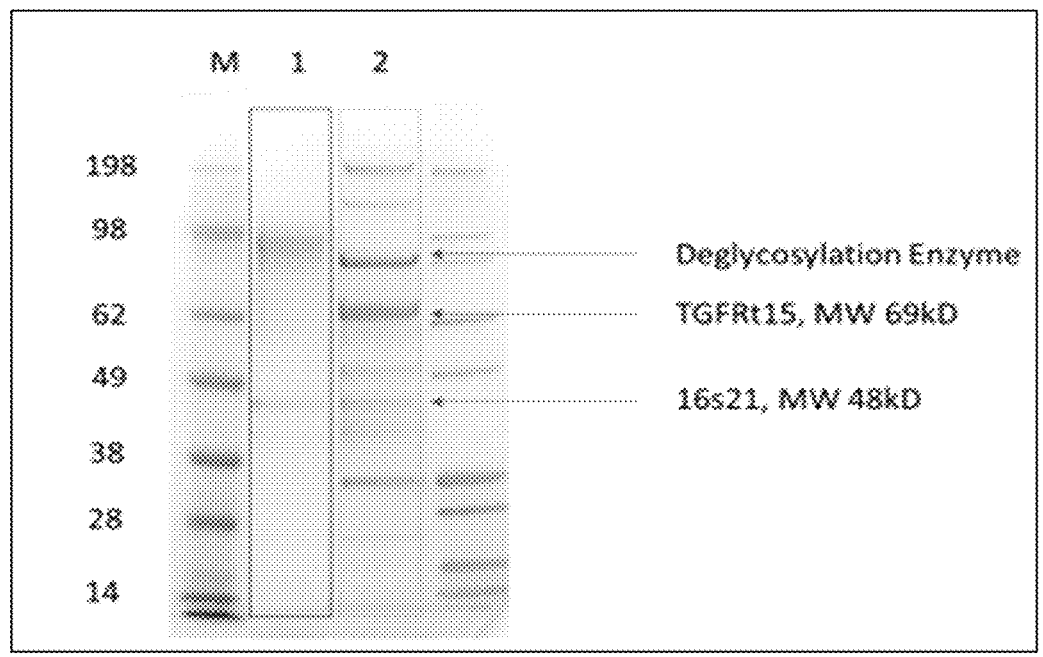
FIG. 72 shows results of a reduced SDS-PAGE analysis of TGFRt15-16s21.

To verify that the TGFRt15-16s21 protein undergoes glycosylation after translation in CHO cells, a deglycosylation experiment was conducted using the Protein Deglycosylation Mix II kit from New England Biolabs according to the manufacturer's instructions. FIG. 72 shows results from the reduced SDS-PAGE analysis of the sample in non-deglycosylated (lane 1 in red outline) and deglycosylated (lane 2 in yellow outline) state. The results showed that the TGFRt15-16s21 protein is glycosylated when expressed in CHO cells. After deglycosylation, the purified sample showed expected molecular weights (69 kDa and 48 kDa) in the reduced SDS gel. Lane M was loaded with 10 μL of SeeBlue Plus2 Prestained Standard.

Example 51: 7t15-7s Fusion Protein Generation and Characterization

Figure 73:
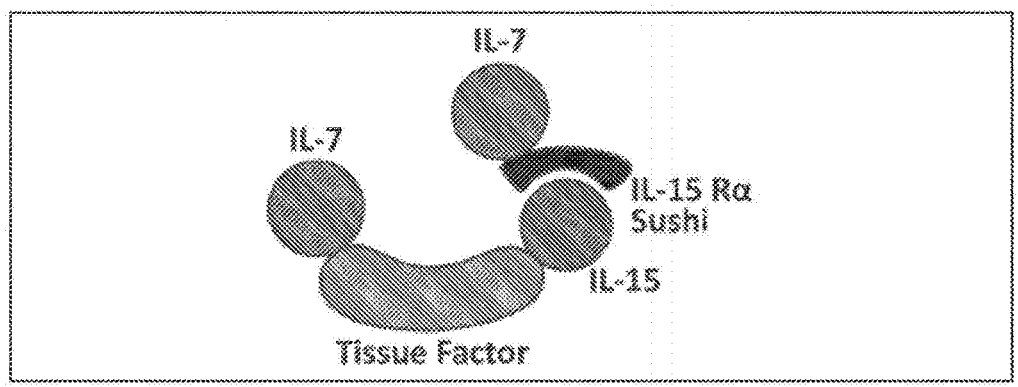
FIG. 73 shows a schematic of the 7t15-7s construct.
Figure 74:
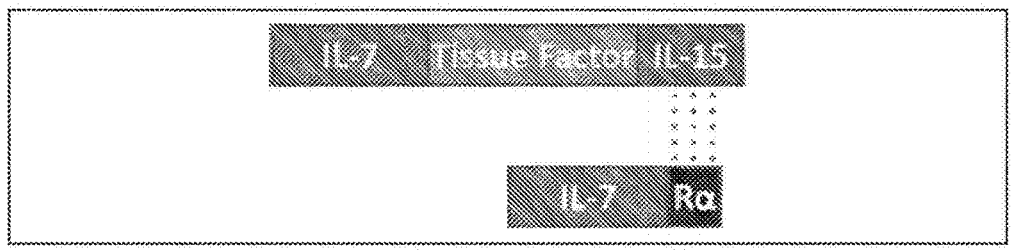
FIG. 74 shows an additional schematic of the 7t15-7s construct.

A fusion protein complex was generated comprising IL-7/TF/IL-15 and IL-7/IL-15RαSu fusion proteins (FIG. 73 and FIG. 74). The human IL-7, tissue factor 219, and IL-15 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15.

The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as follows:

(Signal peptide)
ATGAAGTGGGTGACCTTCATCAGCCTGCTGTTCCTGTTCTCCAGCGCCTA

CTCC (Human IL7)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of 7t15 fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Constructs were also made by linking the IL-7 sequence to the N-terminus coding region of IL-15RαSu chain which was synthesized by Genewiz. The nucleic acid and protein sequences of a construct comprising the IL-7 linked to the N-terminus of IL-15RαSu chain are shown below.

The nucleic acid sequence of 7s construct (including signal peptide sequence) is as follows:

(Signal peptide)
ATGGGAGTGAAAGTTCTTTTTGCCCTTATTTGTATTGCTGTGGCCGAGGC

C (Human IL7)
GATTGTGATATTGAAGGTAAAGATGGCAAACAATATGAGAGTGTTCTAAT

GGTCAGCATCGATCAATTATTGGACAGCATGAAAGAAATTGGTAGCAATT

GCCTGAATAATGAATTTAACTTTTTTAAAAGACATATCTGTGATGCTAAT

AAGGAAGGTATGTTTTTATTCCGTGCTGCTCGCAAGTTGAGGCAATTTCT

TAAAATGAATAGCACTGGTGATTTTGATCTCCACTTATTAAAAGTTTCAG

AAGGCACAACAATACTGTTGAACTGCACTGGCCAGGTTAAAGGAAGAAAA

CCAGCTGCCCTGGGTGAAGCCCAACCAACAAAGAGTTTGGAAGAAAATAA

ATCTTTAAAGGAACAGAAAAAACTGAATGACTTGTGTTTCCTAAAGAGAC

TATTACAAGAGATAAAAACTTGTTGGAATAAAATTTTGATGGGCACTAAA

GAACAC (Human IL-15R α sushi domain)
ATCACGTGCCCTCCCCCCATGTCCGTGGAACACGCAGACATCTGGGTCAA

GAGCTACAGCTTGTACTCCAGGGAGCGGTACATTTGTAACTCTGGTTTCA

AGCGTAAAGCCGGCACGTCCAGCCTGACGGAGTGCGTGTTGAACAAGGCC

ACGAATGTCGCCCACTGGACAACCCCCAGTCTCAAATGCATTAGA

The amino acid sequence of 7s fusion protein (including the leader sequence) is as follows:

(Signal peptide)
MGVKVLFALICIAVAEA (Human IL7)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human IL-15R α sushi domain)
ITCPPPMSVEHADIWVKSYSLYSRERYICNSGFKRKAGTSSLTECVLNKA

TNVAHWTTPSLKCIR

Figure 75:
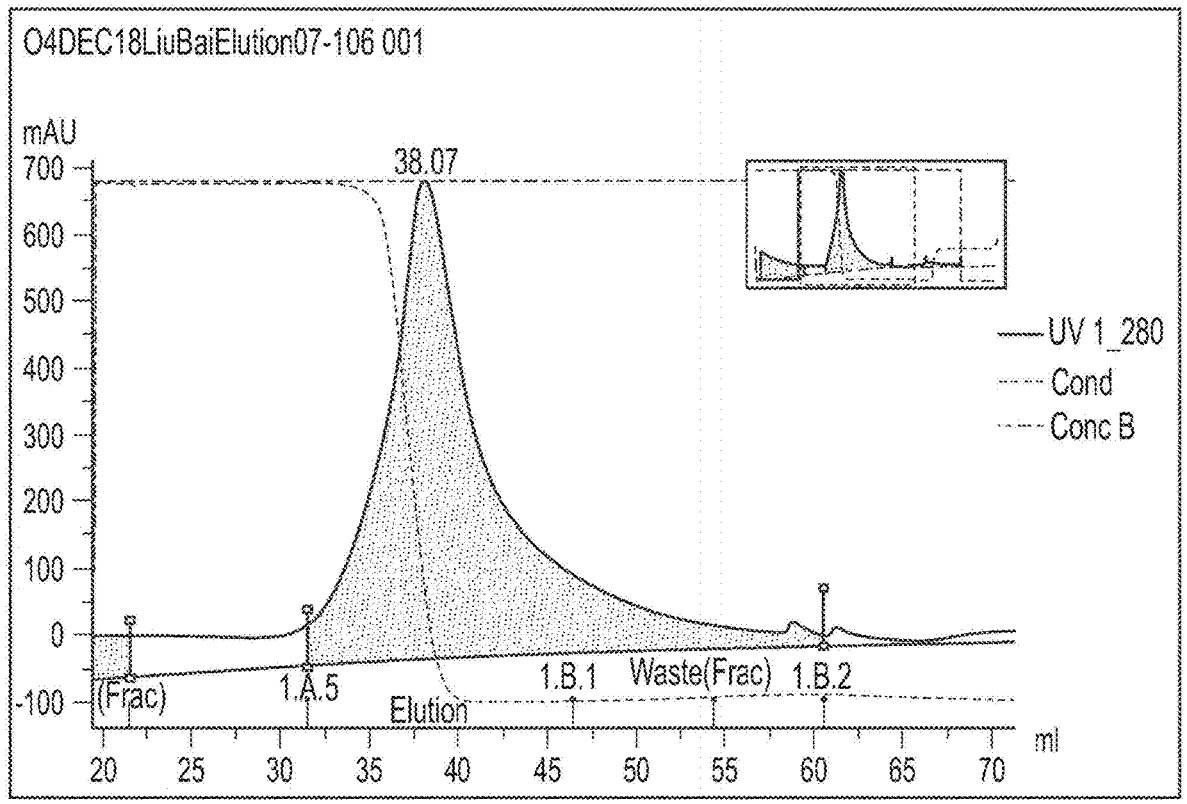
FIG. 75 shows the chromatographic profile of 7t15-7s protein containing cell culture supernatant following binding and elution on anti-TF antibody resin.

The IL-7/TF/IL-15 and IL-7/IL-15RαSu constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15:IL-7/IL-15RαSu protein complex referred to as 7t15-7s, which can be purified by anti-TF IgG1 affinity and other chromatography methods. Purification Elution Chromatograph of 7t15-7s Using Anti-TF Antibody Affinity Column 7t15-7s harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 75, the anti-TF antibody affinity column bound to 7t15-7s which contains tissue factor (TF) as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except the elution step, which was 2 mL/min.

Immunostimulation of 7t15-7s in C57BL/6 Mice

7t15-7s is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of human IL-7 and sushi domain of human IL-15 receptor alpha chain (7s).

Figure 76:
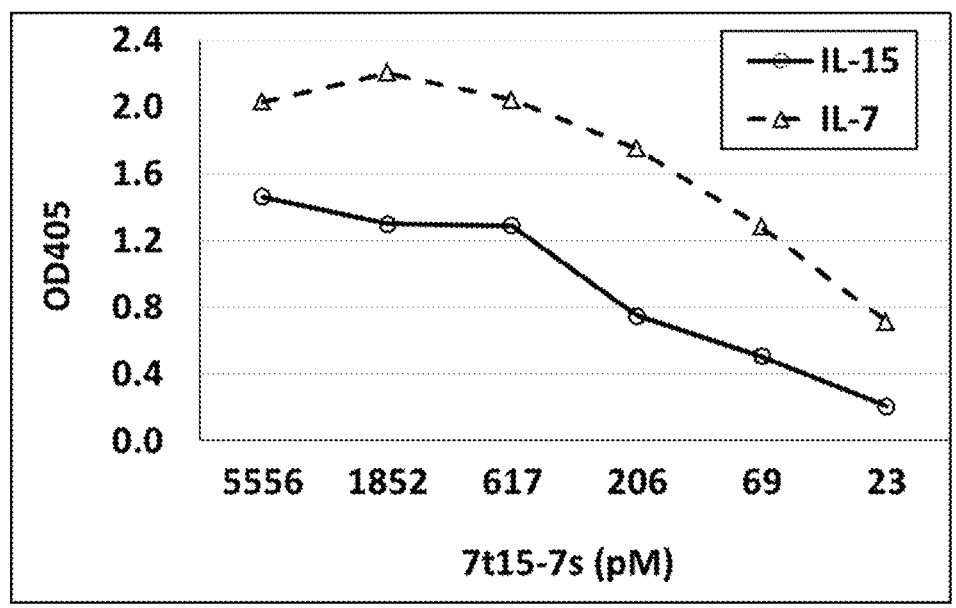
FIG. 76 shows detection of TF, IL-15 and IL-7 in 7t15-7s using ELISA.

CHO cells were co-transfected with the IL7-TF-IL15 (7t15) and IL7-IL15Rα sushi domain (7s) vectors. The 7t15-7s complex was purified from the transfected CHO cell culture supernatant. The IL-7, IL-15 and tissue factor (TF) components were demonstrated in the complex by ELISA as shown in FIG. 76. A humanized anti-TF monoclonal antibody (anti-TF IgG1) was used as the capture antibody to determine TF in 7t15-7s, and biotinylated anti-human IL-15 antibody (R&D systems) and biotinylated anti-human IL-7 antibody (R&D Systems) were used as the detection antibodies to respectively detect IL-15 and IL-7 in 7t15-7s, followed by peroxidase conjugated streptavidin (Jackson ImmunoResearch Lab) and ABTS substrate (Surmodics IVD, Inc.).

Example 52: TGFRt15-TGFRs Fusion Protein Generation and Characterization

Figure 77:
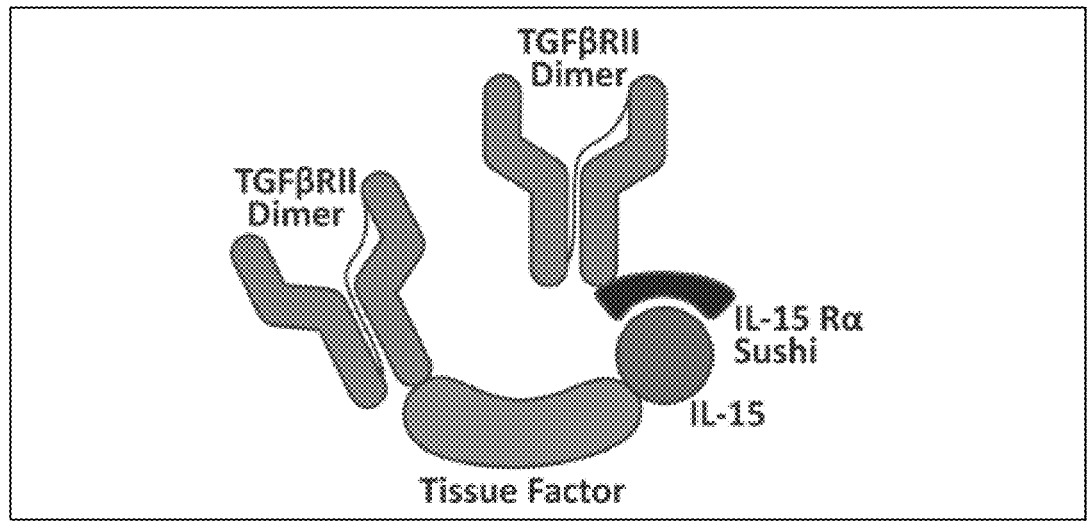
FIG. 77 shows a schematic of the TGFRt15-TGFRs construct.
Figure 78:
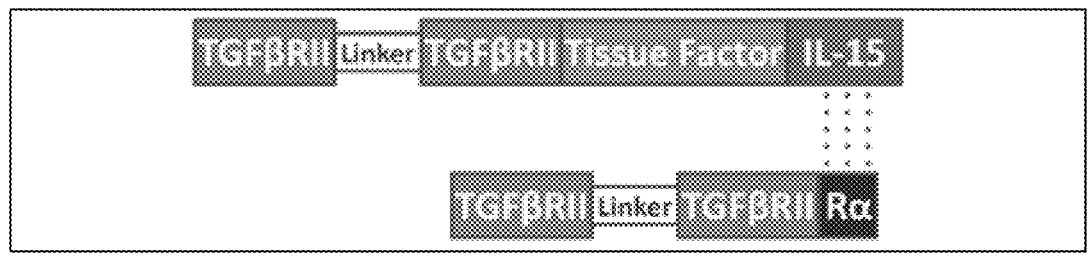
FIG. 78 shows an additional schematic of the TGFRt15-TGFRs construct.

A fusion protein complex was generated comprising of TGFβ Receptor II/IL-15RαSu and TGFβ Receptor II/TF/IL-15 fusion proteins (FIG. 77 and FIG. 78). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G45(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

(Signal peptide)
ATGAAGTGGGTGACCTTCATCAGCCTGCTGTTCCTGTTCTCCAGCGCCTA

CTCC (Two Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of TGFβ Receptor II/TF/IL-15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFβ Receptor II/IL-15 RαSu construct (including signal peptide sequence) is as follows:

(Signal peptide)
ATGAAGTGGGTGACCTTCATCAGCCTGCTGTTCCTGTTCTCCAGCGCCTA

CTCC (Two human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG

The amino acid sequence of the two TGFβ Receptor II/IL-15RαSu construct (including signal peptide sequence) is as follows:

(Signal peptide)
MKWVTFISLLFLFSSAYS (Two human TGFβ Receptor II extra-cellular domains)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNKA

TNVAHWTTPSLKCIR

In some cases, the leader peptide is cleaved from the intact polypeptide to generate the mature form that may be soluble or secreted.

The TGFβR/IL-15RαSu and TGFβR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFβR/TF/IL-15:TGFβR/IL-15RαSu protein complex (referred to as TGFRt15-TGFRs), which can be purified by anti-TF IgG1 affinity and other chromatography methods.

Effect of TGFRt15-TGFRs on TGFβ1 Activity in HEK-Blue TGFβ Cells

To evaluate the activity of TGFβRII in TGFRt15-TGFRs, the effect of TGFRt15-TGFRs on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× gluta-mine) at $5 \times 10^5$ cells/mL. In a flat-bottom 96-well plate, 50 µL cells were added to each well ($2.5 \times 10^4$ cells/well) and followed with 50 µL 0.1 nM TGFβ1 (R&D systems).

TGFRt15-TGFRs or TGFR-Fc (R&D Systems) prepared at a 1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. The $IC_{50}$ of each protein sample was calculated with GraphPad Prism 7.04. The $IC_{50}$ of TGFRt15-TGFRs and TGFR-Fc were 216.9 pM and 460.6 pM respectively. These results showed that the TGFβRII domain in TGFRt15-TGFRs was able to block the activity of TGFβ1 in HEK-Blue TGFβ cells.

Figure 79:
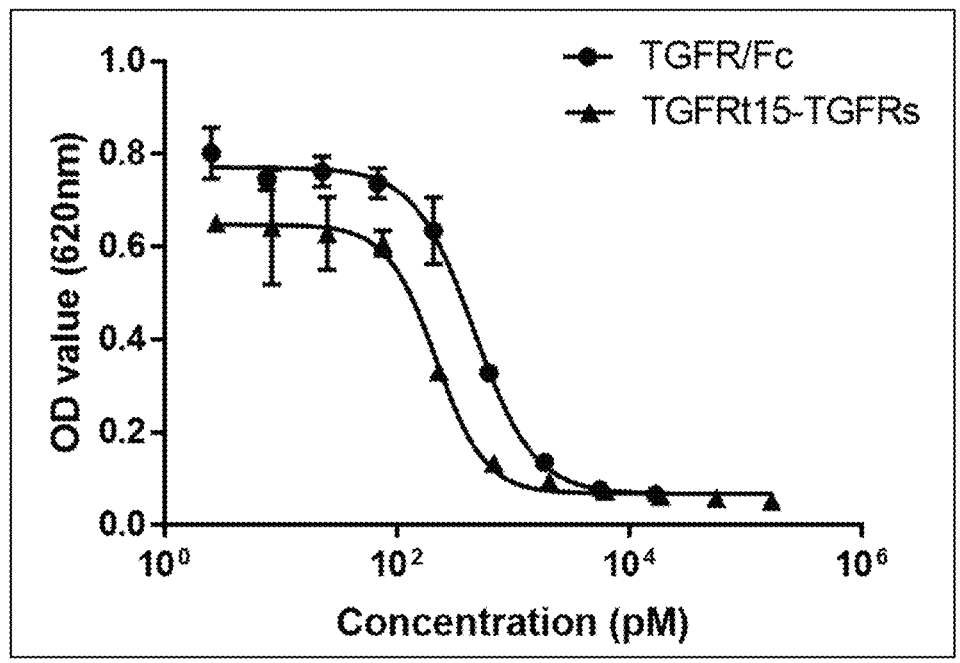
FIG. 79 shows results of TGFβ1 inhibition by TGFRt15-TGFRs and TGFR-Fc.
Figure 80:
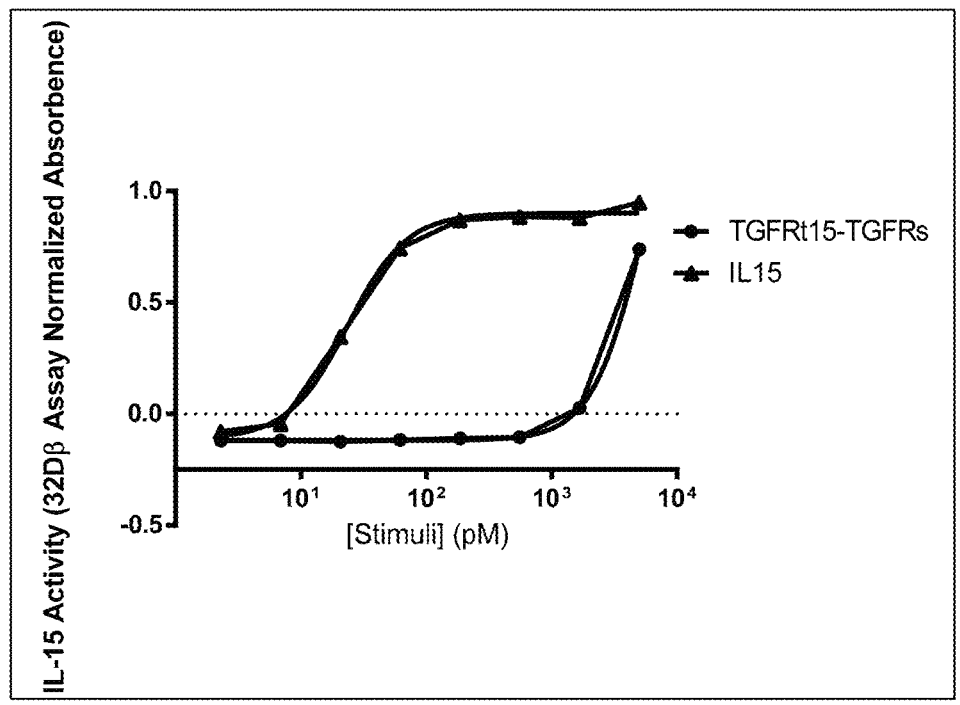
FIG. 80 shows results of 32Dβ cell proliferation assay with TGFRt15-TGFRs or recombinant IL-15

The IL-15 in TGFRt15-TGFRs Promotes IL-2Rβ and Common γ Chain Containing 32Dβ Cell Proliferation To evaluate the activity of IL-15 in TGFRt15-TGFRs, the IL-15 activity of TGFRt15-TGFRs was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-TGFRs or IL-15 were added to the cells (FIG. 79). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The absorbance at 450 nm was measured by analyzing the amount of formazan dye produced. As shown in FIG. 79, TGFRt15-TGFRs and IL-15 promoted 32Dβ cell proliferation, with the $EC_{50}$ of TGFRt15-TGFRs and IL-15 being 1901 pM and 10.63 pM, respectively.

Figure 81A:
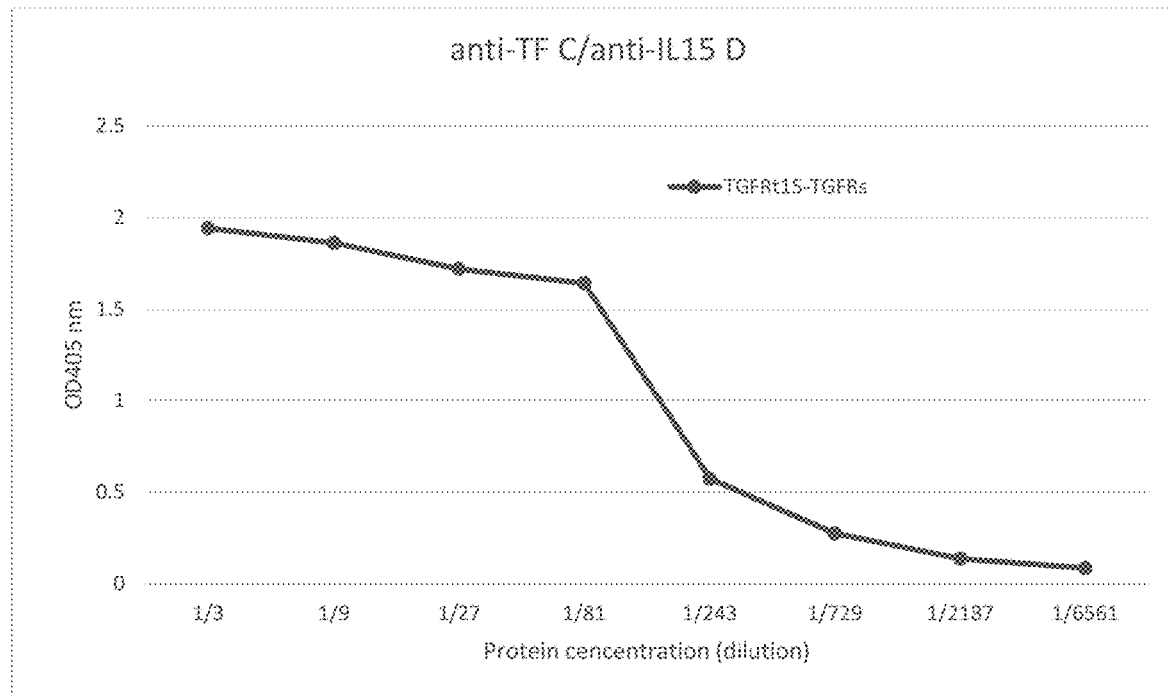
FIGS. 81A and 81B show results of detecting IL-15 and TGFβRII in TGFRt15-TGFRs with corresponding antibodies using ELISA.
Figure 81B:
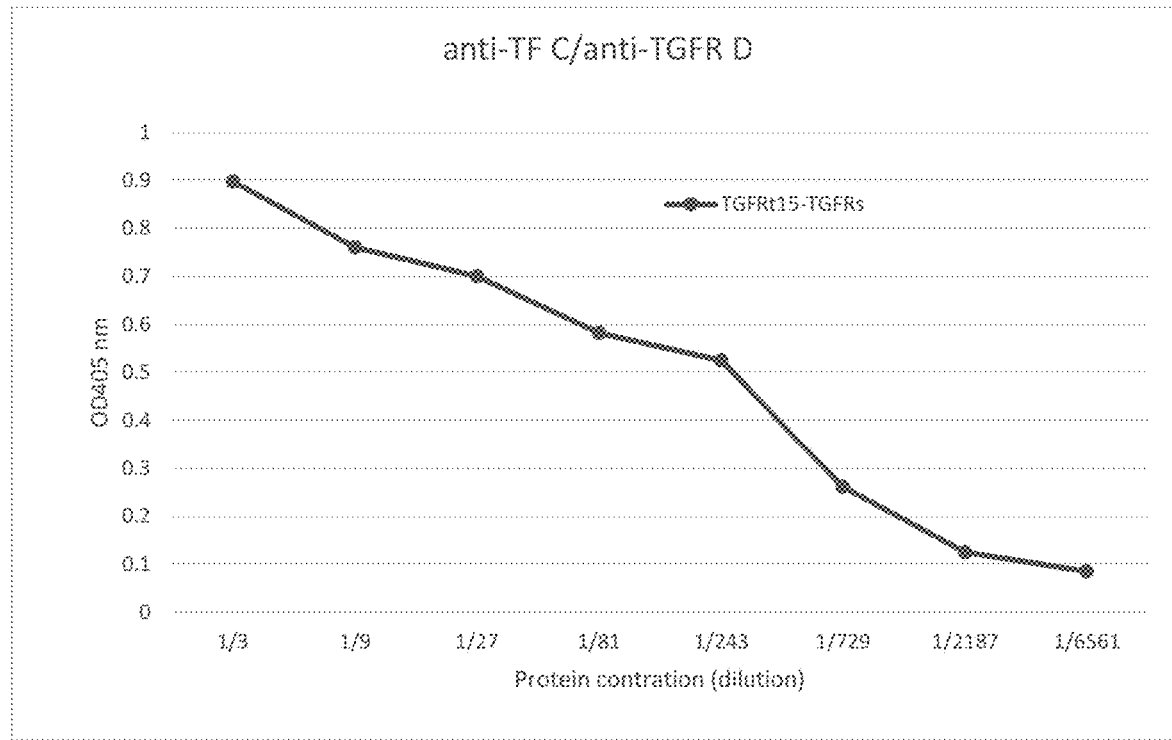

Detection of IL-15 and TGFβRII Domains in TGFRt15-TGFRs with Corresponding Antibodies Using ELISA A 96-well plate was coated with 100 μL (8 μg/mL) of anti-TF IgG1 in R5 (coating buffer) and incubated at room temperature (RT) for 2 hrs. The plates were washed 3 times and blocked with 100 μL of 1% BSA in PBS. TGFRt15-TGFRs was added at a 1:3 serial dilution, and incubated at RT for 60 min. After 3 washes, 50 ng/mL of biotinylated-anti-IL-15 antibody (BAM247, R&D Systems), or 200 ng/mL of biotinylated-anti-TGFβRII antibody (BAF241, R&D Systems) was added to the wells and incubated at RT for 60 min. Next the plates were washed 3 times, and 0.25 μg/mL of HRP-SA (Jackson ImmunoResearch) at 100 μL per well was added and incubated for 30 min at RT, followed by 4 washes and incubation with 100 μL of ABTS for 2 mins at RT. Absorbance at 405 nm was read. As shown in FIGS. 81A and 81B, the IL-15 and TGFβRII domains in TGFRt15-TGFRs were detected by the individual antibodies.

Figure 82:
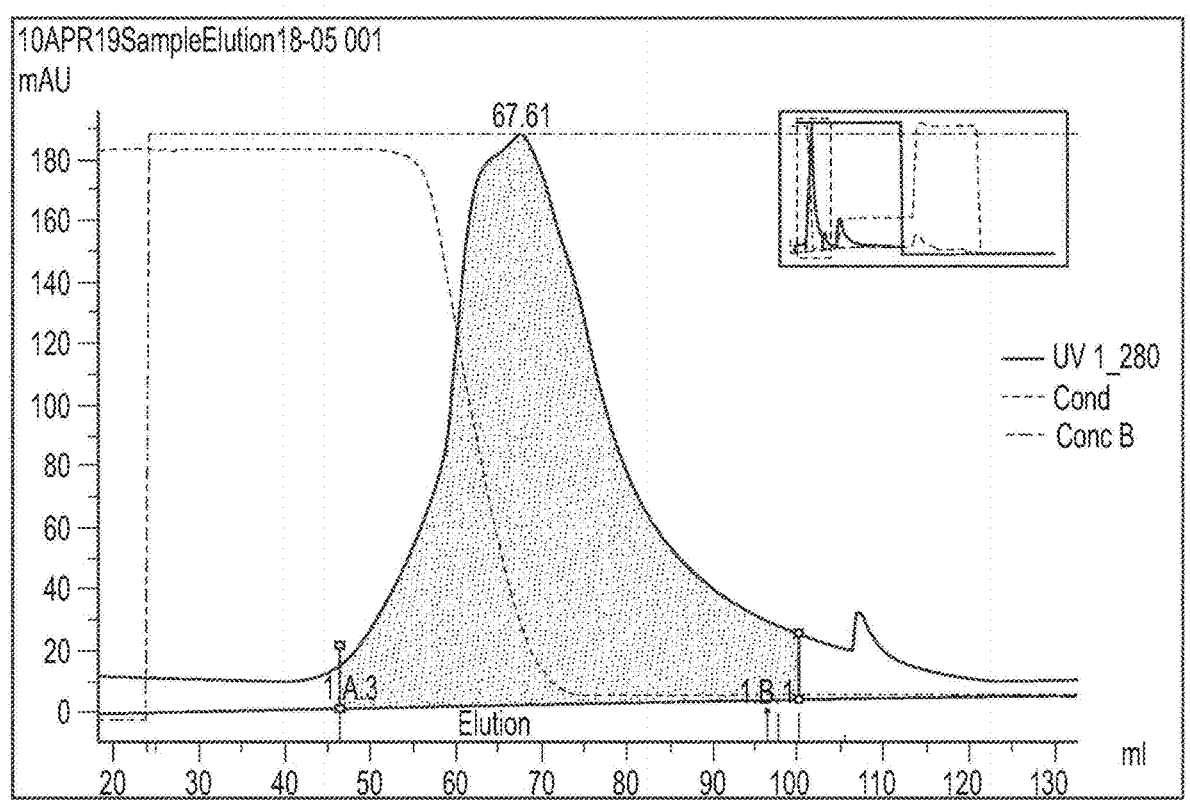
FIG. 82 is a line graph showing the chromatographic profile of TGFRt15-TGFRs protein containing cell culture supernatant following binding and elution on anti-TF antibody resin.

Purification Elution Chromatograph of TGFRt15-TGFRs from Anti-TF Antibody Affinity Column TGFRt15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 82, the anti-TF antibody affinity column bound to TGFRt15-TGFRs which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of TGFRt15-TGFRs

Figure 83:
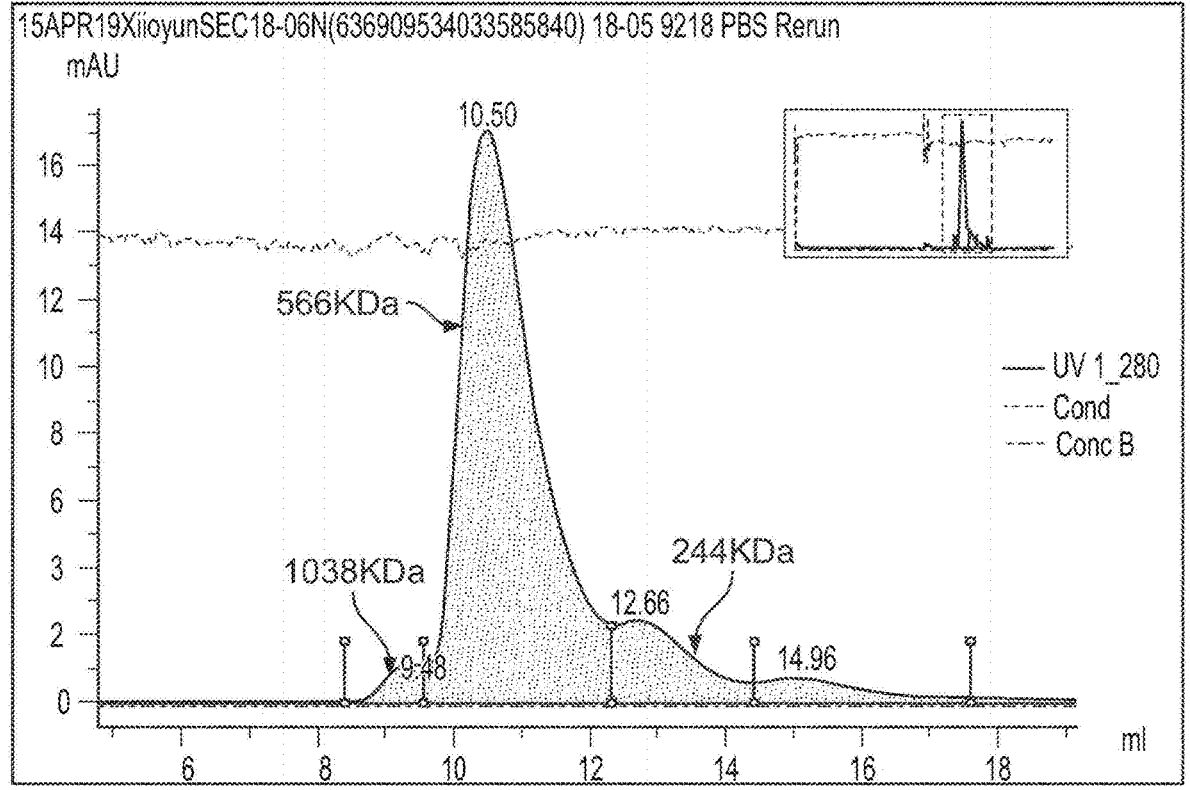
FIG. 83 shows the analytical SEC profile of TGFRt15-TGFRs.

A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing TGFRt15-TGFRs in PBS was injected into the Superdex 200 column using a capillary loop, and analyzed by SEC. The SEC chromatograph of the sample is shown in FIG. 83. The SEC results showed four protein peaks for TGFRt15-TGFRs.

Reduced SDS PAGE Analysis of TGFRt15-TGFRs

To determine the purity and molecular weight of the TGFRt15-TGFRs protein, protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 84:
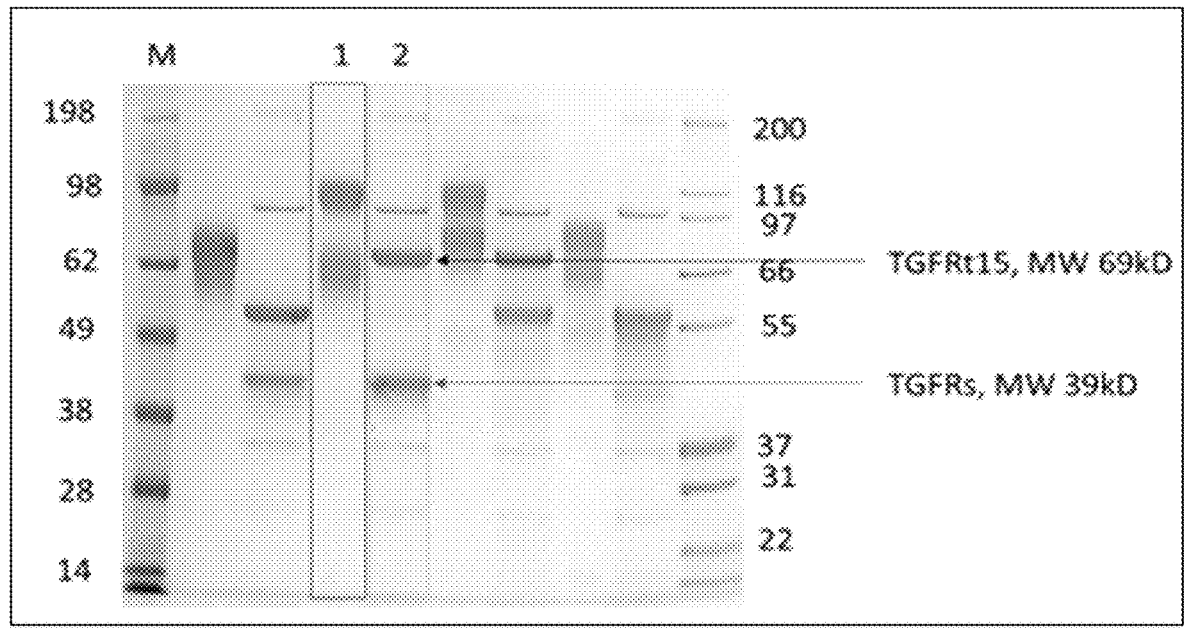
FIG. 84 shows TGFRt15-TGFRs before and after deglycosylation on as analyzed by reduced SDS-PAGE

To verify that the TGFRt15-TGFRs protein undergoes glycosylation after translation in CHO cells, a deglycosylation experiment was conducted using the Protein Deglycosylation Mix II kit from New England Biolabs and the manufacturer's instructions. FIG. 84 shows the reduced SDS-PAGE analysis of the sample in non-deglycosylated (lane 1 in red outline) and deglycosylated (lane 2 in yellow outline) state. The results showed that the TGFRt15-TGFRs protein is glycosylated when expressed in CHO cells. After deglycosylation, the purified sample showed expected molecular weights (69 kDa and 39 kDa) in the reduced SDS gel. Lane M was loaded with 10 ul of SeeBlue Plus2 Prestained Standard.

Immunostimulatory Activity of TGFRt15-TGFRs in C57BL/6 Mice

TGFRt15-TGFRs is a multi-chain polypeptide (a type A multi-chain polypeptide described herein) that includes a first polypeptide that is a soluble fusion of two TGFβRII domains, human tissue factor 219 fragment and human IL-15, and the second polypeptide that is a soluble fusion of two TGFβRII domains and sushi domain of human IL-15 receptor alpha chain.

Figure 85A:
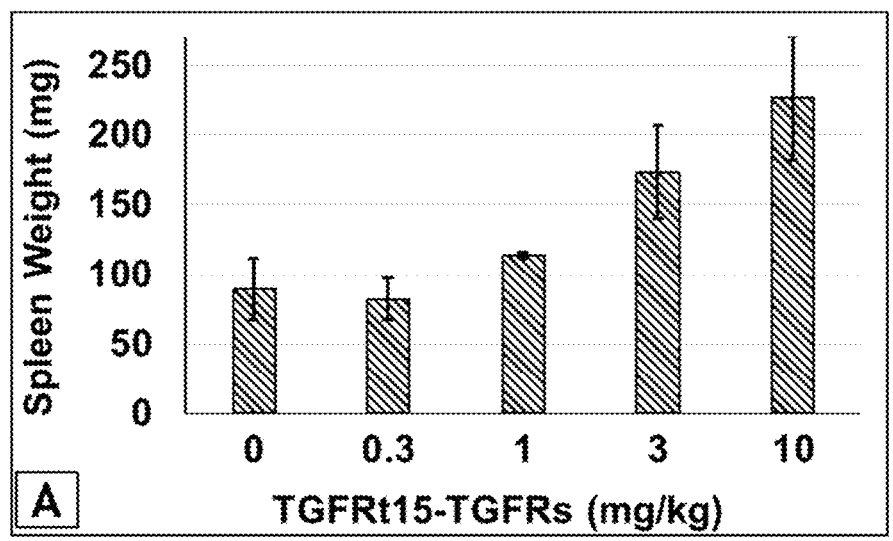
FIGS. 85A and 85B show spleen weight and the percentages of immune cell types in TGFRt15-TGFRs-treated and control-treated mice.
Figure 85B:
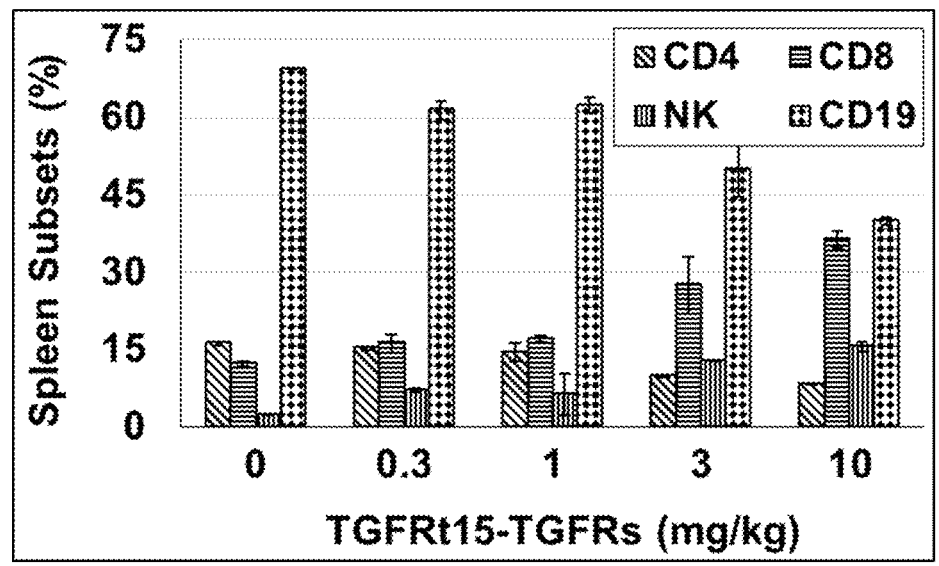

Wild type C57BL/6 mice were treated subcutaneously with either control solution or with TGFRt15-TGFRs at a dosage of 0.3 mg/kg, 1 mg/kg, 3 mg/kg, or 10 mg/kg. Four days after treatment, spleen weight and the percentages of various immune cell types present in the spleen were evaluated. As shown in FIG. 85A, the spleen weight in mice treated with TGFRt15-TGFRs increased with increasing dosage of TGFRt15-TGFRs. Moreover, the spleen weight in mice treated with 1 mg/kg, 3 mg/kg, and 10 mg/kg of TGFRt15-TGFRs were higher as compared to mice treated with the control solution, respectively. In addition, the percentages of $CD4^+$ T cells, $CD8^+$ T cells, NK cells, and $CD19^+$ B cells present in the spleen of control-treated and TGFRt15-TGFRs-treated mice were evaluated. As shown in FIG. 85B, in the spleens of mice treated with TGFRt15-TGFRs, the percentages of $CD8^+$ T cells and NK cells both increased with increasing dosage of TGFRt15-TGFRs. Specifically, the percentages of $CD8^+$ T cells were higher in mice treated with 0.3 mg/kg, 3 mg/kg, and 10 mg/kg of TGFRt15-TGFRs compared to control-treated mice, and the percentages of NK cells were higher in mice treated with 0.3 mg/kg, 1 mg/kg, 3 mg/kg, and 10 mg/kg of TGFRt15-TGFRs compared to control-treated mice. These results demonstrate that TGFRt15-TGFRs is able to stimulate immune cells in the spleen, in particular CD8+ T cells and NK cells.

The pharmacokinetics of TGFRt15-TGFRs molecules were evaluated in wild type C57BL/6 mice. The mice were treated subcutaneously with TGFRt15-TGFRs at a dosage of 3 mg/kg. The mouse blood was drained from tail vein at various time points and the serum was prepared. The TGFRt15-TGFRs concentrations in mouse serum was determined with ELISA (capture: anti-human tissue factor antibody; detection: biotinylated anti-human TGFβ receptor antibody and followed by peroxidase conjugated streptavidin and ABTS substrate). The results showed that the half-life of TGFRt15-TGFRs was 12.66 hours in C57BL/6 mice.

Figure 86A:
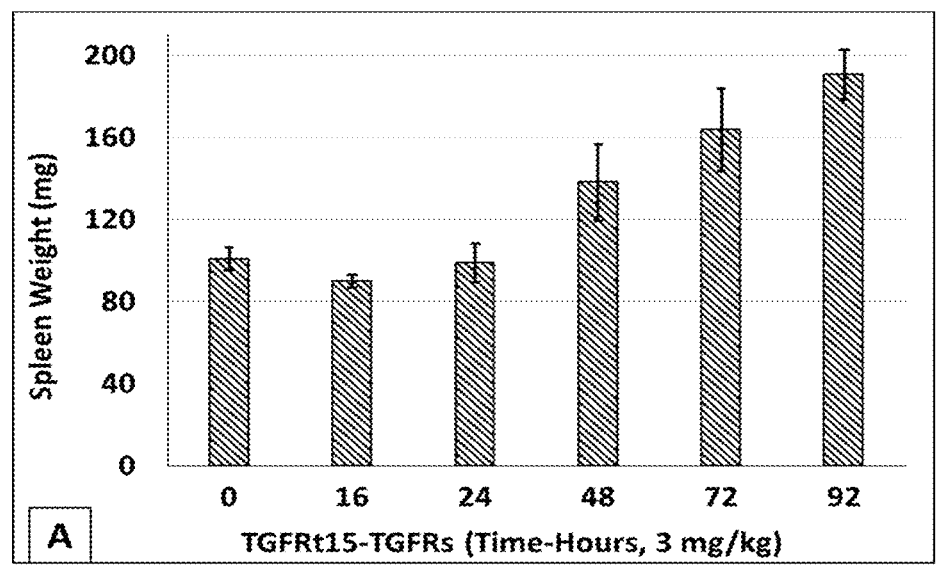
FIGS. 86A and 86B show the spleen weight and immunostimulation over 92 hours in mice treated with TGFRt15-TGFRs.
Figure 86B:
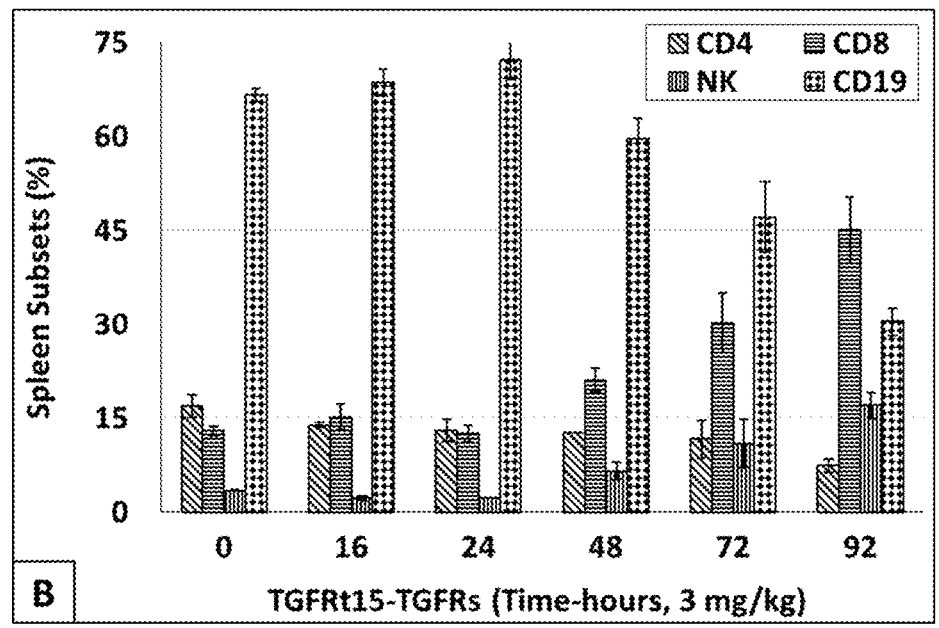

The mouse splenocytes were prepared in order to evaluate the immunostimulatory activity of TGFRt15-TGFRs over time in mice. As shown in FIG. 86A, the spleen weight in mice treated with TGFRt15-TGFRs increased 48 hours posttreatment and continued to increase over time. In addition, the percentages of CD4+ T cells, CD8+ T cells, NK cells, and CD19+ B cells present in the spleen of control-treated and TGFRt15-TGFRs-treated mice were evaluated. As shown in FIG. 86B, in the spleens of mice treated with TGFRt15-TGFRs, the percentages of CD8+ T cells and NK cells both increased at 48 hours after treatment and were higher and higher overtime after the single dose treatment. These results further demonstrate that TGFRt15-TGFRs is able to stimulate immune cells in the spleen, in particular CD8+ T cells and NK cells.

Figure 87A:
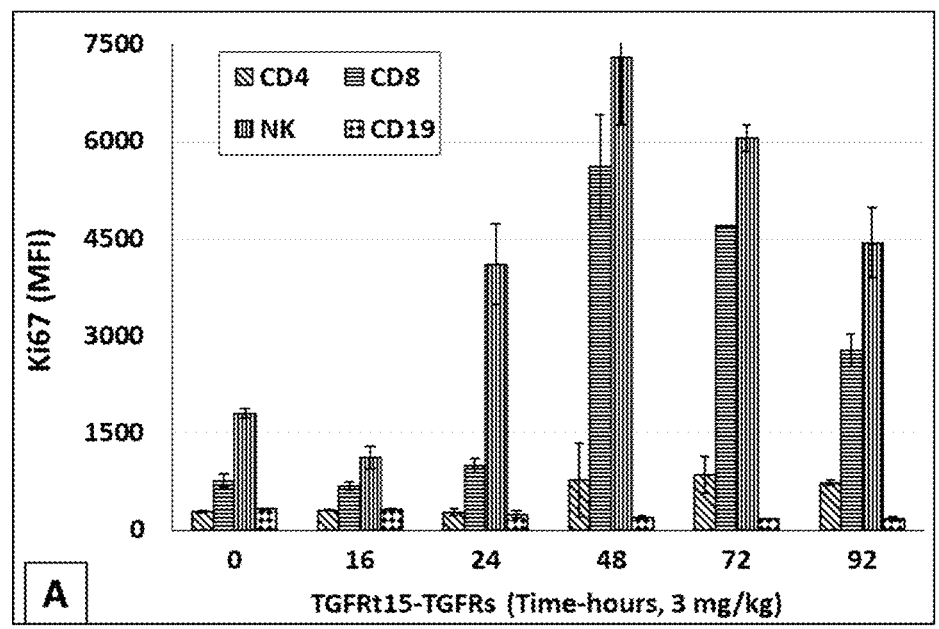
FIGS. 87A and 87B show Ki67 and Granzyme B expression in mice treated with TGFRt15-TGFRs over time.
Figure 87B:
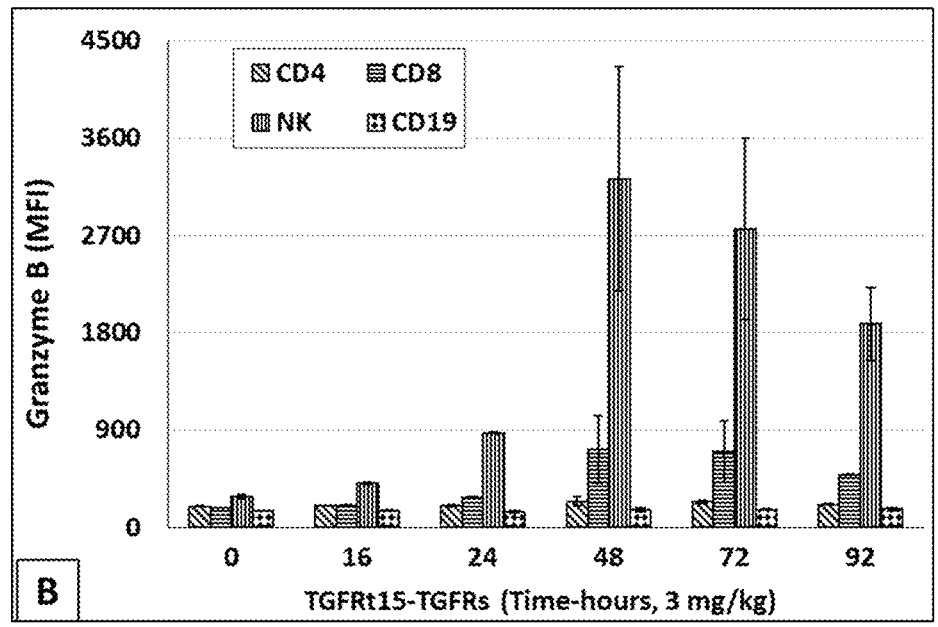

Furthermore, the dynamic proliferation of immune cells based on Ki67 expression of splenocytes and cytotoxicity potential based on granzyme B expression were evaluated in splenocytes isolated from mice following a single dose (3 mg/kg) of TGFRt15-TGFRs. As shown in FIGS. 87A and 87B, in the spleens of mice treated with TGFRt15-TGFRs, the expression of Ki67 and granzyme B by NK cells increased at 24 hours after treatment and its expression of CD8+ T cells and NK cells both increased at 48 hours and later time points after the single dose treatment. These results demonstrate that TGFRt15-TGFRs not only increases the numbers of CD8+ T cells and NK cells but also enhance the cytotoxicity of these cells. The single dose treatment of TGFRt15-TGFRs led CD8+ T cells and NK cells to proliferate for at least 4 days.

Figure 88:
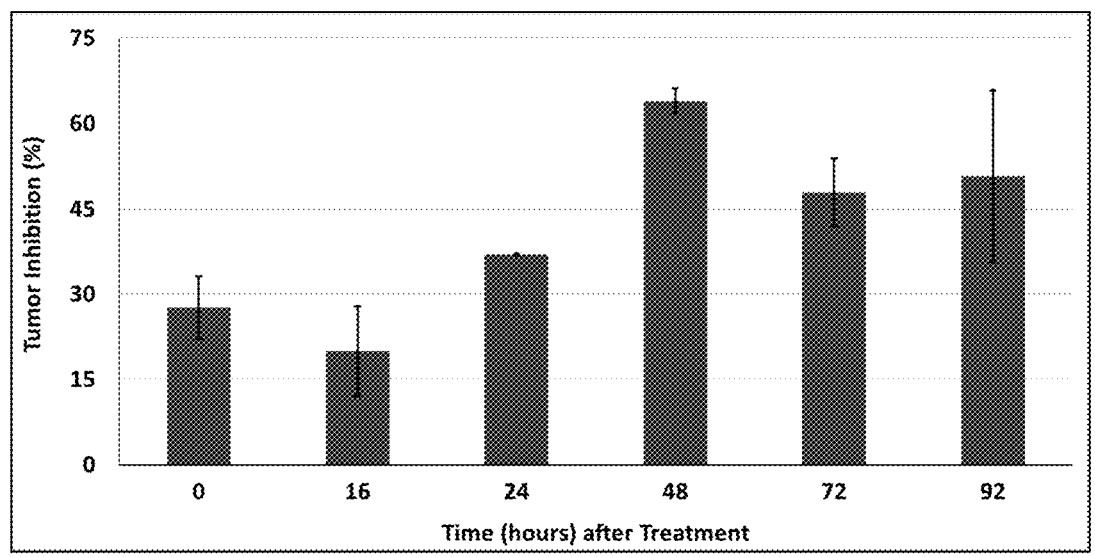
FIG. 88 shows enhancement of cytotoxicity of splenocytes by TGFRt15-TGFRs in C57BL/6 Mice.

The cytotoxicity of the splenocytes from TGFRt15-TGFRs-treated mice against tumor cells was also evaluated. Mouse Moloney leukemia cells (Yac-1) were labeled with CELLTRACE®, violet dye, and were used as tumor target cells. Splenocytes were prepared from TGFRt15-TGFRs (3 mg/kg)-treated mouse spleens at various time points post treatment and were used as effector cells. The target cells were mixed with effector cells at an E:T ratio=10:1 and incubated at 37° C. for 20 hours. Target cell viability was assessed by analysis of propidium iodide positive, violet-labeled Yac-1 cells using flow cytometry. Percentage of Yac-1 tumor inhibition was calculated using the formula, (1−[viable Yac-1 cell number in experimental sample]/[viable Yac-1 cell number in the sample without splenocytes])× 100. As shown in FIG. 88, splenocytes from TGFRt15-TGFRs-treated mice had stronger cytotoxicity against Yac-1 cells than the control mouse splenocytes.

Tumor Size Analysis in Response to Chemotherapy and/or TGFRt15-TGFRs

Figure 89:
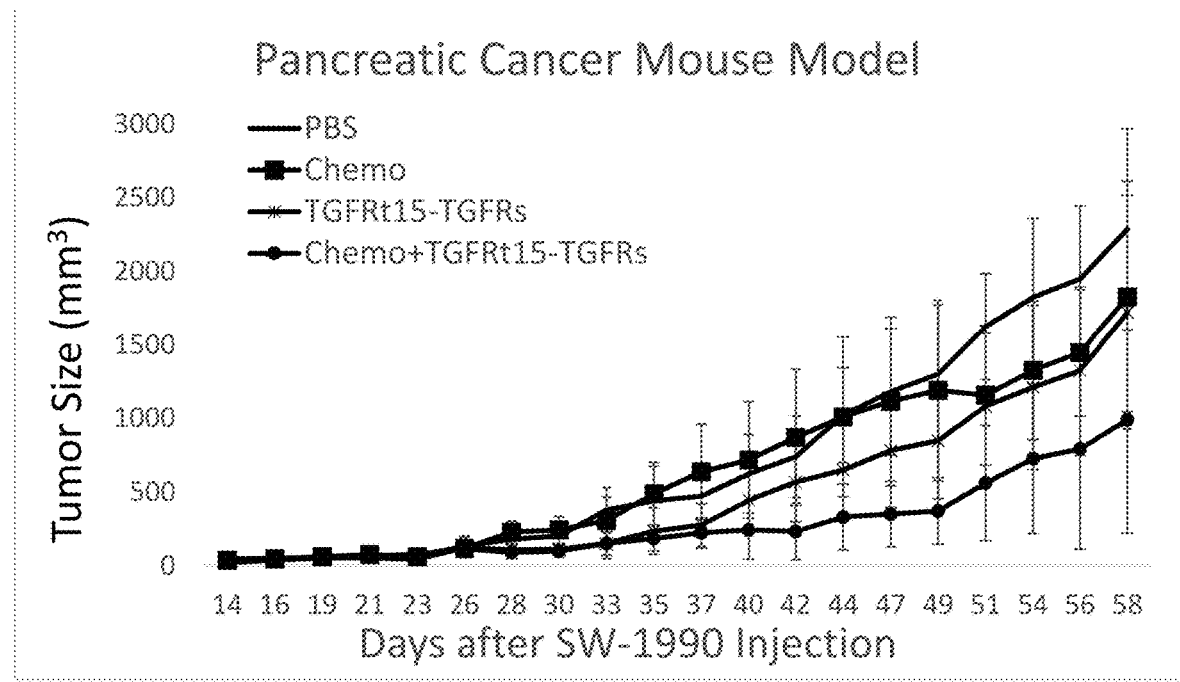
FIG. 89 shows changes in tumor size in response to PBS treatment, chemotherapy alone, TGFRt15-TGFRs alone, or chemotherapy and TGFRt15-TGFRs combination, in a pancreatic cancer mouse model.

Pancreatic cancer cells (SW1990, ATCC® CRL-2172) were subcutaneously (s.c.) injected into C57BL/6 scid mice (The Jackson Laboratory, 001913, 2×10⁶ cells/mouse, in 100 μL HBSS) to establish the pancreatic cancer mouse model. Two weeks after tumor cell injection, chemotherapy was initiated in these mice intraperitoneally with a combination of Abraxane (Celgene, 68817-134, 5 mg/kg, i.p.) and Gemcitabine (Sigma Aldrich, G6423, 40 mg/kg, i.p.), followed by immunotherapy with TGFRt15-TGFRs (3 mg/kg, s.c.) in 2 days. The procedure above was considered one treatment cycle and was repeated for another 3 cycles (1 cycle/week). Control groups were set up as the SW1990-injected mice that received PBS, chemotherapy (Gemcitabine and Abraxane), or TGFRt15-TGFRs alone. Along with the treatment cycles, tumor size of each animal was measured and recorded every other day, until the termination of the experiment 2 months after the SW1990 cells were injected. Measurement of the tumor volumes were analyzed by group and the results indicated that the animals receiving a combination of chemotherapy and TGFRt15-TGFRs had significantly smaller tumors comparing to the PBS group, whereas neither chemotherapy nor TGFRt15-TGFRs therapy alone work as sufficiently as the combination (FIG. 89).

In Vitro Senescent B16F10 Melanoma Model

Figure 90:
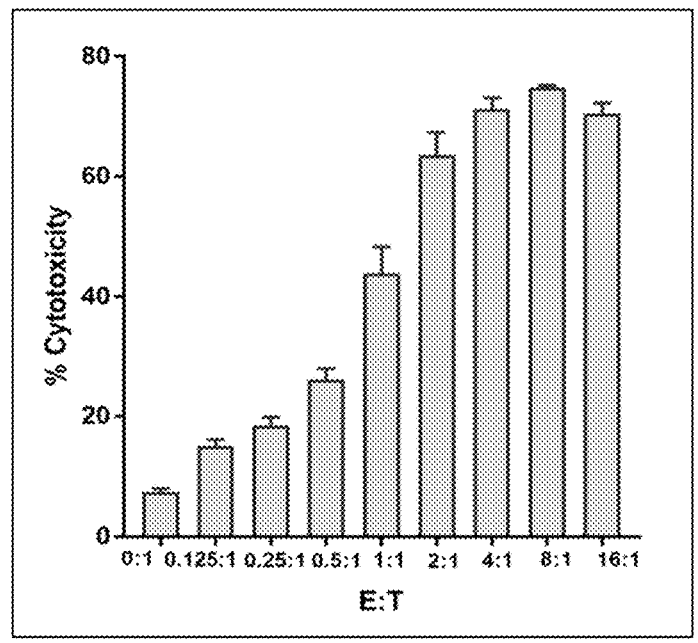
FIG. 90 shows the cytotoxicity of NK cells isolated from mice treated with TGFRt15-TGFRs.

Next, in vitro killing of senescent B16F10 melanoma cells by activated mouse NK cells was evaluated. B16F10 senescence cells (B16F10-SNC) cells were labelled with CELL-TRACE®, violet dye, and incubated for 16 hrs with different E:T ratio of in vitro 2t2-activated mouse NK cells (isolated from spleen of C57BL/6 mice injected with TGFRt15-TGFRs10 mg/kg for 4 days). The cells were trypsinized, washed and resuspended in complete media containing propidium iodide (PI) solution. The cytotoxicity was assessed by flow cytometry (FIG. 90).

Figure 91:
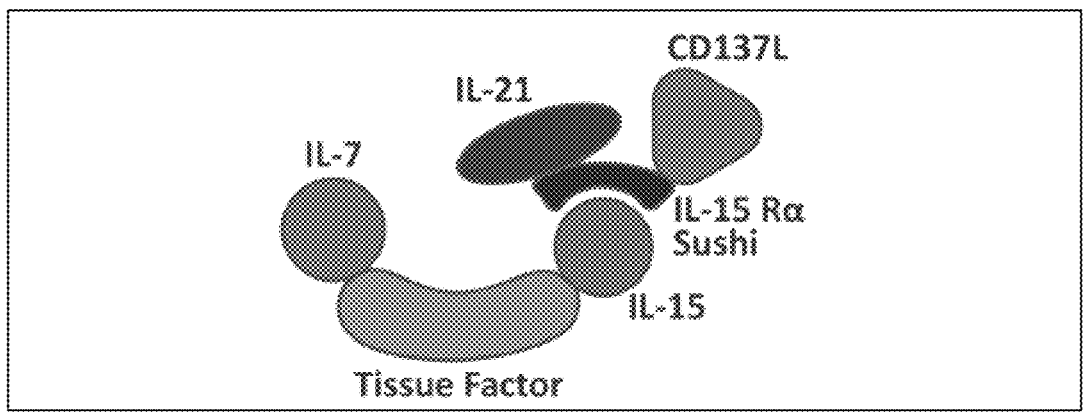
FIG. 91 shows a schematic of the 7t15-21s137L (long version) construct.
Figure 92:
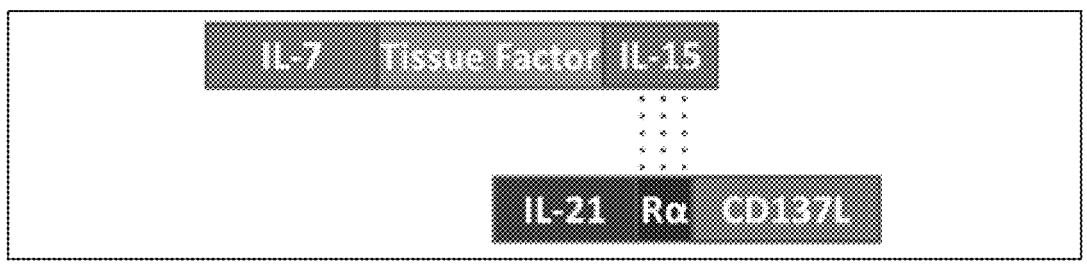
FIG. 92 shows an additional schematic of the 7t15-21s137L (long version) construct.

Example 53: 7t15-21s137L (Long Version) Fusion Protein Creation and Characterization A fusion protein complex was generated comprising of IL-21/IL-15RαSu/CD137L and IL-7/TF/IL-15 fusion proteins (FIG. 91 and FIG. 92). Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as follows:

```
(Signal peptide)
ATGAAGTGGGTGACCTTCATCAGCCTGCTGTTCCTGTTCTCCAGCGCCTA

CTCC (Human IL7)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT
```

-continued (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of 7t15 fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

The nucleic acid and protein sequences of the 21s137L are shown below. The nucleic acid sequence of the 21s137L construct (including signal peptide sequence) is as follows:

(Signal peptide)
ATGAAGTGGGTGACCTTCATCAGCCTGCTGTTCCTGTTCTCCAGCGCCTA

CTCC (Human IL-21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGACCT

GCGGCAGGGCATGTTTGCGCAGCTGGTGGCCCAAAATGTTCTGCTGATCG

ATGGGCCCCTGAGCTGGTACAGTGACCCAGGCCTGGCAGGCGTGTCCCTG

ACGGGGGGCCTGAGCTACAAGAGGACACGAAGGAGCTGGTGGTGGCCAA

GGCTGGAGTCTACTATGTCTTCTTTCAACTAGAGCTGCGGCGCGTGGTGG

CCGGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCACC

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTCGG

AA

The amino acid sequence of 21s137L fusion protein (including the leader sequence) is as follows:

(Signal peptide)
MKWVTFISLLFLFSSAYS (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS

-continued (Human IL-15R α sushi domain)
ITCPPPMSVEHADIWVKSYSLYSRERYICNSGFKRKAGTSSLTECVLNKA

TNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGVSL

TGGLSYKEDTKELVVAKAGVYYVFFQLELRRVVAGEGSGSVSLALHLQPL

RSAAGAAALALTVDLPPASSEARNSAFGFQGRLLHLSAGQRLGVHLHTEA

RARHAWQLTQGATVLGLFRVTPEIPAGLPSPRSE

In some cases, the leader peptide is cleaved from the intact polypeptide to generate the mature form that may be soluble or secreted.

The IL-21/IL-15RαSu/CD137L and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. Hum Gene Ther 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L), which can be purified by anti-TF IgG1 affinity and other chromatography methods.

Figure 93:
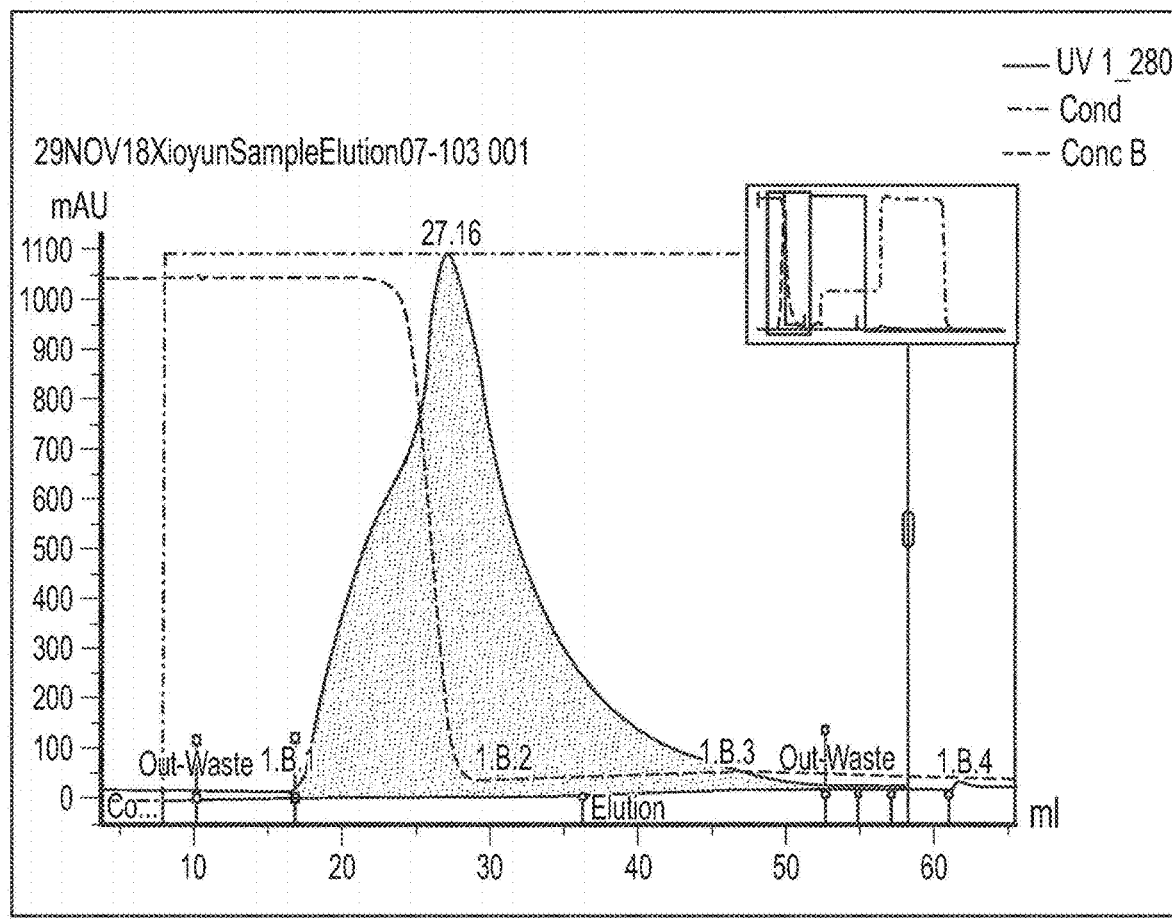
FIG. 93 is a line graph showing the chromatographic profile of 7t15-21s137L (long version) protein containing cell culture supernatant following binding and elution on anti-TF antibody resin.
Figure 94:
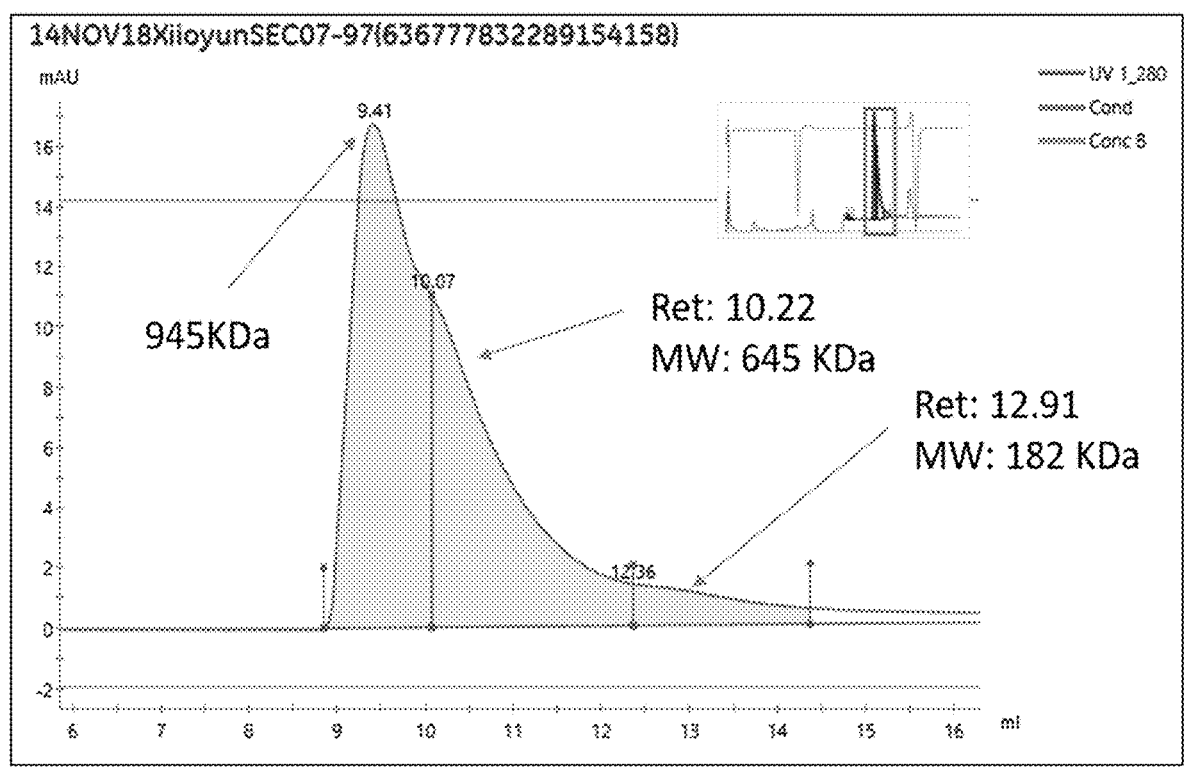
FIG. 94 shows the analytical SEC profile of 7t15-21s137L (long version).
Figure 95:
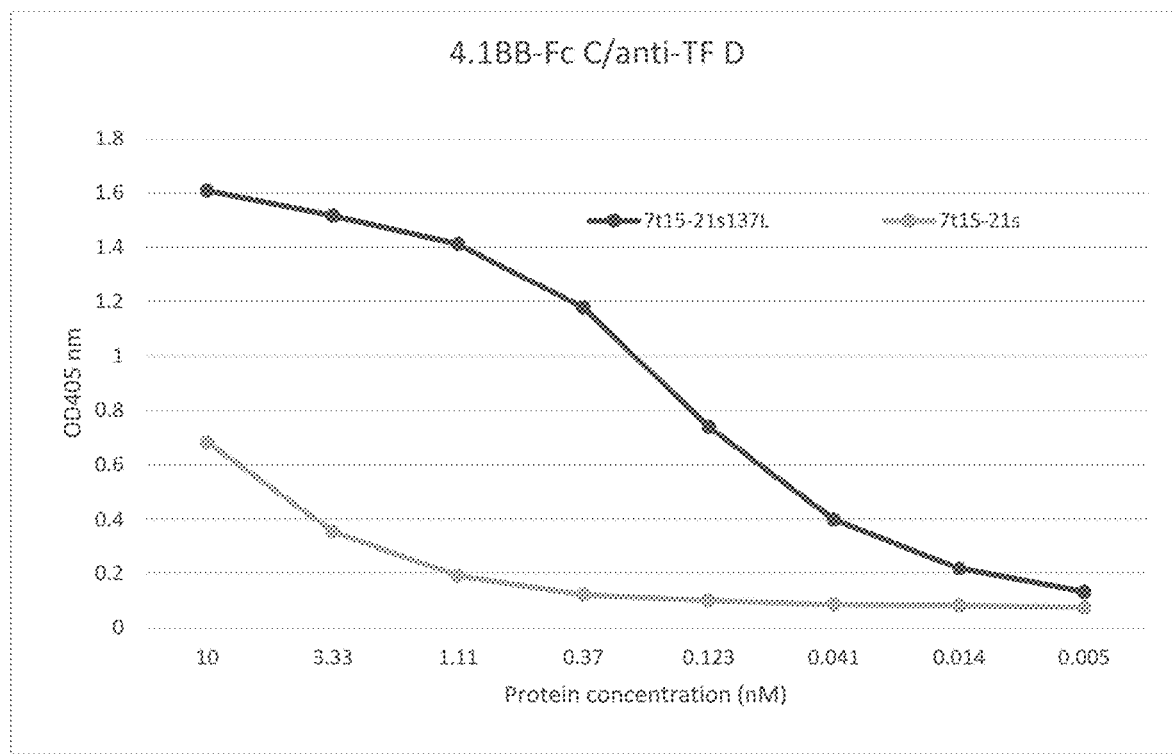
FIG. 95 shows binding of 7t15-21s137L (short version) to CD137L (4.1BBL)

Purification Elution Chromatograph of 7t15-21s137L Using Anti-TF Antibody Affinity Column 7t15-21s137L harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 93, the anti-TF antibody affinity column bound to 7t15-21s137L which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min. FIG. 94 shows the analytical SEC profile of 7t15-21s137L.

Example 54: 7t15-21s137L (Short Version) Fusion Protein Generation and Characterization A fusion protein complex was generated comprising of IL-21/IL-15RαSu/CD137L and IL-7/TF/IL-15 fusion proteins. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as follows:

(Signal peptide)
ATGAAGTGGGTGACCTTCATCAGCCTGCTGTTCCTGTTCTCCAGCGCCTA

CTCC (Human IL7)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of 7t15 fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

The nucleic acid and protein sequences of the 21s137L (short version) are shown below. The nucleic acid sequence of 21s137L (short version) construct (including signal peptide sequence) is as follows:

(Signal peptide)
ATGAAGTGGGTGACCTTCATCAGCCTGCTGTTCCTGTTCTCCAGCGCCTA

CTCC (Human IL-21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137 Ligand short version)
GATCCCGCCGGCCTCTTGGACCTGCGGCAGGGCATGTTTGCGCAGCTGGT

GGCCCAAAATGTTCTGCTGATCGATGGGCCCCTGAGCTGGTACAGTGACC

CAGGCCTGGCAGGCGTGTCCCTGACGGGGGGCCTGAGCTACAAGGAGGAC

ACGAAGGAGCTGGTGGTGGCCAAGGCTGGAGTCTACTATGTCTTCTTTCA

ACTAGAGCTGCGGCGCGTGGTGGCCGGCGAGGGCTCAGGCTCCGTTTCAC

TTGCGCTGCACCTGCAGCCACTGCGCTCTGCTGCTGGGGCCGCCGCCCTG

GCTTTGACCGTGGACCTGCCACCCGCCTCCTCCGAGGCTCGGAACTCGGC

CTTCGGTTTCCAGGGCCGCTTGCTGCACCTGAGTGCCGGCCAGCGCCTGG

GCGTCCATCTTCACACTGAGGCCAGGGCACGCCATGCCTGGCAGCTTACC

CAGGGCGCCACAGTCTTGGGACTCTTCCGGGTGACCCCCGAAATC

The amino acid sequence of the 21s137L (short version) construct (including signal peptide sequence) is as follows:

(Signal peptide)
MKWVTFISLLFLFSSAYS (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLNK

ATNVAHWTTPSLKCIR ((G4S)3 linker)
GGGGSGGGGSGGGGS (Human CD137 Ligand short version)
DPAGLLDLRQGMFAQLVAQNVLLIDGPLSWYSDPGLAGVSLTGGLSYKED

TKELVVAKAGVYYVFFQLELRRVVAGEGSGSVSLALHLQPLRSAAGAAAL

ALTVDLPPASSEARNSAFGFQGRLLHLSAGQRLGVHLHTEARARHAWQLT

QGATVLGLFRVTPEI

The IL-21/IL-15RαSu/CD137L (short version) and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L (short version)), which can be purified by anti-TF IgG1 affinity and other chromatography methods.

Binding of 7t15-21s137L (Short Version) to CD 137 (4.1BB)

On day 1, a 96-well plate was coated with 100 μL (2.5 μg/mL) of GAH IgG Fc (G-102-C, R&D Systems) in R5 (coating buffer) or R5 only and incubated at 4° C., overnight. On day 2, the plates were washed three times and blocked with 300 μL of 1% BSA in PBS at 37° C. for 2 hrs. 10 ng/mL of 4.1BB/Fc (838-4B, R&D Systems) was added at 100 μL/well and incubated for 2 hrs at RT. After three washes, the 7t15-21s137L or 7t15-21s serially diluted at a ⅓ ratio (starting at 10 nM), and incubated at 4° C. overnight. On day 3, following 3 washes, 300 ng/mL of biotinylated-anti-hTF antibody (BAF2339, R&D Systems) was added at 100 μL per well and incubated at RT for 2 hrs. The plate was then washed three times and incubated with 0.25 μg/mL of HRP-SA (Jackson ImmuneResearch) at 100 μL per well for 30 min, followed by 3 washes and incubation with 100 μL of ABTS for 2 mins at RT. Absorbance was read at 405 nm. As shown in FIG. 95, 7t15-21s137L (short version) showed significant interaction with 4.1BB/Fc (blue line) as compared to 7t15-21s.

Detection of IL-15, IL-21, and IL-7 in 7t15-21s137L (Short Version) with ELISA

Figure 96A:
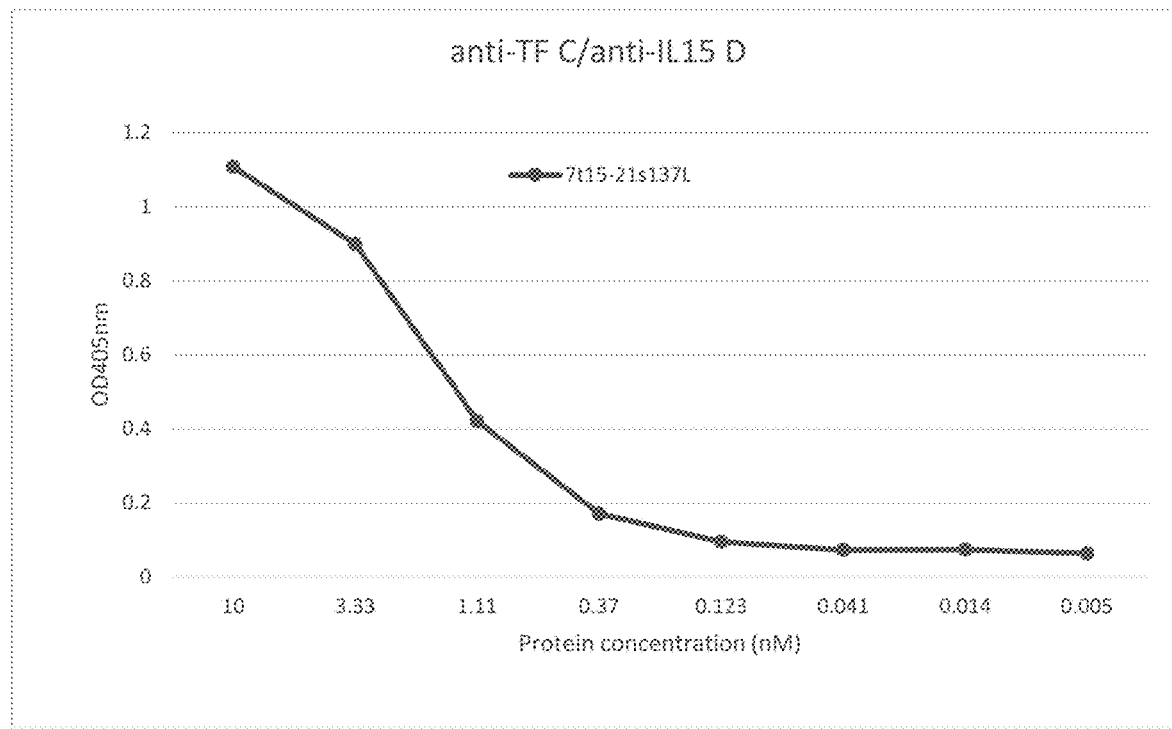
FIGS. 96A-96C show detection of IL15, IL21, and IL7 in 7t15-21s137L (short version) with ELISA.
Figure 96B:
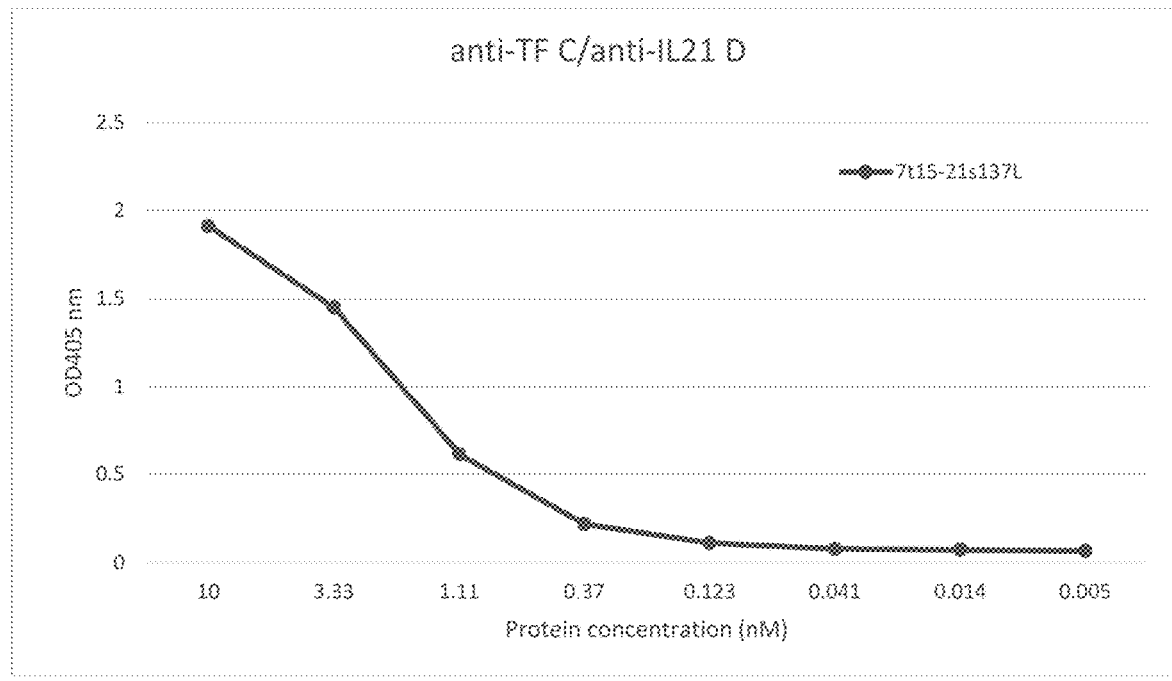
Figure 96C:
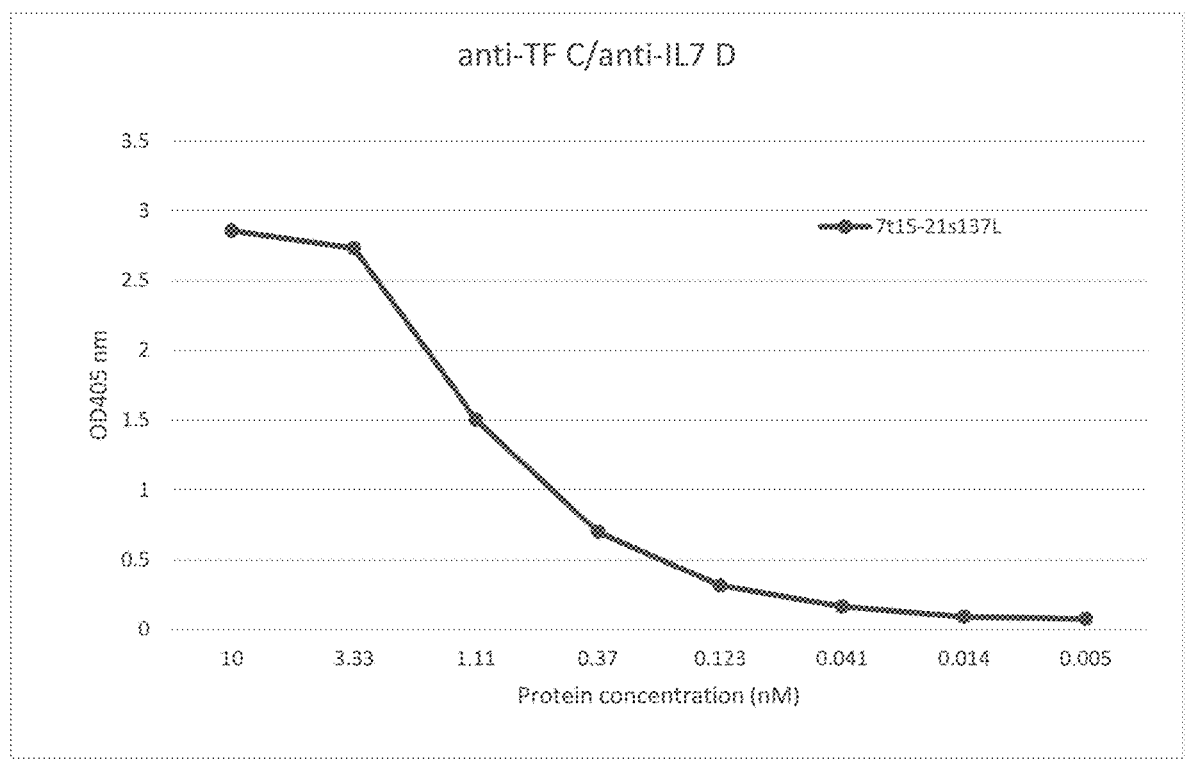

A 96-well plate was coated with 100 μL (8 μg/mL) of anti-TF IgG1 in R5 (coating buffer) and incubated at RT for 2 hrs. The plates were washed 3 times and blocked with 100 μL of 1% BSA in PBS. 7t15-21s137L (short version), serially diluted at a 1:3 ratio was added, and incubated at RT for 60 min. After three washes, 50 ng/mL of biotinylated-anti-IL15 antibody (BAM247, R&D Systems), 500 ng/mL of biotinylated-anti-IL21 antibody (13-7218-81, R&D Systems), or 500 ng/mL of biotinylated-anti-IL7 antibody (506602, R&D Systems) was added to the wells and incubated at RT for 60 min. After three washes and incubation with 0.25 μg/mL of HRP-SA (Jackson ImmunoResearch) at 100 μL per well was carried out for 30 min at RT, followed by four washes and incubation with 100 μL of ABTS for 2 mins at RT. Absorbance was read at 405 nm. As shown in FIGS. 96A-96C, the IL-15, IL-21, and IL-7 domains in 7t15-21s137L (short version) were detected by the respective antibodies.

Figure 97:
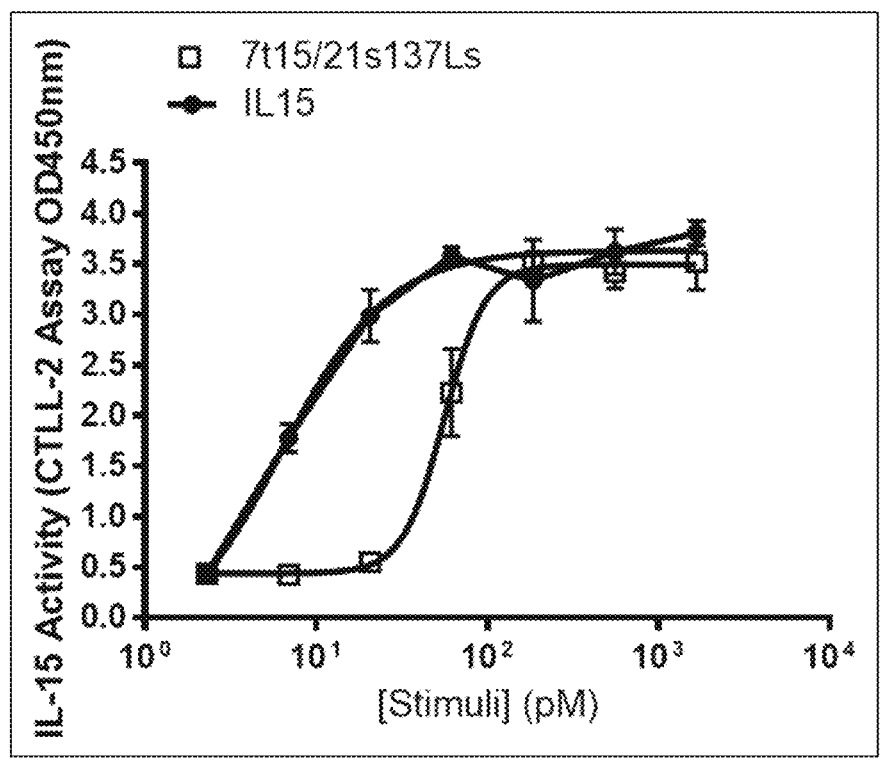
FIG. 97 shows results from a CTLL-2 cell proliferation assay.

The IL-15 in 7t15-1s137L (Short Version) Promotes IL2Rαβγ Containing CTLL2 Cell Proliferation To evaluate the IL-15 activity of 7t15-21s137L (short version), 7t15-21s137L (short version) was compared with recombinant IL15 in promoting proliferation of IL2Rαβγ expressing CTLL2 cells. IL-15-dependent CTLL2 cells were washed 5 times with IMDM-10% FBS and seeded to the wells at 2×10$^4$ cells/well. Serially diluted 7t15-21s137L (short version) or IL-15 were added to the cells (FIG. 97). Cells were incubated in a CO$_2$ incubator at 37° C. for 3 days. Cell proliferation was detected by adding 10 μL of WST1 to each well on day 3 and incubated for an additional 3 hours in a CO$_2$ incubator at 37° C. The amount of formazan dye produced was analyzed by measuring the absorbance at 450 nm. As shown in FIG. 97, 7t15-21s137L (short version) and IL-15 promoted CTLL2 cell proliferation. The EC$_{50}$ of 7t15-21s137L (short version) and IL-15 was 55.91 pM and 6.22 pM, respectively.

Figure 98:
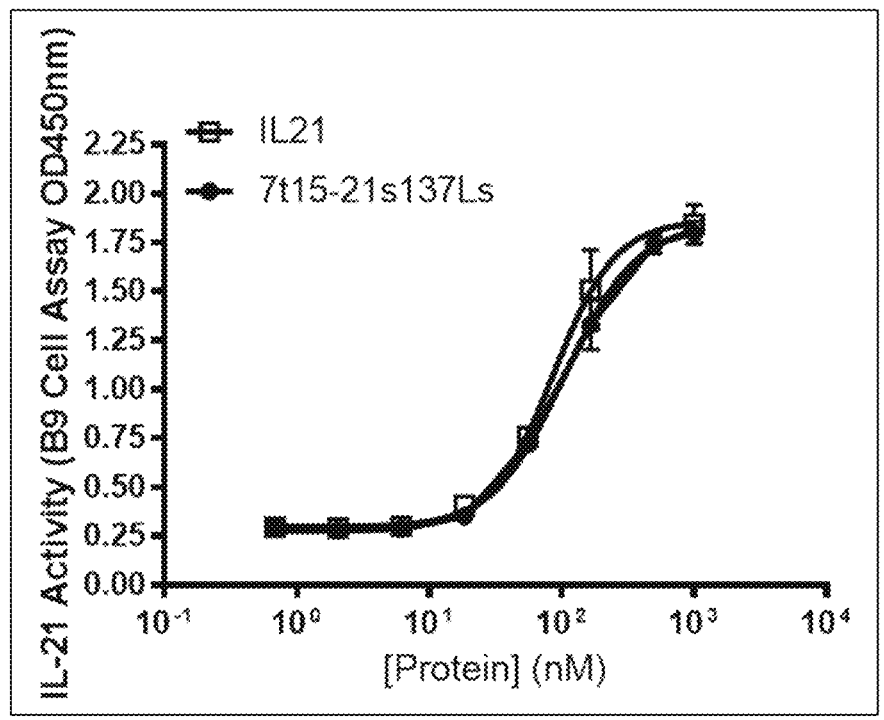
FIG. 98 shows the activity of 7t15-1s137L (short version) in promoting IL21R containing B9 cell proliferation.

The IL-21 in 7t15-1s137L (Short Version) Promotes IL21R Containing B9 Cell Proliferation To evaluate the IL-21 activity of 7t15-21s137L (short version), 7t15-21s137L (short version) was compared with recombinant IL-21 in promoting proliferation of IL-21R expressing B9 cells. IL-21R containing B9 cells were washed 5 times with RPMI-10% FBS and seeded to the wells at 1×10$^4$ cells/well. Serially diluted 7t15-21s137L (short version) or IL-21 were added to the cells (FIG. 98). Cells were incubated in a CO$_2$ incubator at 37° C. for 5 days. Cell proliferation was detected by adding 10 μL of WST1 to each well on day 5 and incubated for an additional 4 hours in a CO$_2$ incubator at 37° C. The amount of formazan dye produced was analyzed by measuring the absorbance at 450 nm. As shown in FIG. 98, 7t15-21s137L (short version) and IL-21 promoted B9 cell proliferation. The EC$_{50}$ of 7t15-21s137L (short version) and was 104.1 nM and 72.55 nM, respectively.

Example 55: 7t15-TGFRs Fusion Protein Generation and Characterization

Figure 99:
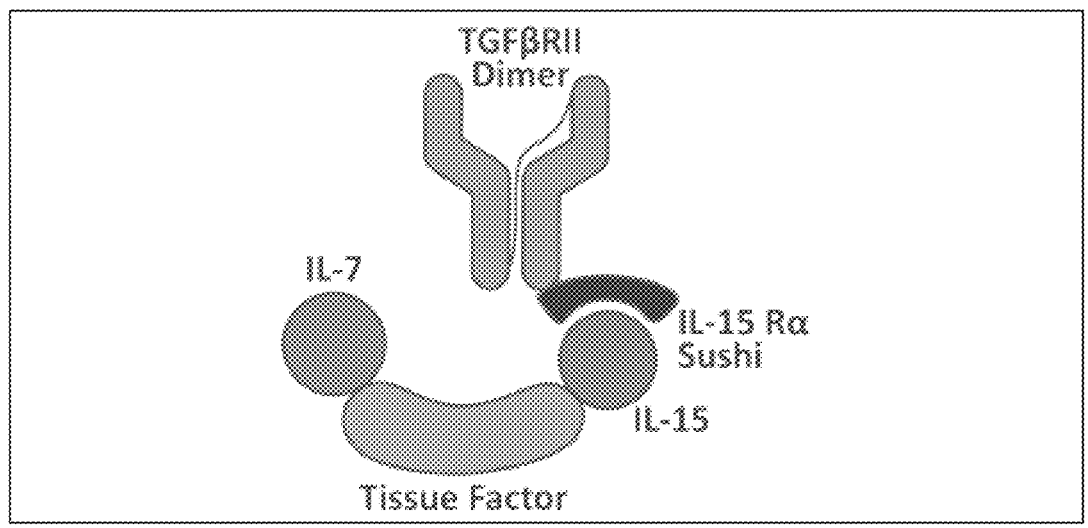
FIG. 99 shows a schematic of the 7t15-TGFRs construct.
Figure 100:
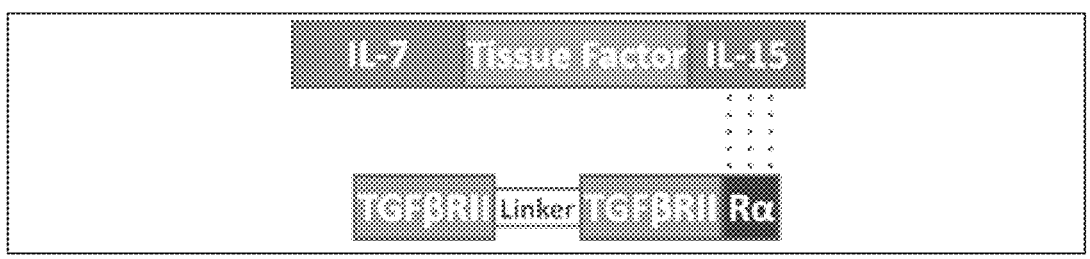
FIG. 100 shows an additional schematic of the 7t15-TGFRs construct.

A fusion protein complex was generated comprising of TGFβ Receptor II/IL-15RαSu and IL-7/TF/IL-15 fusion proteins (FIG. 99 and FIG. 100). The human TGFβ Receptor II (Ile24-Asp159), tissue factor 219, IL-15, and IL-7 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as follows:

```
(Signal peptide)
ATGAAGTGGGTGACCTTCATCAGCCTGCTGTTCCTGTTCTCCAGCGCCT

ACTCC (Human IL7)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG
```

-continued
GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of 7t15 fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICDAN

KEGMPLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFRs construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

-continued
GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG

The amino acid sequence of TGFRs fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNK

ATNVAHWTTPSLKCIR

Effect of 7t15-TGFRs on TGFβ1 Activity in HEK-Blue TGFβ Cells

To evaluate the activity of TGFβR in 7t15-TGFRs, the effect of 7t15-TGFRs on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μL cells were added to each well ($2.5\times10^4$ cells/well) and followed with 50 μL 0.1 nM TGFβ1 (R&D systems). 7t15-TGFRs or TGFR-Fc (R&D Systems) prepared at a1:3 serial dilution was then added to the plate to reach a total volume of 200 μL. After 24 hrs of incubation at 37° C., 40 of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. The $IC_{50}$ of each protein sample was calculated with GraphPad Prism 7.04. The $IC_{50}$ of 7t15-TGFRs and TGFR-Fc were 1142 pM and 558.6 pM respectively. These results showed that the TGFβR in 7t15-TGFRs was able to block the activity of TGFβ1 in HEK-Blue TGFβ cells.

Detection of IL-15, TGFβRII, and IL-7 in 7t15-TGFRs with ELISA

Figure 101:
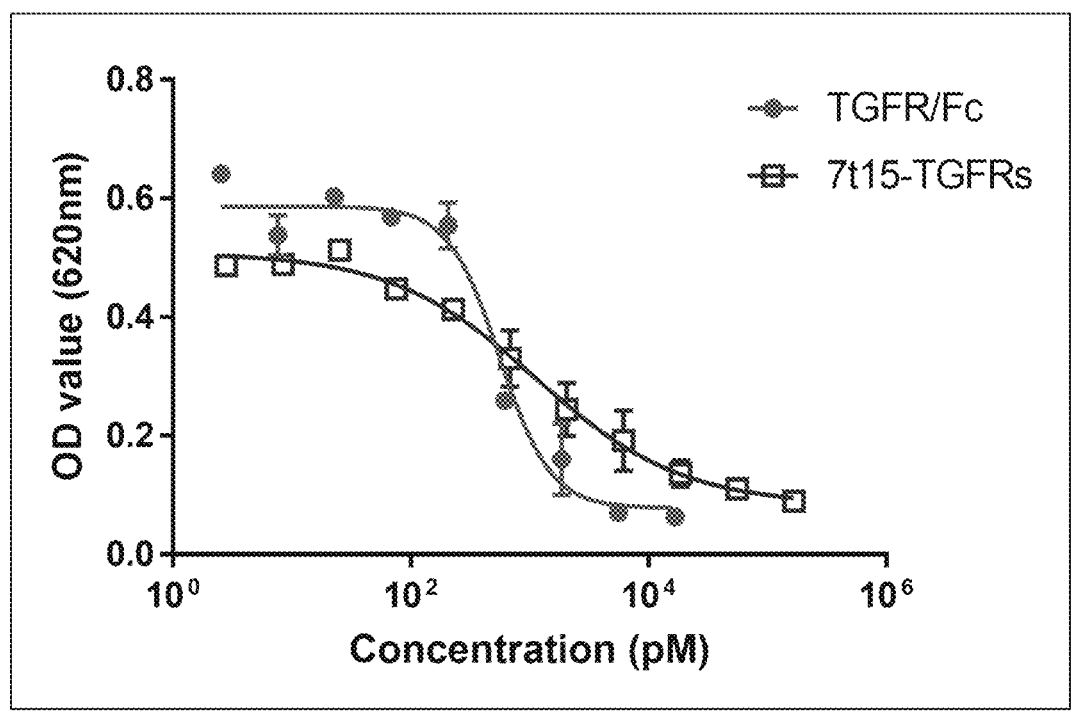
FIG. 101 shows results of TGFβ1 inhibition by 7t15-TGFRs and TGFR-Fc.
Figure 102A:
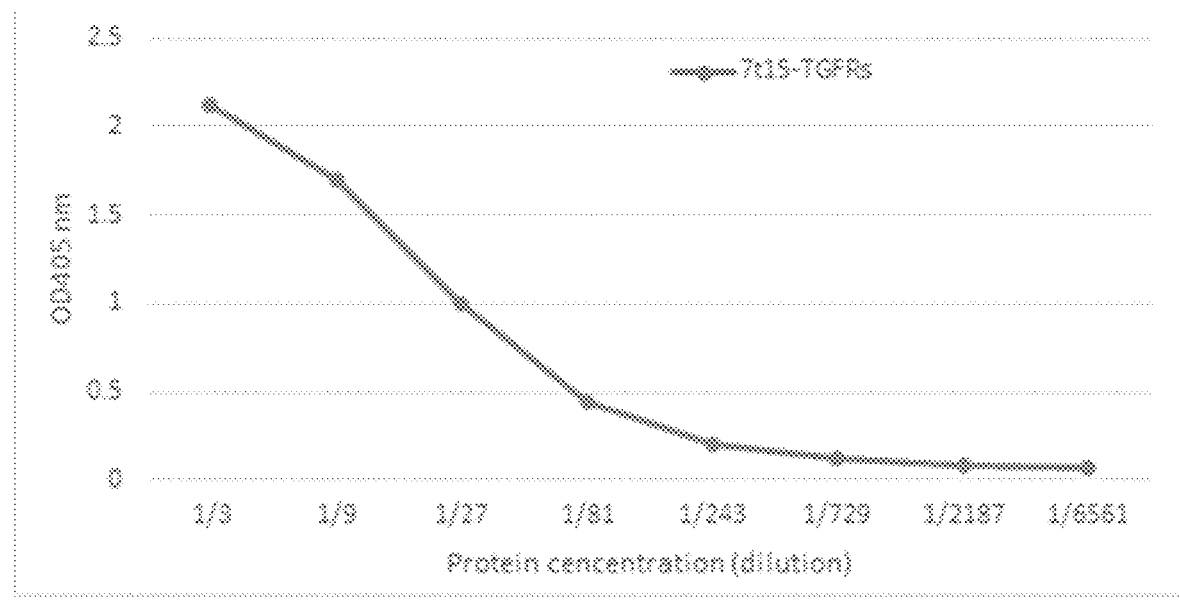
FIGS. 102A-102C show detection of IL-15, TGFβRII, and IL-7 in 7t15-TGFRs with ELISA.
Figure 102B:
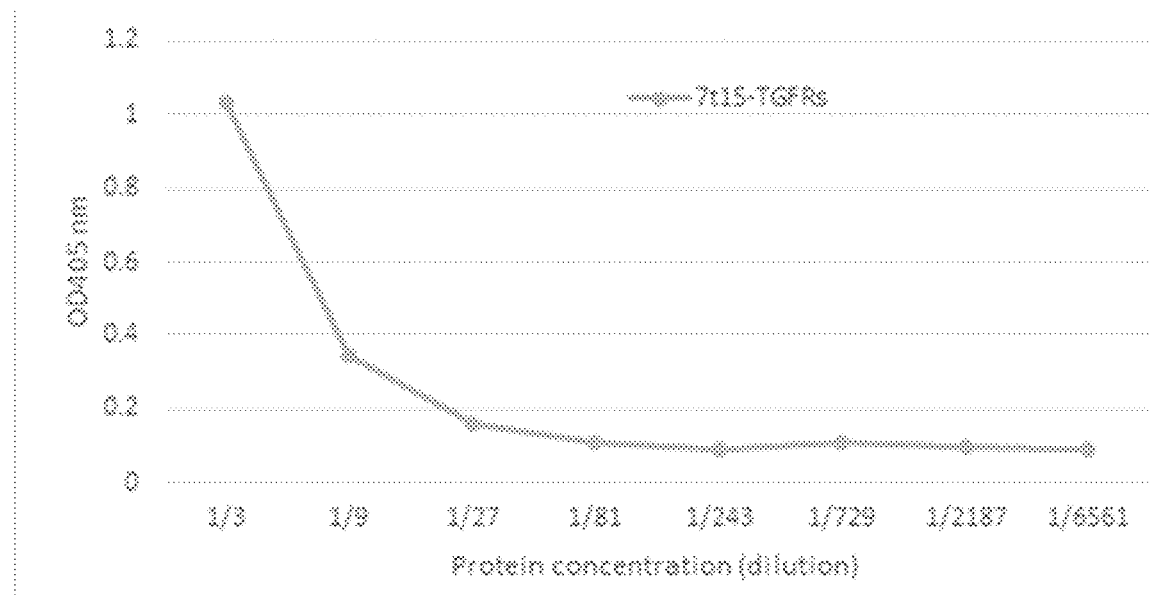
Figure 102C:
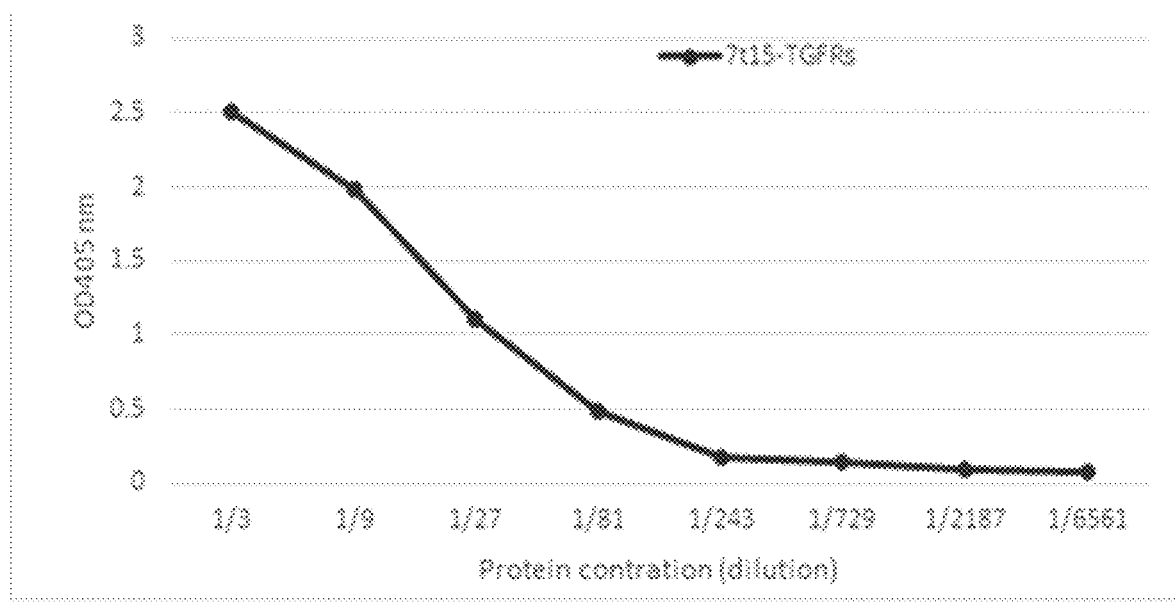

A 96-well plate was coated with 100 μL (8 μg/mL) of anti-TF IgG1 in R5 (coating buffer) and incubated at room temperature (RT) for 2 hrs. The plates were washed three times and blocked with 100 µL of 1% BSA in PBS. Serial dilution of 7t15-TGFRs (1:3 ratio) was added, and incubated at RT for 60 mins. After 3 washes, 50 ng/mL of biotinylated-anti-IL-15 antibody (BAM247, R&D Systems), 200 ng/mL of biotinylated-anti-TGFbRII antibody (BAF241, R&D Systems), or 500 ng/mL of biotinylated-anti-IL-7 antibody (506602, R&D Systems) was added and incubated at RT for 60 min. Following three washes, incubation with 0.25 µg/mL of HRP-SA (Jackson ImmunoResearch) at 100 µL per well was carried out for 30 min at RT, followed by 4 washes and incubation with 100 µL of ABTS for 2 mins at RT. Absorbance was read at 405 nm. The data are shown in FIG. 101. As shown in FIGS. 102A-102C, the IL-15, TGFR, and IL-7 in 7t15-TGFRs were detected by the respective antibodies.

Figure 103:
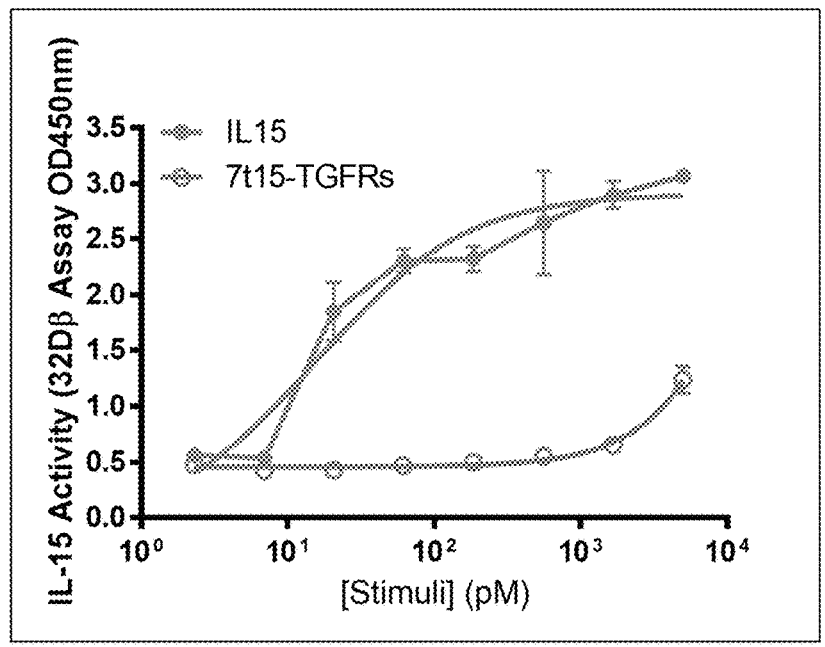
FIG. 103 shows results of a 32Dβ cell proliferation assay with 7t15-TGFRs or recombinant IL-15.

The IL-15 in 7t15-TGFRs Promotes IL-2Rβ and Common γ Chain Containing 32Dβ Cell Proliferation To evaluate the activity of IL-15 in 7t15-TGFRs, 7t15-TGFRs was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted 7t15-TGFRs or IL-15 were added to the cells (FIG. 103). Cells were incubated in a $CO_2$ incubator at 37° C. for 3 days. Cell proliferation was detected by adding 10 µL of WST1 to each well on day 3 and incubating for an additional 3 hours in a $CO_2$ incubator at 37° C. The amount of formazan dye produced was analyzed by measuring the absorbance at 450 nm. As shown in FIG. 103, 7t15-TGFRs and IL-15 promoted 32Dβ cell proliferation, with the $EC_{50}$ of 7t15-TGFRs and IL-15 being 126 nM and 16.63 pM, respectively.

Figure 104:
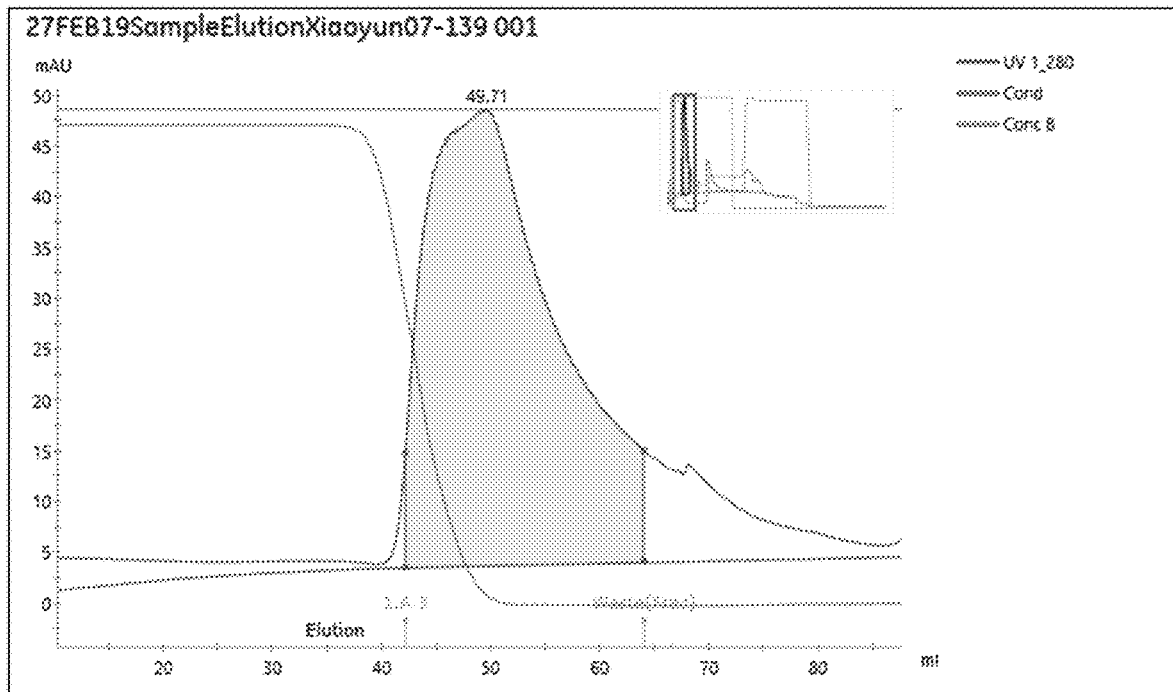
FIG. 104 is a line graph showing the chromatographic profile of 7t15-TGFRs protein containing cell culture supernatant following binding and elution on anti-TF antibody affinity column.

Purification Elution Chromatograph of 7t15-TGFRs Using Anti-TF Antibody Affinity Column 7t15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 104, the anti-TF antibody affinity column can bind 7t15-TGFRs which contains TF as a fusion partner of 7t15-TGFRs. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE Analysis of 7t15-TGFRs

To determine the purity and molecular weight of the protein, 7t15-TGFRs protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 105:
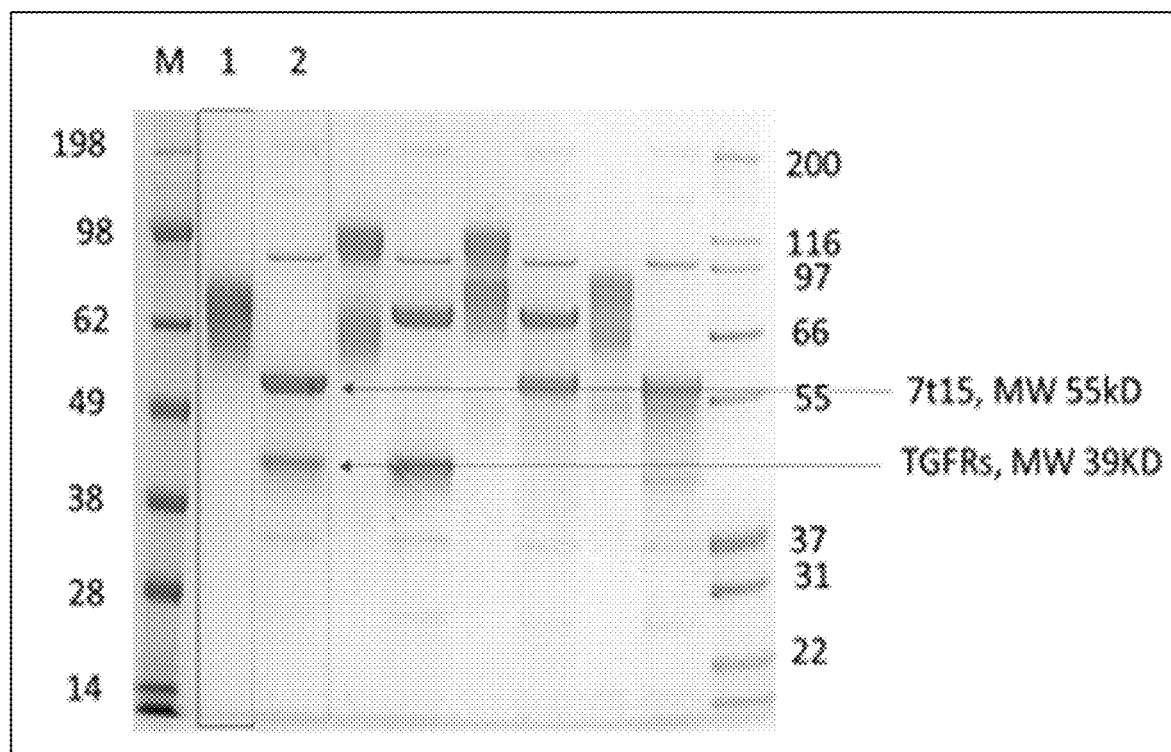
FIG. 105 shows 7t15-TGFRs before and after deglycosylation as analyzed using reduced SDS-PAGE.

To verify that the 7t15-TGFRs protein undergoes glycosylation after translation in CHO cells, a deglycosylation experiment was conducted using the Protein Deglycosylation Mix II kit from New England Biolabs and the manufacturer's instructions. FIG. 105 shows reduced SDS-PAGE analysis of the sample in non-deglycosylated (lane 1 in red outline) and deglycosylated (lane 2 in yellow outline) state. These results showed that the protein is glycosylated when it is expressed in CHO cells. After deglycosylation, the purified sample showed expected molecular weights (55 kDa and 39 kDa) in reduced SDS gel. Lane M was loaded with 10 ul of SeeBlue Plus2 Prestained Standard.

Characterization of 7t15-TGFRs

7t15-TGFRs is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of single chain two TGFβRII domains and sushi domain of human IL-15 receptor alpha chain (TGFRs).

Figure 106:
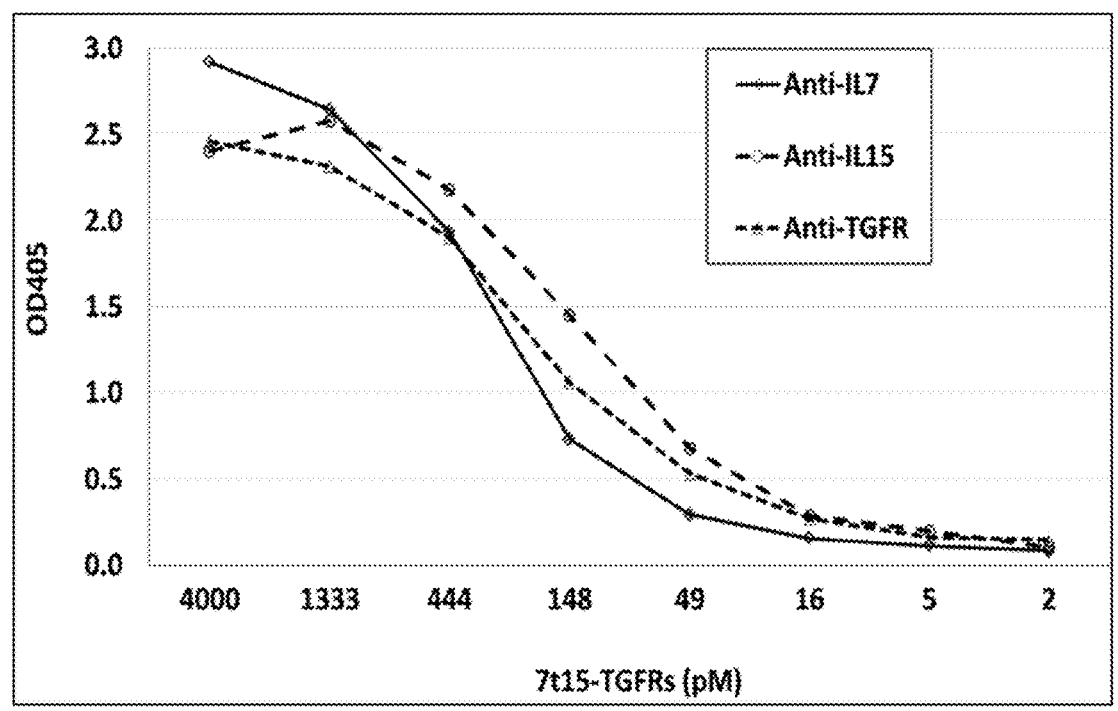
FIG. 106 shows ELISA detection of IL-7, IL-15 and TGFβRII in the 7t15-TGFRs protein.

CHO cells were co-transfected with 7t15 and TGFRs vectors. The 7t15-TGFRs complex was purified from the transfected CHO cell culture supernatant. The IL-7, IL-15, TGFβ receptor and tissue factor (TF) components were demonstrated in the complex by ELISA as shown in FIG. 106. A humanized anti-TF monoclonal antibody (anti-TF IgG1) was used as the capture antibody to determine TF in 7t15-TGFRs, and biotinylated antibodies against human IL-15 antibody (R&D systems), human IL-7 (Biolegend), anti-TGFβ receptor (R&D Systems) were used as the detection antibodies to respectively determine IL-7, IL-15 and TGFβ receptor in 7t15-TGFRs. Peroxidase conjugated streptavidin (Jackson ImmunoResearch Lab) and ABTS substrate (Surmodics IVD, Inc.) were then used to detect the bound biotinylated antibodies. The results were analyzed by ELISA (FIG. 106).

In Vivo Characterization of 7t15-TGFRs in C57BL/6 Mice

Figure 107A:
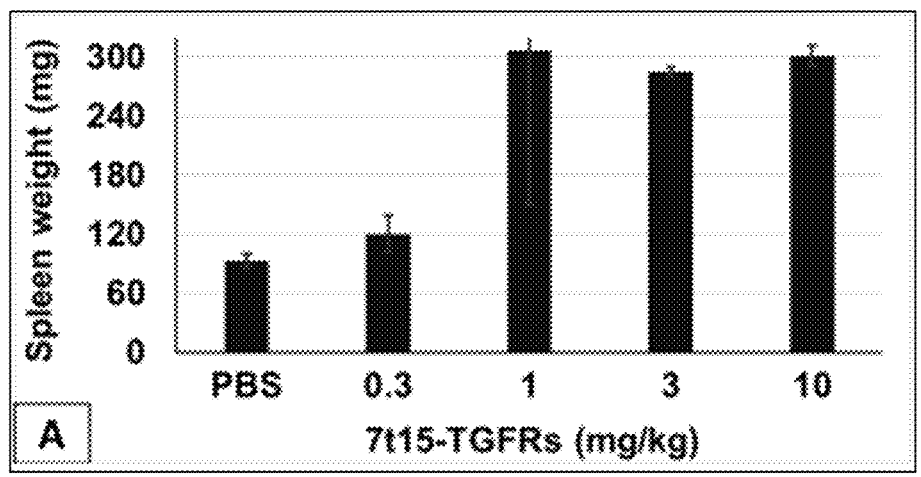
FIGS. 107A and 107B show spleen weight and the percentages of immune cell types in 7t15-TGFRs-treated and control-treated mice.
Figure 107B:
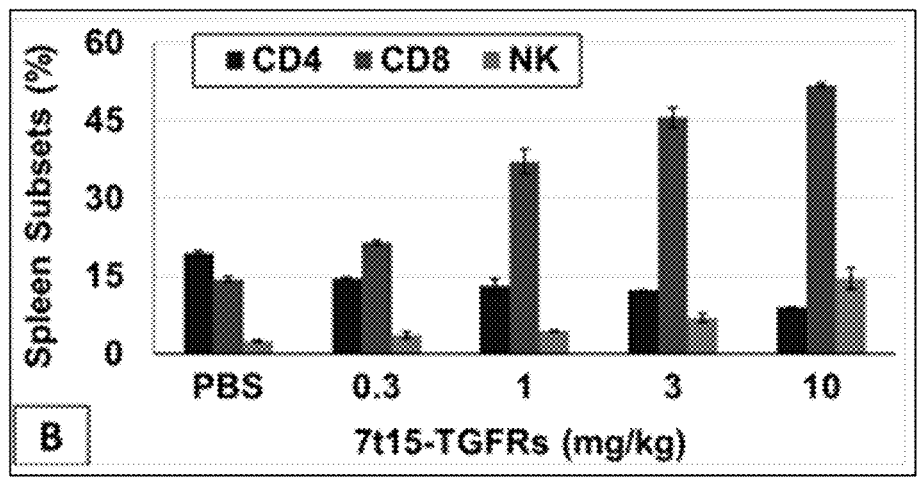
Figure 108A:
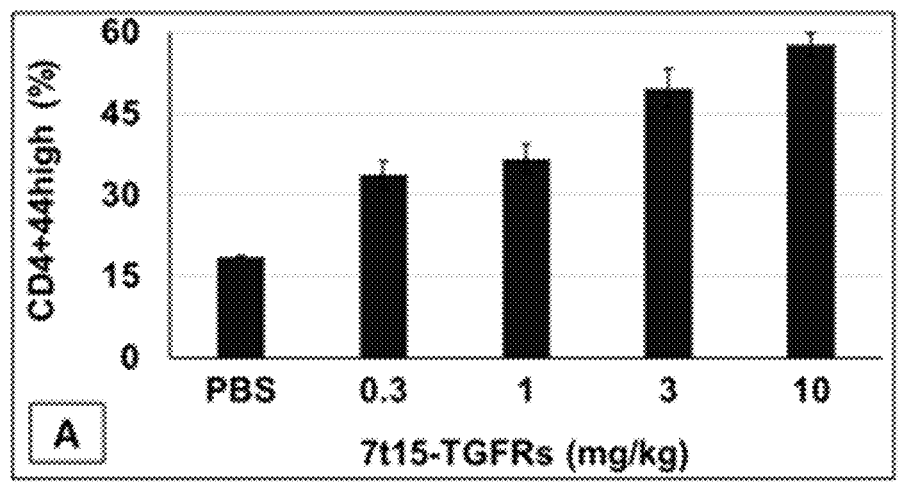
FIGS. 108A and 108B show upregulation of CD44 expression of CD4$^+$ and CD8$^+$ T cells by 7t15-TGFRs in C57BL/6 mice.
Figure 108B:
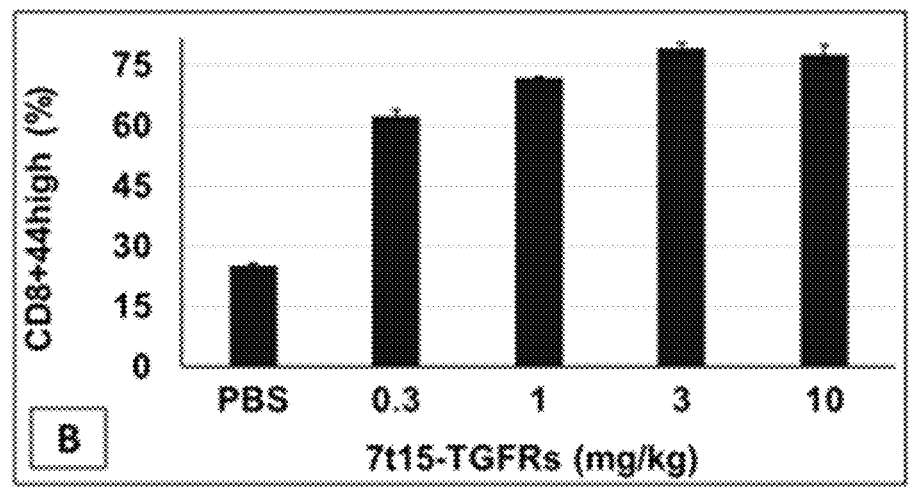

To determine the immunostimulatory activity of 7t15-TGFRs in vivo, C57BL/6 mice were subcutaneously treated with control solution (PBS) or 7t15-TGFRs at 0.3, 1, 3 and 10 mg/kg. The treated mice were euthanized. The mouse spleens were collected and weighed day 4 post treatment. Single splenocyte suspensions were prepared and stained with fluorochrome-conjugated anti-CD4, anti-CD8, and anti-NK1.1 antibodies and the percentage of CD4+ T cells, CD8+ T cells, and NK cells was analyzed by flow cytometry. The results showed that 7t15-TGFRs was effective at expanding splenocytes based on spleen weight (FIG. 107A), especially at 1-10 mg/kg. The percentages of CD8+ T cells and NK cells were higher compared to control-treated mice (FIG. 107B) at all doses tested.

CD44 Expression of CD4+ and CD8+ T Cells

It has been known that IL-15 induces CD44 expression on T cells and development of memory T cells. CD44 expression of CD4+ and CD8+ T cells in the 7t15-TGFRs treated mice were assessed. C57BL/6 mice were subcutaneously treated with 7t15-TGFRs. The splenocytes were stained with fluorochrome-conjugated anti-CD4, anti-CD8 and anti-CD44 monoclonal antibodies for immunocyte subsets. The percentages of CD4+CD44$^{high}$ T cells of total CD4+ T cells and CD8+ CD44$^{high}$ T cells of total CD8+ T cells were analyzed by flow cytometry. As shown in FIGS. 108A and 108B, 7t15-TGFRs significantly activated CD4+ and CD8+ T cells to differentiate into memory T cells.

Figure 109A:
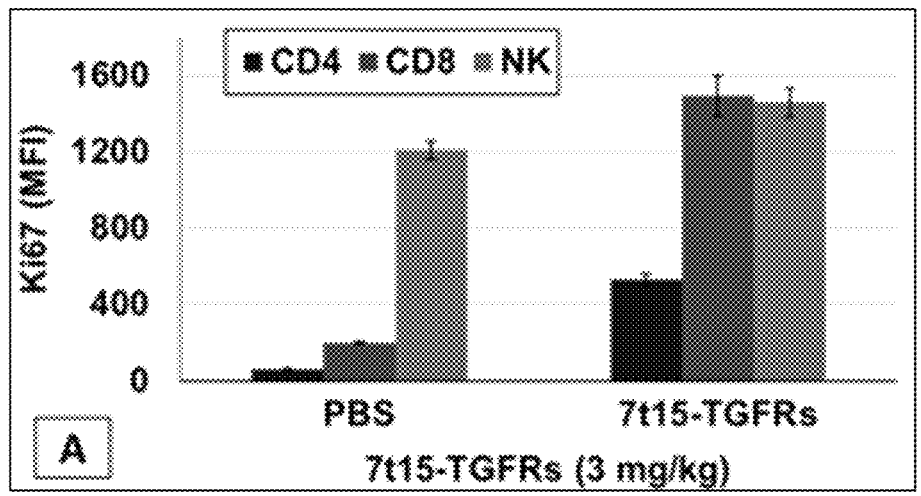
FIGS. 109A and 109B show upregulation of Ki67 expression and Granzyme B expression of CD8$^+$ T cells and NK Cells by 7t15-TGFRs in C57BL/6 mice.
Figure 109B:
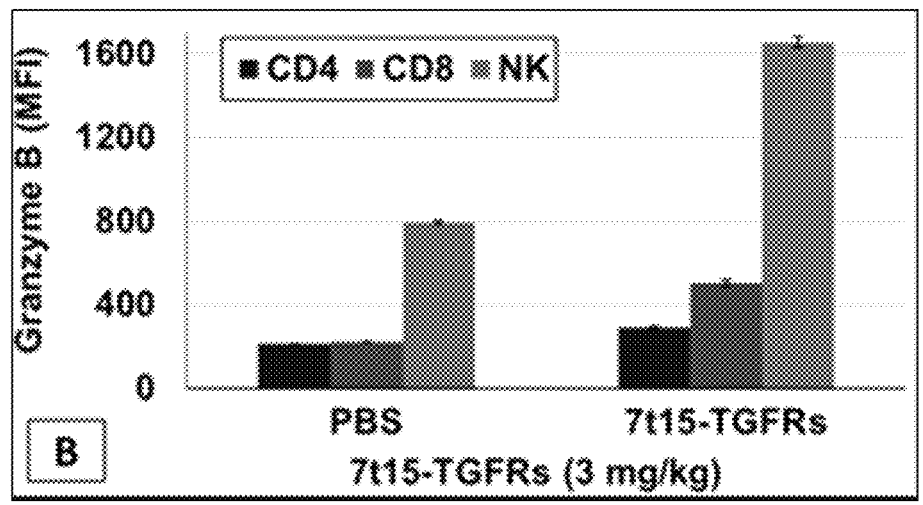

Furthermore, the dynamic proliferation of immune cells based on Ki67 expression of splenocytes and cytotoxicity potential based on granzyme B expression of the splenocytes induced by 7t15-TGFRs after the single dose treatment of mouse were also evaluated. C57BL/6 mice were subcutaneously treated with 7t15-TGFRs at 3 mg/kg. The treated mice were euthanized and the splenocytes were prepared. The prepared splenocytes were stained with fluorochrome-conjugated anti-CD4, anti-CD8, and anti-NK1.1 (NK) antibodies for immunocyte subsets and then intracellularly stained with anti-Ki67 antibody for cell proliferation and anti-granzyme B antibody for cytotoxic marker. The mean fluorescent intensity (MFI) of Ki67 and granzyme B of corresponding immunocyte subsets was analyzed by flow cytometry. As shown in FIGS. 109A and 109B, in the spleens of mice treated with 7t15-TGFRs, the expression of Ki67 and granzyme B by CD8+ T cells and NK cells increased compared with PBS control treatment. These results demonstrate that 7t15-TGFRs is not only to increase numbers of CD8+ T cells and NK cells but also enhance potential cytotoxicity of these cells.

Figure 110:
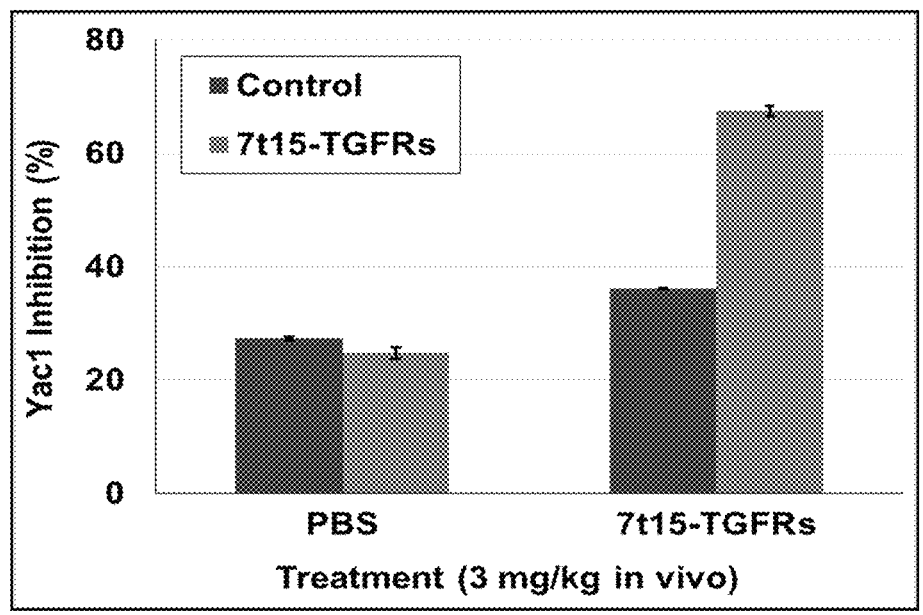
FIG. 110 shows enhancement of cytotoxicity of splenocytes by 7t15-TGFRs in C57BL/6 mice.

Additionally, cytotoxicity of the mouse splenocytes against tumor cells was also evaluated. Mouse Yac-1 cells were labeled with CELLTRACE®, violet dye, and used as tumor target cells. The splenocytes were prepared from 7t15-TGFRs-treated mice and used as effector cells. The target cells were mixed with effector cells at E:T ratio=10:1 in RPMI-10 medium with or without 7t15-TGFRs at 100 nM and incubated at 37° C. for 20 hours. Target Yac-1 cell inhibition was assessed by analysis of viable violet-labeled Yac-1 cells using flow cytometry. Percentage of Yac-1 inhibition was calculated using a formula, (1-viable Yac-1 cell number in experimental sample/viable Yac-1 cell number in the sample without splenocytes)×100. As shown in FIG. 110, 7t15-TGFRs-treated mouse splenocytes had stronger cytotoxicity against Yac-1 cells than the control mouse splenocytes and addition of 7t15-TGFRs during cytotoxic assay further enhanced cytotoxicity of splenocytes against Yac-1 target cells.

Example 56: TGFRt15-21s137L Fusion Protein Generation and Characterization

Figure 111:
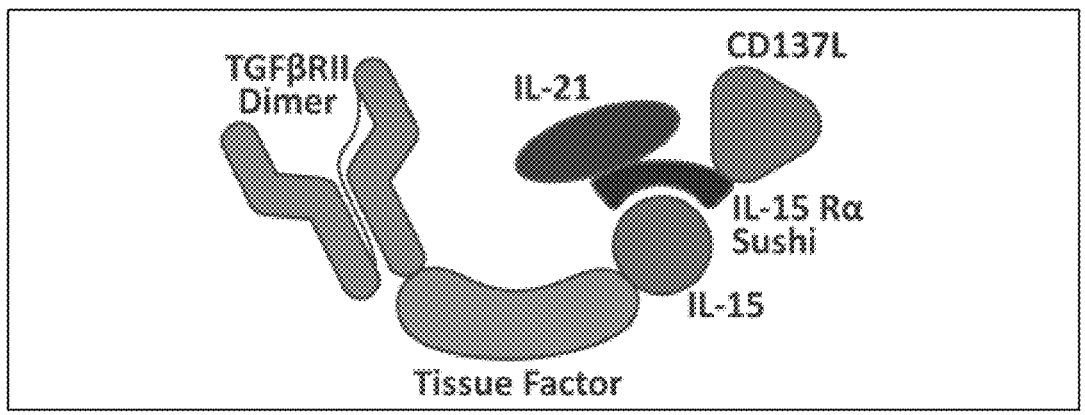
FIG. 111 shows a schematic of the TGFRt15-21s137L construct.
Figure 112:
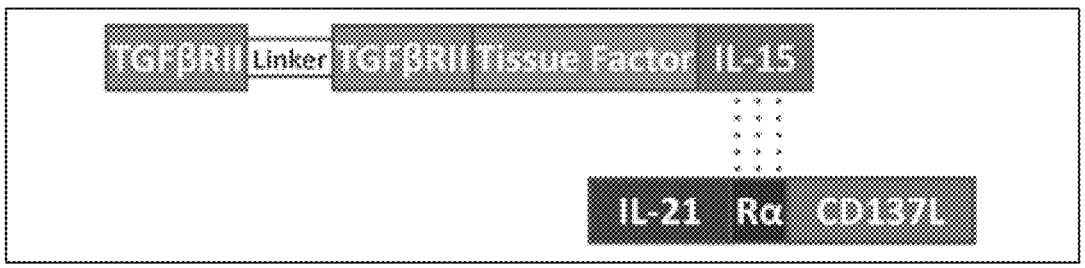
FIG. 112 shows an additional schematic of the TGFRt15-21s137L construct.

A fusion protein complex was generated comprising IL-21/IL-15RαSu/CD137L and TGFβ Receptor IF/TF/IL-15 fusion proteins (FIG. 111 and FIG. 112). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G45(3) linker to generate a single chain version of TGFβ Receptor II and then directly linking to the N-terminus coding region of tissue factor 219 followed by the N-terminus coding region of IL-15.

The nucleic acid sequence of the TGFRt15 construct (including signal peptide effluence) is as follows.

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of TGFRt15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

```
KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

The nucleic acid and protein sequences of the 21s137L are shown below. The nucleic acid sequence of the 21s137L construct (including signal peptide sequence) is as follows:

```
(Signal peptide)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGACCT

GCGGCAGGGCATGTTTGCGCAGCTGGTGGCCCAAAATGTTCTGCTGATCG

ATGGGCCCCTGAGCTGGTACAGTGACCCAGGCCTGGCAGGCGTGTCCCTG

ACGGGGGGCCTGAGCTACAAAGAGGACACGAAGGAGCTGGTGGTGGCCAA

GGCTGGAGTCTACTATGTCTTCTTTCAACTAGAGCTGCGGCGCGTGGTGG

CCGGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCACC

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTC

GGAA
```

The amino acid sequence of 21s137L fusion protein (including the leader sequence) is as follows:

```
(Signal peptide)
MKWVTFISLLFLFSSAYS (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLNK

ATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGVSL

TGGLSYKEDTKELVVAKAGVYYVFFQLELRRVVAGEGSGSVSLALHLQPL

RSAAGAAALALTVDLPPASSEARNSAFGFQGRLLHLSAGQRLGVHLHTEA

RARHAWQLTQGATVLGLFRVTPEIPAGLPSPRSE
```

In some cases, the leader peptide is cleaved from the intact polypeptide to generate the mature form that may be soluble or secreted.

The IL-21/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15: IL-21/IL-15RαSu/CD137L protein complex (referred to as TGFRt15-21s137L), which can be purified by anti-TF IgG1 affinity and other chromatography methods.

Figure 113:
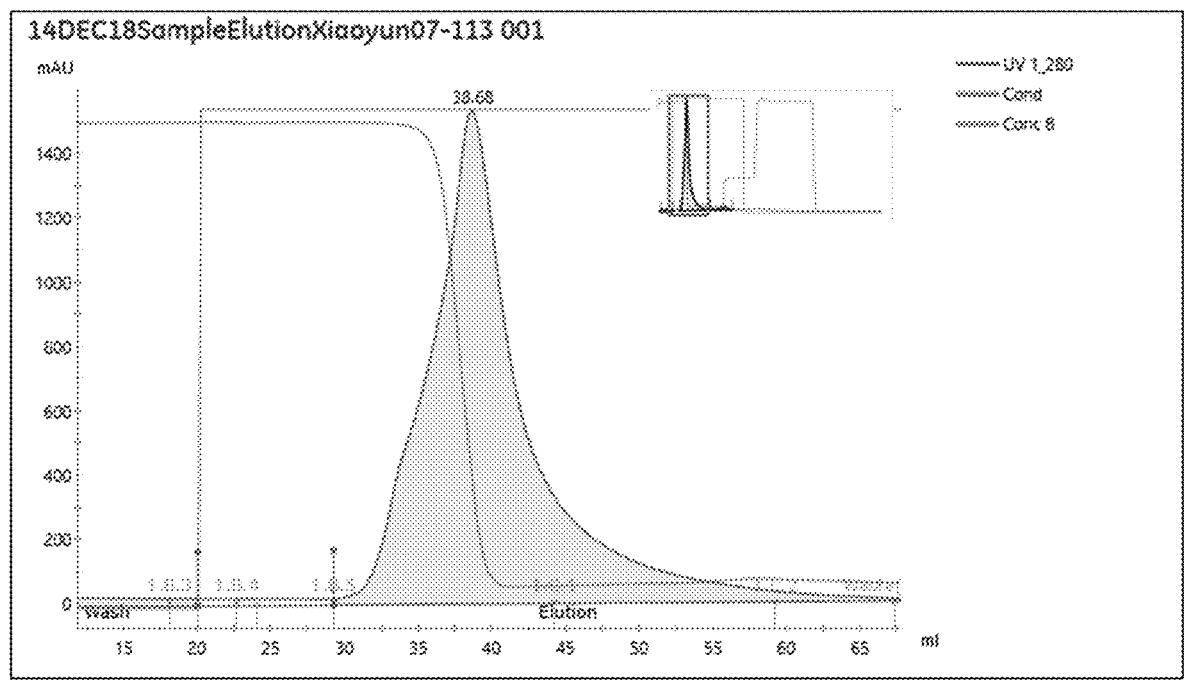
FIG. 113 is a line graph showing the chromatographic profile of TGFRt15-21s137L protein containing cell culture supernatant following binding and elution on anti-TF antibody affinity column.

Purification Elution Chromatograph of TGFRt15-21s137L Using Anti-TF Antibody Affinity Column TGFRt15-21s137L harvest from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 113, the anti-TF antibody affinity column bound to TGFRt15-21s137L which contains TF as a fusion partner of TGFRt15-21s137L. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Example 57: TGFRt15-TGFRs21 Fusion Protein Generation and Characterization

Figure 114:
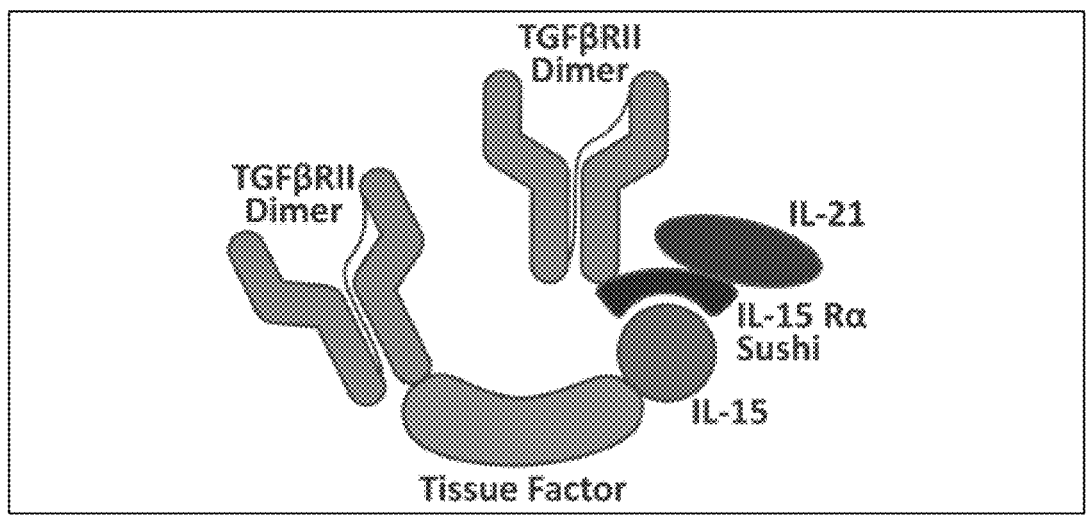
FIG. 114 shows a schematic of the TGFRt15-TGFRs21 construct.
Figure 115:
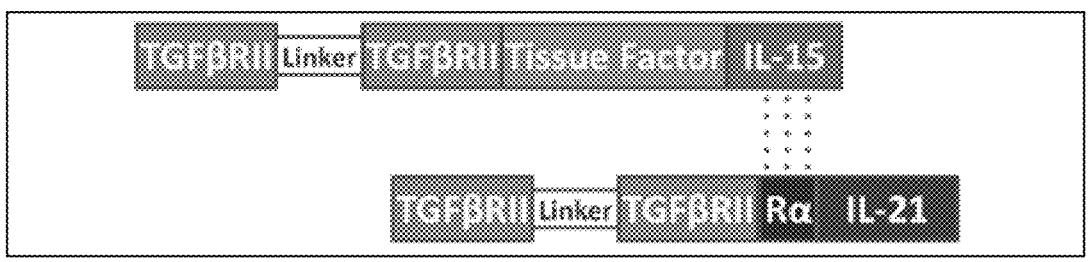
FIG. 115 shows an additional schematic of the TGFRt15-TGFRs21 construct.

A fusion protein complex was generated comprising of TGFβ Receptor II/IL-15RαSu/IL-21 and TGFβ Receptor II/TF/IL-15 fusion proteins (FIG. 114 and FIG. 115). The human TGFβ Receptor II (Ile24-Asp159), tissue factor 219, IL-21, and IL-15 sequences were obtained from the UniProt website and DNA for these sequences was synthesized by Genewiz. Specifically, a construct was made linking two TGFβ Receptor II sequences with a G45(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCCGTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

The amino acid sequence of TGFRt15 fusion protein (including the leader sequence) is as follows:

```
(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE
```

(Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Constructs were also made by attaching two TGFβ Receptor II directly to the IL-15RαSu chain, followed by the N-terminus coding region of IL-21, which was synthesized by Genewiz. The nucleic acid and protein sequences of a construct comprising the TGFβ Receptor II linked to the N-terminus of IL-15RαSu following with the N-terminus of IL-21 are shown below.

The nucleic acid sequence of the TGFRs21 construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG (Human IL-21)
CAAGGTCAAGATCGCCACATGATTAGAATGCGTCAACTTATAGATATTGT

TGATCAGCTGAAAAATTATGTGAATGACTTGGTCCCTGAATTTCTGCCAG

CTCCAGAAGATGTAGAGACAAACTGTGAGTGGTCAGCTTTTTCCTGTTTT

CAGAAGGCCCAACTAAAGTCAGCAAATACAGGAAACAATGAAAGGATAAT

CAATGTATCAATTAAAAAGCTGAAGAGGAAACCACCTTCCACAAATGCAG

GGAGAAGACAGAAACACAGACTAACATGCCCTTCATGTGATTCTTATGAG

AAAAAACCACCCAAAGAATTCCTAGAAAGATTCAAATCACTTCTCCAAAA

GATGATTCATCAGCATCTGTCCTCTAGAACACACGGAAGTGAAGATTCC

The amino acid sequence of TGFRs21 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNKA

TNVAHWTTPSLKCIR (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS

In some cases, the leader peptide is cleaved from the intact polypeptide to generate the mature form that may be soluble or secreted.

The TGFR/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/IL-21 protein complex (referred to as TGFRt15-TGFRs21), which can be purified by anti-TF antibody IgG1 affinity and other chromatography methods.

Figure 116:
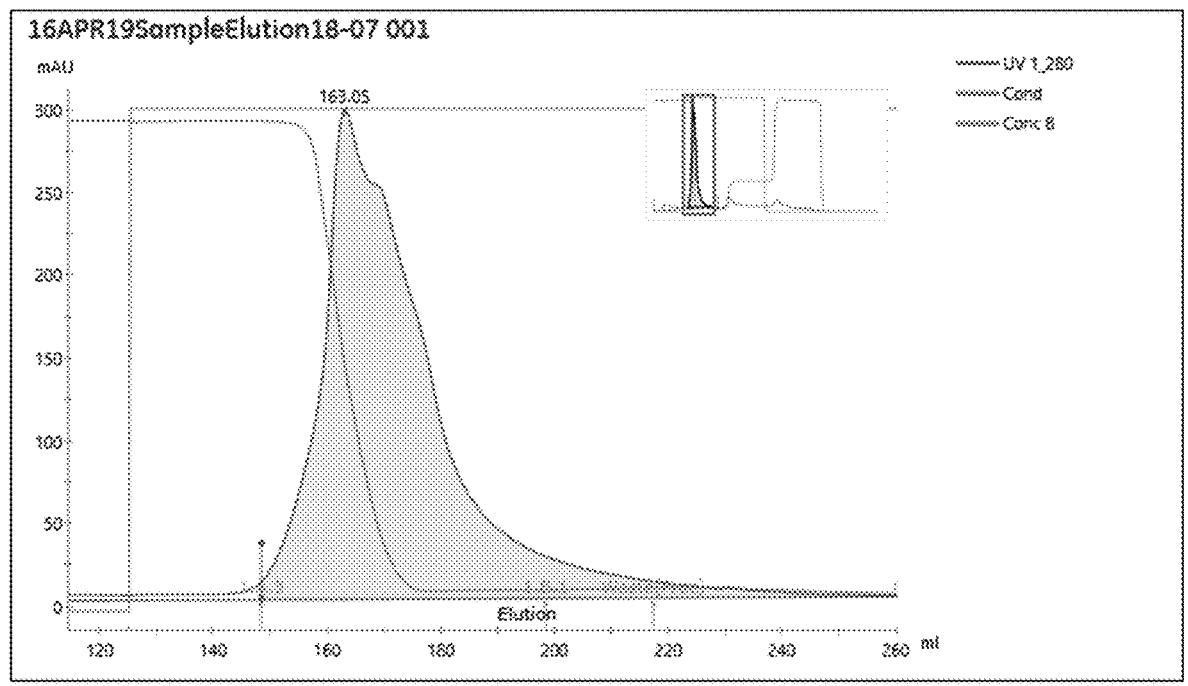
FIG. 116 is a line graph showing the chromatographic profile of TGFRt15-TGFRs21 protein containing cell culture supernatant following binding and elution on anti-TF antibody affinity column.

Purification Elution Chromatograph of TGFRt15-TGFRs21 Using Anti-TF Antibody Affinity Column TGFRt15-TGFRs21 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 116, the anti-TF antibody affinity column bound to TGFRt15-TGFRs21 which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS PAGE Analysis of TGFRt15-TGFRs21

To determine the purity and molecular weight of the protein, TGFRt15-TGFRs21 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 117:
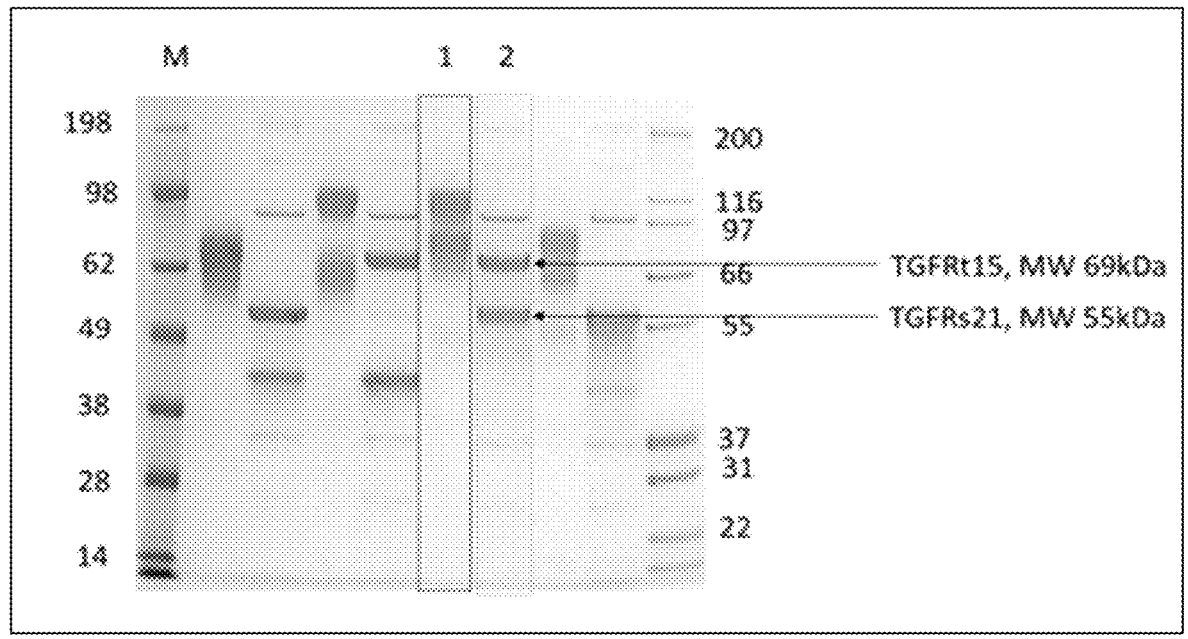
FIG. 117 shows TGFRt15-TGFRs21 before and after deglycosylation as analyzed by reduced SDS-PAGE.

To verify that the TGFRt15-TGFRs21 protein undergoes glycosylation after translation in CHO cells, a deglycosylation experiment was conducted using the Protein Deglycosylation Mix II kit from New England Biolabs and the manufacturer's instructions. FIG. 117 shows the reduced SDS-PAGE analysis of the sample in non-deglycosylated (lane 1 in red outline) and deglycosylated (lane 2 in yellow outline) state. It is clear that the protein is glycosylated when it is expressed in CHO cells. After deglycosylation, the purified sample showed expected molecular weights (69 kDa and 55 kDa) in reduced SDS gel. Lane M was loaded with 10 ul of SeeBlue Plus2 Prestained Standard.

Immunostimulation of TGFRt15-TGFRs21 in C57BL/6 Mice

TGFRt15-TGFRs21 is a multi-chain polypeptide (a type A multi-chain polypeptide described herein) that includes the first polypeptide that is a soluble fusion of single chain two TGFβRII domains, human tissue factor 219 fragment and human IL-15 (TGFRt15), and the second polypeptide that is a soluble fusion of single chain two TGFβRII domains, sushi domain of human IL-15 receptor alpha chain and human IL-21 (TGFRs21).

Figure 118A:
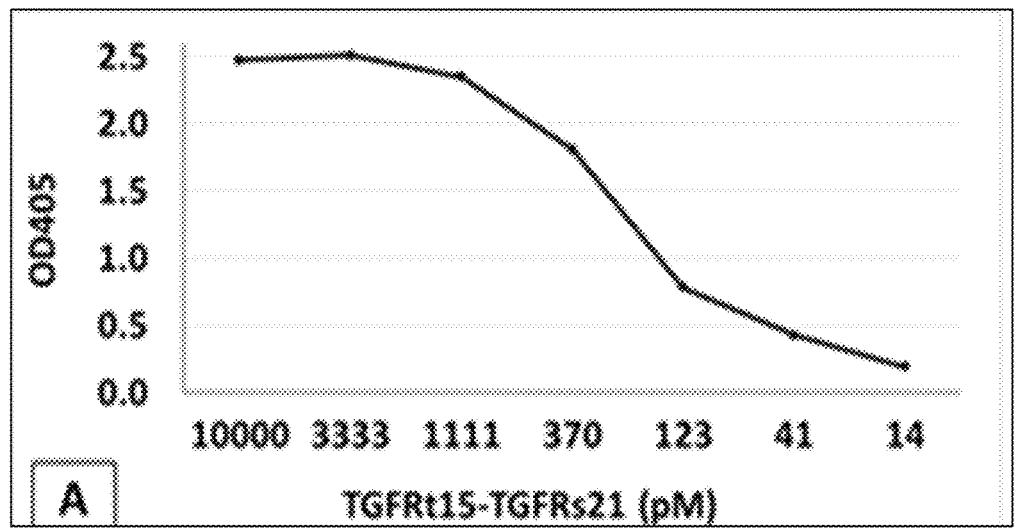
FIGS. 118A and 118B show detection of components of TGFRt15-TGFRs21 using ELISA.
Figure 118B:
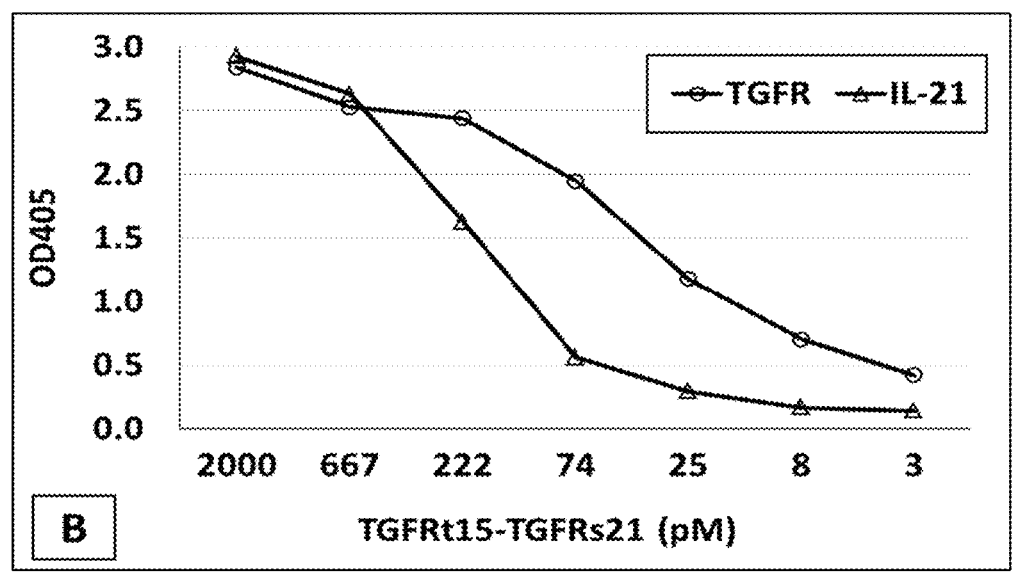

CHO cells were co-transfected with TGFRt15 and TGFRs21 vectors. The TGFRt15-TGFRs21 complex was purified from the transfected CHO cell culture supernatant. The TGFβ receptor, IL-15, IL-21 and tissue factor (TF) components were demonstrated in the complex by ELISA as shown in FIG. 118A-B. A humanized anti-TF monoclonal antibody (anti-TF IgG1) was used as the capture antibody to determine TF in TGFRt15-TGFRs21, biotinylated anti-human IL-15 antibody (R&D systems), biotinylated anti-human TGFβ receptor antibody (R&D systems, and biotinylated anti-human IL-21 antibody (R&D Systems) were used as the detection antibodies to respectively determine IL-15, TGFβ receptor, and IL-21 in TGFRt15-TGFRs21. For detection, peroxidase conjugated streptavidin (Jackson ImmunoResearch Lab) and ABTS were used.

Figure 119A:
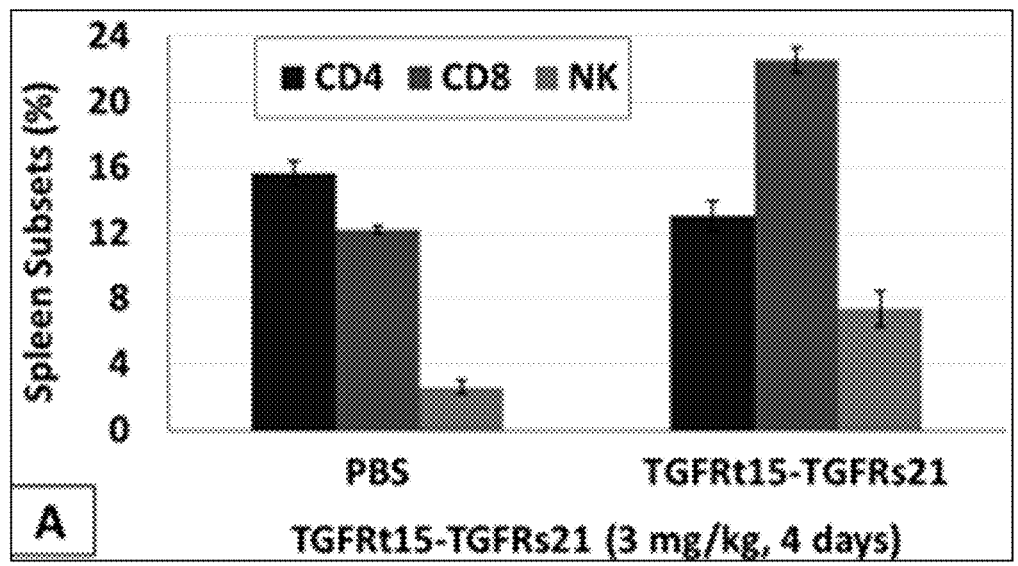
FIGS. 119A and 119B show the percentages and proliferation of CD4$^+$ T cells, CD8$^+$ T cells, and natural killer (NK) cells present in the spleen of control-treated and TGFRt15-TGFRs21-treated mice.
Figure 119B:
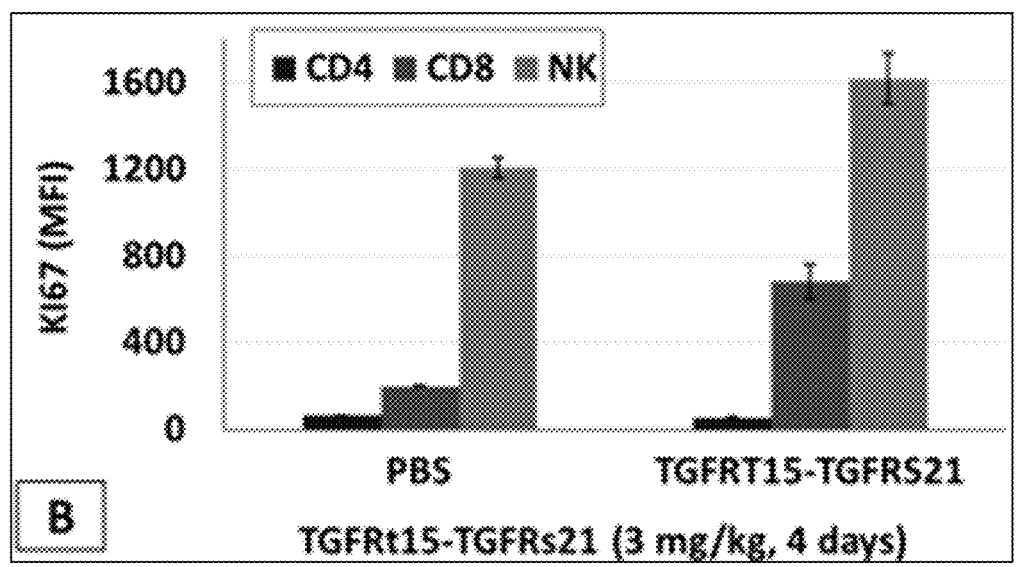
Figure 120:
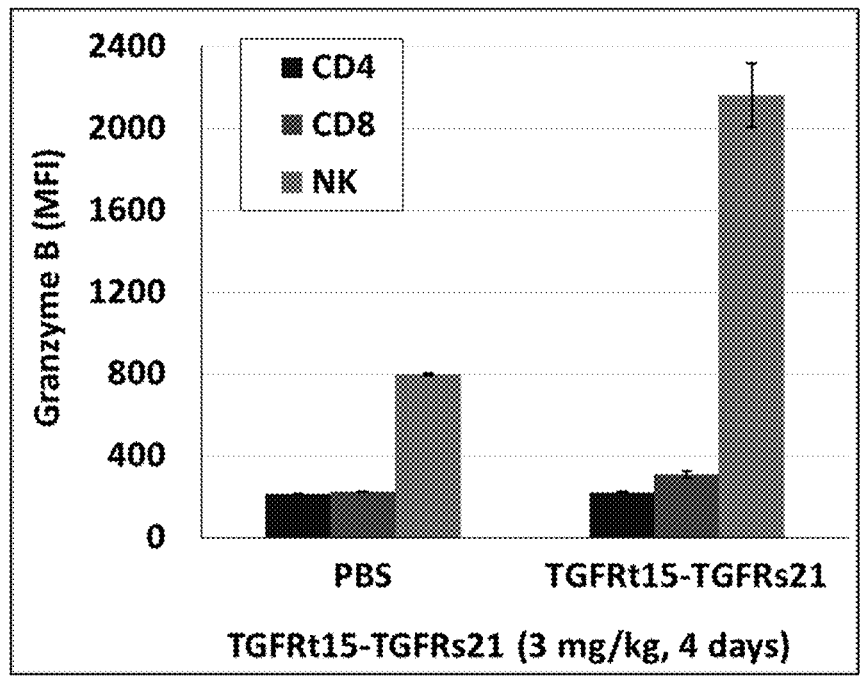
FIG. 120 shows upregulation of Granzyme B expression of splenocytes in mice treated with TGFRt15-TGFRs21.

Wild type C57BL/6 mice were treated subcutaneously with either control solution (PBS) or with TGFRt15-TGFRs21 at 3 mg/kg. Four days after treatment, spleen weight and the percentages of various immune cell types present in the spleen were evaluated. As shown in FIG. 119A, the percentages of CD4$^+$ T cells, CD8$^+$ T cells, and NK cells present in the spleen of control-treated and TGFRt15-TGFRs21-treated mice were evaluated. The dynamic proliferation of immune cells based on Ki67 expression after TGFRt15-TGFRs21 treatment was also evaluated. The splenocytes were stained with fluorochrome-conjugated anti-CD4, anti-CD8, and anti-NK1.1 (NK) antibodies and then intracellularly stained with anti-Ki67 antibody. The percentage of CD4$^+$ T cells, CD8$^+$ T cells, and NK cells and the mean fluorescent intensity (MFI) of Ki67 of corresponding immunocyte subsets were analyzed by flow cytometry (FIGS. 119A and 119B). Furthermore, cytotoxicity potential based on granzyme B expression of the splenocytes induced by TGFRt15-TGFRs21 after the single dose treatment of mouse was also evaluated. As shown in FIG. 120, in the spleens of mice treated with TGFRt15-TGFRs21, the expression of granzyme B by NK cells increased after treatment. The splenocytes from TGFRt15-TGFRs21-treated mice were stained with fluorochrome-conjugated anti-CD4, anti-CD8, and anti-NK1.1 (NK) antibodies and then intracellularly stained with anti-granzyme B antibody. The mean fluorescent intensity (MFI) of granzyme B of corresponding immunocyte subsets was analyzed by flow cytometry (FIG. 120).

As shown in FIG. 119A, in the spleens of mice treated with TGFRt15-TGFRs21, the percentages of CD8$^+$ T cells and NK cells both increased on day 4 after a single TGFRt15-TGFRs21 treatment. These results demonstrate that TGFRt15-TGFRs21 is able to induce immune cells to proliferate in mouse spleen, in particular CD8$^+$ T cells and NK cells.

Figure 121:
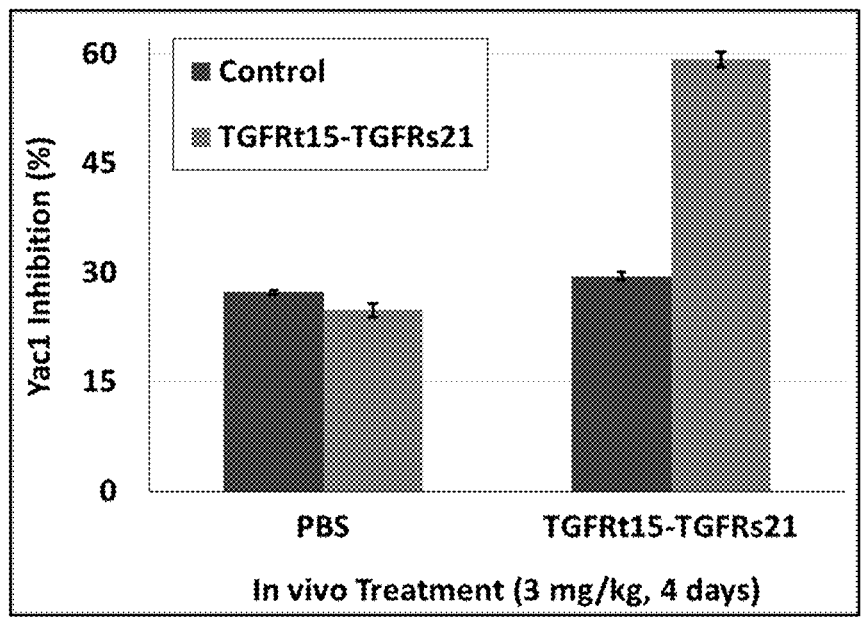
FIG. 121 shows enhancement of cytotoxicity of splenocytes by TGFRt15-TGFRs21 in C57BL/6 Mice.

Additionally, cytotoxicity of the mouse splenocytes against tumor cells was also evaluated. Mouse Yac-1 cells were labeled with CELLTRACE®, violet dye, and used as tumor target cells. The splenocytes were prepared from TGFRt15-TGFRs21-treated mice and used as effector cells. The target cells were mixed with effector cells at E:T ratio=10:1 in RPMI-10 medium with or without TGFRt15-TGFRs21 at 100 nM and incubated at 37° C. for 24 hours. Target Yac-1 cell inhibition was assessed by analysis of viable violet-labeled Yac-1 cells using flow cytometry. Percentage of Yac-1 inhibition was calculated using a formula, (1-[viable Yac-1 cell number in experimental sample]/[viable Yac-1 cell number in the sample without splenocytes])× 100. As shown in FIG. 121, TGFRt15-TGFRs21-treated mouse splenocytes had stronger cytotoxicity against Yac-1 cells than the control mouse cells in the presence of TGFRt15-TGFRs21 during cytotoxic assay (FIG. 121).

Example 58: TGFRt15-TGFRs16 Fusion Protein Generation

Figure 122:
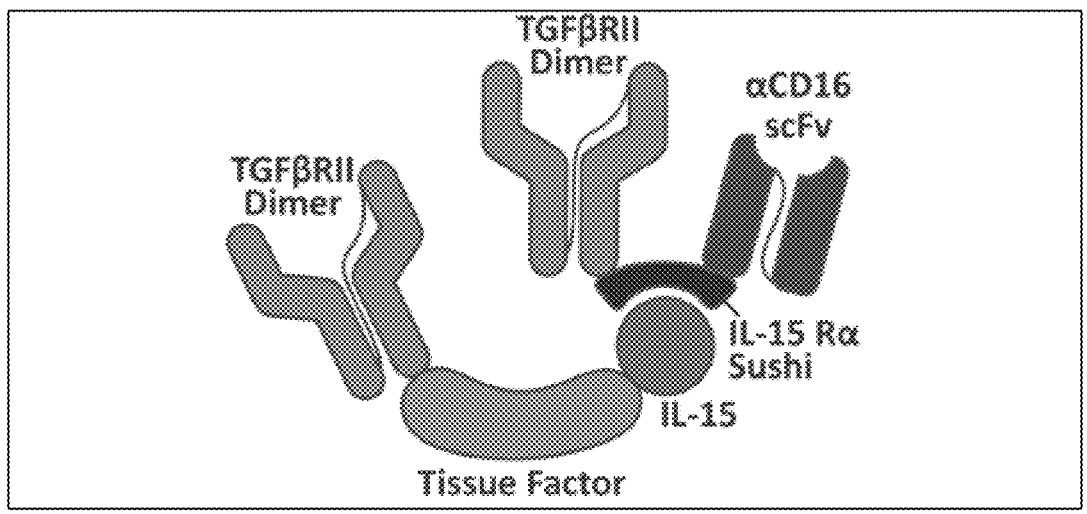
Figure 123:
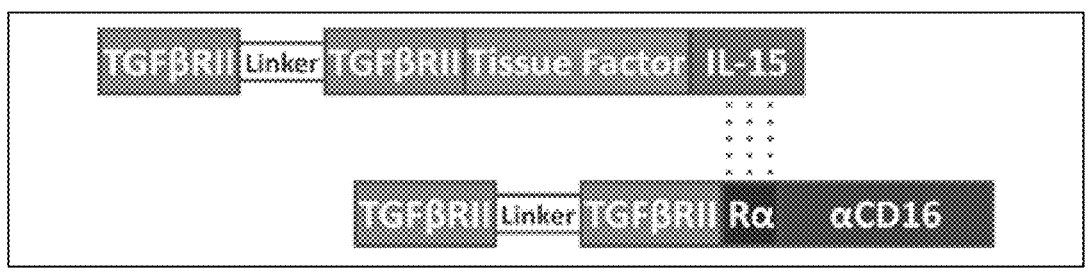

A fusion protein complex was generated comprising of TGFβ Receptor II/IL-15RαSu/anti-CD16scFv and TGFβ Receptor II/TF/IL-15 fusion proteins (FIG. 122 and FIG. 123). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G45(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCTA

CTCC (Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC
```

```
ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

The amino acid sequence of TGFRtl5 fusion protein (including the leader sequence) is as follows:

```
(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

Constructs were also made by attaching two TGFβ Receptor II directly to the IL-15RαSu chain, followed by the anti-CD16scFv sequence, which was synthesized by Genewiz. The nucleic acid and protein sequences of a construct comprising the TGFβ Receptor II linked to the N-terminus of IL-15RαSu following with the anti-CD16scFv sequence are shown below.

The nucleic acid sequence of the TGFRs16 construct (including signal peptide sequence) is as follows:

```
(Signal peptide)
ATGAAGTGGGTGACCTTCATCAGCCTGCTGTTCCTGTTCTCCAGCGCCTA

CTCC (Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC
```

-continued
TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG (Anti-human CD16scFv)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCATGGCGGCGGCGGCTCCGGAGGCGGCGG

CAGCGGCGGAGGAGGATCCGAGGTGCAGCTGGTGGAGTCCGGAGGAGGAG

TGGTGAGGCCTGGAGGCTCCCTGAGGCTGAGCTGTGCTGCCTCCGGCTTC

ACCTTCGACGACTACGGCATGTCCTGGGTGAGGCAGGCTCCTGGAAAGGG

CCTGGAGTGGGTGTCCGGCATCAACTGGAACGGCGGATCCACCGGCTACG

CCGATTCCGTGAAGGGCAGGTTCACCATCAGCAGGGACAACGCCAAGAAC

TCCCTGTACCTGCAGATGAACTCCCTGAGGGCCGAGGACACCGCCGTGTA

CTACTGCGCCAGGGGCAGGTCCCTGCTGTTCGACTACTGGGACAGGGCA

CCCTGGTGACCGTGTCCAGG

The amino acid sequence of TGFRs16 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNKAT

NVAHWTTPSLKCIR (Anti-human CD16scFv)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGHGGGGSGGGGSGGGGSEVQLVESGGGVVRPGGSLRLSCAASGF

TFDDYGMSWVRQAPGKGLEWVSGINWNGGSTGYADSVKGRFTISRDNAKN

SLYLQMNSLRAEDTAVYYCARGRSLLFDYWGQGTLVTVSR

In some cases, the leader peptide is cleaved from the intact polypeptide to generate the mature form that may be soluble or secreted.

The TGFR/IL-15RαSu/anti-CD16scFv and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/anti-CD16scFv protein complex (referred to as TGFRt15-TGFRs16), which can be purified by anti-TF IgG1 affinity and other chromatography methods.

Example 59: The TGFRt15-TGFRs137L Fusion Protein Generation

Figure 124:
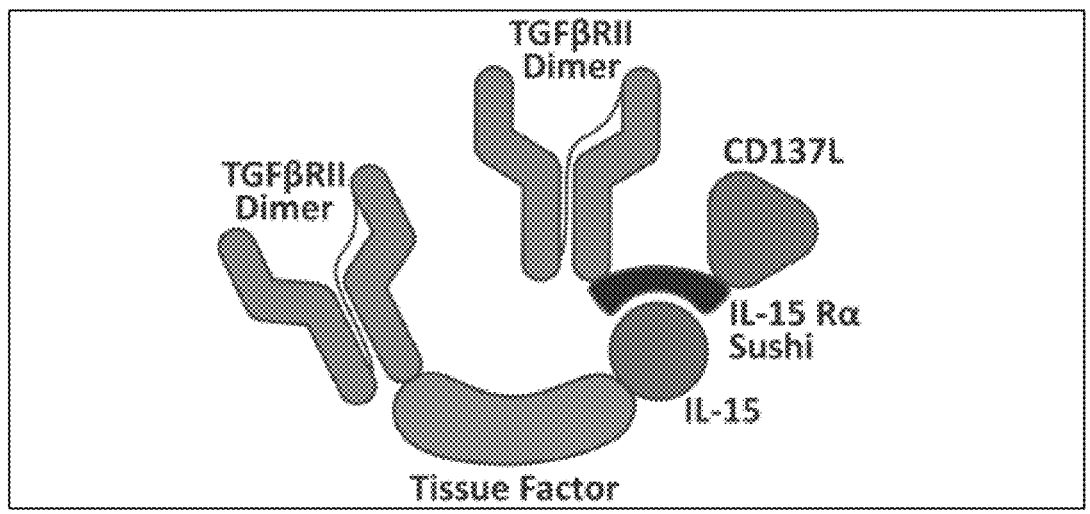
Figure 125:
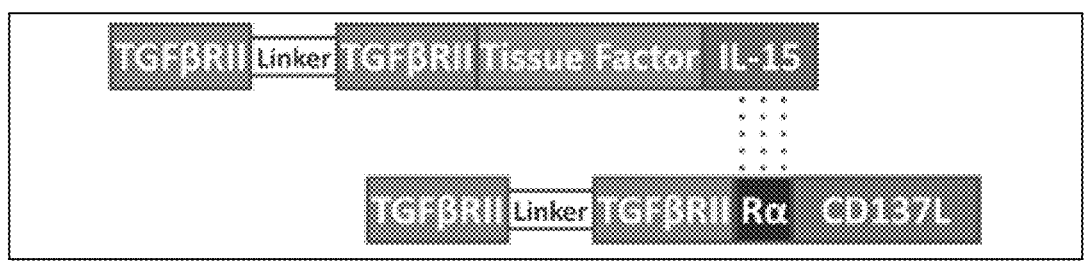

A fusion protein complex was generated comprising of TGFβ Receptor II/IL-15RαSu/CD137L and TGFβ Receptor II/TF/IL-15 fusion proteins (FIG. 124 and FIG. 125). The human TGFβ Receptor II (Ile24-Asp159), tissue factor 219, CD137L, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

(Signal peptide)
ATGAAGTGGGTGACCTTCATCAGCCTGCTGTTCCTGTTCTCCAGCGCCTA

CTCC (Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

```
TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

The amino acid sequence of TGFRt15 fusion protein (including the leader sequence) is as follows:

```
(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

Constructs were also made by attaching two TGFβ Receptor II directly to the IL-15RαSu chain, followed by a (G4S)3 linker and the CD137L sequence, which was synthesized by Genewiz. The nucleic acid and protein sequences of a construct comprising the TGFβ Receptor II linked to the N-terminus of IL-15RαSu following with a (G4S)3 linker and the CD137L sequence are shown below.

The nucleic acid sequence of the TGFRs137L construct (including signal peptide sequence) is as follows:

```
(Signal peptide)
ATGAAGTGGGTGACCTTCATCAGCCTGCTGTTCCTGTTCTCCAGCGCCTA

CTCC (Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA
```

```
-continued
AGAGGAAGGCCGGCACCAGCAGCCTCACCGAGTGCGTGCTGAATAAGGCT

ACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGACCT

GCGGCAGGGCATGTTTGCGCAGCTGGTGGCCCAAAATGTTCTGCTGATCG

ATGGGCCCCTGAGCTGGTACAGTGACCCAGGCCTGGCAGGCGTGTCCCTG

ACGGGGGGCCTGAGCTACAAAGAGGACACGAAGGAGCTGGTGGTGGCCAA

GGCTGGAGTCTACTATGTCTTCTTTCAACTAGAGCTGCGCGCGTGGTGG

CCGGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCACC

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTCGG

AA
```

The amino acid sequence of TGFRs137L fusion protein (including the leader sequence) is as follows:

```
(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNKAT

NVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGVSL

TGGLSYKEDTKELVVAKAGVYYVFFQLELRRVVAGEGSGSVSLALHLQPL

RSAAGAAALALTVDLPPASSEARNSAFGFQGRLLHLSAGQRLGVHLHTEA

RARHAWQLTQGATVLGLFRVTPEIPAGLPSPRSE
```

In some cases, the leader peptide is cleaved from the intact polypeptide to generate the mature form that may be soluble or secreted.

The TGFR/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. Hum Gene Ther 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/CD137L protein complex (referred to as TGFRt15-TGFRs137L), which can be purified by anti-TF IgG1 affinity and other chromatography methods.

Figure 126:
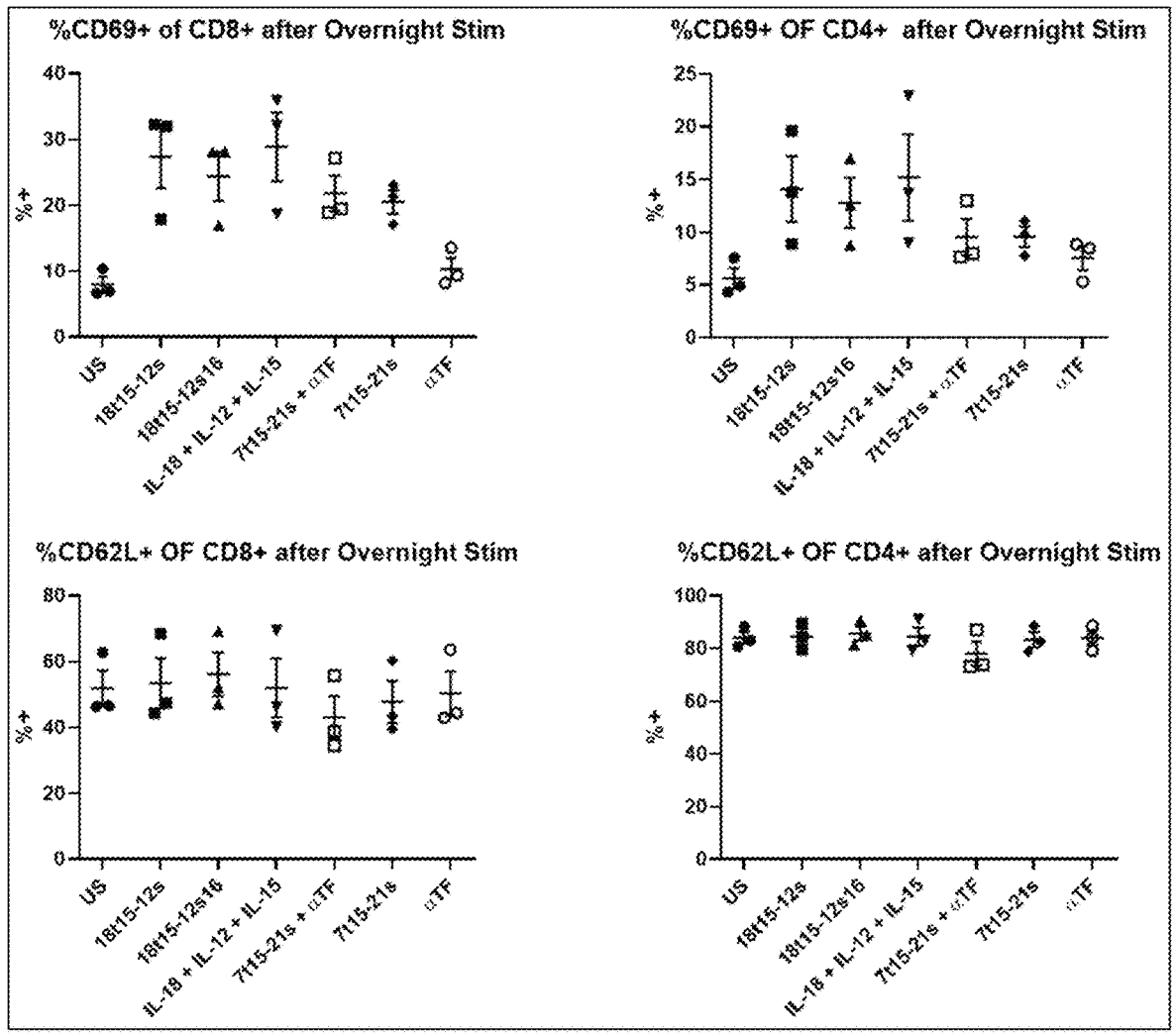

Example 60: Stimulation of NK Cells In Vitro by Multi-Chain Chimeric Polypeptide Constructs A set of experiments was performed to assess changes in the surface phenotype of lymphocyte populations after stimulation with 18t15-12s, 18t15-12s16, and 7t15-21s. In these experiments, fresh human leukocytes were obtained from the blood bank. Peripheral blood lymphocytes were isolated with the Ficoll-PAQUE Plus (GE Healthcare) density gradient media. The cells were counted and resuspended at $0.2 \times 10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 18t15-12s (100 nM); 18t15-12s16 (100 nM), a mixture of single cytokines rhIL15 (50 ng/mL) (Miltenyi), rhIL18 (50 ng/mL) (Invivogen), and rhIL-12 (10 ng/mL) (Peprotech); 7t15-21s (100 nM)+anti-TF antibody (50 nM); 7t15-21s (100 nM); or anti-TF antibody (50 nM) at 37° C. and 5% $CO_2$ for 16 hours. The next day, the cells were harvested and surface stained for 30 minutes with antibodies specific for CD4 or CD8, CD62L, and CD69. After surface staining, cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 126 shows that overnight incubation of purified lymphocyte populations (CD4 and CD8 T cells) with 18t15-12s, 18t15-12s16, or 7t15-21s+anti-TF antibody resulted in an increase in the percentage of CD8 and CD4 T cells expressing CD69. Additionally, incubation with 7t15-21s+anti-TF antibody resulted in an increase in the percentage of CD8 and CD4 T cells expressing CD62L (FIG. 126).

Figure 127:
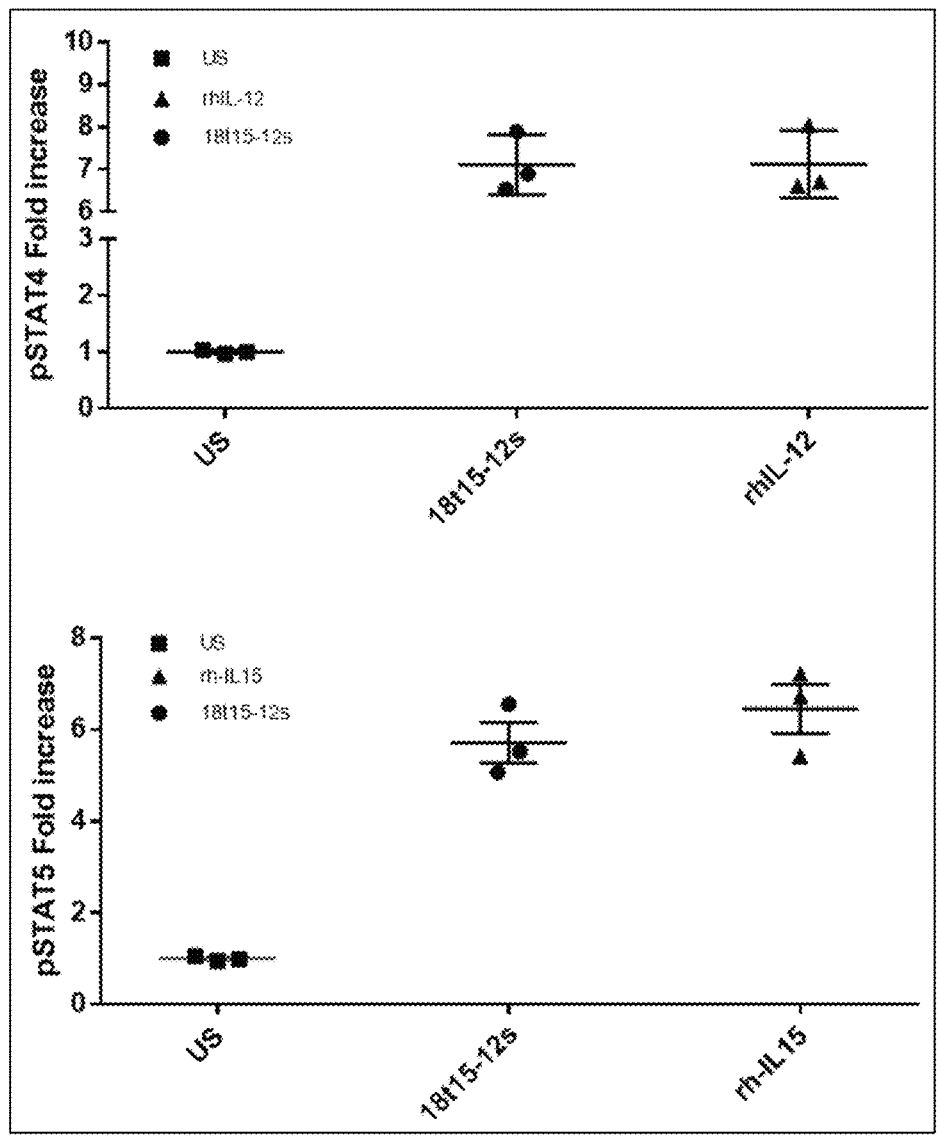

A set of experiments was performed to determine the increase in phospho-STAT4 and phospho-STAT5 levels in NK cells after stimulation with 18t15-12s. In these experiments, fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, and CD69-APCFire750 specific antibodies (BioLegend). The cells were counted and resuspended in $0.05 \times 10^6$/mL in a 96-well flat-bottom plate in 0.1 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with hIL-12 (10 ng/mL) (Biolegend) or hIL-15 (50 ng/mL) (NCI) (Single cytokines), or 18t15-12s (100 nM) at 37° C. and 5% $CO_2$ for 90 minutes. Unstimulated NK cells (US) were used as a control. The cells were harvested and fixed in paraformaldehyde (Sigma) to a final concentration of 1.6%. Plates were incubated in the dark at room temperature for 10 minutes. FACS buffer (1×PBS (Hyclone) with 0.5% BSA (EMD Millipore) and 0.001% sodium azide (Sigma)) (100 μL) was added and cells were transferred to 96-well "V" bottom plate. The cells were washed for 1500 RPM for 5 minutes at room temperature. The cell pellet was mixed with 100 μL chilled methanol by gently pipetting up and down, and cells were incubated for 30 minutes at 4° C. The cells were mixed with 100 mL of FACS buffer and washed for 1500 RPM for 5 minutes at room temperature. The cell pellets were mixed with 50 mL of FACS buffer containing 4 mL of pSTAT4 (BD Bioscience) and pSTAT5 antibodies (BD Bioscience) followed by incubation for 30 minutes at room temperature in the dark. The cells were mixed with 100 mL of FACS buffer and washed for 1500 RPM for 5 minutes at room temperature. The cell pellets were mixed with 50 mL of FACS buffer and cells were analyzed by flow cytometry (Celesta-BD Bioscience). FIG. 127 shows that incubation of NK cells with 18t15-12s induced an increase in pSTAT4 and pSTAT5 (plotted data, normalized fold-change).

Example 61: Stimulation of NK Cells In Vivo by TGFRt15-TGFRs

Figure 128A:
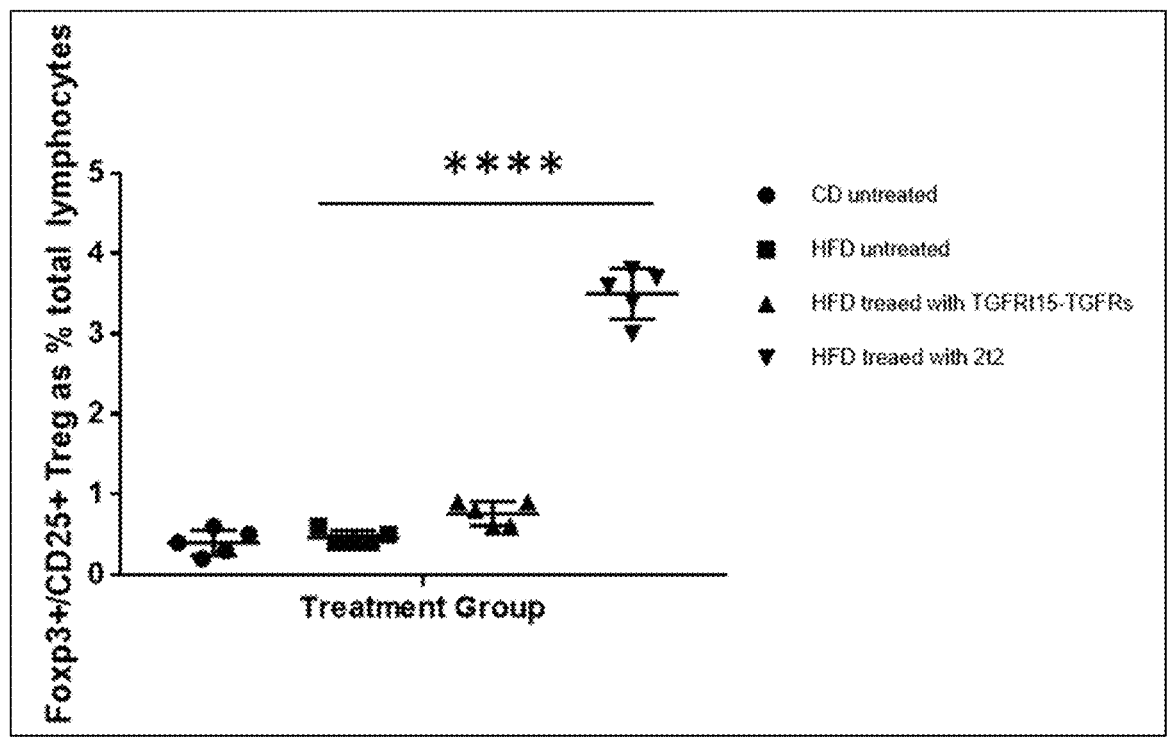
Figure 128B:
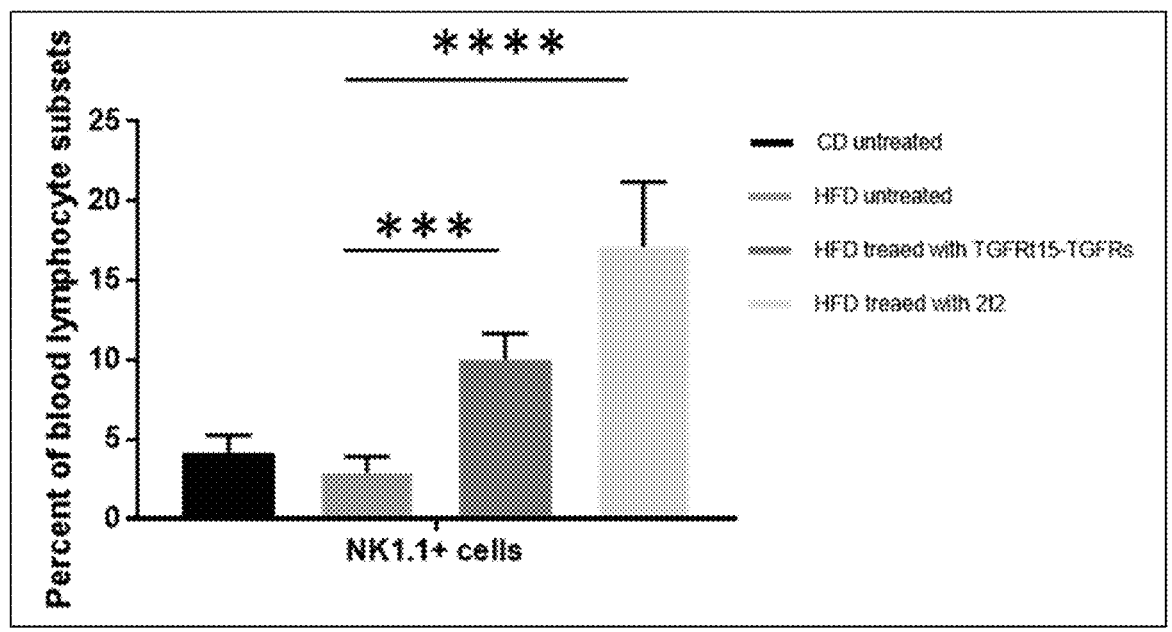
Figure 128C:
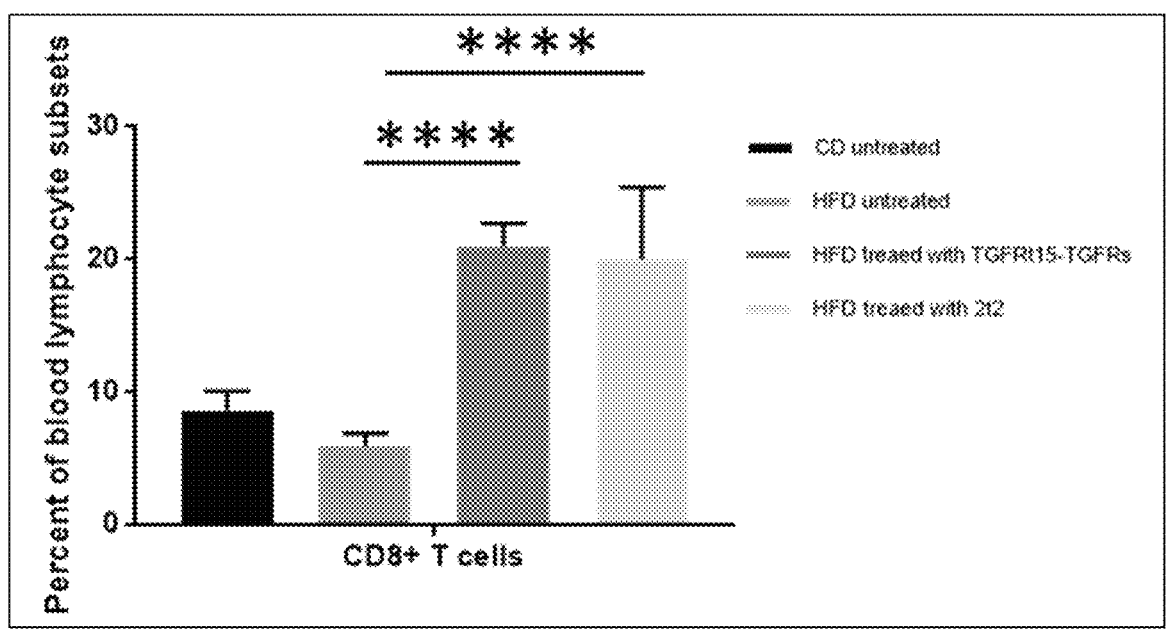

A set of experiments was performed to determine the effect of the TGFRt15-TGFRs construct on immune stimulation in ApoE$^{-/-}$ mice fed with a Western diet. In these experiments, 6-week old female B6.129P2-ApoE$^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with TGFRt15-TGFRs at 3 mg/kg. Three days post treatment, mice were fasted for 16 hours and then blood samples were collected through retro-orbital venous plexus puncture. The blood was mixed with 10 µL 0.5 M EDTA, and 20 µL blood was taken for lymphocyte subsets analysis. The red blood cells were lysed with ACK (0.15 M NH$_4$Cl, 1.0 mM KHCO$_3$, 0.1 mM Na$_2$EDTA, pH 7.4) and the lymphocytes were stained with anti-mouse CD8a and anti-mouse NK1.1 antibodies for 30 minutes at 4° C. in FACS staining buffer (1% BSA in PBS). The cells were washed once and analyzed with a BD FACS Celesta. For Treg staining, ACK treated blood lymphocytes were stained with anti-mouse CD4 and anti-mouse CD25 antibodies for 30 minutes at 4° C. in FACS staining buffer. The cells were washed once and resuspended in fixation/permeabilization working solution and incubated at room temperature for 60 minutes. The cells were washed once and resuspended in permeabilization buffer. The samples were centrifuged at 300-400×g for 5 minutes at room temperature and the supernatant was then discarded. The cell pellet was resuspended in residual volume and the volume adjusted to about 100 µL with 1× permeabilization buffer. Anti-Foxp3 antibody was added to the cells, and the cells were incubated for 30 minutes at room temperature. Permeabilization buffer (200 µL) was added to the cells, and the cells were centrifuged at 300-400×g for 5 minutes at room temperature. The cells were resuspended in flow cytometry staining buffer and analyzed on a flow cytometer. FIGS. 128A-128C show that treatment with TGFRt15-TGFRs increased the percentage of NK cells and CD8$^+$ T cells in ApoE$^{-/-}$ mice fed with Western diet.

Example 62: Induction of Proliferation of Immune Cells In Vivo

Figure 129A:
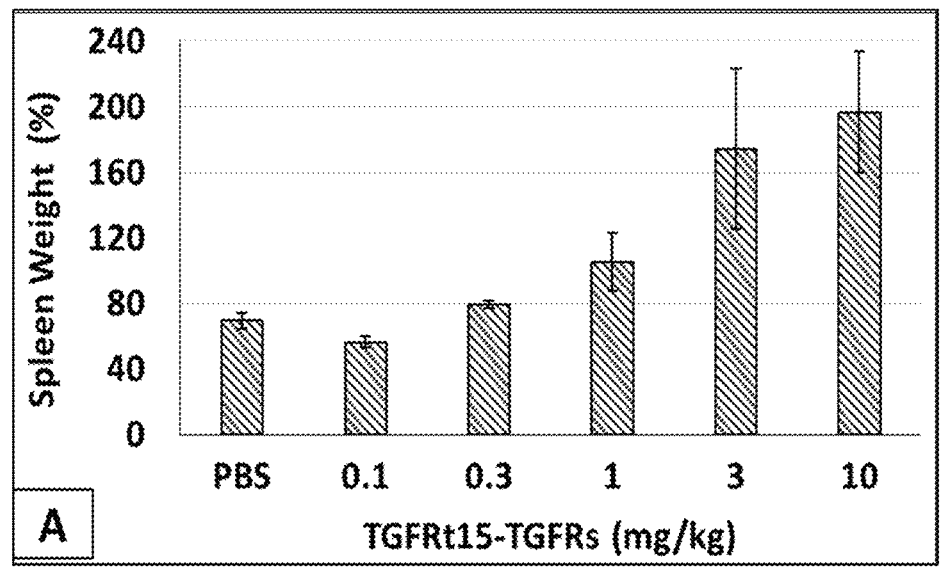
Figure 129B:
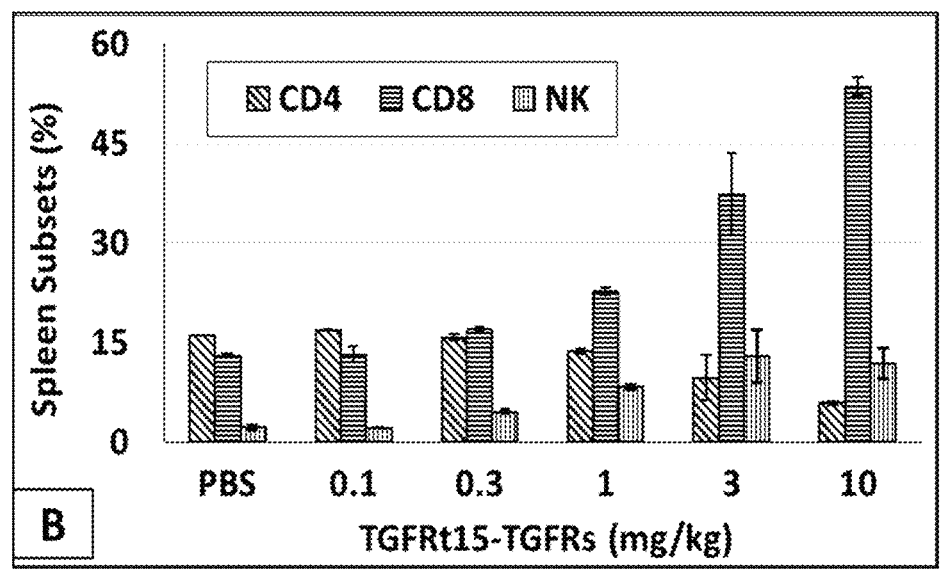
Figure 129C:
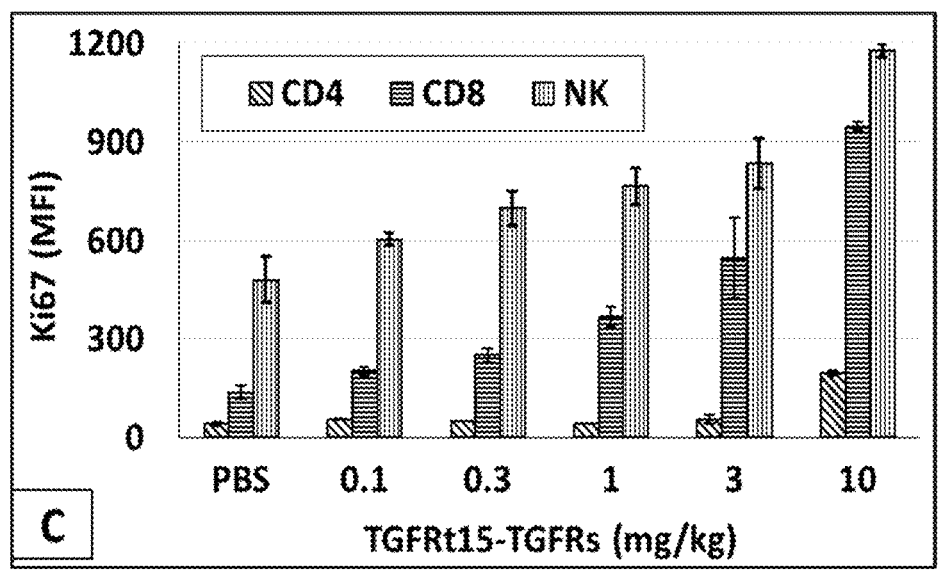

A set of experiments was performed to determine the effect of the TGFRt15-TGFRs construct on immune stimulation in C57BL/6 mice. In these experiments, C57BL/6 mice were subcutaneously treated with control solution (PBS) or TGFRt15-TGFRs at 0.1, 0.3, 1, 3, and 10 mg/kg. The treated mice were euthanized 4 days post-treatment. Spleen weight was measured and splenocyte suspensions were prepared. The splenocyte suspensions were stained with conjugated anti-CD4, anti-CD8, and anti-NK1.1 (NK) antibodies. The cells were additionally stained for proliferation marker Ki67. FIG. 129A shows that spleen weight in mice treated with TGFRt15-TGFRs increased with increasing dosage of TGFRt15-TGFRs. Additionally, spleen weight in mice treated with 1 mg/kg, 3 mg/kg, and 10 mg/kg of TGFRt15-TGFRs was higher as compared to mice treated with just the control solution. The percentages of CD8$^+$ T cells and NK cells both increased with increasing dosage of TGFRt15-TGFRs (FIG. 129B). Finally, TGFRt15-TGFRs significantly upregulated expression of cell proliferation marker Ki67 in both CD8$^+$ T cells and NK cells at all doses of TGFRt15-TGFRs tested (FIG. 129C). These results demonstrate that TGFRt15-TGFRs treatment induced proliferation of both CD8$^+$ T cells and NK cells in C57BL/6 mice.

Figure 130A:
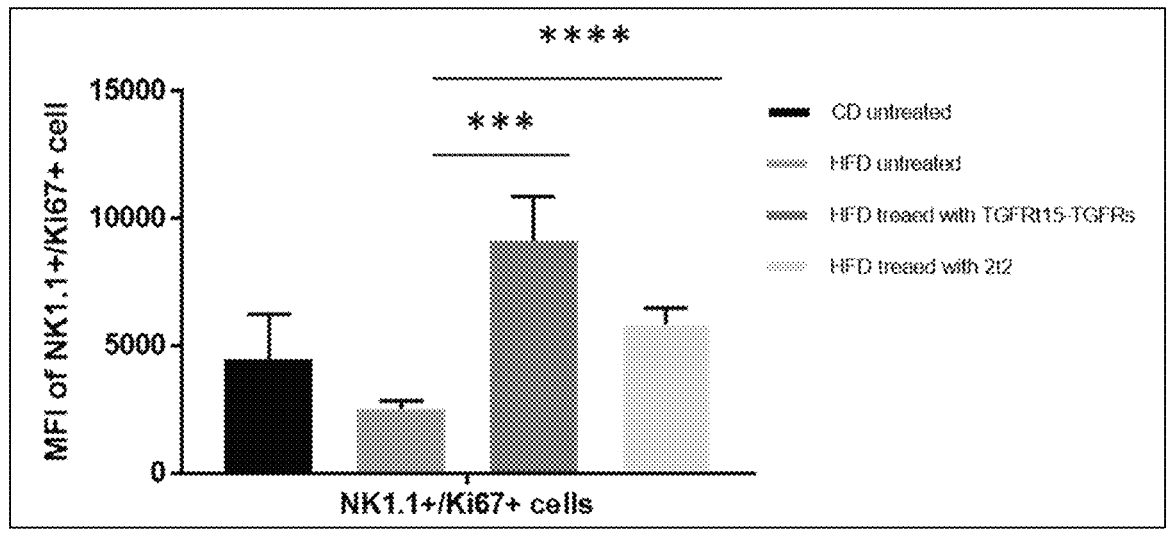
Figure 130B:
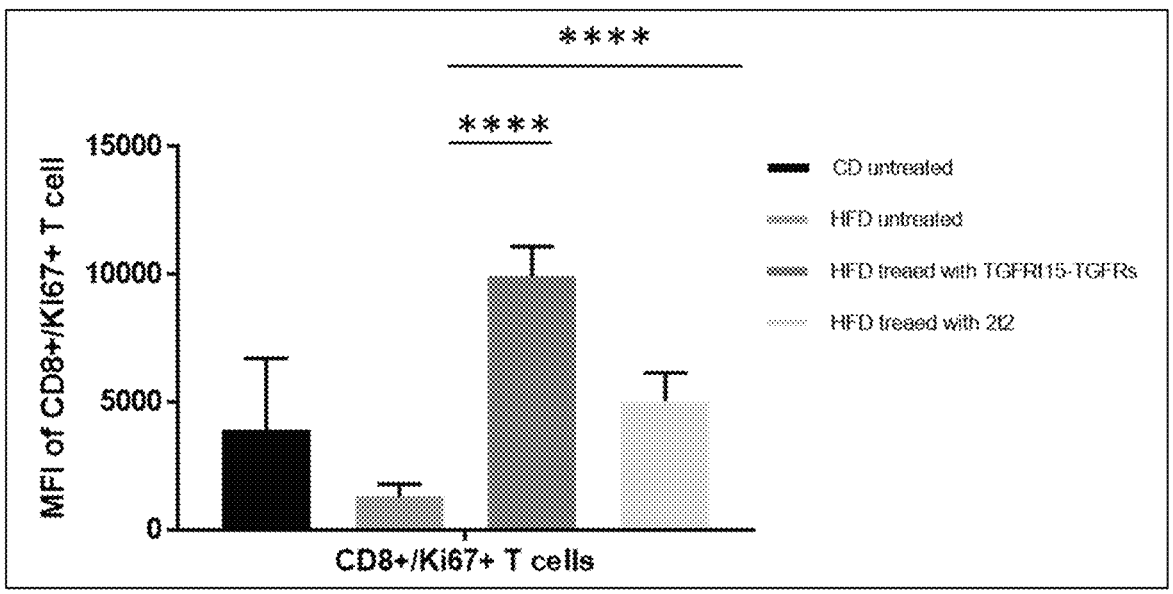

A set of experiments was performed to determine the effect of the TGFRt15-TGFRs construct on immune stimulation in ApoE$^{-/-}$ mice fed with a Western diet. In these experiments, 6-week old female B6.129P2-ApoE$^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-week of the Western diet, the mice were injected subcutaneously with TGFRt15-TGFRs at 3 mg/kg. Three days post-treatment, the mice were fasted for 16 hours and then blood samples were collected through retro-orbital venous plexus puncture. The blood was mixed with 10 µL 0.5 M EDTA and 20 µL blood was taken for lymphocyte subsets analysis. The red blood cells were lysed with ACK (0.15 M NH$_4$Cl, 1.0 mM KHCO$_3$, 0.1 mM Na$_2$EDTA, pH 7.4) and the lymphocytes were stained with anti-mouse CD8a and anti-mouse NK1.1 antibodies for 30 minutes at 4° C. in FACS staining buffer (1% BSA in PBS). The cells were washed once and resuspended in Fixation Buffer (BioLegend Cat #420801) for 20 minutes at room temperature. The cells were centrifuged at 350×g for 5 minutes, the fixed cells were resuspended in Intracellular Staining Permeabilization Wash Buffer (BioLegend Cat #421002) and then centrifuged at 350×g for 5 minutes. The cells were then stained with anti-Ki67 antibody for 20 minutes at RT. The cells were washed twice with Intracellular Staining Permeabilization Wash Buffer and centrifuged at 350×g for 5 minutes. The cells were then resuspended in FACS staining buffer. Lymphocyte subsets were analyzed with a BD FACS Celesta. As described in FIGS. 130A and 130B, treatment of ApoE$^{-/-}$ mice with TGFRt15-TGFRs induced proliferation (Ki67-positive staining) in NK and CD8$^+$ T cells.

Figure 131A:
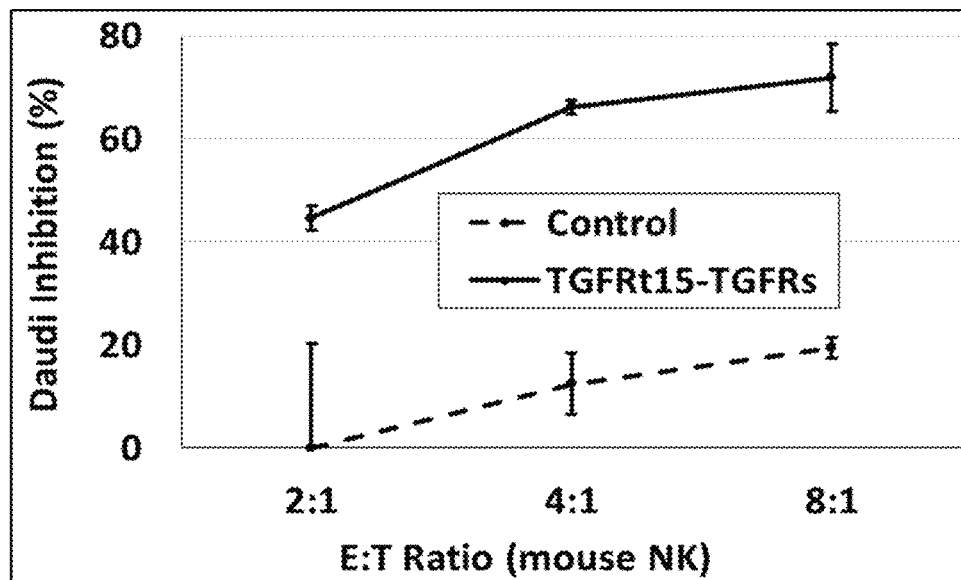
Figure 131B:
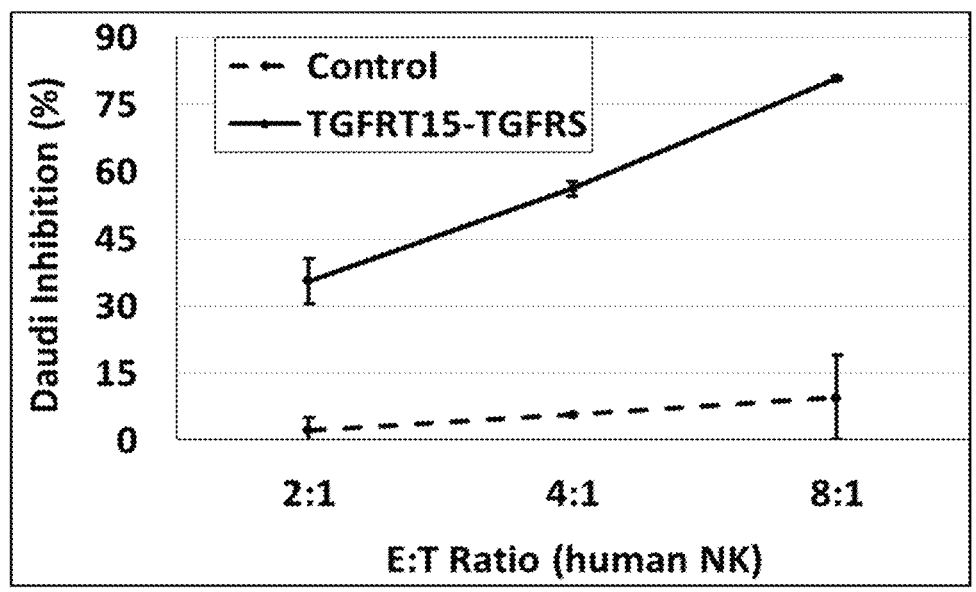

Example 63: NK-Mediated Cytotoxicity Following Treatment with Multi-Chain Construct A set of experiments was performed to determine if treatment of NK cells with TGFRt15-TGFRs enhanced cytotoxicity of NK cells. In these experiments, Human Daudi B lymphoma cells were labeled with CELLTRACE®, violet dye (CTV), and used as tumor target cells. Mouse NK effector cells were isolated with NK1.1-positive selection using a magnetic cell sorting method (Miltenyi Biotec) of C57BL/6 female mouse spleens 4 days post TGFRt15-TGFRs subcutaneous treatment at 3 mg/kg. Human NK effector cells were isolated from peripheral blood mononuclear cells derived from human blood buffy coats with the RosetteSep/human NK cell reagent (Stemcell Technologies). The target cells (Human Daudi B lymphoma cells) were mixed with effector cells (either mouse NK effector cells or human NK effector cells) in the presence of 50 nM TGFRt15-TGFRs or in the absence of TGFRt15-TGFRs (control) and incubated at 37° C. for 44 hours for mouse NK cells and for 20 hours for human NK cells. Target cell (Daudi) viability was assessed by analysis of propidium iodide-positive, CTV-labeled cells using flow cytometry. The percentage of Daudi inhibition was calculated using the formula (1-viable tumor cell number in experimental sample/viable tumor cell number in the sample without NK cells)×100. FIG. 131 shows that mouse (FIG. 131A) and human (FIG. 131B) NK cells had significantly stronger cytotoxicity against Daudi B cells following NK cell activation with TGFRt15-TGFRs than in the absence of TGFRt15-TGFRs activation.

Figure 132A:
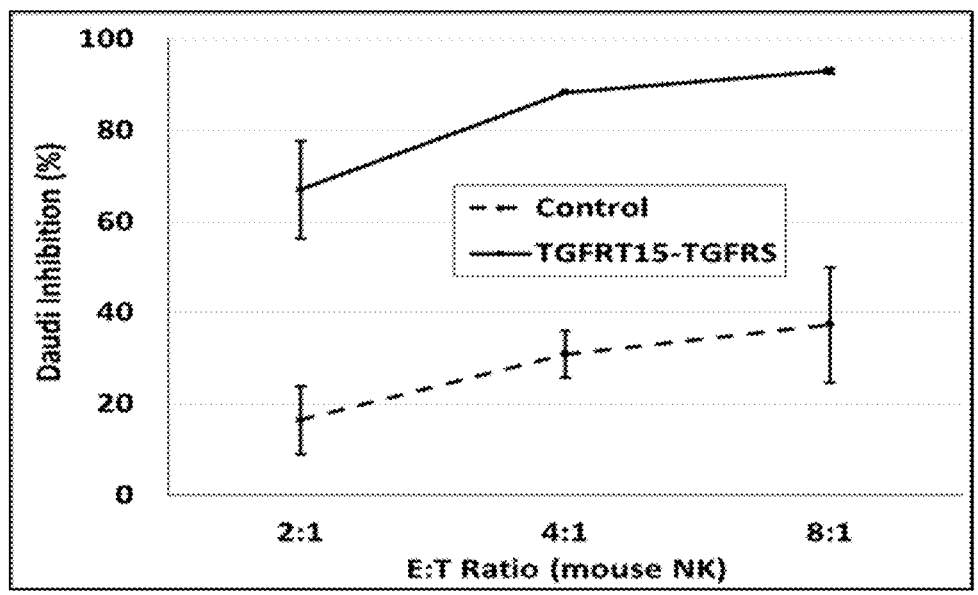
Figure 132B:
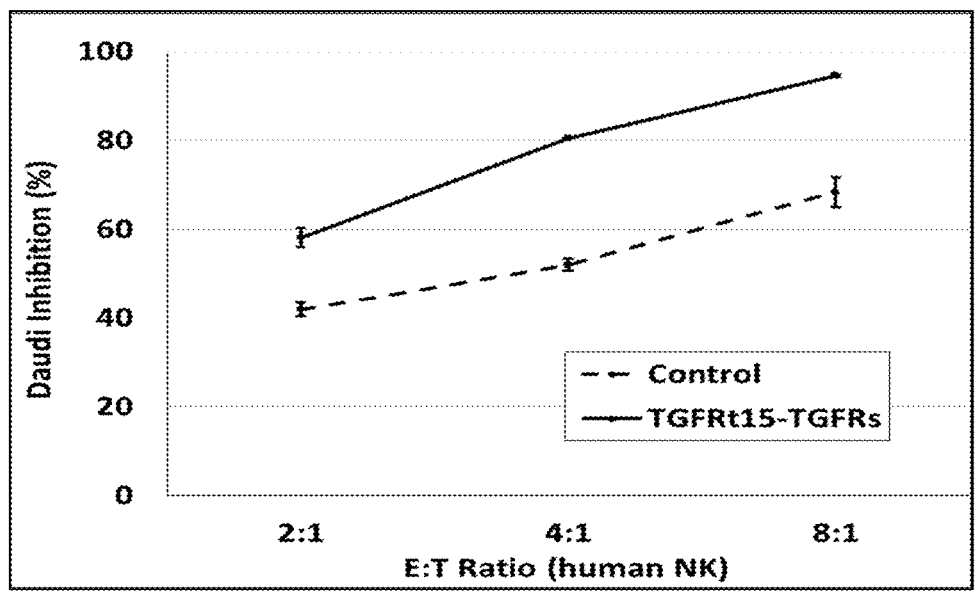

A set of experiments was performed to determine antibody-dependent cellular cytotoxicity (ADCC) of mouse and human NK cells following treatment with TGFRt15-TGFRs. In these experiments, human Daudi B lymphoma cells were labeled with CELLTRACE®, violet dye (CTV), and used as tumor target cells. Mouse NK effector cells were isolated with NK1.1-positive selection using a magnetic cell sorting method (Miltenyi Biotec) of C57BL/6 female mouse spleens 4 days post-TGFRt15-TGFRs subcutaneous treatment at 3 mg/kg. Human NK effector cells were isolated from peripheral blood mononuclear cells derived from human blood buffy coats with the RosetteSep/human NK cell reagent (Stemcell Technologies). The target cells (Daudi B cells) were mixed with effector cells (either mouse NK effector cells or human NK effector cells) in the presence of anti-CD20 antibody (10 nM Rituximab, Genentech) and in the presence of 50 nM TGFRt15-TGFRs, or in the absence of TGFRt15-TGFRs (control) and incubated at 37° C. for 44 hours for mouse NK cells and for 20 hours for human NK cells. The Daudi B cells express the CD20 targets for the anti-CD20 antibody. Target cell viability was assessed after incubation by analysis of propidium iodide-positive, CTV-labeled target cells using flow cytometry. The percentage of Daudi inhibition was calculated using the formula (1-viable tumor cell number in experimental sample/viable tumor cell number in the sample without NK cells)×100. FIG. 132 shows that mouse NK cells (FIG. 132A) and human NK cells (FIG. 132B) had stronger ADCC activity against Daudi B cells following NK cell activation with TGFRt15-TGFRs than in the absence of TGFRt15-TGFRs activation.

Example 64: Treatment of Cancer

Figure 133A:
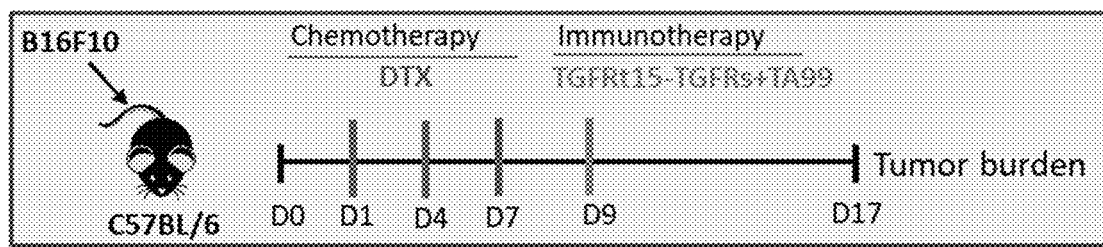
Figure 133B:
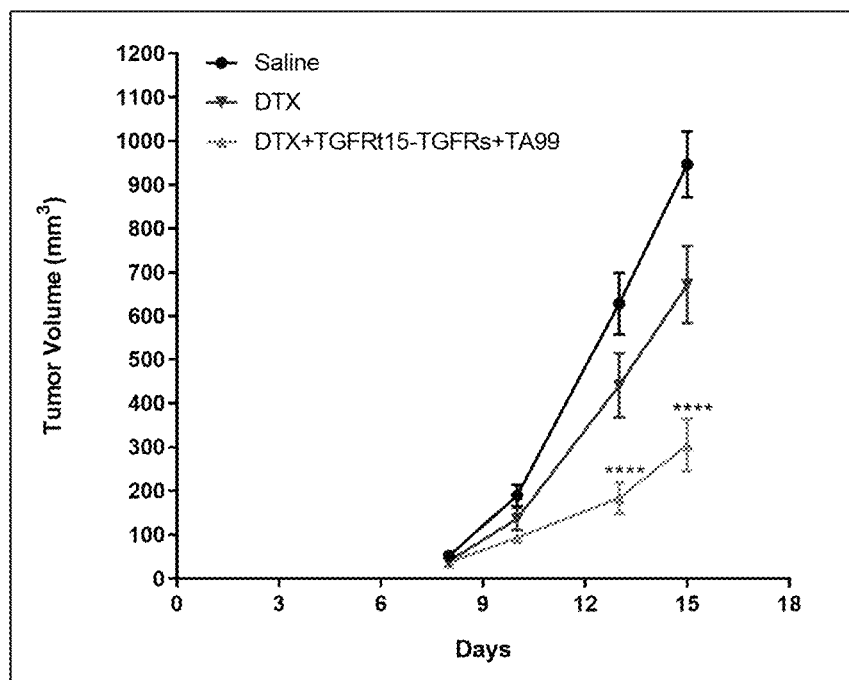

A set of experiments was performed to assess antitumor activity of TGFRt15-TGFRs plus anti-TRP1 antibody (TA99) in combination with chemotherapy in a melanoma mouse model. In these experiments, C57BL/6 mice were subcutaneously injected with 0.5×10⁶ B16F10 melanoma cells. The mice were treated with three doses of chemotherapy docetaxel (10 mg/kg) (DTX) on day 1, day 4, and day 7, followed by treatment with single dose of combination immunotherapy TGFRt15-TGFRs (3 mg/kg)+anti-TRP1 antibody TA99 (200 µg) on day 9. FIG. 133A shows a schematic of the treatment regimen. Tumor growth was monitored by caliper measurement, and tumor volume was calculated using the formula $V=(L \times W^2)/2$, where L is the largest tumor diameter and W is the perpendicular tumor diameter. FIG. 133B shows that treatment with DTX+TGFRt15-TGFRs+TA99 significantly reduced tumor growth compared to saline control and DTX treatment groups (N=10, ****p<0.001, Multiple t test analyses).

Figure 133C:
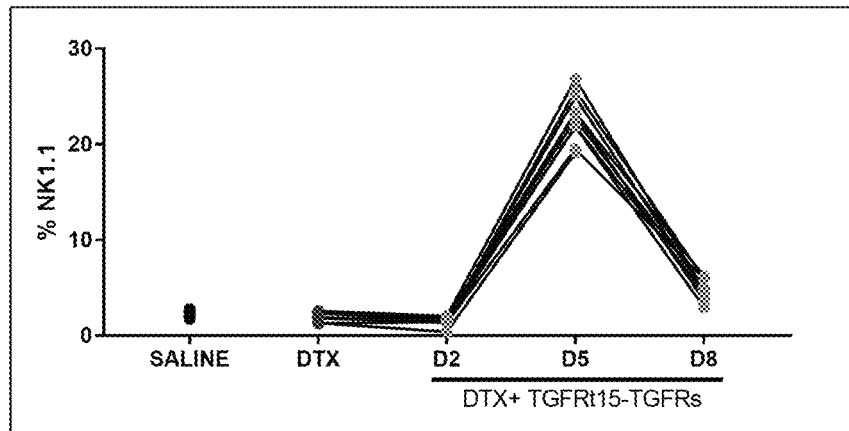
Figure 133D:
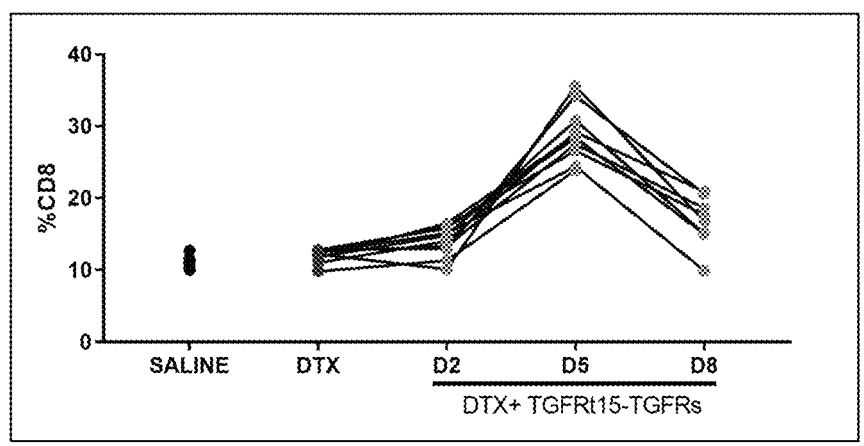
Figure 133E:
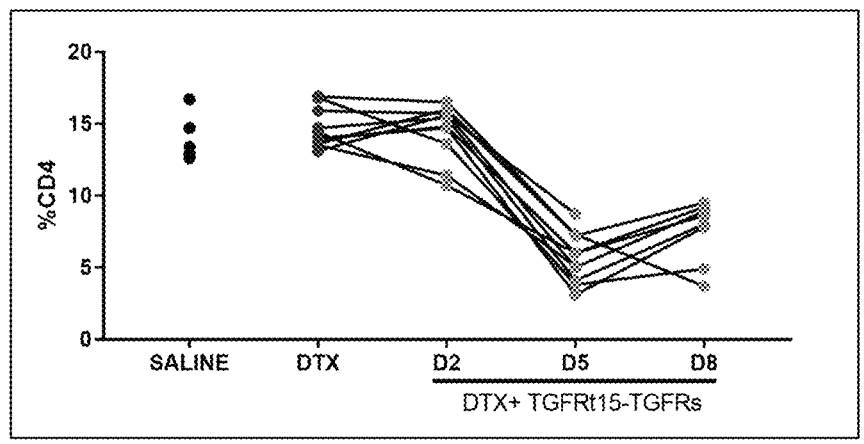

To assess immune cell subsets in the B16F10 tumor model, peripheral blood analysis was performed. In these experiments, C57BL/6 mice were injected with B16F10 cells and treated with DTX, DTX+TGFRt15-TGFRs+TA99, or saline. Blood was drawn from the submandibular vein of B16F10 tumor-bearing mice on days 2, 5, and 8 post-immunotherapy for the DTX+TGFRt15-TGFRs+TA99 group and day 11 post-tumor injection for the DTX and saline groups. RBCs were lysed in ACK lysis buffer and the lymphocytes were washed and stained with anti-NK1.1, anti-CD8, and anti-CD4 antibodies. The cells were analyzed by flow cytometry (Celesta-BD Bioscience). FIGS. 133C-133E show that DTX+TGFRt15-TGFRs+TA99 treatment induced an increase in the percentage of NK cells and CD8⁺ T cells in the tumors compared to the saline and DTX treatment groups.

Figure 133F:
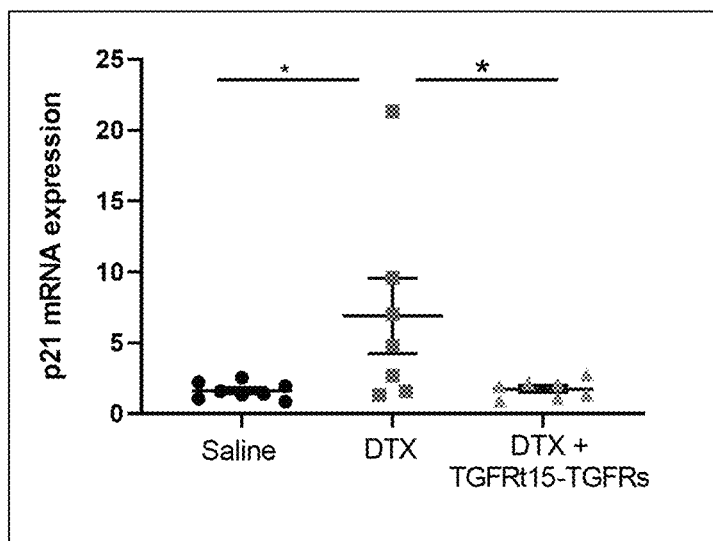
Figure 133G:
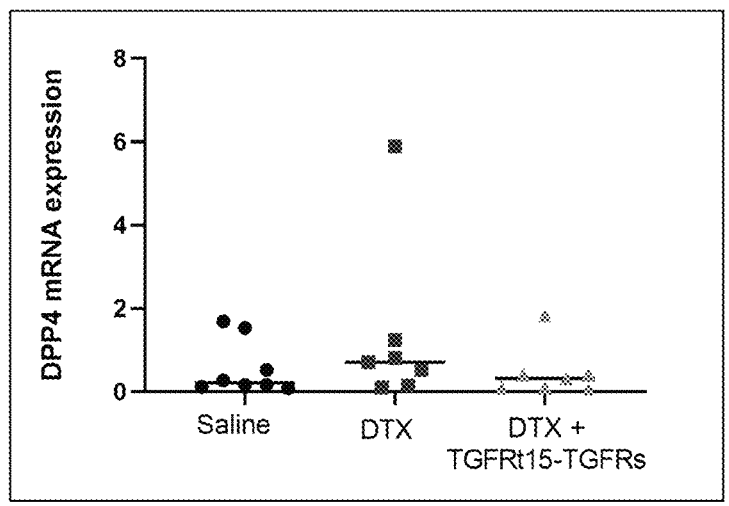
Figure 133H:
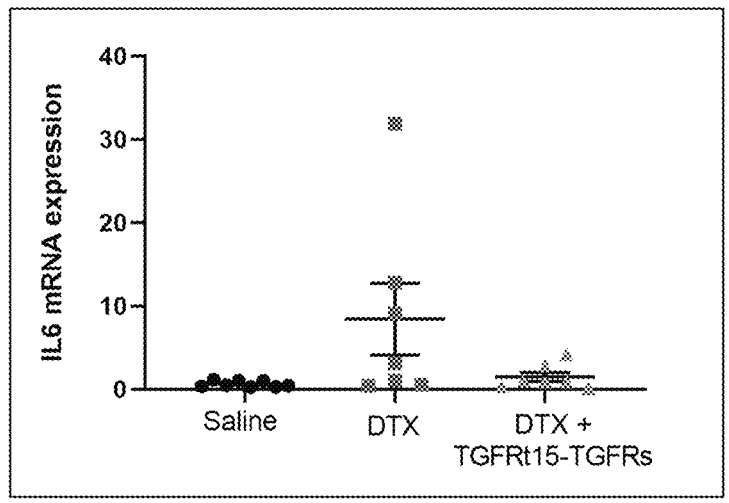

On day 17, total RNA was extracted from tumors of mice treated with saline, DTX or DTX+TGFRt15-TGFRs+TA99 using Trizol. Total RNA (1 µg) was used for cDNA synthesis using the QUANTITECT® Reverse Transcription Kit (Qiagen). Real-time PCR was carried out with CFX96 Detection System (Bio-Rad) using FAM-labeled predesigned primers for senescence cell markers, (F) p21 (G) DPP4 and (H) IL6. The housekeeping gene 18S ribosomal RNA was used as an internal control to normalize the variability in expression levels. The expression of each target mRNA relative to 18S rRNA was calculated based on Ct as 2-Δ(ΔCt), in which ΔCt=Cttarget−Ct18S. The data is presented as fold-change as compared to saline control. FIG. 133F-133H show that DTX treatment induced an increase in senescent tumor cells that were subsequently reduced following treatment with TGFRt15-TGFRs+TA99 immunotherapy.

A set of experiments was performed to investigate amelioration of Western diet-induced hyperglycemia in ApoE$^{-/-}$ mice by TGFRt15-TGFRs. In these experiments, 6-week old female B6.129P2-ApoE$^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with TGFRt15-TGFRs at 3 mg/kg. Three days post-treatment, the mice were fasted for 16 hours and then blood samples were collected through retro-orbital venous plexus puncture. Blood glucose was detected with a glucose meter (One-Touch UltraMini) and GenUltimated test strips using a drop of fresh blood. As shown in FIG. 134A, TGFRt15-TGFRs treatment reduced hyperglycemia induced by the Western diet. The plasma insulin and resistin levels were analyzed with Mouse Rat Metabolic Array by Eve Technologies. HOMA-IR was calculated using the following formula: homeostatic model assessment-insulin resistance=Glucose (mg/dL)*Insulin (mU/mL)/405. As shown in FIG. 134B, TGFRt15-TGFRs treatment reduced insulin resistance compared to the untreated group. TGFRt15-TGFRs (p<0.05) reduced resistin levels significantly compared to the untreated group as shown in FIG. 142C, which may relate to the reduced insulin resistance induced by TGFRt15-TGFRs (FIG. 134B).

Example 65: Induction of Differentiation of NK Cells into Cytokine-Induced Memory Like NK Cells A set of experiments was performed to assess the differentiation of NK cells into cytokine-induced memory like NK Cells (CIMK-NK Cells) after stimulation with 18t15-12s. In these experiments, fresh human leukocytes were obtained from the blood bank and CD56⁺ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in 2×10⁶/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were unstimulated ("No Spike") or stimulated with 18t15-12s (100 nM) or a mixture of single cytokines including rhIL15 (50 ng/mL) (Miltenyi), rhIL18 (50 ng/mL) (Invivogen), and rhIL-12 (10 ng/mL) (Peprotech) ("single cytokines") at 37° C. and 5% $CO_2$ for 16 hrs. The next day, the cells were harvested, and washed two times with warm complete media at 1000 RPM for 10 minutes at room temperature. The cells were resuspended at 2×10⁶/mL in a 24-well flat-bottom plate in 2 mL of complete media with rhIL15 (1 ng/mL). After every 2 days, half of the medium was replaced with fresh complete media containing rhIL15.

To assess the change in memory phenotype of NK cells at day 7, the cells were stained with antibodies to cell-surface CD56, CD16, CD27, CD62L, NKp30, and NKp44 (BioLegend). After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 135 shows that incubation of NK cells with 18t15-12s resulted in an increase in the percentage of $CD16^+CD56^+$ NK cells expressing CD27, CD62L, and NKp44, and an increase in the levels (MFI) of NKp30 in $CD16^+CD56^+$ NK cells.

Example 66: Upregulation of CD44 Memory T Cells

A set of experiments was performed to assess upregulation of CD44 memory T cells upon treatment with TGFRt15-TGFRs. In these experiments, C57BL/6 mice were subcutaneously treated with TGFRt15-TGFRs. The treated mice were euthanized and the single splenocyte suspensions were prepared 4 days (TGFRt15-TGFRs) following the treatment. The prepared splenocytes were stained with fluorochrome-conjugated anti-CD4, anti-CD8 and anti-CD44 antibodies and the percentages of $CD44^{high}$ T cells in $CD4^+$ T cells or $CD8^+$ T cells were analyzed by flow cytometry. The results show that TGFRt15-TGFRs upregulated expression of the memory marker CD44 on $CD4^+$ and $CD8^+$ T cells (FIG. 136). These findings indicate that TGFRt15-TGFRs was able to induce mouse T cells to differentiate into memory T cells.

Example 67: Tissue Factor Coagulation Assays Following Treatment with Single-Chain or Multi-Chain Chimeric Polypeptides A set of experiments was performed to assess blood coagulation following treatment with single-chain or multi-chain chimeric polypeptides. To initiate the blood coagulation cascade pathway, tissue factor (TF) binds to Factor VIIa (FVIIa) to form a TF/FVIIa complex. The TF/FVIIa complex then binds Factor X (FX) and converts FX to FXa.

Factor VIIa (FVIIa) Activity Assay

One assay to measure blood coagulation involves measuring Factor VIIa (FVIIa) activity. This type of assay requires the presence of tissue factor and calcium. The TF/FVIIa complex activity can be measured by a small substrate or by a natural protein substrate, for example, Factor X (FX). When FX is used as a substrate, phospholipids are also required for TF/FVIIa activity. In this assay, FVIIa activity is determined with FVIIa-specific chromogenic substrate S-2288 (Diapharma, West Chester, OH). The color change of the S-2288 substrate can be measured spectrophotometrically and is proportional to the proteolytic activity of FVIIa (e.g., the TF/FVIIa complex).

In these experiments, the FVIIa activity of the following groups were compared: the 219-amino acid extracellular domain of tissue factor domain ($TF_{219}$), a multi-chain chimeric polypeptide with a wild-type tissue factor domain, and a multi-chain chimeric polypeptide with a mutant tissue factor domain. The chimeric polypeptides containing mutant tissue factor molecules were constructed with mutations to the TF domain at amino acid sites: Lys20, Ile22, Asp58, Arg135, and Phe140.

In order to assess activity of FVIIa, FVIIa, and $TF_{219}$ or a $TF_{219}$-containing multi-chain chimeric polypeptide were mixed at an equal molar concentration (10 nM) in all wells of a 96-well ELISA plate in a total volume of 70 μL. After incubation for 10 minutes at 37° C., 10 μL of 8 mM S-2288 substrate was added to start the reaction. The incubation was then kept at 37° C. for 20 minutes. Finally, color change was monitored by reading absorbance at 405 nm. The OD values of different TF/VIIa complexes are shown in Table 1 and Table 2. Table 1 shows a comparison of $TF_{219}$, 21t15-21s wild-type (WT) and 21t15-21s mutant (Mut). Table 2 shows a comparison of $TF_{219}$, 21t15-TGFRs wild-type (WT), and 21t15-TGFRs mutant (Mut). These data show that $TF_{219}$-containing multi-chain chimeric polypeptides (e.g., 21t15-21s-WT, 21t15-21s-Mut, 21t15-TGFRS-WT, and 21t15-TGFRS-Mut) have lower FVIIa activity than $TF_{219}$ when the chromogenic S-2288 was used as a substrate. Notably, the multi-chain chimeric polypeptides containing $TF_{219}$ mutations showed much lower FVIIa activity when compared to multi-chain chimeric polypeptides containing wild type $TF_{219}$.

TABLE 1

| | FVIIa activity |
|---|---|
| Molecule | OD value at 405 nm |
| $TF_{219}$ | 0.307 |
| 21t15/21S-WT | 0.136 |
| 21t15/21S-Mut | 0.095 |

WT: wild type of $TF_{219}$,
Mut: $TF_{219}$ containing mutations.

TABLE 2

| | FVIIa activity |
|---|---|
| Molecule | OD value at 405 nm |
| $TF_{219}$ | 0.345 |
| 21t15/TGFRS-WT | 0.227 |
| 21t15/TGFRS-Mut | 0.100 |

WT: wild type of $TF_{219}$,
Mut: $TF_{219}$ containing mutations.

Factor X (FX) Activation Assay

An additional assay to measure blood coagulation involves measuring activation of Factor X (FX). Briefly, TF/VIIa activates blood coagulation Factor X (FX) to Factor Xa (FXa) in the presence of calcium and phospholipids. $TF_{243}$, which contains the transmembrane domain of TF, has much higher activity in activating FX to FXa than $TF_{219}$, which does not contain the transmembrane domain. TF/VIIa dependent activation of FX is determined by measuring FXa activity using an FXa-specific chromogenic substrate S-2765 (Diapharma, West Chester, OH). The color change of S-2765 can be monitored spectrophotometrically and is proportional to the proteolytic activity of FXa.

In these experiments, FX activation with a multi-chain chimeric polypeptide (18t15-12s, mouse (m)21t15, 21t15-TGFRs, and 21t15-7s) was compared with a positive control (Innovin) or $TF_{219}$. $TF_{219}$ (or $TF_{219}$-containing multi-chain chimeric polypeptides)/FVIIa complexes were mixed at an equal molar concentration (0.1 nM each) in a volume of 50 μL in round bottom wells of a 96-well ELISA plate, after which 10 μL of 180 nM FX was added. After 15 minutes of incubation at 37° C., during which time FX was converted to FXa, 8 μL of 0.5 M EDTA (which chelates calcium and thus terminates FX activation by TF/VIIa) was added to each well to stop FX activation. Next, 10 μL of 3.2 mM S-2765 substrate was added to the reaction mixture. Immediately, the plate absorbance was measured at 405 nm and was recorded as the absorbance at time 0. The plate was then incubated for 10-20 minutes at 37° C. The color change was monitored by reading absorbance at 405 nm following the incubation. Results of FX activation as measured by FXa activity using chromogenic substrate S-2765 are shown in FIG. 137. In this experiment, Innovin, which is a commercial prothrombin reagent containing lipidated recombinant human $TF_{243}$, was used as a positive control for FX activation. Innovin was reconstituted with purified water to about 10 nM of $TF_{243}$. Next, 0.1 nM TF/VIIa complex was made by mixing an equal volume of 0.2 nM of FVIIa with 0.2 nM of Innovin. Innovin demonstrated very potent FX activation activity, while $TF_{219}$ and $TF_{219}$-containing multi-chain chimeric polypeptides had very low FX activation activity, confirming that $TF_{219}$ is not active in a TF/FVIIa complex for activating natural substrate FX in vivo.

Prothrombin Time Test

A third assay to measure blood coagulation is the prothrombin time (PT) test, which measures blood clotting activity. Here, the PT test was performed using commercially available normal human plasma (Ci-Trol Coagulation Control, Level I). For a standard PT test, clot reactions were initiated by addition of Innovin, a lipidated recombinant human $TF_{243}$, in the presence of calcium. Clotting time was monitored and reported by STart PT analyzer (Diagnostica Stago, Parsippany, N.J.). PT assays were started by injecting 0.2 mL of various dilutions of Innovin diluted in PT assay buffer (50 mM Tris-HCl, pH 7.5, 14.6 mM $CaCl_2$), 0.1% BSA) into cuvettes containing 0.1 mL of normal human plasma prewarmed at 37° C. In the PT assay, shorter PT time (clotting time) indicates a higher TF-dependent clotting activity while longer PT (clotting time) means lower TF-dependent clotting activity.

As seen in FIG. 138, addition of different amounts of Innovin (e.g., Innovin reconstituted with purified water equivalent to 10 nM of lipidated recombinant human $TF_{243}$ was considered to be 100% Innovin) to the PT assay demonstrated a dose-response relationship, where lower concentrations of $TF_{243}$ resulted in a longer PT time (lower clotting activity). For example, 0.001% Innovin had a PT time greater than 110 seconds, which was almost the same as buffer alone.

In another experiment, the PT test was conducted on $TF_{219}$ and multi-chain chimeric polypeptides including: 18t15-12s, 7t15-21s, 21 t15-TGFRs-WT, and 21 t15-TGFRs-Mut. FIG. 139 show that $TF_{219}$ and $TF_{219}$-containing multi-chain chimeric polypeptides (at a concentration of 100 nM) had prolonged PT times indicating extremely low or no clotting activity.

Studies were also conducted to evaluate whether incubating the multi-chain chimeric polypeptides in the presence of other cells carrying receptors for the cytokine components of the multi-chain chimeric polypeptide (32Dβ or human PBMCs) would affect the clotting time in the PT assay. To examine whether cells that express IL-15 receptor (32Dβ cells) or IL-15 and IL-21 receptors (PBMCs) would bind IL-15-containing multi-chain chimeric polypeptides to mimic natural TF as a cellular FVIIa receptor, $TF_{219}$-containing multi-chain chimeric polypeptides (at a concentration of 100 nM for each molecule) were diluted in the PT assay buffer and preincubated with 32Dβ cells (at $2 \times 10^5$ cells/mL) or PBMC (at $1 \times 10^5$ cells/mL) for 20-30 minutes at room temperature. The PT assay was then conducted as described above. FIGS. 140 and 141 shows that $TF_{219}$ and $TF_{219}$-containing multi-chain chimeric polypeptides mixed with 32Dβ cells (FIG. 140) or PBMC (FIG. 141) at a final concentration of 100 nM had prolonged PT times similar to 0.001-0.01% Innovin (equivalent to 0.1 pM to 1.0 pM of $TF_{243}$). Expressed in percentage of relative $TF_{243}$ activity, $TF_{219}$-containing multi-chain chimeric polypeptides had 100,000 to 1,000,000 times lower TF dependent clotting activity when compared to Innovin. This demonstrated that $TF_{219}$-containing multi-chain chimeric polypeptides had extremely low or no TF-dependent clotting activity, even while the molecules were bound to an intact cell membrane surface, such as 32Dβ or PBMCs.

Example 68: Characterization of 7t15-21s137L (Long Version)

The nucleic acid sequence of the 7t15 construct (including signal peptide sequence) is as follows (SEQ ID NO: 107):

```
(Signal peptide)
ATGAAGTGGGTGACCTTCATCAGCCTGCTGTTCCTGTTCTCCAGCGCCTA
CTCC (Human IL7)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT
```

-continued
GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of 7t15 fusion protein (including the leader sequence) is as follows (SEQ ID NO: 106):

(Signal peptide)
MKWVTFISLLFLFSSAYS (Human IL7)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

The nucleic acid sequence of the 21s137L construct (including signal peptide sequence) is as follows (SEQ ID NO: 225):

(Signal peptide)
ATGAAGTGGGTGACCTTCATCAGCCTGCTGTTCCTGTTCTCCAGCGCCTA

CTCC

-continued
(Human IL-21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGACCT

GCGGCAGGGCATGTTTGCGCAGCTGGTGGCCCAAAATGTTCTGCTGATCG

ATGGGCCCCTGAGCTGGTACAGTGACCCAGGCCTGGCAGGCGTGTCCCTG

ACGGGGGGCCTGAGCTACAAAGAGGACACGAAGGAGCTGGTGGTGGCCAA

GGCTGGAGTCTACTATGTCTTCTTTCAACTAGAGCTGCGGCGCGTGGTGG

CCGGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCACC

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTCGG

AA

The amino acid sequence of 21s137L fusion protein (including the leader sequence) is as follows (SEQ ID NO: 226):

(Signal peptide)
MKWVTFISLLFLFSSAYS (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLNKA

TNVAHWTTPSLKCIR ((G4S)3 linker)
GGGGSGGGGSGGGGS

-continued (Human CD137L)
REGPELSPDDPAGLLDLRQGMFAQLVAQNVLLIDGPLSWYSDPGLAGVSL

TGGLSYKEDTKELVVAKAGVYYVFFQLELRRVVAGEGSGSVSLALHLQPL

RSAAGAAALALTVDLPPASSEARNSAFGFQGRLLHLSAGQRLGVHLHTEA

RARHAWQLTQGATVLGLFRVTPEIPAGLPSPRSE

The following experiment was conducted to evaluate whether the CD137L portion in 7t15-21s137L was intact to bind to CD137 (4.1BB). On day 1, a 96-well plate was coated with 100 μL (2.5 μg/mL) of GAH IgG Fc (G-102-C, R&D Systems) in R5 (coating buffer), overnight. On day 2, the plates were washed three times and blocked with 300 μL of 1% BSA in PBS at 37° C. for 2 hrs. 10 ng/ml of 4.1BB/Fc (838-4B, R&D Systems) was added at 100 μl/well for 2 hrs at room temperature. Following three washes, 7t15-21s137L (long version) or 7t15-21s137Ls (short version) was added starting at 10 nM, or recombinant human 4.1BBL starting at 180 ng/mL, with ⅓ dilution, followed by incubation at 4° C. overnight. On day 3, the plates were washed three times, and 500 ng/mL of biotinylate-goat anti-human 4.1BBL (BAF2295, R&D Systems) was applied at 100 μL per well, followed by incubation at RT for 2 hrs. The plates were washed three times, and incubated with 0.25 μg/mL of HRP-SA (Jackson ImmuneResearch) at 100 μL per well for 30 min. The plates were then washed three times, and incubated with 100 μL of ABTS for 2 mins at RT. The results were read at 405 nm. As shown in FIG. 142, both 7t15-21s137L (long version) and 7t15-21s137L (short version) could interact with 4.1BB/Fc (dark diamond and gray square) compared to the recombinant human 4.1BB ligand (rhCD137L, light gray star). 7t15-21s137L (long version) (dark diamond) interacted better with 4.1BB/Fc as compared to 7t15-21s137L (short version) (gray square).

The following experiments were conducted to evaluate whether the components IL7, IL21, IL15, and 4.1BBL in 7t15-21s137L (long version) were intact to be detected by the individual antibody using ELISA. A 96-well plate was coated with 100 μL (4 μg/mL) of anti-TF (human IgG1) in R5 (coating buffer) and incubated at RT for 2 hrs. The plates were washed three times, and blocked with 100 μL of 1% BSA in PBS. Purified 7t15-21s137L (long version) was added starting at 10 nM, and at ⅓ dilution, followed by incubation at RT for 60 min. The plates were washed three times, and 500 ng/mL of biotinylate-anti-IL7 (506602, R&D Systems), 500 ng/mL of biotinylate-anti-IL21 (13-7218-81, R&D Systems), 50 ng/mL of biotinylate-anti-IL15 (BAM247, R&D Systems), or 500 ng/ml of biotinylate-goat anti-human 4.1BBL (BAF2295, R&D Systems) was added per well and incubated at room temperature for 60 min. The plates were washed three times and incubated with 0.25 μg/mL of HRP-SA (Jackson ImmunoResearch) at 100 μL per well for 30 min at RT. The plates were washed four times, and incubated with 100 μL of ABTS for 2 mins at room temperature. The absorbance results were read at 405 nm. As shown in FIG. 143A-143D, the components including IL7, IL21, IL15, and 4.1BBL in 7t15-21s137L (long version) were detected by the individual antibodies.

The following experiment was conducted to evaluate the activity of IL15 in 7t15-21s137L (long version) and 7t15-21s137L (short version). The ability of 7t15-21s137L (long version) and 7t15-21s137L (short version) to promote proliferation of IL2Rαβγ-expressing CTLL2 cells was compared with that of recombinant IL15. IL15 dependent CTLL2 cells were washed five times with IMDM-10% FBS and seeded to the wells at $2 \times 10^4$ cells/well. Serially diluted 7t15-21s137L (long version), 7t15-21s137L (short version), or IL15 were added to the cells. Cells were incubated in a $CO_2$ incubator at 37° C. for 3 days. Cell proliferation was detected by adding 20 μL of PrestoBlue (A13261, ThermoFisher) to each well on day 3 and incubated for an additional 4 hours in a $CO_2$ incubator at 37° C. Raw absorbance at 570-610 nm was read in a micro-titer plate reader. As shown in FIG. 144, 7t15-21s137L (long version), 7t15-21s137L (short version), and IL15 all promoted CTLL2 cell proliferation. The $EC_{50}$ of 7t15-21s137L (long version), 7t15-21s137L (short version), and IL15 is 51.19 pM, 55.75 pM, and 4.947 pM, respectively.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

EXEMPLARY EMBODIMENTS

Embodiment A1. A multi-chain chimeric polypeptide comprising:
  (a) a first chimeric polypeptide comprising:
    (i) a first target-binding domain;
    (ii) a soluble tissue factor domain; and
    (iii) a first domain of a pair of affinity domains;
  (b) a second chimeric polypeptide comprising:
    (i) a second domain of a pair of affinity domains; and
    (ii) a second target-binding domain,
  wherein the first chimeric polypeptide and the second chimeric polypeptide associate through the binding of the first domain and the second domain of the pair of affinity domains.

Embodiment A2. The multi-chain chimeric polypeptide of embodiment A1, wherein the first target-binding domain and the soluble tissue factor domain directly abut each other in the first chimeric polypeptide.

Embodiment A3. The multi-chain chimeric polypeptide of embodiment A1, wherein the first chimeric polypeptide further comprises a linker sequence between the first target-binding domain and the soluble tissue factor domain in the first chimeric polypeptide.

Embodiment A4. The multi-chain chimeric polypeptide of any one of embodiments A1-A3, wherein the soluble tissue factor domain and the first domain of the pair of affinity domains directly abut each other in the first chimeric polypeptide.

Embodiment A5. The multi-chain chimeric polypeptide of any one of embodiments A1-A3, wherein the first chimeric polypeptide further comprises a linker sequence between the soluble tissue factor domain and the first domain of the pair of affinity domains in the first chimeric polypeptide.

Embodiment A6. The multi-chain chimeric polypeptide of any one of embodiments A1-A5, wherein the second domain of the pair of affinity domains and the second target-binding domain directly abut each other in the second chimeric polypeptide.

Embodiment A7. The multi-chain chimeric polypeptide of any one of embodiments A1-A5, wherein second chimeric polypeptide further comprises a linker sequence between the second domain of the pair of affinity domains and the second target-binding domain in the second chimeric polypeptide.

Embodiment A8. The multi-chain chimeric polypeptide of any one of embodiments A1-A7, wherein the first target-binding domain and the second target-binding domain bind specifically to the same antigen.

Embodiment A9. The multi-chain chimeric polypeptide of embodiment A8, wherein the first target-binding domain and the second target-binding domain bind specifically to the same epitope.

Embodiment A10. The multi-chain chimeric polypeptide of embodiment A9, wherein the first target-binding domain and the second target-binding domain comprise the same amino acid sequence.

Embodiment A11. The multi-chain chimeric polypeptide of any one of embodiments A1-A7, wherein the first target-binding domain and the second target-binding domain bind specifically to different antigens.

Embodiment A12. The multi-chain chimeric polypeptide of any one of embodiments A1-A11, wherein one or both of the first target-binding domain and the second target-binding domain is an antigen-binding domain.

Embodiment A13. The multi-chain chimeric polypeptide of embodiment A12, wherein the first target-binding domain and the second target-binding domain are each antigen-binding domains.

Embodiment A14. The multi-chain chimeric polypeptide of embodiment A12 or A13, wherein antigen-binding domain comprises a scFv or a single domain antibody.

Embodiment A15. The multi-chain chimeric polypeptide of any one of embodiments A1-A14, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKP30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A16. The multi-chain chimeric polypeptide of any one of embodiments A1-A14, wherein one or both of the first target-binding domain and the second target-binding domain is a soluble interleukin or cytokine protein.

Embodiment A17. The multi-chain chimeric polypeptide of embodiment A16, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment A18. The multi-chain chimeric polypeptide of any one of embodiments A1-A14, wherein one or both of the first target-binding domain and the second target-binding domain is a soluble interleukin or cytokine receptor.

Embodiment A19. The multi-chain chimeric polypeptide of embodiment A18, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment A20. The multi-chain chimeric polypeptide of any one of embodiments A1-A19, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment A21. The multi-chain chimeric polypeptide of embodiment A20, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment A22. The multi-chain chimeric polypeptide of any one of embodiments A1-A19, wherein the first chimeric polypeptide further comprises one or more additional target-binding domains at the N-terminal and/or C-terminal end of the first chimeric polypeptide.

Embodiment A23. The multi-chain chimeric polypeptide of embodiment A22, wherein at least one of the one or more additional target-binding domains directly abuts the first domain of the pair of affinity domains in the first chimeric polypeptide.

Embodiment A24. The multi-chain chimeric polypeptide of embodiment A22, wherein the first chimeric polypeptide further comprises a linker sequence between the at least one of the one or more additional target-binding domains and the first domain of the pair of affinity domains.

Embodiment A25. The multi-chain chimeric polypeptide of embodiment A22, wherein the at least one of the one or more additional target-binding domains directly abuts the first target-binding domain in the first chimeric polypeptide.

Embodiment A26. The multi-chain chimeric polypeptide of embodiment A22, wherein the first chimeric polypeptide further comprises a linker sequence between the at least one of the one or more additional target-binding domains and the first target-binding domain.

Embodiment A27. The multi-chain chimeric polypeptide of embodiment A22, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment A28. The multi-chain chimeric polypeptide of embodiment A27, wherein the at least one additional target-binding domain of the one or more additional target-binding domains disposed at the N-terminus directly abuts the first target-binding domain or the first domain of the pair of affinity domains in the first chimeric Embodiment A29. The multi-chain chimeric polypeptide of embodiment A27, wherein the first chimeric polypeptide further comprises a linker sequence disposed between the at least one additional target-binding domain and the first target-binding domain or the first domain of the pair of affinity domains in the first chimeric polypeptide.

Embodiment A30. The multi-chain chimeric polypeptide of embodiment A27, wherein the at least one additional target-binding domain of the one or more additional target-binding domains disposed at the C-terminus directly abuts the first target-binding domain or the first domain of the pair of affinity domains in the first chimeric polypeptide.

Embodiment A31. The multi-chain chimeric polypeptide of embodiment A27, wherein the first chimeric polypeptide further comprises a linker sequence disposed between the at least one additional target-binding domain and the first target-binding domain or the first domain of the pair of affinity domains in the first chimeric polypeptide.

Embodiment A32. The multi-chain chimeric polypeptide of embodiment A27, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment A33. The multi-chain chimeric polypeptide of embodiment A27, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment A34. The multi-chain chimeric polypeptide of any one of embodiments A1-A33, wherein the second chimeric polypeptide further comprises one or more additional target-binding domains at the N-terminal end or the C-terminal end of the second chimeric polypeptide.

Embodiment A35. The multi-chain chimeric polypeptide of embodiment A34, wherein at least one of the one or more additional target-binding domains directly abuts the second domain of the pair of affinity domains in the second chimeric polypeptide.

Embodiment A36. The multi-chain chimeric polypeptide of embodiment A34, wherein the second chimeric polypeptide further comprises a linker sequence between at least one of the one or more additional target-binding domains and the second domain of the pair of affinity domains in the second chimeric polypeptide.

Embodiment A37. The multi-chain chimeric polypeptide of embodiment A34, wherein at least one of the one or more additional target-binding domains directly abuts the second target-binding domain in the second chimeric polypeptide.

Embodiment A38. The multi-chain chimeric polypeptide of embodiment A34, wherein the second chimeric polypeptide further comprises a linker sequence between at least one of the one or more additional target-binding domains and the second target-binding domain in the second chimeric polypeptide.

Embodiment A39. The multi-chain chimeric polypeptide of any one of embodiments A20-A38, wherein two or more of the first target-binding domain, the second target-binding domain, and the one or more additional target-binding domains bind specifically to the same antigen.

Embodiment A40. The multi-chain chimeric polypeptide of embodiment A39, wherein two or more of the first target-binding domain, the second target-binding domain, and the one or more additional target-binding domains bind specifically to the same epitope.

Embodiment A41. The multi-chain chimeric polypeptide of embodiment A40, wherein two or more of the first target-binding domain, the second target-binding domain, and the one or more additional target-binding domains comprise the same amino acid sequence.

Embodiment A42. The multi-chain chimeric polypeptide of embodiment A39, wherein the first target-binding domain, the second target-binding domain, and the one or more additional target-binding domains each bind specifically to the same antigen.

Embodiment A43. The multi-chain chimeric polypeptide of embodiment A42, wherein the first target-binding domain, the second target-binding domain, and the one or more additional target-binding domains each bind specifically to the same epitope.

Embodiment A44. The multi-chain chimeric polypeptide of embodiment A43, wherein the first target-binding domain, the second target-binding domain, and the one or more additional target-binding domains each comprise the same amino acid sequence.

Embodiment A45. The multi-chain chimeric polypeptide of any one of embodiments A20-A38, wherein the first target-binding domain, the second target-binding domain, and the one or more additional target-binding domains bind specifically to different antigens.

Embodiment A46. The multi-chain chimeric polypeptide of any one of embodiments A20-A45, wherein one or more of the first target-binding domain, the second target-binding domain, and the one or more target-binding domains is an antigen-binding domain.

Embodiment A47. The multi-chain chimeric polypeptide of embodiment A46, wherein the first target-binding domain, the second target-binding domain, and the one or more additional target-binding domains are each an antigen-binding domain.

Embodiment A48. The multi-chain chimeric polypeptide of embodiment A47, wherein antigen-binding domain comprises a scFv.

Embodiment A49. The multi-chain chimeric polypeptide of any one of embodiments A20-A48, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKP30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment A50. The multi-chain chimeric polypeptide of any one of embodiments A20-A48, wherein one or more of the first target-binding domain, the second target-binding domain, and the one or more additional target-binding domains is a soluble interleukin or cytokine protein.

Embodiment A51. The multi-chain chimeric polypeptide of embodiment A50, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment A52. The multi-chain chimeric polypeptide of any one of embodiments A20-A48, wherein one or more of the first target-binding domain, the second target-binding domain, and the one or more additional target-binding domains is a soluble interleukin or cytokine receptor.

Embodiment A53. The multi-chain chimeric polypeptide of embodiment A52, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment A54. The multi-chain chimeric polypeptide of any one of embodiments A1-A53, wherein the first chimeric polypeptide further comprises a peptide tag at the N-terminal end or the C-terminal end of the first chimeric polypeptide.

Embodiment A55. The multi-chain chimeric polypeptide of any one of embodiments A1-A53, wherein the second chimeric polypeptide further comprises a peptide tag at the N-terminal end or the C-terminal end of the second chimeric Embodiment A56. The multi-chain chimeric polypeptide of any one of embodiments A1-A55, wherein the soluble tissue factor domain is a soluble human tissue factor domain.

Embodiment A57. The multi-chain chimeric polypeptide of embodiment A56, wherein the soluble human tissue factor domain comprises a sequence that is at least 80% identical to SEQ ID NO: 1.

Embodiment A58. The multi-chain chimeric polypeptide of embodiment A57, wherein the soluble human tissue factor domain comprises a sequence that is at least 90% identical to SEQ ID NO: 1.

Embodiment A59. The multi-chain chimeric polypeptide of embodiment A58, wherein the soluble human tissue factor domain comprises a sequence that is at least 95% identical to SEQ ID NO: 1.

Embodiment A60. The multi-chain chimeric polypeptide of any one of embodiments A56-A59, wherein the soluble human tissue factor domain does not comprise one or more of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment A61. The multi-chain chimeric polypeptide of embodiment A60, wherein the soluble human tissue factor domain does not comprise any of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment A62. The multi-chain chimeric polypeptide of any one of embodiments A1-A61, wherein the soluble tissue factor domain is not capable of binding to Factor VIIa.

Embodiment A63. The multi-chain chimeric polypeptide of any one of embodiments A1-A62, wherein the soluble tissue factor domain does not convert inactive Factor X into Factor Xa.

Embodiment A64. The multi-chain chimeric polypeptide of any one of embodiments A1-A63, wherein the multi-chain chimeric polypeptide does not stimulate blood coagulation in a mammal.

Embodiment A65. The multi-chain chimeric polypeptide of any one of embodiments A1-A64, wherein the pair of affinity domains is a sushi domain from an alpha chain of human IL-15 receptor (IL15Rα) and a soluble IL-15.

Embodiment A66. The multi-chain chimeric polypeptide of embodiment A65, wherein the soluble IL15 has a D8N or D8A amino acid substitution.

Embodiment A67. The multi-chain chimeric polypeptide of embodiment A65 or A66, wherein the human IL15Rα is a mature full-length IL15Rα.

Embodiment A68. The multi-chain chimeric polypeptide of any one of embodiments A1-A64, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment A69. The multi-chain chimeric polypeptide of any one of embodiments A1-A68, wherein the first chimeric polypeptide and/or the second chimeric polypeptide further comprises a signal sequence at its N-terminal end.

Embodiment A70. A composition comprising any of the multi-chain chimeric polypeptides of embodiments A1-A69.

Embodiment A71. The composition of embodiment A70, wherein the composition is a pharmaceutical composition.

Embodiment A72. A kit comprising at least one dose of the composition of embodiment A70 or A71.

Embodiment A73. A method of stimulating an immune cell, the method comprising:

contacting an immune cell with an effective amount of any of the multi-chain chimeric polypeptides of embodiments A1-A69 or the composition of embodiment A70 or A71.

Embodiment A74. The method of embodiment A73, wherein the immune cell is contacted in vitro.

Embodiment A75. The method of embodiment A74, wherein the immune cell was previously obtained from a subject.

Embodiment A76. The method of embodiment A75, wherein the method further comprises obtaining the immune cell from the subject prior to the contacting step.

Embodiment A77. The method of embodiment A73, wherein the immune cell is contacted in vivo.

Embodiment A78. The method of any one of embodiments A73-A77, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment A79. The method of any one of embodiments A73-A78, wherein the immune cell has previously been genetically modified to express a chimeric antigen receptor or a recombinant T-cell receptor.

Embodiment A80. The method of any one of embodiments A73-A78, wherein the method further comprises, after the contacting step, introducing into the immune cell a nucleic acid encoding a chimeric antigen-receptor or a recombinant T-cell receptor.

Embodiment A81. The method of any one of embodiments A73-A80, wherein the method further comprises administering the immune cell to a subject in need thereof.

Embodiment A82. The method of embodiment A81, wherein the subject has been identified or diagnosed as having an age-related disease or condition.

Embodiment A83. The method of embodiment A82, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A84. The method of embodiment A81, wherein the subject has been identified or diagnosed as having a cancer.

Embodiment A85. The method of embodiment A84, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A86. The method of embodiment A81, wherein the subject has been diagnosed or identified as having an infectious disease.

Embodiment A87. The method of embodiment A86, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A88. A method of inducing or increasing proliferation of an immune cell, the method comprising:

contacting an immune cell with an effective amount of any of the multi-chain chimeric polypeptides of embodiments A1-A69 or the composition of embodiment A70 or A71.

Embodiment A89. The method of embodiment A88, wherein the immune cell is contacted in vitro.

Embodiment A90. The method of embodiment A89, wherein the immune cell was previously obtained from a subject.

Embodiment A91. The method of embodiment A90, wherein the method further comprises obtaining the immune cell from the subject prior to the contacting step.

Embodiment A92. The method of embodiment A88, wherein the immune cell is contacted in vivo.

Embodiment A93. The method of any one of embodiments A88-A92, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment A94. The method of any one of embodiments A88-A93, wherein the immune cell has previously been genetically modified to express a chimeric antigen receptor or a recombinant T-cell receptor.

Embodiment A95. The method of any one of embodiments A88-A93, wherein the method further comprises, after the contacting step, introducing into the immune cell a nucleic acid encoding a chimeric antigen-receptor or a recombinant T-cell receptor.

Embodiment A96. The method of any one of embodiments A88-A95, wherein the method further comprises administering the immune cell to a subject in need thereof.

Embodiment A97. The method of embodiment A96, wherein the subject has been identified or diagnosed as having an age-related disease or condition.

Embodiment A98. The method of embodiment A97, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A99. The method of embodiment A96, wherein the subject has been identified or diagnosed as having a cancer.

Embodiment A100. The method of embodiment A99, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A101. The method of embodiment A96, wherein the subject has been diagnosed or identified as having an infectious disease.

Embodiment A102. The method of embodiment A96, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A103. A method of inducing differentiation of an immune cell into a memory or memory-like immune cell, the method comprising:

contacting an immune cell with an effective amount of any of the multi-chain chimeric polypeptides of embodiments A1-A69 or the composition of embodiment A70 or A71.

Embodiment A104. The method of embodiment A103, wherein the immune cell is contacted in vitro.

Embodiment A105. The method of embodiment A104, wherein the immune cell was previously obtained from a subject.

Embodiment A106. The method of embodiment A105, wherein the method further comprises obtaining the immune cell from the subject prior to the contacting step.

Embodiment A107. The method of embodiment A103, wherein the immune cell is contacted in vivo.

Embodiment A108. The method of any one of embodiments A103-A107, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment A109. The method of any one of embodiments A103-A108, wherein the immune cell has previously been genetically modified to express a chimeric antigen receptor or a recombinant T-cell receptor.

Embodiment A110. The method of any one of embodiments A103-A108, wherein the method further comprises, after the contacting step, introducing into the immune cell a nucleic acid encoding a chimeric antigen-receptor or a recombinant T-cell receptor.

Embodiment A111. The method of any one of embodiments A103-A110, wherein the method further comprises administering the immune cell to a subject in need thereof.

Embodiment A112. The method of embodiment A111, wherein the subject has been identified or diagnosed as having an age-related disease or condition.

Embodiment A113. The method of embodiment A112, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A114. The method of embodiment A111, wherein the subject has been identified or diagnosed as having a cancer.

Embodiment A115. The method of embodiment A114, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A116. The method of embodiment A111, wherein the subject has been diagnosed or identified as having an infectious disease.

Embodiment A117. The method of embodiment A116, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A118. A method of killing a cancer cell, an infected cell, or a senescent cell in a subject in need thereof, the method comprising administering to the subject a therapeutically effective amount of any of the multi-chain chimeric polypeptides of embodiments A1-A69 or the composition of embodiment A70 or A71.

Embodiment A119. The method of embodiment A118, wherein the subject has been identified or diagnosed as having a cancer.

Embodiment A120. The method of embodiment A119, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A121. The method of embodiment A118, wherein the subject has been identified or diagnosed as having an aging-related disease or condition.

Embodiment A122. The method of embodiment A121, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A123. A method of treating a subject in need thereof, the method comprising administering to the subject a therapeutically effective amount of any of the multi-chain chimeric polypeptides of embodiments A1-A69 or the composition of embodiment A70 or A71.

Embodiment A124. The method of embodiment A123, wherein the subject has been identified or diagnosed as having a cancer.

Embodiment A125. The method of embodiment A124, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment A126. The method of embodiment A123, wherein the subject has been identified or diagnosed as having an aging-related disease or condition.

Embodiment A127. The method of embodiment A126, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment A128. The method of embodiment A123, wherein the subject has been diagnosed or identified as having an infectious disease.

Embodiment A129. The method of embodiment A128, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment A130. Nucleic acid encoding any of the multi-chain chimeric polypeptides of any one of embodiments A1-A69.

Embodiment A131. A vector comprising the nucleic acid of embodiment A130.

Embodiment A132. The vector of embodiment A131, wherein the vector is an expression vector.

Embodiment A133. A cell comprising the nucleic acid of embodiment A130 or the vector of embodiment A131 or A132.

Embodiment A134. A method of producing a multi-chain chimeric polypeptide, the method comprising:

culturing the cell of embodiment A133 in a culture medium under conditions sufficient to result in the production of the multi-chain chimeric polypeptide; and recovering the multi-chain chimeric polypeptide from the cell and/or the culture medium.

Embodiment A135. A multi-chain chimeric polypeptide produced by the method of embodiment A134.

Embodiment A136. The multi-chain chimeric polypeptide of embodiment A56, wherein the soluble human tissue factor domain comprises a sequence that is at least 80% identical to SEQ ID NO: 3.

Embodiment A137. The multi-chain chimeric polypeptide of embodiment A136, wherein the soluble human tissue factor domain comprises a sequence that is at least 90% identical to SEQ ID NO: 3.

Embodiment A138. The multi-chain chimeric polypeptide of embodiment A137, wherein the soluble human tissue factor domain comprises a sequence that is at least 95% identical to SEQ ID NO: 3.

Embodiment A139. The multi-chain chimeric polypeptide of embodiment A138, wherein the soluble human tissue factor domain comprises a sequence that is 100% identical to SEQ ID NO: 3.

Embodiment A140. The multi-chain chimeric polypeptide of embodiment A56, wherein the soluble human tissue factor domain comprises a sequence that is at least 80% identical to SEQ ID NO: 4.

Embodiment A141. The multi-chain chimeric polypeptide of embodiment A140, wherein the soluble human tissue factor domain comprises a sequence that is at least 90% identical to SEQ ID NO: 4.

Embodiment A142. The multi-chain chimeric polypeptide of embodiment A141, wherein the soluble human tissue factor domain comprises a sequence that is at least 95% identical to SEQ ID NO: 4.

Embodiment A143. The multi-chain chimeric polypeptide of embodiment A142, wherein the soluble human tissue factor domain comprises a sequence that is 100% identical to SEQ ID NO: 4.

Embodiment A144. The multi-chain chimeric polypeptide of embodiment 56, wherein the human soluble tissue factor domain does not initiate coagulation.

Embodiment A145. The multi-chain chimeric polypeptide of any one of claims 1-59, wherein the soluble tissue factor domain comprises or consists of a sequence from a wildtype soluble human tissue factor.

B. Exemplary Embodiments

Embodiment B1. A multi-chain chimeric polypeptide comprising:
(a) a first chimeric polypeptide comprising:
  (i) a first target-binding domain;
  (ii) a soluble tissue factor domain; and
  (iii) a first domain of a pair of affinity domains;
(b) a second chimeric polypeptide comprising:
  (i) a second domain of a pair of affinity domains; and
  (ii) a second target-binding domain, wherein:

the first chimeric polypeptide and the second chimeric polypeptide associate through the binding of the first domain and the second domain of the pair of affinity domains;
the first target-binding domain and the second targeting-binding domain each independently bind specifically to a receptor of IL-18 or a receptor of IL-12.

Embodiment B2. The multi-chain chimeric polypeptide of embodiment B1, wherein the first target-binding domain and the soluble tissue factor domain directly abut each other in the first chimeric polypeptide.

Embodiment B3. The multi-chain chimeric polypeptide of embodiment B1, wherein the first chimeric polypeptide further comprises a linker sequence between the first target-binding domain and the soluble tissue factor domain in the first chimeric polypeptide.

Embodiment B4. The multi-chain chimeric polypeptide of any one of embodiments B1-B3, wherein the soluble tissue factor domain and the first domain of the pair of affinity domains directly abut each other in the first chimeric polypeptide.

Embodiment B5. The multi-chain chimeric polypeptide of any one of embodiments B1-B3, wherein the first chimeric polypeptide further comprises a linker sequence between the soluble tissue factor domain and the first domain of the pair of affinity domains in the first chimeric polypeptide.

Embodiment B6. The multi-chain chimeric polypeptide of any one of embodiments B1-B5, wherein the second domain of the pair of affinity domains and the second target-binding domain directly abut each other in the second chimeric polypeptide.

Embodiment B7. The multi-chain chimeric polypeptide of any one of embodiments B1-B5, wherein second chimeric polypeptide further comprises a linker sequence between the second domain of the pair of affinity domains and the second target-binding domain in the second chimeric polypeptide.

Embodiment B8. The multi-chain chimeric polypeptide of any one of embodiments B1-B7, wherein the soluble tissue factor domain is a soluble human tissue factor domain.

Embodiment B9. The multi-chain chimeric polypeptide of embodiment B8, wherein the soluble human tissue factor domain comprises a sequence that is at least 80% identical to SEQ ID NO: 1.

Embodiment B10. The multi-chain chimeric polypeptide of embodiment B9, wherein the soluble human tissue factor domain comprises a sequence that is at least 90% identical to SEQ ID NO: 1.

Embodiment B11. The multi-chain chimeric polypeptide of embodiment B10, wherein the soluble human tissue factor domain comprises a sequence that is at least 95% identical to SEQ ID NO: 1.

Embodiment B12. The multi-chain chimeric polypeptide of any one of embodiments B8-B11, wherein the soluble human tissue factor domain does not comprise one or more of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment B13. The multi-chain chimeric polypeptide of embodiment B12, wherein the soluble human tissue factor domain does not comprise any of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment B14. The multi-chain chimeric polypeptide of any one of embodiments B1-B13, wherein the soluble tissue factor domain is not capable of binding to Factor VIIa.

Embodiment B15. The multi-chain chimeric polypeptide of any one of embodiments B1-B14, wherein the soluble tissue factor domain does not convert inactive Factor X into Factor Xa.

Embodiment B16. The multi-chain chimeric polypeptide of any one of embodiments B1-B15, wherein the multi-chain chimeric polypeptide does not stimulate coagulation in a mammal.

Embodiment B17. The multi-chain chimeric polypeptide of any one of embodiments B1-B16, wherein the first chimeric polypeptide further comprises a peptide tag at the N-terminal end or the C-terminal end of the first chimeric polypeptide.

Embodiment B18. The multi-chain chimeric polypeptide of any one of embodiments B1-B17, wherein the second chimeric polypeptide further comprises a peptide tag at the N-terminal end or the C-terminal end of the second chimeric polypeptide.

Embodiment B19. The multi-chain chimeric polypeptide of any one of embodiments B1-18, wherein the first chimeric polypeptide and/or the second chimeric polypeptide further comprises a signal sequence at its N-terminal end.

Embodiment B20. The multi-chain chimeric polypeptide of embodiment B19, wherein the signal sequence comprises SEQ ID NO: 31.

Embodiment B21. The multi-chain chimeric polypeptide of embodiment B20, wherein the signal sequence is SEQ ID NO: 31.

Embodiment B22. The multi-chain chimeric polypeptide of any one of embodiments B1-B21, wherein the pair of affinity domains is a sushi domain from an alpha chain of human IL-15 receptor (IL15Rα) and a soluble IL-15.

Embodiment B23. The multi-chain chimeric polypeptide of embodiment B22, wherein the soluble IL-15 has a D8N or D8A amino acid substitution.

Embodiment B24. The multi-chain chimeric polypeptide of embodiment B22, wherein the soluble IL-15 comprises a sequence that is 80% identical to SEQ ID NO: 14.

Embodiment B25. The multi-chain chimeric polypeptide of embodiment B24, wherein the soluble IL-15 comprises a sequence that is 90% identical to SEQ ID NO: 14.

Embodiment B26. The multi-chain chimeric polypeptide of embodiment B25, wherein the soluble IL-15 comprises a sequence that is 95% identical to SEQ ID NO: 14.

Embodiment B27. The multi-chain chimeric polypeptide of embodiment B26, wherein the soluble IL-15 comprises SEQ ID NO: 14.

Embodiment B28. The multi-chain chimeric polypeptide of any one of embodiments B22-B27, wherein the sushi domain of IL15Rα comprises a sushi domain from human IL15Rα.

Embodiment B29. The multi-chain chimeric polypeptide of embodiment B28, wherein the sushi domain from human IL15Rα comprises a sequence that is 80% identical to SEQ ID NO: 28.

Embodiment B30. The multi-chain chimeric polypeptide of embodiment B29, wherein the sushi domain from human IL15Rα comprises a sequence that is 90% identical to SEQ ID NO: 28.

Embodiment B31. The multi-chain chimeric polypeptide of embodiment B30, wherein the sushi domain from human IL15Rα comprises a sequence that is 95% identical to SEQ ID NO: 28.

Embodiment B32. The multi-chain chimeric polypeptide of embodiment B31, wherein the sushi domain from human IL15Rα comprises SEQ ID NO: 28.

Embodiment B33. The multi-chain chimeric polypeptide of embodiment B28, wherein the sushi domain from human IL15Rα is a mature full-length IL15Rα.

Embodiment B34. The multi-chain chimeric polypeptide of any one of embodiments B1-B21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment B35. The multi-chain chimeric polypeptide of any one of embodiments B1-B34, wherein one or both of the first target-binding domain and the second target-binding domain is an agonistic antigen-binding domain.

Embodiment B36. The multi-chain chimeric polypeptide of embodiment B35, wherein the first target-binding domain and the second target-binding domain are each agonistic antigen-binding domains.

Embodiment B37. The multi-chain chimeric polypeptide of embodiment B35 or B36, wherein antigen-binding domain comprises a scFv or single-domain antibody.

Embodiment B38. The multi-chain chimeric polypeptide of any one of embodiments B1-B34, wherein one or both of the first target-binding domain and the second target-binding domain is a soluble IL-15 or a soluble IL-18.

Embodiment B39. The multi-chain chimeric polypeptide of embodiment B38, wherein the first target-binding domain and the second target-binding domain are each independently a soluble IL-15 or a soluble IL-18.

Embodiment B40. The multi-chain chimeric polypeptide of any one of embodiments B1-B39, wherein the first target-binding domain and the second target-binding domain both bind specifically to a receptor of IL-18 or a receptor of IL-12.

Embodiment B41. The multi-chain chimeric polypeptide of embodiment B40, wherein the first target-binding domain and the second target-binding domain bind specifically to the same epitope.

Embodiment B42. The multi-chain chimeric polypeptide of embodiment B41, wherein the first target-binding domain and the second target-binding domain comprise the same amino acid sequence.

Embodiment B43. The multi-chain chimeric polypeptide of any one of embodiments B1-B39, wherein the first target-binding domain binds specifically to a receptor for IL-12, and the second target-binding domain binds specifically to a receptor for IL-18.

Embodiment B44. The multi-chain chimeric polypeptide of any one of embodiments B1-B39, wherein the first target-binding domain binds specifically to a receptor for IL-18, and the second target-binding domain bind specifically to a receptor for IL-12.

Embodiment B45. The multi-chain chimeric polypeptide of embodiment B44, wherein the first target-binding domain comprises a soluble IL-18.

Embodiment B46. The multi-chain chimeric polypeptide of embodiment B45, wherein the soluble IL-18 is a soluble human IL-18.

Embodiment B47. The multi-chain chimeric polypeptide of embodiment B46, wherein the soluble human IL-18 comprises a sequence at least 80% identical to SEQ ID NO: 16.

Embodiment B48. The multi-chain chimeric polypeptide of embodiment B47, wherein the soluble human IL-18 comprises a sequence at least 90% identical to SEQ ID NO: 16.

Embodiment B49. The multi-chain chimeric polypeptide of embodiment B48, wherein the soluble human IL-18 comprises a sequence at least 95% identical to SEQ ID NO: 16.

Embodiment B50. The multi-chain chimeric polypeptide of embodiment B49, wherein the soluble human IL-18 comprises a sequence of SEQ ID NO: 16.

Embodiment B51. The multi-chain chimeric polypeptide of any one of embodiments B44-B50, wherein the second target-binding domain comprises a soluble IL-12.

Embodiment B52. The multi-chain chimeric polypeptide of embodiment B51, wherein the soluble IL-18 is a soluble human IL-12.

Embodiment B53. The multi-chain chimeric polypeptide of embodiment B52, wherein the soluble human IL-15 comprises a sequence of soluble human IL-12β (p40) and a sequence of soluble human IL-12α (p35).

Embodiment B54. The multi-chain chimeric polypeptide of embodiment B53, wherein the soluble human IL-15 further comprises a linker sequence between the sequence of soluble IL-12β (p40) and the sequence of soluble human IL-12α (p35).

Embodiment B55. The multi-chain chimeric polypeptide of embodiment B54, wherein the linker sequence comprises SEQ ID NO: 7.

Embodiment B56. The multi-chain chimeric polypeptide of any one of embodiments B53-B55, wherein the sequence of soluble human IL-12β (p40) comprises a sequence that is at least 80% identical to SEQ ID NO: 66.

Embodiment B57. The multi-chain chimeric polypeptide of embodiment B56, wherein the sequence of soluble human IL-12β (p40) comprises a sequence that is at least 90% identical to SEQ ID NO: 66.

Embodiment B58. The multi-chain chimeric polypeptide of embodiment B57, wherein the sequence of soluble human IL-12β (p40) comprises a sequence that is at least 95% identical to SEQ ID NO: 66.

Embodiment B59. The multi-chain chimeric polypeptide of embodiment B58, wherein the sequence of soluble human IL-12β (p40) comprises SEQ ID NO: 66.

Embodiment B60. The multi-chain chimeric polypeptide of any one of embodiments B53-B59, wherein the sequence of soluble human IL-12α (p35) comprises a sequence that is at least 80% identical to SEQ ID NO: 68.

Embodiment B61. The multi-chain chimeric polypeptide of embodiment B60, wherein the sequence of soluble human IL-12α (p35) comprises a sequence that is at least 90% identical to SEQ ID NO: 68.

Embodiment B62. The mule-chain chimeric polypeptide of embodiment B61, wherein the sequence of soluble human IL-12α (p35) comprises a sequence that is at least 95% identical to SEQ ID NO: 68.

Embodiment B63. The multi-chain chimeric polypeptide of embodiment B62, wherein the sequence of soluble human IL-12α (p35) comprises SEQ ID NO: 68.

Embodiment B64. The multi-chain chimeric polypeptide of embodiment B1, wherein the first chimeric polypeptide comprises a sequence that is at least 80% identical to SEQ ID NO: 70.

Embodiment B65. The multi-chain chimeric polypeptide of embodiment B64, wherein the first chimeric polypeptide comprises a sequence that is at least 90% identical to SEQ ID NO: 70.

Embodiment B66. The multi-chain chimeric polypeptide of embodiment B65, wherein the first chimeric polypeptide comprises a sequence that is at least 95% identical to SEQ ID NO: 70.

Embodiment B67. The multi-chain chimeric polypeptide of embodiment B66, wherein the first chimeric polypeptide comprises SEQ ID NO: 70.

Embodiment B68. The multi-chain chimeric polypeptide of embodiment B67, wherein the first chimeric polypeptide comprises SEQ ID NO: 72.

Embodiment B69. The multi-chain chimeric polypeptide of any one of embodiments B1 and B64-B68, wherein the second chimeric polypeptide comprises a sequence that is at least 80% identical to SEQ ID NO: 74.

Embodiment B70. The multi-chain chimeric polypeptide of embodiment B69, wherein the second chimeric polypeptide comprises a sequence that is at least 90% identical to SEQ ID NO: 74.

Embodiment B71. The multi-chain chimeric polypeptide of embodiment B70, wherein the second chimeric polypeptide comprises a sequence that is at least 95% identical to SEQ ID NO: 74.

Embodiment B72. The multi-chain chimeric polypeptide of embodiment B71, wherein the second chimeric polypeptide comprises SEQ ID NO: 74.

Embodiment B73. The multi-chain chimeric polypeptide of embodiment B72, wherein the second chimeric polypeptide comprises SEQ ID NO: 74.

Embodiment B74. The multi-chain chimeric polypeptide of any one of embodiments B1-B63, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment B75. The multi-chain chimeric polypeptide of embodiment B74, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment B76. The multi-chain chimeric polypeptide of any one of embodiments B1-B63, wherein the first chimeric polypeptide further comprises one or more additional target-binding domains at the N-terminal and/or C-terminal end of the first chimeric polypeptide.

Embodiment B77. The multi-chain chimeric polypeptide of embodiment B76, wherein at least one of the one or more additional target-binding domains directly abuts the first domain of the pair of affinity domains in the first chimeric polypeptide.

Embodiment B78. The multi-chain chimeric polypeptide of embodiment B76, wherein the first chimeric polypeptide further comprises a linker sequence between the at least one of the one or more additional target-binding domains and the first domain of the pair of affinity domains.

Embodiment B79. The multi-chain chimeric polypeptide of embodiment B76, wherein the at least one of the one or more additional target-binding domains directly abuts the first target-binding domain in the first chimeric polypeptide.

Embodiment B80. The multi-chain chimeric polypeptide of embodiment B76, wherein the first chimeric polypeptide further comprises a linker sequence between the at least one of the one or more additional target-binding domains and the first target-binding domain.

Embodiment B81. The multi-chain chimeric polypeptide of embodiment B76, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment B82. The multi-chain chimeric polypeptide of embodiment B81, wherein the at least one additional target-binding domain of the one or more additional target-binding domains disposed at the N-terminus directly abuts the first target-binding domain or the first domain of the pair of affinity domains in the first chimeric polypeptide.

Embodiment B83. The multi-chain chimeric polypeptide of embodiment B81, wherein the first chimeric polypeptide further comprises a linker sequence disposed between the at least one additional target-binding domain and the first target-binding domain or the first domain of the pair of affinity domains in the first chimeric polypeptide.

Embodiment B84. The multi-chain chimeric polypeptide of embodiment B81, wherein the at least one additional target-binding domain of the one or more additional target-binding domains disposed at the C-terminus directly abuts the first target-binding domain or the first domain of the pair of affinity domains in the first chimeric polypeptide.

Embodiment B85. The multi-chain chimeric polypeptide of embodiment B81, wherein the first chimeric polypeptide further comprises a linker sequence disposed between the at least one additional target-binding domain and the first target-binding domain or the first domain of the pair of affinity domains in the first chimeric Embodiment B86. The multi-chain chimeric polypeptide of embodiment B81, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment B87. The multi-chain chimeric polypeptide of embodiment B81, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment B88. The multi-chain chimeric polypeptide of any one of embodiments B1-B63 and B74-B87, wherein the second chimeric polypeptide further comprises one or more additional target-binding domains at the N-terminal end or the C-terminal end of the second chimeric polypeptide.

Embodiment B89. The multi-chain chimeric polypeptide of embodiment B88, wherein at least one of the one or more additional target-binding domains directly abuts the second domain of the pair of affinity domains in the second chimeric polypeptide.

Embodiment B90. The multi-chain chimeric polypeptide of embodiment B88, wherein the second chimeric polypeptide further comprises a linker sequence between at least one of the one or more additional target-binding domains and the second domain of the pair of affinity domains in the second chimeric polypeptide.

Embodiment B91. The multi-chain chimeric polypeptide of embodiment B88, wherein at least one of the one or more additional target-binding domains directly abuts the second target-binding domain in the second chimeric polypeptide.

Embodiment B92. The multi-chain chimeric polypeptide of embodiment B88, wherein the second chimeric polypeptide further comprises a linker sequence between at least one of the one or more additional target-binding domains and the second target-binding domain in the second chimeric polypeptide.

Embodiment B93. The multi-chain chimeric polypeptide of any one of embodiments B74-B92, wherein two or more of the first target-binding domain, the second target-binding domain, and the one or more additional target-binding domains bind specifically to the same antigen.

Embodiment B94. The multi-chain chimeric polypeptide of embodiment B93, wherein two or more of the first target-binding domain, the second target-binding domain, and the one or more additional target-binding domains bind specifically to the same epitope.

Embodiment B95. The multi-chain chimeric polypeptide of embodiment B94, wherein two or more of the first target-binding domain, the second target-binding domain, and the one or more additional target-binding domains comprise the same amino acid sequence.

Embodiment B96. The multi-chain chimeric polypeptide of any one of embodiments B74-B92, wherein the first target-binding domain, the second target-binding domain, and the one or more additional target-binding domains bind specifically to different antigens.

Embodiment B97. The multi-chain chimeric polypeptide of any one of embodiments B74-B96, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKP30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment B98. The multi-chain chimeric polypeptide of any one of embodiments B74-B96, wherein the one or more additional target-binding domains is a soluble interleukin or cytokine protein.

Embodiment B99. The multi-chain chimeric polypeptide of embodiment B98, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment B100. The multi-chain chimeric polypeptide of any one of embodiments B74-B96, wherein the one or more additional target-binding domains is a soluble interleukin or cytokine receptor.

Embodiment B101. The multi-chain chimeric polypeptide of embodiment B100, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, or a soluble CD28.

Embodiment B102. A composition comprising any of the multi-chain chimeric polypeptides of embodiments B1-B101.

Embodiment B103. The composition of embodiment B102, wherein the composition is a pharmaceutical composition.

Embodiment B104. A kit comprising at least one dose of the composition of embodiment B102 or B103.

Embodiment B105. A method of stimulating an immune cell, the method comprising:

contacting an immune cell with an effective amount of any of the multi-chain chimeric polypeptides of embodiments B1-B101 or the composition of embodiment B102 or B103.

Embodiment B106. The method of embodiment B105, wherein the immune cell is contacted in vitro.

Embodiment B107. The method of embodiment B106, wherein the immune cell was previously obtained from a subject.

Embodiment B108. The method of embodiment B107, wherein the method further comprises obtaining the immune cell from the subject prior to the contacting step.

Embodiment B109. The method of embodiment B105, wherein the immune cell is contacted in vivo.

Embodiment B110. The method of any one of embodiments B105-B109, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment B111. The method of any one of embodiments B105-B110, wherein the immune cell has previously been genetically modified to express a chimeric antigen receptor or a recombinant T-cell receptor.

Embodiment B112. The method of any one of embodiments B105-B110, wherein the method further comprises, after the contacting step, introducing into the immune cell a nucleic acid encoding a chimeric antigen-receptor or a recombinant T-cell receptor.

Embodiment B113. The method of any one of embodiments B105-B112, wherein the method further comprises administering the immune cell to a subject in need thereof.

Embodiment B114. The method of embodiment B113, wherein the subject has been identified or diagnosed as having age-related disease or condition.

Embodiment B115. The method of embodiment B114, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B116. The method of embodiment B113, wherein the subject has been identified or diagnosed as having a cancer.

Embodiment B117. The method of embodiment B116, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B118. The method of embodiment B113, wherein the subject has been diagnosed or identified as having an infectious disease.

Embodiment B119. The method of embodiment B118, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B120. A method of inducing or increasing proliferation of an immune cell, the method comprising:
contacting an immune cell with an effective amount of any of the multi-chain chimeric polypeptides of embodiments B1-B101 or the composition of embodiment B102 or B103.

Embodiment B121. The method of embodiment B120, wherein the immune cell is contacted in vitro.

Embodiment B122. The method of embodiment B121, wherein the immune cell was previously obtained from a subject.

Embodiment B123. The method of embodiment B122, wherein the method further comprises obtaining the immune cell from the subject prior to the contacting step.

Embodiment B124. The method of embodiment B120, wherein the immune cell is contacted in vivo.

Embodiment B125. The method of any one of embodiments B120-B124, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, $\gamma\delta$ T cell, an $\alpha\beta$ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment B126. The method of any one of embodiments B120-B125, wherein the immune cell has previously been genetically modified to express a chimeric antigen receptor or a recombinant T-cell receptor.

Embodiment B127. The method of any one of embodiments B120-B125, wherein the method further comprises, after the contacting step, introducing into the immune cell a nucleic acid encoding a chimeric antigen-receptor or a recombinant T-cell receptor.

Embodiment B128. The method of any one of embodiments B120-B127, wherein the method further comprises administering the immune cell to a subject in need thereof.

Embodiment B129. The method of embodiment B128, wherein the subject has been identified or diagnosed as having an age-related disease or condition.

Embodiment B130. The method of embodiment B129, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B131. The method of embodiment B128, wherein the subject has been identified or diagnosed as having a cancer.

Embodiment B132. The method of embodiment B131, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B133. The method of embodiment B128, wherein the subject has been diagnosed or identified as having an infectious disease.

Embodiment B134. The method of embodiment B128, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B135. A method of inducing differentiation of an immune cell into a memory or memory-like immune cell, the method comprising:
contacting an immune cell with an effective amount of any of the multi-chain chimeric polypeptides of embodiments B1-B101 or the composition of embodiment B102 or B103.

Embodiment B136. The method of embodiment B135, wherein the immune cell is contacted in vitro.

Embodiment B137. The method of embodiment B136, wherein the immune cell was previously obtained from a subject.

Embodiment B138. The method of embodiment B137, wherein the method further comprises obtaining the immune cell from the subject prior to the contacting step.

Embodiment B139. The method of embodiment B135, wherein the immune cell is contacted in vivo.

Embodiment B140. The method of any one of embodiments B135-B139, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment B141. The method of any one of embodiments B135-B140, wherein the immune cell has previously been genetically modified to express a chimeric antigen receptor or a recombinant T-cell receptor.

Embodiment B142. The method of any one of embodiments B135-B140, wherein the method further comprises, after the contacting step, introducing into the immune cell a nucleic acid encoding a chimeric antigen-receptor or a recombinant T-cell receptor.

Embodiment B143. The method of any one of embodiments B135-B142, wherein the method further comprises administering the immune cell to a subject in need thereof.

Embodiment B144. The method of embodiment B143, wherein the subject has been identified or diagnosed as having an age-related disease or condition.

Embodiment B145. The method of embodiment B144, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B146. The method of embodiment B143, wherein the subject has been identified or diagnosed as having a cancer.

Embodiment B147. The method of embodiment B146, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B148. The method of embodiment B143, wherein the subject has been diagnosed or identified as having an infectious disease.

Embodiment B149. The method of embodiment B148, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B150. A method of killing a cancer cell, an infected cell, or a senescent cell in a subject in need thereof, the method comprising administering to the subject a therapeutically effective amount of any of the multi-chain chimeric polypeptides of embodiments B1-B101 or the composition of embodiment B102 or B103.

Embodiment B151. The method of embodiment B150, wherein the subject has been identified or diagnosed as having a cancer.

Embodiment B152. The method of embodiment B151, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B153. The method of embodiment B150, wherein the subject has been identified or diagnosed as having an aging-related disease or condition.

Embodiment B154. The method of embodiment B153, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Hunington's disease, spinocerebellar ataxia, multiple sclerosis, and renal dysfunction Embodiment B155. A method of treating a subject in need thereof, the method comprising administering to the subject a therapeutically effective amount of any of the multi-chain chimeric polypeptides of embodiments B1-B101 or the composition of embodiment B102 or B103.

Embodiment B156. The method of embodiment B155, wherein the subject has been identified or diagnosed as having a cancer or infectious disease.

Embodiment B157. The method of embodiment B156, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment B158. The method of embodiment B155, wherein the subject has been identified or diagnosed as having age-related disease or condition.

Embodiment B159. The method of embodiment B158, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment B160. The method of embodiment B155, wherein the subject has been diagnosed or identified as having an infectious disease.

Embodiment B161. The method of embodiment B160, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment B162. Nucleic acid encoding any of the multi-chain chimeric polypeptides of any one of embodiments B1-B101.

Embodiment B163. A vector comprising the nucleic acid of embodiment B162.

Embodiment B164. The vector of embodiment B163, wherein the vector is an expression vector.

Embodiment B165. A cell comprising the nucleic acid of embodiment B162 or the vector of embodiment B163 or B164.

Embodiment B166. A method of producing a multi-chain chimeric polypeptide, the method comprising:

culturing the cell of embodiment B165 in a culture medium under conditions sufficient to result in the production of the multi-chain chimeric polypeptide; and recovering the multi-chain chimeric polypeptide from the cell and/or the culture medium.

Embodiment B167. A multi-chain chimeric polypeptide produced by the method of embodiment B166.

Embodiment B168. The multi-chain chimeric polypeptide of embodiment B8, wherein the soluble human tissue factor domain comprises a sequence that is at least 80% identical to SEQ ID NO: 3.

Embodiment B169. The multi-chain chimeric polypeptide of embodiment B168, wherein the soluble human tissue factor domain comprises a sequence that is at least 90% identical to SEQ ID NO: 3.

Embodiment B170. The multi-chain chimeric polypeptide of embodiment B169, wherein the soluble human tissue factor domain comprises a sequence that is at least 95% identical to SEQ ID NO: 3.

Embodiment B171. The multi-chain chimeric polypeptide of embodiment B170, wherein the soluble human tissue factor domain comprises a sequence that is 100% identical to SEQ ID NO: 3.

Embodiment B172. The multi-chain chimeric polypeptide of embodiment B8, wherein the soluble human tissue factor domain comprises a sequence that is at least 80% identical to SEQ ID NO: 4.

Embodiment B173. The multi-chain chimeric polypeptide of embodiment B172, wherein the soluble human tissue factor domain comprises a sequence that is at least 90% identical to SEQ ID NO: 4.

Embodiment B174. The multi-chain chimeric polypeptide of embodiment B173, wherein the soluble human tissue factor domain comprises a sequence that is at least 95% identical to SEQ ID NO: 4.

Embodiment B175. The multi-chain chimeric polypeptide of embodiment B174, wherein the soluble human tissue factor domain comprises a sequence that is 100% identical to SEQ ID NO: 4.

C. Exemplary Embodiments

Embodiment C1. A multi-chain chimeric polypeptide comprising:
(a) a first chimeric polypeptide comprising:
 (i) a first target-binding domain;
 (ii) a soluble tissue factor domain; and
 (iii) a first domain of a pair of affinity domains;
(b) a second chimeric polypeptide comprising:
 (i) a second domain of a pair of affinity domains; and
 (ii) a second target-binding domain,
wherein:
the first chimeric polypeptide and the second chimeric polypeptide associate through the binding of the first domain and the second domain of the pair of affinity domains; and
the first target-binding domain and the second targeting-binding domain each independently bind specifically to a receptor of IL-21 or a ligand of tumor growth factor receptor β II (TGFβRII).

Embodiment C2. The multi-chain chimeric polypeptide of embodiment C1, wherein the first target-binding domain and the soluble tissue factor domain directly abut each other in the first chimeric polypeptide.

Embodiment C3. The multi-chain chimeric polypeptide of embodiments C1, wherein the first chimeric polypeptide further comprises a linker sequence between the first target-binding domain and the soluble tissue factor domain in the first chimeric polypeptide.

Embodiment C4. The multi-chain chimeric polypeptide of any one of embodiments C1-C3, wherein the soluble tissue factor domain and the first domain of the pair of affinity domains directly abut each other in the first chimeric polypeptide.

Embodiment C5. The multi-chain chimeric polypeptide of any one of embodiments C1-C3, wherein the first chimeric polypeptide further comprises a linker sequence between the soluble tissue factor domain and the first domain of the pair of affinity domains in the first chimeric polypeptide.

Embodiment C6. The multi-chain chimeric polypeptide of any one of embodiments C1-05, wherein the second domain of the pair of affinity domains and the second target-binding domain directly abut each other in the second chimeric polypeptide.

Embodiment C7. The multi-chain chimeric polypeptide of any one of embodiments C1-05, wherein second chimeric polypeptide further comprises a linker sequence between the second domain of the pair of affinity domains and the second target-binding domain in the second chimeric polypeptide.

Embodiment C8. The multi-chain chimeric polypeptide of any one of embodiments C1-C7, wherein the soluble tissue factor domain is a soluble human tissue factor domain.

Embodiment C9. The multi-chain chimeric polypeptide of embodiment C8, wherein the soluble human tissue factor domain comprises a sequence that is at least 80% identical to SEQ ID NO: 1.

Embodiment C10. The multi-chain chimeric polypeptide of embodiment C9, wherein the soluble human tissue factor domain comprises a sequence that is at least 90% identical to SEQ ID NO: 1.

Embodiment C11. The multi-chain chimeric polypeptide of embodiment C10, wherein the soluble human tissue factor domain comprises a sequence that is at least 95% identical to SEQ ID NO: 1.

Embodiment C12. The multi-chain chimeric polypeptide of any one of embodiments C8-C11, wherein the soluble human tissue factor domain does not comprise one or more of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment C13. The multi-chain chimeric polypeptide of embodiment C12, wherein the soluble human tissue factor domain does not comprise any of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment C14. The multi-chain chimeric polypeptide of any one of embodiments C1-C13, wherein the soluble tissue factor domain is not capable of binding to Factor VIIa.

Embodiment C15. The multi-chain chimeric polypeptide of any one of embodiments C1-C14, wherein the soluble tissue factor domain does not convert inactive Factor X into Factor Xa.

Embodiment C16. The multi-chain chimeric polypeptide of any one of embodiments C1-C15, wherein the multi-chain chimeric polypeptide does not stimulate blood coagulation in a mammal.

Embodiment C17. The multi-chain chimeric polypeptide of any one of embodiments C1-C16, wherein the first chimeric polypeptide further comprises a peptide tag at the N-terminal end or the C-terminal end of the first chimeric polypeptide.

Embodiment C18. The multi-chain chimeric polypeptide of any one of embodiments C1-C17, wherein the second chimeric polypeptide further comprises a peptide tag at the N-terminal end or the C-terminal end of the second chimeric polypeptide.

Embodiment C19. The multi-chain chimeric polypeptide of any one of embodiments C1-C18, wherein the first chimeric polypeptide and/or the second chimeric polypeptide further comprises a signal sequence at its N-terminal end.

Embodiment C20. The multi-chain chimeric polypeptide of embodiment C19, wherein the signal sequence comprises SEQ ID NO: 31.

Embodiment C21. The multi-chain chimeric polypeptide of embodiment C20, wherein the signal sequence is SEQ ID NO: 31.

Embodiment C22. The multi-chain chimeric polypeptide of any one of embodiments C1-C21, wherein the pair of affinity domains is a sushi domain from an alpha chain of human IL-15 receptor (IL15Rα and a soluble IL-15.

Embodiment C23. The multi-chain chimeric polypeptide of embodiment C22, wherein the soluble IL-15 has a D8N or D8A amino acid substitution.

Embodiment C24. The multi-chain chimeric polypeptide of embodiment C22, wherein the soluble IL-15 comprises a sequence that is 80% identical to SEQ ID NO: 14.

Embodiment C25. The multi-chain chimeric polypeptide of embodiment C24, wherein the soluble IL-15 comprises a sequence that is 90% identical to SEQ ID NO: 14.

Embodiment C26. The multi-chain chimeric polypeptide of embodiment C25, wherein the soluble IL-15 comprises a sequence that is 95% identical to SEQ ID NO: 14.

Embodiment C27. The multi-chain chimeric polypeptide of embodiment C26, wherein the soluble IL-15 comprises SEQ ID NO: 14.

Embodiment C28. The multi-chain chimeric polypeptide of any one of embodiments C22-C27, wherein the sushi domain of IL15Rα comprises a sushi domain from human IL15Rα.

Embodiment C29. The multi-chain chimeric polypeptide of embodiment C28, wherein the sushi domain from human IL15Rα comprises a sequence that is 80% identical to SEQ ID NO: 28.

Embodiment C30. The multi-chain chimeric polypeptide of embodiment C29, wherein the sushi domain from human IL15Rα comprises a sequence that is 90% identical to SEQ ID NO: 28.

Embodiment C31. The multi-chain chimeric polypeptide of embodiment C30, wherein the sushi domain from human IL15Rα comprises a sequence that is 95% identical to SEQ ID NO: 28.

Embodiment C32. The multi-chain chimeric polypeptide of embodiment C31, wherein the sushi domain from human IL15Rα comprises SEQ ID NO: 28.

Embodiment C33. The multi-chain chimeric polypeptide of embodiment C28, wherein the sushi domain from human IL15Rα is a mature full-length IL15Rα.

Embodiment C34. The multi-chain chimeric polypeptide of any one of embodiments C1-C21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment C35. The multi-chain chimeric polypeptide of any one of embodiments C1-C34, wherein one or both of the first target-binding domain and the second target-binding domain is an antigen-binding domain.

Embodiment C36. The multi-chain chimeric polypeptide of embodiment C35, wherein the first target-binding domain and the second target-binding domain are antigen-binding domains.

Embodiment C37. The multi-chain chimeric polypeptide of embodiment C35 or C36, wherein antigen-binding domain comprises a scFv or single-domain antibody.

Embodiment C38. The multi-chain chimeric polypeptide of any one of embodiments C1-C34, wherein one or both of the first target-binding domain and the second target-binding domain is a soluble IL-21 or a soluble TGFβRII.

Embodiment C39. The multi-chain chimeric polypeptide of any one of embodiments C1-C38, wherein the first target-binding domain and the second target-binding domain both bind specifically to a receptor of IL-21 or a ligand of TGFβRII.

Embodiment C40. The multi-chain chimeric polypeptide of embodiment C39, wherein the first target-binding domain and the second target-binding domain bind specifically to the same epitope.

Embodiment C41. The multi-chain chimeric polypeptide of embodiment C40, wherein the first target-binding domain and the second target-binding domain comprise the same amino acid sequence.

Embodiment C42. The multi-chain chimeric polypeptide of any one of embodiments C1-C38, wherein the first target-binding domain binds specifically to a ligand of TGFβRII, and the second target-binding domain binds specifically to a receptor for IL-21.

Embodiment C43. The multi-chain chimeric polypeptide of any one of embodiments C1-C38, wherein the first target-binding domain binds specifically to a receptor for IL-21, and the second target-binding domain bind specifically to a ligand of TGFβRII.

Embodiment C44. The multi-chain chimeric polypeptide of embodiment C43, wherein the first target-binding domain comprises a soluble IL-21.

Embodiment C45. The multi-chain chimeric polypeptide of embodiment C44, wherein the soluble IL-21 is a soluble human IL-21.

Embodiment C46. The multi-chain chimeric polypeptide of embodiment C45, wherein the soluble human IL-21 comprises a sequence at least 80% identical to SEQ ID NO: 78.

Embodiment C47. The multi-chain chimeric polypeptide of embodiment C46, wherein the soluble human IL-21 comprises a sequence at least 90% identical to SEQ ID NO: 78.

Embodiment C48. The multi-chain chimeric polypeptide of embodiment C47, wherein the soluble human IL-21 comprises a sequence at least 95% identical to SEQ ID NO: 78.

Embodiment C49. The multi-chain chimeric polypeptide of embodiment C48, wherein the soluble human IL-21 comprises a sequence of SEQ ID NO: 78.

Embodiment C50. The multi-chain chimeric polypeptide of any one of embodiments C43-C49, wherein the second target-binding domain comprises a soluble TGFβRII.

Embodiment C51. The multi-chain chimeric polypeptide of embodiment C50, wherein the soluble TGFβRII is a soluble human TGFβRII.

Embodiment C52. The multi-chain chimeric polypeptide of embodiment C51, wherein the soluble human TGFβRII comprises a first sequence of soluble human TGFβRII and a second sequence of soluble human TGFβRII.

Embodiment C53. The multi-chain chimeric polypeptide of embodiment C52, wherein the soluble human TGFβRII further comprises a linker sequence between the first sequence of soluble human TGFβRII and the second sequence of soluble human TGFβRII.

Embodiment C54. The multi-chain chimeric polypeptide of embodiment C53, wherein the linker sequence comprises SEQ ID NO: 7.

Embodiment C55. The multi-chain chimeric polypeptide of any one of embodiments C52-054, wherein the first sequence of soluble human TGFβRII comprises a sequence that is at least 80% identical to SEQ ID NO: 80.

Embodiment C56. The multi-chain chimeric polypeptide of embodiment C55, wherein the first sequence of soluble human TGFβRII comprises a sequence that is at least 90% identical to SEQ ID NO: 80.

Embodiment C57. The multi-chain chimeric polypeptide of embodiment C56, wherein the first sequence of soluble human TGFβRII comprises a sequence that is at least 95% identical to SEQ ID NO: 80.

Embodiment C58. The multi-chain chimeric polypeptide of embodiment C57, wherein the first sequence of soluble human TGFβRII comprises SEQ ID NO: 80.

Embodiment C59. The multi-chain chimeric polypeptide of any one of embodiments C52-058, wherein the second sequence of soluble human TGFβRII comprises a sequence that is at least 80% identical to SEQ ID NO: 81.

Embodiment C60. The multi-chain chimeric polypeptide of embodiment C59, wherein the second sequence of soluble human TGFβRII comprises a sequence that is at least 90% identical to SEQ ID NO: 81.

Embodiment C61. The mule-chain chimeric polypeptide of embodiment C60, wherein the second sequence of soluble human TGFβRII comprises a sequence that is at least 95% identical to SEQ ID NO: 81.

Embodiment C62. The multi-chain chimeric polypeptide of embodiment C61, wherein the second sequence of soluble human TGFβRII comprises SEQ ID NO: 81.

Embodiment C63. The multi-chain chimeric polypeptide of embodiment C1, wherein the first chimeric polypeptide comprises a sequence that is at least 80% identical to SEQ ID NO: 86.

Embodiment C64. The multi-chain chimeric polypeptide of embodiment C63, wherein the first chimeric polypeptide comprises a sequence that is at least 90% identical to SEQ ID NO: 86.

Embodiment C65. The multi-chain chimeric polypeptide of embodiment C64, wherein the first chimeric polypeptide comprises a sequence that is at least 95% identical to SEQ ID NO: 86.

Embodiment C66. The multi-chain chimeric polypeptide of embodiment C65, wherein the first chimeric polypeptide comprises SEQ ID NO: 86.

Embodiment C67. The multi-chain chimeric polypeptide of embodiment C66, wherein the first chimeric polypeptide comprises SEQ ID NO: 88.

Embodiment C68. The multi-chain chimeric polypeptide of any one of embodiments C1 and C63-C67, wherein the second chimeric polypeptide comprises a sequence that is at least 80% identical to SEQ ID NO: 90.

Embodiment C69. The multi-chain chimeric polypeptide of embodiment C68, wherein the second chimeric polypeptide comprises a sequence that is at least 90% identical to SEQ ID NO: 90.

Embodiment C70. The multi-chain chimeric polypeptide of embodiment C69, wherein the second chimeric polypeptide comprises a sequence that is at least 95% identical to SEQ ID NO: 90.

Embodiment C71. The multi-chain chimeric polypeptide of embodiment C70, wherein the second chimeric polypeptide comprises SEQ ID NO: 90.

Embodiment C72. The multi-chain chimeric polypeptide of embodiment C71, wherein the second chimeric polypeptide comprises SEQ ID NO: 92.

Embodiment C73. The multi-chain chimeric polypeptide of any one of embodiments C1-C62, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment C74. The multi-chain chimeric polypeptide of embodiment C73, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment C75. The multi-chain chimeric polypeptide of any one of embodiments C1-C62, wherein the first chimeric polypeptide further comprises one or more additional target-binding domains at the N-terminal and/or C-terminal end of the first chimeric polypeptide.

Embodiment C76. The multi-chain chimeric polypeptide of embodiment C75, wherein at least one of the one or more additional target-binding domains directly abuts the first domain of the pair of affinity domains in the first chimeric polypeptide.

Embodiment C77. The multi-chain chimeric polypeptide of embodiment C75, wherein the first chimeric polypeptide further comprises a linker sequence between the at least one of the one or more additional target-binding domains and the first domain of the pair of affinity domains.

Embodiment C78. The multi-chain chimeric polypeptide of embodiment C75, wherein the at least one of the one or more additional target-binding domains directly abuts the first target-binding domain in the first chimeric polypeptide.

Embodiment C79. The multi-chain chimeric polypeptide of embodiment C75, wherein the first chimeric polypeptide further comprises a linker sequence between the at least one of the one or more additional target-binding domains and the first target-binding domain.

Embodiment C80. The multi-chain chimeric polypeptide of embodiment C75, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric Embodiment C81. The multi-chain chimeric polypeptide of embodiment C80, wherein the at least one additional target-binding domain of the one or more additional target-binding domains disposed at the N-terminus directly abuts the first target-binding domain or the first domain of the pair of affinity domains in the first chimeric polypeptide.

Embodiment C82. The multi-chain chimeric polypeptide of embodiment C80, wherein the first chimeric polypeptide further comprises a linker sequence disposed between the at least one additional target-binding domain and the first target-binding domain or the first domain of the pair of affinity domains in the first chimeric polypeptide.

Embodiment C83. The multi-chain chimeric polypeptide of embodiment C80, wherein the at least one additional target-binding domain of the one or more additional target-binding domains disposed at the C-terminus directly abuts the first target-binding domain or the first domain of the pair of affinity domains in the first chimeric polypeptide.

Embodiment C84. The multi-chain chimeric polypeptide of embodiment C80, wherein the first chimeric polypeptide further comprises a linker sequence disposed between the at least one additional target-binding domain and the first target-binding domain or the first domain of the pair of affinity domains in the first chimeric polypeptide.

Embodiment C85. The multi-chain chimeric polypeptide of embodiment C80, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment C86. The multi-chain chimeric polypeptide of embodiment C80, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment C87. The multi-chain chimeric polypeptide of any one of embodiments C1-C62 and C73-C86, wherein the second chimeric polypeptide further comprises one or more additional target-binding domains at the N-terminal end or the C-terminal end of the second chimeric polypeptide.

Embodiment C88. The multi-chain chimeric polypeptide of embodiment C87, wherein at least one of the one or more additional target-binding domains directly abuts the second domain of the pair of affinity domains in the second chimeric polypeptide.

Embodiment C89. The multi-chain chimeric polypeptide of embodiment C87, wherein the second chimeric polypeptide further comprises a linker sequence between at least one of the one or more additional target-binding domains and the second domain of the pair of affinity domains in the second chimeric polypeptide.

Embodiment C90. The multi-chain chimeric polypeptide of embodiment C87, wherein at least one of the one or more additional target-binding domains directly abuts the second target-binding domain in the second chimeric polypeptide.

Embodiment C91. The multi-chain chimeric polypeptide of embodiment C87, wherein the second chimeric polypeptide further comprises a linker sequence between at least one of the one or more additional target-binding domains and the second target-binding domain in the second chimeric polypeptide.

Embodiment C92. The multi-chain chimeric polypeptide of any one of embodiments C73-C91, wherein two or more of the first target-binding domain, the second target-binding domain, and the one or more additional target-binding domains bind specifically to the same antigen.

Embodiment C93. The multi-chain chimeric polypeptide of embodiment C92, wherein two or more of the first target-binding domain, the second target-binding domain, and the one or more additional target-binding domains bind specifically to the same epitope.

Embodiment C94. The multi-chain chimeric polypeptide of embodiment C93, wherein two or more of the first target-binding domain, the second target-binding domain, and the one or more additional target-binding domains comprise the same amino acid sequence.

Embodiment C95. The multi-chain chimeric polypeptide of any one of embodiments C73-C91, wherein the first target-binding domain, the second target-binding domain, and the one or more additional target-binding domains bind specifically to different antigens.

Embodiment C96. The multi-chain chimeric polypeptide of any one of embodiments C73-C95, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-D, a ligand of TGF-β receptor II (TGF-RII), a ligand of TGF-βRIII, a ligand of DNAM-1, a ligand of NKp46, a ligand of NKp44, a ligand of NKG2D, a ligand of NKp30, a ligand for a scMRCI, a ligand for a scMRCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment C97. The multi-chain chimeric polypeptide of any one of embodiments C73-C95, wherein the one or more additional target-binding domains is a soluble interleukin or cytokine protein.

Embodiment C98. The multi-chain chimeric polypeptide of embodiment C97, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment C99. The multi-chain chimeric polypeptide of any one of embodiments C73-C95, wherein the one or more additional target-binding domains is a soluble interleukin or cytokine receptor.

Embodiment C100. The multi-chain chimeric polypeptide of embodiment C99, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMRCI, a scMRCII, a scTCR, a soluble CD155, or a soluble CD28.

Embodiment C101. A composition comprising any of the multi-chain chimeric polypeptides of embodiments C1-C100.

Embodiment C102. The composition of embodiment C101, wherein the composition is a pharmaceutical composition.

Embodiment C103. A kit comprising at least one dose of the composition of embodiment C101 or C102.

Embodiment C104. A method of stimulating an immune cell, the method comprising:

contacting an immune cell with an effective amount of any of the multi-chain chimeric polypeptides of embodiments C1-C100 or the composition of embodiment C101 or C102.

Embodiment C105. The method of embodiment C104, wherein the immune cell is contacted in vitro.

Embodiment C106. The method of embodiment C105, wherein the immune cell was previously obtained from a subject.

Embodiment C107. The method of embodiment C106, wherein the method further comprises obtaining the immune cell from the subject prior to the contacting step.

Embodiment C108. The method of embodiment C104, wherein the immune cell is contacted in vivo.

Embodiment C109. The method of any one of embodiments C104-C108, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8$^+$ T cell, a CD4$^+$ T cell, a natural killer T cell, a mast cell, a macrophage, a neutrophil, a dendritic cell, a basophil, an eosinophil, and a natural killer cell.

Embodiment C110. The method of any one of embodiments C104-C109, wherein the immune cell has previously been genetically modified to express a chimeric antigen receptor or a recombinant T-cell receptor.

Embodiment C111. The method of any one of embodiments C104-C109, wherein the method further comprises, after the contacting step, introducing into the immune cell a nucleic acid encoding a chimeric antigen-receptor or a recombinant T-cell receptor.

Embodiment C112. The method of any one of embodiments C104-C111, wherein the method further comprises administering the immune cell to a subject in need thereof.

Embodiment C113. The method of embodiment C112, wherein the subject has been identified or diagnosed as having age-related disease or condition.

Embodiment C114. The method of embodiment C113, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment C115. The method of embodiment C112, wherein the subject has been identified or diagnosed as having a cancer.

Embodiment C116. The method of embodiment C115, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment C117. The method of embodiment C112, wherein the subject has been diagnosed or identified as having an infectious disease.

Embodiment C118. The method of embodiment C117, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment C119. A method of inducing or increasing proliferation of an immune cell, the method comprising:

contacting an immune cell with an effective amount of any of the multi-chain chimeric polypeptides of embodiments C1-C100 or the composition of embodiment C101 or C102.

Embodiment C120. The method of embodiment C119, wherein the immune cell is contacted in vitro.

Embodiment C121. The method of embodiment C120, wherein the immune cell was previously obtained from a subject.

Embodiment C122. The method of embodiment C121, wherein the method further comprises obtaining the immune cell from the subject prior to the contacting step.

Embodiment C123. The method of embodiment C119, wherein the immune cell is contacted in vivo.

Embodiment C124. The method of any one of embodiments C119-C123, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment C125. The method of any one of embodiments C119-C124, wherein the immune cell has previously been genetically modified to express a chimeric antigen receptor or a recombinant T-cell receptor.

Embodiment C126. The method of any one of embodiments C119-C124, wherein the method further comprises, after the contacting step, introducing into the immune cell a nucleic acid encoding a chimeric antigen-receptor or a recombinant T-cell receptor.

Embodiment C127. The method of any one of embodiments C119-C126, wherein the method further comprises administering the immune cell to a subject in need thereof.

Embodiment C128. The method of embodiment C127, wherein the subject has been identified or diagnosed as having an age-related disease or condition.

Embodiment C129. The method of embodiment C128, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment C130. The method of embodiment C127, wherein the subject has been identified or diagnosed as having a cancer.

Embodiment C131. The method of embodiment C130, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment C132. The method of embodiment C127, wherein the subject has been diagnosed or identified as having an infectious disease.

Embodiment C133. The method of embodiment C127, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment C134. A method of inducing differentiation of an immune cell into a memory or memory-like immune cell, the method comprising:
contacting an immune cell with an effective amount of any of the multi-chain chimeric polypeptides of embodiments C1-C100 or the composition of embodiment C101 or C102.

Embodiment C135. The method of embodiment C134, wherein the immune cell is contacted in vitro.

Embodiment C136. The method of embodiment C135, wherein the immune cell was previously obtained from a subject.

Embodiment C137. The method of embodiment C136, wherein the method further comprises obtaining the immune cell from the subject prior to the contacting step.

Embodiment C138. The method of embodiment C134, wherein the immune cell is contacted in vivo.

Embodiment C139. The method of any one of embodiments C134-C138, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment C140. The method of any one of embodiments C134-C139, wherein the immune cell has previously been genetically modified to express a chimeric antigen receptor or a recombinant T-cell receptor.

Embodiment C141. The method of any one of embodiments C134-C139, wherein the method further comprises, after the contacting step, introducing into the immune cell a nucleic acid encoding a chimeric antigen-receptor or a recombinant T-cell receptor.

Embodiment C142. The method of any one of embodiments C134-C141, wherein the method further comprises administering the immune cell to a subject in need thereof.

Embodiment C143. The method of embodiment C142, wherein the subject has been identified or diagnosed as having an age-related disease or condition.

Embodiment C144. The method of embodiment C143, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment C145. The method of embodiment C142, wherein the subject has been identified or diagnosed as having a cancer.

Embodiment C146. The method of embodiment C145, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment C147. The method of embodiment C142, wherein the subject has been diagnosed or identified as having an infectious disease.

Embodiment C148. The method of embodiment C147, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment C149. A method of killing a cancer cell, an infected cell, or a senescent cell in a subject in need thereof, the method comprising administering to the subject a therapeutically effective amount of any of the multi-chain chimeric polypeptides of embodiments C1-C100 or the composition of embodiment C101 or C102.

Embodiment C150. The method of embodiment C149, wherein the subject has been identified or diagnosed as having a cancer.

Embodiment C151. The method of embodiment C150, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment C152. The method of embodiment C149, wherein the subject has been identified or diagnosed as having an aging-related disease or condition.

Embodiment C153. The method of embodiment C152, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Embodiment C154. A method of treating a subject in need thereof, the method comprising administering to the subject a therapeutically effective amount of any of the multi-chain chimeric polypeptides of embodiments C1-C100 or the composition of embodiment C101 or C102.

Embodiment C155. The method of embodiment C154, wherein the subject has been identified or diagnosed as having a cancer or infectious disease.

Embodiment C156. The method of embodiment C157, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment C157. The method of embodiment C154, wherein the subject has been identified or diagnosed as having age-related disease or condition.

Embodiment C158. The method of embodiment C157, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment C159. The method of embodiment C154, wherein the subject has been diagnosed or identified as having an infectious disease.

Embodiment C160. The method of embodiment C159, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment C161. Nucleic acid encoding any of the multi-chain chimeric polypeptides of any one of embodiments C1-C100.

Embodiment C162. A vector comprising the nucleic acid of embodiment C161.

Embodiment C163. The vector of embodiment C162, wherein the vector is an expression vector.

Embodiment C164. A cell comprising the nucleic acid of embodiment C161 or the vector of embodiment C162 or C163.

Embodiment C165. A method of producing a multi-chain chimeric polypeptide, the method comprising:
culturing the cell of embodiment C164 in a culture medium under conditions sufficient to result in the production of the multi-chain chimeric polypeptide; and
recovering the multi-chain chimeric polypeptide from the cell and/or the culture medium.

Embodiment C166. A multi-chain chimeric polypeptide produced by the method of embodiment C165.

Embodiment C167. The multi-chain chimeric polypeptide of embodiment C12, wherein the soluble human tissue factor domain comprises a sequence that is at least 80% identical to SEQ ID NO: 3.

Embodiment C168. The multi-chain chimeric polypeptide of embodiment C167, wherein the soluble human tissue factor domain comprises a sequence that is at least 90% identical to SEQ ID NO: 3.

Embodiment C169. The multi-chain chimeric polypeptide of embodiment C168, wherein the soluble human tissue factor domain comprises a sequence that is at least 95% identical to SEQ ID NO: 3.

Embodiment C170. The multi-chain chimeric polypeptide of embodiment C169, wherein the soluble human tissue factor domain comprises a sequence that is 100% identical to SEQ ID NO: 3.

Embodiment C171. The multi-chain chimeric polypeptide of embodiment C12, wherein the soluble human tissue factor domain comprises a sequence that is at least 80% identical to SEQ ID NO: 4.

Embodiment C172. The multi-chain chimeric polypeptide of embodiment C171, wherein the soluble human tissue factor domain comprises a sequence that is at least 90% identical to SEQ ID NO: 4.

Embodiment C173. The multi-chain chimeric polypeptide of embodiment C172, wherein the soluble human tissue factor domain comprises a sequence that is at least 95% identical to SEQ ID NO: 4.

Embodiment C174. The multi-chain chimeric polypeptide of embodiment C173, wherein the soluble human tissue factor domain comprises a sequence that is 100% identical to SEQ ID NO: 4.

D. Exemplary Embodiments

Embodiment D1. A multi-chain chimeric polypeptide comprising:
(c) a first chimeric polypeptide comprising:
(i) a first target-binding domain;
(ii) a soluble tissue factor domain; and
(iii) a first domain of a pair of affinity domains;
(d) a second chimeric polypeptide comprising:
(i) a second domain of a pair of affinity domains; and
(ii) a second target-binding domain,
wherein:
the first chimeric polypeptide and the second chimeric polypeptide associate through the binding of the first domain and the second domain of the pair of affinity domains;
the first target-binding domain and the second targeting-binding domain each independently bind specifically to a receptor of IL-21 or a receptor of IL-7.

Embodiment D2. The multi-chain chimeric polypeptide of embodiment D1, wherein the first target-binding domain and the soluble tissue factor domain directly abut each other in the first chimeric polypeptide.

Embodiment D3. The multi-chain chimeric polypeptide of embodiment D1, wherein the first chimeric polypeptide further comprises a linker sequence between the first target-binding domain and the soluble tissue factor domain in the first chimeric polypeptide.

Embodiment D4. The multi-chain chimeric polypeptide of any one of embodiments D1-D3, wherein the soluble tissue factor domain and the first domain of the pair of affinity domains directly abut each other in the first chimeric polypeptide.

Embodiment D5. The multi-chain chimeric polypeptide of any one of embodiments D1-D3, wherein the first chimeric polypeptide further comprises a linker sequence between the soluble tissue factor domain and the first domain of the pair of affinity domains in the first chimeric polypeptide.

Embodiment D6. The multi-chain chimeric polypeptide of any one of embodiments D1-D5, wherein the second domain of the pair of affinity domains and the second target-binding domain directly abut each other in the second chimeric polypeptide.

Embodiment D7. The multi-chain chimeric polypeptide of any one of embodiments D1-D5, wherein second chimeric polypeptide further comprises a linker sequence between the second domain of the pair of affinity domains and the second target-binding domain in the second chimeric polypeptide.

Embodiment D8. The multi-chain chimeric polypeptide of any one of embodiments D1-D7, wherein the soluble tissue factor domain is a soluble human tissue factor domain.

Embodiment D9. The multi-chain chimeric polypeptide of embodiment D8, wherein the soluble human tissue factor domain comprises a sequence that is at least 80% identical to SEQ ID NO: 1.

Embodiment D10. The multi-chain chimeric polypeptide of embodiment D9, wherein the soluble human tissue factor domain comprises a sequence that is at least 90% identical to SEQ ID NO: 1.

Embodiment D11. The multi-chain chimeric polypeptide of embodiment D10, wherein the soluble human tissue factor domain comprises a sequence that is at least 95% identical to SEQ ID NO: 1.

Embodiment D12. The multi-chain chimeric polypeptide of embodiment D11, wherein the soluble human tissue factor domain comprises SEQ ID NO: 1.

Embodiment D13. The multi-chain chimeric polypeptide of embodiment D8, wherein the soluble human tissue factor domain comprises a sequence that is at least 80% identical to SEQ ID NO: 3.

Embodiment D14. The multi-chain chimeric polypeptide of embodiment D13, wherein the soluble human tissue factor domain comprises a sequence that is at least 90% identical to SEQ ID NO: 3.

Embodiment D15. The multi-chain chimeric polypeptide of embodiment D14, wherein the soluble human tissue factor domain comprises a sequence that is at least 95% identical to SEQ ID NO: 3.

Embodiment D16. The multi-chain chimeric polypeptide of embodiment D15, wherein the soluble human tissue factor domain comprises SEQ ID NO: 3.

Embodiment D17. The multi-chain chimeric polypeptide of embodiment D8, wherein the soluble human tissue factor domain comprises a sequence that is at least 80% identical to SEQ ID NO: 4.

Embodiment D18. The multi-chain chimeric polypeptide of embodiment D17, wherein the soluble human tissue factor domain comprises a sequence that is at least 90% identical to SEQ ID NO: 4.

Embodiment D19. The multi-chain chimeric polypeptide of embodiment D18, wherein the soluble human tissue factor domain comprises a sequence that is at least 95% identical to SEQ ID NO: 4.

Embodiment D20. The multi-chain chimeric polypeptide of embodiment D19, wherein the soluble human tissue factor domain comprises SEQ ID NO: 4.

Embodiment D21. The multi-chain chimeric polypeptide of any one of embodiments D8-D11, D13-D15, and D17-D19, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D22. The multi-chain chimeric polypeptide of embodiment D21, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D23. The multi-chain chimeric polypeptide of any one of embodiments D1-D22, wherein the soluble tissue factor domain is not capable of binding to Factor VIIa.

Embodiment D24. The multi-chain chimeric polypeptide of any one of embodiments D1-D23, wherein the soluble tissue factor domain does not convert inactive Factor X into Factor Xa.

Embodiment D25. The multi-chain chimeric polypeptide of any one of embodiments D1-D24, wherein the multi-chain chimeric polypeptide does not stimulate coagulation in a mammal.

Embodiment D26. The multi-chain chimeric polypeptide of any one of embodiments D1-D25, wherein the first chimeric polypeptide further comprises a peptide tag at the N-terminal end or the C-terminal end of the first chimeric polypeptide.

Embodiment D27. The multi-chain chimeric polypeptide of any one of embodiments D1-D26, wherein the second chimeric polypeptide further comprises a peptide tag at the N-terminal end or the C-terminal end of the second chimeric Embodiment D28. The multi-chain chimeric polypeptide of any one of embodiments D1-D27, wherein the first chimeric polypeptide and/or the second chimeric polypeptide further comprises a signal sequence at its N-terminal end.

Embodiment D29. The multi-chain chimeric polypeptide of embodiment D28, wherein the signal sequence comprises SEQ ID NO: 31.

Embodiment D30. The multi-chain chimeric polypeptide of embodiment D28, wherein the signal sequence is SEQ ID NO: 223.

Embodiment D31. The multi-chain chimeric polypeptide of any one of embodiments D1-D30, wherein the pair of affinity domains is a sushi domain from an alpha chain of human IL-15 receptor (IL15Rα) and a soluble IL-15.

Embodiment D32. The multi-chain chimeric polypeptide of embodiment D31, wherein the soluble IL-15 has a D8N or D8A amino acid substitution.

Embodiment D33. The multi-chain chimeric polypeptide of embodiment D31, wherein the soluble IL-15 comprises a sequence that is at least 80% identical to SEQ ID NO: 14.

Embodiment D34. The multi-chain chimeric polypeptide of embodiment D33, wherein the soluble IL-15 comprises a sequence that is at least 90% identical to SEQ ID NO: 14.

Embodiment D35. The multi-chain chimeric polypeptide of embodiment D34, wherein the soluble IL-15 comprises a sequence that is at least 95% identical to SEQ ID NO: 14.

Embodiment D36. The multi-chain chimeric polypeptide of embodiment D35, wherein the soluble IL-15 comprises SEQ ID NO: 14.

Embodiment D37. The multi-chain chimeric polypeptide of any one of embodiments D31-D36, wherein the sushi domain of IL15Rα comprises a sushi domain from human IL15Rα.

Embodiment D38. The multi-chain chimeric polypeptide of embodiment D37, wherein the sushi domain from human IL15Rα comprises a sequence that is at least 80% identical to SEQ ID NO: 28.

Embodiment D39. The multi-chain chimeric polypeptide of embodiment D38, wherein the sushi domain from human IL15Rα comprises a sequence that is at least 90% identical to SEQ ID NO: 28.

Embodiment D40. The multi-chain chimeric polypeptide of embodiment D39, wherein the sushi domain from human IL15Rα comprises a sequence that is at least 95% identical to SEQ ID NO: 28.

Embodiment D41. The multi-chain chimeric polypeptide of embodiment D40, wherein the sushi domain from human IL15Rα comprises SEQ ID NO: 28.

Embodiment D42. The multi-chain chimeric polypeptide of embodiment D37, wherein the sushi domain from human IL15Rα is a mature full-length IL15Rα.

Embodiment D43. The multi-chain chimeric polypeptide of any one of embodiments D1-D30, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment D44. The multi-chain chimeric polypeptide of any one of embodiments D1-D43, wherein one or both of the first target-binding domain and the second target-binding domain is an agonistic antigen-binding domain.

Embodiment D45. The multi-chain chimeric polypeptide of embodiment D44, wherein the first target-binding domain and the second target-binding domain are each agonistic antigen-binding domains.

Embodiment D46. The multi-chain chimeric polypeptide of embodiment D44 or D45, wherein antigen-binding domain comprises a scFv or single-domain antibody.

Embodiment D47. The multi-chain chimeric polypeptide of any one of embodiments D1-D43, wherein one or both of the first target-binding domain and the second target-binding domain is a soluble IL-21 or a soluble IL-7.

Embodiment D48. The multi-chain chimeric polypeptide of embodiment D47, wherein the first target-binding domain and the second target-binding domain are each independently a soluble IL-21 or a soluble IL-7.

Embodiment D49. The multi-chain chimeric polypeptide of any one of embodiments D1-D48, wherein the first target-binding domain and the second target-binding domain both bind specifically to a receptor of IL-21 or a receptor of IL-7.

Embodiment D50. The multi-chain chimeric polypeptide of embodiment D49, wherein the first target-binding domain and the second target-binding domain bind specifically to the same epitope.

Embodiment D51. The multi-chain chimeric polypeptide of embodiment D50, wherein the first target-binding domain and the second target-binding domain comprise the same amino acid sequence.

Embodiment D52. The multi-chain chimeric polypeptide of any one of embodiments D1-D48, wherein the first target-binding domain binds specifically to a receptor for IL-21, and the second target-binding domain binds specifically to a receptor for IL-7.

Embodiment D53. The multi-chain chimeric polypeptide of any one of embodiments D1-D48, wherein the first target-binding domain binds specifically to a receptor for IL-7, and the second target-binding domain bind specifically to a receptor for IL-21.

Embodiment D54. The multi-chain chimeric polypeptide of embodiment D53, wherein the first target-binding domain comprises a soluble IL-21.

Embodiment D55. The multi-chain chimeric polypeptide of embodiment D54, wherein the soluble IL-21 is a soluble human IL-21.

Embodiment D56. The multi-chain chimeric polypeptide of embodiment D55, wherein the soluble human IL-21 comprises a sequence at least 80% identical to SEQ ID NO: 78.

Embodiment D57. The multi-chain chimeric polypeptide of embodiment D56, wherein the soluble human IL-21 comprises a sequence at least 90% identical to SEQ ID NO: 78.

Embodiment D58. The multi-chain chimeric polypeptide of embodiment D57, wherein the soluble human IL-21 comprises a sequence at least 95% identical to SEQ ID NO: 78.

Embodiment D59. The multi-chain chimeric polypeptide of embodiment D58, wherein the soluble human IL-21 comprises a sequence of SEQ ID NO: 78.

Embodiment D60. The multi-chain chimeric polypeptide of any one of embodiments D53-D59, wherein the second target-binding domain comprises a soluble IL-7.

Embodiment D61. The multi-chain chimeric polypeptide of embodiment D60, wherein the soluble IL-7 is a soluble human IL-7.

Embodiment D62. The multi-chain chimeric polypeptide of embodiment D61, wherein the soluble human IL-7 comprises a sequence at least 80% identical to SEQ ID NO: 11.

Embodiment D63. The multi-chain chimeric polypeptide of embodiment D62, wherein the soluble human IL-7 comprises a sequence at least 90% identical to SEQ ID NO: 11.

Embodiment D64. The multi-chain chimeric polypeptide of embodiment D63, wherein the soluble human IL-7 comprises a sequence at least 95% identical to SEQ ID NO: 11.

Embodiment D65. The multi-chain chimeric polypeptide of embodiment D64, wherein the soluble human IL-7 comprises a sequence of SEQ ID NO: 11.

Embodiment D66. The multi-chain chimeric polypeptide of embodiment D1, wherein the first chimeric polypeptide comprises a sequence that is at least 80% identical to SEQ ID NO: 104.

Embodiment D67. The multi-chain chimeric polypeptide of embodiment D66, wherein the first chimeric polypeptide comprises a sequence that is at least 90% identical to SEQ ID NO: 104.

Embodiment D68. The multi-chain chimeric polypeptide of embodiment D67, wherein the first chimeric polypeptide comprises a sequence that is at least 95% identical to SEQ ID NO: 104.

Embodiment D69. The multi-chain chimeric polypeptide of embodiment D68, wherein the first chimeric polypeptide comprises SEQ ID NO: 104.

Embodiment D70. The multi-chain chimeric polypeptide of embodiment D69, wherein the first chimeric polypeptide comprises SEQ ID NO: 106.

Embodiment D71. The multi-chain chimeric polypeptide of any one of embodiments D1 and D66-D70, wherein the second chimeric polypeptide comprises a sequence that is at least 80% identical to SEQ ID NO: 108.

Embodiment D72. The multi-chain chimeric polypeptide of embodiment D71, wherein the second chimeric polypeptide comprises a sequence that is at least 90% identical to SEQ ID NO: 108.

Embodiment D73. The multi-chain chimeric polypeptide of embodiment D72, wherein the second chimeric polypeptide comprises a sequence that is at least 95% identical to SEQ ID NO: 108.

Embodiment D74. The multi-chain chimeric polypeptide of embodiment D73, wherein the second chimeric polypeptide comprises SEQ ID NO: 108.

Embodiment D75. The multi-chain chimeric polypeptide of embodiment D74, wherein the second chimeric polypeptide comprises SEQ ID NO: 110.

Embodiment D76. The multi-chain chimeric polypeptide of embodiment D1, wherein the first chimeric polypeptide comprises a sequence that is at least 80% identical to SEQ ID NO: 96.

Embodiment D77. The multi-chain chimeric polypeptide of embodiment D76, wherein the first chimeric polypeptide comprises a sequence that is at least 90% identical to SEQ ID NO: 96.

Embodiment D78. The multi-chain chimeric polypeptide of embodiment D77, wherein the first chimeric polypeptide comprises a sequence that is at least 95% identical to SEQ ID NO: 96.

Embodiment D79. The multi-chain chimeric polypeptide of embodiment D68, wherein the first chimeric polypeptide comprises SEQ ID NO: 96.

Embodiment D80. The multi-chain chimeric polypeptide of embodiment D69, wherein the first chimeric polypeptide comprises SEQ ID NO: 98.

Embodiment D81. The multi-chain chimeric polypeptide of any one of embodiments D1 and D76-D80, wherein the second chimeric polypeptide comprises a sequence that is at least 80% identical to SEQ ID NO: 100.

Embodiment D82. The multi-chain chimeric polypeptide of embodiment D81, wherein the second chimeric polypeptide comprises a sequence that is at least 90% identical to SEQ ID NO: 100.

Embodiment D83. The multi-chain chimeric polypeptide of embodiment D82, wherein the second chimeric polypeptide comprises a sequence that is at least 95% identical to SEQ ID NO: 100.

Embodiment D84. The multi-chain chimeric polypeptide of embodiment D83, wherein the second chimeric polypeptide comprises SEQ ID NO: 100.

Embodiment D85. The multi-chain chimeric polypeptide of embodiment D84, wherein the second chimeric polypeptide comprises SEQ ID NO: 106.

Embodiment D86. The multi-chain chimeric polypeptide of any one of embodiments D1-D65, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment D87. The multi-chain chimeric polypeptide of embodiment D86, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment D88. The multi-chain chimeric polypeptide of any one of embodiments D1-D65, wherein the first chimeric polypeptide further comprises one or more additional target-binding domains at the N-terminal and/or C-terminal end of the first chimeric polypeptide.

Embodiment D89. The multi-chain chimeric polypeptide of embodiment D88, wherein at least one of the one or more additional target-binding domains directly abuts the first domain of the pair of affinity domains in the first chimeric polypeptide.

Embodiment D90. The multi-chain chimeric polypeptide of embodiment D88, wherein the first chimeric polypeptide further comprises a linker sequence between the at least one of the one or more additional target-binding domains and the first domain of the pair of affinity domains.

Embodiment D91. The multi-chain chimeric polypeptide of embodiment D88, wherein the at least one of the one or more additional target-binding domains directly abuts the first target-binding domain in the first chimeric polypeptide.

Embodiment D92. The multi-chain chimeric polypeptide of embodiment D88, wherein the first chimeric polypeptide further comprises a linker sequence between the at least one of the one or more additional target-binding domains and the first target-binding domain.

Embodiment D93. The multi-chain chimeric polypeptide of embodiment D88, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment D94. The multi-chain chimeric polypeptide of embodiment D93, wherein the at least one additional target-binding domain of the one or more additional target-binding domains disposed at the N-terminus directly abuts the first target-binding domain or the first domain of the pair of affinity domains in the first chimeric polypeptide.

Embodiment D95. The multi-chain chimeric polypeptide of embodiment D93, wherein the first chimeric polypeptide further comprises a linker sequence disposed between the at least one additional target-binding domain and the first target-binding domain or the first domain of the pair of affinity domains in the first chimeric Embodiment D96. The multi-chain chimeric polypeptide of embodiment D93, wherein the at least one additional target-binding domain of the one or more additional target-binding domains disposed at the C-terminus directly abuts the first target-binding domain or the first domain of the pair of affinity domains in the first chimeric polypeptide.

Embodiment D97. The multi-chain chimeric polypeptide of embodiment D93, wherein the first chimeric polypeptide further comprises a linker sequence disposed between the at least one additional target-binding domain and the first target-binding domain or the first domain of the pair of affinity domains in the first chimeric polypeptide.

Embodiment D98. The multi-chain chimeric polypeptide of embodiment D93, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment D99. The multi-chain chimeric polypeptide of embodiment D93, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment D100. The multi-chain chimeric polypeptide of any one of embodiments D1-D65 and D86-D99, wherein the second chimeric polypeptide further comprises one or more additional target-binding domains at the N-terminal end or the C-terminal end of the second chimeric polypeptide.

Embodiment D101. The multi-chain chimeric polypeptide of embodiment D100, wherein at least one of the one or more additional target-binding domains directly abuts the second domain of the pair of affinity domains in the second chimeric polypeptide.

Embodiment D102. The multi-chain chimeric polypeptide of embodiment D100, wherein the second chimeric polypeptide further comprises a linker sequence between at least one of the one or more additional target-binding domains and the second domain of the pair of affinity domains in the second chimeric polypeptide.

Embodiment D103. The multi-chain chimeric polypeptide of embodiment D100, wherein at least one of the one or more additional target-binding domains directly abuts the second target-binding domain in the second chimeric polypeptide.

Embodiment D104. The multi-chain chimeric polypeptide of embodiment D100, wherein the second chimeric polypeptide further comprises a linker sequence between at least one of the one or more additional target-binding domains and the second target-binding domain in the second chimeric polypeptide.

Embodiment D105. The multi-chain chimeric polypeptide of any one of embodiments D86-D104, wherein two or more of the first target-binding domain, the second target-binding domain, and the one or more additional target-binding domains bind specifically to the same antigen.

Embodiment D106. The multi-chain chimeric polypeptide of embodiment D105, wherein two or more of the first target-binding domain, the second target-binding domain, and the one or more additional target-binding domains bind specifically to the same epitope.

Embodiment D107. The multi-chain chimeric polypeptide of embodiment D106, wherein two or more of the first target-binding domain, the second target-binding domain, and the one or more additional target-binding domains comprise the same amino acid sequence.

Embodiment D108. The multi-chain chimeric polypeptide of any one of embodiments D86-D104, wherein the first target-binding domain, the second target-binding domain, and the one or more additional target-binding domains bind specifically to different antigens.

Embodiment D109. The multi-chain chimeric polypeptide of any one of embodiments D86-D108, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment D110. The multi-chain chimeric polypeptide of any one of embodiments D86-D108, wherein the one or more additional target-binding domains is a soluble interleukin or cytokine protein.

Embodiment D111. The multi-chain chimeric polypeptide of embodiment D110, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment D112. The multi-chain chimeric polypeptide of any one of embodiments D86-D108, wherein the one or more additional target-binding domains is a soluble interleukin or cytokine receptor.

Embodiment D113. The multi-chain chimeric polypeptide of embodiment D112, wherein the soluble receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, or a soluble CD28.

Embodiment D114. A composition comprising any of the multi-chain chimeric polypeptides of embodiments D1-D113.

Embodiment D115. The composition of embodiment D114, wherein the composition is a pharmaceutical composition.

Embodiment D116. A kit comprising at least one dose of the composition of embodiment D114 or D115.

Embodiment D117. A method of stimulating an immune cell, the method comprising:

contacting an immune cell with an effective amount of any of the multi-chain chimeric polypeptides of embodiments D1-D113 or the composition of embodiment D114 or D115.

Embodiment D118. The method of embodiment D117, wherein the immune cell is contacted in vitro.

Embodiment D119. The method of embodiment D118, wherein the immune cell was previously obtained from a subject.

Embodiment D120. The method of embodiment D119, wherein the method further comprises obtaining the immune cell from the subject prior to the contacting step.

Embodiment D121. The method of embodiment D117, wherein the immune cell is contacted in vivo.

Embodiment D122. The method of any one of embodiments D117-D121, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, $\gamma\delta$ T cell, an $\alpha\beta$ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment D123. The method of any one of embodiments D117-D122, wherein the immune cell has previously been genetically modified to express a chimeric antigen receptor or a recombinant T-cell receptor.

Embodiment D124. The method of any one of embodiments D117-D122, wherein the method further comprises, after the contacting step, introducing into the immune cell a nucleic acid encoding a chimeric antigen-receptor or a recombinant T-cell receptor.

Embodiment D125. The method of any one of embodiments D117-D124, wherein the method further comprises administering the immune cell to a subject in need thereof.

Embodiment D126. The method of embodiment D125, wherein the subject has been identified or diagnosed as having age-related disease or condition.

Embodiment D127. The method of embodiment D126, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment D128. The method of embodiment D125, wherein the subject has been identified or diagnosed as having a cancer.

Embodiment D129. The method of embodiment D128, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment D130. The method of embodiment D125, wherein the subject has been diagnosed or identified as having an infectious disease.

Embodiment D131. The method of embodiment D130, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Embodiment D132. A method of inducing or increasing proliferation of an immune cell, the method comprising:

contacting an immune cell with an effective amount of any of the multi-chain chimeric polypeptides of embodiments D1-D113 or the composition of embodiment D114 or D115.

Embodiment D133. The method of embodiment D132, wherein the immune cell is contacted in vitro.

Embodiment D134. The method of embodiment D133, wherein the immune cell was previously obtained from a subject.

Embodiment D135. The method of embodiment D134, wherein the method further comprises obtaining the immune cell from the subject prior to the contacting step.

Embodiment D136. The method of embodiment D132, wherein the immune cell is contacted in vivo.

Embodiment D137. The method of any one of embodiments D132-D136, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, $\gamma\delta$ T cell, an $\alpha\beta$ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment D138. The method of any one of embodiments D132-D137, wherein the immune cell has previously been genetically modified to express a chimeric antigen receptor or a recombinant T-cell receptor.

Embodiment D139. The method of any one of embodiments D132-D137, wherein the method further comprises, after the contacting step, introducing into the immune cell a nucleic acid encoding a chimeric antigen-receptor or a recombinant T-cell receptor.

Embodiment D140. The method of any one of embodiments D132-D139, wherein the method further comprises administering the immune cell to a subject in need thereof.

Embodiment D141. The method of embodiment D140, wherein the subject has been identified or diagnosed as having an age-related disease or condition.

Embodiment D142. The method of embodiment D141, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment D143. The method of embodiment D140, wherein the subject has been identified or diagnosed as having a cancer.

Embodiment D144. The method of embodiment D143, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment D145. The method of embodiment D140, wherein the subject has been diagnosed or identified as having an infectious disease.

Embodiment D146. The method of embodiment D140, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Embodiment D147. A method of inducing differentiation of an immune cell into a memory or memory-like immune cell, the method comprising:

contacting an immune cell with an effective amount of any of the multi-chain chimeric polypeptides of embodiments D1-D113 or the composition of embodiment D114 or D115.

Embodiment D148. The method of embodiment D147, wherein the immune cell is contacted in vitro.

Embodiment D149. The method of embodiment D148, wherein the immune cell was previously obtained from a subject.

Embodiment D150. The method of embodiment D149, wherein the method further comprises obtaining the immune cell from the subject prior to the contacting step.

Embodiment D151. The method of embodiment D147, wherein the immune cell is contacted in vivo.

Embodiment D152. The method of any one of embodiments D147-D151, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment D153. The method of any one of embodiments D147-D152, wherein the immune cell has previously been genetically modified to express a chimeric antigen receptor or a recombinant T-cell receptor.

Embodiment D154. The method of any one of embodiments D147-D152, wherein the method further comprises, after the contacting step, introducing into the immune cell a nucleic acid encoding a chimeric antigen-receptor or a recombinant T-cell receptor.

Embodiment D155: The method of any one of embodiments D147-D153, wherein the immune cell is contacted with anti-TF IgG antibody to create a memory or memory like immune cell.

Embodiment D156. The method of any one of embodiments D147-D155, wherein the method further comprises administering the immune cell to a subject in need thereof.

Embodiment D157. The method of embodiment D156, wherein the subject has been identified or diagnosed as having an age-related disease or condition.

Embodiment D158. The method of embodiment D156, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment D159. The method of embodiment D156, wherein the subject has been identified or diagnosed as having a cancer.

Embodiment D160. The method of embodiment D159, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment D161. The method of embodiment D156, wherein the subject has been diagnosed or identified as having an infectious disease.

Embodiment D162. The method of embodiment D161, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Embodiment D163. A method of killing a cancer cell, an infected cell, or a senescent cell in a subject in need thereof, the method comprising administering to the subject a therapeutically effective amount of any of the multi-chain chimeric polypeptides of embodiments D1-D113 or the composition of embodiment D114 or D115.

Embodiment D164. The method of embodiment D163, wherein the subject has been identified or diagnosed as having a cancer.

Embodiment D165. The method of embodiment D164, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment D166. The method of embodiment D163, wherein the subject has been identified or diagnosed as having an aging-related disease or condition.

Embodiment D167. The method of embodiment D166, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Embodiment D168. A method of treating a subject in need thereof, the method comprising administering to the subject a therapeutically effective amount of any of the multi-chain chimeric polypeptides of embodiments D1-D113 or the composition of embodiment D114 or D115.

Embodiment D169. The method of embodiment D168, wherein the subject has been identified or diagnosed as having a cancer or infectious disease.

Embodiment D170. The method of embodiment D169, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment D171. The method of embodiment D168, wherein the subject has been identified or diagnosed as having age-related disease or condition.

Embodiment D172. The method of embodiment D171, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment D173. The method of embodiment D168, wherein the subject has been diagnosed or identified as having an infectious disease.

Embodiment D174. The method of embodiment D173, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Embodiment D175. Nucleic acid encoding any of the multi-chain chimeric polypeptides of any one of embodiments D1-D113.

Embodiment D176. A vector comprising the nucleic acid of embodiment D174.

Embodiment D177. The vector of embodiment D176, wherein the vector is an expression vector.

Embodiment D178. A cell comprising the nucleic acid of embodiment D175 or the vector of embodiment D175 or D176.

Embodiment D179. A method of producing a multi-chain chimeric polypeptide, the method comprising:

culturing the cell of embodiment D177 in a culture medium under conditions sufficient to result in the production of the multi-chain chimeric polypeptide; and recovering the multi-chain chimeric polypeptide from the cell and/or the culture medium.

Embodiment D180. A multi-chain chimeric polypeptide produced by the method of embodiment D179.

E. Exemplary Embodiments

Embodiment E1. A multi-chain chimeric polypeptide comprising:
(e) a first chimeric polypeptide comprising:
(i) a first target-binding domain;
(ii) a soluble tissue factor domain; and
(iii) a first domain of a pair of affinity domains;
(f) a second chimeric polypeptide comprising:
(i) a second domain of a pair of affinity domains; and
(ii) a second target-binding domain,
wherein:
the first chimeric polypeptide and the second chimeric polypeptide associate through the binding of the first domain and the second domain of the pair of affinity domains; and
the first target-binding domain and the second targeting-binding domain each independently bind specifically to: a receptor for IL-7, CD16, a receptor for IL-21, TGF-β, or a receptor for CD137L.

Embodiment E2. The multi-chain chimeric polypeptide of embodiment E1, wherein the first target-binding domain and the soluble tissue factor domain directly abut each other in the first chimeric polypeptide.

Embodiment E3. The multi-chain chimeric polypeptide of embodiment E1, wherein the first chimeric polypeptide further comprises a linker sequence between the first target-binding domain and the soluble tissue factor domain in the first chimeric Embodiment E4. The multi-chain chimeric polypeptide of any one of embodiments E1-E3, wherein the soluble tissue factor domain and the first domain of the pair of affinity domains directly abut each other in the first chimeric polypeptide.

Embodiment E5. The multi-chain chimeric polypeptide of any one of embodiments E1-E3, wherein the first chimeric polypeptide further comprises a linker sequence between the soluble tissue factor domain and the first domain of the pair of affinity domains in the first chimeric polypeptide.

Embodiment E6. The multi-chain chimeric polypeptide of any one of embodiments E1-E5, wherein the second domain of the pair of affinity domains and the second target-binding domain directly abut each other in the second chimeric polypeptide.

Embodiment E7. The multi-chain chimeric polypeptide of any one of embodiments E1-E5, wherein second chimeric polypeptide further comprises a linker sequence between the second domain of the pair of affinity domains and the second target-binding domain in the second chimeric polypeptide.

Embodiment E8. The multi-chain chimeric polypeptide of any one of embodiments E1-E7, wherein the soluble tissue factor domain is a soluble human tissue factor domain.

Embodiment E9. The multi-chain chimeric polypeptide of embodiment E8, wherein the soluble human tissue factor domain comprises a sequence that is at least 80% identical to SEQ ID NO: 1.

Embodiment E10. The multi-chain chimeric polypeptide of embodiment E9, wherein the soluble human tissue factor domain comprises a sequence that is at least 90% identical to SEQ ID NO: 1.

Embodiment E11. The multi-chain chimeric polypeptide of embodiment E10, wherein the soluble human tissue factor domain comprises a sequence that is at least 95% identical to SEQ ID NO: 1.

Embodiment E12. The multi-chain chimeric polypeptide of any one of embodiments E8-E11, wherein the soluble human tissue factor domain does not comprise one or more of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment E13. The multi-chain chimeric polypeptide of embodiment E12, wherein the soluble human tissue factor domain does not comprise any of:
a lysine at an amino acid position that corresponds to amino acid position 20 of mature wildtype human tissue factor protein;
an isoleucine at an amino acid position that corresponds to amino acid position 22 of mature wildtype human tissue factor protein;
a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and
a phenylalanine at an amino acid position that corresponds to amino acid position 140 of mature wildtype human tissue factor protein.

Embodiment E14. The multi-chain chimeric polypeptide of any one of embodiments E1-E13, wherein the soluble tissue factor domain is not capable of binding to Factor VIIa.

Embodiment E15. The multi-chain chimeric polypeptide of any one of embodiments E1-E14, wherein the soluble tissue factor domain does not convert inactive Factor X into Factor Xa.

Embodiment E16. The multi-chain chimeric polypeptide of any one of embodiments E1-E15, wherein the multi-chain chimeric polypeptide does not stimulate coagulation in a mammal.

Embodiment E17. The multi-chain chimeric polypeptide of any one of embodiments E1-E16, wherein the first chimeric polypeptide further comprises a peptide tag at the N-terminal end or the C-terminal end of the first chimeric polypeptide.

Embodiment E18. The multi-chain chimeric polypeptide of any one of embodiments E1-E17, wherein the second chimeric polypeptide further comprises a peptide tag at the N-terminal end or the C-terminal end of the second chimeric Embodiment E19. The multi-chain chimeric polypeptide of any one of embodiments E1-E18, wherein the first chimeric polypeptide and/or the second chimeric polypeptide further comprises a signal sequence at its N-terminal end.

Embodiment E20. The multi-chain chimeric polypeptide of embodiment E19, wherein the signal sequence comprises SEQ ID NO: 31.

Embodiment E21. The multi-chain chimeric polypeptide of embodiment E20, wherein the signal sequence is SEQ ID NO: 31.

Embodiment E22. The multi-chain chimeric polypeptide of any one of embodiments E1-E21, wherein the pair of affinity domains is a sushi domain from an alpha chain of human IL-15 receptor (IL15Rα) and a soluble IL-15.

Embodiment E23. The multi-chain chimeric polypeptide of embodiment E22, wherein the soluble IL-15 has a D8N or D8 amino acid substitution.

Embodiment E24. The multi-chain chimeric polypeptide of embodiment E22, wherein the soluble IL-15 comprises a sequence that is 80% identical to SEQ ID NO: 14.

Embodiment E25. The multi-chain chimeric polypeptide of embodiment E24, wherein the soluble IL-15 comprises a sequence that is 90% identical to SEQ ID NO: 14.

Embodiment E26. The multi-chain chimeric polypeptide of embodiment E25, wherein the soluble IL-15 comprises a sequence that is 95% identical to SEQ ID NO: 14.

Embodiment E27. The multi-chain chimeric polypeptide of embodiment E26, wherein the soluble IL-15 comprises SEQ ID NO: 14.

Embodiment E28. The multi-chain chimeric polypeptide of any one of embodiments E22-E27, wherein the sushi domain of IL15Rα comprises a sushi domain from human IL15Rα.

Embodiment E29. The multi-chain chimeric polypeptide of embodiment E28, wherein the sushi domain from human IL15Rα comprises a sequence that is 80% identical to SEQ ID NO: 28.

Embodiment E30. The multi-chain chimeric polypeptide of embodiment E29, wherein the sushi domain from human IL15Rα comprises a sequence that is 90% identical to SEQ ID NO: 28.

Embodiment E31. The multi-chain chimeric polypeptide of embodiment E30, wherein the sushi domain from human IL15Rα comprises a sequence that is 95% identical to SEQ ID NO: 28.

Embodiment E32. The multi-chain chimeric polypeptide of embodiment E31, wherein the sushi domain from human IL15Rα comprises SEQ ID NO: 28.

Embodiment E33. The multi-chain chimeric polypeptide of embodiment E28, wherein the sushi domain from human IL15Rα is a mature full-length IL15Rα.

Embodiment E34. The multi-chain chimeric polypeptide of any one of embodiments E1-E21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment E35. The multi-chain chimeric polypeptide of any one of embodiments E1-E34, wherein the first target-binding domain and the second targeting-binding domain each independently bind specifically to a receptor for IL-7, CD16, or a receptor for IL-21.

Embodiment E36. The multi-chain chimeric polypeptide of embodiment E35, wherein the first target-binding domain binds specifically to a receptor IL-7 and the second target-binding domain binds specifically to CD16 or a receptor for IL-21.

Embodiment E37. The multi-chain chimeric polypeptide of embodiment E36, wherein the first target-binding domain comprises a soluble IL-7 protein.

Embodiment E38. The multi-chain chimeric polypeptide of embodiment E37, wherein the soluble IL-7 protein is a soluble human IL-7.

Embodiment E39. The multi-chain chimeric polypeptide of any one of embodiments E36-E38, wherein the second antigen-binding domain comprises an antigen-binding domain that binds specifically to CD16.

Embodiment E40. The multi-chain chimeric polypeptide of embodiment E39, wherein the second antigen-binding domain comprises an scFv that binds specifically to CD16.

Embodiment E41. The multi-chain chimeric polypeptide of any one of embodiments E36-E38, wherein the second antigen-binding domain bind specifically to a receptor for IL-21.

Embodiment E42. The multi-chain chimeric polypeptide of embodiment E41, wherein the second antigen-binding domain comprises a soluble IL-21.

Embodiment E43. The multi-chain chimeric polypeptide of embodiment E42, wherein the soluble IL-21 is a soluble human IL-21.

Embodiment E44. The multi-chain chimeric polypeptide of any one of embodiments E36-E40, wherein the second chimeric polypeptide further comprises an additional target-binding domain that binds specifically to a receptor for IL-21.

Embodiment E45. The multi-chain chimeric polypeptide of embodiment E44, wherein the additional target-binding domain comprises a soluble IL-21.

Embodiment E46. The multi-chain chimeric polypeptide of embodiment E45, wherein the soluble IL-21 is a soluble human IL-12.

Embodiment E47. The multi-chain chimeric polypeptide of any one of embodiments E1-E34, wherein the first target-binding domain and the second targeting-binding domain each independently bind specifically to TGF-β, CD16, or a receptor for IL-21.

Embodiment E48. The multi-chain chimeric polypeptide of embodiment E47, wherein the first target-binding domain binds specifically to a TGF-β and the second target-binding domain binds specifically to CD16 or a receptor of IL-21.

Embodiment E49. The multi-specific chimeric polypeptide of embodiment E48, wherein the first target-binding domain is a soluble TGF-β receptor.

Embodiment E50. The multi-specific chimeric polypeptide of embodiment E49, wherein soluble TGF-β receptor is a soluble TGFβRII receptor.

Embodiment E51. The multi-specific chimeric polypeptide of any one of embodiments E48-E50, wherein the second target-binding domain binds specifically to CD16.

Embodiment E52. The multi-specific chimeric polypeptide of embodiment E51, wherein the second antigen-binding domain comprises an antigen-binding domain that binds specifically to CD16.

Embodiment E53. The multi-chain chimeric polypeptide of embodiment E52, wherein the second antigen-binding domain comprises an scFv that binds specifically to CD16.

Embodiment E54. The multi-chain chimeric polypeptide of any one of embodiments E48-E50, wherein the second target-binding domain binds specifically to a receptor for IL-21.

Embodiment E55. The multi-chain chimeric polypeptide of embodiment E54, wherein the second target-binding domain comprises a soluble IL-21.

Embodiment E56. The multi-chain chimeric polypeptide of embodiment E55, wherein the second target-binding domain comprises a soluble human IL-21.

Embodiment E57. The multi-chain chimeric polypeptide of any one of embodiments E48-E53, wherein the second chimeric polypeptide further comprises an additional target-binding domain that binds specifically to a receptor for IL-21.

Embodiment E58. The multi-chain chimeric polypeptide of embodiment E57, wherein the additional target-binding domain comprises a soluble IL-21.

Embodiment E59. The multi-chain chimeric polypeptide of embodiment E58, wherein the soluble IL-21 is a soluble human IL-21.

Embodiment E60. The multi-chain chimeric polypeptide of any one of embodiments E1-E34, wherein the first target-binding domain and the second target-binding domain each independently bind specifically to a receptor for IL-7.

Embodiment E61. The multi-chain chimeric polypeptide of embodiment E60, wherein the first target-binding domain and the second target-binding domain include a soluble IL-7.

Embodiment E62. The multi-chain chimeric polypeptide of embodiment E61, wherein the soluble IL-7 is a soluble human IL-7.

Embodiment E63. The multi-chain chimeric polypeptide of any one of embodiments E1-E34, wherein the first target-binding domain and the second target-binding domain each independently bind specifically to TGF-β.

Embodiment E64. The multi-specific chimeric polypeptide of embodiment E63, wherein the first target-binding domain and the second target-binding domain is a soluble TGF-β receptor.

Embodiment E65. The multi-specific chimeric polypeptide of embodiment E64, wherein the soluble TGF-β receptor is a soluble TGFβRII receptor.

Embodiment E66. The multi-specific chimeric polypeptide of any one of embodiments E1-E34, wherein the first target-binding domain and the second targeting-binding domain each independently bind specifically to a receptor for IL-7, a receptor for IL-21, or a receptor for CD137L.

Embodiment E67. The multi-chain chimeric polypeptide of embodiment E66, wherein the first target-binding domain binds specifically to a receptor for IL-7 and the second target-binding domain binds specifically to a receptor for IL-21 or a receptor for CD137L.

Embodiment E68. The multi-specific chimeric polypeptide of embodiment E67, wherein the first target-binding domain is a soluble IL-7.

Embodiment E69. The multi-specific chimeric polypeptide of embodiment E68, wherein the soluble IL-7 is a soluble human IL-7.

Embodiment E70. The multi-chain chimeric polypeptide of any one of embodiments E67-E69, wherein the second target-binding domain binds specifically to a receptor for IL-21.

Embodiment E71. The multi-chain chimeric polypeptide of embodiment E70, wherein the second target-binding domain is a soluble IL-21.

Embodiment E72. The multi-chain chimeric polypeptide of embodiment E71, wherein the soluble IL-21 is a soluble human IL-21.

Embodiment E73. The multi-chain chimeric polypeptide of any one of embodiments E67-E69, wherein the second antigen-binding domain binds specifically to a receptor for CD137L.

Embodiment E74. The multi-chain chimeric polypeptide of embodiment E73, wherein the second antigen-binding domain is a soluble CD137L.

Embodiment E75. The multi-chain chimeric polypeptide of embodiment E74, wherein the soluble CD137L is a soluble human CD137L.

Embodiment E76. The multi-chain chimeric polypeptide of any one of embodiments E67-E72, wherein the second chimeric polypeptide further comprises an additional target-binding domain that binds specifically to a receptor for CD137L.

Embodiment E77. The multi-chain chimeric polypeptide of embodiment E76, wherein the additional target-binding domain comprises a soluble CD137L.

Embodiment E78. The multi-chain chimeric polypeptide of embodiment E77, wherein the soluble CD137L is a soluble human CD137L.

Embodiment E79. The multi-chain chimeric polypeptide of any one of embodiments E1-E34, wherein the first target-binding domain and the second targeting-binding domain each independently bind specifically to a receptor for IL-7 or TGF-β.

Embodiment E80. The multi-chain chimeric polypeptide of embodiment E79, wherein the first target-binding domain binds specifically to a receptor IL-7 and the second target-binding domain binds specifically to TGF-β.

Embodiment E81. The multi-chain chimeric polypeptide of embodiment E80, wherein the first target-binding domain comprises a soluble IL-7 protein.

Embodiment E82. The multi-chain chimeric polypeptide of embodiment E81, wherein the soluble IL-7 protein is a soluble human IL-7.

Embodiment E83. The multi-chain chimeric polypeptide of any one of embodiments E80-E82, wherein the second antigen-binding domain comprises an antigen-binding domain that binds specifically to TGF-β.

Embodiment E84. The multi-specific chimeric polypeptide of embodiment E83, wherein the second target-binding domain is a soluble TGF-β receptor.

Embodiment E85. The multi-specific chimeric polypeptide of embodiment E84, wherein the soluble TGF-β receptor is a soluble TGFβRII receptor.

Embodiment E86. The multi-chain chimeric polypeptide of any one of embodiments E1-E34, wherein the first target-binding domain and the second targeting-binding domain each independently bind specifically to TGF-β, a receptor for IL-21, or a receptor for CD137L.

Embodiment E87. The multi-chain chimeric polypeptide of embodiment E86, wherein the first target-binding domain binds specifically to a TGF-β and the second target-binding domain binds specifically to a receptor for IL-21 or a receptor for CD137L.

Embodiment E88. The multi-specific chimeric polypeptide of embodiment E87, wherein the first target-binding domain is a soluble TGF-β receptor.

Embodiment E89. The multi-specific chimeric polypeptide of embodiment E88, wherein the soluble TGF-β receptor is a soluble TGFβRII receptor.

Embodiment E90. The multi-specific chimeric polypeptide of any one of embodiments E87-E89, wherein the second target-binding domain binds specifically to a receptor for IL-21.

Embodiment E91. The multi-chain chimeric polypeptide of embodiment E90, wherein the second target-binding domain comprises a soluble IL-21.

Embodiment E92. The multi-chain chimeric polypeptide of embodiment E91, wherein the second target-binding domain comprises a soluble human IL-21.

Embodiment E93. The multi-specific chimeric polypeptide of any one of embodiments E87-E89, wherein the second target-binding domain binds specifically to a receptor for CD137L.

Embodiment E94. The multi-chain chimeric polypeptide of embodiment E93, wherein the second target-binding domain comprises a soluble CD137L.

Embodiment E95. The multi-chain chimeric polypeptide of embodiment E94, wherein the second target-binding domain comprises a soluble human CD137L.

Embodiment E96. The multi-chain chimeric polypeptide of any one of embodiments E87-E92, wherein the second chimeric polypeptide further comprises an additional target-binding domain that binds specifically to a receptor for CD137L.

Embodiment E97. The multi-chain chimeric polypeptide of embodiment E96, wherein the additional target-binding domain comprises a soluble CD137L.

Embodiment E98. The multi-chain chimeric polypeptide of embodiment E97, wherein the soluble CD137L is a soluble human CD137L.

Embodiment E99. The multi-chain chimeric polypeptide of any one of embodiments E1-E34, wherein the first target-binding domain and the second targeting-binding domain each independently bind specifically to TGF-β or a receptor for IL-21.

Embodiment E100. The multi-chain chimeric polypeptide of embodiment E99, wherein the first target-binding domain binds specifically to a TGF-β and the second target-binding domain binds specifically to TGF-β or a receptor for IL-21.

Embodiment E101. The multi-specific chimeric polypeptide of embodiment E100, wherein the first target-binding domain is a soluble TGF-β receptor.

Embodiment E102. The multi-specific chimeric polypeptide of embodiment E101, wherein the soluble TGF-β receptor is a soluble TGFβRII receptor.

Embodiment E103. The multi-specific chimeric polypeptide of any one of embodiments E100-E102, wherein the second target-binding domain binds specifically to a receptor for IL-21.

Embodiment E104. The multi-chain chimeric polypeptide of embodiment E103, wherein the second target-binding domain comprises a soluble IL-21.

Embodiment E105. The multi-chain chimeric polypeptide of embodiment E104, wherein the second target-binding domain comprises a soluble human IL-21.

Embodiment E106. The multi-specific chimeric polypeptide of any one of embodiments E100-E102, wherein the second target-binding domain binds specifically to TGF-β.

Embodiment E107. The multi-specific chimeric polypeptide of embodiment E106, wherein the first target-binding domain is a soluble TGF-β receptor.

Embodiment E108. The multi-specific chimeric polypeptide of embodiment E107, wherein the soluble TGF-β receptor is a soluble TGFβRII receptor.

Embodiment E109. The multi-specific chimeric polypeptide of any one of embodiments E100-E105, wherein the second polypeptide further comprises an additional target-binding domain that binds specifically to TGF-β.

Embodiment E110. The multi-specific chimeric polypeptide of embodiment E109, wherein the first target-binding domain is a soluble TGF-β receptor.

Embodiment E111. The multi-specific chimeric polypeptide of embodiment E110, wherein the soluble TGF-β receptor is a soluble TGFβRII receptor.

Embodiment E112. The multi-chain chimeric polypeptide of any one of embodiments E1-E34, wherein the first target-binding domain and the second targeting-binding domain each independently bind specifically to TGF-β or IL-16.

Embodiment E113. The multi-chain chimeric polypeptide of embodiment E112, wherein the first target-binding domain binds specifically to a TGF-β and the second target-binding domain binds specifically to TGF-β or IL-16.

Embodiment E114. The multi-specific chimeric polypeptide of embodiment E113, wherein the first target-binding domain is a soluble TGF-β receptor.

Embodiment E115. The multi-specific chimeric polypeptide of embodiment E114, wherein the soluble TGF-β receptor is a soluble TGFβRII receptor.

Embodiment E116. The multi-specific chimeric polypeptide of any one of embodiments E113-E115, wherein the second target-binding domain binds specifically to IL-16.

Embodiment E117. The multi-specific chimeric polypeptide of embodiment E116, wherein the second antigen-binding domain comprises an antigen-binding domain that binds specifically to CD16.

Embodiment E118. The multi-chain chimeric polypeptide of embodiment E117, wherein the second antigen-binding domain comprises an scFv that binds specifically to CD16.

Embodiment E119. The multi-specific chimeric polypeptide of any one of embodiments E113-E115, wherein the second target-binding domain binds specifically to TGF-β.

Embodiment E120. The multi-specific chimeric polypeptide of embodiment E119, wherein the first target-binding domain is a soluble TGF-β receptor.

Embodiment E121. The multi-specific chimeric polypeptide of embodiment E120, wherein the soluble TGF-β receptor is a soluble TGFβRII receptor.

Embodiment E122. The multi-specific chimeric polypeptide of any one of embodiments E113-E118, wherein the second chimeric polypeptide further comprises an additional target-binding domain that binds specifically to TGF-β.

Embodiment E123. The multi-specific chimeric polypeptide of embodiment E122, wherein the first target-binding domain is a soluble TGF-β receptor.

Embodiment E124. The multi-specific chimeric polypeptide of embodiment E123, wherein the soluble TGF-β receptor is a soluble TGFβRII receptor.

Embodiment E125. The multi-chain chimeric polypeptide of any one of embodiments E1-E34, wherein the first target-binding domain and the second targeting-binding domain each independently bind specifically to a TGF-β or a receptor for CD137L.

Embodiment E126. The multi-chain chimeric polypeptide of embodiment E125, wherein the first target-binding domain binds specifically to TGF-β and the second target-binding domain binds specifically to a receptor for CD137L.

Embodiment E127. The multi-specific chimeric polypeptide of embodiment E126, wherein the first target-binding domain is a soluble TGF-β receptor.

Embodiment E128. The multi-specific chimeric polypeptide of embodiment E127, wherein the soluble TGF-β receptor is a soluble TGFβRII receptor.

Embodiment E129. The multi-chain chimeric polypeptide of embodiment E128, wherein the second target-binding domain comprises a soluble CD137L protein.

Embodiment E130. The multi-chain chimeric polypeptide of embodiment E129, wherein the soluble CD137L protein is a soluble human CD137L.

Embodiment E131. The multi-chain chimeric polypeptide of any one of embodiments E126-E130, wherein the second chimeric polypeptide further comprises an additional target-binding domain that binds specifically to TGF-β.

Embodiment E132. The multi-specific chimeric polypeptide of embodiment E131, wherein the additional target-binding domain is a soluble TGF-β receptor.

Embodiment E133. The multi-specific chimeric polypeptide of embodiment E132, wherein the soluble TGF-β receptor is a soluble TGFβRII receptor.

Embodiment E134. The multi-chain chimeric polypeptide of embodiment E1, wherein the first chimeric polypeptide comprises a sequence that is at least 80% identical to SEQ ID NO: 104.

Embodiment E135. The multi-chain chimeric polypeptide of embodiment E134, wherein the first chimeric polypeptide comprises a sequence that is at least 90% identical to SEQ ID NO: 104.

Embodiment E136. The multi-chain chimeric polypeptide of embodiment E135, wherein the first chimeric polypeptide comprises a sequence that is at least 95% identical to SEQ ID NO: 104.

Embodiment E137. The multi-chain chimeric polypeptide of embodiment E136, wherein the first chimeric polypeptide comprises SEQ ID NO: 104.

Embodiment E138. The multi-chain chimeric polypeptide of embodiment E137, wherein the first chimeric polypeptide comprises SEQ ID NO: 106.

Embodiment E139. The multi-chain chimeric polypeptide of any one of embodiments E1 and E134-E138, wherein the second chimeric polypeptide comprises a sequence that is at least 80% identical to SEQ ID NO: 129.

Embodiment E140. The multi-chain chimeric polypeptide of embodiment E139, wherein the second chimeric polypeptide comprises a sequence that is at least 90% identical to SEQ ID NO: 129.

Embodiment E141. The multi-chain chimeric polypeptide of embodiment E140, wherein the second chimeric polypeptide comprises a sequence that is at least 95% identical to SEQ ID NO: 129.

Embodiment E142. The multi-chain chimeric polypeptide of embodiment E141, wherein the second chimeric polypeptide comprises SEQ ID NO: 129.

Embodiment E143. The multi-chain chimeric polypeptide of embodiment E142, wherein the second chimeric polypeptide comprises SEQ ID NO: 131.

Embodiment E144. The multi-chain chimeric polypeptide of embodiment E1, wherein the first chimeric polypeptide comprises a sequence that is at least 80% identical to SEQ ID NO: 133.

Embodiment E145. The multi-chain chimeric polypeptide of embodiment E144, wherein the first chimeric polypeptide comprises a sequence that is at least 90% identical to SEQ ID NO: 133.

Embodiment E146. The multi-chain chimeric polypeptide of embodiment E145, wherein the first chimeric polypeptide comprises a sequence that is at least 95% identical to SEQ ID NO: 133.

Embodiment E147. The multi-chain chimeric polypeptide of embodiment E146, wherein the first chimeric polypeptide comprises SEQ ID NO: 133.

Embodiment E148. The multi-chain chimeric polypeptide of embodiment E147, wherein the first chimeric polypeptide comprises SEQ ID NO: 135.

Embodiment E149. The multi-chain chimeric polypeptide of any one of embodiments E1 and E144-E148, wherein the second chimeric polypeptide comprises a sequence that is at least 80% identical to SEQ ID NO: 137.

Embodiment E150. The multi-chain chimeric polypeptide of embodiment E149, wherein the second chimeric polypeptide comprises a sequence that is at least 90% identical to SEQ ID NO: 137.

Embodiment E151. The multi-chain chimeric polypeptide of embodiment E150, wherein the second chimeric polypeptide comprises a sequence that is at least 95% identical to SEQ ID NO: 137.

Embodiment E152. The multi-chain chimeric polypeptide of embodiment E151, wherein the second chimeric polypeptide comprises SEQ ID NO: 137.

Embodiment E153. The multi-chain chimeric polypeptide of embodiment E152, wherein the second chimeric polypeptide comprises SEQ ID NO: 139.

Embodiment E154. The multi-chain chimeric polypeptide of embodiment E1, wherein the first chimeric polypeptide comprises a sequence that is at least 80% identical to SEQ ID NO: 141.

Embodiment E155. The multi-chain chimeric polypeptide of embodiment E154, wherein the first chimeric polypeptide comprises a sequence that is at least 90% identical to SEQ ID NO: 141.

Embodiment E156. The multi-chain chimeric polypeptide of embodiment E155, wherein the first chimeric polypeptide comprises a sequence that is at least 95% identical to SEQ ID NO: 141.

Embodiment E157. The multi-chain chimeric polypeptide of embodiment E156, wherein the first chimeric polypeptide comprises SEQ ID NO: 141.

Embodiment E158. The multi-chain chimeric polypeptide of embodiment E157, wherein the first chimeric polypeptide comprises SEQ ID NO: 143.

Embodiment E159. The multi-chain chimeric polypeptide of any one of embodiments E1 and E154-E158, wherein the second chimeric polypeptide comprises a sequence that is at least 80% identical to SEQ ID NO: 145.

Embodiment E160. The multi-chain chimeric polypeptide of embodiment E159, wherein the second chimeric polypeptide comprises a sequence that is at least 90% identical to SEQ ID NO: 145.

Embodiment E161. The multi-chain chimeric polypeptide of embodiment E160, wherein the second chimeric polypeptide comprises a sequence that is at least 95% identical to SEQ ID NO: 145.

Embodiment E162. The multi-chain chimeric polypeptide of embodiment E161, wherein the second chimeric polypeptide comprises SEQ ID NO: 145.

Embodiment E163. The multi-chain chimeric polypeptide of embodiment E162, wherein the second chimeric polypeptide comprises SEQ ID NO: 147.

Embodiment E164. The multi-chain chimeric polypeptide of embodiment E1, wherein the first chimeric polypeptide comprises a sequence that is at least 80% identical to SEQ ID NO: 149.

Embodiment E165. The multi-chain chimeric polypeptide of embodiment E164, wherein the first chimeric polypeptide comprises a sequence that is at least 90% identical to SEQ ID NO: 149.

Embodiment E166. The multi-chain chimeric polypeptide of embodiment E165, wherein the first chimeric polypeptide comprises a sequence that is at least 95% identical to SEQ ID NO: 149.

Embodiment E167. The multi-chain chimeric polypeptide of embodiment E166, wherein the first chimeric polypeptide comprises SEQ ID NO: 149.

Embodiment E168. The multi-chain chimeric polypeptide of embodiment E167, wherein the first chimeric polypeptide comprises SEQ ID NO: 151.

Embodiment E169. The multi-chain chimeric polypeptide of any one of embodiments E1 and E164-E168, wherein the second chimeric polypeptide comprises a sequence that is at least 80% identical to SEQ ID NO: 153.

Embodiment E170. The multi-chain chimeric polypeptide of embodiment E169, wherein the second chimeric polypeptide comprises a sequence that is at least 90% identical to SEQ ID NO: 153.

Embodiment E171. The multi-chain chimeric polypeptide of embodiment E170, wherein the second chimeric polypeptide comprises a sequence that is at least 95% identical to SEQ ID NO: 153.

Embodiment E172. The multi-chain chimeric polypeptide of embodiment E171, wherein the second chimeric polypeptide comprises SEQ ID NO: 153.

Embodiment E173. The multi-chain chimeric polypeptide of embodiment E172, wherein the second chimeric polypeptide comprises SEQ ID NO: 155.

Embodiment E174. The multi-chain chimeric polypeptide of embodiment E1, wherein the first chimeric polypeptide comprises a sequence that is at least 80% identical to SEQ ID NO: 161.

Embodiment E175. The multi-chain chimeric polypeptide of embodiment E174, wherein the first chimeric polypeptide comprises a sequence that is at least 90% identical to SEQ ID NO: 161.

Embodiment E176. The multi-chain chimeric polypeptide of embodiment E175, wherein the first chimeric polypeptide comprises a sequence that is at least 95% identical to SEQ ID NO: 161.

Embodiment E177. The multi-chain chimeric polypeptide of embodiment E176, wherein the first chimeric polypeptide comprises SEQ ID NO: 161.

Embodiment E178. The multi-chain chimeric polypeptide of embodiment E177, wherein the first chimeric polypeptide comprises SEQ ID NO: 163.

Embodiment E179. The multi-chain chimeric polypeptide of any one of embodiments E1 and E174-E178, wherein the second chimeric polypeptide comprises a sequence that is at least 80% identical to SEQ ID NO: 165.

Embodiment E180. The multi-chain chimeric polypeptide of embodiment E179, wherein the second chimeric polypeptide comprises a sequence that is at least 90% identical to SEQ ID NO: 165.

Embodiment E181. The multi-chain chimeric polypeptide of embodiment E180, wherein the second chimeric polypeptide comprises a sequence that is at least 95% identical to SEQ ID NO: 165.

Embodiment E182. The multi-chain chimeric polypeptide of embodiment E181, wherein the second chimeric polypeptide comprises SEQ ID NO: 165.

Embodiment E183. The multi-chain chimeric polypeptide of embodiment E182, wherein the second chimeric polypeptide comprises SEQ ID NO: 167.

Embodiment E184. The multi-chain chimeric polypeptide of embodiment E1, wherein the first chimeric polypeptide comprises a sequence that is at least 80% identical to SEQ ID NO: 173.

Embodiment E185. The multi-chain chimeric polypeptide of embodiment E184, wherein the first chimeric polypeptide comprises a sequence that is at least 90% identical to SEQ ID NO: 173.

Embodiment E186. The multi-chain chimeric polypeptide of embodiment E185, wherein the first chimeric polypeptide comprises a sequence that is at least 95% identical to SEQ ID NO: 173.

Embodiment E187. The multi-chain chimeric polypeptide of embodiment E186, wherein the first chimeric polypeptide comprises SEQ ID NO: 173.

Embodiment E188. The multi-chain chimeric polypeptide of embodiment E187, wherein the first chimeric polypeptide comprises SEQ ID NO: 175.

Embodiment E189. The multi-chain chimeric polypeptide of any one of embodiments E1 and E184-E188, wherein the second chimeric polypeptide comprises a sequence that is at least 80% identical to SEQ ID NO: 189.

Embodiment E190. The multi-chain chimeric polypeptide of embodiment E189, wherein the second chimeric polypeptide comprises a sequence that is at least 90% identical to SEQ ID NO: 189.

Embodiment E191. The multi-chain chimeric polypeptide of embodiment E190, wherein the second chimeric polypeptide comprises a sequence that is at least 95% identical to SEQ ID NO: 189.

Embodiment E192. The multi-chain chimeric polypeptide of embodiment E191, wherein the second chimeric polypeptide comprises SEQ ID NO: 189.

Embodiment E193. The multi-chain chimeric polypeptide of embodiment E192, wherein the second chimeric polypeptide comprises SEQ ID NO: 191.

Embodiment E194. The multi-chain chimeric polypeptide of embodiment E1, wherein the first chimeric polypeptide comprises a sequence that is at least 80% identical to SEQ ID NO: 173.

Embodiment E195. The multi-chain chimeric polypeptide of embodiment E194, wherein the first chimeric polypeptide comprises a sequence that is at least 90% identical to SEQ ID NO: 173.

Embodiment E196. The multi-chain chimeric polypeptide of embodiment E195, wherein the first chimeric polypeptide comprises a sequence that is at least 95% identical to SEQ ID NO: 173.

Embodiment E197. The multi-chain chimeric polypeptide of embodiment E196, wherein the first chimeric polypeptide comprises SEQ ID NO: 173.

Embodiment E198. The multi-chain chimeric polypeptide of embodiment E197, wherein the first chimeric polypeptide comprises SEQ ID NO: 175.

Embodiment E199. The multi-chain chimeric polypeptide of any one of embodiments E1 and E194-E198, wherein the second chimeric polypeptide comprises a sequence that is at least 80% identical to SEQ ID NO: 177.

Embodiment E200. The multi-chain chimeric polypeptide of embodiment E199, wherein the second chimeric polypeptide comprises a sequence that is at least 90% identical to SEQ ID NO: 177.

Embodiment E201. The multi-chain chimeric polypeptide of embodiment E200, wherein the second chimeric polypeptide comprises a sequence that is at least 95% identical to SEQ ID NO: 177.

Embodiment E202. The multi-chain chimeric polypeptide of embodiment E201, wherein the second chimeric polypeptide comprises SEQ ID NO: 177.

Embodiment E203. The multi-chain chimeric polypeptide of embodiment E202, wherein the second chimeric polypeptide comprises SEQ ID NO: 179.

Embodiment E204. The multi-chain chimeric polypeptide of embodiment E1, wherein the first chimeric polypeptide comprises a sequence that is at least 80% identical to SEQ ID NO: 181.

Embodiment E205. The multi-chain chimeric polypeptide of embodiment E204, wherein the first chimeric polypeptide comprises a sequence that is at least 90% identical to SEQ ID NO: 181.

Embodiment E206. The multi-chain chimeric polypeptide of embodiment E205, wherein the first chimeric polypeptide comprises a sequence that is at least 95% identical to SEQ ID NO: 181.

Embodiment E207. The multi-chain chimeric polypeptide of embodiment E206, wherein the first chimeric polypeptide comprises SEQ ID NO: 181.

Embodiment E208. The multi-chain chimeric polypeptide of embodiment E207, wherein the first chimeric polypeptide comprises SEQ ID NO: 183.

Embodiment E209. The multi-chain chimeric polypeptide of any one of embodiments E1 and E204-E208, wherein the second chimeric polypeptide comprises a sequence that is at least 80% identical to SEQ ID NO: 185.

Embodiment E210. The multi-chain chimeric polypeptide of embodiment E209, wherein the second chimeric polypeptide comprises a sequence that is at least 90% identical to SEQ ID NO: 185.

Embodiment E211. The multi-chain chimeric polypeptide of embodiment E210, wherein the second chimeric polypeptide comprises a sequence that is at least 95% identical to SEQ ID NO: 185.

Embodiment E212. The multi-chain chimeric polypeptide of embodiment E211, wherein the second chimeric polypeptide comprises SEQ ID NO: 185.

Embodiment E213. The multi-chain chimeric polypeptide of embodiment E212, wherein the second chimeric polypeptide comprises SEQ ID NO: 187.

Embodiment E214. The multi-chain chimeric polypeptide of embodiment E1, wherein the first chimeric polypeptide comprises a sequence that is at least 80% identical to SEQ ID NO: 193.

Embodiment E215. The multi-chain chimeric polypeptide of embodiment E214, wherein the first chimeric polypeptide comprises a sequence that is at least 90% identical to SEQ ID NO: 193.

Embodiment E216. The multi-chain chimeric polypeptide of embodiment E215, wherein the first chimeric polypeptide comprises a sequence that is at least 95% identical to SEQ ID NO: 193.

Embodiment E217. The multi-chain chimeric polypeptide of embodiment E216, wherein the first chimeric polypeptide comprises SEQ ID NO: 193.

Embodiment E218. The multi-chain chimeric polypeptide of embodiment E217, wherein the first chimeric polypeptide comprises SEQ ID NO: 195.

Embodiment E219. The multi-chain chimeric polypeptide of any one of embodiments E1 and E214-E218, wherein the second chimeric polypeptide comprises a sequence that is at least 80% identical to SEQ ID NO: 197.

Embodiment E220. The multi-chain chimeric polypeptide of embodiment E219, wherein the second chimeric polypeptide comprises a sequence that is at least 90% identical to SEQ ID NO: 197.

Embodiment E221. The multi-chain chimeric polypeptide of embodiment E220, wherein the second chimeric polypeptide comprises a sequence that is at least 95% identical to SEQ ID NO: 197.

Embodiment E222. The multi-chain chimeric polypeptide of embodiment E221, wherein the second chimeric polypeptide comprises SEQ ID NO: 197.

Embodiment E223. The multi-chain chimeric polypeptide of embodiment E222, wherein the second chimeric polypeptide comprises SEQ ID NO: 199.

Embodiment E224. The multi-chain chimeric polypeptide of embodiment E1, wherein the first chimeric polypeptide comprises a sequence that is at least 80% identical to SEQ ID NO: 201.

Embodiment E225. The multi-chain chimeric polypeptide of embodiment E224, wherein the first chimeric polypeptide comprises a sequence that is at least 90% identical to SEQ ID NO: 201.

Embodiment E226. The multi-chain chimeric polypeptide of embodiment E225, wherein the first chimeric polypeptide comprises a sequence that is at least 95% identical to SEQ ID NO: 201.

Embodiment E227. The multi-chain chimeric polypeptide of embodiment E226, wherein the first chimeric polypeptide comprises SEQ ID NO: 201.

Embodiment E228. The multi-chain chimeric polypeptide of embodiment E227, wherein the first chimeric polypeptide comprises SEQ ID NO: 203.

Embodiment E229. The multi-chain chimeric polypeptide of any one of embodiments E1 and E224-E228, wherein the second chimeric polypeptide comprises a sequence that is at least 80% identical to SEQ ID NO: 205.

Embodiment E230. The multi-chain chimeric polypeptide of embodiment E229, wherein the second chimeric polypeptide comprises a sequence that is at least 90% identical to SEQ ID NO: 205.

Embodiment E231. The multi-chain chimeric polypeptide of embodiment E230, wherein the second chimeric polypeptide comprises a sequence that is at least 95% identical to SEQ ID NO: 205.

Embodiment E232. The multi-chain chimeric polypeptide of embodiment E231, wherein the second chimeric polypeptide comprises SEQ ID NO: 205.

Embodiment E233. The multi-chain chimeric polypeptide of embodiment E232, wherein the second chimeric polypeptide comprises SEQ ID NO: 207.

Embodiment E234. The multi-chain chimeric polypeptide of embodiment E1, wherein the first chimeric polypeptide comprises a sequence that is at least 80% identical to SEQ ID NO: 209.

Embodiment E235. The multi-chain chimeric polypeptide of embodiment E234, wherein the first chimeric polypeptide comprises a sequence that is at least 90% identical to SEQ ID NO: 209.

Embodiment E236. The multi-chain chimeric polypeptide of embodiment E235, wherein the first chimeric polypeptide comprises a sequence that is at least 95% identical to SEQ ID NO: 209.

Embodiment E237. The multi-chain chimeric polypeptide of embodiment E236, wherein the first chimeric polypeptide comprises SEQ ID NO: 209.

Embodiment E238. The multi-chain chimeric polypeptide of embodiment E237, wherein the first chimeric polypeptide comprises SEQ ID NO: 211.

Embodiment E239. The multi-chain chimeric polypeptide of any one of embodiments E1 and E234-E238, wherein the second chimeric polypeptide comprises a sequence that is at least 80% identical to SEQ ID NO: 213.

Embodiment E240. The multi-chain chimeric polypeptide of embodiment E239, wherein the second chimeric polypeptide comprises a sequence that is at least 90% identical to SEQ ID NO: 213.

Embodiment E241. The multi-chain chimeric polypeptide of embodiment E240, wherein the second chimeric polypeptide comprises a sequence that is at least 95% identical to SEQ ID NO: 213.

Embodiment E242. The multi-chain chimeric polypeptide of embodiment E241, wherein the second chimeric polypeptide comprises SEQ ID NO: 213.

Embodiment E243. The multi-chain chimeric polypeptide of embodiment E242, wherein the second chimeric polypeptide comprises SEQ ID NO: 215.

Embodiment E244. The multi-chain chimeric polypeptide of any one of embodiments E1-E133, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment E245. The multi-chain chimeric polypeptide of embodiment E244, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment E246. The multi-chain chimeric polypeptide of any one of embodiments E1-E133, wherein the first chimeric polypeptide further comprises one or more additional target-binding domains at the N-terminal and/or C-terminal end of the first chimeric polypeptide.

Embodiment E247. The multi-chain chimeric polypeptide of embodiment E246, wherein at least one of the one or more additional target-binding domains directly abuts the first domain of the pair of affinity domains in the first chimeric polypeptide.

Embodiment E248. The multi-chain chimeric polypeptide of embodiment E246, wherein the first chimeric polypeptide further comprises a linker sequence between the at least one of the one or more additional target-binding domains and the first domain of the pair of affinity domains.

Embodiment E249. The multi-chain chimeric polypeptide of embodiment E246, wherein the at least one of the one or more additional target-binding domains directly abuts the first target-binding domain in the first chimeric polypeptide.

Embodiment E250. The multi-chain chimeric polypeptide of embodiment E246, wherein the first chimeric polypeptide further comprises a linker sequence between the at least one of the one or more additional target-binding domains and the first target-binding domain.

Embodiment E251. The multi-chain chimeric polypeptide of embodiment E246, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment E252. The multi-chain chimeric polypeptide of embodiment E251, wherein the at least one additional target-binding domain of the one or more additional target-binding domains disposed at the N-terminus directly abuts the first target-binding domain or the first domain of the pair of affinity domains in the first chimeric Embodiment E253. The multi-chain chimeric polypeptide of embodiment E251, wherein the first chimeric polypeptide further comprises a linker sequence disposed between the at least one additional target-binding domain and the first target-binding domain or the first domain of the pair of affinity domains in the first chimeric polypeptide.

Embodiment E254. The multi-chain chimeric polypeptide of embodiment E251, wherein the at least one additional target-binding domain of the one or more additional target-binding domains disposed at the C-terminus directly abuts the first target-binding domain or the first domain of the pair of affinity domains in the first chimeric polypeptide.

Embodiment E255. The multi-chain chimeric polypeptide of embodiment E251, wherein the first chimeric polypeptide further comprises a linker sequence disposed between the at least one additional target-binding domain and the first target-binding domain or the first domain of the pair of affinity domains in the first chimeric polypeptide.

Embodiment E256. The multi-chain chimeric polypeptide of embodiment E251, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment E257. The multi-chain chimeric polypeptide of embodiment E251, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment E258. The multi-chain chimeric polypeptide of any one of embodiments E44-E46, E57-E59, E76-E78, E96-E98, E109-E111, E122-E124, and E131-E133, wherein the second chimeric polypeptide further comprises the additional target-binding domain at the N-terminal end or the C-terminal end of the second chimeric polypeptide.

Embodiment E259. The multi-chain chimeric polypeptide of embodiment E258, wherein the additional target-binding domain directly abuts the second domain of the pair of affinity domains in the second chimeric polypeptide.

Embodiment E260. The multi-chain chimeric polypeptide of embodiment E258, wherein the second chimeric polypeptide further comprises a linker sequence between the additional target-binding domain and the second domain of the pair of affinity domains in the second chimeric polypeptide.

Embodiment E261. The multi-chain chimeric polypeptide of embodiment E258, wherein the additional target-binding domain directly abuts the second target-binding domain in the second chimeric polypeptide.

Embodiment E262. The multi-chain chimeric polypeptide of embodiment E258, wherein the second chimeric polypeptide further comprises a linker sequence between the additional target-binding domain and the second target-binding domain in the second chimeric polypeptide.

Embodiment E263. A composition comprising any of the multi-chain chimeric polypeptides of embodiments E1-E262.

Embodiment E264. The composition of embodiment E263, wherein the composition is a pharmaceutical composition.

Embodiment E265. A kit comprising at least one dose of the composition of embodiment E263 or E264.

Embodiment E266. A method of stimulating an immune cell, the method comprising:
contacting an immune cell with an effective amount of any of the multi-chain chimeric polypeptides of embodiments E1-E262 or the composition of embodiment E263 or E264.

Embodiment E267. The method of embodiment E266, wherein the immune cell is contacted in vitro.

Embodiment E268. The method of embodiment E267, wherein the immune cell was previously obtained from a subject.

Embodiment E269. The method of embodiment E268, wherein the method further comprises obtaining the immune cell from the subject prior to the contacting step.

Embodiment E270. The method of embodiment E266, wherein the immune cell is contacted in vivo.

Embodiment E271. The method of any one of embodiments E266-E270, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell.

Embodiment E272. The method of any one of embodiments E266-E271, wherein the immune cell has previously been genetically modified to express a chimeric antigen receptor or a recombinant T-cell receptor.

Embodiment E273. The method of any one of embodiments E266-E271, wherein the method further comprises, after the contacting step, introducing into the immune cell a nucleic acid encoding a chimeric antigen-receptor or a recombinant T-cell receptor.

Embodiment E274. The method of any one of embodiments E266-E273, wherein the method further comprises administering the immune cell to a subject in need thereof.

Embodiment E275. The method of embodiment E274, wherein the subject has been identified or diagnosed as having age-related disease or condition.

Embodiment E276. The method of embodiment E275, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment E277. The method of embodiment E274, wherein the subject has been identified or diagnosed as having a cancer.

Embodiment E278. The method of embodiment E277, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment E279. The method of embodiment E274, wherein the subject has been diagnosed or identified as having an infectious disease.

Embodiment E280. The method of embodiment E279, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment E281. A method of inducing or increasing proliferation of an immune cell, the method comprising:
contacting an immune cell with an effective amount of any of the multi-chain chimeric polypeptides of embodiments E1-E262 or the composition of embodiment E263 or E264.

Embodiment E282. The method of embodiment E281, wherein the immune cell is contacted in vitro.

Embodiment E283. The method of embodiment E282, wherein the immune cell was previously obtained from a subject.

Embodiment E284. The method of embodiment E283, wherein the method further comprises obtaining the immune cell from the subject prior to the contacting step.

Embodiment E285. The method of embodiment E281, wherein the immune cell is contacted in vivo.

Embodiment E286. The method of any one of embodiments E281-E285, wherein the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment E287. The method of any one of embodiments E281-E286, wherein the immune cell has previously been genetically modified to express a chimeric antigen receptor or a recombinant T-cell receptor.

Embodiment E288. The method of any one of embodiments E281-E286, wherein the method further comprises, after the contacting step, introducing into the immune cell a nucleic acid encoding a chimeric antigen-receptor or a recombinant T-cell receptor.

Embodiment E289. The method of any one of embodiments E281-E288, wherein the method further comprises administering the immune cell to a subject in need thereof.

Embodiment E290. The method of embodiment E289, wherein the subject has been identified or diagnosed as having an age-related disease or condition.

Embodiment E291. The method of embodiment E290, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment E292. The method of embodiment E289, wherein the subject has been identified or diagnosed as having a cancer.

Embodiment E293. The method of embodiment E292, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment E294. The method of embodiment E289, wherein the subject has been diagnosed or identified as having an infectious disease.

Embodiment E295. The method of embodiment E289, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment E296. A method of inducing differentiation of an immune cell into a memory or memory-like immune cell, the method comprising:
contacting an immune cell with an effective amount of any of the multi-chain chimeric polypeptides of embodiments E1-E262 or the composition of embodiment E263 or E264.

Embodiment E297. The method of embodiment E296, wherein the immune cell is contacted in vitro.

Embodiment E298. The method of embodiment E297, wherein the immune cell was previously obtained from a subject.

Embodiment E299. The method of embodiment E298, wherein the method further comprises obtaining the immune cell from the subject prior to the contacting step.

Embodiment E300. The method of embodiment E296, wherein the immune cell is contacted in vivo.

Embodiment E301. The method of any one of embodiments E296-E300, wherein the immune cell is selected from the group consisting of: an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell.

Embodiment E302. The method of any one of embodiments E296-E301, wherein the immune cell has previously been genetically modified to express a chimeric antigen receptor or a recombinant T-cell receptor.

Embodiment E303. The method of any one of embodiments E296-E301, wherein the method further comprises, after the contacting step, introducing into the immune cell a nucleic acid encoding a chimeric antigen-receptor or a recombinant T-cell receptor.

Embodiment E304. The method of any one of embodiments E296-E303, wherein the method further comprises administering the immune cell to a subject in need thereof.

Embodiment E305. The method of embodiment E304, wherein the subject has been identified or diagnosed as having an age-related disease or condition.

Embodiment E306. The method of embodiment E305, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment E307. The method of embodiment E304, wherein the subject has been identified or diagnosed as having a cancer.

Embodiment E308. The method of embodiment E307, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment E309. The method of embodiment E304, wherein the subject has been diagnosed or identified as having an infectious disease.

Embodiment E310. The method of embodiment E309, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment E311. A method of killing a cancer cell, an infected cell, or a senescent cell in a subject in need thereof, the method comprising administering to the subject a therapeutically effective amount of any of the multi-chain chimeric polypeptides of embodiments E1-E262 or the composition of embodiment E263 or E264.

Embodiment E312. The method of embodiment E311, wherein the subject has been identified or diagnosed as having a cancer.

Embodiment E313. The method of embodiment E312, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment E314. The method of embodiment E311, wherein the subject has been identified or diagnosed as having an aging-related disease or condition.

Embodiment E315. The method of embodiment E314, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment E316. A method of treating a subject in need thereof, the method comprising administering to the subject a therapeutically effective amount of any of the multi-chain chimeric polypeptides of embodiments E1-E262 or the composition of embodiment E263 or E264.

Embodiment E317. The method of embodiment E316, wherein the subject has been identified or diagnosed as having a cancer or infectious disease.

Embodiment E318. The method of embodiment E317, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment E319. The method of embodiment E316, wherein the subject has been identified or diagnosed as having age-related disease or condition.

Embodiment E320. The method of embodiment E319, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment E321. The method of embodiment E316, wherein the subject has been diagnosed or identified as having an infectious disease.

Embodiment E322. The method of embodiment E321, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment E323. Nucleic acid encoding any of the multi-chain chimeric polypeptides of any one of embodiments E1-E262.

Embodiment E324. A vector comprising the nucleic acid of embodiment E323.

Embodiment E325. The vector of embodiment E324, wherein the vector is an expression vector.

Embodiment E326. A cell comprising the nucleic acid of embodiment E323 or the vector of embodiment E324 or E325.

Embodiment E327. A method of producing a multi-chain chimeric polypeptide, the method comprising:
culturing the cell of embodiment E326 in a culture medium under conditions sufficient to result in the production of the multi-chain chimeric polypeptide; and
recovering the multi-chain chimeric polypeptide from the cell and/or the culture medium.

Embodiment E328. A multi-chain chimeric polypeptide produced by the method of embodiment E327.

Embodiment E329. The multi-chain chimeric polypeptide of embodiment E8, wherein the soluble human tissue factor domain comprises a sequence that is at least 80% identical to SEQ ID NO: 3.

Embodiment E330. The multi-chain chimeric polypeptide of embodiment E329, wherein the soluble human tissue factor domain comprises a sequence that is at least 90% identical to SEQ ID NO: 3.

Embodiment E331. The multi-chain chimeric polypeptide of embodiment E330, wherein the soluble human tissue factor domain comprises a sequence that is at least 95% identical to SEQ ID NO: 3.

Embodiment E332. The multi-chain chimeric polypeptide of embodiment E331, wherein the soluble human tissue factor domain comprises a sequence that is 100% identical to SEQ ID NO: 3.

Embodiment E333. The multi-chain chimeric polypeptide of embodiment E8, wherein the soluble human tissue factor domain comprises a sequence that is at least 80% identical to SEQ ID NO: 4.

Embodiment E334. The multi-chain chimeric polypeptide of embodiment E333, wherein the soluble human tissue factor domain comprises a sequence that is at least 90% identical to SEQ ID NO: 4.

Embodiment E335. The multi-chain chimeric polypeptide of embodiment E334, wherein the soluble human tissue factor domain comprises a sequence that is at least 95% identical to SEQ ID NO: 4.

Embodiment E336. The multi-chain chimeric polypeptide of embodiment E335, wherein the soluble human tissue factor domain comprises a sequence that is 100% identical to SEQ ID NO: 4.

F. Exemplary Embodiments

Embodiment F1. A multi-chain chimeric polypeptide comprising:
(a) a first chimeric polypeptide comprising:
(i) a first target-binding domain;
(ii) a linker domain; and
(iii) a first domain of a pair of affinity domains;
(b) a second chimeric polypeptide comprising:
(i) a second domain of a pair of affinity domains; and
(ii) a second target-binding domain,
wherein the first chimeric polypeptide and the second chimeric polypeptide associate through the binding of the first domain and the second domain of the pair of affinity domains.

Embodiment F2. The multi-chain chimeric polypeptide of embodiment F1, wherein the first target-binding domain and the linker domain directly abut each other in the first chimeric polypeptide.

Embodiment F3. The multi-chain chimeric polypeptide of embodiment F1, wherein the first chimeric polypeptide further comprises a linker sequence between the first target-binding domain and the linker domain in the first chimeric polypeptide.

Embodiment F4. The multi-chain chimeric polypeptide of any one of embodiments F1-F3, wherein the linker domain and the first domain of the pair of affinity domains directly abut each other in the first chimeric polypeptide.

Embodiment F5. The multi-chain chimeric polypeptide of any one of embodiments F1-F3, wherein the first chimeric polypeptide further comprises a linker sequence between the linker domain and the first domain of the pair of affinity domains in the first chimeric polypeptide.

Embodiment F6. The multi-chain chimeric polypeptide of any one of embodiments F1-F5, wherein the second domain of the pair of affinity domains and the second target-binding domain directly abut each other in the second chimeric polypeptide.

Embodiment F7. The multi-chain chimeric polypeptide of any one of embodiments F1-F5, wherein the second chimeric polypeptide further comprises a linker sequence between the second domain of the pair of affinity domains and the second target-binding domain in the second chimeric polypeptide.

Embodiment F8. The multi-chain chimeric polypeptide of any one of embodiments F1-F7, wherein the first target-binding domain and the second target-binding domain bind specifically to the same antigen.

Embodiment F9. The multi-chain chimeric polypeptide of embodiment F8, wherein the first target-binding domain and the second target-binding domain bind specifically to the same epitope.

Embodiment F10. The multi-chain chimeric polypeptide of embodiment F9, wherein the first target-binding domain and the second target-binding domain comprise the same amino acid sequence.

Embodiment F11. The multi-chain chimeric polypeptide of any one of embodiments F1-F7, wherein the first target-binding domain and the second target-binding domain bind specifically to different antigens.

Embodiment F12. The multi-chain chimeric polypeptide of any one of embodiments F1-F11, wherein one or both of the first target-binding domain and the second target-binding domain is an antigen-binding domain.

Embodiment F13. The multi-chain chimeric polypeptide of embodiment F12, wherein the first target-binding domain and the second target-binding domain are each antigen-binding domains.

Embodiment F14. The multi-chain chimeric polypeptide of embodiment F12 or F13, wherein the antigen-binding domain comprises a scFv or a single domain antibody.

Embodiment F15. The multi-chain chimeric polypeptide of any one of embodiments F1-F14, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment F16. The multi-chain chimeric polypeptide of any one of embodiments F1-F14, wherein one or both of the first target-binding domain and the second target-binding domain is a soluble interleukin or cytokine protein.

Embodiment F17. The multi-chain chimeric polypeptide of embodiment F16, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, and FLT3L.

Embodiment F18. The multi-chain chimeric polypeptide of any one of embodiments F1-F14, wherein one or both of the first target-binding domain and the second target-binding domain is a soluble interleukin or cytokine receptor.

Embodiment F19. The multi-chain chimeric polypeptide of embodiment F18, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment F20. The multi-chain chimeric polypeptide of any one of embodiments F1-F19, wherein the first chimeric polypeptide further comprises one or more additional target-binding domain(s), where at least one of the one or more target-binding domain(s) is positioned between the linker domain and the first domain of the pair of affinity domains.

Embodiment F21. The multi-chain chimeric polypeptide of embodiment F20, wherein the first chimeric polypeptide further comprises a linker sequence between the linker domain and the at least one of the one or more target antigen-binding domain(s), and/or a linker sequence between the at least one of the one or more target antigen-binding domain(s) and the first domain of the pair of affinity domains.

Embodiment F22. The multi-chain chimeric polypeptide of any one of embodiments F1-F19, wherein the first chimeric polypeptide further comprises one or more additional target-binding domains at the N-terminal and/or C-terminal end of the first chimeric polypeptide.

Embodiment F23. The multi-chain chimeric polypeptide of embodiment F22, wherein at least one of the one or more additional target-binding domains directly abuts the first domain of the pair of affinity domains in the first chimeric polypeptide.

Embodiment F24. The multi-chain chimeric polypeptide of embodiment F22, wherein the first chimeric polypeptide further comprises a linker sequence between the at least one of the one or more additional target-binding domains and the first domain of the pair of affinity domains.

Embodiment F25. The multi-chain chimeric polypeptide of embodiment F22, wherein the at least one of the one or more additional target-binding domains directly abuts the first target-binding domain in the first chimeric polypeptide.

Embodiment F26. The multi-chain chimeric polypeptide of embodiment F22, wherein the first chimeric polypeptide further comprises a linker sequence between the at least one of the one or more additional target-binding domains and the first target-binding domain.

Embodiment F27. The multi-chain chimeric polypeptide of embodiment F22, wherein at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide.

Embodiment F28. The multi-chain chimeric polypeptide of embodiment F27, wherein the at least one additional target-binding domain of the one or more additional target-binding domains disposed at the N-terminus directly abuts the first target-binding domain or the first domain of the pair of affinity domains in the first chimeric Embodiment F29. The multi-chain chimeric polypeptide of embodiment F27, wherein the first chimeric polypeptide further comprises a linker sequence disposed between the at least one additional target-binding domain and the first target-binding domain or the first domain of the pair of affinity domains in the first chimeric polypeptide.

Embodiment F30. The multi-chain chimeric polypeptide of embodiment F27, wherein the at least one additional target-binding domain of the one or more additional target-binding domains disposed at the C-terminus directly abuts the first target-binding domain or the first domain of the pair of affinity domains in the first chimeric polypeptide.

Embodiment F31. The multi-chain chimeric polypeptide of embodiment F27, wherein the first chimeric polypeptide further comprises a linker sequence disposed between the at least one additional target-binding domain and the first target-binding domain or the first domain of the pair of affinity domains in the first chimeric polypeptide.

Embodiment F32. The multi-chain chimeric polypeptide of embodiment F27, wherein the at least one of the one or more additional target-binding domains positioned between the linker domain and the first domain of the pair of affinity domains, directly abuts the linker domain and/or the first domain of the pair of affinity domains.

Embodiment F33. The multi-chain chimeric polypeptide of embodiment F27, wherein the first chimeric polypeptide further comprises a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

Embodiment F34. The multi-chain chimeric polypeptide of any one of embodiments F1-F33, wherein the second chimeric polypeptide further comprises one or more additional target-binding domains at the N-terminal end and/or the C-terminal end of the second chimeric polypeptide.

Embodiment F35. The multi-chain chimeric polypeptide of embodiment F34, wherein at least one of the one or more additional target-binding domains directly abuts the second domain of the pair of affinity domains in the second chimeric polypeptide.

Embodiment F36. The multi-chain chimeric polypeptide of embodiment F34, wherein the second chimeric polypeptide further comprises a linker sequence between at least one of the one or more additional target-binding domains and the second domain of the pair of affinity domains in the second chimeric polypeptide.

Embodiment F37. The multi-chain chimeric polypeptide of embodiment F34, wherein at least one of the one or more additional target-binding domains directly abuts the second target-binding domain in the second chimeric polypeptide.

Embodiment F38. The multi-chain chimeric polypeptide of embodiment F34, wherein the second chimeric polypeptide further comprises a linker sequence between at least one of the one or more additional target-binding domains and the second target-binding domain in the second chimeric polypeptide.

Embodiment F39. The multi-chain chimeric polypeptide of any one of embodiments F20-F38, wherein two or more of the first target-binding domain, the second target-binding domain, and the one or more additional target-binding domains bind specifically to the same antigen.

Embodiment F40. The multi-chain chimeric polypeptide of embodiment F39, wherein two or more of the first target-binding domain, the second target-binding domain, and the one or more additional target-binding domains bind specifically to the same epitope.

Embodiment F41. The multi-chain chimeric polypeptide of embodiment F40, wherein two or more of the first target-binding domain, the second target-binding domain, and the one or more additional target-binding domains comprise the same amino acid sequence.

Embodiment F42. The multi-chain chimeric polypeptide of embodiment F39, wherein the first target-binding domain, the second target-binding domain, and the one or more additional target-binding domains each bind specifically to the same antigen.

Embodiment F43. The multi-chain chimeric polypeptide of embodiment F42, wherein the first target-binding domain, the second target-binding domain, and the one or more additional target-binding domains each bind specifically to the same epitope.

Embodiment F44. The multi-chain chimeric polypeptide of embodiment F43, wherein the first target-binding domain, the second target-binding domain, and the one or more additional target-binding domains each comprise the same amino acid sequence.

Embodiment F45. The multi-chain chimeric polypeptide of any one of embodiments F20-F38, wherein the first target-binding domain, the second target-binding domain, and the one or more additional target-binding domains bind specifically to different antigens.

Embodiment F46. The multi-chain chimeric polypeptide of any one of embodiments F20-F45, wherein one or more of the first target-binding domain, the second target-binding domain, and the one or more target-binding domains is an antigen-binding domain.

Embodiment F47. The multi-chain chimeric polypeptide of embodiment F46, wherein the first target-binding domain, the second target-binding domain, and the one or more additional target-binding domains are each an antigen-binding domain.

Embodiment F48. The multi-chain chimeric polypeptide of embodiment F46 or F47, wherein the antigen-binding domain comprises a scFv.

Embodiment F49. The multi-chain chimeric polypeptide of any one of embodiments F20-F48, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKp30, a ligand of NKG2D, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment F50. The multi-chain chimeric polypeptide of any one of embodiments F20-F48, wherein one or more of the first target-binding domain, the second target-binding domain, and the one or more additional target-binding domains is a soluble interleukin or cytokine protein.

Embodiment F52. The multi-chain chimeric polypeptide of any one of embodiments F20-F48, wherein one or more of the first target-binding domain, the second target-binding domain, and the one or more additional target-binding domains is a soluble interleukin or cytokine receptor.

Embodiment F53. The multi-chain chimeric polypeptide of embodiment F52, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment F54. The multi-chain chimeric polypeptide of any one of embodiments F1-F53, wherein the first chimeric polypeptide further comprises a peptide tag at the N-terminal end or the C-terminal end of the first chimeric polypeptide.

Embodiment F55. The multi-chain chimeric polypeptide of any one of embodiments F1-F53, wherein the second chimeric polypeptide further comprises a peptide tag at the N-terminal end or the C-terminal end of the second chimeric polypeptide.

Embodiment F56. The multi-chain chimeric polypeptide of any one of embodiments F1-F55, wherein the linker domain is a soluble tissue factor domain.

Embodiment F57. The multi-chain chimeric polypeptide of embodiment F56, wherein the soluble tissue factor domain is a soluble human tissue factor domain.

Embodiment F58. The multi-chain chimeric polypeptide of embodiment F57, wherein the soluble human tissue factor domain comprises a sequence that is at least 80% identical to SEQ ID NO: 1.

Embodiment F59. The multi-chain chimeric polypeptide of embodiment F58, wherein the soluble human tissue factor domain comprises a sequence that is at least 90% identical to SEQ ID NO: 1.

Embodiment F60. The multi-chain chimeric polypeptide of embodiment F59, wherein the soluble human tissue factor domain comprises a sequence that is at least 95% identical to SEQ ID NO: 1.

Embodiment F61. The multi-chain chimeric polypeptide of any one of embodiments F57-F60, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F62. The multi-chain chimeric polypeptide of embodiment F61, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F63. The multi-chain chimeric polypeptide of any one of embodiments F56-F62, wherein the soluble tissue factor domain is not capable of binding to Factor VIIa.

Embodiment F64. The multi-chain chimeric polypeptide of any one of embodiments F56-F63, wherein the soluble tissue factor domain does not convert inactive Factor X into Factor Xa.

Embodiment F65. The multi-chain chimeric polypeptide of any one of embodiments F56-F64, wherein the multi-chain chimeric polypeptide does not stimulate blood coagulation in a mammal.

Embodiment F66. The multi-chain chimeric polypeptide of any one of embodiments F1-F55, wherein the linker domain is selected from the group consisting of: a kappa chain and a lambda chain.

Embodiment F67. The multi-chain chimeric polypeptide of any one of embodiments F1-F66, wherein the pair of affinity domains is a sushi domain from an alpha chain of human IL-15 receptor (IL15Rα) and a soluble IL-15.

Embodiment F68. The multi-chain chimeric polypeptide of embodiment F67, wherein the soluble IL15 has a D8N or D8A amino acid substitution.

Embodiment F69. The multi-chain chimeric polypeptide of embodiment F67 or F68, wherein the human IL15Rα is a mature full-length IL15Rα.

Embodiment F70. The multi-chain chimeric polypeptide of any one of embodiments F1-F66, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment F71. The multi-chain chimeric polypeptide of any one of embodiments F1-F70, wherein the first chimeric polypeptide and/or the second chimeric polypeptide further comprises a signal sequence at its N-terminal end.

Embodiment F72. The multi-chain chimeric polypeptide of any one of embodiments F1-F70, wherein the first chimeric polypeptide and/or the second chimeric polypeptide lacks a signal sequence at its N-terminal end.

Embodiment F73. A composition comprising any of the multi-chain chimeric polypeptides of embodiments F1-F72.

Embodiment F74. The composition of embodiment F73, wherein the composition is a pharmaceutical composition.

Embodiment F75. A kit comprising at least one dose of the composition of embodiment F73 or F74.

Embodiment F76. Nucleic acid encoding any of the multi-chain chimeric polypeptides of any one of embodiments F1-F72.

Embodiment F77. A vector comprising the nucleic acid of embodiment F76.

Embodiment F78. The vector of embodiment F77, wherein the vector is an expression vector.

Embodiment F79. A cell comprising the nucleic acid of embodiment F76 or the vector of embodiment F77 or F78.

Embodiment F80. A method of producing a multi-chain chimeric polypeptide, the method comprising:
culturing the cell of embodiment F79 in a culture medium under conditions sufficient to result in the production of the multi-chain chimeric polypeptide; and
recovering the multi-chain chimeric polypeptide from the cell and/or the culture medium.

Embodiment F81. A multi-chain chimeric polypeptide produced by the method of embodiment F80.

---

What is claimed is:

1. A multi-chain chimeric polypeptide comprising:
   (a) a first chimeric polypeptide comprising:
      (i) a first target-binding domain;
      (ii) a soluble tissue factor domain comprising a sequence at least 80% identical to SEQ ID NO: 1; and
      (iii) a first domain of a pair of affinity domains comprising a sequence that is at least 80% identical to SEQ ID NO: 14;
   (b) a second chimeric polypeptide comprising:
      (i) a second domain of a pair of affinity domains comprising a sequence that is at least 80% identical to SEQ ID NO: 28; and
      (ii) a second target-binding domain,
   wherein the first chimeric polypeptide and the second chimeric polypeptide associate through the binding of the first domain and the second domain of the pair of affinity domains; and
   wherein (A) the first target-binding domain comprises a sequence at least 80% identical to SEQ ID NO: 16 and the second target-binding domain comprises a first sequence that is at least 80% identical to SEQ ID NO: 66 and a second sequence that is at least 80% identical to SEQ ID NO: 68, or (B) the first target-binding domain comprises a first sequence that is at least 80% identical to SEQ ID NO: 66 and a second sequence that is at least 80% identical to SEQ ID NO: 68, and the second target-binding domain comprises a sequence at least 80% identical to SEQ ID NO: 16.

2. The multi-chain chimeric polypeptide of claim 1, wherein the first target-binding domain and the soluble tissue factor domain directly abut each other in the first chimeric polypeptide.

3. The multi-chain chimeric polypeptide of claim 1, wherein the first chimeric polypeptide further comprises a linker sequence between the first target-binding domain and the soluble tissue factor domain in the first chimeric polypeptide.

4. The multi-chain chimeric polypeptide of claim 1, wherein the soluble tissue factor domain and the first domain of the pair of affinity domains directly abut each other in the first chimeric polypeptide.

5. The multi-chain chimeric polypeptide of claim 1, wherein the first chimeric polypeptide further comprises a linker sequence between the soluble tissue factor domain and the first domain of the pair of affinity domains in the first chimeric polypeptide.

6. The multi-chain chimeric polypeptide of claim 1, wherein the second domain of the pair of affinity domains and the second target-binding domain directly abut each other in the second chimeric polypeptide.

7. The multi-chain chimeric polypeptide of claim 1, wherein second chimeric polypeptide further comprises a linker sequence between the second domain of the pair of affinity domains and the second target-binding domain in the second chimeric polypeptide.

8. The multi-chain chimeric polypeptide of claim 1, wherein the soluble tissue factor domain is a soluble human tissue factor domain.

9. The multi-chain chimeric polypeptide of claim 8, wherein the human soluble tissue factor domain does not initiate blood coagulation.

10. The multi-chain chimeric polypeptide of claim 1, wherein the first target-binding domain comprises a sequence at least 80% identical to SEQ ID NO: 16 and the second target-binding domain comprises a first sequence that is at least 80% identical to SEQ ID NO: 66 and a second sequence that is at least 80% identical to SEQ ID NO: 68.

11. The multi-chain chimeric polypeptide of claim 1, wherein the first chimeric polypeptide comprises a sequence that is at least 80% identical to SEQ ID NO: 70 and the second chimeric polypeptide comprises a sequence that is at least 80% identical to SEQ ID NO: 74.

12. The multi-chain chimeric polypeptide of claim 10, wherein the first and second sequence are separated by a linker.

13. The multi-chain chimeric polypeptide of claim 12, wherein the linker comprises a sequence of SEQ ID NO: 7.

14. The multi-chain chimeric polypeptide of claim 1, wherein the first chimeric polypeptide comprises a sequence that is at least 80% identical to SEQ ID NO: 72 and the second chimeric polypeptide comprises a sequence that is at least 80% identical to SEQ ID NO: 76.

15. The multi-chain chimeric polypeptide of claim 1, wherein the first chimeric polypeptide comprises a sequence that is at least 90% identical to SEQ ID NO: 72 and the second chimeric polypeptide comprises a sequence that is at least 90% identical to SEQ ID NO: 76.

16. The multi-chain chimeric polypeptide of claim 1, wherein the first chimeric polypeptide comprises a sequence that is at least 96% identical to SEQ ID NO: 72 and the second chimeric polypeptide comprises a sequence that is at least 96% identical to SEQ ID NO: 76.

17. The multi-chain chimeric polypeptide of claim 1, wherein the first chimeric polypeptide comprises a sequence of SEQ ID NO: 72 and the second chimeric polypeptide comprises a sequence of SEQ ID NO: 76.

18. The multi-chain chimeric polypeptide of claim 1, wherein the first chimeric polypeptide comprises a sequence of SEQ ID NO: 70 and the second chimeric polypeptide comprises a sequence of SEQ ID NO: 74.

19. A composition comprising the multi-chain chimeric polypeptide of claim 1.

20. The composition of claim 19, wherein the composition is a pharmaceutical composition.

21. The multi-chain chimeric polypeptide of claim 1, wherein:
the first target-binding domain comprises a sequence that is at least 90% identical to SEQ ID NO: 16;
the soluble tissue factor domain comprises a sequence that is at least 90% identical to SEQ ID NO: 1;
the first domain of the pair of affinity domains comprises a sequence that is at least 90% identical to SEQ ID NO: 14;
the second target-binding domain comprises a first sequence that is at least 90% identical to SEQ ID NO: 66 and a second sequence that is at least 90% identical to SEQ ID NO: 68; and
the second domain of the pair of affinity domains comprises a sequence that is at least 90% identical to SEQ ID NO: 28.

22. The multi-chain chimeric polypeptide of claim 1, wherein:
the first target-binding domain comprises a sequence that is at least 95% identical to SEQ ID NO: 16;
the soluble tissue factor domain comprises a sequence that is at least 95% identical to SEQ ID NO: 1;
the first domain of the pair of affinity domains comprises a sequence that is at least 95% identical to SEQ ID NO: 14;
the second target-binding domain comprises a first sequence that is at least 95% identical to SEQ ID NO: 66 and a second sequence that is at least 95% identical to SEQ ID NO: 68; and
the second domain of the pair of affinity domains comprises a sequence that is at least 95% identical to SEQ ID NO: 28.

23. The multi-chain chimeric polypeptide of claim 1, wherein:
the first target-binding domain comprises SEQ ID NO: 16;
the soluble tissue factor domain comprises SEQ ID NO: 1;
the first domain of the pair of affinity domains comprises SEQ ID NO: 14;
the second target-binding domain comprises a first sequence of SEQ ID NO: 66 and a second sequence of SEQ ID NO: 68; and
the second domain of the pair of affinity domains comprises SEQ ID NO: 28.

24. The multi-chain chimeric polypeptide of claim 1, wherein:
the first chimeric polypeptide comprises a sequence that is at least 90% identical to SEQ ID NO: 70; and
the second chimeric polypeptide comprises a sequence that is at least 90% identical to SEQ ID NO: 74.

25. The multi-chain chimeric polypeptide of claim 1, wherein:
the first chimeric polypeptide comprises a sequence that is at least 95% identical to SEQ ID NO: 70; and
the second chimeric polypeptide comprises a sequence that is at least 95% identical to SEQ ID NO: 74.

26. The multi-chain chimeric polypeptide of claim 21, wherein the first and second sequence are separated by a linker.

27. The multi-chain chimeric polypeptide of claim 22, wherein the first and second sequence are separated by a linker.

28. The multi-chain chimeric polypeptide of claim 23, wherein the first and second sequence are separated by a linker.

29. The multi-chain chimeric polypeptide of claim 1, wherein the first target-binding domain comprises a first sequence that is at least 80% identical to SEQ ID NO: 66 and a second sequence that is at least 80% identical to SEQ ID NO: 68, and the second target-binding domain comprises a sequence at least 80% identical to SEQ ID NO: 16.

30. The multi-chain chimeric polypeptide of claim 29, wherein the first and second sequence are separated by a linker.

31. The multi-chain chimeric polypeptide of claim 1, wherein:
the first target-binding domain comprises a first sequence that is at least 90% identical to SEQ ID NO: 66 and a second sequence that is at least 90% identical to SEQ ID NO: 68;
the soluble tissue factor domain comprises a sequence that is at least 90% identical to SEQ ID NO: 1;
the first domain of the pair of affinity domains comprises a sequence that is at least 90% identical to SEQ ID NO: 14;
the second target-binding domain comprises a sequence at least 90% identical to SEQ ID NO: 16; and
the second domain of the pair of affinity domains comprises a sequence that is at least 90% identical to SEQ ID NO: 28.

32. The multi-chain chimeric polypeptide of claim 31, wherein the first and second sequence are separated by a linker.

33. The multi-chain chimeric polypeptide of claim 1, wherein:
the first target-binding domain comprises a first sequence that is at least 95% identical to SEQ ID NO: 66 and a second sequence that is at least 95% identical to SEQ ID NO: 68;
the soluble tissue factor domain comprises a sequence that is at least 95% identical to SEQ ID NO: 1;
the first domain of the pair of affinity domains comprises a sequence that is at least 95% identical to SEQ ID NO: 14;
the second target-binding domain comprises a sequence at least 95% identical to SEQ ID NO: 16; and
the second domain of the pair of affinity domains comprises a sequence that is at least 95% identical to SEQ ID NO: 28.

34. The multi-chain chimeric polypeptide of claim 33, wherein the first and second sequence are separated by a linker.

35. The multi-chain chimeric polypeptide of claim 1, wherein:
- the first target-binding domain comprises a first sequence of SEQ ID NO: 66 and a second sequence of SEQ ID NO: 68;
- the soluble tissue factor domain comprises SEQ ID NO: 1;
- the first domain of the pair of affinity domains comprises SEQ ID NO: 14;
- the second target-binding domain comprises SEQ ID NO: 16; and
- the second domain of the pair of affinity domains comprises SEQ ID NO: 28.

36. The multi-chain chimeric polypeptide of claim 35, wherein the first and second sequence are separated by a linker.

* * * * *

UNITED STATES PATENT AND TRADEMARK OFFICE
CERTIFICATE OF CORRECTION

| | | |
|---|---|---|
| PATENT NO. | : 12,269,854 B2 | Page 1 of 1 |
| APPLICATION NO. | : 16/952848 | |
| DATED | : April 8, 2025 | |
| INVENTOR(S) | : Hing Wong | |

It is certified that error appears in the above-identified patent and that said Letters Patent is hereby corrected as shown below:

On the Title Page

Item (71) Applicant, delete "HCW Biologics, Inc., Miramar, FL (US)" and insert --ImmunityBio, Inc., San Diego, CA (US)--

Signed and Sealed this
Twenty-second Day of July, 2025

Coke Morgan Stewart
*Acting Director of the United States Patent and Trademark Office*

SEQUENCE LISTING

```
<160> NUMBER OF SEQ ID NOS: 226

<210> SEQ ID NO 1
<211> LENGTH: 219
<212> TYPE: PRT
<213> ORGANISM: Homo sapiens
<220> FEATURE:
<221> NAME/KEY: source
<223> OTHER INFORMATION: /note="Tissue factor"

<400> SEQUENCE: 1

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110
```

```
Ile Gln Ser Phe Glu Gln Val Gly Thr Lys Val Asn Val Thr Val Glu
            115                 120                 125
Asp Glu Arg Thr Leu Val Arg Arg Asn Asn Thr Phe Leu Ser Leu Arg
    130                 135                 140
Asp Val Phe Gly Lys Asp Leu Ile Tyr Thr Leu Tyr Tyr Trp Lys Ser
145                 150                 155                 160
Ser Ser Ser Gly Lys Lys Thr Ala Lys Thr Asn Thr Asn Glu Phe Leu
                165                 170                 175
Ile Asp Val Asp Lys Gly Glu Asn Tyr Cys Phe Ser Val Gln Ala Val
            180                 185                 190
Ile Pro Ser Arg Thr Val Asn Arg Lys Ser Thr Asp Ser Pro Val Glu
        195                 200                 205
Cys Met Gly Gln Glu Lys Gly Glu Phe Arg Glu
    210                 215
```

<210> SEQ ID NO 2
<211> LENGTH: 657
<212> TYPE: DNA
<213> ORGANISM: Homo sapiens
<220> FEATURE:
<221> NAME/KEY: source
<223> OTHER INFORMATION: /note="Tissue factor"

<400> SEQUENCE: 2

```
agcggcacaa ccaacacagt cgctgcctat aacctcactt ggaagagcac caacttcaaa      60
accatcctcg aatgggaacc caaacccgtt aaccaagttt acaccgtgca gatcagcacc     120
aagtccggcg actggaagtc caaatgtttc tataccaccg acaccgagtg cgatctcacc     180
gatgagatcg tgaaagatgt gaaacagacc tacctcgccc gggtgtttag ctaccccgcc     240
ggcaatgtgg agagcactgg ttccgctggc gagcctttat acgagaacag ccccgaattt     300
accccttacc tcgagaccaa tttaggacag cccaccatcc aaagctttga gcaagttggc     360
acaaaggtga atgtgacagt ggaggacgag cggactttag tgcggcggaa caacacctt     420
ctcagcctcc gggatgtgtt cggcaaagat ttaatctaca cactgtatta ctggaagtcc     480
tcttcctccg gcaagaagac agctaaaacc aacacaaacg agtttttaat cgacgtggat     540
aaaggcgaaa actactgttt cagcgtgcaa gctgtgatcc cctcccggac cgtgaatagg     600
aaaagcaccg atagcccgt tgagtgcatg ggccaagaaa agggcgagtt ccgggag         657
```

<210> SEQ ID NO 3
<211> LENGTH: 219
<212> TYPE: PRT
<213> ORGANISM: Homo sapiens
<220> FEATURE:
<221> NAME/KEY: source
<223> OTHER INFORMATION: /note="Tissue factor"

<400> SEQUENCE: 3

```
Ser Gly Thr Thr Asn Thr Val Ala Ala Tyr Asn Leu Thr Trp Lys Ser
1               5                   10                  15
Thr Asn Phe Ala Thr Ala Leu Glu Trp Glu Pro Lys Pro Val Asn Gln
            20                  25                  30
Val Tyr Thr Val Gln Ile Ser Thr Lys Ser Gly Asp Trp Lys Ser Lys
        35                  40                  45
Cys Phe Tyr Thr Thr Asp Thr Glu Cys Ala Leu Thr Asp Glu Ile Val
    50                  55                  60
Lys Asp Val Lys Gln Thr Tyr Leu Ala Arg Val Phe Ser Tyr Pro Ala
65                  70                  75                  80
```

```
Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Ala Arg Asn Asn Thr Ala Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
        210                 215

<210> SEQ ID NO 4
<211> LENGTH: 219
<212> TYPE: PRT
<213> ORGANISM: Homo sapiens
<220> FEATURE:
<221> NAME/KEY: source
<223> OTHER INFORMATION: /note="Tissue factor"

<400> SEQUENCE: 4

Ser Gly Thr Thr Asn Thr Val Ala Ala Tyr Asn Leu Thr Trp Lys Ser
1               5                   10                  15

Thr Asn Phe Ala Thr Ala Leu Glu Trp Glu Pro Lys Pro Val Asn Gln
            20                  25                  30

Val Tyr Thr Val Gln Ile Ser Thr Lys Ser Gly Asp Ala Lys Ser Lys
        35                  40                  45

Cys Phe Tyr Thr Thr Asp Thr Glu Cys Ala Leu Thr Asp Glu Ile Val
50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Ala Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Ala Arg Asn Asn Thr Ala Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
```

-continued

<210> SEQ ID NO 5
<211> LENGTH: 223
<212> TYPE: PRT
<213> ORGANISM: Mus musculus
<220> FEATURE:
<221> NAME/KEY: source
<223> OTHER INFORMATION: /note="Tissue factor"

<400> SEQUENCE: 5

Ala Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
                20                  25                  30

Thr Val Gln Ile Ser Asp Arg Ser Arg Asn Trp Lys Asn Lys Cys Phe
            35                  40                  45

Ser Thr Thr Asp Thr Glu Cys Asp Leu Thr Asp Glu Ile Val Lys Asp
        50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
            100                 105                 110

Gly Gln Pro Val Ile Gln Gln Phe Glu Gln Asp Gly Arg Lys Leu Asn
        115                 120                 125

Val Val Val Lys Asp Ser Leu Thr Leu Val Arg Lys Asn Gly Thr Phe
    130                 135                 140

Leu Thr Leu Arg Gln Val Phe Gly Lys Asp Leu Gly Tyr Ile Ile Thr
145                 150                 155                 160

Tyr Arg Lys Gly Ser Ser Thr Gly Lys Lys Thr Asn Ile Thr Asn Thr
                165                 170                 175

Asn Glu Phe Ser Ile Asp Val Glu Glu Gly Val Ser Tyr Cys Phe Phe
            180                 185                 190

Val Gln Ala Met Ile Phe Ser Arg Lys Thr Asn Gln Asn Ser Pro Gly
        195                 200                 205

Ser Ser Thr Val Cys Thr Glu Gln Trp Lys Ser Phe Leu Gly Glu
    210                 215                 220

<210> SEQ ID NO 6
<211> LENGTH: 224
<212> TYPE: PRT
<213> ORGANISM: Rattus rattus
<220> FEATURE:
<221> NAME/KEY: source
<223> OTHER INFORMATION: /note="Tissue factor"

<400> SEQUENCE: 6

Ala Gly Thr Pro Pro Gly Lys Ala Phe Asn Leu Thr Trp Ile Ser Thr
1               5                   10                  15

Asp Phe Lys Thr Ile Leu Glu Trp Gln Pro Lys Pro Thr Asn Tyr Thr
                20                  25                  30

Tyr Thr Val Gln Ile Ser Asp Arg Ser Arg Asn Trp Lys Tyr Lys Cys
            35                  40                  45

Thr Gly Thr Thr Asp Thr Glu Cys Asp Leu Thr Asp Glu Ile Val Lys
        50                  55                  60

Asp Val Asn Trp Thr Tyr Glu Ala Arg Val Leu Ser Val Pro Trp Arg

```
                65                  70                  75                  80
Asn Ser Thr His Gly Lys Glu Thr Leu Phe Gly Thr His Gly Glu Glu
                    85                  90                  95

Pro Pro Phe Thr Asn Ala Arg Lys Phe Leu Pro Tyr Arg Asp Thr Lys
                    100                 105                 110

Ile Gly Gln Pro Val Ile Gln Lys Tyr Glu Gln Gly Thr Lys Leu
            115                 120                 125

Lys Val Thr Val Lys Asp Ser Phe Thr Leu Val Arg Lys Asn Gly Thr
            130                 135                 140

Phe Leu Thr Leu Arg Gln Val Phe Gly Asn Asp Leu Gly Tyr Ile Leu
145                 150                 155                 160

Thr Tyr Arg Lys Asp Ser Ser Thr Gly Arg Lys Thr Asn Thr Thr His
                    165                 170                 175

Thr Asn Glu Phe Leu Ile Asp Val Glu Lys Gly Val Ser Tyr Cys Phe
                    180                 185                 190

Phe Ala Gln Ala Val Ile Phe Ser Arg Lys Thr Asn His Lys Ser Pro
                    195                 200                 205

Glu Ser Ile Thr Lys Cys Thr Glu Gln Trp Lys Ser Val Leu Gly Glu
            210                 215                 220

<210> SEQ ID NO 7
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Linker sequence"

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic Linker sequence"

<400> SEQUENCE: 8
ggcggtggag gatccggagg aggtggctcc ggcggcggag gatct           45

<210> SEQ ID NO 9
<211> LENGTH: 133
<212> TYPE: PRT
<213> ORGANISM: Homo sapiens
<220> FEATURE:
<221> NAME/KEY: source
<223> OTHER INFORMATION: /note="IL-2"

<400> SEQUENCE: 9

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                    20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
```

```
                    50                  55                  60
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                     85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 10
<211> LENGTH: 133
<212> TYPE: PRT
<213> ORGANISM: Homo sapiens
<220> FEATURE:
<221> NAME/KEY: source
<223> OTHER INFORMATION: /note="IL-3"

<400> SEQUENCE: 10

Ala Pro Met Thr Gln Thr Thr Pro Leu Lys Thr Ser Trp Val Asn Cys
 1               5                  10                  15

Ser Asn Met Ile Asp Glu Ile Ile Thr His Leu Lys Gln Pro Pro Leu
                20                  25                  30

Pro Leu Leu Asp Phe Asn Asn Leu Asn Gly Glu Asp Gln Asp Ile Leu
            35                  40                  45

Met Glu Asn Asn Leu Arg Arg Pro Asn Leu Glu Ala Phe Asn Arg Ala
 50                  55                  60

Val Lys Ser Leu Gln Asn Ala Ser Ala Ile Glu Ser Ile Leu Lys Asn
 65                  70                  75                  80

Leu Leu Pro Cys Leu Pro Leu Ala Thr Ala Ala Pro Thr Arg His Pro
                85                  90                  95

Ile His Ile Lys Asp Gly Asp Trp Asn Glu Phe Arg Arg Lys Leu Thr
                100                 105                 110

Phe Tyr Leu Lys Thr Leu Glu Asn Ala Gln Ala Gln Thr Thr Thr Leu
            115                 120                 125

Ser Leu Ala Ile Phe
            130

<210> SEQ ID NO 11
<211> LENGTH: 152
<212> TYPE: PRT
<213> ORGANISM: Homo sapiens
<220> FEATURE:
<221> NAME/KEY: source
<223> OTHER INFORMATION: /note="IL-7"

<400> SEQUENCE: 11

Asp Cys Asp Ile Glu Gly Lys Asp Gly Lys Gln Tyr Glu Ser Val Leu
 1               5                  10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
 50                  55                  60

Gln Phe Leu Lys Met Asn Ser Thr Gly Asp Phe Asp Leu His Leu Leu
```

```
                65                  70                  75                  80
Lys Val Ser Glu Gly Thr Thr Ile Leu Leu Asn Cys Thr Gly Gln Val
                    85                  90                  95

Lys Gly Arg Lys Pro Ala Ala Leu Gly Glu Ala Gln Pro Thr Lys Ser
                100                 105                 110

Leu Glu Glu Asn Lys Ser Leu Lys Glu Gln Lys Lys Leu Asn Asp Leu
                115                 120                 125

Cys Phe Leu Lys Arg Leu Leu Gln Glu Ile Lys Thr Cys Trp Asn Lys
130                 135                 140

Ile Leu Met Gly Thr Lys Glu His
145                 150

<210> SEQ ID NO 12
<211> LENGTH: 79
<212> TYPE: PRT
<213> ORGANISM: Homo sapiens
<220> FEATURE:
<221> NAME/KEY: source
<223> OTHER INFORMATION: /note="IL-8"

<400> SEQUENCE: 12

Glu Gly Ala Val Leu Pro Arg Ser Ala Lys Glu Leu Arg Cys Gln Cys
1               5                   10                  15

Ile Lys Thr Tyr Ser Lys Pro Phe His Pro Lys Phe Ile Lys Glu Leu
                20                  25                  30

Arg Val Ile Glu Ser Gly Pro His Cys Ala Asn Thr Glu Ile Ile Val
            35                  40                  45

Lys Leu Ser Asp Gly Arg Glu Leu Cys Leu Asp Pro Lys Glu Asn Trp
        50                  55                  60

Val Gln Arg Val Val Glu Lys Phe Leu Lys Arg Ala Glu Asn Ser
65                  70                  75

<210> SEQ ID NO 13
<211> LENGTH: 160
<212> TYPE: PRT
<213> ORGANISM: Homo sapiens
<220> FEATURE:
<221> NAME/KEY: source
<223> OTHER INFORMATION: /note="IL-10"

<400> SEQUENCE: 13

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
        50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
                100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
```

```
                130                 135                 140
Ile Phe Ile Asn Tyr Ile Glu Ala Tyr Met Thr Met Lys Ile Arg Asn
145                 150                 155                 160

<210> SEQ ID NO 14
<211> LENGTH: 114
<212> TYPE: PRT
<213> ORGANISM: Homo sapiens
<220> FEATURE:
<221> NAME/KEY: source
<223> OTHER INFORMATION: /note="IL-15"

<400> SEQUENCE: 14

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 15
<211> LENGTH: 132
<212> TYPE: PRT
<213> ORGANISM: Homo sapiens
<220> FEATURE:
<221> NAME/KEY: source
<223> OTHER INFORMATION: /note="IL-17"

<400> SEQUENCE: 15

Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
                20                  25                  30

Thr Asn Thr Asn Pro Lys Arg Ser Ser Asp Tyr Tyr Asn Arg Ser Thr
            35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Ile Asn Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
            100                 105                 110

Glu Lys Ile Leu Val Ser Val Gly Cys Thr Cys Val Thr Pro Ile Val
            115                 120                 125

His His Val Ala
            130

<210> SEQ ID NO 16
```

```
<211> LENGTH: 157
<212> TYPE: PRT
<213> ORGANISM: Homo sapiens
<220> FEATURE:
<221> NAME/KEY: source
<223> OTHER INFORMATION: /note="IL-18"

<400> SEQUENCE: 16

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 17
<211> LENGTH: 352
<212> TYPE: PRT
<213> ORGANISM: Homo sapiens
<220> FEATURE:
<221> NAME/KEY: source
<223> OTHER INFORMATION: /note="PDGF-DD"

<400> SEQUENCE: 17

Arg Asp Thr Ser Ala Thr Pro Gln Ser Ala Ser Ile Lys Ala Leu Arg
1               5                   10                  15

Asn Ala Asn Leu Arg Arg Asp Glu Ser Asn His Leu Thr Asp Leu Tyr
            20                  25                  30

Arg Arg Asp Glu Thr Ile Gln Val Lys Gly Asn Gly Tyr Val Gln Ser
        35                  40                  45

Pro Arg Phe Pro Asn Ser Tyr Pro Arg Asn Leu Leu Leu Thr Trp Arg
    50                  55                  60

Leu His Ser Gln Glu Asn Thr Arg Ile Gln Leu Val Phe Asp Asn Gln
65                  70                  75                  80

Phe Gly Leu Glu Glu Ala Glu Asn Asp Ile Cys Arg Tyr Asp Phe Val
                85                  90                  95

Glu Val Glu Asp Ile Ser Glu Thr Ser Thr Ile Ile Arg Gly Arg Trp
            100                 105                 110

Cys Gly His Lys Glu Val Pro Pro Arg Ile Lys Ser Arg Thr Asn Gln
        115                 120                 125

Ile Lys Ile Thr Phe Lys Ser Asp Asp Tyr Phe Val Ala Lys Pro Gly
    130                 135                 140

Phe Lys Ile Tyr Tyr Ser Leu Leu Glu Asp Phe Gln Pro Ala Ala Ala
145                 150                 155                 160
```

```
Ser Glu Thr Asn Trp Glu Ser Val Thr Ser Ser Ile Ser Gly Val Ser
            165                 170                 175

Tyr Asn Ser Pro Ser Val Thr Asp Pro Thr Leu Ile Ala Asp Ala Leu
        180                 185                 190

Asp Lys Lys Ile Ala Glu Phe Asp Thr Val Glu Asp Leu Leu Lys Tyr
    195                 200                 205

Phe Asn Pro Glu Ser Trp Gln Glu Asp Leu Glu Asn Met Tyr Leu Asp
210                 215                 220

Thr Pro Arg Tyr Arg Gly Arg Ser Tyr His Asp Arg Lys Ser Lys Val
225                 230                 235                 240

Asp Leu Asp Arg Leu Asn Asp Asp Ala Lys Arg Tyr Ser Cys Thr Pro
                245                 250                 255

Arg Asn Tyr Ser Val Asn Ile Arg Glu Glu Leu Lys Leu Ala Asn Val
            260                 265                 270

Val Phe Phe Pro Arg Cys Leu Leu Val Gln Arg Cys Gly Gly Asn Cys
        275                 280                 285

Gly Cys Gly Thr Val Asn Trp Arg Ser Cys Thr Cys Asn Ser Gly Lys
    290                 295                 300

Thr Val Lys Lys Tyr His Glu Val Leu Gln Phe Glu Pro Gly His Ile
305                 310                 315                 320

Lys Arg Arg Gly Arg Ala Lys Thr Met Ala Leu Val Asp Ile Gln Leu
                325                 330                 335

Asp His His Glu Arg Cys Asp Cys Ile Cys Ser Ser Arg Pro Pro Arg
            340                 345                 350

<210> SEQ ID NO 18
<211> LENGTH: 248
<212> TYPE: PRT
<213> ORGANISM: Homo sapiens
<220> FEATURE:
<221> NAME/KEY: source
<223> OTHER INFORMATION: /note="SCF"

<400> SEQUENCE: 18

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
            20                  25                  30

Val Pro Gly Met Asp Val Leu Pro Ser His Cys Trp Ile Ser Glu Met
        35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Glu Thr Ser Asp Cys Val Val Ser Ser Thr Leu
    130                 135                 140

Ser Pro Glu Lys Asp Ser Arg Val Ser Val Thr Lys Pro Phe Met Leu
145                 150                 155                 160

Pro Pro Val Ala Ala Ser Ser Leu Arg Asn Asp Ser Ser Ser Ser Asn
```

```
                    165                 170                 175
Arg Lys Ala Lys Asn Pro Pro Gly Asp Ser Ser Leu His Trp Ala Ala
            180                 185                 190

Met Ala Leu Pro Ala Leu Phe Ser Leu Ile Ile Gly Phe Ala Phe Gly
        195                 200                 205

Ala Leu Tyr Trp Lys Lys Arg Gln Pro Ser Leu Thr Arg Ala Val Glu
    210                 215                 220

Asn Ile Gln Ile Asn Glu Glu Asp Asn Glu Ile Ser Met Leu Gln Glu
225                 230                 235                 240

Lys Glu Arg Glu Phe Gln Glu Val
                245
```

<210> SEQ ID NO 19
<211> LENGTH: 209
<212> TYPE: PRT
<213> ORGANISM: Homo sapiens
<220> FEATURE:
<221> NAME/KEY: source
<223> OTHER INFORMATION: /note="FLT3L"

<400> SEQUENCE: 19

```
Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Leu Ala Ala Ala
                165                 170                 175

Trp Cys Leu His Trp Gln Arg Thr Arg Arg Arg Thr Pro Arg Pro Gly
            180                 185                 190

Glu Gln Val Pro Pro Val Pro Ser Pro Gln Asp Leu Leu Leu Val Glu
        195                 200                 205

His
```

<210> SEQ ID NO 20
<211> LENGTH: 360
<212> TYPE: PRT
<213> ORGANISM: Homo sapiens
<220> FEATURE:
<221> NAME/KEY: source
<223> OTHER INFORMATION: /note="MICA"

<400> SEQUENCE: 20

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser Gly Lys Val Leu Val Leu Gln Ser His Trp Gln Thr Phe His
        275                 280                 285

Val Ser Ala Val Ala Ala Ala Ile Phe Val Ile Ile Phe Tyr
290                 295                 300

Val Arg Cys Cys Lys Lys Lys Thr Ser Ala Ala Glu Gly Pro Glu Leu
305                 310                 315                 320

Val Ser Leu Gln Val Leu Asp Gln His Pro Val Gly Thr Ser Asp His
                325                 330                 335

Arg Asp Ala Thr Gln Leu Gly Phe Gln Pro Leu Met Ser Asp Leu Gly
            340                 345                 350

Ser Thr Gly Ser Thr Glu Gly Ala
        355                 360

<210> SEQ ID NO 21
<211> LENGTH: 361
<212> TYPE: PRT
<213> ORGANISM: Homo sapiens
<220> FEATURE:
<221> NAME/KEY: source
<223> OTHER INFORMATION: /note="MICB"

<400> SEQUENCE: 21

```
Ala Glu Pro His Ser Leu Arg Tyr Asn Leu Met Val Leu Ser Gln Asp
1               5                   10                  15
Glu Ser Val Gln Ser Gly Phe Leu Ala Glu Gly His Leu Asp Gly Gln
            20                  25                  30
Pro Phe Leu Arg Tyr Asp Arg Gln Lys Arg Arg Ala Lys Pro Gln Gly
        35                  40                  45
Gln Trp Ala Glu Asp Val Leu Gly Ala Lys Thr Trp Asp Thr Glu Thr
    50                  55                  60
Glu Asp Leu Thr Glu Asn Gly Gln Asp Leu Arg Arg Thr Leu Thr His
65                  70                  75                  80
Ile Lys Asp Gln Lys Gly Gly Leu His Ser Leu Gln Glu Ile Arg Val
                85                  90                  95
Cys Glu Ile His Glu Asp Ser Ser Thr Arg Gly Ser Arg His Phe Tyr
            100                 105                 110
Tyr Asp Gly Glu Leu Phe Leu Ser Gln Asn Leu Glu Thr Gln Glu Ser
        115                 120                 125
Thr Val Pro Gln Ser Ser Arg Ala Gln Thr Leu Ala Met Asn Val Thr
    130                 135                 140
Asn Phe Trp Lys Glu Asp Ala Met Lys Thr Lys Thr His Tyr Arg Ala
145                 150                 155                 160
Met Gln Ala Asp Cys Leu Gln Lys Leu Gln Arg Tyr Leu Lys Ser Gly
                165                 170                 175
Val Ala Ile Arg Arg Thr Val Pro Pro Met Val Asn Val Thr Cys Ser
            180                 185                 190
Glu Val Ser Glu Gly Asn Ile Thr Val Thr Cys Arg Ala Ser Ser Phe
        195                 200                 205
Tyr Pro Arg Asn Ile Thr Leu Thr Trp Arg Gln Asp Gly Val Ser Leu
    210                 215                 220
Ser His Asn Thr Gln Gln Trp Gly Asp Val Leu Pro Asp Gly Asn Gly
225                 230                 235                 240
Thr Tyr Gln Thr Trp Val Ala Thr Arg Ile Arg Gln Gly Glu Glu Gln
                245                 250                 255
Arg Phe Thr Cys Tyr Met Glu His Ser Gly Asn His Gly Thr His Pro
            260                 265                 270
Val Pro Ser Gly Lys Val Leu Val Leu Gln Ser Gln Arg Thr Asp Phe
        275                 280                 285
Pro Tyr Val Ser Ala Ala Met Pro Cys Phe Val Ile Ile Ile Ile Leu
    290                 295                 300
Cys Val Pro Cys Cys Lys Lys Lys Thr Ser Ala Ala Glu Gly Pro Glu
305                 310                 315                 320
Leu Val Ser Leu Gln Val Leu Asp Gln His Pro Val Gly Thr Gly Asp
                325                 330                 335
His Arg Asp Ala Ala Gln Leu Gly Phe Gln Pro Leu Met Ser Ala Thr
            340                 345                 350
Gly Ser Thr Gly Ser Thr Glu Gly Ala
        355                 360
```

<210> SEQ ID NO 22
<211> LENGTH: 190
<212> TYPE: PRT
<213> ORGANISM: Homo sapiens
<220> FEATURE:
<221> NAME/KEY: source
<223> OTHER INFORMATION: /note="ULBP1"

<400> SEQUENCE: 22

Trp Val Asp Thr His Cys Leu Cys Tyr Asp Phe Ile Ile Thr Pro Lys
1               5                   10                  15

Ser Arg Pro Glu Pro Gln Trp Cys Glu Val Gln Gly Leu Val Asp Glu
            20                  25                  30

Arg Pro Phe Leu His Tyr Asp Cys Val Asn His Lys Ala Lys Ala Phe
        35                  40                  45

Ala Ser Leu Gly Lys Lys Val Asn Val Thr Lys Thr Trp Glu Glu Gln
    50                  55                  60

Thr Glu Thr Leu Arg Asp Val Val Asp Phe Leu Lys Gly Gln Leu Leu
65                  70                  75                  80

Asp Ile Gln Val Glu Asn Leu Ile Pro Ile Glu Pro Leu Thr Leu Gln
                85                  90                  95

Ala Arg Met Ser Cys Glu His Glu Ala His Gly His Gly Arg Gly Ser
            100                 105                 110

Trp Gln Phe Leu Phe Asn Gly Gln Lys Phe Leu Leu Phe Asp Ser Asn
        115                 120                 125

Asn Arg Lys Trp Thr Ala Leu His Pro Gly Ala Lys Lys Met Thr Glu
    130                 135                 140

Lys Trp Glu Lys Asn Arg Asp Val Thr Met Phe Phe Gln Lys Ile Ser
145                 150                 155                 160

Leu Gly Asp Cys Lys Met Trp Leu Glu Glu Phe Leu Met Tyr Trp Glu
                165                 170                 175

Gln Met Leu Asp Pro Thr Lys Pro Pro Ser Leu Ala Pro Gly
            180                 185                 190

<210> SEQ ID NO 23
<211> LENGTH: 191
<212> TYPE: PRT
<213> ORGANISM: Homo sapiens
<220> FEATURE:
<221> NAME/KEY: source
<223> OTHER INFORMATION: /note="ULBP2"

<400> SEQUENCE: 23

Gly Arg Ala Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Asn Lys Thr Val Thr Pro
        35                  40                  45

Val Ser Pro Leu Gly Lys Lys Leu Asn Val Thr Thr Ala Trp Lys Ala
    50                  55                  60

Gln Asn Pro Val Leu Arg Glu Val Val Asp Ile Leu Thr Glu Gln Leu
65                  70                  75                  80

Arg Asp Ile Gln Leu Glu Asn Tyr Thr Pro Lys Glu Pro Leu Thr Leu
                85                  90                  95

Gln Ala Arg Met Ser Cys Glu Gln Lys Ala Glu Gly His Ser Ser Gly
            100                 105                 110

Ser Trp Gln Phe Ser Phe Asp Gly Gln Ile Phe Leu Leu Phe Asp Ser
        115                 120                 125

Glu Lys Arg Met Trp Thr Thr Val His Pro Gly Ala Arg Lys Met Lys
    130                 135                 140

Glu Lys Trp Glu Asn Asp Lys Val Val Ala Met Ser Phe His Tyr Phe
145                 150                 155                 160

```
Ser Met Gly Asp Cys Ile Gly Trp Leu Glu Asp Phe Leu Met Gly Met
            165                 170                 175

Asp Ser Thr Leu Glu Pro Ser Ala Gly Ala Pro Leu Ala Met Ser
            180                 185                 190

<210> SEQ ID NO 24
<211> LENGTH: 188
<212> TYPE: PRT
<213> ORGANISM: Homo sapiens
<220> FEATURE:
<221> NAME/KEY: source
<223> OTHER INFORMATION: /note="ULBP3"

<400> SEQUENCE: 24

Asp Ala His Ser Leu Trp Tyr Asn Phe Thr Ile Ile His Leu Pro Arg
1               5                   10                  15

His Gly Gln Gln Trp Cys Glu Val Gln Ser Gln Val Asp Gln Lys Asn
            20                  25                  30

Phe Leu Ser Tyr Asp Cys Gly Ser Asp Lys Val Leu Ser Met Gly His
        35                  40                  45

Leu Glu Glu Gln Leu Tyr Ala Thr Asp Ala Trp Gly Lys Gln Leu Glu
50                  55                  60

Met Leu Arg Glu Val Gly Gln Arg Leu Arg Leu Glu Leu Ala Asp Thr
65                  70                  75                  80

Glu Leu Glu Asp Phe Thr Pro Ser Gly Pro Leu Thr Leu Gln Val Arg
                85                  90                  95

Met Ser Cys Glu Cys Glu Ala Asp Gly Tyr Ile Arg Gly Ser Trp Gln
            100                 105                 110

Phe Ser Phe Asp Gly Arg Lys Phe Leu Leu Phe Asp Ser Asn Asn Arg
        115                 120                 125

Lys Trp Thr Val Val His Ala Gly Ala Arg Arg Met Lys Glu Lys Trp
130                 135                 140

Glu Lys Asp Ser Gly Leu Thr Thr Phe Phe Lys Met Val Ser Met Arg
145                 150                 155                 160

Asp Cys Lys Ser Trp Leu Arg Asp Phe Leu Met His Arg Lys Lys Arg
                165                 170                 175

Leu Glu Pro Thr Ala Pro Pro Thr Met Ala Pro Gly
            180                 185

<210> SEQ ID NO 25
<211> LENGTH: 233
<212> TYPE: PRT
<213> ORGANISM: Homo sapiens
<220> FEATURE:
<221> NAME/KEY: source
<223> OTHER INFORMATION: /note="ULBP4"

<400> SEQUENCE: 25

His Ser Leu Cys Phe Asn Phe Thr Ile Lys Ser Leu Ser Arg Pro Gly
1               5                   10                  15

Gln Pro Trp Cys Glu Ala Gln Val Phe Leu Asn Lys Asn Leu Phe Leu
            20                  25                  30

Gln Tyr Asn Ser Asp Asn Asn Met Val Lys Pro Leu Gly Leu Leu Gly
        35                  40                  45

Lys Lys Val Tyr Ala Thr Ser Thr Trp Gly Glu Leu Thr Gln Thr Leu
50                  55                  60

Gly Glu Val Gly Arg Asp Leu Arg Met Leu Leu Cys Asp Ile Lys Pro
65                  70                  75                  80
```

```
Gln Ile Lys Thr Ser Asp Pro Ser Thr Leu Gln Val Glu Met Phe Cys
                85                  90                  95

Gln Arg Glu Ala Glu Arg Cys Thr Gly Ala Ser Trp Gln Phe Ala Thr
            100                 105                 110

Asn Gly Glu Lys Ser Leu Leu Phe Asp Ala Met Asn Thr Trp Thr
        115                 120                 125

Val Ile Asn His Glu Ala Ser Lys Ile Lys Glu Thr Trp Lys Lys Asp
    130                 135                 140

Arg Gly Leu Glu Lys Tyr Phe Arg Lys Leu Ser Lys Gly Asp Cys Asp
145                 150                 155                 160

His Trp Leu Arg Glu Phe Leu Gly His Trp Glu Ala Met Pro Glu Pro
                165                 170                 175

Thr Val Ser Pro Val Asn Ala Ser Asp Ile His Trp Ser Ser Ser
            180                 185                 190

Leu Pro Asp Arg Trp Ile Ile Leu Gly Ala Phe Ile Leu Leu Val Leu
            195                 200                 205

Met Gly Ile Val Leu Ile Cys Val Trp Trp Gln Asn Gly Glu Trp Gln
    210                 215                 220

Ala Gly Leu Trp Pro Leu Arg Thr Ser
225                 230

<210> SEQ ID NO 26
<211> LENGTH: 193
<212> TYPE: PRT
<213> ORGANISM: Homo sapiens
<220> FEATURE:
<221> NAME/KEY: source
<223> OTHER INFORMATION: /note="ULBP5"

<400> SEQUENCE: 26

Gly Leu Ala Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Ser Lys Thr Val Thr Pro
        35                  40                  45

Val Ser Pro Leu Gly Lys Lys Leu Asn Val Thr Thr Ala Trp Lys Ala
    50                  55                  60

Gln Asn Pro Val Leu Arg Glu Val Val Asp Ile Leu Thr Glu Gln Leu
65                  70                  75                  80

Leu Asp Ile Gln Leu Glu Asn Tyr Ile Pro Lys Glu Pro Leu Thr Leu
                85                  90                  95

Gln Ala Arg Met Ser Cys Glu Gln Lys Ala Glu Gly His Gly Ser Gly
            100                 105                 110

Ser Trp Gln Leu Ser Phe Asp Gly Gln Ile Phe Leu Leu Phe Asp Ser
        115                 120                 125

Glu Asn Arg Met Trp Thr Thr Val His Pro Gly Ala Arg Lys Met Lys
    130                 135                 140

Glu Lys Trp Glu Asn Asp Lys Asp Met Thr Met Ser Phe His Tyr Ile
145                 150                 155                 160

Ser Met Gly Asp Cys Thr Gly Trp Leu Glu Asp Phe Leu Met Gly Met
                165                 170                 175

Asp Ser Thr Leu Glu Pro Ser Ala Gly Ala Pro Pro Thr Met Ser Ser
            180                 185                 190

Gly
```

```
<210> SEQ ID NO 27
<211> LENGTH: 193
<212> TYPE: PRT
<213> ORGANISM: Homo sapiens
<220> FEATURE:
<221> NAME/KEY: source
<223> OTHER INFORMATION: /note="ULBP6"

<400> SEQUENCE: 27

Arg Arg Asp Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Asn Lys Thr Val Thr Pro
        35                  40                  45

Val Ser Pro Leu Gly Lys Lys Leu Asn Val Thr Met Ala Trp Lys Ala
    50                  55                  60

Gln Asn Pro Val Leu Arg Glu Val Val Asp Ile Leu Thr Glu Gln Leu
65                  70                  75                  80

Leu Asp Ile Gln Leu Glu Asn Tyr Thr Pro Lys Glu Pro Leu Thr Leu
                85                  90                  95

Gln Ala Arg Met Ser Cys Glu Gln Lys Ala Glu Gly His Ser Ser Gly
            100                 105                 110

Ser Trp Gln Phe Ser Ile Asp Gly Gln Thr Phe Leu Leu Phe Asp Ser
        115                 120                 125

Glu Lys Arg Met Trp Thr Thr Val His Pro Gly Ala Arg Lys Met Lys
130                 135                 140

Glu Lys Trp Glu Asn Asp Lys Asp Val Ala Met Ser Phe His Tyr Ile
145                 150                 155                 160

Ser Met Gly Asp Cys Ile Gly Trp Leu Glu Asp Phe Leu Met Gly Met
                165                 170                 175

Asp Ser Thr Leu Glu Pro Ser Ala Gly Ala Pro Leu Ala Met Ser Ser
            180                 185                 190

Gly

<210> SEQ ID NO 28
<211> LENGTH: 65
<212> TYPE: PRT
<213> ORGANISM: Homo sapiens
<220> FEATURE:
<221> NAME/KEY: source
<223> OTHER INFORMATION: /note="IL15Ralpha"

<400> SEQUENCE: 28

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 29
<211> LENGTH: 195
```

```
<212> TYPE: DNA
<213> ORGANISM: Homo sapiens
<220> FEATURE:
<221> NAME/KEY: source
<223> OTHER INFORMATION: /note="IL15Ralpha"

<400> SEQUENCE: 29
attacatgcc cccctcccat gagcgtggag cacgccgaca tctgggtgaa gagctatagc    60
ctctacagcc gggagaggta tatctgtaac agcggcttca agaggaaggc cggcaccagc   120
agcctcaccg agtgcgtgct gaataaggct accaacgtgg ctcactggac aacaccctct   180
ttaaagtgca tccgg                                                    195

<210> SEQ ID NO 30
<211> LENGTH: 342
<212> TYPE: DNA
<213> ORGANISM: Homo sapiens
<220> FEATURE:
<221> NAME/KEY: source
<223> OTHER INFORMATION: /note="IL-15"

<400> SEQUENCE: 30
aactgggtga acgtcatcag cgatttaaag aagatcgaag atttaattca gtccatgcat    60
atcgacgcca ctttatacac agaatccgac gtgcaccccc ttgtaaggt gaccgccatg    120 aaatgttttt tactggagct gcaagttatc tctttagaga gcggagacgc tagcatccac   180
gacaccgtgg agaatttaat catttta gcc aataactctt tatccagcaa cggcaacgtg   240
acagagtccg gctgcaagga gtgcgaagag ctggaggaga gaacatcaa ggagtttctg   300 caatcctttg tgcacattgt ccagatgttc atcaatacct cc                       342

<210> SEQ ID NO 31
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Met Lys Trp Val Thr Phe Ile Ser Leu Leu Phe Leu Phe Ser Ser Ala
1               5                   10                  15

Tyr Ser

<210> SEQ ID NO 32
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
atgaaatggg tgacctttat ttctttactg ttcctcttta gcagcgccta ctcc          54

<210> SEQ ID NO 33
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 33
atgaagtggg tcacatttat ctctttactg ttcctcttct ccagcgccta cagc          54

<210> SEQ ID NO 34
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
atgaaatggg tgacctttat ttctttactg ttcctcttta gcagcgccta ctcc          54

<210> SEQ ID NO 35
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Met Lys Cys Leu Leu Tyr Leu Ala Phe Leu Phe Leu Gly Val Asn Cys
1               5                   10                  15

<210> SEQ ID NO 36
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Gly Gln Ile Val Thr Met Phe Glu Ala Leu Pro His Ile Ile Asp
1               5                   10                  15

Glu Val Ile Asn Ile Val Ile Val Leu Ile Ile Thr Ser Ile
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly
    50                  55

<210> SEQ ID NO 37
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Met Pro Asn His Gln Ser Gly Ser Pro Thr Gly Ser Ser Asp Leu Leu
1               5                   10                  15

Leu Ser Gly Lys Lys Gln Arg Pro His Leu Ala Leu Arg Arg Lys Arg
            20                  25                  30

Arg Arg Glu Met Arg Lys Ile Asn Arg Lys Val Arg Arg Met Asn Leu
        35                  40                  45
```

```
Ala Pro Ile Lys Glu Lys Thr Ala Trp Gln His Leu Gln Ala Leu Ile
        50                  55                  60

Ser Glu Ala Glu Val Leu Lys Thr Ser Gln Thr Pro Gln Asn Ser
 65              70                  75                  80

Leu Thr Leu Phe Leu Ala Leu Leu Ser Val Leu Gly Pro Pro Val Thr
                85                  90                  95

Gly

<210> SEQ ID NO 38
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Asp Ser Lys Gly Ser Ser Gln Lys Gly Ser Arg Leu Leu Leu Leu
 1               5                  10                  15

Leu Val Val Ser Asn Leu Leu Leu Cys Gln Gly Val Val Ser
             20                  25                  30

<210> SEQ ID NO 39
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic AviTag sequence"

<400> SEQUENCE: 39

Gly Leu Asn Asp Ile Phe Glu Ala Gln Lys Ile Glu Trp His Glu
 1               5                  10                  15

<210> SEQ ID NO 40
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 40

Lys Arg Arg Trp Lys Lys Asn Phe Ile Ala Val Ser Ala Ala Asn Arg
 1               5                  10                  15

Phe Lys Lys Ile Ser Ser Ser Gly Ala Leu
             20                  25

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 41

Glu Glu Glu Glu Glu Glu Thr
 1               5

<210> SEQ ID NO 42
```

```
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 42

Gly Ala Pro Val Pro Tyr Pro Asp Pro Leu Glu Pro Arg
1               5                   10

<210> SEQ ID NO 43
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 43

Asp Tyr Lys Asp Asp Asp Asp Lys
1               5

<210> SEQ ID NO 44
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 44

Tyr Pro Tyr Asp Val Pro Asp Tyr Ala
1               5

<210> SEQ ID NO 45
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 45

His His His His His
1               5

<210> SEQ ID NO 46
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 46

His His His His His His
1               5

<210> SEQ ID NO 47
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic Tag sequence"

<400> SEQUENCE: 47

His His His His His His His
1               5

<210> SEQ ID NO 48
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 48

His His His His His His His His
1               5

<210> SEQ ID NO 49
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 49

His His His His His His His His His
1               5

<210> SEQ ID NO 50
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 50

His His His His His His His His His His
1               5                   10

<210> SEQ ID NO 51
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 51

Glu Gln Lys Leu Ile Ser Glu Glu Asp Leu
1               5                   10

<210> SEQ ID NO 52
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"
```

```
<400> SEQUENCE: 52

Thr Lys Glu Asn Pro Arg Ser Asn Gln Glu Glu Ser Tyr Asp Asp Asn
1               5                   10                  15

Glu Ser

<210> SEQ ID NO 53
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 53

Lys Glu Thr Ala Ala Ala Lys Phe Glu Arg Gln His Met Asp Ser
1               5                   10                  15

<210> SEQ ID NO 54
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 54

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 55
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 55

Ser Leu Ala Glu Leu Leu Asn Ala Gly Leu Gly Gly Ser
1               5                   10

<210> SEQ ID NO 56
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 56

Thr Gln Asp Pro Ser Arg Val Gly
1               5

<210> SEQ ID NO 57
<211> LENGTH: 12
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic Tag sequence"

<400> SEQUENCE: 57

Pro Asp Arg Val Arg Ala Val Ser His Trp Ser Ser
1               5                   10

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 58

Trp Ser His Pro Gln Phe Glu Lys
1               5

<210> SEQ ID NO 59
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 59

Cys Cys Pro Gly Cys Cys
1               5

<210> SEQ ID NO 60
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 60

Glu Val His Thr Asn Gln Asp Pro Leu Asp
1               5                   10

<210> SEQ ID NO 61
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 61

Gly Lys Pro Ile Pro Asn Pro Leu Leu Gly Leu Asp Ser Thr
1               5                   10

<210> SEQ ID NO 62
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"
```

<400> SEQUENCE: 62

Tyr Thr Asp Ile Glu Met Asn Arg Leu Gly Lys
1               5                   10

<210> SEQ ID NO 63
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 63

Asp Leu Tyr Asp Asp Asp Asp Lys
1               5

<210> SEQ ID NO 64
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Tag sequence"

<400> SEQUENCE: 64

Glu Gln Lys Leu Ile Ser Glu Glu Asp Leu
1               5                   10

<210> SEQ ID NO 65
<211> LENGTH: 471
<212> TYPE: DNA
<213> ORGANISM: Homo sapiens
<220> FEATURE:
<221> NAME/KEY: source
<223> OTHER INFORMATION: /note="IL-18"

<400> SEQUENCE: 65
tacttcggca aactggaatc caagctgagc gtgatccgga atttaaacga ccaagttctg      60
tttatcgatc aaggtaaccg gcctctgttc gaggacatga ccgactccga ttgccgggac     120
aatgcccccc ggaccatctt cattatctcc atgtacaagg acagccagcc ccggggcatg     180
gctgtgacaa ttagcgtgaa gtgtgagaaa atcagcactt tatcttgtga gaacaagatc     240
atctccttta aggaaatgaa cccccccgat aacatcaagg acaccaagtc cgatatcatc     300
ttcttccagc ggtccgtgcc cggtcacgat aacaagatgc agttcgaatc ctcctcctac     360
gagggctact ttttagcttg tgaaaaggag agggatttat tcaagctgat cctcaagaag     420
gaggacgagc tgggcgatcg ttccatcatg ttcaccgtcc aaaacgagga t             471

<210> SEQ ID NO 66
<211> LENGTH: 306
<212> TYPE: PRT
<213> ORGANISM: Homo sapiens
<220> FEATURE:
<221> NAME/KEY: source
<223> OTHER INFORMATION: /note="IL-12Beta"

<400> SEQUENCE: 66

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

```
Glu Asp Gly Ile Thr Trp Thr Leu Asp Gln Ser Ser Glu Val Leu Gly
            35                  40                  45
Ser Gly Lys Thr Leu Thr Ile Gln Val Lys Glu Phe Gly Asp Ala Gly
 50                  55                  60
Gln Tyr Thr Cys His Lys Gly Gly Glu Val Leu Ser His Ser Leu Leu
 65                  70                  75                  80
Leu Leu His Lys Lys Glu Asp Gly Ile Trp Ser Thr Asp Ile Leu Lys
                 85                  90                  95
Asp Gln Lys Glu Pro Lys Asn Lys Thr Phe Leu Arg Cys Glu Ala Lys
            100                 105                 110
Asn Tyr Ser Gly Arg Phe Thr Cys Trp Trp Leu Thr Thr Ile Ser Thr
            115                 120                 125
Asp Leu Thr Phe Ser Val Lys Ser Ser Arg Gly Ser Ser Asp Pro Gln
130                 135                 140
Gly Val Thr Cys Gly Ala Ala Thr Leu Ser Ala Glu Arg Val Arg Gly
145                 150                 155                 160
Asp Asn Lys Glu Tyr Glu Tyr Ser Val Glu Cys Gln Glu Asp Ser Ala
                165                 170                 175
Cys Pro Ala Ala Glu Glu Ser Leu Pro Ile Glu Val Met Val Asp Ala
            180                 185                 190
Val His Lys Leu Lys Tyr Glu Asn Tyr Thr Ser Ser Phe Phe Ile Arg
195                 200                 205
Asp Ile Ile Lys Pro Asp Pro Pro Lys Asn Leu Gln Leu Lys Pro Leu
            210                 215                 220
Lys Asn Ser Arg Gln Val Glu Val Ser Trp Glu Tyr Pro Asp Thr Trp
225                 230                 235                 240
Ser Thr Pro His Ser Tyr Phe Ser Leu Thr Phe Cys Val Gln Val Gln
                245                 250                 255
Gly Lys Ser Lys Arg Glu Lys Lys Asp Arg Val Phe Thr Asp Lys Thr
            260                 265                 270
Ser Ala Thr Val Ile Cys Arg Lys Asn Ala Ser Ile Ser Val Arg Ala
            275                 280                 285
Gln Asp Arg Tyr Tyr Ser Ser Ser Trp Ser Glu Trp Ala Ser Val Pro
290                 295                 300
Cys Ser
305

<210> SEQ ID NO 67
<211> LENGTH: 918
<212> TYPE: DNA
<213> ORGANISM: Homo sapiens
<220> FEATURE:
<221> NAME/KEY: source
<223> OTHER INFORMATION: /note="IL-12Beta"

<400> SEQUENCE: 67
atttgggaac tgaagaagga cgtctacgtg gtcgaactgg actggtatcc cgatgctccc      60
ggcgaaatgg tggtgctcac ttgtgacacc cccgaagaag acggcatcac ttggaccctc     120
gatcagagca gcgaggtgct gggctccgga aagaccctca caatccaagt taaggagttc     180
ggagacgctg gccaatacac atgccacaag ggaggcgagt gctcagcca ttccttatta      240 ttattacaca agaaggaaga cggaatctgg tccaccgaca ttttaaaaga tcagaaggag     300
cccaagaata gacctttttt aaggtgtgag gccaaaaact acagcggtcg tttcacttgt     360
tggtggctga ccaccatttc caccgattta accttctccg tgaaaagcag ccggggaagc     420
```

```
tccgaccctc aaggtgtgac atgtggagcc gctaccctca gcgctgagag ggttcgtggc    480
gataacaagg aatacgagta cagcgtggag tgccaagaag atagcgcttg tcccgctgcc    540
gaagaatctt tacccattga ggtgatggtg acgccgtgc acaaactcaa gtacgagaac     600
tacacctcct ccttctttat ccgggacatc attaagcccg atcctcctaa gaatttacag    660
ctgaagcctc tcaaaaatag ccggcaagtt gaggtctctt gggaatatcc cgacacttgg    720
agcacacccc acagctactt ctctttaacc ttttgtgtgc aagttcaagg taaaagcaag    780
cgggagaaga agaccgggt gtttaccgac aaaaccagcg ccaccgtcat ctgtcggaag     840
aacgcctcca tcagcgtgag ggctcaagat cgttattact ccagcagctg gtccgagtgg    900
gccagcgtgc cttgttcc                                                  918
```

<210> SEQ ID NO 68
<211> LENGTH: 197
<212> TYPE: PRT
<213> ORGANISM: Homo sapiens
<220> FEATURE:
<221> NAME/KEY: source
<223> OTHER INFORMATION: /note="IL-12alpha"

<400> SEQUENCE: 68

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195
```

<210> SEQ ID NO 69
<211> LENGTH: 591
<212> TYPE: DNA
<213> ORGANISM: Homo sapiens
<220> FEATURE:
<221> NAME/KEY: source
<223> OTHER INFORMATION: /note="IL-12alpha"

<400> SEQUENCE: 69

```
cgtaacctcc ccgtggctac ccccgatccc ggaatgttcc cttgtttaca ccacagccag    60
aatttactga gggccgtgag caacatgctg cagaaagcta ggcagacttt agaattttac   120
ccttgcacca gcgaggagat cgaccatgaa gatatcacca aggacaagac atccaccgtg   180
gaggcttgtt tacctctgga gctgacaaag aacgagtctt gtctcaactc tcgtgaaacc   240
agcttcatca caaatggctc ttgtttagct tcccggaaga cctcctttat gatggcttta   300
tgcctcagct ccatctacga ggatttaaag atgtaccaag tggagttcaa gaccatgaac   360
gccaagctgc tcatggaccc taaacggcag atcttttag accagaacat gctggctgtg   420
attgatgagc tgatgcaagc tttaaacttc aactccgaga ccgtccctca gaagtcctcc   480
ctcgaggagc ccgattttta caagacaaag atcaaactgt gcattttact ccacgccttt   540
aggatccggg ccgtgaccat tgaccgggtc atgagctatt taaacgccag c           591
```

<210> SEQ ID NO 70
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 18t15-12s sequence"

<400> SEQUENCE: 70

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp Ser Gly Thr
145                 150                 155                 160

Thr Asn Thr Val Ala Ala Tyr Asn Leu Thr Trp Lys Ser Thr Asn Phe
                165                 170                 175

Lys Thr Ile Leu Glu Trp Glu Pro Lys Pro Val Asn Gln Val Tyr Thr
            180                 185                 190

Val Gln Ile Ser Thr Lys Ser Gly Asp Trp Lys Ser Lys Cys Phe Tyr
        195                 200                 205

Thr Thr Asp Thr Glu Cys Asp Leu Thr Asp Glu Ile Val Lys Asp Val
    210                 215                 220

Lys Gln Thr Tyr Leu Ala Arg Val Phe Ser Tyr Pro Ala Gly Asn Val
225                 230                 235                 240

Glu Ser Thr Gly Ser Ala Gly Glu Pro Leu Tyr Glu Asn Ser Pro Glu
                245                 250                 255
```

Phe Thr Pro Tyr Leu Glu Thr Asn Leu Gly Gln Pro Thr Ile Gln Ser
            260                 265                 270

Phe Glu Gln Val Gly Thr Lys Val Asn Val Thr Val Glu Asp Glu Arg
        275                 280                 285

Thr Leu Val Arg Arg Asn Asn Thr Phe Leu Ser Leu Arg Asp Val Phe
    290                 295                 300

Gly Lys Asp Leu Ile Tyr Thr Leu Tyr Tyr Trp Lys Ser Ser Ser Ser
305                 310                 315                 320

Gly Lys Lys Thr Ala Lys Thr Asn Thr Asn Glu Phe Leu Ile Asp Val
                325                 330                 335

Asp Lys Gly Glu Asn Tyr Cys Phe Ser Val Gln Ala Val Ile Pro Ser
            340                 345                 350

Arg Thr Val Asn Arg Lys Ser Thr Asp Ser Pro Val Glu Cys Met Gly
        355                 360                 365

Gln Glu Lys Gly Glu Phe Arg Glu Asn Trp Val Asn Val Ile Ser Asp
370                 375                 380

Leu Lys Lys Ile Glu Asp Leu Ile Gln Ser Met His Ile Asp Ala Thr
385                 390                 395                 400

Leu Tyr Thr Glu Ser Asp Val His Pro Ser Cys Lys Val Thr Ala Met
            405                 410                 415

Lys Cys Phe Leu Leu Glu Leu Gln Val Ile Ser Leu Glu Ser Gly Asp
        420                 425                 430

Ala Ser Ile His Asp Thr Val Glu Asn Leu Ile Ile Leu Ala Asn Asn
    435                 440                 445

Ser Leu Ser Ser Asn Gly Asn Val Thr Glu Ser Gly Cys Lys Glu Cys
    450                 455                 460

Glu Glu Leu Glu Glu Lys Asn Ile Lys Glu Phe Leu Gln Ser Phe Val
465                 470                 475                 480

His Ile Val Gln Met Phe Ile Asn Thr Ser
            485                 490

<210> SEQ ID NO 71
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 18t15-12s sequence"

<400> SEQUENCE: 71
tacttcggca aactggaatc caagctgagc gtgatccgga atttaaacga ccaagttctg      60
tttatcgatc aaggtaaccg gcctctgttc gaggacatga ccgactccga ttgccgggac     120 aatgccccc ggaccatctt cattatctcc atgtacaagg acagccagcc ccggggcatg      180
gctgtgacaa ttagcgtgaa gtgtgagaaa atcagcactt tatcttgtga gaacaagatc     240
atctccttta aggaaatgaa cccccccgat aacatcaagg acaccaagtc cgatatcatc     300
ttcttccagc ggtccgtgcc cggtcacgat aacaagatgc agttcgaatc tcctcctac     360 gagggctact ttttagcttg tgaaaaggag agggatttat tcaagctgat cctcaagaag     420
gaggacgagc tgggcgatcg ttccatcatg ttcaccgtcc aaaacgagga tagcggcaca     480
accaacacag tcgctgccta taacctcact tggaagagca ccaacttcaa aaccatcctc     540
gaatgggaac ccaaacccgt taaccaagtt tacaccgtgc agatcagcac caagtccggc     600
gactggaagt ccaaatgttt ctataccacc gacaccgagt gcgatctcac cgatgagatc     660

```
gtgaaagatg tgaaacagac ctacctcgcc cgggtgttta gctacccgc cggcaatgtg    720 gagagcactg gttccgctgg cgagccttta tacgagaaca gccccgaatt taccccttac    780
ctcgagacca atttaggaca gcccaccatc caaagctttg agcaagttgg cacaaaggtg    840
aatgtgacag tggaggacga gcggacttta gtgcggcgga acaacacctt tctcagcctc    900
cgggatgtgt tcggcaaaga tttaatctac acactgtatt actggaagtc ctcttcctcc    960
ggcaagaaga cagctaaaac caacacaaac gagtttttaa tcgacgtgga taaaggcgaa   1020
aactactgtt tcagcgtgca agctgtgatc ccctcccgga ccgtgaatag gaaaagcacc   1080
gatagccccg ttgagtgcat gggccaagaa aagggcgagt tccgggagaa ctgggtgaac   1140
gtcatcagcg atttaaagaa gatcgaagat ttaattcagt ccatgcatat cgacgccact   1200
ttatacacag aatccgacgt gcaccctct tgtaaggtga ccgccatgaa atgtttttta   1260
ctggagctgc aagttatctc tttagagagc ggagacgcta gcatccacga caccgtggag   1320
aatttaatca ttttagccaa taactcttta tccagcaacg gcaacgtgac agagtccggc   1380
tgcaaggagt gcgaagagct ggaggagaag aacatcaagg agtttctgca atcctttgtg   1440
cacattgtcc agatgttcat caatacctcc                                    1470
```

<210> SEQ ID NO 72
<211> LENGTH: 508
<212> TYPE: PRT
<213> ORGANISM: Artificial Sequence
<220> FEATURE:
<221> NAME/KEY: source
<223> OTHER INFORMATION: /note="Description of Artificial Sequence:
   Synthetic 18t15-12s sequence"

<400> SEQUENCE: 72

```
Met Lys Trp Val Thr Phe Ile Ser Leu Leu Phe Leu Phe Ser Ser Ala
1               5                   10                  15

Tyr Ser Tyr Phe Gly Lys Leu Glu Ser Lys Leu Ser Val Ile Arg Asn
            20                  25                  30

Leu Asn Asp Gln Val Leu Phe Ile Asp Gln Gly Asn Arg Pro Leu Phe
        35                  40                  45

Glu Asp Met Thr Asp Ser Asp Cys Arg Asp Asn Ala Pro Arg Thr Ile
    50                  55                  60

Phe Ile Ile Ser Met Tyr Lys Asp Ser Gln Pro Arg Gly Met Ala Val
65                  70                  75                  80

Thr Ile Ser Val Lys Cys Glu Lys Ile Ser Thr Leu Ser Cys Glu Asn
                85                  90                  95

Lys Ile Ile Ser Phe Lys Glu Met Asn Pro Pro Asp Asn Ile Lys Asp
            100                 105                 110

Thr Lys Ser Asp Ile Ile Phe Phe Gln Arg Ser Val Pro Gly His Asp
        115                 120                 125

Asn Lys Met Gln Phe Glu Ser Ser Ser Tyr Glu Gly Tyr Phe Leu Ala
    130                 135                 140

Cys Glu Lys Glu Arg Asp Leu Phe Lys Leu Ile Leu Lys Lys Glu Asp
145                 150                 155                 160

Glu Leu Gly Asp Arg Ser Ile Met Phe Thr Val Gln Asn Glu Asp Ser
                165                 170                 175

Gly Thr Thr Asn Thr Val Ala Ala Tyr Asn Leu Thr Trp Lys Ser Thr
            180                 185                 190

Asn Phe Lys Thr Ile Leu Glu Trp Glu Pro Lys Pro Val Asn Gln Val
        195                 200                 205
```

Tyr Thr Val Gln Ile Ser Thr Lys Ser Gly Asp Trp Lys Ser Lys Cys
            210                 215                 220

Phe Tyr Thr Thr Asp Thr Glu Cys Asp Leu Thr Asp Glu Ile Val Lys
225                 230                 235                 240

Asp Val Lys Gln Thr Tyr Leu Ala Arg Val Phe Ser Tyr Pro Ala Gly
                245                 250                 255

Asn Val Glu Ser Thr Gly Ser Ala Gly Glu Pro Leu Tyr Glu Asn Ser
            260                 265                 270

Pro Glu Phe Thr Pro Tyr Leu Glu Thr Asn Leu Gly Gln Pro Thr Ile
        275                 280                 285

Gln Ser Phe Glu Gln Val Gly Thr Lys Val Asn Val Thr Val Glu Asp
290                 295                 300

Glu Arg Thr Leu Val Arg Arg Asn Asn Thr Phe Leu Ser Leu Arg Asp
305                 310                 315                 320

Val Phe Gly Lys Asp Leu Ile Tyr Thr Leu Tyr Tyr Trp Lys Ser Ser
                325                 330                 335

Ser Ser Gly Lys Lys Thr Ala Lys Thr Asn Thr Asn Glu Phe Leu Ile
            340                 345                 350

Asp Val Asp Lys Gly Glu Asn Tyr Cys Phe Ser Val Gln Ala Val Ile
        355                 360                 365

Pro Ser Arg Thr Val Asn Arg Lys Ser Thr Asp Ser Pro Val Glu Cys
370                 375                 380

Met Gly Gln Glu Lys Gly Glu Phe Arg Glu Asn Trp Val Asn Val Ile
385                 390                 395                 400

Ser Asp Leu Lys Lys Ile Glu Asp Leu Ile Gln Ser Met His Ile Asp
                405                 410                 415

Ala Thr Leu Tyr Thr Glu Ser Asp Val His Pro Ser Cys Lys Val Thr
            420                 425                 430

Ala Met Lys Cys Phe Leu Leu Glu Leu Gln Val Ile Ser Leu Glu Ser
        435                 440                 445

Gly Asp Ala Ser Ile His Asp Thr Val Glu Asn Leu Ile Ile Leu Ala
450                 455                 460

Asn Asn Ser Leu Ser Ser Asn Gly Asn Val Thr Glu Ser Gly Cys Lys
465                 470                 475                 480

Glu Cys Glu Glu Leu Glu Glu Lys Asn Ile Lys Glu Phe Leu Gln Ser
                485                 490                 495

Phe Val His Ile Val Gln Met Phe Ile Asn Thr Ser
            500                 505

<210> SEQ ID NO 73
<211> LENGTH: 1524
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic 18t15-12s sequence"

<400> SEQUENCE: 73
atgaagtggg tcacatttat ctctttactg ttcctcttct ccagcgccta cagctacttc      60
ggcaaactgg aatccaagct gagcgtgatc cggaatttaa acgaccaagt tctgtttatc     120
gatcaaggta accggcctct gttcgaggac atgaccgact ccgattgccg ggacaatgcc     180
ccccggacca tcttcattat ctccatgtac aaggacagcc agccccgggg catggctgtg     240
acaattagcg tgaagtgtga gaaaatcagc actttatctt gtgagaacaa gatcatctcc     300

```
tttaaggaaa tgaacccccc cgataacatc aaggacacca agtccgatat catcttcttc    360
cagcggtccg tgcccggtca cgataacaag atgcagttcg aatcctcctc ctacgagggc    420 tacttttag cttgtgaaaa ggagagggat ttattcaagc tgatcctcaa gaaggaggac     480
gagctgggcg atcgttccat catgttcacc gtccaaaacg aggatagcgg cacaaccaac    540
acagtcgctg cctataacct cacttggaag agcaccaact tcaaaaccat cctcgaatgg    600
gaacccaaac ccgttaacca agtttacacc gtgcagatca gcaccaagtc cggcgactgg    660
aagtccaaat gtttctatac caccgacacc gagtgcgatc tcaccgatga gatcgtgaaa    720
gatgtgaaaa agacctacct cgcccgggtg tttagctacc ccgccggcaa tgtggagagc    780
actggttccg ctggcgagcc tttatacgag aacagccccg aatttacccc ttacctcgag    840
accaatttag acagcccac catccaaagc tttgagcaag ttggcacaaa ggtgaatgtg     900
acagtggagg acgagcggac tttagtgcgg cggaacaaca cctttctcag cctccgggat   960
gtgttcggca agatttaat ctacacactg tattactgga agtcctcttc ctccggcaag    1020
aagacagcta aaccaacac aaacgagttt taatcgacg tggataaagg cgaaaactac     1080
tgtttcagcg tgcaagctgt gatcccctcc cggaccgtga ataggaaaag caccgatagc   1140
cccgttgagt gcatgggcca agaaaagggc gagttccggg agaactgggt gaacgtcatc   1200
agcgatttaa agaagatcga agatttaatt cagtccatgc atatcgacgc cactttatac   1260
acagaatccg acgtgcaccc ctcttgtaag gtgaccgcca tgaaatgttt tttactggag   1320
ctgcaagtta tctctttaga gagcggagac gctagcatcc acgacaccgt ggagaattta   1380
atcattttag ccaataactc tttatccagc aacggcaacg tgacagagtc cggctgcaag   1440
gagtgcgaag agctggagga gaagaacatc aaggagtttc tgcaatcctt tgtgcacatt   1500
gtccagatgt tcatcaatac ctcc                                         1524
```

<210> SEQ ID NO 74
<211> LENGTH: 583
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 18t15-12s sequence"

<400> SEQUENCE: 74

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
                100                 105                 110

Asn Tyr Ser Gly Arg Phe Thr Cys Trp Trp Leu Thr Thr Ile Ser Thr
            115                 120                 125

```
Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
                180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
290                 295                 300

Cys Ser Gly Gly Gly Ser Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
                340                 345                 350

Lys Ala Arg Gln Thr Leu Glu Phe Tyr Pro Cys Thr Ser Glu Glu Ile
            355                 360                 365

Asp His Glu Asp Ile Thr Lys Asp Lys Thr Ser Thr Val Glu Ala Cys
            370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
                420                 425                 430

Tyr Gln Val Glu Phe Lys Thr Met Asn Ala Lys Leu Leu Met Asp Pro
            435                 440                 445

Lys Arg Gln Ile Phe Leu Asp Gln Asn Met Leu Ala Val Ile Asp Glu
450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Ile Thr Cys Pro Pro Met Ser Val Glu
            515                 520                 525

His Ala Asp Ile Trp Val Lys Ser Tyr Ser Leu Tyr Ser Arg Glu Arg
530                 535                 540

Tyr Ile Cys Asn Ser Gly Phe Lys Arg Lys Ala Gly Thr Ser Ser Leu
```

545                 550                 555                 560
Thr Glu Cys Val Leu Asn Lys Ala Thr Asn Val Ala His Trp Thr Thr
                    565                 570                 575

Pro Ser Leu Lys Cys Ile Arg
            580

<210> SEQ ID NO 75
<211> LENGTH: 1749
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 18t15-12s sequence"

<400> SEQUENCE: 75

```
atttgggaac tgaagaagga cgtctacgtg gtcgaactgg actggtatcc cgatgctccc        60
ggcgaaatgg tggtgctcac ttgtgacacc cccgaagaag acggcatcac ttggaccctc       120
gatcagagca gcgaggtgct gggctccgga aagacccctca caatccaagt taaggagttc     180
ggagacgctg gccaatacac atgccacaag ggaggcgagg tgctcagcca ttccttatta      240
ttattacaca agaaggaaga cggaatctgg tccaccgaca ttttaaaaga tcagaaggag      300
cccaagaata agacctttt aaggtgtgag gccaaaaact acagcggtcg tttcacttgt       360
tggtggctga ccaccatttc caccgattta accttctccg tgaaaagcag ccggggaagc     420
tccgaccctc aaggtgtgac atgtggagcc gctaccctca gcgctgagag ggttcgtggc      480
gataacaagg aatacgagta cagcgtggag tgccaagaag atagcgcttg ccccgctgcc      540
gaagaatctt tacccattga ggtgatggtg acgccgtgc acaaactcaa gtacgagaac      600
tacacctcct ccttctttat ccgggacatc attaagcccg atcctcctaa gaatttacag     660
ctgaagcctc tcaaaaatag ccggcaagtt gaggtctctt gggaatatcc cgacacttgg     720
agcacacccc acagctactt ctcttttaacc ttttgtgtgc aagttcaagg taaaagcaag     780
cgggagaaga agaccgggt gtttaccgac aaaaccagcg ccaccgtcat ctgtcggaag      840
aacgcctcca tcagcgtgag ggctcaagat cgttattact ccagcagctg gtccgagtgg     900
gccagcgtgc cttgttccgg cggtggagga tccggaggag gtggctccgg cggcggagga     960
tctcgtaacc tccccgtggc taccccgat cccggaatgt tcccttgttt acaccacagc     1020
cagaatttac tgagggccgt gagcaacatg ctgcagaaag ctaggcagac tttagaattt    1080
tacccttgca ccagcgagga gatcgaccat gaagatatca ccaaggacaa gacatccacc    1140
gtggaggctt gtttacctct ggagctgaca agaacgagt cttgtctcaa ctctcgtgaa    1200
accagcttca tcacaaatgg ctcttgttta gcttcccgga agacctcctt tatgatggct    1260
ttatgcctca gctccatcta cgaggattta aagatgtacc aagtggagtt caagaccatg    1320
aacgccaagc tgctcatgga ccctaaacgg cagatcttt tagaccagaa catgctggct    1380
gtgattgatg agctgatgca agctttaaac ttcaactccg agaccgtccc tcagaagtcc    1440
tccctcgagg agcccgattt ttacaagaca aagatcaaac tgtgcatttt actccacgcc    1500
tttaggatcc gggccgtgac cattgaccgg gtcatgagct atttaaacgc cagcattaca    1560
tgcccccctc ccatgagcgt ggagcacgcc gacatctggg tgaagagcta gcctctac     1620 agccgggaga ggtatatctg taacagcggc ttcaagagga aggccggcac cagcagcctc    1680
accgagtgcg tgctgaataa ggctaccaac gtggctcact ggacaacacc ctcttttaaag   1740 tgcatccgg                                                             1749
```

<210> SEQ ID NO 76
<211> LENGTH: 601
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 18t15-12s sequence"

<400> SEQUENCE: 76

```
Met Lys Trp Val Thr Phe Ile Ser Leu Leu Phe Leu Phe Ser Ser Ala
1               5                   10                  15

Tyr Ser Ile Trp Glu Leu Lys Lys Asp Val Tyr Val Val Glu Leu Asp
            20                  25                  30

Trp Tyr Pro Asp Ala Pro Gly Glu Met Val Val Leu Thr Cys Asp Thr
        35                  40                  45

Pro Glu Glu Asp Gly Ile Thr Trp Thr Leu Asp Gln Ser Ser Glu Val
50                  55                  60

Leu Gly Ser Gly Lys Thr Leu Thr Ile Gln Val Lys Glu Phe Gly Asp
65                  70                  75                  80

Ala Gly Gln Tyr Thr Cys His Lys Gly Gly Glu Val Leu Ser His Ser
                85                  90                  95

Leu Leu Leu Leu His Lys Lys Glu Asp Gly Ile Trp Ser Thr Asp Ile
            100                 105                 110

Leu Lys Asp Gln Lys Glu Pro Lys Asn Lys Thr Phe Leu Arg Cys Glu
        115                 120                 125

Ala Lys Asn Tyr Ser Gly Arg Phe Thr Cys Trp Trp Leu Thr Thr Ile
130                 135                 140

Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175

Arg Gly Asp Asn Lys Glu Tyr Glu Tyr Ser Val Glu Cys Gln Glu Asp
            180                 185                 190

Ser Ala Cys Pro Ala Ala Glu Glu Ser Leu Pro Ile Glu Val Met Val
        195                 200                 205

Asp Ala Val His Lys Leu Lys Tyr Glu Asn Tyr Thr Ser Ser Phe Phe
210                 215                 220

Ile Arg Asp Ile Ile Lys Pro Asp Pro Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
        275                 280                 285

Lys Thr Ser Ala Thr Val Ile Cys Arg Lys Asn Ala Ser Ile Ser Val
290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Ser Gly Gly Gly Ser Gly Gly
                325                 330                 335

Gly Gly Ser Arg Asn Leu Pro Val Ala Thr Pro Asp Pro Gly Met Phe
            340                 345                 350
```

Pro Cys Leu His His Ser Gln Asn Leu Leu Arg Ala Val Ser Asn Met
            355                 360                 365

Leu Gln Lys Ala Arg Gln Thr Leu Glu Phe Tyr Pro Cys Thr Ser Glu
    370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
        435                 440                 445

Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
        515                 520                 525

Val Met Ser Tyr Leu Asn Ala Ser Ile Thr Cys Pro Pro Met Ser
    530                 535                 540

Val Glu His Ala Asp Ile Trp Val Lys Ser Tyr Ser Leu Tyr Ser Arg
545                 550                 555                 560

Glu Arg Tyr Ile Cys Asn Ser Gly Phe Lys Arg Lys Ala Gly Thr Ser
                565                 570                 575

Ser Leu Thr Glu Cys Val Leu Asn Lys Ala Thr Asn Val Ala His Trp
            580                 585                 590

Thr Thr Pro Ser Leu Lys Cys Ile Arg
        595                 600

<210> SEQ ID NO 77
<211> LENGTH: 1803
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 18t15-12s sequence"

<400> SEQUENCE: 77
atgaaatggg tgacctttat ttctttactg ttcctcttta gcagcgccta ctccatttgg    60
gaactgaaga aggacgtcta cgtggtcgaa ctggactggt atcccgatgc tcccggcgaa   120
atggtggtgc tcacttgtga cacccccgaa aagacggca tcacttggac cctcgatcag   180
agcagcgagg tgctgggctc cggaaagacc ctcacaatcc aagttaagga gttcggagac   240
gctggccaat acacatgcca agggaggc gaggtgctca gccattcctt attattata     300 cacaagaagg aagacggaat ctggtccacc gacatttaa aagatcagaa ggagcccaag   360
aataagacct ttttaaggtg tgaggccaaa aactacagcg gtcgtttcac ttgttggtgg   420
ctgaccacca tttccaccga tttaaccttc tccgtgaaaa gcagccgggg aagctccgac   480
cctcaaggtg tgacatgtgg agccgctacc ctcagcgctg agggggttcg tggcgataac   540
aaggaatacg agtacagcgt ggagtgccaa gaagatagcg cttgtccgc tgccgaagaa   600

```
tctttaccca ttgaggtgat ggtggacgcc gtgcacaaac tcaagtacga gaactacacc      660
tcctccttct ttatccggga catcattaag cccgatcctc ctaagaattt acagctgaag      720
cctctcaaaa atagccggca agttgaggtc tcttgggaat atcccgacac ttggagcaca      780
ccccacagct acttctcttt aacctttttgt gtgcaagttc aaggtaaaag caagcgggag     840
aagaaagacc gggtgtttac cgacaaaacc agcgccaccg tcatctgtcg aagaacgcc      900 tccatcagcg tgagggctca agatcgttat tactccagca gctggtccga gtgggccagc      960
gtgccttgtt ccggcggtgg aggatccgga ggaggtggct ccggcggcgg aggatctcgt     1020
aacctccccg tggctacccc cgatcccgga atgttcccct gtttacacca cagccagaat    1080
ttactgaggg ccgtgagcaa catgctgcag aaagctaggc agactttaga attttaccct     1140
tgcaccagcg aggagatcga ccatgaagat atcaccaagg acaagacatc caccgtggag    1200
gcttgtttac ctctggagct gacaaagaac gagtcttgtc tcaactctcg tgaaaccagc    1260
ttcatcacaa atggctcttg tttagcttcc cggaagacct cctttatgat ggctttatgc    1320
ctcagctcca tctacgagga tttaaagatg taccaagtgg agttcaagac catgaacgcc    1380
aagctgctca tggaccctaa acggcagatc tttttagacc agaacatgct ggctgtgatt    1440
gatgagctga tgcaagcttt aaacttcaac tccgagaccg tccctcagaa gtcctccctc    1500
gaggagcccg attttacaa gacaaagatc aaactgtgca ttttactcca cgcctttagg    1560
atccgggccg tgaccattga ccgggtcatg agctatttaa acgccagcat acatgcccc    1620 cctcccatga gcgtggagca cgccgacatc tgggtgaaga gctatagcct ctacagccgg    1680
gagaggtata tctgtaacag cggcttcaag aggaaggccg gcaccagcag cctcaccgag    1740
tgcgtgctga ataaggctac caacgtggct cactggacaa caccctcttt aaagtgcatc    1800
cgg                                                                    1803
```

<210> SEQ ID NO 78
<211> LENGTH: 133
<212> TYPE: PRT
<213> ORGANISM: Homo sapiens
<220> FEATURE:
<221> NAME/KEY: source
<223> OTHER INFORMATION: /note="IL-21"

<400> SEQUENCE: 78

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
        130
```

<210> SEQ ID NO 79
<211> LENGTH: 399
<212> TYPE: DNA
<213> ORGANISM: Artificial Sequence
<220> FEATURE:
<221> NAME/KEY: source
<223> OTHER INFORMATION: /note="Description of Artificial Sequence: Synthetic IL7RA MCP insert sequence"

<400> SEQUENCE: 79

```
cagggccagg acaggcacat gatccggatg aggcagctca tcgacatcgt cgaccagctg      60
aagaactacg tgaacgacct ggtgcccgag tttctgcctg cccccgagga cgtggagacc     120
aactgcgagt ggtccgcctt ctcctgcttt cagaaggccc agctgaagtc cgccaacacc     180
ggcaacaacg agcggatcat caacgtgagc atcaagaagc tgaagcggaa gcctccctcc     240
acaaacgccg gcaggaggca gaagcacagg ctgacctgcc ccagctgtga ctcctacgag     300
aagaagcccc ccaaggagtt cctggagagg ttcaagtccc tgctgcagaa gatgatccat     360
cagcacctgt cctccaggac ccacggctcc gaggactcc                            399
```

<210> SEQ ID NO 80
<211> LENGTH: 136
<212> TYPE: PRT
<213> ORGANISM: Homo sapiens
<220> FEATURE:
<221> NAME/KEY: source
<223> OTHER INFORMATION: /note="TGFRbetaRII"

<400> SEQUENCE: 80

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135
```

<210> SEQ ID NO 81
<211> LENGTH: 136
<212> TYPE: PRT
<213> ORGANISM: Homo sapiens
<220> FEATURE:
<221> NAME/KEY: source
<223> OTHER INFORMATION: /note="TGFRbetaRII"

<400> SEQUENCE: 81

```
Ile Pro Pro His Val Gln Lys Ser Val Asn Asn Asp Met Ile Val Thr
1               5                   10                  15
```

Asp Asn Asn Gly Ala Val Lys Phe Pro Gln Leu Cys Lys Phe Cys Asp
            20                  25                  30
Val Arg Phe Ser Thr Cys Asp Asn Gln Lys Ser Cys Met Ser Asn Cys
         35                  40                  45
Ser Ile Thr Ser Ile Cys Glu Lys Pro Gln Glu Val Cys Val Ala Val
     50                  55                  60
Trp Arg Lys Asn Asp Glu Asn Ile Thr Leu Glu Thr Val Cys His Asp
65                  70                  75                  80
Pro Lys Leu Pro Tyr His Asp Phe Ile Leu Glu Asp Ala Ala Ser Pro
                85                  90                  95
Lys Cys Ile Met Lys Glu Lys Lys Lys Pro Gly Glu Thr Phe Phe Met
            100                 105                 110
Cys Ser Cys Ser Ser Asp Glu Cys Asn Asp Asn Ile Ile Phe Ser Glu
            115                 120                 125
Glu Tyr Asn Thr Ser Asn Pro Asp
    130                 135

<210> SEQ ID NO 82
<211> LENGTH: 408
<212> TYPE: DNA
<213> ORGANISM: Homo sapiens
<220> FEATURE:
<221> NAME/KEY: source
<223> OTHER INFORMATION: /note="TGFRbetaRII"

<400> SEQUENCE: 82 atccccccc atgtgcaaaa gagcgtgaac aacgatatga tcgtgaccga caacaacggc        60
gccgtgaagt ttcccagct ctgcaagttc tgcgatgtca ggttcagcac ctgcgataat      120
cagaagtcct gcatgtccaa ctgcacgatc acctccatct gcgagaagcc ccaagaagtg   180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga gaagcccgg agagaccttc tttatgtgtt cctgtagcag cgacgagtgt  360
aacgacaaca tcatcttcag cgaagagtac aacaccagca ccctgat              408

<210> SEQ ID NO 83
<211> LENGTH: 408
<212> TYPE: DNA
<213> ORGANISM: Homo sapiens
<220> FEATURE:
<221> NAME/KEY: source
<223> OTHER INFORMATION: /note="TGFRbetaRII"

<400> SEQUENCE: 83
attcctcccc acgtgcagaa gagcgtgaat aatgacatga tcgtgaccga taacaatggc        60
gccgtgaaat ttcccagct gtgcaaattc tgcgatgtga ggttttccac ctgcgacaac      120
cagaagtcct gtatgagcaa ctgcacaatc acctccatct gtgagaagcc tcaggaggtg   180
tgcgtggctg tctggcggaa gaatgacgag aatatcaccc tggaaaccgt ctgccacgat  240
cccaagctgc cctaccacga tttcatcctg gaagacgccg ccagccctaa gtgcatcatg  300
aaagagaaaa gaagcctggg cgagaccttt ttcatgtgct cctgcagcag cgacgaatgc  360
aacgacaata tcatctttag cgaggaatac aataccagca ccccgac              408

<210> SEQ ID NO 84
<211> LENGTH: 960
<212> TYPE: DNA

```
<213> ORGANISM: Homo sapiens
<220> FEATURE:
<221> NAME/KEY: source
<223> OTHER INFORMATION: /note="TGFRbetaRII"

<400> SEQUENCE: 84
aactgggtga atgtgatcag cgacctgaag aagatcgagg atctgatcca gagcatgcac    60
attgatgcca ccctgtacac agaatctgat gtgcaccta tcccccccca tgtgcaaaag    120
agcgtgaaca acgatatgat cgtgaccgac aacaacggcg ccgtgaagtt ccccagctc    180 tgcaagttct gcgatgtcag gttcagcacc tgcgataatc agaagtcctg catgtccaac    240
tgcacgatca cctccatctg cgagaagccc aagaagtgt gcgtggccgt gtggcggaaa    300
aatgacgaga acatcaccct ggagaccgtg tgtcacgacc caagctccc ttatcacgac    360 ttcattctgg aggacgctgc ctccccaaaa tgcatcatga aggagaagaa gaagcccgga    420
gagaccttct ttatgtgttc ctgtagcagc gacgagtgta cgacaacat catcttcagc    480 gaagagtaca acaccagcaa ccctgatgga ggtggcggat ccggaggtgg aggttctggt    540
ggaggtggga gtattcctcc ccacgtgcag aagagcgtga ataatgacat gatcgtgacc    600
gataacaatg gcgccgtgaa atttccccag ctgtgcaaat ctgcgatgt gaggttttcc    660 acctgcgaca accagaagtc ctgtatgagc aactgcacaa tcacctccat ctgtgagaag    720
cctcaggagg tgtgcgtggc tgtctggcgg aagaatgacg agaatatcac cctgaaaacc    780
gtctgccacg atcccaagct gccctaccac gatttcatcc tggaagacgc cgccagccct    840
aagtgcatca tgaaagagaa aaagaagcct ggcgagacct ttttcatgtg ctcctgcagc    900
agcgacgaat gcaacgacaa tatcatcttt agcgaggaat acaataccag caaccccgac    960

<210> SEQ ID NO 85
<211> LENGTH: 287
<212> TYPE: PRT
<213> ORGANISM: Homo sapiens
<220> FEATURE:
<221> NAME/KEY: source
<223> OTHER INFORMATION: /note="TGFRbetaRII"

<400> SEQUENCE: 85

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Gly Ser Ile Pro Pro His Val Gln Lys Ser Val
145                 150                 155                 160
```

```
Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp
        275                 280                 285
```

<210> SEQ ID NO 86
<211> LENGTH: 466
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21t15-TGFRs sequence"

<400> SEQUENCE: 86

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ser Gly Thr Thr Asn Thr Val Ala Ala Tyr Asn
    130                 135                 140

Leu Thr Trp Lys Ser Thr Asn Phe Lys Thr Ile Leu Glu Trp Glu Pro
145                 150                 155                 160

Lys Pro Val Asn Gln Val Tyr Thr Val Gln Ile Ser Thr Lys Ser Gly
                165                 170                 175

Asp Trp Lys Ser Lys Cys Phe Tyr Thr Thr Asp Thr Glu Cys Asp Leu
            180                 185                 190

Thr Asp Glu Ile Val Lys Asp Val Lys Gln Thr Tyr Leu Ala Arg Val
        195                 200                 205

Phe Ser Tyr Pro Ala Gly Asn Val Glu Ser Thr Gly Ser Ala Gly Glu
    210                 215                 220
```

Pro Leu Tyr Glu Asn Ser Pro Glu Phe Thr Pro Tyr Leu Glu Thr Asn
225                 230                 235                 240

Leu Gly Gln Pro Thr Ile Gln Ser Phe Glu Gln Val Gly Thr Lys Val
            245                 250                 255

Asn Val Thr Val Glu Asp Glu Arg Thr Leu Val Arg Arg Asn Asn Thr
            260                 265                 270

Phe Leu Ser Leu Arg Asp Val Phe Gly Lys Asp Leu Ile Tyr Thr Leu
            275                 280                 285

Tyr Tyr Trp Lys Ser Ser Ser Gly Lys Lys Thr Ala Lys Thr Asn
290                 295                 300

Thr Asn Glu Phe Leu Ile Asp Val Asp Lys Gly Glu Asn Tyr Cys Phe
305                 310                 315                 320

Ser Val Gln Ala Val Ile Pro Ser Arg Thr Val Asn Arg Lys Ser Thr
            325                 330                 335

Asp Ser Pro Val Glu Cys Met Gly Gln Glu Lys Gly Glu Phe Arg Glu
            340                 345                 350

Asn Trp Val Asn Val Ile Ser Asp Leu Lys Lys Ile Glu Asp Leu Ile
            355                 360                 365

Gln Ser Met His Ile Asp Ala Thr Leu Tyr Thr Glu Ser Asp Val His
370                 375                 380

Pro Ser Cys Lys Val Thr Ala Met Lys Cys Phe Leu Leu Glu Leu Gln
385                 390                 395                 400

Val Ile Ser Leu Glu Ser Gly Asp Ala Ser Ile His Asp Thr Val Glu
            405                 410                 415

Asn Leu Ile Ile Leu Ala Asn Asn Ser Leu Ser Ser Asn Gly Asn Val
            420                 425                 430

Thr Glu Ser Gly Cys Lys Glu Cys Glu Glu Leu Glu Glu Lys Asn Ile
            435                 440                 445

Lys Glu Phe Leu Gln Ser Phe Val His Ile Val Gln Met Phe Ile Asn
450                 455                 460

Thr Ser
465

<210> SEQ ID NO 87
<211> LENGTH: 1398
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21t15-TGFRs sequence"

<400> SEQUENCE: 87
cagggccagg acaggcacat gatccggatg aggcagctca tcgacatcgt cgaccagctg      60
aagaactacg tgaacgacct ggtgcccgag tttctgcctg cccccgagga cgtggagacc     120
aactgcgagt ggtccgcctt ctcctgcttt cagaaggccc agctgaagtc cgccaacacc     180
ggcaacaacg agcggatcat caacgtgagc atcaagaagc tgaagcggaa gcctccctcc     240
acaaacgccg gcaggaggca gaagcacagg ctgacctgcc ccagctgtga ctcctacgag     300
aagaagcccc ccaaggagtt cctggagagg ttcaagtccc tgctgcagaa gatgatccat     360
cagcacctgt cctccaggac ccacggctcc gaggactcct ccggcaccac caataccgtg     420
gccgcttata acctcacatg gaagagcacc aacttcaaga caattctgga atgggaaccc     480
aagcccgtca atcaagttta caccgtgcag atctccacca atccggaga ctggaagagc     540 aagtgcttct acacaacaga caccgagtgt gatttaaccg acgaaatcgt caaggacgtc     600

```
aagcaaacct atctggctcg ggtcttttcc tacccgctg gcaatgtcga gtccaccggc    660
tccgctggcg agcctctcta cgagaattcc cccgaattca ccccttattt agagaccaat   720
ttaggccagc ctaccatcca gagcttcgag caagttggca ccaaggtgaa cgtcaccgtc   780
gaggatgaaa ggactttagt gcggcggaat aacacatttt tatccctccg ggatgtgttc   840
ggcaaagacc tcatctacac actgtactat tggaagtcca gctcctccgg caaaaagacc   900
gctaagacca acaccaacga gttttaatt gactgggaca aaggcgagaa ctactgcttc    960
agcgtgcaag ccgtgatccc ttctcgtacc gtcaaccgga agagcacaga ttcccccgtt   1020
gagtgcatgg gccaagaaaa gggcgagttc cgggagaact gggtgaacgt catcagcgat   1080
ttaaagaaga tcgaagattt aattcagtcc atgcatatcg acgccacttt atacacagaa   1140
tccgacgtgc acccctcttg taaggtgacc gccatgaaat gtttttact ggagctgcaa    1200 gttatctctt tagagagcgg agacgctagc atccacgaca ccgtggagaa tttaatcatt   1260
ttagccaata actctttatc cagcaacggc aacgtgacag agtccggctg caaggagtgc   1320
gaagagctgg aggagaagaa catcaaggag tttctgcaat cctttgtgca cattgtccag   1380
atgttcatca atacctcc                                                 1398
```

<210> SEQ ID NO 88
<211> LENGTH: 484
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21t15-TGFRs sequence"

<400> SEQUENCE: 88

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ser Gly Thr Thr Asn Thr Val Ala Ala
145                 150                 155                 160

Tyr Asn Leu Thr Trp Lys Ser Thr Asn Phe Lys Thr Ile Leu Glu Trp
                165                 170                 175

Glu Pro Lys Pro Val Asn Gln Val Tyr Thr Val Gln Ile Ser Thr Lys
            180                 185                 190

Ser Gly Asp Trp Lys Ser Lys Cys Phe Tyr Thr Thr Asp Thr Glu Cys
        195                 200                 205
```

Asp Leu Thr Asp Glu Ile Val Lys Asp Val Lys Gln Thr Tyr Leu Ala
    210                 215                 220

Arg Val Phe Ser Tyr Pro Ala Gly Asn Val Glu Ser Thr Gly Ser Ala
225                 230                 235                 240

Gly Glu Pro Leu Tyr Glu Asn Ser Pro Glu Phe Thr Pro Tyr Leu Glu
                245                 250                 255

Thr Asn Leu Gly Gln Pro Thr Ile Gln Ser Phe Glu Gln Val Gly Thr
            260                 265                 270

Lys Val Asn Val Thr Val Glu Asp Glu Arg Thr Leu Val Arg Arg Asn
        275                 280                 285

Asn Thr Phe Leu Ser Leu Arg Asp Val Phe Gly Lys Asp Leu Ile Tyr
    290                 295                 300

Thr Leu Tyr Tyr Trp Lys Ser Ser Ser Gly Lys Lys Thr Ala Lys
305                 310                 315                 320

Thr Asn Thr Asn Glu Phe Leu Ile Asp Val Asp Lys Gly Glu Asn Tyr
                325                 330                 335

Cys Phe Ser Val Gln Ala Val Ile Pro Ser Arg Thr Val Asn Arg Lys
            340                 345                 350

Ser Thr Asp Ser Pro Val Glu Cys Met Gly Gln Glu Lys Gly Glu Phe
        355                 360                 365

Arg Glu Asn Trp Val Asn Val Ile Ser Asp Leu Lys Lys Ile Glu Asp
    370                 375                 380

Leu Ile Gln Ser Met His Ile Asp Ala Thr Leu Tyr Thr Glu Ser Asp
385                 390                 395                 400

Val His Pro Ser Cys Lys Val Thr Ala Met Lys Cys Phe Leu Leu Glu
                405                 410                 415

Leu Gln Val Ile Ser Leu Glu Ser Gly Asp Ala Ser Ile His Asp Thr
            420                 425                 430

Val Glu Asn Leu Ile Ile Leu Ala Asn Asn Ser Leu Ser Ser Asn Gly
        435                 440                 445

Asn Val Thr Glu Ser Gly Cys Lys Glu Cys Glu Glu Leu Glu Glu Lys
    450                 455                 460

Asn Ile Lys Glu Phe Leu Gln Ser Phe Val His Ile Val Gln Met Phe
465                 470                 475                 480

Ile Asn Thr Ser

<210> SEQ ID NO 89
<211> LENGTH: 1452
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21t15-TGFRs sequence"

<400> SEQUENCE: 89
atgaagtggg tgaccttcat cagcctgctg ttcctgttct ccagcgccta ctcccagggc    60
caggacaggc acatgatccg gatgaggcag ctcatcgaca tcgtcgacca gctgaagaac   120
tacgtgaacg acctggtgcc cgagtttctg cctgccccg aggacgtgga gaccaactgc   180
gagtggtccg ccttctcctg ctttcagaag gcccagctga agtccgccaa caccggcaac   240
aacgagcgga tcatcaacgt gagcatcaag aagctgaagc ggaagcctcc ctccacaaac   300
gccggcagga ggcagaagca caggctgacc tgccccagct gtgactccta cgagaagaag   360
cccccccaag gagttcctgga gaggttcaag tccctgctgc agaagatgat ccatcagcac   420

```
ctgtcctcca ggacccacgg ctccgaggac tcctccggca ccaccaatac cgtggccgct    480
tataacctca catggaagag caccaacttc aagacaattc tggaatggga acccaagccc    540
gtcaatcaag tttacaccgt gcagatctcc accaaatccg agactggaa gagcaagtgc    600 ttctacacaa cagacaccga gtgtgattta accgacgaaa tcgtcaagga cgtcaagcaa    660
acctatctgg ctcgggtctt ttcctacccc gctggcaatg tcgagtccac cggctccgct    720
ggcgagcctc tctacgagaa ttcccccgaa ttcaccccttt atttagagac caatttaggc    780
cagcctacca tccagagctt cgagcaagtt ggcaccaagg tgaacgtcac cgtcgaggat    840
gaaaggactt tagtgcggcg aataacaca tttttatccc tccgggatgt gttcggcaaa    900
gacctcatct acacactgta ctattggaag tccagctcct ccggcaaaaa gaccgctaag    960
accaacacca cgagttttt aattgacgtg acaaaggcg agaactactg cttcagcgtg    1020
caagccgtga tcccttctcg taccgtcaac cggaagagca cagattcccc cgttgagtgc    1080
atgggccaag aaaagggcga gttccggag aactgggtga acgtcatcag cgatttaaag    1140
aagatcgaag atttaattca gtccatgcat atcgacgcca ctttatacac agaatccgac    1200
gtgcacccct cttgtaaggt gaccgccatg aaatgttttt tactggagct gcaagttatc    1260
tctttagaga gcggagacgc tagcatccac gacaccgtgg agaatttaat cattttagcc    1320
aataactctt tatccagcaa cggcaacgtg acagagtccg gctgcaagga gtgcgaagag    1380
ctggaggaga agaacatcaa ggagtttctg caatcctttg tgcacattgt ccagatgttc    1440 atcaataccct cc                                                        1452
```

<210> SEQ ID NO 90
<211> LENGTH: 352
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 21t15-TGFRs sequence"

<400> SEQUENCE: 90

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Gly Ser Ile Pro Pro His Val Gln Lys Ser Val
145                 150                 155                 160
```

Asn Asn Asp Met Ile Val Thr Asp Asn Asn Gly Ala Val Lys Phe Pro
            165                 170                 175

Gln Leu Cys Lys Phe Cys Asp Val Arg Phe Ser Thr Cys Asp Asn Gln
        180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
            245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ile
        275                 280                 285

Thr Cys Pro Pro Met Ser Val Glu His Ala Asp Ile Trp Val Lys
        290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
            325                 330                 335

Ala Thr Asn Val Ala His Trp Thr Thr Pro Ser Leu Lys Cys Ile Arg
            340                 345                 350

<210> SEQ ID NO 91
<211> LENGTH: 1056
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21t15-TGFRs sequence"

<400> SEQUENCE: 91
atcccccccc atgtgcaaaa gagcgtgaac aacgatatga tcgtgaccga caacaacggc    60
gccgtgaagt ttccccagct ctgcaagttc tgcgatgtca ggttcagcac ctgcgataat   120
cagaagtcct gcatgtccaa ctgcacgatc acctccatct gcgagaagcc caagaagtg   180 tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga agaagcccgg agagaccttc tttatgtgtt cctgtagcag cgacgagtgt   360
aacgacaaca tcatcttcag cgaagagtac aacaccagca accctgatgg aggtggcgga   420
tccggaggtg gaggttctgg tggaggtggg agtattcctc cccacgtgca gaagagcgtg   480
aataatgaca tgatcgtgac cgataacaat ggcgccgtga aatttccccca gctgtgcaaa   540 ttctgcgatg tgaggttttc cacctgcgac aaccagaagt cctgtatgag caactgcaca   600
atcacctcca tctgtgagaa gcctcaggag gtgtgcgtgg ctgtctggcg gaagaatgac   660
gagaatatca ccctggaaac cgtctgccac gatcccaagc tgccctacca cgatttcatc   720
ctggaagacg ccgccagccc taagtgcatc atgaaagaga aaaagaagcc tggcgagacc   780 ttttcatgt gctcctgcag cagcgacgaa tgcaacgaca atatcatctt tagcgaggaa   840
tacaatacca gcaaccccga catcacgtgt cctcctccta tgtccgtgga acacgcagac   900
atctgggtca gagctacag cttgtactcc agggagcggt acatttgtaa ctctggtttc   960

```
aagcgtaaag ccggcacgtc cagcctgacg gagtgcgtgt tgaacaaggc cacgaatgtc      1020
gcccactgga caaccccag tctcaaatgt attaga                                 1056
```

<210> SEQ ID NO 92
<211> LENGTH: 370
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21t15-TGFRs sequence"

<400> SEQUENCE: 92

Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

```
Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365

Ile Arg
    370

<210> SEQ ID NO 93
<211> LENGTH: 1110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21t15-TGFRs sequence"

<400> SEQUENCE: 93
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcac gatcacctcc atctgcgaga agccccaaga agtgtgcgtg     240
gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaaccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg cacaatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gccctaagtg catcatgaaa gagaaaaaga gcctggcga gacctttttc     840 atgtgctcct gcagcagcga cgaatgcaac gacaatatca tctttagcga ggaatacaat     900
accagcaacc ccgacatcac cgtgtcctcct cctatgtccg tggaacacgc agacatctgg     960
gtcaagagct acagcttgta ctccagggag cggtacattt gtaactctgg tttcaagcgt    1020
aaagccggca cgtccagcct gacggagtgc gtgttgaaca aggccacgaa tgtcgcccac    1080
tggacaaccc ccagtctcaa atgtattaga                                    1110

<210> SEQ ID NO 94
<211> LENGTH: 399
<212> TYPE: DNA
<213> ORGANISM: Homo sapiens
<220> FEATURE:
<221> NAME/KEY: source
<223> OTHER INFORMATION: /note="IL-21"

<400> SEQUENCE: 94
caaggtcaag atcgccacat gattagaatg cgtcaactta gatatattgt tgatcagctg      60
aaaaattatg tgaatgactt ggtccctgaa tttctgccag ctccagaaga tgtagagaca     120
aactgtgagt ggtcagcttt ttcctgtttt cagaaggccc aactaaagtc agcaaataca     180
ggaaacaatg aaaggataat caatgtatca attaaaaagc tgaagaggaa accaccttcc     240
```
acaaatgcag ggagaagaca gaaacacaga ctaacatgcc cttcatgtga ttcttatgag    300
aaaaaaccac ccaaagaatt cctagaaaga ttcaaatcac ttctccaaaa gatgattcat    360
cagcatctgt cctctagaac acacggaagt gaagattcc    399

<210> SEQ ID NO 95
<211> LENGTH: 456
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic IL-7 sequence"

<400> SEQUENCE: 95
gattgtgata ttgaaggtaa agatggcaaa caatatgaga gtgttctaat ggtcagcatc     60
gatcaattat tggacagcat gaaagaaatt ggtagcaatt gcctgaataa tgaatttaac    120
ttttttaaaa gacatatctg tgatgctaat aaggaaggta tgttttttatt ccgtgctgct    180 cgcaagttga ggcaatttct taaatgaat agcactggtg attttgatct ccacttatta    240
aaagtttcag aaggcacaac aatactgttg aactgcactg ccaggttaa aggaagaaaa    300 ccagctgccc tgggtgaagc ccaaccaaca aagagtttgg aagaaaataa atctttaaag    360
gaacagaaaa aactgaatga cttgtgtttc ctaaagagac tattacaaga gataaaaact    420
tgttggaata aaattttgat gggcactaaa gaacac    456

<210> SEQ ID NO 96
<211> LENGTH: 466
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ser Gly Thr Thr Asn Thr Val Ala Ala Tyr Asn
    130                 135                 140

Leu Thr Trp Lys Ser Thr Asn Phe Lys Thr Ile Leu Glu Trp Glu Pro
145                 150                 155                 160

Lys Pro Val Asn Gln Val Tyr Thr Val Gln Ile Ser Thr Lys Ser Gly
                165                 170                 175

```
Asp Trp Lys Ser Lys Cys Phe Tyr Thr Thr Asp Thr Glu Cys Asp Leu
            180                 185                 190

Thr Asp Glu Ile Val Lys Asp Val Lys Gln Thr Tyr Leu Ala Arg Val
        195                 200                 205

Phe Ser Tyr Pro Ala Gly Asn Val Glu Ser Thr Gly Ser Ala Gly Glu
    210                 215                 220

Pro Leu Tyr Glu Asn Ser Pro Glu Phe Thr Pro Tyr Leu Glu Thr Asn
225                 230                 235                 240

Leu Gly Gln Pro Thr Ile Gln Ser Phe Glu Gln Val Gly Thr Lys Val
            245                 250                 255

Asn Val Thr Val Glu Asp Glu Arg Thr Leu Val Arg Arg Asn Asn Thr
        260                 265                 270

Phe Leu Ser Leu Arg Asp Val Phe Gly Lys Asp Leu Ile Tyr Thr Leu
    275                 280                 285

Tyr Tyr Trp Lys Ser Ser Ser Gly Lys Lys Thr Ala Lys Thr Asn
            290                 295                 300

Thr Asn Glu Phe Leu Ile Asp Val Asp Lys Gly Glu Asn Tyr Cys Phe
305                 310                 315                 320

Ser Val Gln Ala Val Ile Pro Ser Arg Thr Val Asn Arg Lys Ser Thr
            325                 330                 335

Asp Ser Pro Val Glu Cys Met Gly Gln Glu Lys Gly Glu Phe Arg Glu
        340                 345                 350

Asn Trp Val Asn Val Ile Ser Asp Leu Lys Lys Ile Glu Asp Leu Ile
    355                 360                 365

Gln Ser Met His Ile Asp Ala Thr Leu Tyr Thr Glu Ser Asp Val His
370                 375                 380

Pro Ser Cys Lys Val Thr Ala Met Lys Cys Phe Leu Leu Glu Leu Gln
385                 390                 395                 400

Val Ile Ser Leu Glu Ser Gly Asp Ala Ser Ile His Asp Thr Val Glu
            405                 410                 415

Asn Leu Ile Ile Leu Ala Asn Asn Ser Leu Ser Ser Asn Gly Asn Val
        420                 425                 430

Thr Glu Ser Gly Cys Lys Glu Cys Glu Glu Leu Glu Glu Lys Asn Ile
    435                 440                 445

Lys Glu Phe Leu Gln Ser Phe Val His Ile Val Gln Met Phe Ile Asn
450                 455                 460

Thr Ser
465
```

<210> SEQ ID NO 97
<211> LENGTH: 1398
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 21t15-7s sequence"

<400> SEQUENCE: 97

```
caaggtcaag atcgccacat gattagaatg cgtcaactta tagatattgt tgatcagctg      60
aaaaattatg tgaatgactt ggtccctgaa tttctgccag ctccagaaga tgtagagaca     120
aactgtgagt ggtcagcttt ttcctgtttt cagaaggccc aactaaagtc agcaaataca     180
ggaaacaatg aaaggataat caatgtatca attaaaaagc tgaagaggaa accaccttcc     240
acaaatgcag ggagaagaca gaaacacaga ctaacatgcc cttcatgtga ttcttatgag     300
```

```
aaaaaaccac ccaaagaatt cctagaaaga ttcaaatcac ttctccaaaa gatgattcat    360
cagcatctgt cctctagaac acacggaagt gaagattcct caggcactac aaatactgtg    420
gcagcatata atttaacttg gaaatcaact aatttcaaga caattttgga gtgggaaccc    480
aaacccgtca atcaagtcta cactgttcaa ataagcacta agtcaggaga ttggaaaagc    540
aaatgctttt acacaacaga cacagagtgt gacctcaccg acgagattgt gaaggatgtg    600
aagcagacgt acttggcacg ggtcttctcc tacccggcag ggaatgtgga gagcaccggt    660
tctgctgggg agcctctgta tgagaactcc ccagagttca caccttacct ggagacaaac    720
ctcggacagc caacaattca gagttttgaa caggtgggaa caaaagtgaa tgtgaccgta    780
gaagatgaac ggactttagt cagaaggaac aacactttcc taagcctccg ggatgttttt    840
ggcaaggact taatttatac actttattat tggaaatctt caagttcagg aaagaaaaca    900
gccaaaacaa acactaatga ttttttgatt gatgtggata aggagaaaaa ctactgtttc    960
agtgttcaag cagtgattcc ctcccgaaca gttaaccgga agagtacaga cagcccggta   1020
gagtgtatgg gccaggagaa aggggaattc agagaaaact gggtgaacgt catcagcgat   1080
ttaaagaaga tcgaagattt aattcagtcc atgcatatcg acgccacttt atacacagaa   1140
tccgacgtgc acccctcttg taaggtgacc gccatgaaat gttttttact ggagctgcaa   1200
gttatctctt tagagagcgg agacgctagc atccacgaca ccgtggagaa tttaatcatt   1260
ttagccaata actctttatc cagcaacggc aacgtgacag agtccggctg caaggagtgc   1320
gaagagctgg aggagaagaa catcaaggag tttctgcaat cctttgtgca cattgtccag   1380
atgttcatca atacctcc                                                 1398
```

<210> SEQ ID NO 98
<211> LENGTH: 483
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21t15-7s sequence"

<400> SEQUENCE: 98

```
Met Gly Val Lys Val Leu Phe Ala Leu Ile Cys Ile Ala Val Ala Glu
1               5                   10                  15

Ala Gln Gly Gln Asp Arg His Met Ile Arg Met Arg Gln Leu Ile Asp
            20                  25                  30

Ile Val Asp Gln Leu Lys Asn Tyr Val Asn Asp Leu Val Pro Glu Phe
        35                  40                  45

Leu Pro Ala Pro Glu Asp Val Glu Thr Asn Cys Glu Trp Ser Ala Phe
    50                  55                  60

Ser Cys Phe Gln Lys Ala Gln Leu Lys Ser Ala Asn Thr Gly Asn Asn
65                  70                  75                  80

Glu Arg Ile Ile Asn Val Ser Ile Lys Lys Leu Lys Arg Lys Pro Pro
                85                  90                  95

Ser Thr Asn Ala Gly Arg Arg Gln Lys His Arg Leu Thr Cys Pro Ser
            100                 105                 110

Cys Asp Ser Tyr Glu Lys Lys Pro Pro Lys Glu Phe Leu Glu Arg Phe
        115                 120                 125

Lys Ser Leu Leu Gln Lys Met Ile His Gln His Leu Ser Ser Arg Thr
    130                 135                 140

His Gly Ser Glu Asp Ser Ser Gly Thr Thr Asn Thr Val Ala Ala Tyr
145                 150                 155                 160
```

Asn Leu Thr Trp Lys Ser Thr Asn Phe Lys Thr Ile Leu Glu Trp Glu
           165                 170                 175

Pro Lys Pro Val Asn Gln Val Tyr Thr Val Gln Ile Ser Thr Lys Ser
        180                 185                 190

Gly Asp Trp Lys Ser Lys Cys Phe Tyr Thr Asp Thr Glu Cys Asp
        195                 200                 205

Leu Thr Asp Glu Ile Val Lys Asp Val Lys Gln Thr Tyr Leu Ala Arg
        210                 215                 220

Val Phe Ser Tyr Pro Ala Gly Asn Val Glu Ser Thr Gly Ser Ala Gly
225                 230                 235                 240

Glu Pro Leu Tyr Glu Asn Ser Pro Glu Phe Thr Pro Tyr Leu Glu Thr
                245                 250                 255

Asn Leu Gly Gln Pro Thr Ile Gln Ser Phe Glu Gln Val Gly Thr Lys
            260                 265                 270

Val Asn Val Thr Val Glu Asp Glu Arg Thr Leu Val Arg Arg Asn Asn
        275                 280                 285

Thr Phe Leu Ser Leu Arg Asp Val Phe Gly Lys Asp Leu Ile Tyr Thr
        290                 295                 300

Leu Tyr Tyr Trp Lys Ser Ser Ser Gly Lys Lys Thr Ala Lys Thr
305                 310                 315                 320

Asn Thr Asn Glu Phe Leu Ile Asp Val Asp Lys Gly Glu Asn Tyr Cys
                325                 330                 335

Phe Ser Val Gln Ala Val Ile Pro Ser Arg Thr Val Asn Arg Lys Ser
            340                 345                 350

Thr Asp Ser Pro Val Glu Cys Met Gly Gln Glu Lys Gly Glu Phe Arg
        355                 360                 365

Glu Asn Trp Val Asn Val Ile Ser Asp Leu Lys Lys Ile Glu Asp Leu
        370                 375                 380

Ile Gln Ser Met His Ile Asp Ala Thr Leu Tyr Thr Glu Ser Asp Val
385                 390                 395                 400

His Pro Ser Cys Lys Val Thr Ala Met Lys Cys Phe Leu Leu Glu Leu
                405                 410                 415

Gln Val Ile Ser Leu Glu Ser Gly Asp Ala Ser Ile His Asp Thr Val
            420                 425                 430

Glu Asn Leu Ile Ile Leu Ala Asn Asn Ser Leu Ser Ser Asn Gly Asn
        435                 440                 445

Val Thr Glu Ser Gly Cys Lys Glu Cys Glu Glu Leu Glu Glu Lys Asn
        450                 455                 460

Ile Lys Glu Phe Leu Gln Ser Phe Val His Ile Val Gln Met Phe Ile
465                 470                 475                 480

Asn Thr Ser

<210> SEQ ID NO 99
<211> LENGTH: 1449
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21t15-7s sequence"

<400> SEQUENCE: 99
atgggagtga aagttctttt tgcccttatt tgtattgctg tggccgaggc ccaaggtcaa      60
gatcgccaca tgattagaat gcgtcaactt atagatattg ttgatcagct gaaaaattat    120

```
gtgaatgact tggtccctga atttctgcca gctccagaag atgtagagac aaactgtgag    180
tggtcagctt tttcctgttt tcagaaggcc caactaaagt cagcaaatac aggaaacaat    240
gaaaggataa tcaatgtatc aattaaaaag ctgaaggga aaccaccttc cacaaatgca    300
gggagaagac agaaacacag actaacatgc ccttcatgtg attcttatga gaaaaaacca    360
cccaaagaat tcctagaaag attcaaatca cttctccaaa agatgattca tcagcatctg    420
tcctctagaa cacacggaag tgaagattcc tcaggcacta caaatactgt ggcagcatat    480
aatttaactt ggaaatcaac taatttcaag acaattttgg agtgggaacc caaacccgtc    540
aatcaagtct acactgttca aataagcact aagtcaggag attggaaaag caaatgcttt    600
tacacaacag acacagagtg tgacctcacc gacgagattg tgaaggatgt gaagcagacg    660
tacttggcac gggtcttctc ctacccggca gggaatgtgg agagcaccgg ttctgctggg    720
gagcctctgt atgagaactc cccagagttc acaccttacc tggagacaaa cctcggacag    780
ccaacaattc agagttttga acaggtggga acaaaagtga atgtgaccgt agaagatgaa    840
cggactttag tcagaaggaa caacactttc ctaagcctcc gggatgtttt tggcaaggac    900
ttaatttata cactttatta ttggaaatct tcaagttcag gaaagaaaac agccaaaaca    960
aacactaatg agttttgat tgatgtggat aaaggagaaa actactgttt cagtgttcaa   1020
gcagtgattc cctcccgaac agttaaccgg aagagtacag acagcccggt agagtgtatg   1080
ggccaggaga aggggaatt cagagaaaac tgggtgaacg tcatcagcga tttaaagaag   1140
atcgaagatt taattcagtc catgcatatc gacgccactt tatacacaga atccgacgtg   1200 caccctctt gtaaggtgac cgccatgaaa tgtttttac tggagctgca agttatctct   1260
ttagagagcg gagacgctag catccacgac accgtggaga atttaatcat tttagccaat   1320
aactctttat ccagcaacgg caacgtgaca gagtccggct gcaaggagtg cgaagagctg   1380
gaggagaaga acatcaagga gtttctgcaa tcctttgtgc acattgtcca gatgttcatc   1440
aatacctcc                                                          1449
```

<210> SEQ ID NO 100
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic 21t15-7s sequence"

<400> SEQUENCE: 100

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110
```

```
Leu Glu Glu Asn Lys Ser Leu Lys Glu Gln Lys Lys Leu Asn Asp Leu
            115                 120                 125

Cys Phe Leu Lys Arg Leu Leu Gln Glu Ile Lys Thr Cys Trp Asn Lys
130                 135                 140

Ile Leu Met Gly Thr Lys Glu His Ile Thr Cys Pro Pro Pro Met Ser
145                 150                 155                 160

Val Glu His Ala Asp Ile Trp Val Lys Ser Tyr Ser Leu Tyr Ser Arg
                165                 170                 175

Glu Arg Tyr Ile Cys Asn Ser Gly Phe Lys Arg Lys Ala Gly Thr Ser
            180                 185                 190

Ser Leu Thr Glu Cys Val Leu Asn Lys Ala Thr Asn Val Ala His Trp
        195                 200                 205

Thr Thr Pro Ser Leu Lys Cys Ile Arg
    210                 215
```

<210> SEQ ID NO 101
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21t15-7s sequence"

<400> SEQUENCE: 101

```
gattgtgata ttgaaggtaa agatggcaaa caatatgaga gtgttctaat ggtcagcatc      60
gatcaattat tggacagcat gaaagaaatt ggtagcaatt gcctgaataa tgaatttaac     120
ttttttaaaa gacatatctg tgatgctaat aaggaaggta tgttttttatt ccgtgctgct     180
cgcaagttga ggcaatttct taaaatgaat agcactggtg attttgatct ccacttatta     240
aaagtttcag aaggcacaac aatactgttg aactgcactg ccaggttaa aggaagaaaa      300
ccagctgccc tgggtgaagc ccaaccaaca aagagtttgg aagaaaataa atctttaaag     360
gaacagaaaa aactgaatga cttgtgtttc ctaaagagac tattacaaga gataaaaact     420
tgttggaata aaattttgat gggcactaaa gaacacatca cgtgccctcc ccccatgtcc     480
gtggaacacg cagacatctg ggtcaagagc tacagcttgt actccaggga gcggtacatt     540
tgtaactctg gtttcaagcg taaagccggc acgtccagcc tgacggagtg cgtgttgaac     600
aaggccacga atgtcgccca ctggacaacc cccagtctca atgcattag a              651
```

<210> SEQ ID NO 102
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21t15-7s sequence"

<400> SEQUENCE: 102

```
Met Gly Val Lys Val Leu Phe Ala Leu Ile Cys Ile Ala Val Ala Glu
1               5                   10                  15

Ala Asp Cys Asp Ile Glu Gly Lys Asp Gly Lys Gln Tyr Glu Ser Val
            20                  25                  30

Leu Met Val Ser Ile Asp Gln Leu Leu Asp Ser Met Lys Glu Ile Gly
        35                  40                  45

Ser Asn Cys Leu Asn Asn Glu Phe Asn Phe Phe Lys Arg His Ile Cys
50                  55                  60
```

```
Asp Ala Asn Lys Glu Gly Met Phe Leu Phe Arg Ala Ala Arg Lys Leu
 65                  70                  75                  80

Arg Gln Phe Leu Lys Met Asn Ser Thr Gly Asp Phe Asp Leu His Leu
                 85                  90                  95

Leu Lys Val Ser Glu Gly Thr Thr Ile Leu Leu Asn Cys Thr Gly Gln
            100                 105                 110

Val Lys Gly Arg Lys Pro Ala Ala Leu Gly Glu Ala Gln Pro Thr Lys
        115                 120                 125

Ser Leu Glu Glu Asn Lys Ser Leu Lys Glu Gln Lys Lys Leu Asn Asp
130                 135                 140

Leu Cys Phe Leu Lys Arg Leu Leu Gln Glu Ile Lys Thr Cys Trp Asn
145                 150                 155                 160

Lys Ile Leu Met Gly Thr Lys Glu His Ile Thr Cys Pro Pro Pro Met
                165                 170                 175

Ser Val Glu His Ala Asp Ile Trp Val Lys Ser Tyr Ser Leu Tyr Ser
            180                 185                 190

Arg Glu Arg Tyr Ile Cys Asn Ser Gly Phe Lys Arg Lys Ala Gly Thr
        195                 200                 205

Ser Ser Leu Thr Glu Cys Val Leu Asn Lys Ala Thr Asn Val Ala His
210                 215                 220

Trp Thr Thr Pro Ser Leu Lys Cys Ile Arg
225                 230
```

<210> SEQ ID NO 103
<211> LENGTH: 702
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21t15-7s sequence"

<400> SEQUENCE: 103

```
atgggagtga aagttctttt tgcccttatt tgtattgctg tggccgaggc cgattgtgat     60
attgaaggta agatggcaa acaatatgag agtgttctaa tggtcagcat cgatcaatta    120
ttggacagca tgaaagaaat tggtagcaat tgcctgaata atgaatttaa cttttttaaa    180
agacatatct gtgatgctaa taggaaggt atgtttttat ccgtgctgc tcgcaagttg     240 aggcaatttc ttaaaatgaa tagcactggt gattttgatc tccacttatt aaaagtttca    300
gaaggcacaa caatactgtt gaactgcact ggccaggtta aggaagaaa accagctgcc    360 ctgggtgaag cccaaccaac aaagagtttg gaagaaaata atctttaaa ggaacagaaa     420 aaactgaatg acttgtgttt cctaaagaga ctattacaag ataaaaac ttgttggaat     480 aaaattttga tgggcactaa agaacacatc acgtgccctc ccccatgtc cgtggaacac    540 gcagacatct gggtcaagag ctacagcttg tactccaggg agcggtacat ttgtaactct    600
ggtttcaagc gtaaagccgg cacgtccagc ctgacggagt gcgtgttgaa caaggccacg    660
aatgtcgccc actggacaac ccccagtctc aaatgcatta ga                      702
```

<210> SEQ ID NO 104
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-21s sequence"

```
<400> SEQUENCE: 104

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Ser Gly Thr Thr Asn Thr Val Ala
145                 150                 155                 160

Ala Tyr Asn Leu Thr Trp Lys Ser Thr Asn Phe Lys Thr Ile Leu Glu
                165                 170                 175

Trp Glu Pro Lys Pro Val Asn Gln Val Tyr Thr Val Gln Ile Ser Thr
            180                 185                 190

Lys Ser Gly Asp Trp Lys Ser Lys Cys Phe Tyr Thr Thr Asp Thr Glu
        195                 200                 205

Cys Asp Leu Thr Asp Glu Ile Val Lys Asp Val Lys Gln Thr Tyr Leu
    210                 215                 220

Ala Arg Val Phe Ser Tyr Pro Ala Gly Asn Val Glu Ser Thr Gly Ser
225                 230                 235                 240

Ala Gly Glu Pro Leu Tyr Glu Asn Ser Pro Glu Phe Thr Pro Tyr Leu
                245                 250                 255

Glu Thr Asn Leu Gly Gln Pro Thr Ile Gln Ser Phe Glu Gln Val Gly
            260                 265                 270

Thr Lys Val Asn Val Thr Val Glu Asp Glu Arg Thr Leu Val Arg Arg
        275                 280                 285

Asn Asn Thr Phe Leu Ser Leu Arg Asp Val Phe Gly Lys Asp Leu Ile
    290                 295                 300

Tyr Thr Leu Tyr Tyr Trp Lys Ser Ser Ser Gly Lys Lys Thr Ala
305                 310                 315                 320

Lys Thr Asn Thr Asn Glu Phe Leu Ile Asp Val Asp Lys Gly Glu Asn
                325                 330                 335

Tyr Cys Phe Ser Val Gln Ala Val Ile Pro Ser Arg Thr Val Asn Arg
            340                 345                 350

Lys Ser Thr Asp Ser Pro Val Glu Cys Met Gly Gln Glu Lys Gly Glu
        355                 360                 365

Phe Arg Glu Asn Trp Val Asn Val Ile Ser Asp Leu Lys Lys Ile Glu
    370                 375                 380

Asp Leu Ile Gln Ser Met His Ile Asp Ala Thr Leu Tyr Thr Glu Ser
385                 390                 395                 400

Asp Val His Pro Ser Cys Lys Val Thr Ala Met Lys Cys Phe Leu Leu
                405                 410                 415
```

Glu Leu Gln Val Ile Ser Leu Glu Ser Gly Asp Ala Ser Ile His Asp
                420                 425                 430

Thr Val Glu Asn Leu Ile Ile Leu Ala Asn Asn Ser Leu Ser Ser Asn
            435                 440                 445

Gly Asn Val Thr Glu Ser Gly Cys Lys Glu Cys Glu Glu Leu Glu Glu
        450                 455                 460

Lys Asn Ile Lys Glu Phe Leu Gln Ser Phe Val His Ile Val Gln Met
465                 470                 475                 480

Phe Ile Asn Thr Ser
                485

<210> SEQ ID NO 105
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-21s sequence"

<400> SEQUENCE: 105
gattgcgaca tcgagggcaa ggacggcaag cagtacgaga gcgtgctgat ggtgtccatc       60
gaccagctgc tggacagcat gaaggagatc ggctccaact gcctcaacaa cgagttcaac      120
ttcttcaagc ggcacatctg cgacgccaac aaggagggca tgttcctgtt cagggccgcc      180
aggaaactgc ggcagttcct gaagatgaac tccaccggcg acttcgacct gcacctgctg      240
aaggtgtccg agggcaccac catcctgctg aactgcaccg acaggtgaa gggccggaaa      300 cctgctgctc tgggagaggc ccaacccacc aagagcctgg aggagaacaa gtccctgaag      360
gagcagaaga agctgaacga cctgtgcttc ctgaagaggc tgctgcagga gatcaagacc      420
tgctggaaca agatcctgat gggcaccaag gagcatagcg gcacaaccaa cacagtcgct      480
gcctataacc tcacttggaa gagcaccaac ttcaaaacca tcctcgaatg gaacccaaaa      540
cccgttaacc aagtttacac cgtgcagatc agcaccaagt ccggcgactg aagtccaaa      600 tgtttctata ccaccgacac cgagtgcgat ctcaccgatg agatcgtgaa agatgtgaaa      660
cagacctacc tcgcccgggt gtttagctac cccgccggca atgtggagag cactggttcc      720
gctggcgagc ctttatacga gaacagcccc gaatttaccc cttacctcga gaccaattta      780
ggacagccca ccatccaaag cttttgagcaa gttggcacaa aggtgaatgt gacagtggag      840
gacgagcgga ctttagtgcg gcggaacaac acctttctca gcctccggga tgtgttcggc      900
aaagatttaa tctacacact gtattactgg aagtcctctt cctccggcaa gaagacagct      960
aaaaccaaca caaacgagtt tttaatcgac gtggataaag cgaaaacta ctgttttcagc     1020 gtgcaagctg tgatcccctc ccggaccgtg aataggaaaa gcaccgatag ccccgttgag     1080
tgcatgggcc aagaaaaggg cgagttccgg gagaactggg tgaacgtcat cagcgattta     1140
aagaagatcg aagatttaat tcagtccatg catatcgacg ccactttata cacagaatcc     1200
gacgtgcacc cctcttgtaa ggtgaccgcc atgaaatgtt ttttactgga gctgcaagtt     1260 atctcttttag agagcggaga cgctagcatc cacgacaccg tggagaattt aatcatttta     1320
gccaataact ctttatccag caacggcaac gtgacagagt ccggctgcaa ggagtgcgaa     1380
gagctggagg agaagaacat caaggagttt ctgcaatcct tgtgcacat tgtccagatg     1440 ttcatcaata cctcc                                                      1455

-continued

```
<210> SEQ ID NO 106
<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-21s sequence"

<400> SEQUENCE: 106

Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
            100                 105                 110

Gln Val Lys Gly Arg Lys Pro Ala Ala Leu Gly Glu Ala Gln Pro Thr
        115                 120                 125

Lys Ser Leu Glu Glu Asn Lys Ser Leu Lys Glu Gln Lys Lys Leu Asn
    130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ser Gly Thr Thr Asn Thr
                165                 170                 175

Val Ala Ala Tyr Asn Leu Thr Trp Lys Ser Thr Asn Phe Lys Thr Ile
            180                 185                 190

Leu Glu Trp Glu Pro Lys Pro Val Asn Gln Val Tyr Thr Val Gln Ile
        195                 200                 205

Ser Thr Lys Ser Gly Asp Trp Lys Ser Lys Cys Phe Tyr Thr Thr Asp
    210                 215                 220

Thr Glu Cys Asp Leu Thr Asp Glu Ile Val Lys Asp Val Lys Gln Thr
225                 230                 235                 240

Tyr Leu Ala Arg Val Phe Ser Tyr Pro Ala Gly Asn Val Glu Ser Thr
                245                 250                 255

Gly Ser Ala Gly Glu Pro Leu Tyr Glu Asn Ser Pro Glu Phe Thr Pro
            260                 265                 270

Tyr Leu Glu Thr Asn Leu Gly Gln Pro Thr Ile Gln Ser Phe Glu Gln
        275                 280                 285

Val Gly Thr Lys Val Asn Val Thr Val Glu Asp Glu Arg Thr Leu Val
    290                 295                 300

Arg Arg Asn Asn Thr Phe Leu Ser Leu Arg Asp Val Phe Gly Lys Asp
305                 310                 315                 320

Leu Ile Tyr Thr Leu Tyr Tyr Trp Lys Ser Ser Ser Gly Lys Lys
                325                 330                 335

Thr Ala Lys Thr Asn Thr Asn Glu Phe Leu Ile Asp Val Asp Lys Gly
            340                 345                 350

Glu Asn Tyr Cys Phe Ser Val Gln Ala Val Ile Pro Ser Arg Thr Val
        355                 360                 365
```

Asn Arg Lys Ser Thr Asp Ser Pro Val Glu Cys Met Gly Gln Glu Lys
    370                 375                 380

Gly Glu Phe Arg Glu Asn Trp Val Asn Val Ile Ser Asp Leu Lys Lys
385                 390                 395                 400

Ile Glu Asp Leu Ile Gln Ser Met His Ile Asp Ala Thr Leu Tyr Thr
                405                 410                 415

Glu Ser Asp Val His Pro Ser Cys Lys Val Thr Ala Met Lys Cys Phe
                420                 425                 430

Leu Leu Glu Leu Gln Val Ile Ser Leu Glu Ser Gly Asp Ala Ser Ile
            435                 440                 445

His Asp Thr Val Glu Asn Leu Ile Ile Leu Ala Asn Asn Ser Leu Ser
    450                 455                 460

Ser Asn Gly Asn Val Thr Glu Ser Gly Cys Lys Glu Cys Glu Glu Leu
465                 470                 475                 480

Glu Glu Lys Asn Ile Lys Glu Phe Leu Gln Ser Phe Val His Ile Val
                485                 490                 495

Gln Met Phe Ile Asn Thr Ser
            500

<210> SEQ ID NO 107
<211> LENGTH: 1508
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-21s sequence"

<400> SEQUENCE: 107

| | | | | | |
|---|---|---|---|---|---|
| atgaagtggg | tgaccttcat | cagcctgctg | ttcctgttct | ccagcgccta | ctccgattgc | 60 |
| gacatcgagg | gcaaggacgg | caagcagtac | gagagcgtgc | tgatggtgtc | catcgaccag | 120 |
| ctgctggaca | gcatgaagga | gatcggctcc | aactgcctca | caacgagtt | caacttcttc | 180 |
| aagcggcaca | tctgcgacgc | caacaaggag | ggcatgttcc | tgttcagggc | cgccaggaaa | 240 |
| ctgcggcagt | tcctgaagat | gaactccacc | ggcgacttcg | acctgcacct | gctgaaggtg | 300 |
| tccgagggca | ccaccatcct | gctgaactgc | accggacagg | tgaagggccg | gaaacctgct | 360 |
| gctctgggag | aggcccaacc | caccaagagc | tggaggaga | caagtccct | gaaggagcag | 420 |
| aagaagctga | cgacctgtg | cttcctgaag | aggctgctgc | aggagatcaa | gacctgctgg | 480 |
| aacaagatcc | tgatgggcac | caaggagcat | agcggcacaa | ccaacacagt | cgctgcctat | 540 |
| aacctcactt | ggaagagcac | caacttcaaa | accatcctcg | aatgggaacc | caaacccgtt | 600 |
| aaccaagttt | acaccgtgca | gatcagcacc | aagtccggcg | actggaagtc | caaatgtttc | 660 |
| tataccaccg | acaccgagtg | cgatctcacc | gatgagatcg | tgaaagatgt | gaaacagacc | 720 |
| tacctcgccc | gggtgtttag | ctaccccgcc | ggcaatgtgg | agagcactgg | ttccgctggc | 780 |
| gagcctttat | acgagaacag | ccccgaattt | accccttacc | tcgagaccaa | tttaggacag | 840 |
| cccaccatcc | aaagctttga | gcaagttggc | acaaggtga | atgtgacagt | ggaggacgag | 900 |
| cggactttag | tgcggcggaa | caacaccttt | ctcagcctcc | gggatgtgtt | cggcaaagat | 960 |
| ttaatctaca | cactgtatta | ctggaagtcc | tcttcctccg | gcaagaagac | agctaaaacc | 1020 |
| aacacaaacg | agttttaat | cgacgtggat | aaaggcgaaa | actactgttt | cagcgtgcaa | 1080 |
| gctgtgatcc | cctccggac | cgtgaatagg | aaaagcaccg | atagcccgt | tgagtgcatg | 1140 |
| ggccaagaaa | agggcgagtt | ccgggagaac | tgggtgaacg | tcatcagcga | tttaaagaag | 1200 |

```
atcgaagatt taattcagtc catgcatatc gacgccactt tatacacaga atccgacgtg    1260 caccccctctt gtaaggtgac cgccatgaaa tgttttttac tggagctgca agttatctct    1320
ttagagagcg gagacgctag catccacgac accgtggaga atttaatcat tttagccaat    1380
aactctttat ccagcaacgg caacgtgaca gagtccggct gcaaggagtg cgaagagctg    1440
gaggagaaga acatcaagga gtttctgcaa tcctttgtgc acattgtcca gatgttcatc    1500
aatacctc                                                              1508
```

<210> SEQ ID NO 108
<211> LENGTH: 198
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-21s sequence"

<400> SEQUENCE: 108

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ile Thr Cys Pro Pro Met Ser Val Glu His
    130                 135                 140

Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

Glu Cys Val Leu Asn Lys Ala Thr Asn Val Ala His Trp Thr Thr Pro
            180                 185                 190

Ser Leu Lys Cys Ile Arg
        195
```

<210> SEQ ID NO 109
<211> LENGTH: 594
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-21s sequence"

<400> SEQUENCE: 109

```
cagggccagg acaggcacat gatccggatg aggcagctca tcgacatcgt cgaccagctg     60
aagaactacg tgaacgacct ggtgcccgag tttctgcctg cccccgagga cgtggagacc    120
```

```
aactgcgagt ggtccgcctt ctcctgcttt cagaaggccc agctgaagtc cgccaacacc      180
ggcaacaacg agcggatcat caacgtgagc atcaagaagc tgaagcggaa gcctccctcc      240
acaaacgccg gcaggaggca gaagcacagg ctgacctgcc ccagctgtga ctcctacgag      300
aagaagcccc ccaaggagtt cctggagagg ttcaagtccc tgctgcagaa gatgatccat      360
cagcacctgt cctccaggac ccacggctcc gaggactcca ttacatgccc ccctcccatg      420
agcgtggagc acgccgacat ctgggtgaag agctatagcc tctacagccg ggagaggtat      480
atctgtaaca gcggcttcaa gaggaaggcc ggcaccagca gcctcaccga gtgcgtgctg      540
aataaggcta ccaacgtggc tcactggaca cacccctctt taaagtgcat ccgg            594
```

<210> SEQ ID NO 110
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic 7t15-21s sequence"

<400> SEQUENCE: 110

```
Met Lys Trp Val Thr Phe Ile Ser Leu Leu Phe Leu Phe Ser Ser Ala
1               5                  10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr
        195                 200                 205

Thr Pro Ser Leu Lys Cys Ile Arg
    210                 215
```

<210> SEQ ID NO 111
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic 7t15-21s sequence"

<400> SEQUENCE: 111

```
atgaagtggg tgaccttcat cagcctgctg ttcctgttct ccagcgccta ctcccagggc    60
caggacaggc acatgatccg gatgaggcag ctcatcgaca tcgtcgacca gctgaagaac   120
tacgtgaacg acctggtgcc cgagtttctg cctgccccg aggacgtgga gaccaactgc   180
gagtggtccg ccttctcctg ctttcagaag gcccagctga agtccgccaa caccggcaac   240
aacgagcgga tcatcaacgt gagcatcaag aagctgaagc ggaagcctcc ctccacaaac   300
gccggcagga ggcagaagca caggctgacc tgccccagct gtgactccta cgagaagaag   360
ccccccaagg agttcctgga gaggttcaag tccctgctgc agaagatgat ccatcagcac   420
ctgtcctcca ggacccacgg ctccgaggac tccattacat gccccctcc catgagcgtg   480
gagcacgccg acatctgggt gaagagctat agcctctaca gccgggagag gtatatctgt   540
aacagcggct tcaagaggaa ggccggcacc agcagcctca ccgagtgcgt gctgaataag   600
gctaccaacg tggctcactg gacaacaccc tctttaaagt gcatccgg               648
```

<210> SEQ ID NO 112
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic CD16 LC sequence"

<400> SEQUENCE: 112

```
Ser Glu Leu Thr Gln Asp Pro Ala Val Ser Val Ala Leu Gly Gln Thr
1               5                   10                  15
Val Arg Ile Thr Cys Gln Gly Asp Ser Leu Arg Ser Tyr Tyr Ala Ser
            20                  25                  30
Trp Tyr Gln Gln Lys Pro Gly Gln Ala Pro Val Leu Val Ile Tyr Gly
        35                  40                  45
Lys Asn Asn Arg Pro Ser Gly Ile Pro Asp Arg Phe Ser Gly Ser Ser
    50                  55                  60
Ser Gly Asn Thr Ala Ser Leu Thr Ile Thr Gly Ala Gln Ala Glu Asp
65                  70                  75                  80
Glu Ala Asp Tyr Tyr Cys Asn Ser Arg Asp Ser Ser Gly Asn His Val
                85                  90                  95
Val Phe Gly Gly Gly Thr Lys Leu Thr Val Gly His
            100                 105
```

<210> SEQ ID NO 113
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic CD16 LC sequence"

<400> SEQUENCE: 113

```
tccgagctga cccaggaccc tgctgtgtcc gtggctctgg gccagaccgt gaggatcacc    60
tgccagggcg actccctgag gtcctactac gcctcctggt accagcagaa gcccggccag   120
gctcctgtgc tggtgatcta cggcaagaac aacaggccct ccggcatccc tgacaggttc   180
tccggatcct cctccggcaa caccgcctcc ctgaccatca caggcgctca ggccgaggac   240
```

```
gaggctgact actactgcaa ctccagggac tcctccggca accatgtggt gttcggcggc    300
ggcaccaagc tgaccgtggg ccat                                           324
```

<210> SEQ ID NO 114
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic CD16 HC sequence"

<400> SEQUENCE: 114

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Leu Leu Phe Asp Tyr Trp Gly Gln Gly Thr Leu
            100                 105                 110

Val Thr Val Ser Arg
        115
```

<210> SEQ ID NO 115
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic CD16 HC sequence"

<400> SEQUENCE: 115

```
gaggtgcagc tggtggagtc cggaggagga gtggtgaggc ctggaggctc cctgaggctg    60
agctgtgctg cctccggctt caccttcgac gactacggca tgtcctgggt gaggcaggct   120
cctggaaagg gcctggagtg ggtgtccggc atcaactgga cggcggatc caccggctac   180 gccgattccg tgaagggcag gttcaccatc agcagggaca cgccaagaa ctccctgtac   240 ctgcagatga actccctgag ggccgaggac accgccgtgt actactgcgc caggggcagg   300
tccctgctgt tcgactactg gggacagggc accctggtga ccgtgtccag g            351
```

<210> SEQ ID NO 116
<211> LENGTH: 490
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 18t15-12s16 sequence"

<400> SEQUENCE: 116

```
Tyr Phe Gly Lys Leu Glu Ser Lys Leu Ser Val Ile Arg Asn Leu Asn
1               5                   10                  15
```

-continued

Asp Gln Val Leu Phe Ile Asp Gln Gly Asn Arg Pro Leu Phe Glu Asp
             20                  25                  30

Met Thr Asp Ser Asp Cys Arg Asp Asn Ala Pro Arg Thr Ile Phe Ile
         35                  40                  45

Ile Ser Met Tyr Lys Asp Ser Gln Pro Arg Gly Met Ala Val Thr Ile
     50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp Ser Gly Thr
145                 150                 155                 160

Thr Asn Thr Val Ala Ala Tyr Asn Leu Thr Trp Lys Ser Thr Asn Phe
                165                 170                 175

Lys Thr Ile Leu Glu Trp Glu Pro Lys Pro Val Asn Gln Val Tyr Thr
            180                 185                 190

Val Gln Ile Ser Thr Lys Ser Gly Asp Trp Lys Ser Lys Cys Phe Tyr
        195                 200                 205

Thr Thr Asp Thr Glu Cys Asp Leu Thr Asp Glu Ile Val Lys Asp Val
    210                 215                 220

Lys Gln Thr Tyr Leu Ala Arg Val Phe Ser Tyr Pro Ala Gly Asn Val
225                 230                 235                 240

Glu Ser Thr Gly Ser Ala Gly Glu Pro Leu Tyr Glu Asn Ser Pro Glu
                245                 250                 255

Phe Thr Pro Tyr Leu Glu Thr Asn Leu Gly Gln Pro Thr Ile Gln Ser
            260                 265                 270

Phe Glu Gln Val Gly Thr Lys Val Asn Val Thr Val Glu Asp Glu Arg
        275                 280                 285

Thr Leu Val Arg Arg Asn Asn Thr Phe Leu Ser Leu Arg Asp Val Phe
    290                 295                 300

Gly Lys Asp Leu Ile Tyr Thr Leu Tyr Tyr Trp Lys Ser Ser Ser Ser
305                 310                 315                 320

Gly Lys Lys Thr Ala Lys Thr Asn Thr Asn Glu Phe Leu Ile Asp Val
                325                 330                 335

Asp Lys Gly Glu Asn Tyr Cys Phe Ser Val Gln Ala Val Ile Pro Ser
            340                 345                 350

Arg Thr Val Asn Arg Lys Ser Thr Asp Ser Pro Val Glu Cys Met Gly
        355                 360                 365

Gln Glu Lys Gly Glu Phe Arg Glu Asn Trp Val Asn Val Ile Ser Asp
    370                 375                 380

Leu Lys Lys Ile Glu Asp Leu Ile Gln Ser Met His Ile Asp Ala Thr
385                 390                 395                 400

Leu Tyr Thr Glu Ser Asp Val His Pro Ser Cys Lys Val Thr Ala Met
                405                 410                 415

Lys Cys Phe Leu Leu Glu Leu Gln Val Ile Ser Leu Glu Ser Gly Asp
            420                 425                 430

Ala Ser Ile His Asp Thr Val Glu Asn Leu Ile Ile Leu Ala Asn Asn

```
            435                 440                 445
Ser Leu Ser Ser Asn Gly Asn Val Thr Glu Ser Gly Cys Lys Glu Cys
    450                 455                 460

Glu Glu Leu Glu Glu Lys Asn Ile Lys Glu Phe Leu Gln Ser Phe Val
465                 470                 475                 480

His Ile Val Gln Met Phe Ile Asn Thr Ser
                485                 490

<210> SEQ ID NO 117
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 18t15-12s16 sequence"

<400> SEQUENCE: 117
tacttcggca aactggaatc caagctgagc gtgatccgga atttaaacga ccaagttctg      60
tttatcgatc aaggtaaccg gcctctgttc gaggacatga ccgactccga ttgccgggac     120 aatgccccccc ggaccatctt cattatctcc atgtacaagg acagccagcc ccggggcatg    180
gctgtgacaa ttagcgtgaa gtgtgagaaa atcagcactt tatcttgtga gaacaagatc     240
atctccttta aggaaatgaa cccccccgat aacatcaagg acaccaagtc cgatatcatc     300
ttcttccagc ggtccgtgcc cggtcacgat aacaagatgc agttcgaatc ctcctcctac     360
gagggctact ttttagcttg tgaaaaggag agggatttat tcaagctgat cctcaagaag    420
gaggacgagc tgggcgatcg ttccatcatg ttcaccgtcc aaaacgagga tagcggcaca    480
accaacacag tcgctgccta aacctcact tggaagagca ccaacttcaa aaccatcctc     540
gaatgggaac ccaaacccgt taaccaagtt tacaccgtgc agatcagcac caagtccggc    600
gactggaagt ccaaatgttt ctataccacc gacaccgagt gcgatctcac cgatgagatc    660
gtgaaagatg tgaaacagac ctacctcgcc cgggtgttta gctaccccgc cggcaatgtg   720
gagagcactg gttccgctgg cgagccttta tacgagaaca gccccgaatt taccccttac    780
ctcgagacca atttaggaca gcccaccatc caaagctttg agcaagttgg cacaaaggtg    840
aatgtgacag tggaggacga gcggacttta gtgcggcgga acaacacctt tctcagcctc    900
cgggatgtgt tcggcaaaga tttaatctac acactgtatt actggaagtc ctcttcctcc    960
ggcaagaaga cagctaaaac caacacaaac gagtttttaa tcgacgtgga taaaggcgaa   1020
aactactgtt tcagcgtgca agctgtgatc ccctcccgga ccgtgaatag gaaaagcacc   1080
gatagccccg ttgagtgcat gggccaagaa aagggcgagt tccgggagaa ctgggtgaac   1140
gtcatcagcg atttaaagaa gatcgaagat ttaattcagt ccatgcatat cgacgccact   1200
ttatacacag aatccgacgt gcaccctct tgtaaggtga ccgccatgaa atgtttttta     1260
ctggagctgc aagttatctc tttagagagc ggagacgcta gcatccacga caccgtggag   1320
aatttaatca tttttagccaa taactctta tccagcaacg gcaacgtgac agagtccggc   1380
tgcaaggagt gcgaagagct ggaggagaag aacatcaagg agtttctgca atcctttgtg   1440
cacattgtcc agatgttcat caatacctcc                                    1470

<210> SEQ ID NO 118
<211> LENGTH: 508
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic 18t15-12s16 sequence"

<400> SEQUENCE: 118
```

| | | | | | | | | | | | | | | | |
|---|---|---|---|---|---|---|---|---|---|---|---|---|---|---|---|
| Met | Lys | Trp | Val | Thr | Phe | Ile | Ser | Leu | Leu | Phe | Leu | Phe | Ser | Ser | Ala |
| 1 | | | | 5 | | | | | 10 | | | | | 15 | |
| Tyr | Ser | Tyr | Phe | Gly | Lys | Leu | Glu | Ser | Lys | Leu | Ser | Val | Ile | Arg | Asn |
| | | | 20 | | | | | 25 | | | | | 30 | | |
| Leu | Asn | Asp | Gln | Val | Leu | Phe | Ile | Asp | Gln | Gly | Asn | Arg | Pro | Leu | Phe |
| | | 35 | | | | | 40 | | | | | 45 | | | |
| Glu | Asp | Met | Thr | Asp | Ser | Asp | Cys | Arg | Asp | Asn | Ala | Pro | Arg | Thr | Ile |
| 50 | | | | | 55 | | | | | 60 | | | | | |
| Phe | Ile | Ile | Ser | Met | Tyr | Lys | Asp | Ser | Gln | Pro | Arg | Gly | Met | Ala | Val |
| 65 | | | | | 70 | | | | | 75 | | | | | 80 |
| Thr | Ile | Ser | Val | Lys | Cys | Glu | Lys | Ile | Ser | Thr | Leu | Ser | Cys | Glu | Asn |
| | | | | 85 | | | | | 90 | | | | | 95 | |
| Lys | Ile | Ile | Ser | Phe | Lys | Glu | Met | Asn | Pro | Pro | Asp | Asn | Ile | Lys | Asp |
| | | | 100 | | | | | 105 | | | | | 110 | | |
| Thr | Lys | Ser | Asp | Ile | Ile | Phe | Phe | Gln | Arg | Ser | Val | Pro | Gly | His | Asp |
| | | 115 | | | | | 120 | | | | | 125 | | | |
| Asn | Lys | Met | Gln | Phe | Glu | Ser | Ser | Ser | Tyr | Glu | Gly | Tyr | Phe | Leu | Ala |
| 130 | | | | | 135 | | | | | 140 | | | | | |
| Cys | Glu | Lys | Glu | Arg | Asp | Leu | Phe | Lys | Leu | Ile | Leu | Lys | Lys | Glu | Asp |
| 145 | | | | | 150 | | | | | 155 | | | | | 160 |
| Glu | Leu | Gly | Asp | Arg | Ser | Ile | Met | Phe | Thr | Val | Gln | Asn | Glu | Asp | Ser |
| | | | | 165 | | | | | 170 | | | | | 175 | |
| Gly | Thr | Thr | Asn | Thr | Val | Ala | Ala | Tyr | Asn | Leu | Thr | Trp | Lys | Ser | Thr |
| | | | 180 | | | | | 185 | | | | | 190 | | |
| Asn | Phe | Lys | Thr | Ile | Leu | Glu | Trp | Glu | Pro | Lys | Pro | Val | Asn | Gln | Val |
| | | 195 | | | | | 200 | | | | | 205 | | | |
| Tyr | Thr | Val | Gln | Ile | Ser | Thr | Lys | Ser | Gly | Asp | Trp | Lys | Ser | Lys | Cys |
| 210 | | | | | 215 | | | | | 220 | | | | | |
| Phe | Tyr | Thr | Thr | Asp | Thr | Glu | Cys | Asp | Leu | Thr | Asp | Glu | Ile | Val | Lys |
| 225 | | | | | 230 | | | | | 235 | | | | | 240 |
| Asp | Val | Lys | Gln | Thr | Tyr | Leu | Ala | Arg | Val | Phe | Ser | Tyr | Pro | Ala | Gly |
| | | | | 245 | | | | | 250 | | | | | 255 | |
| Asn | Val | Glu | Ser | Thr | Gly | Ser | Ala | Gly | Glu | Pro | Leu | Tyr | Glu | Asn | Ser |
| | | | 260 | | | | | 265 | | | | | 270 | | |
| Pro | Glu | Phe | Thr | Pro | Tyr | Leu | Glu | Thr | Asn | Leu | Gly | Gln | Pro | Thr | Ile |
| | | 275 | | | | | 280 | | | | | 285 | | | |
| Gln | Ser | Phe | Glu | Gln | Val | Gly | Thr | Lys | Val | Asn | Val | Thr | Val | Glu | Asp |
| 290 | | | | | 295 | | | | | 300 | | | | | |
| Glu | Arg | Thr | Leu | Val | Arg | Arg | Asn | Asn | Thr | Phe | Leu | Ser | Leu | Arg | Asp |
| 305 | | | | | 310 | | | | | 315 | | | | | 320 |
| Val | Phe | Gly | Lys | Asp | Leu | Ile | Tyr | Thr | Leu | Tyr | Tyr | Trp | Lys | Ser | Ser |
| | | | | 325 | | | | | 330 | | | | | 335 | |
| Ser | Ser | Gly | Lys | Lys | Thr | Ala | Lys | Thr | Asn | Thr | Asn | Glu | Phe | Leu | Ile |
| | | | 340 | | | | | 345 | | | | | 350 | | |
| Asp | Val | Asp | Lys | Gly | Glu | Asn | Tyr | Cys | Phe | Ser | Val | Gln | Ala | Val | Ile |
| | | 355 | | | | | 360 | | | | | 365 | | | |
| Pro | Ser | Arg | Thr | Val | Asn | Arg | Lys | Ser | Thr | Asp | Ser | Pro | Val | Glu | Cys |
| 370 | | | | | 375 | | | | | 380 | | | | | |
| Met | Gly | Gln | Glu | Lys | Gly | Glu | Phe | Arg | Glu | Asn | Trp | Val | Asn | Val | Ile |

```
                385                 390                 395                 400
Ser Asp Leu Lys Lys Ile Glu Asp Leu Ile Gln Ser Met His Ile Asp
                405                 410                 415

Ala Thr Leu Tyr Thr Glu Ser Asp Val His Pro Ser Cys Lys Val Thr
            420                 425                 430

Ala Met Lys Cys Phe Leu Leu Glu Leu Gln Val Ile Ser Leu Glu Ser
        435                 440                 445

Gly Asp Ala Ser Ile His Asp Thr Val Glu Asn Leu Ile Ile Leu Ala
    450                 455                 460

Asn Asn Ser Leu Ser Ser Asn Gly Asn Val Thr Glu Ser Gly Cys Lys
465                 470                 475                 480

Glu Cys Glu Glu Leu Glu Glu Lys Asn Ile Lys Glu Phe Leu Gln Ser
                485                 490                 495

Phe Val His Ile Val Gln Met Phe Ile Asn Thr Ser
                500                 505
```

<210> SEQ ID NO 119
<211> LENGTH: 1524
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 18t15-12s16 sequence"

<400> SEQUENCE: 119

```
atgaagtggg tcacatttat ctctttactg ttcctcttct ccagcgccta cagctacttc      60
ggcaaactgg aatccaagct gagcgtgatc cggaatttaa acgaccaagt tctgtttatc     120
gatcaaggta accggcctct gttcgaggac atgaccgact ccgattgccg ggacaatgcc     180
ccccggacca tcttcattat ctccatgtac aaggacagcc agccccgggg catggctgtg     240
acaattagcg tgaagtgtga aaaatcagc actttatctt gtgagaacaa gatcatctcc     300
tttaaggaaa tgaaccccccc cgataacatc aaggacacca gtccgatat catcttcttc     360 cagcggtccg tgcccggtca cgataacaag atgcagttcg aatcctcctc ctacgagggc     420
tactttttag cttgtgaaaa ggagagggat ttattcaagc tgatcctcaa gaaggaggac     480
gagctgggcg atcgttccat catgttcacc gtccaaaacg aggatagcgg cacaaccaac     540
acagtcgctg cctataacct cacttggaag agcaccaact tcaaaaccat cctcgaatgg     600
gaacccaaac ccgttaacca agtttacacc gtgcagatca gcaccaagtc cggcgactgg     660
aagtccaaat gtttctatac caccgacacc gagtgcgatc tcaccgatga gatcgtgaaa     720
gatgtgaaac agacctacct cgcccgggtg tttagctacc ccgccggcaa tgtggagagc     780
actggttccg ctggcgagcc tttatacgag aacagcccg aatttacccc ttacctcgag     840
accaatttag acagcccac catccaaagc tttgagcaag ttggcacaaa ggtgaatgtg     900
acagtggagg acgagcggac tttagtgcgg cggaacaaca cctttctcag cctccgggat     960
gtgttcggca agatttaat ctacacactg tattactgga agtcctcttc ctccggcaag    1020
aagacagcta aaccaacac aaacgagttt ttaatcgacg tggataaagg cgaaaactac    1080
tgtttcagcg tgcaagctgt gatccctcc cggaccgtga ataggaaaag caccgatagc    1140
cccgttgagt gcatgggcca agaaaagggc gagttccggg agaactgggt gaacgtcatc    1200
agcgatttaa agaagatcga agatttaatt cagtccatgc atatcgacgc cacttttatac    1260 acagaatccg acgtgcaccc ctcttgtaag gtgaccgcca tgaaatgttt tttactggag    1320
```

```
ctgcaagtta tctctttaga gagcggagac gctagcatcc acgacaccgt ggagaattta   1380
atcattttag ccaataactc tttatccagc aacggcaacg tgacagagtc cggctgcaag   1440
gagtgcgaag agctggagga gaagaacatc aaggagtttc tgcaatcctt tgtgcacatt   1500
gtccagatgt tcatcaatac ctcc                                          1524
```

<210> SEQ ID NO 120
<211> LENGTH: 823
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 18t15-12s16 sequence"

<400> SEQUENCE: 120

```
Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320
```

```
Ser Arg Asn Leu Pro Val Ala Thr Pro Asp Pro Gly Met Phe Pro Cys
            325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
            355                 360                 365

Asp His Glu Asp Ile Thr Lys Asp Lys Thr Ser Thr Val Glu Ala Cys
            370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
                420                 425                 430

Tyr Gln Val Glu Phe Lys Thr Met Asn Ala Lys Leu Leu Met Asp Pro
                435                 440                 445

Lys Arg Gln Ile Phe Leu Asp Gln Asn Met Leu Ala Val Ile Asp Glu
            450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
                500                 505                 510

Ser Tyr Leu Asn Ala Ser Ile Thr Cys Pro Pro Met Ser Val Glu
            515                 520                 525

His Ala Asp Ile Trp Val Lys Ser Tyr Ser Leu Tyr Ser Arg Glu Arg
            530                 535                 540

Tyr Ile Cys Asn Ser Gly Phe Lys Arg Lys Ala Gly Thr Ser Ser Leu
545                 550                 555                 560

Thr Glu Cys Val Leu Asn Lys Ala Thr Asn Val Ala His Trp Thr Thr
                565                 570                 575

Pro Ser Leu Lys Cys Ile Arg Ser Glu Leu Thr Gln Asp Pro Ala Val
                580                 585                 590

Ser Val Ala Leu Gly Gln Thr Val Arg Ile Thr Cys Gln Gly Asp Ser
            595                 600                 605

Leu Arg Ser Tyr Tyr Ala Ser Trp Tyr Gln Gln Lys Pro Gly Gln Ala
            610                 615                 620

Pro Val Leu Val Ile Tyr Gly Lys Asn Asn Arg Pro Ser Gly Ile Pro
625                 630                 635                 640

Asp Arg Phe Ser Gly Ser Ser Gly Asn Thr Ala Ser Leu Thr Ile
                645                 650                 655

Thr Gly Ala Gln Ala Glu Asp Glu Ala Asp Tyr Tyr Cys Asn Ser Arg
                660                 665                 670

Asp Ser Ser Gly Asn His Val Val Phe Gly Gly Gly Thr Lys Leu Thr
            675                 680                 685

Val Gly His Gly Gly Gly Gly Ser Gly Gly Gly Ser Gly Gly Gly
            690                 695                 700

Gly Ser Glu Val Gln Leu Val Glu Ser Gly Gly Val Val Arg Pro
705                 710                 715                 720

Gly Gly Ser Leu Arg Leu Ser Cys Ala Ala Ser Gly Phe Thr Phe Asp
                725                 730                 735
```

```
Asp Tyr Gly Met Ser Trp Val Arg Gln Ala Pro Gly Lys Gly Leu Glu
            740                 745                 750

Trp Val Ser Gly Ile Asn Trp Asn Gly Gly Ser Thr Gly Tyr Ala Asp
        755                 760                 765

Ser Val Lys Gly Arg Phe Thr Ile Ser Arg Asp Asn Ala Lys Asn Ser
    770                 775                 780

Leu Tyr Leu Gln Met Asn Ser Leu Arg Ala Glu Asp Thr Ala Val Tyr
785                 790                 795                 800

Tyr Cys Ala Arg Gly Arg Ser Leu Leu Phe Asp Tyr Trp Gly Gln Gly
                805                 810                 815

Thr Leu Val Thr Val Ser Arg
            820

<210> SEQ ID NO 121
<211> LENGTH: 2469
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 18t15-12s16 sequence"

<400> SEQUENCE: 121
atttgggaac tgaagaagga cgtctacgtg gtcgaactgg actggtatcc cgatgctccc      60
ggcgaaatgg tggtgctcac ttgtgacacc cccgaagaag acggcatcac ttggaccctc     120
gatcagagca gcgaggtgct gggctccgga agaccctcaa caatccaagt taaggagttc     180
ggagacgctg ccaatacac atgccacaag ggaggcgagg tgctcagcca ttccttatta      240
ttattacaca agaaggaaga cggaatctgg tccaccgaca ttttaaaaga tcagaaggag     300
cccaagaata agaccttttt aaggtgtgag gccaaaaact acagcggtcg tttcacttgt     360
tggtggctga ccaccatttc caccgattta accttctccg tgaaaagcag ccggggaagc     420
tccgaccctc aaggtgtgac atgtggagcc gctaccctca gcgctgagag ggttcgtggc     480
gataacaagg aatacgagta cagcgtggag tgccaagaag atagcgcttg tcccgctgcc     540
gaagaatctt tacccattga ggtgatggtg gacgccgtgc acaaactcaa gtacgagaac     600
tacacctcct ccttctttat ccgggacatc attaagcccg atcctcctaa gaatttacag     660
ctgaagcctc tcaaaaatag ccggcaagtt gaggtctctt gggaatatcc cgacacttgg     720
agcacacccc acagctactt ctctttaacc ttttgtgtgc aagttcaagg taaaagcaag     780
cgggagaaga aagaccgggt gtttaccgac aaaaccagcg ccaccgtcat ctgtcggaag     840
aacgcctcca tcagcgtgag ggctcaagat cgttattact ccagcagctg gtccgagtgg     900
gccagcgtgc cttgttccgg cggtggagga tccggaggag gtggctccgg cggcggagga     960
tctcgtaacc tccccgtggc tacccccgat cccggaatgt tcccttgttt acaccacagc    1020
cagaatttac tgagggccgt gagcaacatg ctgcagaaag ctaggcagac tttagaattt    1080
tacccttgca ccagcgagga gatcgaccat gaagatatca ccaaggacaa gacatccacc    1140
gtggaggctt gtttacctct ggagctgaca agaacgagt cttgtctcaa ctctcgtgaa    1200
accagcttca tcacaaatgg ctcttgttta gcttcccgga agacctcctt tatgatggct    1260
ttatgcctca gctccatcta cgaggattta aagatgtacc aagtggagtt caagaccatg    1320
aacgccaagc tgctcatgga ccctaaacgg cagatctttt tagaccagaa catgctggct    1380
gtgattgatg agctgatgca agcttttaaac ttcaactccg agaccgtccc tcagaagtcc    1440
tccctcgagg agcccgattt ttacaagaca aagatcaaac tgtgcatttt actccacgcc    1500
```

```
tttaggatcc gggccgtgac cattgaccgg gtcatgagct atttaaacgc cagcattaca    1560
tgcccccctc ccatgagcgt ggagcacgcc gacatctggg tgaagagcta tagcctctac    1620
agccgggaga ggtatatctg taacagcggc ttcaagagga aggccggcac cagcagcctc    1680
accgagtgcg tgctgaataa ggctaccaac gtggctcact ggacaacacc ctctttaaag    1740
tgcatccggt ccgagctgac ccaggaccct gctgtgtccg tggctctggg ccagaccgtg    1800
aggatcaccc tgccagggcga ctccctgagg tcctactacg cctcctggta ccagcagaag    1860
cccggccagg ctcctgtgct ggtgatctac ggcaagaaca acaggccctc cggcatccct    1920
gacaggttct ccgatcctc ctccggcaac accgcctccc tgaccatcac aggcgctcag    1980
gccgaggacg aggctgacta ctactgcaac tccagggact cctccggcaa ccatgtggtg    2040
ttcggcggcg gcaccaagct gaccgtgggc catggcggcg cggctccgg aggcggcggc    2100 agcggcggag gaggatccga ggtgcagctg gtggagtccg aggaggagt ggtgaggcct    2160 ggaggctccc tgaggctgag ctgtgctgcc tccggcttca ccttcgacga ctacggcatg    2220
tcctgggtga ggcaggctcc tggaaagggc ctggagtggg tgtccggcat caactggaac    2280
ggcggatcca ccggctacgc cgattccgtg aagggcaggt tcaccatcag cagggacaac    2340
gccaagaact ccctgtacct gcagatgaac tccctgaggg ccgaggacac cgccgtgtac    2400
tactgcgcca ggggcaggtc cctgctgttc gactactggg gacagggcac cctggtgacc    2460
gtgtccagg                                                            2469
```

<210> SEQ ID NO 122
<211> LENGTH: 841
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 18t15-12s16 sequence"

<400> SEQUENCE: 122

```
Met Lys Trp Val Thr Phe Ile Ser Leu Leu Phe Leu Phe Ser Ser Ala
1               5                   10                  15

Tyr Ser Ile Trp Glu Leu Lys Lys Asp Val Tyr Val Val Glu Leu Asp
                20                  25                  30

Trp Tyr Pro Asp Ala Pro Gly Glu Met Val Val Leu Thr Cys Asp Thr
            35                  40                  45

Pro Glu Glu Asp Gly Ile Thr Trp Thr Leu Asp Gln Ser Ser Glu Val
        50                  55                  60

Leu Gly Ser Gly Lys Thr Leu Thr Ile Gln Val Lys Glu Phe Gly Asp
65                  70                  75                  80

Ala Gly Gln Tyr Thr Cys His Lys Gly Gly Glu Val Leu Ser His Ser
                85                  90                  95

Leu Leu Leu Leu His Lys Lys Glu Asp Gly Ile Trp Ser Thr Asp Ile
                100                 105                 110

Leu Lys Asp Gln Lys Glu Pro Lys Asn Lys Thr Phe Leu Arg Cys Glu
            115                 120                 125

Ala Lys Asn Tyr Ser Gly Arg Phe Thr Cys Trp Trp Leu Thr Thr Ile
        130                 135                 140

Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175
```

```
Arg Gly Asp Asn Lys Glu Tyr Glu Tyr Ser Val Glu Cys Gln Glu Asp
            180                 185                 190

Ser Ala Cys Pro Ala Ala Glu Glu Ser Leu Pro Ile Glu Val Met Val
        195                 200                 205

Asp Ala Val His Lys Leu Lys Tyr Glu Asn Tyr Thr Ser Ser Phe Phe
    210                 215                 220

Ile Arg Asp Ile Ile Lys Pro Asp Pro Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
        275                 280                 285

Lys Thr Ser Ala Thr Val Ile Cys Arg Lys Asn Ala Ser Ile Ser Val
    290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Ser Gly Gly Gly Ser Gly Gly
                325                 330                 335

Gly Gly Ser Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
            355                 360                 365

Leu Gln Lys Ala Arg Gln Thr Leu Glu Phe Tyr Pro Cys Thr Ser Glu
        370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
        435                 440                 445

Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
        515                 520                 525

Val Met Ser Tyr Leu Asn Ala Ser Ile Thr Cys Pro Pro Met Ser
    530                 535                 540

Val Glu His Ala Asp Ile Trp Val Lys Ser Tyr Ser Leu Tyr Ser Arg
545                 550                 555                 560

Glu Arg Tyr Ile Cys Asn Ser Gly Phe Lys Arg Lys Ala Gly Thr Ser
                565                 570                 575

Ser Leu Thr Glu Cys Val Leu Asn Lys Ala Thr Asn Val Ala His Trp
            580                 585                 590
```

Thr Thr Pro Ser Leu Lys Cys Ile Arg Ser Glu Leu Thr Gln Asp Pro
            595                 600                 605

Ala Val Ser Val Ala Leu Gly Gln Thr Val Arg Ile Thr Cys Gln Gly
        610                 615                 620

Asp Ser Leu Arg Ser Tyr Tyr Ala Ser Trp Tyr Gln Gln Lys Pro Gly
625                 630                 635                 640

Gln Ala Pro Val Leu Val Ile Tyr Gly Lys Asn Asn Arg Pro Ser Gly
                645                 650                 655

Ile Pro Asp Arg Phe Ser Gly Ser Ser Ser Gly Asn Thr Ala Ser Leu
            660                 665                 670

Thr Ile Thr Gly Ala Gln Ala Glu Asp Glu Ala Asp Tyr Tyr Cys Asn
        675                 680                 685

Ser Arg Asp Ser Ser Gly Asn His Val Val Phe Gly Gly Gly Thr Lys
    690                 695                 700

Leu Thr Val Gly His Gly Gly Gly Ser Gly Gly Gly Ser Gly
705                 710                 715                 720

Gly Gly Gly Ser Glu Val Gln Leu Val Glu Ser Gly Gly Val Val
                725                 730                 735

Arg Pro Gly Gly Ser Leu Arg Leu Ser Cys Ala Ala Ser Gly Phe Thr
            740                 745                 750

Phe Asp Asp Tyr Gly Met Ser Trp Val Arg Gln Ala Pro Gly Lys Gly
        755                 760                 765

Leu Glu Trp Val Ser Gly Ile Asn Trp Asn Gly Gly Ser Thr Gly Tyr
    770                 775                 780

Ala Asp Ser Val Lys Gly Arg Phe Thr Ile Ser Arg Asp Asn Ala Lys
785                 790                 795                 800

Asn Ser Leu Tyr Leu Gln Met Asn Ser Leu Arg Ala Glu Asp Thr Ala
                805                 810                 815

Val Tyr Tyr Cys Ala Arg Gly Arg Ser Leu Leu Phe Asp Tyr Trp Gly
            820                 825                 830

Gln Gly Thr Leu Val Thr Val Ser Arg
        835                 840

<210> SEQ ID NO 123
<211> LENGTH: 2523
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 18t15-12s16 sequence"

<400> SEQUENCE: 123
atgaaatggg tgacctttat ttctttactg ttcctcttta gcagcgccta ctccatttgg      60
gaactgaaga aggacgtcta cgtggtcgaa ctggactggt atcccgatgc tcccggcgaa     120
atggtggtgc tcacttgtga cacccccgaa gaagacggca tcacttggac cctcgatcag     180
agcagcgagg tgctgggctc cggaaagacc ctcacaatcc aagttaagga gttcggagac     240
gctggccaat acacatgcca agggaggc gaggtgctca gccattcctt attattata         300 cacaagaagg aagacggaat ctggtccacc gacattttaa agatcagaa ggagcccaag      360 aataagacct ttttaaggtg tgaggccaaa aactacagcg tcgtttcac ttgttggtgg       420 ctgaccacca tttccaccga tttaaccttc tccgtgaaaa gcagccgggg aagctccgac     480
cctcaaggtg tgcatgtgg agccgctacc ctcagcgctg agggggttcg tggcgataac      540
aaggaatacg agtacagcgt ggagtgccaa gaagatagcg cttgtccgc tgccgaagaa      600

```
tctttaccca ttgaggtgat ggtggacgcc gtgcacaaac tcaagtacga gaactacacc    660
tcctccttct ttatccggga catcattaag cccgatcctc ctaagaattt acagctgaag    720
cctctcaaaa atagccggca agttgaggtc tcttgggaat atcccgacac ttggagcaca    780
ccccacagct acttctcttt aacctttgt gtgcaagttc aaggtaaaag caagcgggag     840
aagaaagacc gggtgtttac cgacaaaacc agcgccaccg tcatctgtcg gaagaacgcc    900
tccatcagcg tgagggctca agatcgttat tactccagca gctggtccga gtgggccagc    960
gtgccttgtt ccggcggtgg aggatccgga ggaggtggct ccggcggcgg aggatctcgt   1020
aacctccccg tggctacccc cgatcccgga atgttccctt gtttacacca cagccagaat   1080
ttactgaggg ccgtgagcaa catgctgcag aaagctaggc agactttaga attttaccct   1140
tgcaccagcg aggagatcga ccatgaagat atcaccaagg acaagacatc caccgtggag   1200
gcttgtttac ctctggagct gacaaagaac gagtcttgtc tcaactctcg tgaaaccagc   1260
ttcatcacaa atggctcttg tttagcttcc cggaagacct cctttatgat ggctttatgc   1320
ctcagctcca tctacgagga tttaaagatg taccaagtgg agttcaagac catgaacgcc   1380
aagctgctca tggaccctaa acggcagatc ttttagacc agaacatgct ggctgtgatt    1440
gatgagctga tgcaagcttt aaacttcaac tccgagaccg tccctcagaa gtcctccctc   1500
gaggagcccg attttacaa gacaaagatc aaactgtgca ttttactcca cgcctttagg    1560
atccgggccg tgaccattga ccgggtcatg agctatttaa acgccagcat acatgcccc    1620 cctcccatga gcgtggagca cgccgacatc tgggtgaaga gctatagcct ctacagccgg   1680
gagaggtata tctgtaacag cggcttcaag aggaaggccg gcaccagcag cctcaccgag   1740
tgcgtgctga ataaggctac caacgtggct cactggacaa cccctctctt aaagtgcatc   1800
cggtccgagc tgacccagga ccctgctgtg tccgtggctc tgggccagac cgtgaggatc   1860
acctgccagg gcgactccct gaggtcctac tacgcctcct ggtaccagca gaagcccggc   1920
caggctcctg tgctggtgat ctacggcaag aacaacaggc cctccggcat ccctgacagg   1980
ttctccggat cctcctccgg caacaccgcc tccctgacca tcacaggcgc tcaggccgag   2040
gacgaggctg actactactg caactccagg gactcctccg caaccatgt ggtgttcggc    2100 ggcggcacca agctgaccgt gggccatggc ggcggcggct ccggaggcgg cggcagcggc   2160
ggaggaggat ccgaggtgca gctggtggag tccggaggag gagtggtgag gcctggaggc   2220
tccctgaggc tgagctgtgc tgcctccggc ttcaccttcg acgactacgg catgtcctgg   2280
gtgaggcagg ctcctggaaa gggcctggag tgggtgtccg gcatcaactg aacggcgga   2340 tccaccggct acgccgattc cgtgaagggc aggttcacca tcagcaggga caacgccaag   2400
aactccctgt acctgcagat gaactccctg agggccgagg acaccgccgt gtactactgc   2460 gccagggca ggtccctgct gttcgactac tggggacagg gcaccctggt gaccgtgtcc    2520
agg                                                                  2523
```

<210> SEQ ID NO 124
<211> LENGTH: 456
<212> TYPE: DNA
<213> ORGANISM: Artificial Sequence
<220> FEATURE:
<221> NAME/KEY: source
<223> OTHER INFORMATION: /note="Description of Artificial Sequence: Synthetic IL-7 sequence"

<400> SEQUENCE: 124

```
gattgcgaca tcgagggcaa ggacggcaag cagtacgaga gcgtgctgat ggtgtccatc    60
gaccagctgc tggacagcat gaaggagatc ggctccaact gcctcaacaa cgagttcaac   120
ttcttcaagc ggcacatctg cgacgccaac aaggagggca tgttcctgtt cagggccgcc   180
aggaaactgc ggcagttcct gaagatgaac tccaccggcg acttcgacct gcacctgctg   240
aaggtgtccg agggcaccac catcctgctg aactgcaccg acaggtgaa gggccggaaa    300 cctgctgctc tgggagaggc ccaacccacc aagagcctgg aggagaacaa gtccctgaag   360
gagcagaaga agctgaacga cctgtgcttc ctgaagaggc tgctgcagga gatcaagacc   420
tgctggaaca agatcctgat gggcaccaag gagcat                              456
```

<210> SEQ ID NO 125
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-16s21 sequence"

<400> SEQUENCE: 125

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Ser Gly Thr Thr Asn Thr Val Ala
145                 150                 155                 160

Ala Tyr Asn Leu Thr Trp Lys Ser Thr Asn Phe Lys Thr Ile Leu Glu
                165                 170                 175

Trp Glu Pro Lys Pro Val Asn Gln Val Tyr Thr Val Gln Ile Ser Thr
            180                 185                 190

Lys Ser Gly Asp Trp Lys Ser Lys Cys Phe Tyr Thr Thr Asp Thr Glu
        195                 200                 205

Cys Asp Leu Thr Asp Glu Ile Val Lys Asp Val Lys Gln Thr Tyr Leu
    210                 215                 220

Ala Arg Val Phe Ser Tyr Pro Ala Gly Asn Val Glu Ser Thr Gly Ser
225                 230                 235                 240

Ala Gly Glu Pro Leu Tyr Glu Asn Ser Pro Glu Phe Thr Pro Tyr Leu
                245                 250                 255

Glu Thr Asn Leu Gly Gln Pro Thr Ile Gln Ser Phe Gly Gln Val Gly
            260                 265                 270
```

```
Thr Lys Val Asn Val Thr Val Glu Asp Glu Arg Thr Leu Val Arg Arg
            275                 280                 285

Asn Asn Thr Phe Leu Ser Leu Arg Asp Val Phe Gly Lys Asp Leu Ile
        290                 295                 300

Tyr Thr Leu Tyr Tyr Trp Lys Ser Ser Ser Gly Lys Lys Thr Ala
305                 310                 315                 320

Lys Thr Asn Thr Asn Glu Phe Leu Ile Asp Val Asp Lys Gly Glu Asn
                325                 330                 335

Tyr Cys Phe Ser Val Gln Ala Val Ile Pro Ser Arg Thr Val Asn Arg
            340                 345                 350

Lys Ser Thr Asp Ser Pro Val Glu Cys Met Gly Gln Glu Lys Gly Glu
        355                 360                 365

Phe Arg Glu Asn Trp Val Asn Val Ile Ser Asp Leu Lys Lys Ile Glu
370                 375                 380

Asp Leu Ile Gln Ser Met His Ile Asp Ala Thr Leu Tyr Thr Glu Ser
385                 390                 395                 400

Asp Val His Pro Ser Cys Lys Val Thr Ala Met Lys Cys Phe Leu Leu
                405                 410                 415

Glu Leu Gln Val Ile Ser Leu Glu Ser Gly Asp Ala Ser Ile His Asp
            420                 425                 430

Thr Val Glu Asn Leu Ile Ile Leu Ala Asn Asn Ser Leu Ser Ser Asn
        435                 440                 445

Gly Asn Val Thr Glu Ser Gly Cys Lys Glu Cys Glu Glu Leu Glu Glu
    450                 455                 460

Lys Asn Ile Lys Glu Phe Leu Gln Ser Phe Val His Ile Val Gln Met
465                 470                 475                 480

Phe Ile Asn Thr Ser
                485

<210> SEQ ID NO 126
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-16s21 sequence"

<400> SEQUENCE: 126
gattgcgaca tcgagggcaa ggacggcaag cagtacgaga gcgtgctgat ggtgtccatc      60
gaccagctgc tggacagcat gaaggagatc ggctccaact gcctcaacaa cgagttcaac     120
ttcttcaagc ggcacatctg cgacgccaac aaggagggca tgttcctgtt cagggccgcc     180
aggaaactgc ggcagttcct gaagatgaac tccaccggcg acttcgacct gcacctgctg     240
aaggtgtccg agggcaccac catcctgctg aactgcaccg acaggtgaa gggccggaaa      300 cctgctgctc tgggagaggc ccaacccacc aagagcctgg aggagaacaa gtccctgaag     360
gagcagaaga agctgaacga cctgtgcttc ctgaagaggc tgctgcagga gatcaagacc     420
tgctggaaca agatcctgat gggcaccaag gagcatagcg cacaaccaa cacagtcgct      480 gcctataacc tcacttggaa gagcaccaac ttcaaaacca tcctcgaatg ggaacccaaa     540
cccgttaacc aagtttacac cgtgcagatc agcaccaagt ccggcgactg gaagtccaaa     600
tgtttctata ccaccgacac cgagtgcgat ctcaccgatg agatcgtgaa agatgtgaaa     660
cagacctacc tcgcccgggt gtttagctac cccgccggca atgtggagag cactggttcc     720
gctggcgagc ctttatacga gaacagcccc gaatttaccc cttacctcga gaccaattta     780
```

```
ggacagccca ccatccaaag ctttgagcaa gttggcacaa aggtgaatgt gacagtggag    840
gacgagcgga ctttagtgcg gcggaacaac acctttctca gcctccggga tgtgttcggc    900
aaagatttaa tctacacact gtattactgg aagtcctctt cctccggcaa gaagacagct    960
aaaaccaaca caaacgagtt tttaatcgac gtggataaag gcgaaaacta ctgtttcagc   1020
gtgcaagctg tgatcccctc ccggaccgtg aataggaaaa gcaccgatag ccccgttgag   1080
tgcatgggcc aagaaaaggg cgagttccgg gagaactggg tgaacgtcat cagcgattta   1140
aagaagatcg aagatttaat tcagtccatg catatcgacg ccactttata cacagaatcc   1200
gacgtgcacc cctcttgtaa ggtgaccgcc atgaaatgtt ttttactgga gctgcaagtt   1260
atctctttag agagcggaga cgctagcatc cacgacaccg tggagaattt aatcattta    1320 gccaataact ctttatccag caacggcaac gtgacagagt ccggctgcaa ggagtgcgaa   1380
gagctggagg agaagaacat caaggagttt ctgcaatcct ttgtgcacat tgtccagatg   1440
ttcatcaata cctcc                                                   1455
```

<210> SEQ ID NO 127
<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-16s21 sequence"

<400> SEQUENCE: 127

```
Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
                20                  25                  30

Val Leu Met Val Ser Ile Asp Gln Leu Leu Asp Ser Met Lys Glu Ile
            35                  40                  45

Gly Ser Asn Cys Leu Asn Asn Glu Phe Asn Phe Phe Lys Arg His Ile
        50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
            100                 105                 110

Gln Val Lys Gly Arg Lys Pro Ala Ala Leu Gly Glu Ala Gln Pro Thr
        115                 120                 125

Lys Ser Leu Glu Glu Asn Lys Ser Leu Lys Glu Gln Lys Lys Leu Asn
    130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ser Gly Thr Thr Asn Thr
                165                 170                 175

Val Ala Ala Tyr Asn Leu Thr Trp Lys Ser Thr Asn Phe Lys Thr Ile
            180                 185                 190

Leu Glu Trp Glu Pro Lys Pro Val Asn Gln Val Tyr Thr Val Gln Ile
        195                 200                 205

Ser Thr Lys Ser Gly Asp Trp Lys Ser Lys Cys Phe Tyr Thr Thr Asp
    210                 215                 220
```

```
Thr Glu Cys Asp Leu Thr Asp Glu Ile Val Lys Asp Val Lys Gln Thr
225                 230                 235                 240

Tyr Leu Ala Arg Val Phe Ser Tyr Pro Ala Gly Asn Val Glu Ser Thr
            245                 250                 255

Gly Ser Ala Gly Glu Pro Leu Tyr Glu Asn Ser Pro Glu Phe Thr Pro
        260                 265                 270

Tyr Leu Glu Thr Asn Leu Gly Gln Pro Thr Ile Gln Ser Phe Glu Gln
    275                 280                 285

Val Gly Thr Lys Val Asn Val Thr Val Glu Asp Glu Arg Thr Leu Val
290                 295                 300

Arg Arg Asn Asn Thr Phe Leu Ser Leu Arg Asp Val Phe Gly Lys Asp
305                 310                 315                 320

Leu Ile Tyr Thr Leu Tyr Tyr Trp Lys Ser Ser Ser Gly Lys Lys
            325                 330                 335

Thr Ala Lys Thr Asn Thr Asn Glu Phe Leu Ile Asp Val Asp Lys Gly
                340                 345                 350

Glu Asn Tyr Cys Phe Ser Val Gln Ala Val Ile Pro Ser Arg Thr Val
            355                 360                 365

Asn Arg Lys Ser Thr Asp Ser Pro Val Glu Cys Met Gly Gln Glu Lys
370                 375                 380

Gly Glu Phe Arg Glu Asn Trp Val Asn Val Ile Ser Asp Leu Lys Lys
385                 390                 395                 400

Ile Glu Asp Leu Ile Gln Ser Met His Ile Asp Ala Thr Leu Tyr Thr
                405                 410                 415

Glu Ser Asp Val His Pro Ser Cys Lys Val Thr Ala Met Lys Cys Phe
            420                 425                 430

Leu Leu Glu Leu Gln Val Ile Ser Leu Glu Ser Gly Asp Ala Ser Ile
        435                 440                 445

His Asp Thr Val Glu Asn Leu Ile Ile Leu Ala Asn Asn Ser Leu Ser
    450                 455                 460

Ser Asn Gly Asn Val Thr Glu Ser Gly Cys Lys Glu Cys Glu Glu Leu
465                 470                 475                 480

Glu Glu Lys Asn Ile Lys Glu Phe Leu Gln Ser Phe Val His Ile Val
                485                 490                 495

Gln Met Phe Ile Asn Thr Ser
            500

<210> SEQ ID NO 128
<211> LENGTH: 1509
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-16s21 sequence"

<400> SEQUENCE: 128
atgaagtggg tgaccttcat cagcctgctg ttcctgttct ccagcgccta ctccgattgc      60
gacatcgagg gcaaggacgg caagcagtac gagagcgtgc tgatggtgtc catcgaccag    120
ctgctggaca gcatgaagga gatcggctcc aactgcctca caacgagtt caacttcttc     180 aagcggcaca tctgcgacgc caacaaggag ggcatgttcc tgttcagggc cgccaggaaa    240
ctgcggcagt cctgaagat gaactccacc ggcgacttcg acctgcacct gctgaaggtg     300
tccgagggca ccaccatcct gctgaactgc accggacagg tgaagggccg aaacctgct    360 gctctgggag aggcccaacc caccaagagc ctggaggaga caagtccct gaaggagcag    420
```

```
aagaagctga acgacctgtg cttcctgaag aggctgctgc aggagatcaa gacctgctgg    480
aacaagatcc tgatgggcac caaggagcat agcggcacaa ccaacacagt cgctgcctat    540
aacctcactt ggaagagcac caacttcaaa accatcctcg aatgggaacc caaacccgtt    600
aaccaagttt acaccgtgca gatcagcacc aagtccggcg actggaagtc caaatgtttc    660
tataccaccg acaccgagtg cgatctcacc gatgagatcg tgaaagatgt gaaacagacc    720
tacctcgccc gggtgtttag ctaccccgcc ggcaatgtgg agagcactgg ttccgctggc    780
gagcctttat acgagaacag ccccgaattt accccttacc tcgagaccaa tttaggacag    840
cccaccatcc aaagctttga gcaagttggc acaaaggtga atgtgacagt ggaggacgag    900
cggactttag tgcggcggaa caacaccttt ctcagcctcc gggatgtgtt cggcaaagat    960
ttaatctaca cactgtatta ctggaagtcc tcttcctccg gcaagaagac agctaaaacc   1020
aacacaaacg agttttaat cgacgtggat aaaggcgaaa actactgttt cagcgtgcaa   1080
gctgtgatcc cctcccggac cgtgaatagg aaaagcaccg atagcccccgt tgagtgcatg   1140
ggccaagaaa agggcgagtt ccgggagaac tgggtgaacg tcatcagcga tttaaagaag   1200
atcgaagatt taattcagtc catgcatatc gacgccactt tatacacaga atccgacgtg   1260
cacccctctt gtaaggtgac cgccatgaaa tgttttttac tggagctgca agttatctct   1320
ttagagagcg gagacgctag catccacgac accgtggaga atttaatcat tttagccaat   1380
aactctttat ccagcaacgg caacgtgaca gagtccggct gcaaggagtg cgaagagctg   1440
gaggagaaga acatcaagga gtttctgcaa tcctttgtgc acattgtcca gatgttcatc   1500
aatacctcc                                                            1509
```

<210> SEQ ID NO 129
<211> LENGTH: 438
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-16s21 sequence"

<400> SEQUENCE: 129

```
Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Gly Asn His Val
                85                  90                  95

Val Phe Gly Gly Gly Thr Lys Leu Thr Val Gly His Gly Gly Gly
            100                 105                 110

Ser Gly Gly Gly Gly Ser Gly Gly Gly Ser Glu Val Gln Leu Val
        115                 120                 125

Glu Ser Gly Gly Gly Val Val Arg Pro Gly Gly Ser Leu Arg Leu Ser
    130                 135                 140

Cys Ala Ala Ser Gly Phe Thr Phe Asp Asp Tyr Gly Met Ser Trp Val
```

```
            145                 150                 155                 160
Arg Gln Ala Pro Gly Lys Gly Leu Glu Trp Val Ser Gly Ile Asn Trp
                165                 170                 175

Asn Gly Gly Ser Thr Gly Tyr Ala Asp Ser Val Lys Gly Arg Phe Thr
            180                 185                 190

Ile Ser Arg Asp Asn Ala Lys Asn Ser Leu Tyr Leu Gln Met Asn Ser
        195                 200                 205

Leu Arg Ala Glu Asp Thr Ala Val Tyr Tyr Cys Ala Arg Gly Arg Ser
    210                 215                 220

Leu Leu Phe Asp Tyr Trp Gly Gln Gly Thr Leu Val Thr Val Ser Arg
225                 230                 235                 240

Ile Thr Cys Pro Pro Pro Met Ser Val Glu His Ala Asp Ile Trp Val
                245                 250                 255

Lys Ser Tyr Ser Leu Tyr Ser Arg Glu Arg Tyr Ile Cys Asn Ser Gly
                260                 265                 270

Phe Lys Arg Lys Ala Gly Thr Ser Ser Leu Thr Glu Cys Val Leu Asn
            275                 280                 285

Lys Ala Thr Asn Val Ala His Trp Thr Thr Pro Ser Leu Lys Cys Ile
    290                 295                 300

Arg Gln Gly Gln Asp Arg His Met Ile Arg Met Arg Gln Leu Ile Asp
305                 310                 315                 320

Ile Val Asp Gln Leu Lys Asn Tyr Val Asn Asp Leu Val Pro Glu Phe
                325                 330                 335

Leu Pro Ala Pro Glu Asp Val Glu Thr Asn Cys Glu Trp Ser Ala Phe
                340                 345                 350

Ser Cys Phe Gln Lys Ala Gln Leu Lys Ser Ala Asn Thr Gly Asn Asn
            355                 360                 365

Glu Arg Ile Ile Asn Val Ser Ile Lys Lys Leu Lys Arg Lys Pro Pro
    370                 375                 380

Ser Thr Asn Ala Gly Arg Arg Gln Lys His Arg Leu Thr Cys Pro Ser
385                 390                 395                 400

Cys Asp Ser Tyr Glu Lys Lys Pro Pro Lys Glu Phe Leu Glu Arg Phe
                405                 410                 415

Lys Ser Leu Leu Gln Lys Met Ile His Gln His Leu Ser Ser Arg Thr
            420                 425                 430

His Gly Ser Glu Asp Ser
        435

<210> SEQ ID NO 130
<211> LENGTH: 1314
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-16s21 sequence"

<400> SEQUENCE: 130
tccgagctga cccaggaccc tgctgtgtcc gtggctctgg ccagaccgt gaggatcacc      60 tgccagggcg actccctgag gtcctactac gcctcctggt accagcagaa gcccggccag     120
gctcctgtgc tggtgatcta cggcaagaac aacaggccct ccggcatccc tgacaggttc     180
tccggatcct cctccggcaa caccgcctcc ctgaccatca caggcgctca ggccgaggac     240
gaggctgact actactgcaa ctccagggac tcctccggca accatgtggt gttcggcggc     300
ggcaccaagc tgaccgtggg ccatggcggc ggcggctccg gaggcggcgg cagcggcgga     360
```

```
ggaggatccg aggtgcagct ggtggagtcc ggaggaggag tggtgaggcc tggaggctcc    420
ctgaggctga gctgtgctgc ctccggcttc accttcgacg actacggcat gtcctgggtg    480
aggcaggctc ctggaaaggg cctggagtgg gtgtccggca tcaactggaa cggcggatcc    540
accggctacg ccgattccgt gaagggcagg ttcaccatca gcagggacaa cgccaagaac    600
tccctgtacc tgcagatgaa ctccctgagg gccgaggaca ccgccgtgta ctactgcgcc    660
aggggcaggt ccctgctgtt cgactactgg ggacagggca cctggtgac cgtgtccagg    720 attacatgcc ccctcccat gagcgtggag cacgccgaca tctgggtgaa gagctatagc    780
ctctacagcc gggagaggta tatctgtaac agcggcttca agaggaaggc cggcaccagc    840
agcctcaccg agtgcgtgct gaataaggct accaacgtgg ctcactggac aacaccctct    900
ttaaagtgca tccggcaggg ccaggacagg cacatgatcc ggatgaggca gctcatcgac    960
atcgtcgacc agctgaagaa ctacgtgaac gacctggtgc ccgagtttct gcctgccccc   1020
gaggacgtgg agaccaactg cgagtggtcc gccttctcct gctttcagaa ggcccagctg   1080
aagtccgcca acaccggcaa caacgagcgg atcatcaacg tgagcatcaa gaagctgaag   1140
cggaagcctc cctccacaaa cgccggcagg aggcagaagc acaggctgac ctgccccagc   1200
tgtgactcct acgagaagaa gccccccaag gagttcctgg agaggttcaa gtccctgctg   1260
cagaagatga tccatcagca cctgtcctcc aggacccacg gctccgagga ctcc          1314
```

<210> SEQ ID NO 131
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-16s21 sequence"

<400> SEQUENCE: 131

```
Met Lys Trp Val Thr Phe Ile Ser Leu Leu Phe Leu Phe Ser Ser Ala
1               5                   10                  15

Tyr Ser Ser Glu Leu Thr Gln Asp Pro Ala Val Ser Val Ala Leu Gly
            20                  25                  30

Gln Thr Val Arg Ile Thr Cys Gln Gly Asp Ser Leu Arg Ser Tyr Tyr
        35                  40                  45

Ala Ser Trp Tyr Gln Gln Lys Pro Gly Gln Ala Pro Val Leu Val Ile
    50                  55                  60

Tyr Gly Lys Asn Asn Arg Pro Ser Gly Ile Pro Asp Arg Phe Ser Gly
65                  70                  75                  80

Ser Ser Ser Gly Asn Thr Ala Ser Leu Thr Ile Thr Gly Ala Gln Ala
                85                  90                  95

Glu Asp Glu Ala Asp Tyr Tyr Cys Asn Ser Arg Asp Ser Ser Gly Asn
            100                 105                 110

His Val Val Phe Gly Gly Gly Thr Lys Leu Thr Val Gly His Gly Gly
        115                 120                 125

Gly Gly Ser Gly Gly Gly Gly Ser Gly Gly Gly Ser Glu Val Gln
    130                 135                 140

Leu Val Glu Ser Gly Gly Gly Val Val Arg Pro Gly Gly Ser Leu Arg
145                 150                 155                 160

Leu Ser Cys Ala Ala Ser Gly Phe Thr Phe Asp Asp Tyr Gly Met Ser
                165                 170                 175

Trp Val Arg Gln Ala Pro Gly Lys Gly Leu Glu Trp Val Ser Gly Ile
```

```
                    180                 185                 190
Asn Trp Asn Gly Gly Ser Thr Gly Tyr Ala Asp Ser Val Lys Gly Arg
            195                 200                 205
Phe Thr Ile Ser Arg Asp Asn Ala Lys Asn Ser Leu Tyr Leu Gln Met
        210                 215                 220
Asn Ser Leu Arg Ala Glu Asp Thr Ala Val Tyr Tyr Cys Ala Arg Gly
225                 230                 235                 240
Arg Ser Leu Leu Phe Asp Tyr Trp Gly Gln Gly Thr Leu Val Thr Val
                245                 250                 255
Ser Arg Ile Thr Cys Pro Pro Met Ser Val Glu His Ala Asp Ile
            260                 265                 270
Trp Val Lys Ser Tyr Ser Leu Tyr Ser Arg Glu Arg Tyr Ile Cys Asn
        275                 280                 285
Ser Gly Phe Lys Arg Lys Ala Gly Thr Ser Ser Leu Thr Glu Cys Val
    290                 295                 300
Leu Asn Lys Ala Thr Asn Val Ala His Trp Thr Thr Pro Ser Leu Lys
305                 310                 315                 320
Cys Ile Arg Gln Gly Gln Asp Arg His Met Ile Arg Met Arg Gln Leu
                325                 330                 335
Ile Asp Ile Val Asp Gln Leu Lys Asn Tyr Val Asn Asp Leu Val Pro
            340                 345                 350
Glu Phe Leu Pro Ala Pro Glu Asp Val Glu Thr Asn Cys Glu Trp Ser
        355                 360                 365
Ala Phe Ser Cys Phe Gln Lys Ala Gln Leu Lys Ser Ala Asn Thr Gly
    370                 375                 380
Asn Asn Glu Arg Ile Ile Asn Val Ser Ile Lys Lys Leu Lys Arg Lys
385                 390                 395                 400
Pro Pro Ser Thr Asn Ala Gly Arg Arg Gln Lys His Arg Leu Thr Cys
                405                 410                 415
Pro Ser Cys Asp Ser Tyr Glu Lys Lys Pro Pro Lys Glu Phe Leu Glu
            420                 425                 430
Arg Phe Lys Ser Leu Leu Gln Lys Met Ile His Gln His Leu Ser Ser
        435                 440                 445
Arg Thr His Gly Ser Glu Asp Ser
    450                 455

<210> SEQ ID NO 132
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-16s21 sequence"

<400> SEQUENCE: 132
atgaagtggg tgaccttcat cagcctgctg ttcctgttct ccagcgccta ctcctccgag      60
ctgacccagg accctgctgt gtccgtggct ctgggccaga ccgtgaggat cacctgccag     120
ggcgactccc tgaggtccta ctacgcctcc tggtaccagc agaagcccgg ccaggctcct     180
gtgctggtga tctacggcaa gaacaacagg ccctccggca tccctgacag gttctccgga     240
tcctcctccg gcaacaccgc ctccctgacc atcacaggcg ctcaggccga ggacgaggct     300
gactactact gcaactccag ggactcctcc ggcaaccatg tggtgttcgg cggcggcacc     360
aagctgaccg tgggccatgg cggcggcggc tccggaggcg gcggcagcgg cggaggagga     420
```

```
tccgaggtgc agctggtgga gtccggagga ggagtggtga ggcctggagg ctccctgagg    480
ctgagctgtg ctgcctccgg cttcaccttc gacgactacg catgtcctg ggtgaggcag     540
gctcctggaa agggcctgga gtgggtgtcc ggcatcaact ggaacggcgg atccaccggc    600
tacgccgatt ccgtgaaggg caggttcacc atcagcaggg acaacgccaa gaactccctg    660
tacctgcaga tgaactccct gagggccgag gacaccgccg tgtactactg cgccaggggc    720
aggtccctgc tgttcgacta ctggggacag ggcaccctgg tgaccgtgtc caggattaca    780
tgccccctc ccatgagcgt ggagcacgcc gacatctggg tgaagagcta tagcctctac     840
agccgggaga ggtatatctg taacagcggc ttcaagagga aggccggcac cagcagcctc    900
accgagtgcg tgctgaataa ggctaccaac gtggctcact ggacaacacc ctctttaaag    960
tgcatccggc agggccagga caggcacatg atccggatga ggcagctcat cgacatcgtc    1020
gaccagctga agaactacgt gaacgacctg gtgcccgagt ttctgcctgc ccccgaggac    1080
gtggagacca actgcgagtg gtccgccttc tcctgctttc agaaggccca gctgaagtcc    1140
gccaacaccg caacaacga gcggatcatc aacgtgagca tcaagaagct gaagcggaag    1200
cctccctcca caaacgccgg caggaggcag aagcacaggc tgacctgccc cagctgtgac    1260
tcctacgaga gaagccccc caaggagttc tggagaggg tcaagtccct gctgcagaag     1320
atgatccatc agcacctgtc ctccaggacc cacggctccg aggactcc                1368
```

<210> SEQ ID NO 133
<211> LENGTH: 620
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-16s21 sequence"

<400> SEQUENCE: 133

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Gly Ala Val Lys Phe Pro
                165                 170                 175

Gln Leu Cys Lys Phe Cys Asp Val Arg Phe Ser Thr Cys Asp Asn Gln
            180                 185                 190
```

-continued

```
Lys Ser Cys Met Ser Asn Cys Ser Ile Thr Ser Ile Cys Glu Lys Pro
            195                 200                 205

Gln Glu Val Cys Val Ala Val Trp Arg Lys Asn Asp Glu Asn Ile Thr
            210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
                260                 265                 270

Asp Asn Ile Ile Phe Ser Glu Glu Tyr Asn Thr Ser Asn Pro Asp Ser
                275                 280                 285

Gly Thr Thr Asn Thr Val Ala Ala Tyr Asn Leu Thr Trp Lys Ser Thr
        290                 295                 300

Asn Phe Lys Thr Ile Leu Glu Trp Glu Pro Lys Pro Val Asn Gln Val
305                 310                 315                 320

Tyr Thr Val Gln Ile Ser Thr Lys Ser Gly Asp Trp Lys Ser Lys Cys
                325                 330                 335

Phe Tyr Thr Thr Asp Thr Glu Cys Asp Leu Thr Asp Glu Ile Val Lys
                340                 345                 350

Asp Val Lys Gln Thr Tyr Leu Ala Arg Val Phe Ser Tyr Pro Ala Gly
            355                 360                 365

Asn Val Glu Ser Thr Gly Ser Ala Gly Glu Pro Leu Tyr Glu Asn Ser
        370                 375                 380

Pro Glu Phe Thr Pro Tyr Leu Glu Thr Asn Leu Gly Gln Pro Thr Ile
385                 390                 395                 400

Gln Ser Phe Glu Gln Val Gly Thr Lys Val Asn Val Thr Val Glu Asp
                405                 410                 415

Glu Arg Thr Leu Val Arg Arg Asn Asn Thr Phe Leu Ser Leu Arg Asp
            420                 425                 430

Val Phe Gly Lys Asp Leu Ile Tyr Thr Leu Tyr Tyr Trp Lys Ser Ser
            435                 440                 445

Ser Ser Gly Lys Lys Thr Ala Lys Thr Asn Thr Asn Glu Phe Leu Ile
        450                 455                 460

Asp Val Asp Lys Gly Glu Asn Tyr Cys Phe Ser Val Gln Ala Val Ile
465                 470                 475                 480

Pro Ser Arg Thr Val Asn Arg Lys Ser Thr Asp Ser Pro Val Glu Cys
                485                 490                 495

Met Gly Gln Glu Lys Gly Glu Phe Arg Glu Asn Trp Val Asn Val Ile
                500                 505                 510

Ser Asp Leu Lys Lys Ile Glu Asp Leu Ile Gln Ser Met His Ile Asp
            515                 520                 525

Ala Thr Leu Tyr Thr Glu Ser Asp Val His Pro Ser Cys Lys Val Thr
            530                 535                 540

Ala Met Lys Cys Phe Leu Leu Glu Leu Gln Val Ile Ser Leu Glu Ser
545                 550                 555                 560

Gly Asp Ala Ser Ile His Asp Thr Val Glu Asn Leu Ile Ile Leu Ala
                565                 570                 575

Asn Asn Ser Leu Ser Ser Asn Gly Asn Val Thr Glu Ser Gly Cys Lys
            580                 585                 590

Glu Cys Glu Glu Leu Glu Glu Lys Asn Ile Lys Glu Phe Leu Gln Ser
            595                 600                 605
```

Phe Val His Ile Val Gln Met Phe Ile Asn Thr Ser
    610             615             620

<210> SEQ ID NO 134
<211> LENGTH: 1860
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic TGFRt15-16s21 sequence"

<400> SEQUENCE: 134

| | | | | | |
|---|---|---|---|---|---|
| atccccccc | atgtgcaaaa | gagcgtgaac | aacgatatga | tcgtgaccga | caacaacggc | 60 |
| gccgtgaagt | ttccccagct | ctgcaagttc | tgcgatgtca | ggttcagcac | ctgcgataat | 120 |
| cagaagtcct | gcatgtccaa | ctgcagcatc | acctccatct | gcgagaagcc | caagaagtg | 180 |
| tgcgtggccg | tgtggcggaa | aaatgacgag | aacatcaccc | tggagaccgt | gtgtcacgac | 240 |
| cccaagctcc | cttatcacga | cttcattctg | gaggacgctg | cctcccccaa | atgcatcatg | 300 |
| aaggagaaga | agaagcccgg | agagaccttc | tttatgtgtt | cctgtagcag | cgacgagtgt | 360 |
| aacgacaaca | tcatcttcag | cgaagagtac | aacaccagca | accctgatgg | aggtggcgga | 420 |
| tccggaggtg | gaggttctgg | tggaggtggg | agtattcctc | cccacgtgca | gaagagcgtg | 480 |
| aataatgaca | tgatcgtgac | cgataacaat | ggcgccgtga | aatttcccca | gctgtgcaaa | 540 |
| ttctgcgatg | tgaggttttc | cacctgcgac | aaccagaagt | cctgtatgag | caactgctcc | 600 |
| atcacctcca | tctgtgagaa | gcctcaggag | gtgtgcgtgg | ctgtctggcg | gaagaatgac | 660 |
| gagaatatca | ccctggaaac | cgtctgccac | gatcccaagc | tgccctacca | cgatttcatc | 720 |
| ctggaagacg | ccgccagccc | taagtgcatc | atgaaagaga | aaagaagcc | tggcgagacc | 780 |
| tttttcatgt | gctcctgcag | cagcgacgaa | tgcaacgaca | atatcatctt | tagcgaggaa | 840 |
| tacaatacca | gcaaccccga | cagcggcaca | accaacacag | tcgctgccta | taacctcact | 900 |
| tggaagagca | ccaacttcaa | aaccatcctc | gaatgggaac | ccaaacccgt | taaccaagtt | 960 |
| tacaccgtgc | agatcagcac | caagtccggc | gactggaagt | ccaaatgttt | ctataccacc | 1020 |
| gacaccgagt | gcgatctcac | cgatgagatc | gtgaaagatg | tgaaacagac | ctacctcgcc | 1080 |
| cgggtgttta | gctaccccgc | cggcaatgtg | gagagcactg | gttccgctgg | cgagccttta | 1140 |
| tacgagaaca | gccccgaatt | tacccttac | ctcgagacca | atttaggaca | gcccaccatc | 1200 |
| caaagctttg | agcaagttgg | cacaaaggtg | aatgtgacag | tggaggacga | gcggacttta | 1260 |
| gtgcggcgga | acaacacctt | tctcagcctc | cgggatgtgt | tcggcaaaga | tttaatctac | 1320 |
| acactgtatt | actggaagtc | ctcttcctcc | ggcaagaaga | cagctaaaac | caacacaaac | 1380 |
| gagtttttaa | tcgacgtgga | taaggcgaa | aactactgtt | tcagcgtgca | agctgtgatc | 1440 |
| ccctcccgga | ccgtgaatag | gaaaagcacc | gatagccccg | ttgagtgcat | gggccaagaa | 1500 |
| aagggcgagt | tccgggagaa | ctgggtgaac | gtcatcagcg | atttaaagaa | gatcgaagat | 1560 |
| ttaattcagt | ccatgcatat | cgacgccact | ttatacacag | aatccgacgt | gcacccctct | 1620 |
| tgtaaggtga | ccgccatgaa | atgttttta | ctggagctgc | aagttatctc | tttagagagc | 1680 |
| ggagacgcta | gcatccacga | caccgtggag | aatttaatca | ttttagccaa | taactctttta | 1740 |
| tccagcaacg | gcaacgtgac | agagtccggc | tgcaaggagt | gcgaagagct | ggaggagaag | 1800 |
| aacatcaagg | agtttctgca | atcctttgtg | cacattgtcc | agatgttcat | caataccctcc | 1860 |

<210> SEQ ID NO 135

-continued

```
<211> LENGTH: 638
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-16s21 sequence"

<400> SEQUENCE: 135

Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
                325                 330                 335

Gln Val Tyr Thr Val Gln Ile Ser Thr Lys Ser Gly Asp Trp Lys Ser
            340                 345                 350

Lys Cys Phe Tyr Thr Thr Asp Thr Glu Cys Asp Leu Thr Asp Glu Ile
        355                 360                 365
```

```
Val Lys Asp Val Lys Gln Thr Tyr Leu Ala Arg Val Phe Ser Tyr Pro
370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415

Thr Ile Gln Ser Phe Glu Gln Val Gly Thr Lys Val Asn Val Thr Val
                420                 425                 430

Glu Asp Glu Arg Thr Leu Val Arg Arg Asn Asn Thr Phe Leu Ser Leu
            435                 440                 445

Arg Asp Val Phe Gly Lys Asp Leu Ile Tyr Thr Leu Tyr Tyr Trp Lys
450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                485                 490                 495

Val Ile Pro Ser Arg Thr Val Asn Arg Lys Ser Thr Asp Ser Pro Val
                500                 505                 510

Glu Cys Met Gly Gln Glu Lys Gly Glu Phe Arg Glu Asn Trp Val Asn
            515                 520                 525

Val Ile Ser Asp Leu Lys Lys Ile Glu Asp Leu Ile Gln Ser Met His
530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
                580                 585                 590

Leu Ala Asn Asn Ser Leu Ser Ser Asn Gly Asn Val Thr Glu Ser Gly
            595                 600                 605

Cys Lys Glu Cys Glu Glu Leu Glu Glu Lys Asn Ile Lys Glu Phe Leu
610                 615                 620

Gln Ser Phe Val His Ile Val Gln Met Phe Ile Asn Thr Ser
625                 630                 635

<210> SEQ ID NO 136
<211> LENGTH: 1914
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-16s21 sequence"

<400> SEQUENCE: 136
atgaagtggg tgaccttcat cagcctgctg ttcctgttct ccagcgccta ctccatcccc     60
ccccatgtgc aaaagagcgt gaacaacgat atgatcgtga ccgacaacaa cggcgccgtg    120
aagtttcccc agctctgcaa gttctgcgat gtcaggttca gcacctgcga taatcagaag    180
tcctgcatgt ccaactgcag catcacctcc atctgcgaga agccccaaga agtgtgcgtg    240
gccgtgtggc ggaaaaatga cgagaacatc accctggaga ccgtgtgtca cgaccccaag    300
ctcccttatc acgacttcat tctggaggac gctgcctccc ccaaatgcat catgaaggag    360
aagaagaagc ccgagagac cttctttatg tgttcctgta gcagcgacga gtgtaacgac    420
aacatcatct tcagcgaaga gtacaacacc agcaaccctg atggaggtgg cggatccgga    480
```

```
ggtggaggtt ctggtggagg tgggagtatt cctccccacg tgcagaagag cgtgaataat    540
gacatgatcg tgaccgataa caatggcgcc gtgaaatttc cccagctgtg caaattctgc    600
gatgtgaggt tttccacctg cgacaaccag aagtcctgta tgagcaactg ctccatcacc    660
tccatctgtg agaagcctca ggaggtgtgc gtggctgtct ggcggaagaa tgacgagaat    720
atcaccctgg aaaccgtctg ccacgatccc aagctgccct accacgattt catcctggaa    780
gacgccgcca gccctaagtg catcatgaaa gagaaaaaga agcctggcga gaccttttc     840 atgtgctcct gcagcagcga cgaatgcaac gacaatatca tctttagcga ggaatacaat    900
accagcaacc ccgacagcgg cacaaccaac acagtcgctg cctataacct cacttggaag    960
agcaccaact tcaaaaccat cctcgaatgg gaacccaaac ccgttaacca agtttacacc   1020
gtgcagatca gcaccaagtc cggcgactgg aagtccaaat gtttctatac caccgacacc   1080
gagtgcgatc tcaccgatga gatcgtgaaa gatgtgaaac agacctacct cgcccgggtg   1140
tttagctacc ccgccggcaa tgtggagagc actggttccg ctggcgagcc tttatacgag   1200
aacagccccg aatttacccc ttacctcgag accaatttag acagccacac catccaaagc   1260
tttgagcaag ttggcacaaa ggtgaatgtg acagtggagg acgagcggac tttagtgcgg   1320
cggaacaaca ccttttctcag cctccgggat gtgttcggca agatttaat ctacacactg   1380 tattactgga agtcctcttc ctccggcaag aagacagcta aaccaacac aaacgagttt    1440 ttaatcgacg tggataaagg cgaaaactac tgtttcagcg tgcaagctgt gatcccctcc   1500
cggaccgtga ataggaaaag caccgatagc cccgttgagt gcatgggcca agaaaagggc   1560
gagttccggg agaactgggt gaacgtcatc agcgatttaa agaagatcga agatttaatt   1620
cagtccatgc atatcgacgc cactttatac acagaatccg acgtgcaccc ctcttgtaag   1680
gtgaccgcca tgaaatgttt tttactggag ctgcaagtta tctctttaga gagcggagac   1740
gctagcatcc acgacaccgt ggagaattta atcatttag ccaataactc tttatccagc    1800
aacggcaacg tgacagagtc cggctgcaag gagtgcgaag agctggagga agaacatc     1860 aaggagtttc tgcaatcctt tgtgcacatt gtccagatgt tcatcaatac ctcc          1914
```

<210> SEQ ID NO 137
<211> LENGTH: 438
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-16s21 sequence"

<400> SEQUENCE: 137

```
Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn His Val
                85                  90                  95

Val Phe Gly Gly Gly Thr Lys Leu Thr Val Gly His Gly Gly Gly Gly
```

```
            100                 105                 110
Ser Gly Gly Gly Ser Gly Gly Gly Ser Glu Val Gln Leu Val
        115                 120                 125
Glu Ser Gly Gly Gly Val Val Arg Pro Gly Gly Ser Leu Arg Leu Ser
130                 135                 140
Cys Ala Ala Ser Gly Phe Thr Phe Asp Asp Tyr Gly Met Ser Trp Val
145                 150                 155                 160
Arg Gln Ala Pro Gly Lys Gly Leu Glu Trp Val Ser Gly Ile Asn Trp
                165                 170                 175
Asn Gly Gly Ser Thr Gly Tyr Ala Asp Ser Val Lys Gly Arg Phe Thr
            180                 185                 190
Ile Ser Arg Asp Asn Ala Lys Asn Ser Leu Tyr Leu Gln Met Asn Ser
        195                 200                 205
Leu Arg Ala Glu Asp Thr Ala Val Tyr Tyr Cys Ala Arg Gly Arg Ser
    210                 215                 220
Leu Leu Phe Asp Tyr Trp Gly Gln Gly Thr Leu Val Thr Val Ser Arg
225                 230                 235                 240
Ile Thr Cys Pro Pro Pro Met Ser Val Glu His Ala Asp Ile Trp Val
                245                 250                 255
Lys Ser Tyr Ser Leu Tyr Ser Arg Glu Arg Tyr Ile Cys Asn Ser Gly
            260                 265                 270
Phe Lys Arg Lys Ala Gly Thr Ser Ser Leu Thr Glu Cys Val Leu Asn
        275                 280                 285
Lys Ala Thr Asn Val Ala His Trp Thr Thr Pro Ser Leu Lys Cys Ile
    290                 295                 300
Arg Gln Gly Gln Asp Arg His Met Ile Arg Met Arg Gln Leu Ile Asp
305                 310                 315                 320
Ile Val Asp Gln Leu Lys Asn Tyr Val Asn Asp Leu Val Pro Glu Phe
                325                 330                 335
Leu Pro Ala Pro Glu Asp Val Glu Thr Asn Cys Glu Trp Ser Ala Phe
            340                 345                 350
Ser Cys Phe Gln Lys Ala Gln Leu Lys Ser Ala Asn Thr Gly Asn Asn
        355                 360                 365
Glu Arg Ile Ile Asn Val Ser Ile Lys Lys Leu Lys Arg Lys Pro Pro
    370                 375                 380
Ser Thr Asn Ala Gly Arg Arg Gln Lys His Arg Leu Thr Cys Pro Ser
385                 390                 395                 400
Cys Asp Ser Tyr Glu Lys Lys Pro Pro Lys Glu Phe Leu Glu Arg Phe
                405                 410                 415
Lys Ser Leu Leu Gln Lys Met Ile His Gln His Leu Ser Ser Arg Thr
            420                 425                 430
His Gly Ser Glu Asp Ser
        435

<210> SEQ ID NO 138
<211> LENGTH: 1314
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-16s21 sequence"

<400> SEQUENCE: 138
tccgagctga cccaggaccc tgctgtgtcc gtggctctgg gccagaccgt gaggatcacc    60
```

-continued

```
tgccagggcg actccctgag gtcctactac gcctcctggt accagcagaa gcccggccag      120
gctcctgtgc tggtgatcta cggcaagaac aacaggccct ccggcatccc tgacaggttc      180
tccggatcct cctccggcaa caccgcctcc ctgaccatca caggcgctca ggccgaggac      240
gaggctgact actactgcaa ctccaggac tcctccggca accatgtggt gttcggcggc       300
ggcaccaagc tgaccgtggg ccatggcggc ggcggctccg gaggcggcgg cagcggcgga      360
ggaggatccg aggtgcagct ggtggagtcc ggaggaggag tggtgaggcc tggaggctcc      420
ctgaggctga gctgtgctgc ctccggcttc accttcgacg actacggcat gtcctgggtg      480
aggcaggctc ctggaaaggg cctggagtgg gtgtccggca tcaactgaa cggcggatcc       540 accggctacg ccgattccgt gaagggcagg ttcaccatca gcagggacaa cgccaagaac      600
tccctgtacc tgcagatgaa ctccctgagg gccgaggaca ccgccgtgta ctactgcgcc      660
aggggcaggt ccctgctgtt cgactactgg ggacagggca ccctggtgac cgtgtccagg      720
attacatgcc cccctcccat gagcgtggag cacgccgaca tctgggtgaa gagctatagc      780
ctctacagcc gggagaggta tctgtgtaac agcggcttca agaggaaggc cggcaccagc      840
agcctcaccg agtgcgtgct gaataaggct accaacgtgg ctcactggac aacaccctct      900
ttaaagtgca tccggcaggg ccaggacagg cacatgatcc ggatgaggca gctcatcgac      960
atcgtcgacc agctgaagaa ctacgtgaac gacctggtgc ccgagtttct gcctgccccc     1020
gaggacgtgg agaccaactg cgagtggtcc gccttctcct gctttcagaa ggcccagctg     1080
aagtccgcca caccggcaa caacgagcgg atcatcaacg tgagcatcaa gaagctgaag      1140
cggaagcctc cctccacaaa cgccggcagg aggcagaagc acaggctgac ctgccccagc     1200
tgtgactcct acgagaagaa gccccccaag gagttcctgg agaggttcaa gtccctgctg     1260
cagaagatga tccatcagca cctgtcctcc aggacccacg gctccgagga ctcc            1314
```

<210> SEQ ID NO 139
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-16s21 sequence"

<400> SEQUENCE: 139

```
Met Lys Trp Val Thr Phe Ile Ser Leu Leu Phe Leu Phe Ser Ser Ala
1               5                   10                  15

Tyr Ser Ser Glu Leu Thr Gln Asp Pro Ala Val Ser Val Ala Leu Gly
            20                  25                  30

Gln Thr Val Arg Ile Thr Cys Gln Gly Asp Ser Leu Arg Ser Tyr Tyr
        35                  40                  45

Ala Ser Trp Tyr Gln Gln Lys Pro Gly Gln Ala Pro Val Leu Val Ile
    50                  55                  60

Tyr Gly Lys Asn Asn Arg Pro Ser Gly Ile Pro Asp Arg Phe Ser Gly
65                  70                  75                  80

Ser Ser Ser Gly Asn Thr Ala Ser Leu Thr Ile Thr Gly Ala Gln Ala
                85                  90                  95

Glu Asp Glu Ala Asp Tyr Tyr Cys Asn Ser Arg Asp Ser Ser Gly Asn
            100                 105                 110

His Val Val Phe Gly Gly Gly Thr Lys Leu Thr Val Gly His Gly Gly
        115                 120                 125

Gly Gly Ser Gly Gly Gly Gly Ser Gly Gly Gly Gly Ser Glu Val Gln
```

```
            130                 135                 140
Leu Val Glu Ser Gly Gly Gly Val Val Arg Pro Gly Gly Ser Leu Arg
145                 150                 155                 160

Leu Ser Cys Ala Ala Ser Gly Phe Thr Phe Asp Asp Tyr Gly Met Ser
                165                 170                 175

Trp Val Arg Gln Ala Pro Gly Lys Gly Leu Glu Trp Val Ser Gly Ile
            180                 185                 190

Asn Trp Asn Gly Gly Ser Thr Gly Tyr Ala Asp Ser Val Lys Gly Arg
        195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Val Tyr Tyr Cys Ala Arg Gly
225                 230                 235                 240

Arg Ser Leu Leu Phe Asp Tyr Trp Gly Gln Gly Thr Leu Val Thr Val
                245                 250                 255

Ser Arg Ile Thr Cys Pro Pro Pro Met Ser Val Glu His Ala Asp Ile
            260                 265                 270

Trp Val Lys Ser Tyr Ser Leu Tyr Ser Arg Glu Arg Tyr Ile Cys Asn
        275                 280                 285

Ser Gly Phe Lys Arg Lys Ala Gly Thr Ser Ser Leu Thr Glu Cys Val
    290                 295                 300

Leu Asn Lys Ala Thr Asn Val Ala His Trp Thr Thr Pro Ser Leu Lys
305                 310                 315                 320

Cys Ile Arg Gln Gly Gln Asp Arg His Met Ile Arg Met Arg Gln Leu
                325                 330                 335

Ile Asp Ile Val Asp Gln Leu Lys Asn Tyr Val Asn Asp Leu Val Pro
            340                 345                 350

Glu Phe Leu Pro Ala Pro Glu Asp Val Glu Thr Asn Cys Glu Trp Ser
        355                 360                 365

Ala Phe Ser Cys Phe Gln Lys Ala Gln Leu Lys Ser Ala Asn Thr Gly
    370                 375                 380

Asn Asn Glu Arg Ile Ile Asn Val Ser Ile Lys Lys Leu Lys Arg Lys
385                 390                 395                 400

Pro Pro Ser Thr Asn Ala Gly Arg Arg Gln Lys His Arg Leu Thr Cys
                405                 410                 415

Pro Ser Cys Asp Ser Tyr Glu Lys Lys Pro Pro Lys Glu Phe Leu Glu
            420                 425                 430

Arg Phe Lys Ser Leu Leu Gln Lys Met Ile His Gln His Leu Ser Ser
        435                 440                 445

Arg Thr His Gly Ser Glu Asp Ser
    450                 455

<210> SEQ ID NO 140
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-16s21 sequence"

<400> SEQUENCE: 140
atgaagtggg tgaccttcat cagcctgctg ttcctgttct ccagcgccta ctcctccgag     60
ctgacccagg accctgctgt gtccgtggct ctgggccaga ccgtgaggat cacctgccag    120
ggcgactccc tgaggtccta ctacgcctcc tggtaccagc agaagcccgg ccaggctcct    180
```

-continued

```
gtgctggtga tctacggcaa gaacaacagg ccctccggca tccctgacag gttctccgga    240
tcctcctccg gcaacaccgc ctccctgacc atcacaggcg ctcaggccga ggacgaggct    300
gactactact gcaactccag ggactcctcc ggcaaccatg tggtgttcgg cggcggcacc    360
aagctgaccg tgggccatgg cggcggcggc tccggaggcg gcggcagcgg cggaggagga    420
tccgaggtgc agctggtgga gtccggagga ggagtggtga ggcctggagg ctccctgagg    480
ctgagctgtg ctgcctccgg cttcaccttc gacgactacg catgtcctg gtgaggcag    540 gctcctggaa agggcctgga gtgggtgtcc ggcatcaact ggaacggcgg atccaccggc    600
tacgccgatt ccgtgaaggg caggttcacc atcagcaggg acaacgccaa gaactccctg    660
tacctgcaga tgaactccct gagggccgag gacaccgccg tgtactactg cgccagggc    720 aggtccctgc tgttcgacta ctggggacag ggcaccctgg tgaccgtgtc caggattaca    780 tgccccctc ccatgagcgt ggagcacgcc gacatctggg tgaagagcta tagcctctac    840
agccgggaga ggtatatctg taacagcggc ttcaagagga aggccggcac cagcagcctc    900
accgagtgcg tgctgaataa ggctaccaac gtggctcact ggacaacacc ctctttaaag    960
tgcatccggc agggccagga caggcacatg atccggatga ggcagctcat cgacatcgtc    1020
gaccagctga agaactacgt gaacgacctg gtgcccgagt tctgcctgc ccccgaggac    1080 gtggagacca actgcgagtg gtccgccttc tcctgctttc agaaggccca gctgaagtcc    1140
gccaacaccg gcaacaacga gcggatcatc aacgtgagca tcaagaagct gaagcggaag    1200 cctcccctcca caaacgccgg caggaggcag aagcacaggc tgacctgccc cagctgtgac    1260
tcctacgaga agaagccccc caaggagttc ctggagaggt tcaagtccct gctgcagaag    1320
atgatccatc agcacctgtc ctccaggacc cacggctccg aggactcc                 1368
```

<210> SEQ ID NO 141
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-7s sequence"

<400> SEQUENCE: 141

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140
```

```
Ile Leu Met Gly Thr Lys Glu His Ser Gly Thr Thr Asn Thr Val Ala
145                 150                 155                 160

Ala Tyr Asn Leu Thr Trp Lys Ser Thr Asn Phe Lys Thr Ile Leu Glu
            165                 170                 175

Trp Glu Pro Lys Pro Val Asn Gln Val Tyr Thr Val Gln Ile Ser Thr
        180                 185                 190

Lys Ser Gly Asp Trp Lys Ser Lys Cys Phe Tyr Thr Thr Asp Thr Glu
    195                 200                 205

Cys Asp Leu Thr Asp Glu Ile Val Lys Asp Val Lys Gln Thr Tyr Leu
210                 215                 220

Ala Arg Val Phe Ser Tyr Pro Ala Gly Asn Val Glu Ser Thr Gly Ser
225                 230                 235                 240

Ala Gly Glu Pro Leu Tyr Glu Asn Ser Pro Glu Phe Thr Pro Tyr Leu
            245                 250                 255

Glu Thr Asn Leu Gly Gln Pro Thr Ile Gln Ser Phe Glu Gln Val Gly
        260                 265                 270

Thr Lys Val Asn Val Thr Val Glu Asp Glu Arg Thr Leu Val Arg Arg
    275                 280                 285

Asn Asn Thr Phe Leu Ser Leu Arg Asp Val Phe Gly Lys Asp Leu Ile
290                 295                 300

Tyr Thr Leu Tyr Tyr Trp Lys Ser Ser Ser Gly Lys Lys Thr Ala
305                 310                 315                 320

Lys Thr Asn Thr Asn Glu Phe Leu Ile Asp Val Asp Lys Gly Glu Asn
            325                 330                 335

Tyr Cys Phe Ser Val Gln Ala Val Ile Pro Ser Arg Thr Val Asn Arg
        340                 345                 350

Lys Ser Thr Asp Ser Pro Val Glu Cys Met Gly Gln Glu Lys Gly Glu
    355                 360                 365

Phe Arg Glu Asn Trp Val Asn Val Ile Ser Asp Leu Lys Lys Ile Glu
370                 375                 380

Asp Leu Ile Gln Ser Met His Ile Asp Ala Thr Leu Tyr Thr Glu Ser
385                 390                 395                 400

Asp Val His Pro Ser Cys Lys Val Thr Ala Met Lys Cys Phe Leu Leu
            405                 410                 415

Glu Leu Gln Val Ile Ser Leu Glu Ser Gly Asp Ala Ser Ile His Asp
        420                 425                 430

Thr Val Glu Asn Leu Ile Ile Leu Ala Asn Asn Ser Leu Ser Ser Asn
    435                 440                 445

Gly Asn Val Thr Glu Ser Gly Cys Lys Glu Cys Glu Glu Leu Glu Glu
450                 455                 460

Lys Asn Ile Lys Glu Phe Leu Gln Ser Phe Val His Ile Val Gln Met
465                 470                 475                 480

Phe Ile Asn Thr Ser
            485

<210> SEQ ID NO 142
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-7s sequence"

<400> SEQUENCE: 142
```

```
gattgcgaca tcgagggcaa ggacggcaag cagtacgaga gcgtgctgat ggtgtccatc    60
gaccagctgc tggacagcat gaaggagatc ggctccaact gcctcaacaa cgagttcaac   120
ttcttcaagc ggcacatctg cgacgccaac aaggagggca tgttcctgtt cagggccgcc   180
aggaaactgc ggcagttcct gaagatgaac tccaccggcg acttcgacct gcacctgctg   240
aaggtgtccg agggcaccac catcctgctg aactgcaccg acaggtgaa gggccggaaa    300 cctgctgctc tgggagaggc ccaacccacc aagagcctgg aggagaacaa gtccctgaag   360
gagcagaaga agctgaacga cctgtgcttc ctgaagaggc tgctgcagga gatcaagacc   420
tgctggaaca gatcctgat gggcaccaag gagcatagcg gcacaaccaa cacagtcgct    480
gcctataacc tcacttggaa gagcaccaac ttcaaaacca tcctcgaatg ggaacccaaa   540
cccgttaacc aagtttacac cgtgcagatc agcaccaagt ccggcgactg gaagtccaaa   600
tgtttctata ccaccgacac cgagtgcgat ctcaccgatg agatcgtgaa agatgtgaaa   660
cagacctacc tcgcccgggt gtttagctac cccgccggca atgtggagag cactggttcc   720
gctggcgagc ctttatacga gaacagcccc gaatttaccc cttacctcga gaccaattta   780
ggacagccca ccatccaaag ctttgagcaa gttggcacaa aggtgaatgt gacagtggag   840
gacgagcgga ctttagtgcg gcggaacaac acctttctca gcctccggga tgtgttcggc   900
aaagatttaa tctacacact gtattactgg aagtcctctt cctccggcaa gaagacagct   960
aaaaccaaca caaacgagtt tttaatcgac gtggataaag cgaaaactat ctgtttcagc  1020
gtgcaagctg tgatcccctc ccggaccgtg aataggaaaa gcaccgatag ccccgttgag  1080
tgcatgggcc aagaaaaggg cgagttccgg gagaactggg tgaacgtcat cagcgattta  1140
aagaagatcg aagatttaat tcagtccatg catatcgacg ccactttata cacagaatcc  1200
gacgtgcacc cctcttgtaa ggtgaccgcc atgaaatgtt ttttactgga gctgcaagtt  1260
atctctttag agagcggaga cgctagcatc cacgacaccg tggagaattt aatcattta   1320 gccaataact ctttatccag caacggcaac gtgacagagt ccggctgcaa ggagtgcgaa  1380
gagctggagg agaagaacat caaggagttt ctgcaatcct tgtgcacat tgtccagatg   1440 ttcatcaata cctcc                                                   1455
```

<210> SEQ ID NO 143
<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-7s sequence"

<400> SEQUENCE: 143

```
Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95
```

```
Leu Leu Lys Val Ser Glu Gly Thr Thr Ile Leu Leu Asn Cys Thr Gly
            100                 105                 110

Gln Val Lys Gly Arg Lys Pro Ala Leu Gly Glu Ala Gln Pro Thr
        115                 120                 125

Lys Ser Leu Glu Glu Asn Lys Ser Leu Lys Glu Gln Lys Lys Leu Asn
130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ser Gly Thr Thr Asn Thr
                165                 170                 175

Val Ala Ala Tyr Asn Leu Thr Trp Lys Ser Thr Asn Phe Lys Thr Ile
                180                 185                 190

Leu Glu Trp Glu Pro Lys Pro Val Asn Gln Val Tyr Thr Val Gln Ile
                195                 200                 205

Ser Thr Lys Ser Gly Asp Trp Lys Ser Lys Cys Phe Tyr Thr Thr Asp
        210                 215                 220

Thr Glu Cys Asp Leu Thr Asp Glu Ile Val Lys Asp Val Lys Gln Thr
225                 230                 235                 240

Tyr Leu Ala Arg Val Phe Ser Tyr Pro Ala Gly Asn Val Glu Ser Thr
                245                 250                 255

Gly Ser Ala Gly Glu Pro Leu Tyr Glu Asn Ser Pro Glu Phe Thr Pro
                260                 265                 270

Tyr Leu Glu Thr Asn Leu Gly Gln Pro Thr Ile Gln Ser Phe Glu Gln
                275                 280                 285

Val Gly Thr Lys Val Asn Val Thr Val Glu Asp Glu Arg Thr Leu Val
                290                 295                 300

Arg Arg Asn Asn Thr Phe Leu Ser Leu Arg Asp Val Phe Gly Lys Asp
305                 310                 315                 320

Leu Ile Tyr Thr Leu Tyr Tyr Trp Lys Ser Ser Ser Ser Gly Lys Lys
                325                 330                 335

Thr Ala Lys Thr Asn Thr Asn Glu Phe Leu Ile Asp Val Asp Lys Gly
                340                 345                 350

Glu Asn Tyr Cys Phe Ser Val Gln Ala Val Ile Pro Ser Arg Thr Val
                355                 360                 365

Asn Arg Lys Ser Thr Asp Ser Pro Val Glu Cys Met Gly Gln Glu Lys
370                 375                 380

Gly Glu Phe Arg Glu Asn Trp Val Asn Val Ile Ser Asp Leu Lys Lys
385                 390                 395                 400

Ile Glu Asp Leu Ile Gln Ser Met His Ile Asp Ala Thr Leu Tyr Thr
                405                 410                 415

Glu Ser Asp Val His Pro Ser Cys Lys Val Thr Ala Met Lys Cys Phe
                420                 425                 430

Leu Leu Glu Leu Gln Val Ile Ser Leu Glu Ser Gly Asp Ala Ser Ile
            435                 440                 445

His Asp Thr Val Glu Asn Leu Ile Ile Leu Ala Asn Asn Ser Leu Ser
                450                 455                 460

Ser Asn Gly Asn Val Thr Glu Ser Gly Cys Lys Glu Cys Glu Glu Leu
465                 470                 475                 480

Glu Glu Lys Asn Ile Lys Glu Phe Leu Gln Ser Phe Val His Ile Val
                485                 490                 495

Gln Met Phe Ile Asn Thr Ser
            500
```

<210> SEQ ID NO 144
<211> LENGTH: 1509
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 144

```
atgaagtggg tgaccttcat cagcctgctg ttcctgttct ccagcgccta ctccgattgc    60
gacatcgagg gcaaggacgg caagcagtac gagagcgtgc tgatggtgtc catcgaccag   120
ctgctggaca gcatgaagga gatcggctcc aactgcctca caacgagtt caacttcttc   180
aagcggcaca tctgcgacgc caacaaggag ggcatgttcc tgttcagggc cgccaggaaa   240
ctgcggcagt tcctgaagat gaactccacc ggcgacttcg acctgcacct gctgaaggtg   300
tccgagggca ccaccatcct gctgaactgc accggacagg tgaagggccg aaacctgct   360
gctctgggag aggcccaacc caccaagagc ctggaggaga caagtccct gaggagcag   420
aagaagctga cgacctgtg cttcctgaag aggctgctgc aggagatcaa gacctgctgg   480
aacaagatcc tgatgggcac caaggagcat agcggcacaa ccaacacagt cgctgcctat   540
aacctcactt ggaagagcac caacttcaaa accatcctcg aatgggaacc caaacccgtt   600
aaccaagttt acaccgtgca gatcagcacc aagtccggcg actggaagtc caatgtttc   660
tataccaccg acaccgagtg cgatctcacc gatgagatcg tgaaagatgt gaaacagacc   720
tacctcgccc gggtgtttag ctaccccgcc ggcaatgtgg agagcactgg ttccgctggc   780
gagcctttat acgagaacag ccccgaattt accccttacc tcgagaccaa tttaggacag   840
cccaccatcc aaagctttga gcaagttggc acaaaggtga atgtgacagt ggaggacgag   900
cggactttag tgcggcggaa caacaccttt ctcagcctcc gggatgtgtt cggcaaagat   960
ttaatctaca cactgtatta ctggaagtcc tcttcctccg gcaagaagac agctaaaacc  1020
aacacaaacg agttttttaat cgacgtggat aaaggcgaaa actactgttt cagcgtgcaa  1080
gctgtgatcc cctcccggac cgtgaatagg aaaagcaccg atagccccgt tgagtgcatg  1140
ggccaagaaa agggcgagtt ccgggagaac tgggtgaacg tcatcagcga tttaaagaag  1200
atcgaagatt taattcagtc catgcatatc gacgccactt tatacacaga tccgacgtg  1260
caccctctt gtaaggtgac cgccatgaaa tgtttttac tggagctgca agttatctct  1320
ttagagagcg gagacgctag catccacgac accgtggaga atttaatcat tttagccaat  1380
aactcttat ccagcaacgg caacgtgaca gagtccggct gcaaggagtg cgaagagctg  1440
gaggagaaga acatcaagga gtttctgcaa tcctttgtgc acattgtcca gatgttcatc  1500
aatacctcc                                                          1509
```

<210> SEQ ID NO 145
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-7s sequence"

<400> SEQUENCE: 145

```
Asp Cys Asp Ile Glu Gly Lys Asp Gly Lys Gln Tyr Glu Ser Val Leu
1               5                   10                  15
```

```
Met Val Ser Ile Asp Gln Leu Leu Asp Ser Met Lys Glu Ile Gly Ser
         20                  25                  30

Asn Cys Leu Asn Asn Glu Phe Asn Phe Phe Lys Arg His Ile Cys Asp
     35                  40                  45

Ala Asn Lys Glu Gly Met Phe Leu Phe Arg Ala Ala Arg Lys Leu Arg
 50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
             85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
            115                 120                 125

Cys Phe Leu Lys Arg Leu Leu Gln Glu Ile Lys Thr Cys Trp Asn Lys
    130                 135                 140

Ile Leu Met Gly Thr Lys Glu His Ile Thr Cys Pro Pro Pro Met Ser
145                 150                 155                 160

Val Glu His Ala Asp Ile Trp Val Lys Ser Tyr Ser Leu Tyr Ser Arg
                165                 170                 175

Glu Arg Tyr Ile Cys Asn Ser Gly Phe Lys Arg Lys Ala Gly Thr Ser
            180                 185                 190

Ser Leu Thr Glu Cys Val Leu Asn Lys Ala Thr Asn Val Ala His Trp
            195                 200                 205

Thr Thr Pro Ser Leu Lys Cys Ile Arg
    210                 215
```

<210> SEQ ID NO 146
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-7s sequence"

<400> SEQUENCE: 146

```
gattgtgata ttgaaggtaa agatggcaaa caatatgaga gtgttctaat ggtcagcatc      60
gatcaattat tggacagcat gaaagaaatt ggtagcaatt gcctgaataa tgaatttaac     120
ttttttaaaa gacatatctg tgatgctaat aaggaaggta tgttttttatt ccgtgctgct     180
cgcaagttga ggcaatttct taaaatgaat agcactggtg attttgatct ccacttatta     240
aaagtttcag aaggcacaac aatactgttg aactgcactg ccaggttaa aggaagaaaa      300
ccagctgccc tgggtgaagc ccaaccaaca aagagtttgg aagaaaataa atctttaaag     360
gaacagaaaa aactgaatga cttgtgtttc ctaaagagac tattacaaga gataaaaact     420
tgttggaata aaattttgat gggcactaaa gaacacatca cgtgccctcc ccccatgtcc     480
gtggaacacg cagacatctg ggtcaagagc tacagcttgt actccaggga gcggtacatt     540
tgtaactctg gtttcaagcg taaagccggc acgtccagcc tgacggagtg cgtgttgaac     600
aaggccacga atgtcgccca ctggacaacc cccagtctca aatgcattag a              651
```

<210> SEQ ID NO 147
<211> LENGTH: 235
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic 7t15-7s sequence"

<400> SEQUENCE: 147
```

| | | | | | | | | | | | | | | | |
|---|---|---|---|---|---|---|---|---|---|---|---|---|---|---|---|
|Met|Lys|Trp|Val|Thr|Phe|Ile|Ser|Leu|Leu|Phe|Leu|Phe|Ser|Ser|Ala|
|1| | |5| | | | |10| | | | |15| | |
|Tyr|Ser|Asp|Cys|Asp|Ile|Glu|Gly|Lys|Asp|Gly|Lys|Gln|Tyr|Glu|Ser|
| | | |20| | | | |25| | | | |30| | |
|Val|Leu|Met|Val|Ser|Ile|Asp|Gln|Leu|Leu|Asp|Ser|Met|Lys|Glu|Ile|
| | |35| | | | |40| | | | |45| | | |
|Gly|Ser|Asn|Cys|Leu|Asn|Asn|Glu|Phe|Asn|Phe|Phe|Lys|Arg|His|Ile|
| |50| | | | |55| | | | |60| | | | |
|Cys|Asp|Ala|Asn|Lys|Glu|Gly|Met|Phe|Leu|Phe|Arg|Ala|Ala|Arg|Lys|
|65| | | |70| | | | |75| | | | |80| | |
|Leu|Arg|Gln|Phe|Leu|Lys|Met|Asn|Ser|Thr|Gly|Asp|Phe|Asp|Leu|His|
| | | | |85| | | | |90| | | | |95| | |
|Leu|Leu|Lys|Val|Ser|Glu|Gly|Thr|Thr|Ile|Leu|Leu|Asn|Cys|Thr|Gly|
| | | |100| | | | |105| | | | |110| | | |
|Gln|Val|Lys|Gly|Arg|Lys|Pro|Ala|Ala|Leu|Gly|Glu|Ala|Gln|Pro|Thr|
| | |115| | | | |120| | | | |125| | | |
|Lys|Ser|Leu|Glu|Glu|Asn|Lys|Ser|Leu|Lys|Glu|Gln|Lys|Lys|Leu|Asn|
| |130| | | | |135| | | | |140| | | | |
|Asp|Leu|Cys|Phe|Leu|Lys|Arg|Leu|Leu|Gln|Glu|Ile|Lys|Thr|Cys|Trp|
|145| | | |150| | | | |155| | | | |160| | |
|Asn|Lys|Ile|Leu|Met|Gly|Thr|Lys|Glu|His|Ile|Thr|Cys|Pro|Pro|Pro|
| | | | |165| | | | |170| | | | |175| | |
|Met|Ser|Val|Glu|His|Ala|Asp|Ile|Trp|Val|Lys|Ser|Tyr|Ser|Leu|Tyr|
| | | |180| | | | |185| | | | |190| | | |
|Ser|Arg|Glu|Arg|Tyr|Ile|Cys|Asn|Ser|Gly|Phe|Lys|Arg|Lys|Ala|Gly|
| | |195| | | | |200| | | | |205| | | |
|Thr|Ser|Ser|Leu|Thr|Glu|Cys|Val|Leu|Asn|Lys|Ala|Thr|Asn|Val|Ala|
| |210| | | | |215| | | | |220| | | | |
|His|Trp|Thr|Thr|Pro|Ser|Leu|Lys|Cys|Ile|Arg| | | | | |
|225| | | |230| | | | |235| | | | | | |

```
<210> SEQ ID NO 148
<211> LENGTH: 705
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-7s sequence"

<400> SEQUENCE: 148
atgaagtggg tgaccttcat cagcctgctg ttcctgttct ccagcgccta ctccgattgc      60
gacatcgagg gcaaggacgg caagcagtac gagagcgtgc tgatggtgtc catcgaccag     120
ctgctggaca gcatgaagga gatcggctcc aactgcctca caacgagtt caacttcttc      180 aagcggcaca tctgcgacgc caacaaggag ggcatgttcc tgttcagggc cgccaggaaa     240
ctgcggcagt tcctgaagat gaactccacc ggcgacttcg acctgcacct gctgaaggtg     300
tccgagggca ccaccatcct gctgaactgc accggacagg tgaagggccg gaaacctgct     360
gctctgggag aggcccaacc caccaagagc ctggaggaga caagtccct gaaggagcag      420 aagaagctga cgacctgtg cttcctgaag aggctgctgc aggagatcaa gacctgctgg      480
```

```
aacaagatcc tgatgggcac caaggagcat attacatgcc ccctcccat gagcgtggag    540 cacgccgaca tctgggtgaa gagctatagc ctctacagcc gggagaggta tatctgtaac    600
agcggcttca agaggaaggc cggcaccagc agcctcaccg agtgcgtgct gaataaggct    660
accaacgtgg ctcactggac aacaccctct ttaaagtgca tccgg                   705
```

```
<210> SEQ ID NO 149
<211> LENGTH: 620
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-TGFR sequence"

<400> SEQUENCE: 149
```

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ser
        275                 280                 285

Gly Thr Thr Asn Thr Val Ala Ala Tyr Asn Leu Thr Trp Lys Ser Thr
    290                 295                 300

Asn Phe Lys Thr Ile Leu Glu Trp Glu Pro Lys Pro Val Asn Gln Val
305                 310                 315                 320
```

Tyr Thr Val Gln Ile Ser Thr Lys Ser Gly Asp Trp Lys Ser Lys Cys
             325                 330                 335

Phe Tyr Thr Thr Asp Thr Glu Cys Asp Leu Thr Asp Glu Ile Val Lys
             340                 345                 350

Asp Val Lys Gln Thr Tyr Leu Ala Arg Val Phe Ser Tyr Pro Ala Gly
             355                 360                 365

Asn Val Glu Ser Thr Gly Ser Ala Gly Glu Pro Leu Tyr Glu Asn Ser
             370                 375                 380

Pro Glu Phe Thr Pro Tyr Leu Glu Thr Asn Leu Gly Gln Pro Thr Ile
385                 390                 395                 400

Gln Ser Phe Glu Gln Val Gly Thr Lys Val Asn Val Thr Val Glu Asp
             405                 410                 415

Glu Arg Thr Leu Val Arg Arg Asn Asn Thr Phe Leu Ser Leu Arg Asp
             420                 425                 430

Val Phe Gly Lys Asp Leu Ile Tyr Thr Leu Tyr Tyr Trp Lys Ser Ser
             435                 440                 445

Ser Ser Gly Lys Lys Thr Ala Lys Thr Asn Thr Asn Glu Phe Leu Ile
             450                 455                 460

Asp Val Asp Lys Gly Glu Asn Tyr Cys Phe Ser Val Gln Ala Val Ile
465                 470                 475                 480

Pro Ser Arg Thr Val Asn Arg Lys Ser Thr Asp Ser Pro Val Glu Cys
             485                 490                 495

Met Gly Gln Glu Lys Gly Glu Phe Arg Glu Asn Trp Val Asn Val Ile
             500                 505                 510

Ser Asp Leu Lys Lys Ile Glu Asp Leu Ile Gln Ser Met His Ile Asp
             515                 520                 525

Ala Thr Leu Tyr Thr Glu Ser Asp Val His Pro Ser Cys Lys Val Thr
             530                 535                 540

Ala Met Lys Cys Phe Leu Leu Glu Leu Gln Val Ile Ser Leu Glu Ser
545                 550                 555                 560

Gly Asp Ala Ser Ile His Asp Thr Val Glu Asn Leu Ile Ile Leu Ala
             565                 570                 575

Asn Asn Ser Leu Ser Ser Asn Gly Asn Val Thr Glu Ser Gly Cys Lys
             580                 585                 590

Glu Cys Glu Glu Leu Glu Glu Lys Asn Ile Lys Glu Phe Leu Gln Ser
             595                 600                 605

Phe Val His Ile Val Gln Met Phe Ile Asn Thr Ser
610                 615                 620

<210> SEQ ID NO 150
<211> LENGTH: 1860
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic TGFRt15-TGFR sequence"

<400> SEQUENCE: 150
atcccccccc atgtgcaaaa gagcgtgaac aacgatatga tcgtgaccga caacaacggc      60
gccgtgaagt ttccccagct ctgcaagttc tgcgatgtca ggttcagcac ctgcgataat     120
cagaagtcct gcatgtccaa ctgcagcatc acctccatct gcgagaagcc ccaagaagtg     180
tgcgtggccg tgtggcggaa aaatgacgag aacatcaccc tggagaccgt gtgtcacgac     240
cccaagctcc cttatcacga cttcattctg gaggacgctg cctcccccaa atgcatcatg     300

```
aaggagaaga agaagcccgg agagaccttc tttatgtgtt cctgtagcag cgacgagtgt    360
aacgacaaca tcatcttcag cgaagagtac aacaccagca accctgatgg aggtggcgga    420
tccggaggtg gaggttctgg tggaggtggg agtattcctc cccacgtgca agagagcgtg    480
aataatgaca tgatcgtgac cgataacaat ggcgccgtga aatttcccca gctgtgcaaa    540
ttctgcgatg tgaggttttc cacctgcgac aaccagaagt cctgtatgag caactgctcc    600
atcacctcca tctgtgagaa gcctcaggag gtgtgcgtgg ctgtctggcg aagaatgac    660
gagaatatca ccctggaaac cgtctgccac gatcccaagc tgccctacca cgatttcatc    720
ctggaagacg ccgccagccc taagtgcatc atgaaagaga aaagaagcc tggcgagacc    780
tttttcatgt gctcctgcag cagcgacgaa tgcaacgaca atatcatctt tagcgaggaa    840
tacaatacca gcaaccccga cagcggcaca accaacacag tcgctgccta aacctcact    900
tggaagagca ccaacttcaa aaccatcctc gaatgggaac ccaaacccgt taaccaagtt    960
tacaccgtgc agatcagcac caagtccggc gactggaagt ccaaatgttt ctataccacc   1020
gacaccgagt gcgatctcac cgatgagatc gtgaaagatg tgaaacagac ctacctcgcc   1080
cgggtgttta gctaccccgc cggcaatgtg gagagcactg gttccgctgg cgagcccttta  1140
tacgagaaca gccccgaatt taccccttac ctcgagacca atttaggaca gcccaccatc   1200
caaagctttg agcaagttgg cacaaaggtg aatgtgacag tggaggacga gcggacttta   1260
gtgcggcgga acaacacctt tctcagcctc cgggatgtgt tcggcaaaga tttaatctac   1320
acactgtatt actggaagtc ctcttcctcc ggcaagaaga cagctaaaac caacacaaac   1380
gagtttttaa tcgacgtgga taaaggcgaa aactactgtt tcagcgtgca agctgtgatc   1440
ccctcccgga ccgtgaatag gaaaagcacc gatagccccg ttgagtgcat gggccaagaa   1500
aagggcgagt tccgggagaa ctgggtgaac gtcatcagcg atttaaagaa gatcgaagat   1560
ttaattcagt ccatgcatat cgacgccact ttatacacag aatccgacgt gcacccctct   1620
tgtaaggtga ccgccatgaa atgttttta ctggagctgc aagttatctc tttagagagc   1680
ggagacgcta gcatccacga caccgtggag aatttaatca ttttagccaa taactcttta   1740
tccagcaacg gcaacgtgac agagtccggc tgcaaggagt gcgaagagct ggaggagaag   1800
aacatcaagg agtttctgca atcctttgtg cacattgtcc agatgttcat caatacctcc   1860
```

<210> SEQ ID NO 151
<211> LENGTH: 638
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-TGFR sequence"

<400> SEQUENCE: 151

Met Lys Trp Val Thr Phe Ile Ser Leu Leu Phe Leu Phe Ser Ser Ala
1               5                  10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

-continued

```
Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
        180                 185                 190

Phe Pro Gln Leu Cys Lys Phe Cys Asp Val Arg Phe Ser Thr Cys Asp
    195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
                260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
                325                 330                 335

Gln Val Tyr Thr Val Gln Ile Ser Thr Lys Ser Gly Asp Trp Lys Ser
            340                 345                 350

Lys Cys Phe Tyr Thr Thr Asp Thr Glu Cys Asp Leu Thr Asp Glu Ile
        355                 360                 365

Val Lys Asp Val Lys Gln Thr Tyr Leu Ala Arg Val Phe Ser Tyr Pro
370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415

Thr Ile Gln Ser Phe Glu Gln Val Gly Thr Lys Val Asn Val Thr Val
            420                 425                 430

Glu Asp Glu Arg Thr Leu Val Arg Arg Asn Asn Thr Phe Leu Ser Leu
        435                 440                 445

Arg Asp Val Phe Gly Lys Asp Leu Ile Tyr Thr Leu Tyr Tyr Trp Lys
    450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                485                 490                 495
```

```
Val Ile Pro Ser Arg Thr Val Asn Arg Lys Ser Thr Asp Ser Pro Val
                500                 505                 510

Glu Cys Met Gly Gln Glu Lys Gly Glu Phe Arg Glu Asn Trp Val Asn
            515                 520                 525

Val Ile Ser Asp Leu Lys Lys Ile Glu Asp Leu Ile Gln Ser Met His
        530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
        595                 600                 605

Cys Lys Glu Cys Glu Glu Leu Glu Glu Lys Asn Ile Lys Glu Phe Leu
610                 615                 620

Gln Ser Phe Val His Ile Val Gln Met Phe Ile Asn Thr Ser
625                 630                 635

<210> SEQ ID NO 152
<211> LENGTH: 1914
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFR sequence"

<400> SEQUENCE: 152
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agccccaaga agtgtgcgtg     240
gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaaccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg ctccatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gccctaagtg catcatgaaa gagaaaaaga gcctggcga gacctttttc     840 atgtgctcct gcagcagcga cgaatgcaac gacaatatca tctttagcga ggaatacaat     900
accagcaacc ccgacagcgg cacaaccaac acagtcgctg cctataacct cacttggaag     960
agcaccaact tcaaaaccat cctcgaatgg gaacccaaac ccgttaacca agtttacacc    1020
gtgcagatca gcaccaagtc cggcgactgg aagtccaaat gtttctatac caccgacacc    1080
gagtgcgatc tcaccgatga gatcgtgaaa gatgtgaaac agaacctacct cgcccgggtg    1140 tttagctacc ccgccggcaa tgtggagagc actggttccg ctggcgagcc tttatacgag    1200
```

```
aacagcccccg aatttacccc ttacctcgag accaatttag gacagcccac catccaaagc   1260
tttgagcaag ttggcacaaa ggtgaatgtg acagtggagg acgagcggac tttagtgcgg   1320
cggaacaaca cctttctcag cctccgggat gtgttcggca agatttaat ctacacactg    1380 tattactgga agtcctcttc ctccggcaag aagacagcta aaccaacac aaacgagttt    1440 ttaatcgacg tggataaagg cgaaaactac tgtttcagcg tgcaagctgt gatcccctcc   1500
cggaccgtga ataggaaaag caccgatagc cccgttgagt gcatgggcca agaaaagggc   1560
gagttccggg agaactgggt gaacgtcatc agcgatttaa agaagatcga agatttaatt   1620
cagtccatgc atatcgacgc cactttatac acagaatccg acgtgcaccc ctcttgtaag   1680
gtgaccgcca tgaaatgttt tttactggag ctgcaagtta tctctttaga gagcggagac   1740
gctagcatcc acgacaccgt ggagaattta atcattttag ccaataactc tttatccagc   1800
aacggcaacg tgacagagtc cggctgcaag gagtgcgaag agctggagga gaagaacatc   1860
aaggagtttc tgcaatcctt tgtgcacatt gtccagatgt tcatcaatac ctcc         1914
```

<210> SEQ ID NO 153
<211> LENGTH: 352
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-TGFR sequence"

<400> SEQUENCE: 153

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
```

```
                225                 230                 235                 240
Leu Glu Asp Ala Ala Ser Pro Lys Cys Ile Met Lys Glu Lys Lys
                    245                 250                 255

Pro Gly Glu Thr Phe Phe Met Cys Ser Cys Ser Ser Asp Glu Cys Asn
                260                 265                 270

Asp Asn Ile Ile Phe Ser Glu Glu Tyr Asn Thr Ser Asn Pro Asp Ile
                275                 280                 285

Thr Cys Pro Pro Pro Met Ser Val Glu His Ala Asp Ile Trp Val Lys
            290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
                    325                 330                 335

Ala Thr Asn Val Ala His Trp Thr Thr Pro Ser Leu Lys Cys Ile Arg
                340                 345                 350
```

<210> SEQ ID NO 154
<211> LENGTH: 1056
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFR sequence"

<400> SEQUENCE: 154

```
atccccccc  atgtgcaaaa  gagcgtgaac  aacgatatga  tcgtgaccga  caacaacggc    60
gccgtgaagt  ttccccagct  ctgcaagttc  tgcgatgtca  ggttcagcac  ctgcgataat  120
cagaagtcct  gcatgtccaa  ctgcagcatc  acctccatct  gcgagaagcc  ccaagaagtg  180
tgcgtggccg  tgtggcggaa  aaatgacgag  aacatcaccc  tggagaccgt  gtgtcacgac  240
cccaagctcc  cttatcacga  cttcattctg  gaggacgctg  cctcccccaa  atgcatcatg  300
aaggagaaga  agaagcccgg  agagaccttc  tttatgtgtt  cctgtagcag  cgacgagtgt  360
aacgacaaca  tcatcttcag  cgaagagtac  aacaccagca  accctgatgg  aggtggcgga  420
tccggaggtg  gaggttctgg  tggaggtggg  agtattcctc  cccacgtgca  gaagagcgtg  480
aataatgaca  tgatcgtgac  cgataacaat  ggcgccgtga  aatttcccca  gctgtgcaaa  540
ttctgcgatg  tgaggttttc  cacctgcgac  aaccagaagt  cctgtatgag  caactgctcc  600
atcacctcca  tctgtgagaa  gcctcaggag  gtgtgcgtgg  ctgtctggcg  gaagaatgac  660
gagaatatca  ccctggaaac  cgtctgccac  gatcccaagc  tgccctacca  cgatttcatc  720
ctggaagacg  ccgccagccc  taagtgcatc  atgaaagaga  aaagaagcc  tggcgagacc  780
tttttcatgt  gctcctgcag  cagcgacgaa  tgcaacgaca  tatcatcttt  agcgaggaa  840
tacaatacca  gcaaccccga  cattacatgc  ccccctccca  tgagcgtgga  gcacgccgac  900
atctgggtga  agagctatag  cctctacagc  cgggagaggt  atatctgtaa  cagcggcttc  960
aagaggaagg  ccggcaccag  cagcctcacc  gagtgcgtgc  tgaataaggc  taccaacgtg  1020
gctcactgga  caacaccctc  tttaaagtgc  atccgg                              1056
```

<210> SEQ ID NO 155
<211> LENGTH: 370
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic TGFRt15-TGFR sequence"

<400> SEQUENCE: 155

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
            115                 120                 125

Phe Met Cys Ser Cys Ser Ser Asp Glu Cys Asn Asp Asn Ile Ile Phe
130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
            195                 200                 205

Asn Gln Lys Ser Cys Met Ser Asn Cys Ser Ile Thr Ser Ile Cys Glu
            210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
            275                 280                 285

Cys Asn Asp Asn Ile Ile Phe Ser Glu Glu Tyr Asn Thr Ser Asn Pro
290                 295                 300

Asp Ile Thr Cys Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
            325                 330                 335

Gly Phe Lys Arg Lys Ala Gly Thr Ser Ser Leu Thr Glu Cys Val Leu
                340                 345                 350

Asn Lys Ala Thr Asn Val Ala His Trp Thr Thr Pro Ser Leu Lys Cys
            355                 360                 365

Ile Arg
370
```

<210> SEQ ID NO 156
<211> LENGTH: 1110

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic TGFRt15-TGFR sequence"

<400> SEQUENCE: 156

```
atgaagtggg tgaccttcat cagcctgctg ttcctgttct ccagcgccta ctccatcccc    60
ccccatgtgc aaaagagcgt gaacaacgat atgatcgtga ccgacaacaa cggcgccgtg   120
aagtttcccc agctctgcaa gttctgcgat gtcaggttca gcacctgcga taatcagaag   180
tcctgcatgt ccaactgcag catcacctcc atctgcgaga agccccaaga agtgtgcgtg   240
gccgtgtggc ggaaaaatga cgagaacatc accctggaga ccgtgtgtca cgaccccaag   300
ctcccttatc acgacttcat tctggaggac gctgcctccc ccaaatgcat catgaaggag   360
aagaagaagc ccggagagac cttctttatg tgttcctgta gcagcgacga gtgtaacgac   420
aacatcatct tcagcgaaga gtacaacacc agcaaccctg atggaggtgg cggatccgga   480
ggtggaggtt ctggtggagg tgggagtatt cctccccacg tgcagaagag cgtgaataat   540
gacatgatcg tgaccgataa caatggcgcc gtgaaatttc cccagctgtg caaattctgc   600
gatgtgaggt tttccacctg cgacaaccag aagtcctgta tgagcaactg ctccatcacc   660
tccatctgtg agaagcctca ggaggtgtgc gtggctgtct ggcggaagaa tgacgagaat   720
atcacccctg gaaaccgtct gccacgatcc caagctgccct accacgattt catcctggaa   780
gacgccgcca gccctaagtg catcatgaaa gagaaaaaga gcctggcga gaccttttc   840
atgtgctcct gcagcagcga cgaatgcaac gacaatatca tctttagcga ggaatacaat   900
accagcaacc ccgacattac atgccccct cccatgagcg tggagcacgc cgacatctgg   960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
tggacaacac cctcttttaa agtgcatccgg                                  1110
```

<210> SEQ ID NO 157
<211> LENGTH: 184
<212> TYPE: PRT
<213> ORGANISM: Homo sapiens
<220> FEATURE:
<221> NAME/KEY: source
<223> OTHER INFORMATION: /note="CD137L"

<400> SEQUENCE: 157

```
Arg Glu Gly Pro Glu Leu Ser Pro Asp Asp Pro Ala Gly Leu Leu Asp
1               5                   10                  15
Leu Arg Gln Gly Met Phe Ala Gln Leu Val Ala Gln Asn Val Leu Leu
            20                  25                  30
Ile Asp Gly Pro Leu Ser Trp Tyr Ser Asp Pro Gly Leu Ala Gly Val
        35                  40                  45
Ser Leu Thr Gly Gly Leu Ser Tyr Lys Glu Asp Thr Lys Glu Leu Val
    50                  55                  60
Val Ala Lys Ala Gly Val Tyr Tyr Val Phe Phe Gln Leu Glu Leu Arg
65                  70                  75                  80
Arg Val Val Ala Gly Glu Gly Ser Gly Ser Val Ser Leu Ala Leu His
                85                  90                  95
Leu Gln Pro Leu Arg Ser Ala Ala Gly Ala Ala Ala Leu Ala Leu Thr
            100                 105                 110
```

```
Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180

<210> SEQ ID NO 158
<211> LENGTH: 552
<212> TYPE: DNA
<213> ORGANISM: Homo sapiens
<220> FEATURE:
<221> NAME/KEY: source
<223> OTHER INFORMATION: /note="CD137L"

<400> SEQUENCE: 158
cgcgagggtc ccgagctttc gcccgacgat cccgccggcc tcttggacct gcggcagggc      60
atgtttgcgc agctggtggc ccaaaatgtt ctgctgatcg atgggcccct gagctggtac     120
agtgacccag gcctggcagg cgtgtccctg acgggggggcc tgagctacaa gaggacacg     180 aaggagctgt tggtggccaa ggctggagtc tactatgtct ctttcaact agagctgcgg     240 cgcgtggtgg ccggcgaggg ctcaggctcc gtttcacttg cgctgcacct gcagccactg     300
cgctctgctg ctggggccgc cgccctggct ttgaccgtgg acctgccacc cgcctcctcc     360
gaggctcgga actcggcctt cggtttccag gccgcttgc tgcacctgag tgccggccag     420
cgcctgggcg tccatcttca cactgaggcc agggcacgcc atgcctggca gcttacccag     480
ggcgccacag tcttgggact cttccggtg accccgaaa tcccagccgg actcccttca     540
ccgaggtcgg aa                                                         552

<210> SEQ ID NO 159
<211> LENGTH: 165
<212> TYPE: PRT
<213> ORGANISM: Homo sapiens
<220> FEATURE:
<221> NAME/KEY: source
<223> OTHER INFORMATION: /note="CD137L"

<400> SEQUENCE: 159

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
```

```
                115                 120                 125
Ala Gly Gln Arg Leu Gly Val His Leu His Thr Glu Ala Arg Ala Arg
            130                 135                 140

His Ala Trp Gln Leu Thr Gln Gly Ala Thr Val Leu Gly Leu Phe Arg
145                 150                 155                 160

Val Thr Pro Glu Ile
                165

<210> SEQ ID NO 160
<211> LENGTH: 495
<212> TYPE: DNA
<213> ORGANISM: Homo sapiens
<220> FEATURE:
<221> NAME/KEY: source
<223> OTHER INFORMATION: /note="CD137L"

<400> SEQUENCE: 160
gatcccgccg gcctcttgga cctgcggcag ggcatgtttg cgcagctggt ggcccaaaat      60
gttctgctga tcgatgggcc cctgagctgg tacagtgacc aggcctggc aggcgtgtcc      120 ctgacggggg gcctgagcta caaagaggac acgaaggagc tggtggtggc caaggctgga    180
gtctactatg tcttctttca actagagctg cggcgcgtgg tggccggcga gggctcaggc    240
tccgtttcac ttgcgctgca cctgcagcca ctgcgctctg ctgctggggc cgccgccctg    300
gctttgaccg tggacctgcc acccgcctcc tccgaggctc ggaactcggc cttcggtttc    360
cagggccgct tgctgcacct gagtgccggc cagcgcctgg cgtccatct tcacactgag     420 gccagggcac gccatgcctg gcagcttacc cagggcgcca cagtcttggg actcttccgg    480 gtgaccccg aaatc                                                      495

<210> SEQ ID NO 161
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-21s137L sequence"

<400> SEQUENCE: 161

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140
```

```
Ile Leu Met Gly Thr Lys Glu His Ser Gly Thr Asn Thr Val Ala
145                 150                 155                 160

Ala Tyr Asn Leu Thr Trp Lys Ser Thr Asn Phe Lys Thr Ile Leu Glu
            165                 170                 175

Trp Glu Pro Lys Pro Val Asn Gln Val Tyr Thr Val Gln Ile Ser Thr
                180                 185                 190

Lys Ser Gly Asp Trp Lys Ser Lys Cys Phe Tyr Thr Thr Asp Thr Glu
            195                 200                 205

Cys Asp Leu Thr Asp Glu Ile Val Lys Asp Val Lys Gln Thr Tyr Leu
210                 215                 220

Ala Arg Val Phe Ser Tyr Pro Ala Gly Asn Val Glu Ser Thr Gly Ser
225                 230                 235                 240

Ala Gly Glu Pro Leu Tyr Glu Asn Ser Pro Glu Phe Thr Pro Tyr Leu
                245                 250                 255

Glu Thr Asn Leu Gly Gln Pro Thr Ile Gln Ser Phe Glu Gln Val Gly
            260                 265                 270

Thr Lys Val Asn Val Thr Val Glu Asp Glu Arg Thr Leu Val Arg Arg
        275                 280                 285

Asn Asn Thr Phe Leu Ser Leu Arg Asp Val Phe Gly Lys Asp Leu Ile
290                 295                 300

Tyr Thr Leu Tyr Tyr Trp Lys Ser Ser Ser Gly Lys Lys Thr Ala
305                 310                 315                 320

Lys Thr Asn Thr Asn Glu Phe Leu Ile Asp Val Asp Lys Gly Glu Asn
                325                 330                 335

Tyr Cys Phe Ser Val Gln Ala Val Ile Pro Ser Arg Thr Val Asn Arg
            340                 345                 350

Lys Ser Thr Asp Ser Pro Val Glu Cys Met Gly Gln Glu Lys Gly Glu
        355                 360                 365

Phe Arg Glu Asn Trp Val Asn Val Ile Ser Asp Leu Lys Lys Ile Glu
370                 375                 380

Asp Leu Ile Gln Ser Met His Ile Asp Ala Thr Leu Tyr Thr Glu Ser
385                 390                 395                 400

Asp Val His Pro Ser Cys Lys Val Thr Ala Met Lys Cys Phe Leu Leu
                405                 410                 415

Glu Leu Gln Val Ile Ser Leu Glu Ser Gly Asp Ala Ser Ile His Asp
            420                 425                 430

Thr Val Glu Asn Leu Ile Ile Leu Ala Asn Asn Ser Leu Ser Ser Asn
        435                 440                 445

Gly Asn Val Thr Glu Ser Gly Cys Lys Glu Cys Glu Glu Leu Glu Glu
450                 455                 460

Lys Asn Ile Lys Glu Phe Leu Gln Ser Phe Val His Ile Val Gln Met
465                 470                 475                 480

Phe Ile Asn Thr Ser
                485
```

<210> SEQ ID NO 162
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-21s137L sequence"

<400> SEQUENCE: 162
gattgcgaca tcgagggcaa ggacggcaag cagtacgaga gcgtgctgat ggtgtccatc          60

```
gaccagctgc tggacagcat gaaggagatc ggctccaact gcctcaacaa cgagttcaac    120
ttcttcaagc ggcacatctg cgacgccaac aaggagggca tgttcctgtt cagggccgcc    180
aggaaactgc ggcagttcct gaagatgaac tccaccggcg acttcgacct gcacctgctg    240
aaggtgtccg agggcaccac catcctgctg aactgcaccg acaggtgaa gggccggaaa    300
cctgctgctc tgggagaggc ccaacccacc aagagcctgg aggagaacaa gtccctgaag    360
gagcagaaga agctgaacga cctgtgcttc ctgaagaggc tgctgcagga gatcaagacc    420
tgctggaaca agatcctgat gggcaccaag gagcatagcg gcacaaccaa cacagtcgct    480
gcctataacc tcacttggaa gagcaccaac ttcaaaacca tcctcgaatg gaacccaaa    540
cccgttaacc aagtttacac cgtgcagatc agcaccaagt ccggcgactg aagtccaaa    600
tgtttctata ccaccgacac cgagtgcgat ctcaccgatg agatcgtgaa agatgtgaaa    660
cagacctacc tcgcccgggt gtttagctac cccgccggca atgtggagag cactggttcc    720
gctggcgagc cttatacga gaacagcccc gaatttaccc cttacctcga gaccaattta    780
ggacagccca ccatccaaag ctttgagcaa gttggcacaa aggtgaatgt gacagtggag    840
gacgagcgga ctttagtgcg gcggaacaac accttctca gcctccggga tgtgttcggc    900
aaagatttaa tctacacact gtattactgg aagtcctctt cctccggcaa gaagacagct    960
aaaaccaaca caaacgagtt tttaatcgac gtggataaag gcgaaaacta ctgtttcagc   1020
gtgcaagctg tgatcccctc ccggaccgtg aataggaaaa gcaccgatag ccccgttgag   1080
tgcatgggcc aagaaaaggg cgagttccgg gagaactggg tgaacgtcat cagcgattta   1140
aagaagatcg aagatttaat tcagtccatg catatcgacg ccactttata cacagaatcc   1200
gacgtgcacc cctcttgtaa ggtgaccgcc atgaaatgtt ttttactgga gctgcaagtt   1260
atctctttag agagcggaga cgctagcatc cacgacaccg tggagaattt aatcattta   1320
gccataact ctttatccag caacggcaac gtgacagagt ccggctgcaa ggagtgcgaa   1380
gagctggagg agaagaacat caaggagttt ctgcaatcct tgtgcacat tgtccagatg   1440
ttcatcaata cctcc                                                    1455
```

<210> SEQ ID NO 163
<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-21s137L sequence"

<400> SEQUENCE: 163

```
Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95
```

-continued

```
Leu Leu Lys Val Ser Glu Gly Thr Thr Ile Leu Leu Asn Cys Thr Gly
            100                 105                 110

Gln Val Lys Gly Arg Lys Pro Ala Ala Leu Gly Glu Ala Gln Pro Thr
        115                 120                 125

Lys Ser Leu Glu Glu Asn Lys Ser Leu Lys Glu Gln Lys Lys Leu Asn
130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ser Gly Thr Thr Asn Thr
                165                 170                 175

Val Ala Ala Tyr Asn Leu Thr Trp Lys Ser Thr Asn Phe Lys Thr Ile
            180                 185                 190

Leu Glu Trp Glu Pro Lys Pro Val Asn Gln Val Tyr Thr Val Gln Ile
        195                 200                 205

Ser Thr Lys Ser Gly Asp Trp Lys Ser Lys Cys Phe Tyr Thr Thr Asp
    210                 215                 220

Thr Glu Cys Asp Leu Thr Asp Glu Ile Val Lys Asp Val Lys Gln Thr
225                 230                 235                 240

Tyr Leu Ala Arg Val Phe Ser Tyr Pro Ala Gly Asn Val Glu Ser Thr
                245                 250                 255

Gly Ser Ala Gly Glu Pro Leu Tyr Glu Asn Ser Pro Glu Phe Thr Pro
            260                 265                 270

Tyr Leu Glu Thr Asn Leu Gly Gln Pro Thr Ile Gln Ser Phe Glu Gln
        275                 280                 285

Val Gly Thr Lys Val Asn Val Thr Val Glu Asp Glu Arg Thr Leu Val
    290                 295                 300

Arg Arg Asn Asn Thr Phe Leu Ser Leu Arg Asp Val Phe Gly Lys Asp
305                 310                 315                 320

Leu Ile Tyr Thr Leu Tyr Tyr Trp Lys Ser Ser Ser Gly Lys Lys
                325                 330                 335

Thr Ala Lys Thr Asn Thr Asn Glu Phe Leu Ile Asp Val Asp Lys Gly
            340                 345                 350

Glu Asn Tyr Cys Phe Ser Val Gln Ala Val Ile Pro Ser Arg Thr Val
        355                 360                 365

Asn Arg Lys Ser Thr Asp Ser Pro Val Glu Cys Met Gly Gln Glu Lys
370                 375                 380

Gly Glu Phe Arg Glu Asn Trp Val Asn Val Ile Ser Asp Leu Lys Lys
385                 390                 395                 400

Ile Glu Asp Leu Ile Gln Ser Met His Ile Asp Ala Thr Leu Tyr Thr
                405                 410                 415

Glu Ser Asp Val His Pro Ser Cys Lys Val Thr Ala Met Lys Cys Phe
            420                 425                 430

Leu Leu Glu Leu Gln Val Ile Ser Leu Glu Ser Gly Asp Ala Ser Ile
        435                 440                 445

His Asp Thr Val Glu Asn Leu Ile Ile Leu Ala Asn Asn Ser Leu Ser
    450                 455                 460

Ser Asn Gly Asn Val Thr Glu Ser Gly Cys Lys Glu Cys Glu Glu Leu
465                 470                 475                 480

Glu Glu Lys Asn Ile Lys Glu Phe Leu Gln Ser Phe Val His Ile Val
                485                 490                 495

Gln Met Phe Ile Asn Thr Ser
            500
```

<210> SEQ ID NO 164
<211> LENGTH: 1509
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-21s137L sequence"

<400> SEQUENCE: 164

```
atgaagtggg tgaccttcat cagcctgctg ttcctgttct ccagcgccta ctccgattgc      60
gacatcgagg gcaaggacgg caagcagtac gagagcgtgc tgatggtgtc catcgaccag     120
ctgctggaca gcatgaagga gatcggctcc aactgcctca caacgagtt caacttcttc      180
aagcggcaca tctgcgacgc caacaaggag ggcatgttcc tgttcagggc cgccaggaaa     240
ctgcggcagt cctgaagat gaactccacc ggcgacttcg acctgcacct gctgaaggtg     300
tccgagggca ccaccatcct gctgaactgc accggacagg tgaagggccg gaaacctgct     360
gctctgggag aggcccaacc caccaagagc ctggaggaga caagtccct gaaggagcag     420
aagaagctga cgacctgtg cttcctgaag aggctgctgc aggagatcaa gacctgctgg     480
aacaagatcc tgatgggcac caaggagcat agcggcacaa ccaacacagt cgctgcctat     540
aacctcactt ggaagagcac caacttcaaa accatcctcg aatgggaacc caaaccccgtt     600
aaccaagttt acaccgtgca gatcagcacc aagtccggcg actggaagtc caaatgtttc     660
tataccaccg acaccgagtg cgatctcacc gatgagatcg tgaaagatgt gaaacagacc     720
tacctcgccc gggtgtttag ctaccccgcc ggcaatgtgg agagcactgg ttccgctggc     780
gagcctttat acgagaacag ccccgaattt accccttacc tcgagaccaa tttaggacag     840
cccaccatcc aaagctttga gcaagttggc acaaaggtga atgtgacagt ggaggacgag     900
cggactttag tgcggcggaa caacaccttt ctcagcctcc gggatgtgtt cggcaaagat     960
ttaatctaca cactgtatta ctggaagtcc tcttcctccg gcaagaagac agctaaaacc    1020
aacacaaacg agttttttaat cgacgtggat aaaggcgaaa actactgttt cagcgtgcaa    1080
gctgtgatcc cctcccggac cgtgaatagg aaaagcaccg atagccccgt tgagtgcatg    1140
ggccaagaaa agggcgagtt ccgggagaac tgggtgaacg tcatcagcga tttaaagaag    1200
atcgaagatt taattcagtc catgcatatc gacgccactt tatacacaga atccgacgtg    1260
caccccctctt gtaaggtgac cgccatgaaa tgttttttac tggagctgca agttatctct    1320
ttagagagcg gagacgctag catccacgac accgtggaga atttaatcat tttagccaat    1380
aactcttttat ccagcaacgg caacgtgaca gagtccggct gcaaggagtg cgaagagctg    1440
gaggagaaga acatcaagga gtttctgcaa tcctttgtgc acattgtcca gatgttcatc    1500
aatacctcc                                                             1509
```

<210> SEQ ID NO 165
<211> LENGTH: 397
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-21s137L sequence"

<400> SEQUENCE: 165

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
```

```
            20                  25                  30
Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
            115                 120                 125

Gly Ser Glu Asp Ser Ile Thr Cys Pro Pro Met Ser Val Glu His
            130                 135                 140

Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

Glu Cys Val Leu Asn Lys Ala Thr Asn Val Ala His Trp Thr Thr Pro
            180                 185                 190

Ser Leu Lys Cys Ile Arg Gly Gly Gly Ser Gly Gly Gly Gly Ser
            195                 200                 205

Gly Gly Gly Gly Ser Arg Glu Gly Pro Glu Leu Ser Pro Asp Asp Pro
        210                 215                 220

Ala Gly Leu Leu Asp Leu Arg Gln Gly Met Phe Ala Gln Leu Val Ala
225                 230                 235                 240

Gln Asn Val Leu Leu Ile Asp Gly Pro Leu Ser Trp Tyr Ser Asp Pro
                245                 250                 255

Gly Leu Ala Gly Val Ser Leu Thr Gly Gly Leu Ser Tyr Lys Glu Asp
            260                 265                 270

Thr Lys Glu Leu Val Val Ala Lys Ala Gly Val Tyr Tyr Val Phe Phe
            275                 280                 285

Gln Leu Glu Leu Arg Arg Val Val Ala Gly Glu Gly Ser Gly Ser Val
            290                 295                 300

Ser Leu Ala Leu His Leu Gln Pro Leu Arg Ser Ala Ala Gly Ala Ala
305                 310                 315                 320

Ala Leu Ala Leu Thr Val Asp Leu Pro Pro Ala Ser Ser Glu Ala Arg
                325                 330                 335

Asn Ser Ala Phe Gly Phe Gln Gly Arg Leu Leu His Leu Ser Ala Gly
            340                 345                 350

Gln Arg Leu Gly Val His Leu His Thr Glu Ala Arg Ala Arg His Ala
            355                 360                 365

Trp Gln Leu Thr Gln Gly Ala Thr Val Leu Gly Leu Phe Arg Val Thr
        370                 375                 380

Pro Glu Ile Pro Ala Gly Leu Pro Ser Pro Arg Ser Glu
385                 390                 395
```

<210> SEQ ID NO 166
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic 7t15-21s137L sequence"

<400> SEQUENCE: 166

```
cagggccagg acaggcacat gatccggatg aggcagctca tcgacatcgt cgaccagctg    60
aagaactacg tgaacgacct ggtgcccgag tttctgcctg cccccgagga cgtggagacc   120
aactgcgagt ggtccgcctt ctcctgcttt cagaaggccc agctgaagtc cgccaacacc   180
ggcaacaacg agcggatcat caacgtgagc atcaagaagc tgaagcggaa gcctccctcc   240
acaaacgccg gcaggaggca gaagcacagg ctgacctgcc ccagctgtga ctcctacgag   300
aagaagcccc ccaaggagtt cctggagagg ttcaagtccc tgctgcagaa gatgatccat   360
cagcacctgt cctccaggac ccacggctcc gaggactcca ttacatgccc ccctcccatg   420
agcgtggagc acgccgacat ctgggtgaag agctatagcc tctacagccg ggagaggtat   480
atctgtaaca gcggcttcaa gaggaaggcc ggcaccagca gcctcaccga gtgcgtgctg   540
aataaggcta ccaacgtggc tcactggaca cacccctctt aaagtgcat ccggggcggt    600
ggaggatccg gaggaggtgg ctccggcggc ggaggatctc gcgagggtcc cgagctttcg   660
cccgacgatc ccgccggcct cttggacctg cggcagggca tgtttgcgca gctggtggcc   720
caaaatgttc tgctgatcga tgggcccctg agctggtaca gtgacccagg cctggcaggc   780
gtgtccctga cgggggggcct gagctacaaa gaggacacga aggagctggt ggtggccaag   840
gctggagtct actatgtctt ctttcaacta gagctgcggc gcgtggtggc cggcgagggc   900
tcaggctccg tttcacttgc gctgcacctg cagccactgc gctctgctgc tggggccgcc   960
gccctggctt tgaccgtgga cctgccaccc gcctcctccg aggctcggaa ctcggccttc   1020
ggtttccagg gccgcttgct gcacctgagt gccggccagc gcctgggcgt ccatcttcac  1080
actgaggcca gggcacgcca tgcctggcag cttaccagg gcgccacagt cttgggactc    1140
ttccgggtga ccccgaaat cccagccgga ctcccttcac cgaggtcgga a             1191
```

<210> SEQ ID NO 167
<211> LENGTH: 415
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-21s137L sequence"

<400> SEQUENCE: 167

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
                20                  25                  30

Asp Ile Val Asp Gln Leu Lys Asn Tyr Val Asn Asp Leu Val Pro Glu
            35                  40                  45

Phe Leu Pro Ala Pro Glu Asp Val Glu Thr Asn Cys Glu Trp Ser Ala
        50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
                100                 105                 110

Ser Cys Asp Ser Tyr Glu Lys Lys Pro Pro Lys Glu Phe Leu Glu Arg
            115                 120                 125
```

```
Phe Lys Ser Leu Leu Gln Lys Met Ile His Gln His Leu Ser Ser Arg
    130                 135                 140
Thr His Gly Ser Glu Asp Ser Ile Thr Cys Pro Pro Met Ser Val
145                 150                 155                 160
Glu His Ala Asp Ile Trp Val Lys Ser Tyr Ser Leu Tyr Ser Arg Glu
                165                 170                 175
Arg Tyr Ile Cys Asn Ser Gly Phe Lys Arg Lys Ala Gly Thr Ser Ser
            180                 185                 190
Leu Thr Glu Cys Val Leu Asn Lys Ala Thr Asn Val Ala His Trp Thr
        195                 200                 205
Thr Pro Ser Leu Lys Cys Ile Arg Gly Gly Gly Ser Gly Gly Gly
    210                 215                 220
Gly Ser Gly Gly Gly Gly Ser Arg Glu Gly Pro Glu Leu Ser Pro Asp
225                 230                 235                 240
Asp Pro Ala Gly Leu Leu Asp Leu Arg Gln Gly Met Phe Ala Gln Leu
                245                 250                 255
Val Ala Gln Asn Val Leu Leu Ile Asp Gly Pro Leu Ser Trp Tyr Ser
            260                 265                 270
Asp Pro Gly Leu Ala Gly Val Ser Leu Thr Gly Leu Ser Tyr Lys
        275                 280                 285
Glu Asp Thr Lys Glu Leu Val Val Ala Lys Ala Gly Val Tyr Tyr Val
    290                 295                 300
Phe Phe Gln Leu Glu Leu Arg Arg Val Val Ala Gly Glu Gly Ser Gly
305                 310                 315                 320
Ser Val Ser Leu Ala Leu His Leu Gln Pro Leu Arg Ser Ala Ala Gly
                325                 330                 335
Ala Ala Ala Leu Ala Leu Thr Val Asp Leu Pro Pro Ala Ser Ser Glu
            340                 345                 350
Ala Arg Asn Ser Ala Phe Gly Phe Gln Gly Arg Leu Leu His Leu Ser
        355                 360                 365
Ala Gly Gln Arg Leu Gly Val His Leu His Thr Glu Ala Arg Ala Arg
    370                 375                 380
His Ala Trp Gln Leu Thr Gln Gly Ala Thr Val Leu Gly Leu Phe Arg
385                 390                 395                 400
Val Thr Pro Glu Ile Pro Ala Gly Leu Pro Ser Pro Arg Ser Glu
                405                 410                 415

<210> SEQ ID NO 168
<211> LENGTH: 1245
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-21s137L sequence"

<400> SEQUENCE: 168
atgaagtggg tgaccttcat cagcctgctg ttcctgttct ccagcgccta ctcccagggc    60
caggacaggc acatgatccg gatgaggcag ctcatcgaca tcgtcgacca gctgaagaac   120
tacgtgaacg acctggtgcc cgagtttctg cctgccccg aggacgtgga gaccaactgc   180
gagtggtccg ccttctcctg ctttcagaag gcccagctga agtccgccaa caccggcaac   240
aacgagcgga tcatcaacgt gagcatcaag aagctgaagc ggaagcctcc ctccacaaac   300
gccggcagga ggcagaagca caggctgacc tgccccagct gtgactccta cgagaagaag   360
```

-continued

```
cccccccaagg agttcctgga gaggttcaag tccctgctgc agaagatgat ccatcagcac    420
ctgtcctcca ggacccacgg ctccgaggac tccattacat gccccctcc catgagcgtg     480
gagcacgccg acatctgggt gaagagctat agcctctaca gccgggagag gtatatctgt    540
aacagcggct tcaagaggaa ggccggcacc agcagcctca ccgagtgcgt gctgaataag    600
gctaccaacg tggctcactg gacaacaccc tctttaaagt gcatccgggg cggtggagga    660
tccggaggag gtggctccgg cggcggagga tctcgcgagg gtcccgagct ttcgcccgac    720
gatcccgccg gcctcttgga cctgcgcag ggcatgtttg cgcagctggt ggcccaaaat    780
gttctgctga tcgatgggcc cctgagctgg tacagtgacc caggcctggc aggcgtgtcc    840
ctgacggggg gcctgagcta caagaggac acgaaggagc tggtggtggc caaggctgga    900
gtctactatg tcttctttca actagagctg cggcgcgtgg tggccggcga gggctcaggc    960
tccgtttcac ttgcgctgca cctgcagcca ctgcgctctg ctgctgggc cgccgccctg   1020
gctttgaccg tggacctgcc acccgcctcc tccgaggctc ggaactcggc cttcggtttc   1080
cagggccgct tgctgcacct gagtgccggc cagcgcctgg gcgtccatct tcacactgag   1140
gccagggcac gccatgcctg gcagcttacc cagggcgcca cagtcttggg actcttccgg   1200
gtgaccccg aaatcccagc cggactccct tcaccgaggt cggaa                  1245
```

<210> SEQ ID NO 169
<211> LENGTH: 378
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-21s137L sequence"

<400> SEQUENCE: 169

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ile Thr Cys Pro Pro Met Ser Val Glu His
    130                 135                 140

Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

Glu Cys Val Leu Asn Lys Ala Thr Asn Val Ala His Trp Thr Thr Pro
            180                 185                 190

Ser Leu Lys Cys Ile Arg Gly Gly Gly Gly Ser Gly Gly Gly Gly Ser

```
                195                 200                 205
Gly Gly Gly Gly Ser Asp Pro Ala Gly Leu Leu Asp Leu Arg Gln Gly
        210                 215                 220

Met Phe Ala Gln Leu Val Ala Gln Asn Val Leu Leu Ile Asp Gly Pro
225                 230                 235                 240

Leu Ser Trp Tyr Ser Asp Pro Gly Leu Ala Gly Val Ser Leu Thr Gly
                245                 250                 255

Gly Leu Ser Tyr Lys Glu Asp Thr Lys Glu Leu Val Val Ala Lys Ala
            260                 265                 270

Gly Val Tyr Tyr Val Phe Phe Gln Leu Glu Leu Arg Arg Val Val Ala
        275                 280                 285

Gly Glu Gly Ser Gly Ser Val Ser Leu Ala Leu His Leu Gln Pro Leu
    290                 295                 300

Arg Ser Ala Ala Gly Ala Ala Ala Leu Ala Leu Thr Val Asp Leu Pro
305                 310                 315                 320

Pro Ala Ser Ser Glu Ala Arg Asn Ser Ala Phe Gly Phe Gln Gly Arg
                325                 330                 335

Leu Leu His Leu Ser Ala Gly Gln Arg Leu Gly Val His Leu His Thr
            340                 345                 350

Glu Ala Arg Ala Arg His Ala Trp Gln Leu Thr Gln Gly Ala Thr Val
        355                 360                 365

Leu Gly Leu Phe Arg Val Thr Pro Glu Ile
    370                 375
```

<210> SEQ ID NO 170
<211> LENGTH: 1134
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic 7t15-21s137L sequence"

<400> SEQUENCE: 170

```
cagggccagg acaggcacat gatccggatg aggcagctca tcgacatcgt cgaccagctg    60
aagaactacg tgaacgacct ggtgcccgag tttctgcctg cccccgagga cgtggagacc   120
aactgcgagt ggtccgcctt ctcctgcttt cagaaggccc agctgaagtc cgccaacacc   180
ggcaacaacg agcggatcat caacgtgagc atcaagaagc tgaagcggaa gcctccctcc   240
acaaacgccg gcaggaggca gaagcacagg ctgacctgcc ccagctgtga ctcctacgag   300
aagaagcccc ccaaggagtt cctggagagg ttcaagtccc tgctgcagaa gatgatccat   360
cagcacctgt cctccaggac ccacggctcc gaggactcca ttacatgccc cctcccatg    420 agcgtggagc acgccgacat ctgggtgaag agctatagcc tctacagccg ggagaggtat   480
atctgtaaca gcggcttcaa gaggaaggcc ggcaccagca gcctcaccga gtgcgtgctg   540
aataaggcta ccaacgtggc tcactggaca caccctctt taaagtgcat ccggggcggt   600
ggaggatccg gaggaggtgg ctccggcggc ggaggatctg atcccgccgg cctcttggac   660
ctgcggcagg gcatgtttgc gcagctggtg gcccaaaatg ttctgctgat cgatgggccc   720
ctgagctggt acagtgaccc aggcctggca ggcgtgtccc tgacgggggg cctgagctac   780
aaagaggaca cgaaggagct ggtggtggcc aaggctggag tctactatgt cttctttcaa   840
ctagagctgc ggcgcgtggt ggccggcgag ggctcaggct ccgtttcact tgcgctgcac   900
ctgcagccac tgcgctctgc tgctggggcc gcgccctgg ctttgaccgt ggacctgcca   960
```

```
cccgcctcct ccgaggctcg gaactcggcc ttcggtttcc agggccgctt gctgcacctg   1020
agtgccggcc agcgcctggg cgtccatctt cacactgagg ccagggcacg ccatgcctgg   1080
cagcttaccc agggcgccac agtcttggga ctcttccggg tgaccccga aatc          1134
```

<210> SEQ ID NO 171
<211> LENGTH: 396
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-21s137L sequence"

<400> SEQUENCE: 171

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr
        195                 200                 205

Thr Pro Ser Leu Lys Cys Ile Arg Gly Gly Gly Ser Gly Gly Gly
    210                 215                 220

Gly Ser Gly Gly Gly Gly Ser Asp Pro Ala Gly Leu Leu Asp Leu Arg
225                 230                 235                 240

Gln Gly Met Phe Ala Gln Leu Val Ala Gln Asn Val Leu Leu Ile Asp
                245                 250                 255

Gly Pro Leu Ser Trp Tyr Ser Asp Pro Gly Leu Ala Gly Val Ser Leu
            260                 265                 270

Thr Gly Gly Leu Ser Tyr Lys Glu Asp Thr Lys Glu Leu Val Val Ala
        275                 280                 285

Lys Ala Gly Val Tyr Tyr Val Phe Phe Gln Leu Glu Leu Arg Arg Val
    290                 295                 300

Val Ala Gly Glu Gly Ser Gly Ser Val Ser Leu Ala Leu His Leu Gln
305                 310                 315                 320

Pro Leu Arg Ser Ala Ala Gly Ala Ala Ala Leu Ala Leu Thr Val Asp
```

```
                    325                 330                 335
Leu Pro Pro Ala Ser Ser Glu Ala Arg Asn Ser Ala Phe Gly Phe Gln
            340                 345                 350
Gly Arg Leu Leu His Leu Ser Ala Gly Gln Arg Leu Gly Val His Leu
        355                 360                 365
His Thr Glu Ala Arg Ala Arg His Ala Trp Gln Leu Thr Gln Gly Ala
    370                 375                 380
Thr Val Leu Gly Leu Phe Arg Val Thr Pro Glu Ile
385                 390                 395
```

<210> SEQ ID NO 172
<211> LENGTH: 1188
<212> TYPE: DNA
<213> ORGANISM: Artificial Sequence
<220> FEATURE:
<221> NAME/KEY: source
<223> OTHER INFORMATION: /note="Description of Artificial Sequence: Synthetic 7t15-21s137L sequence"

<400> SEQUENCE: 172

```
atgaagtggg tgaccttcat cagcctgctg ttcctgttct ccagcgccta ctcccagggc    60
caggacaggc acatgatccg gatgaggcag ctcatcgaca tcgtcgacca gctgaagaac   120
tacgtgaacg acctggtgcc cgagtttctg cctgcccccg aggacgtgga gaccaactgc   180
gagtggtccg ccttctcctg ctttcagaag gcccagctga gtccgccaa caccggcaac   240
aacgagcgga tcatcaacgt gagcatcaag aagctgaagc ggaagcctcc ctccacaaac   300
gccggcagga ggcagaagca caggctgacc tgccccagct gtgactccta cgagaagaag   360
ccccccaagg agttcctgga gaggttcaag tccctgctgc agaagatgat ccatcagcac   420
ctgtcctcca ggacccacgg ctccgaggac tccattacat gccccctcc catgagcgtg   480
gagcacgccg acatctgggt gaagagctat agcctctaca gccgggagag gtatatctgt   540
aacagcggct tcaagaggaa ggccggcacc agcagcctca ccgagtgcgt gctgaataag   600
gctaccaacg tggctcactg gacaacaccc tctttaaagt gcatccgggg cggtggagga   660
tccggaggag gtggctccgg cggcggagga tctgatcccg ccggcctctt ggacctgcgg   720
cagggcatgt ttgcgcagct ggtggcccaa atgttctgc tgatcgatgg gcccctgagc   780
tggtacagtg acccaggcct ggcaggcgtg tccctgacgg ggggcctgag ctacaaagag   840
gacacgaagg agctggtggt ggccaaggct ggagtctact atgtcttctt caactagag   900
ctgcggcgcg tggtggccgg cgagggctca ggctccgttt cacttgcgct gcacctgcag   960
ccactgcgct ctgctgctgg ggccgccgcc ctggctttga ccgtggacct gccacccgcc  1020
tcctccgagg ctcggaactc ggccttcggt ttccagggcc gcttgctgca cctgagtgcc  1080
ggccagcgcc tgggcgtcca tcttcacact gaggccaggg cacgccatgc ctggcagctt  1140
acccagggcg ccacagtctt gggactcttc cgggtgaccc ccgaaatc              1188
```

<210> SEQ ID NO 173
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-TGFRs sequence"

<400> SEQUENCE: 173

Asp Cys Asp Ile Glu Gly Lys Asp Gly Lys Gln Tyr Glu Ser Val Leu

-continued

```
1               5                   10                  15
Met Val Ser Ile Asp Gln Leu Leu Asp Ser Met Lys Glu Ile Gly Ser
                20                  25                  30
Asn Cys Leu Asn Asn Glu Phe Asn Phe Phe Lys Arg His Ile Cys Asp
                35                  40                  45
Ala Asn Lys Glu Gly Met Phe Leu Phe Arg Ala Ala Arg Lys Leu Arg
            50                  55                  60
Gln Phe Leu Lys Met Asn Ser Thr Gly Asp Phe Asp Leu His Leu Leu
65                  70                  75                  80
Lys Val Ser Glu Gly Thr Thr Ile Leu Leu Asn Cys Thr Gly Gln Val
                    85                  90                  95
Lys Gly Arg Lys Pro Ala Ala Leu Gly Glu Ala Gln Pro Thr Lys Ser
                100                 105                 110
Leu Glu Glu Asn Lys Ser Leu Lys Glu Gln Lys Lys Leu Asn Asp Leu
                115                 120                 125
Cys Phe Leu Lys Arg Leu Leu Gln Glu Ile Lys Thr Cys Trp Asn Lys
            130                 135                 140
Ile Leu Met Gly Thr Lys Glu His Ser Gly Thr Thr Asn Thr Val Ala
145                 150                 155                 160
Ala Tyr Asn Leu Thr Trp Lys Ser Thr Asn Phe Lys Thr Ile Leu Glu
                    165                 170                 175
Trp Glu Pro Lys Pro Val Asn Gln Val Tyr Thr Val Gln Ile Ser Thr
                180                 185                 190
Lys Ser Gly Asp Trp Lys Ser Lys Cys Phe Tyr Thr Thr Asp Thr Glu
                195                 200                 205
Cys Asp Leu Thr Asp Glu Ile Val Lys Asp Val Lys Gln Thr Tyr Leu
            210                 215                 220
Ala Arg Val Phe Ser Tyr Pro Ala Gly Asn Val Glu Ser Thr Gly Ser
225                 230                 235                 240
Ala Gly Glu Pro Leu Tyr Glu Asn Ser Pro Glu Phe Thr Pro Tyr Leu
                    245                 250                 255
Glu Thr Asn Leu Gly Gln Pro Thr Ile Gln Ser Phe Glu Gln Val Gly
                260                 265                 270
Thr Lys Val Asn Val Thr Val Glu Asp Glu Arg Thr Leu Val Arg Arg
                275                 280                 285
Asn Asn Thr Phe Leu Ser Leu Arg Asp Val Phe Gly Lys Asp Leu Ile
            290                 295                 300
Tyr Thr Leu Tyr Tyr Trp Lys Ser Ser Ser Gly Lys Lys Thr Ala
305                 310                 315                 320
Lys Thr Asn Thr Asn Glu Phe Leu Ile Asp Val Asp Lys Gly Glu Asn
                    325                 330                 335
Tyr Cys Phe Ser Val Gln Ala Val Ile Pro Ser Arg Thr Val Asn Arg
                340                 345                 350
Lys Ser Thr Asp Ser Pro Val Glu Cys Met Gly Gln Glu Lys Gly Glu
                355                 360                 365
Phe Arg Glu Asn Trp Val Asn Val Ile Ser Asp Leu Lys Lys Ile Glu
            370                 375                 380
Asp Leu Ile Gln Ser Met His Ile Asp Ala Thr Leu Tyr Thr Glu Ser
385                 390                 395                 400
Asp Val His Pro Ser Cys Lys Val Thr Ala Met Lys Cys Phe Leu Leu
                    405                 410                 415
Glu Leu Gln Val Ile Ser Leu Glu Ser Gly Asp Ala Ser Ile His Asp
                420                 425                 430
```

Thr Val Glu Asn Leu Ile Ile Leu Ala Asn Asn Ser Leu Ser Ser Asn
        435                 440                 445

Gly Asn Val Thr Glu Ser Gly Cys Lys Glu Cys Glu Glu Leu Glu Glu
    450                 455                 460

Lys Asn Ile Lys Glu Phe Leu Gln Ser Phe Val His Ile Val Gln Met
465                 470                 475                 480

Phe Ile Asn Thr Ser
                485

<210> SEQ ID NO 174
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-TGFRs sequence"

<400> SEQUENCE: 174

```
gattgcgaca tcgagggcaa ggacggcaag cagtacgaga gcgtgctgat ggtgtccatc      60
gaccagctgc tggacagcat gaaggagatc ggctccaact gcctcaacaa cgagttcaac     120
ttcttcaagc ggcacatctg cgacgccaac aaggagggca tgttcctgtt cagggccgcc     180
aggaaactgc ggcagttcct gaagatgaac tccaccggcg acttcgacct gcacctgctg     240
aaggtgtccg agggcaccac catcctgctg aactgcaccg acaggtgaa gggccggaaa      300 cctgctgctc tgggagaggc ccaacccacc aagagcctgg aggagaacaa gtccctgaag     360
gagcagaaga agctgaacga cctgtgcttc ctgaagaggc tgctgcagga gatcaagacc     420
tgctggaaca gatcctgat gggcaccaag gagcatagcg gcacaaccaa cacagtcgct      480
gcctataacc tcacttggaa gagcaccaac ttcaaaacca tcctcgaatg gaacccaaa      540 cccgttaacc aagtttacac cgtgcagatc agcaccaagt ccggcgactg gaagtccaaa     600
tgtttctata ccaccgacac cgagtgcgat ctcaccgatg agatcgtgaa agatgtgaaa     660
cagacctacc tcgcccgggt gtttagctac ccgccggca atgtggagag cactggttcc      720
gctggcgagc ctttatacga aacagcccc gaatttaccc cttacctcga ccaatttta       780 ggacagccca ccatccaaag ctttgagcaa gttggcacaa aggtgaatgt gacagtggag     840
gacgagcgga ctttagtgcg gcggaacaac acctttctca gcctccggga tgtgttcggc     900
aaagatttaa tctacacact gtattactgg aagtcctctt cctccggcaa gaagacagct     960
aaaaccaaca caaacgagtt tttaatcgac gtggataaag cgaaaactac tgtttcagc    1020 gtgcaagctg tgatcccctc ccggaccgtg aataggaaaa gcaccgatag ccccgttgag    1080
tgcatgggcc aagaaaaggg cgagttccgg gagaactggg tgaacgtcat cagcgattta    1140
aagaagatcg aagatttaat tcagtccatg catatcgacg ccactttata cacagaatcc    1200
gacgtgcacc cctcttgtaa ggtgaccgcc atgaaatgtt ttttactgga gctgcaagtt    1260
atctctttag agagcggaga cgctagcatc cacgacaccg tggagaattt aatcatttta    1320
gccaataact ctttatccag caacggcaac gtgacagagt ccggctgcaa ggagtgcgaa    1380
gagctggagg agaagaacat caaggagttt ctgcaatcct tgtgcacat tgtccagatg    1440 ttcatcaata cctcc                                                    1455
```

<210> SEQ ID NO 175
<211> LENGTH: 502
<212> TYPE: PRT

<213> ORGANISM: Artificial Sequence
<220> FEATURE:
<221> NAME/KEY: source
<223> OTHER INFORMATION: /note="Description of Artificial Sequence: Synthetic 7t15-TGFRs sequence"

<400> SEQUENCE: 175

Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
            100                 105                 110

Gln Val Lys Gly Arg Lys Pro Ala Ala Leu Gly Glu Ala Gln Pro Thr
        115                 120                 125

Lys Ser Leu Glu Glu Asn Lys Ser Leu Lys Glu Gln Lys Lys Leu Asn
130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ser Gly Thr Thr Asn Thr
                165                 170                 175

Val Ala Ala Tyr Asn Leu Thr Trp Lys Ser Thr Asn Phe Lys Thr Ile
            180                 185                 190

Leu Glu Trp Glu Pro Lys Pro Val Asn Gln Val Tyr Thr Val Gln Ile
        195                 200                 205

Ser Thr Lys Ser Gly Asp Trp Lys Ser Lys Cys Phe Tyr Thr Thr Asp
210                 215                 220

Thr Glu Cys Asp Leu Thr Asp Glu Ile Val Lys Asp Val Lys Gln Thr
225                 230                 235                 240

Tyr Leu Ala Arg Val Phe Ser Tyr Pro Ala Gly Asn Val Glu Ser Thr
                245                 250                 255

Gly Ser Ala Gly Glu Pro Leu Tyr Glu Asn Ser Pro Glu Phe Thr Pro
            260                 265                 270

Tyr Leu Glu Thr Asn Leu Gly Gln Pro Thr Ile Gln Ser Phe Glu Gln
        275                 280                 285

Val Gly Thr Lys Val Asn Val Thr Val Glu Asp Glu Arg Thr Leu Val
290                 295                 300

Arg Arg Asn Asn Thr Phe Leu Ser Leu Arg Asp Val Phe Gly Lys Asp
305                 310                 315                 320

Leu Ile Tyr Thr Leu Tyr Tyr Trp Lys Ser Ser Ser Gly Lys Lys
                325                 330                 335

Thr Ala Lys Thr Asn Thr Asn Glu Phe Leu Ile Asp Val Asp Lys Gly
            340                 345                 350

Glu Asn Tyr Cys Phe Ser Val Gln Ala Val Ile Pro Ser Arg Thr Val
        355                 360                 365

Asn Arg Lys Ser Thr Asp Ser Pro Val Glu Cys Met Gly Gln Glu Lys
370                 375                 380

```
Gly Glu Phe Arg Glu Asn Trp Val Asn Val Ile Ser Asp Leu Lys Lys
385                 390                 395                 400

Ile Glu Asp Leu Ile Gln Ser Met His Ile Asp Ala Thr Leu Tyr Thr
            405                 410                 415

Glu Ser Asp Val His Pro Ser Cys Lys Val Thr Ala Met Lys Cys Phe
        420                 425                 430

Leu Leu Glu Leu Gln Val Ile Ser Leu Glu Ser Gly Asp Ala Ser Ile
    435                 440                 445

His Asp Thr Val Glu Asn Leu Ile Ile Leu Ala Asn Asn Ser Leu Ser
        450                 455                 460

Ser Asn Gly Asn Val Thr Glu Ser Gly Cys Lys Glu Cys Glu Glu Leu
465                 470                 475                 480

Glu Glu Lys Asn Ile Lys Glu Phe Leu Gln Ser Phe Val His Ile Val
            485                 490                 495

Gln Met Phe Ile Asn Thr
            500

<210> SEQ ID NO 176
<211> LENGTH: 1509
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-TGFRs sequence"

<400> SEQUENCE: 176
```

| | | | | | |
|---|---|---|---|---|---|
| atgaagtggg | tgaccttcat | cagcctgctg | ttcctgttct | ccagcgccta | ctccgattgc | 60 |
| gacatcgagg | gcaaggacgg | caagcagtac | gagagcgtgc | tgatggtgtc | catcgaccag | 120 |
| ctgctggaca | gcatgaagga | gatcggctcc | aactgcctca | caacgagtt | caacttcttc | 180 |
| aagcggcaca | tctgcgacgc | caacaaggag | ggcatgttcc | tgttcagggc | cgccaggaaa | 240 |
| ctgcggcagt | tcctgaagat | gaactccacc | ggcgacttcg | acctgcacct | gctgaaggtg | 300 |
| tccgagggca | ccaccatcct | gctgaactgc | accggacagg | tgaagggccg | gaaacctgct | 360 |
| gctctgggag | aggcccaacc | caccaagagc | ctggaggaga | caagtccct | gaaggagcag | 420 |
| aagaagctga | cgacctgtg | cttcctgaag | aggctgctgc | aggagatcaa | gacctgctgg | 480 |
| aacaagatcc | tgatgggcac | caaggagcat | agcggcacaa | ccaacacagt | cgctgcctat | 540 |
| aacctcactt | ggaagagcac | caacttcaaa | accatcctcg | aatgggaacc | caaacccgtt | 600 |
| aaccaagttt | acaccgtgca | gatcagcacc | aagtccggcg | actggaagtc | caatgtttc | 660 |
| tataccaccg | acaccgagtg | cgatctcacc | gatgagatcg | tgaaagatgt | gaaacagacc | 720 |
| tacctcgccc | gggtgtttag | ctaccccgcc | ggcaatgtgg | agagcactgg | ttccgctggc | 780 |
| gagcctttat | acgagaacag | ccccgaattt | accccttacc | tcgagaccaa | tttaggacag | 840 |
| cccaccatcc | aaagctttga | gcaagttggc | acaaaggtga | atgtgacagt | ggaggacgag | 900 |
| cggactttag | tgcggcggaa | caacaccttt | ctcagcctcc | gggatgtgtt | cggcaaagat | 960 |
| ttaatctaca | cactgtatta | ctggaagtcc | tcttcctccg | gcaagaagac | agctaaaacc | 1020 |
| aacacaaacg | agttttaat | cgacgtggat | aaaggcgaaa | actactgttt | cagcgtgcaa | 1080 |
| gctgtgatcc | cctcccggac | cgtgaatagg | aaaagcaccg | atagccccgt | tgagtgcatg | 1140 |
| ggccaagaaa | agggcgagtt | ccgggagaac | tgggtgaacg | tcatcagcga | tttaaagaag | 1200 |
| atcgaagatt | taattcagtc | catgcatatc | gacgccactt | tatacacaga | atccgacgtg | 1260 |

-continued

```
cacccctctt gtaaggtgac cgccatgaaa tgttttttac tggagctgca agttatctct    1320
ttagagagcg gagacgctag catccacgac accgtggaga atttaatcat tttagccaat    1380
aactctttat ccagcaacgg caacgtgaca gagtccggct gcaaggagtg cgaagagctg    1440
gaggagaaga acatcaagga gtttctgcaa tcctttgtgc acattgtcca gatgttcatc    1500
aatacctcc                                                            1509
```

<210> SEQ ID NO 177
<211> LENGTH: 352
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 7t15-TGFRs sequence"

<400> SEQUENCE: 177

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ile
        275                 280                 285

Thr Cys Pro Pro Met Ser Val Glu His Ala Asp Ile Trp Val Lys
    290                 295                 300
```

```
Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
                325                 330                 335

Ala Thr Asn Val Ala His Trp Thr Thr Pro Ser Leu Lys Cys Ile Arg
            340                 345                 350
```

<210> SEQ ID NO 178
<211> LENGTH: 1056
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-TGFRs sequence"

<400> SEQUENCE: 178

```
atcccccccc atgtgcaaaa gagcgtgaac aacgatatga tcgtgaccga caacaacggc      60
gccgtgaagt ttccccagct ctgcaagttc tgcgatgtca ggttcagcac ctgcgataat     120
cagaagtcct gcatgtccaa ctgcagcatc acctccatct gcgagaagcc caagaagtg     180
tgcgtggccg tgtggcggaa aaatgacgag aacatcaccc tggagaccgt gtgtcacgac     240
cccaagctcc cttatcacga cttcattctg gaggacgctg cctcccccaa atgcatcatg     300
aaggagaaga agaagcccgg agagaccttc tttatgtgtt cctgtagcag cgacgagtgt     360
aacgacaaca tcatcttcag cgaagagtac aacaccagca ccctgatgg aggtggcgga     420
tccggaggtg gaggttctgg tggaggtggg agtattcctc ccacgtgca gaagagcgtg     480
aataatgaca tgatcgtgac cgataacaat ggcgccgtga atttcccca gctgtgcaaa     540
ttctgcgatg tgaggttttc cacctgcgac aaccagaagt cctgtatgag caactgctcc     600
atcacctcca tctgtgagaa gcctcaggag gtgtgcgtgg ctgtctggcg gaagaatgac     660
gagaatatca ccctggaaac cgtctgccac gatcccaagc tgcctaccct cgatttcatc     720
ctggaagacg ccgccagccc taagtgcatc atgaaagaga aaagaagcc tggcgagacc     780
ttttcatgt gctcctgcag cagcgacgaa tgcaacgaca tatcatctt agcgaggaa     840
tacaatacca gcaacccga cattacatgc cccctccca tgagcgtgga gcacgccgac     900
atctgggtga agagctatag cctctacagc cgggagaggt atatctgtaa cagcggcttc     960
aagaggaagg ccggcaccag cagcctcacc gagtgcgtgc tgaataaggc taccaacgtg    1020
gctcactgga caacaccctc tttaaagtgc atccgg                              1056
```

<210> SEQ ID NO 179
<211> LENGTH: 370
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 7t15-TGFRs sequence"

<400> SEQUENCE: 179

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
                20                  25                  30

Val Thr Asp Asn Asn Gly Ala Val Lys Phe Pro Gln Leu Cys Lys Phe
            35                  40                  45

Cys Asp Val Arg Phe Ser Thr Cys Asp Asn Gln Lys Ser Cys Met Ser
```

```
            50                  55                  60
Asn Cys Ser Ile Thr Ser Ile Cys Glu Lys Pro Gln Glu Val Cys Val
 65                  70                  75                  80

Ala Val Trp Arg Lys Asn Asp Glu Asn Ile Thr Leu Glu Thr Val Cys
                 85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365

Ile Arg
    370

<210> SEQ ID NO 180
<211> LENGTH: 1110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 7t15-TGFRs sequence"

<400> SEQUENCE: 180
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
```

```
tcctgcatgt ccaactgcag catcacctcc atctgcgaga agccccaaga agtgtgcgtg    240
gccgtgtggc ggaaaaatga cgagaacatc accctggaga ccgtgtgtca cgaccccaag    300
ctcccttatc acgacttcat tctggaggac gctgcctccc ccaaatgcat catgaaggag    360
aagaagaagc ccggagagac cttctttatg tgttcctgta gcagcgacga gtgtaacgac    420
aacatcatct tcagcgaaga gtacaacacc agcaaccctg atggaggtgg cggatccgga    480
ggtggaggtt ctggtggagg tgggagtatt cctccccacg tgcagaagag cgtgaataat    540
gacatgatcg tgaccgataa caatggcgcc gtgaaatttc cccagctgtg caattctgc     600 gatgtgaggt tttccacctg cgacaaccag aagtcctgta tgagcaactg ctccatcacc    660
tccatctgtg agaagcctca ggaggtgtgc gtggctgtct ggcggaagaa tgacgagaat    720
atcaccctgg aaaccgtctg ccacgatccc aagctgccct accacgattt catcctggaa    780
gacgccgcca gccctaagtg catcatgaaa gagaaaaaga gcctggcga gacctttttc     840 atgtgctcct gcagcagcga cgaatgcaac gacaatatca tctttagcga ggaatacaat    900
accagcaacc ccgacattac atgccccccc cccatgagcg tggagcacgc cgacatctgg    960
gtgaagagct atagcctcta cagccgggag aggtatatct gtaacagcgg cttcaagagg    1020
aaggccggca ccagcagcct caccgagtgc gtgctgaata aggctaccaa cgtggctcac    1080
tggacaacac cctctttaaa gtgcatccgg                                     1110
```

<210> SEQ ID NO 181
<211> LENGTH: 620
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-21s137L sequence"

<400> SEQUENCE: 181

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
```

```
            180                 185                 190
Lys Ser Cys Met Ser Asn Cys Ser Ile Thr Ser Ile Cys Glu Lys Pro
            195                 200                 205
Gln Glu Val Cys Val Ala Val Trp Arg Lys Asn Asp Glu Asn Ile Thr
            210                 215                 220
Leu Glu Thr Val Cys His Asp Pro Lys Leu Pro Tyr His Asp Phe Ile
225                 230                 235                 240
Leu Glu Asp Ala Ala Ser Pro Lys Cys Ile Met Lys Glu Lys Lys Lys
            245                 250                 255
Pro Gly Glu Thr Phe Phe Met Cys Ser Cys Ser Ser Asp Glu Cys Asn
            260                 265                 270
Asp Asn Ile Ile Phe Ser Glu Glu Tyr Asn Thr Ser Asn Pro Asp Ser
            275                 280                 285
Gly Thr Thr Asn Thr Val Ala Ala Tyr Asn Leu Thr Trp Lys Ser Thr
            290                 295                 300
Asn Phe Lys Thr Ile Leu Glu Trp Glu Pro Lys Pro Val Asn Gln Val
305                 310                 315                 320
Tyr Thr Val Gln Ile Ser Thr Lys Ser Gly Asp Trp Lys Ser Lys Cys
            325                 330                 335
Phe Tyr Thr Thr Asp Thr Glu Cys Asp Leu Thr Asp Glu Ile Val Lys
            340                 345                 350
Asp Val Lys Gln Thr Tyr Leu Ala Arg Val Phe Ser Tyr Pro Ala Gly
            355                 360                 365
Asn Val Glu Ser Thr Gly Ser Ala Gly Glu Pro Leu Tyr Glu Asn Ser
            370                 375                 380
Pro Glu Phe Thr Pro Tyr Leu Glu Thr Asn Leu Gly Gln Pro Thr Ile
385                 390                 395                 400
Gln Ser Phe Glu Gln Val Gly Thr Lys Val Asn Val Thr Val Glu Asp
            405                 410                 415
Glu Arg Thr Leu Val Arg Arg Asn Asn Thr Phe Leu Ser Leu Arg Asp
            420                 425                 430
Val Phe Gly Lys Asp Leu Ile Tyr Thr Leu Tyr Tyr Trp Lys Ser Ser
            435                 440                 445
Ser Ser Gly Lys Lys Thr Ala Lys Thr Asn Thr Asn Glu Phe Leu Ile
            450                 455                 460
Asp Val Asp Lys Gly Glu Asn Tyr Cys Phe Ser Val Gln Ala Val Ile
465                 470                 475                 480
Pro Ser Arg Thr Val Asn Arg Lys Ser Thr Asp Ser Pro Val Glu Cys
            485                 490                 495
Met Gly Gln Glu Lys Gly Glu Phe Arg Glu Asn Trp Val Asn Val Ile
            500                 505                 510
Ser Asp Leu Lys Lys Ile Glu Asp Leu Ile Gln Ser Met His Ile Asp
            515                 520                 525
Ala Thr Leu Tyr Thr Glu Ser Asp Val His Pro Ser Cys Lys Val Thr
            530                 535                 540
Ala Met Lys Cys Phe Leu Leu Glu Leu Gln Val Ile Ser Leu Glu Ser
545                 550                 555                 560
Gly Asp Ala Ser Ile His Asp Thr Val Glu Asn Leu Ile Ile Leu Ala
            565                 570                 575
Asn Asn Ser Leu Ser Ser Asn Gly Asn Val Thr Glu Ser Gly Cys Lys
            580                 585                 590
Glu Cys Glu Glu Leu Glu Glu Lys Asn Ile Lys Glu Phe Leu Gln Ser
            595                 600                 605
```

Phe Val His Ile Val Gln Met Phe Ile Asn Thr Ser
    610                 615                 620

<210> SEQ ID NO 182
<211> LENGTH: 1860
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-21s137L sequence"

<400> SEQUENCE: 182

```
atccccnccc atgtgcaaaa gagcgtgaac aacgatatga tcgtgaccga caacaacggc    60
gccgtgaagt ttccccagct ctgcaagttc tgcgatgtca ggttcagcac ctgcgataat   120
cagaagtcct gcatgtccaa ctgcagcatc acctccatct gcgagaagcc ccaagaagtg   180
tgcgtggccg tgtggcggaa aaatgacgag aacatcaccc tggagaccgt gtgtcacgac   240
cccaagctcc cttatcacga cttcattctg gaggacgctg cctccccaa atgcatcatg    300
aaggagaaga agaagcccgg agagaccttc tttatgtgtt cctgtagcag cgacgagtgt   360
aacgacaaca tcatcttcag cgaagagtac aacaccagca ccctgatgg aggtggcgga   420
tccggaggtg gaggttctgg tggaggtggg agtattcctc ccacgtgca agagcgtg    480
aataatgaca tgatcgtgac cgataacaat ggcgccgtga atttcccca gctgtgcaaa    540
ttctgcgatg tgaggttttc cacctgcgac aaccagaagt cctgtatgag caactgctcc   600
atcacctcca tctgtgagaa gcctcaggag gtgtgcgtgg ctgtctggcg gaagaatgac   660
gagaatatca ccctggaaac cgtctgccac gatcccaagc tgccctacca cgatttcatc   720
ctggaagacg ccgccagccc taagtgcatc atgaaagaga aaagaagcc tggcgagacc    780
tttttcatgt gctcctgcag cagcgacgaa tgcaacgaca atatcatctt tagcgaggaa   840
tacaatacca gcaccccga cagcggcaca accaacacag tcgctgccta acctcact    900
tggaagagca ccaacttcaa aaccatcctc gaatgggaac ccaaacccgt taaccaagtt   960
tacaccgtgc agatcagcac caagtccggc gactggaagt ccaaatgttt ctataccacc  1020
gacaccgagt gcgatctcac cgatgagatc gtgaaagatg tgaaacagac ctacctcgcc  1080
cgggtgttta gctaccccgc cggcaatgtg gagagcactg gttccgctgg cgagccttta  1140
tacgagaaca gccccgaatt tacccctac ctcgagacca atttaggaca gcccaccatc   1200
caaagctttg agcaagttgg cacaaaggtg aatgtgacag tggaggacga gcggacttta  1260
gtgcggcgga caacacctt tctcagcctc cgggatgtgt tcggcaaaga tttaatctac  1320
acactgtatt actggaagtc ctcttcctcc ggcaagaaga cagctaaaac caacacaaac  1380
gagttttaa tcgacgtgga taaaggcgaa aactactgtt tcagcgtgca agctgtgatc  1440
ccctcccgga ccgtgaatag gaaaagcacc gatagcccg ttgagtgcat gggccaagaa   1500
aagggcgagt tccggagaa ctgggtgaac gtcatcagcg atttaaagaa gatcgaagat   1560
ttaattcagt ccatgcatat cgacgccact ttatacacag aatccgacgt gcacccctct  1620
tgtaaggtga ccgccatgaa atgttttta ctggagctgc aagttatctc tttagagagc   1680
ggagacgcta gcatccacga caccgtggag aatttaatca ttttagccaa taactcttta  1740
tccagcaacg gcaacgtgac agagtccggc tgcaaggagt gcgaagagct ggaggagaag  1800
aacatcaagg agttctgca atcctttgtg cacattgtcc agatgttcat caataccctcc  1860
```

```
<210> SEQ ID NO 183
<211> LENGTH: 638
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-21s137L sequence"

<400> SEQUENCE: 183
```

| | | | | | | | | | | | | | | |
|---|---|---|---|---|---|---|---|---|---|---|---|---|---|---|
| Met | Lys | Trp | Val | Thr | Phe | Ile | Ser | Leu | Leu | Phe | Leu | Phe | Ser | Ala |
| 1 | | | | 5 | | | | | 10 | | | | | 15 |
| Tyr | Ser | Ile | Pro | Pro | His | Val | Gln | Lys | Ser | Val | Asn | Asn | Asp | Met |
| | | | 20 | | | | | 25 | | | | | 30 | |
| Ile | Val | Thr | Asp | Asn | Asn | Gly | Ala | Val | Lys | Phe | Pro | Gln | Leu | Cys |
| | | 35 | | | | | 40 | | | | | 45 | | |
| Lys | Phe | Cys | Asp | Val | Arg | Phe | Ser | Thr | Cys | Asp | Asn | Gln | Lys | Ser |
| 50 | | | | | 55 | | | | | 60 | | | | |
| Cys | Met | Ser | Asn | Cys | Ser | Ile | Thr | Ser | Ile | Cys | Glu | Lys | Pro | Gln |
| 65 | | | | | 70 | | | | | 75 | | | | 80 |
| Glu | Val | Cys | Val | Ala | Val | Trp | Arg | Lys | Asn | Asp | Glu | Asn | Ile | Thr |
| | | | | 85 | | | | | 90 | | | | | 95 |
| Leu | Glu | Thr | Val | Cys | His | Asp | Pro | Lys | Leu | Pro | Tyr | His | Asp | Phe |
| | | | 100 | | | | | 105 | | | | | 110 | |
| Ile | Leu | Glu | Asp | Ala | Ala | Ser | Pro | Lys | Cys | Ile | Met | Lys | Glu | Lys |
| | | 115 | | | | | 120 | | | | | 125 | | |
| Lys | Pro | Gly | Glu | Thr | Phe | Phe | Met | Cys | Ser | Cys | Ser | Ser | Asp | Glu |
| 130 | | | | | 135 | | | | | 140 | | | | |
| Cys | Asn | Asp | Asn | Ile | Ile | Phe | Ser | Glu | Glu | Tyr | Asn | Thr | Ser | Asn |
| 145 | | | | | 150 | | | | | 155 | | | | 160 |
| Pro | Asp | Gly | Gly | Gly | Gly | Ser | Gly | Gly | Gly | Gly | Ser | Ile | Pro | Pro |
| | | | | 165 | | | | | 170 | | | | | 175 |
| His | Val | Gln | Lys | Ser | Val | Asn | Asn | Asp | Met | Ile | Val | Thr | Asp | Asn |
| | | | | 180 | | | | | 185 | | | | | 190 |
| Asn | Gly | Ala | Val | Lys | Phe | Pro | Gln | Leu | Cys | Lys | Phe | Cys | Asp | Val |
| | | | 195 | | | | | 200 | | | | | 205 | |
| Arg | Phe | Ser | Thr | Cys | Asp | Asn | Gln | Lys | Ser | Cys | Met | Ser | Asn | Cys |
| | | 210 | | | | | 215 | | | | | 220 | | |
| Ser | Ile | Thr | Ser | Ile | Cys | Glu | Lys | Pro | Gln | Glu | Val | Cys | Val | Ala |
| 225 | | | | | 230 | | | | | 235 | | | | 240 |
| Val | Trp | Arg | Lys | Asn | Asp | Glu | Asn | Ile | Thr | Leu | Glu | Thr | Val | Cys |
| | | | | 245 | | | | | 250 | | | | | 255 |
| His | Asp | Pro | Lys | Leu | Pro | Tyr | His | Asp | Phe | Ile | Leu | Glu | Asp | Ala |
| | | | | 260 | | | | | 265 | | | | | 270 |
| Ala | Ser | Pro | Lys | Cys | Ile | Met | Lys | Glu | Lys | Lys | Pro | Gly | Glu | Thr |
| | | | 275 | | | | | 280 | | | | | 285 | |
| Phe | Phe | Met | Cys | Ser | Cys | Ser | Ser | Asp | Glu | Cys | Asn | Asp | Asn | Ile |
| | | 290 | | | | | 295 | | | | | 300 | | |
| Ile | Phe | Ser | Glu | Glu | Tyr | Asn | Thr | Ser | Asn | Pro | Asp | Ser | Gly | Thr |
| 305 | | | | | 310 | | | | | 315 | | | | 320 |
| Thr | Asn | Thr | Val | Ala | Ala | Tyr | Asn | Leu | Thr | Trp | Lys | Ser | Thr | Asn |
| | | | | 325 | | | | | 330 | | | | | 335 |
| Phe | Lys | Thr | Ile | Leu | Glu | Trp | Glu | Pro | Lys | Pro | Val | Asn | Gln | Val |
| | | | | 340 | | | | | 345 | | | | | 350 |
| Tyr | Thr | Val | Gln | Ile | Ser | Thr | Lys | Ser | Gly | Asp | Trp | Lys | Ser | Lys |
| | | | 355 | | | | | 360 | | | | | 365 | |
| Cys | Phe | Tyr | Thr | Thr | Asp | Thr | Glu | Cys | Asp | Leu | Thr | Asp | Glu | Ile |

Val Lys Asp Val Lys Gln Thr Tyr Leu Ala Arg Val Phe Ser Tyr Pro
    370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415

Thr Ile Gln Ser Phe Glu Gln Val Gly Thr Lys Val Asn Val Thr Val
            420                 425                 430

Glu Asp Glu Arg Thr Leu Val Arg Arg Asn Asn Thr Phe Leu Ser Leu
        435                 440                 445

Arg Asp Val Phe Gly Lys Asp Leu Ile Tyr Thr Leu Tyr Tyr Trp Lys
    450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                485                 490                 495

Val Ile Pro Ser Arg Thr Val Asn Arg Lys Ser Thr Asp Ser Pro Val
            500                 505                 510

Glu Cys Met Gly Gln Glu Lys Gly Glu Phe Arg Glu Asn Trp Val Asn
        515                 520                 525

Val Ile Ser Asp Leu Lys Lys Ile Glu Asp Leu Ile Gln Ser Met His
    530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
        595                 600                 605

Cys Lys Glu Cys Glu Glu Leu Glu Glu Lys Asn Ile Lys Glu Phe Leu
    610                 615                 620

Gln Ser Phe Val His Ile Val Gln Met Phe Ile Asn Thr Ser
625                 630                 635

<210> SEQ ID NO 184
<211> LENGTH: 1914
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-21s137L sequence"

<400> SEQUENCE: 184
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agcccaagaa agtgtgcgtg     240
gccgtgtggc ggaaaaatga cgagaacatc accctggaga ccgtgtgtca cgaccccaag     300
ctcccttatc acgacttcat tctggaggac gctgcctccc caaatgcat catgaaggag     360 aagaagaagc ccgagagac cttctttatg tgttcctgta gcagcgacga gtgtaacgac     420
aacatcatct tcagcgaaga gtacaacacc agcaaccctg atggaggtgg cggatccgga     480

```
ggtggaggtt ctggtggagg tgggagtatt cctccccacg tgcagaagag cgtgaataat    540
gacatgatcg tgaccgataa caatggcgcc gtgaaatttc cccagctgtg caaattctgc    600
gatgtgaggt tttccacctg cgacaaccag aagtcctgta tgagcaactg ctccatcacc    660
tccatctgtg agaagcctca ggaggtgtgc gtggctgtct ggcggaagaa tgacgagaat    720
atcaccctgg aaaccgtctg ccacgatccc aagctgccct accacgattt catcctggaa    780
gacgccgcca gccctaagtg catcatgaaa gagaaaaaga agcctggcga gacctttttc    840
atgtgctcct gcagcagcga cgaatgcaac gacaatatca tctttagcga ggaatacaat    900
accagcaacc ccgacagcgg cacaaccaac acagtcgctg cctataacct cacttggaag    960
agcaccaact tcaaaaccat cctcgaatgg gaacccaaac ccgttaacca agtttacacc   1020
gtgcagatca gcaccaagtc cggcgactgg aagtccaaat gtttctatac caccgacacc   1080
gagtgcgatc tcaccgatga gatcgtgaaa gatgtgaaac agacctacct cgcccgggtg   1140
tttagctacc ccgccggcaa tgtggagagc actggttccg ctggcgagcc tttatacgag   1200
aacagccccg aatttacccc ttacctcgag accaatttag gacagcccac catccaaagc   1260
tttgagcaag ttggcacaaa ggtgaatgtg acagtggagg acgagcggac tttagtgcgg   1320
cggaacaaca cctttctcag cctccgggat gtgttcggca agatttaat ctacacactg    1380
tattactgga gtcctcttc ctccggcaag aagacagcta aaaccaacac aaacgagttt    1440
ttaatcgacg tggataaagg cgaaaactac tgtttcagcg tgcaagctgt gatcccctcc    1500
cggaccgtga ataggaaaag caccgatagc cccgttgagt gcatgggcca agaaaagggc   1560
gagttccggg agaactgggt gaacgtcatc agcgatttaa agaagatcga agatttaatt   1620
cagtccatgc atatcgacgc cactttatac acagaatccg acgtgcaccc ctcttgtaag   1680
gtgaccgcca tgaaatgttt tttactggag ctgcaagtta tctctttaga gagcggagac   1740
gctagcatcc acgacaccgt ggagaattta atcattttag ccaataactc tttatccagc   1800
aacggcaacg tgacagagtc cggctgcaag gagtgcgaag agctggagga agaacatc    1860
aaggagtttc tgcaatcctt tgtgcacatt gtccagatgt tcatcaatac ctcc           1914
```

<210> SEQ ID NO 185
<211> LENGTH: 397
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-21s137L sequence"

<400> SEQUENCE: 185

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
        100                 105                 110

Ser Leu Leu Gln Lys Met Ile His Gln His Leu Ser Ser Arg Thr His
    115                 120                 125

Gly Ser Glu Asp Ser Ile Thr Cys Pro Pro Met Ser Val Glu His
130                 135                 140

Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

Glu Cys Val Leu Asn Lys Ala Thr Asn Val Ala His Trp Thr Thr Pro
            180                 185                 190

Ser Leu Lys Cys Ile Arg Gly Gly Gly Ser Gly Gly Gly Gly Ser
        195                 200                 205

Gly Gly Gly Gly Ser Arg Glu Gly Pro Glu Leu Ser Pro Asp Asp Pro
210                 215                 220

Ala Gly Leu Leu Asp Leu Arg Gln Gly Met Phe Ala Gln Leu Val Ala
225                 230                 235                 240

Gln Asn Val Leu Leu Ile Asp Gly Pro Leu Ser Trp Tyr Ser Asp Pro
                245                 250                 255

Gly Leu Ala Gly Val Ser Leu Thr Gly Gly Leu Ser Tyr Lys Glu Asp
            260                 265                 270

Thr Lys Glu Leu Val Val Ala Lys Ala Gly Val Tyr Tyr Val Phe Phe
        275                 280                 285

Gln Leu Glu Leu Arg Arg Val Val Ala Gly Glu Gly Ser Gly Ser Val
    290                 295                 300

Ser Leu Ala Leu His Leu Gln Pro Leu Arg Ser Ala Ala Gly Ala Ala
305                 310                 315                 320

Ala Leu Ala Leu Thr Val Asp Leu Pro Pro Ala Ser Ser Glu Ala Arg
                325                 330                 335

Asn Ser Ala Phe Gly Phe Gln Gly Arg Leu Leu His Leu Ser Ala Gly
            340                 345                 350

Gln Arg Leu Gly Val His Leu His Thr Glu Ala Arg Ala Arg His Ala
        355                 360                 365

Trp Gln Leu Thr Gln Gly Ala Thr Val Leu Gly Leu Phe Arg Val Thr
    370                 375                 380

Pro Glu Ile Pro Ala Gly Leu Pro Ser Pro Arg Ser Glu
385                 390                 395

<210> SEQ ID NO 186
<211> LENGTH: 1191
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic TGFRt15-21s137L sequence"

<400> SEQUENCE: 186
cagggccagg acaggcacat gatccggatg aggcagctca tcgacatcgt cgaccagctg        60
aagaactacg tgaacgacct ggtgcccgag tttctgcctg cccccgagga cgtggagacc       120
aactgcgagt ggtccgcctt ctcctgcttt cagaaggccc agctgaagtc cgccaacacc       180
ggcaacaacg agcggatcat caacgtgagc atcaagaagc tgaagcggaa gcctcccctcc      240 acaaacgccg gcaggaggca gaagcacagg ctgacctgcc ccagctgtga ctcctacgag       300

-continued

```
aagaagcccc ccaaggagtt cctggagagg ttcaagtccc tgctgcagaa gatgatccat    360
cagcacctgt cctccaggac ccacggctcc gaggactcca ttacatgccc ccctcccatg    420
agcgtggagc acgccgacat ctgggtgaag agctatagcc tctacagccg ggagaggtat    480
atctgtaaca gcggcttcaa gaggaaggcc ggcaccagca gcctcaccga gtgcgtgctg    540
aataaggcta ccaacgtggc tcactggaca acaccctctt taaagtgcat ccggggcggt    600
ggaggatccg gaggaggtgg ctccggcggc ggaggatctc gcgagggtcc cgagctttcg    660
cccgacgatc ccgccggcct cttggacctg cggcagggca tgtttgcgca gctggtggcc    720
caaaatgttc tgctgatcga tgggcccctg agctggtaca gtgacccagg cctggcaggc    780
gtgtccctga cggggggcct gagctacaaa gaggacacga aggagctggt ggtggccaag    840
gctggagtct actatgtctt ctttcaacta gagctgcggc gcgtggtggc cggcgagggc    900
tcaggctccg tttcacttgc gctgcacctg cagccactgc gctctgctgc tggggccgcc    960
gccctggctt tgaccgtgga cctgccaccc gcctcctccg aggctcggaa ctcggccttc   1020
ggtttccagg gccgcttgct gcacctgagt gccggccagc gcctgggcgt ccatcttcac   1080
actgaggcca gggcacgcca tgcctggcag cttacccagg gcgccacagt cttgggactc   1140
ttccgggtga cccccgaaat cccagccgga ctcccttcac cgaggtcgga a            1191
```

<210> SEQ ID NO 187
<211> LENGTH: 415
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-21s137L sequence"

<400> SEQUENCE: 187

Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr

|  |  |  |  | 195 |  |  |  | 200 |  |  |  | 205 |  |  |
|---|---|---|---|---|---|---|---|---|---|---|---|---|---|---|
| Thr | Pro | Ser | Leu | Lys | Cys | Ile | Arg | Gly | Gly | Gly | Ser | Gly | Gly | Gly |
|  |  |  | 210 |  |  |  |  | 215 |  |  |  |  | 220 |  |
| Gly | Ser | Gly | Gly | Gly | Ser | Arg | Glu | Gly | Pro | Glu | Leu | Ser | Pro | Asp |
| 225 |  |  |  |  | 230 |  |  |  |  | 235 |  |  |  | 240 |
| Asp | Pro | Ala | Gly | Leu | Leu | Asp | Leu | Arg | Gln | Gly | Met | Phe | Ala | Gln | Leu |
|  |  |  |  | 245 |  |  |  |  | 250 |  |  |  |  | 255 |
| Val | Ala | Gln | Asn | Val | Leu | Leu | Ile | Asp | Gly | Pro | Leu | Ser | Trp | Tyr | Ser |
|  |  |  | 260 |  |  |  |  | 265 |  |  |  |  | 270 |  |
| Asp | Pro | Gly | Leu | Ala | Gly | Val | Ser | Leu | Thr | Gly | Gly | Leu | Ser | Tyr | Lys |
|  |  |  | 275 |  |  |  |  | 280 |  |  |  |  | 285 |  |
| Glu | Asp | Thr | Lys | Glu | Leu | Val | Val | Ala | Lys | Ala | Gly | Val | Tyr | Tyr | Val |
|  |  |  | 290 |  |  |  |  | 295 |  |  |  |  | 300 |  |
| Phe | Phe | Gln | Leu | Glu | Leu | Arg | Arg | Val | Val | Ala | Gly | Glu | Gly | Ser | Gly |
| 305 |  |  |  |  | 310 |  |  |  |  | 315 |  |  |  |  | 320 |
| Ser | Val | Ser | Leu | Ala | Leu | His | Leu | Gln | Pro | Leu | Arg | Ser | Ala | Ala | Gly |
|  |  |  |  | 325 |  |  |  |  | 330 |  |  |  |  | 335 |  |
| Ala | Ala | Ala | Leu | Ala | Leu | Thr | Val | Asp | Leu | Pro | Pro | Ala | Ser | Ser | Glu |
|  |  |  | 340 |  |  |  |  | 345 |  |  |  |  | 350 |  |
| Ala | Arg | Asn | Ser | Ala | Phe | Gly | Phe | Gln | Gly | Arg | Leu | Leu | His | Leu | Ser |
|  |  |  | 355 |  |  |  |  | 360 |  |  |  |  | 365 |  |
| Ala | Gly | Gln | Arg | Leu | Gly | Val | His | Leu | His | Thr | Glu | Ala | Arg | Ala | Arg |
|  |  |  | 370 |  |  |  |  | 375 |  |  |  |  | 380 |  |
| His | Ala | Trp | Gln | Leu | Thr | Gln | Gly | Ala | Thr | Val | Leu | Gly | Leu | Phe | Arg |
| 385 |  |  |  |  | 390 |  |  |  |  | 395 |  |  |  |  | 400 |
| Val | Thr | Pro | Glu | Ile | Pro | Ala | Gly | Leu | Pro | Ser | Pro | Arg | Ser | Glu |  |
|  |  |  |  | 405 |  |  |  |  | 410 |  |  |  |  | 415 |  |

<210> SEQ ID NO 188
<211> LENGTH: 1245
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic TGFRt15-21s137L sequence"

<400> SEQUENCE: 188

| atgaagtggg tgaccttcat cagcctgctg ttcctgttct ccagcgccta ctcccagggc | 60 |
|---|---|
| caggacaggc acatgatccg gatgaggcag ctcatcgaca tcgtcgacca gctgaagaac | 120 |
| tacgtgaacg acctggtgcc cgagtttctg cctgccccg aggacgtgga gaccaactgc | 180 |
| gagtggtccg ccttctcctg ctttcagaag gcccagctga agtccgccaa caccggcaac | 240 |
| aacgagcgga tcatcaacgt gagcatcaag aagctgaagc ggaagcctcc ctccacaaac | 300 |
| gccggcagga ggcagaagca caggctgacc tgccccagct gtgactccta cgagaagaag | 360 |
| cccccaagg agttcctgga gaggttcaag tccctgctgc agaagatgat ccatcagcac | 420 |
| ctgtcctcca ggacccacgg ctccgaggac tccattacat gcccccctcc catgagcgtg | 480 |
| gagcacgccg acatctgggt gaagagctat agcctctaca gccgggagag gtatatctgt | 540 |
| aacagcggct tcaagaggaa ggccggcacc agcagcctca ccgagtgcgt gctgaataag | 600 |
| gctaccaacg tggctcactg gacaacaccc tctttaaagt gcatccgggg cggtggagga | 660 |
| tccggaggag gtggctccgg cggcggagga tctcgcgagg gtcccgagct ttcgcccgac | 720 |
| gatcccgccg gcctcttgga cctgcggcag ggcatgtttg cgcagctggt ggcccaaaat | 780 |

```
gttctgctga tcgatgggcc cctgagctgg tacagtgacc caggcctggc aggcgtgtcc    840
ctgacggggg gcctgagcta caaagaggac acgaaggagc tggtggtggc caaggctgga    900
gtctactatg tcttctttca actagagctg cggcgcgtgg tggccggcga gggctcaggc    960
tccgtttcac ttgcgctgca cctgcagcca ctgcgctctg ctgctggggc cgccgccctg    1020
gctttgaccg tggacctgcc accgcctcc tccgaggctc ggaactcggc cttcggtttc     1080
cagggccgct tgctgcacct gagtgccggc cagcgcctgg gcgtccatct tcacactgag    1140
gccagggcac gccatgcctg cagcttacc cagggcgcca cagtcttggg actcttccgg     1200 gtgaccccg aaatcccagc cggactccct tcaccgaggt cggaa                     1245
```

<210> SEQ ID NO 189
<211> LENGTH: 378
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-21s137L sequence"

<400> SEQUENCE: 189

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ile Thr Cys Pro Pro Met Ser Val Glu His
    130                 135                 140

Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

Glu Cys Val Leu Asn Lys Ala Thr Asn Val Ala His Trp Thr Thr Pro
            180                 185                 190

Ser Leu Lys Cys Ile Arg Gly Gly Gly Ser Gly Gly Gly Gly Ser
        195                 200                 205

Gly Gly Gly Gly Ser Asp Pro Ala Gly Leu Leu Asp Leu Arg Gln Gly
    210                 215                 220

Met Phe Ala Gln Leu Val Ala Gln Asn Val Leu Leu Ile Asp Gly Pro
225                 230                 235                 240

Leu Ser Trp Tyr Ser Asp Pro Gly Leu Ala Gly Val Ser Leu Thr Gly
                245                 250                 255

Gly Leu Ser Tyr Lys Glu Asp Thr Lys Glu Leu Val Val Ala Lys Ala
            260                 265                 270
```

Gly Val Tyr Tyr Val Phe Phe Gln Leu Glu Leu Arg Arg Val Val Ala
                275                 280                 285

Gly Glu Gly Ser Gly Ser Val Ser Leu Ala Leu His Leu Gln Pro Leu
    290                 295                 300

Arg Ser Ala Ala Gly Ala Ala Ala Leu Ala Leu Thr Val Asp Leu Pro
305                 310                 315                 320

Pro Ala Ser Ser Glu Ala Arg Asn Ser Ala Phe Gly Phe Gln Gly Arg
                325                 330                 335

Leu Leu His Leu Ser Ala Gly Gln Arg Leu Gly Val His Leu His Thr
                340                 345                 350

Glu Ala Arg Ala Arg His Ala Trp Gln Leu Thr Gln Gly Ala Thr Val
                355                 360                 365

Leu Gly Leu Phe Arg Val Thr Pro Glu Ile
    370                 375

<210> SEQ ID NO 190
<211> LENGTH: 1134
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-21s137L sequence"

<400> SEQUENCE: 190
cagggccagg acaggcacat gatccggatg aggcagctca tcgacatcgt cgaccagctg     60
aagaactacg tgaacgacct ggtgcccgag tttctgcctg cccccgagga cgtggagacc    120
aactgcgagt ggtccgcctt ctcctgcttt cagaaggccc agctgaagtc cgccaacacc    180
ggcaacaacg agcggatcat caacgtgagc atcaagaagc tgaagcggaa gcctcccctcc   240 acaaacgccg gcaggaggca gaagcacagg ctgacctgcc cagctgtgac tcctacgag    300 aagaagcccc ccaaggagtt cctggagagg ttcaagtccc tgctgcagaa gatgatccat    360
cagcacctgt cctccaggac ccacggctcc gaggactcca ttacatgccc ccctcccatg    420
agcgtggagc acgccgacat ctgggtgaag agctatagcc tctacagccg ggagaggtat    480
atctgtaaca gcggcttcaa gaggaaggcc ggcaccagca gcctcaccga gtgcgtgctg    540
aataaggcta ccaacgtggc tcactggaca cacccctctt taaagtgcat ccggggcggt    600
ggaggatccg gaggaggtgg ctccggcggc ggaggatctg atcccgccgg cctcttggac    660
ctgcggcagg gcatgtttgc gcagctggtg gcccaaaatg ttctgctgat cgatgggccc    720
ctgagctggt acagtgaccc aggcctggca ggcgtgtccc tgacgggggg cctgagctac    780
aaagaggaca cgaaggagct ggtggtggcc aaggctggag tctactatgt cttctttcaa    840
ctagagctgc ggcgcgtggt ggccggcgag ggctcaggct ccgtttcact gcgcgctgcac   900 ctgcagccac tgcgctctgc tgctggggcc gccgccctgg ctttgaccgt ggacctgcca    960
cccgcctcct ccgaggctcg gaactcggcc ttcggttttcc agggccgctt gctgcacctg   1020
agtgccggcc agcgcctggg cgtccatctt cacactgagg ccagggcacg ccatgcctgg   1080
cagcttaccc agggcgccac agtcttggga ctcttccggg tgaccccccga aatc        1134

<210> SEQ ID NO 191
<211> LENGTH: 396
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic TGFRt15-21s137L sequence"

<400> SEQUENCE: 191

Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
130                 135                 140

Thr His Gly Ser Glu Asp Ser Ile Thr Cys Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr
        195                 200                 205

Thr Pro Ser Leu Lys Cys Ile Arg Gly Gly Gly Ser Gly Gly Gly
210                 215                 220

Gly Ser Gly Gly Gly Ser Asp Pro Ala Gly Leu Leu Asp Leu Arg
225                 230                 235                 240

Gln Gly Met Phe Ala Gln Leu Val Ala Gln Asn Val Leu Leu Ile Asp
                245                 250                 255

Gly Pro Leu Ser Trp Tyr Ser Asp Pro Gly Leu Ala Gly Val Ser Leu
            260                 265                 270

Thr Gly Gly Leu Ser Tyr Lys Glu Asp Thr Lys Glu Leu Val Val Ala
        275                 280                 285

Lys Ala Gly Val Tyr Tyr Val Phe Phe Gln Leu Glu Leu Arg Arg Val
    290                 295                 300

Val Ala Gly Glu Gly Ser Gly Ser Val Ser Leu Ala Leu His Leu Gln
305                 310                 315                 320

Pro Leu Arg Ser Ala Ala Gly Ala Ala Ala Leu Ala Leu Thr Val Asp
                325                 330                 335

Leu Pro Pro Ala Ser Ser Glu Ala Arg Asn Ser Ala Phe Gly Phe Gln
            340                 345                 350

Gly Arg Leu Leu His Leu Ser Ala Gly Gln Arg Leu Gly Val His Leu
        355                 360                 365

His Thr Glu Ala Arg Ala Arg His Ala Trp Gln Leu Thr Gln Gly Ala
370                 375                 380

Thr Val Leu Gly Leu Phe Arg Val Thr Pro Glu Ile
385                 390                 395

<210> SEQ ID NO 192
<211> LENGTH: 1188
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic TGFRt15-21s137L sequence"

<400> SEQUENCE: 192

```
atgaagtggg tgaccttcat cagcctgctg ttcctgttct ccagcgccta ctcccagggc     60
caggacaggc acatgatccg gatgaggcag ctcatcgaca tcgtcgacca gctgaagaac    120
tacgtgaacg acctggtgcc cgagtttctg cctgcccccg aggacgtgga gaccaactgc    180
gagtggtccg ccttctcctg ctttcagaag gcccagctga gtccgccaa caccggcaac    240
aacgagcgga tcatcaacgt gagcatcaag aagctgaagc ggaagcctcc ctccacaaac    300
gccggcagga ggcagaagca caggctgacc tgccccagct gtgactccta cgagaagaag    360
cccccccaagg agttcctgga gaggttcaag tccctgctgc agaagatgat ccatcagcac    420
ctgtcctcca ggacccacgg ctccgaggac tccattacat gccccctcc catgagcgtg    480
gagcacgccg acatctgggt gaagagctat agcctctaca gccgggagag gtatatctgt    540
aacagcggct tcaagaggaa ggccggcacc agcagcctca ccgagtgcgt gctgaataag    600
gctaccaacg tggctcactg gacaacaccc tctttaaagt gcatccgggg cggtggagga    660
tccggaggag gtggctccgg cggcggagga tctgatcccg ccggcctctt ggacctgcgg    720
cagggcatgt tgcgcagct ggtggcccaa aatgttctgc tgatcgatgg cccctgagc    780
tggtacagtg acccaggcct ggcaggcgtg tccctgacgg ggggcctgag ctacaaagag    840
gacacgaagg agctggtggt ggccaaggct ggagtctact atgtcttctt caactagag    900
ctgcggcgcg tggtggccgg cgagggctca ggctccgttt cacttgcgct gcacctgcag    960
ccactgcgct ctgctgctgg ggccgccgcc ctggctttga ccgtggacct gccacccgcc   1020
tcctccgagg ctcggaactc ggccttcggt ttccagggcc gcttgctgca cctgagtgcc   1080
ggccagcgcc tgggcgtcca tcttcacact gaggccaggg cacgccatgc ctggcagctt   1140
acccagggcg ccacagtctt gggactcttc cgggtgaccc ccgaaatc              1188
```

<210> SEQ ID NO 193
<211> LENGTH: 620
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic TGFRt15-TGFRs21 sequence"

<400> SEQUENCE: 193

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80
```

-continued

```
Pro Lys Leu Pro Tyr His Asp Phe Ile Leu Glu Asp Ala Ala Ser Pro
                85                  90                  95
Lys Cys Ile Met Lys Glu Lys Lys Pro Gly Glu Thr Phe Phe Met
            100                 105                 110
Cys Ser Cys Ser Ser Asp Glu Cys Asn Asp Asn Ile Ile Phe Ser Glu
            115                 120                 125
Glu Tyr Asn Thr Ser Asn Pro Asp Gly Gly Gly Ser Gly Gly Gly
        130                 135                 140
Gly Ser Gly Gly Gly Ser Ile Pro Pro His Val Gln Lys Ser Val
145                 150                 155                 160
Asn Asn Asp Met Ile Val Thr Asp Asn Asn Gly Ala Val Lys Phe Pro
                165                 170                 175
Gln Leu Cys Lys Phe Cys Asp Val Arg Phe Ser Thr Cys Asp Asn Gln
            180                 185                 190
Lys Ser Cys Met Ser Asn Cys Ser Ile Thr Ser Ile Cys Glu Lys Pro
            195                 200                 205
Gln Glu Val Cys Val Ala Val Trp Arg Lys Asn Asp Glu Asn Ile Thr
    210                 215                 220
Leu Glu Thr Val Cys His Asp Pro Lys Leu Pro Tyr His Asp Phe Ile
225                 230                 235                 240
Leu Glu Asp Ala Ala Ser Pro Lys Cys Ile Met Lys Glu Lys Lys
                245                 250                 255
Pro Gly Glu Thr Phe Phe Met Cys Ser Cys Ser Ser Asp Glu Cys Asn
            260                 265                 270
Asp Asn Ile Ile Phe Ser Glu Glu Tyr Asn Thr Ser Asn Pro Asp Ser
        275                 280                 285
Gly Thr Thr Asn Thr Val Ala Ala Tyr Asn Leu Thr Trp Lys Ser Thr
    290                 295                 300
Asn Phe Lys Thr Ile Leu Glu Trp Glu Pro Lys Pro Val Asn Gln Val
305                 310                 315                 320
Tyr Thr Val Gln Ile Ser Thr Lys Ser Gly Asp Trp Lys Ser Lys Cys
                325                 330                 335
Phe Tyr Thr Thr Asp Thr Glu Cys Asp Leu Thr Asp Glu Ile Val Lys
            340                 345                 350
Asp Val Lys Gln Thr Tyr Leu Ala Arg Val Phe Ser Tyr Pro Ala Gly
            355                 360                 365
Asn Val Glu Ser Thr Gly Ser Ala Gly Glu Pro Leu Tyr Glu Asn Ser
        370                 375                 380
Pro Glu Phe Thr Pro Tyr Leu Glu Thr Asn Leu Gly Gln Pro Thr Ile
385                 390                 395                 400
Gln Ser Phe Glu Gln Val Gly Thr Lys Val Asn Val Thr Val Glu Asp
                405                 410                 415
Glu Arg Thr Leu Val Arg Arg Asn Asn Thr Phe Leu Ser Leu Arg Asp
            420                 425                 430
Val Phe Gly Lys Asp Leu Ile Tyr Thr Leu Tyr Trp Lys Ser Ser
            435                 440                 445
Ser Ser Gly Lys Lys Thr Ala Lys Thr Asn Thr Asn Glu Phe Leu Ile
    450                 455                 460
Asp Val Asp Lys Gly Glu Asn Tyr Cys Phe Ser Val Gln Ala Val Ile
465                 470                 475                 480
Pro Ser Arg Thr Val Asn Arg Lys Ser Thr Asp Ser Pro Val Glu Cys
                485                 490                 495
Met Gly Gln Glu Lys Gly Glu Phe Arg Glu Asn Trp Val Asn Val Ile
```

|  |  |  | 500 |  |  |  |  | 505 |  |  |  |  | 510 |  |
|---|---|---|---|---|---|---|---|---|---|---|---|---|---|---|
| Ser | Asp | Leu | Lys | Lys | Ile | Glu | Asp | Leu | Ile | Gln | Ser | Met | His | Ile | Asp |
|  |  |  | 515 |  |  |  |  | 520 |  |  |  |  | 525 |  |  |

Ala Thr Leu Tyr Thr Glu Ser Asp Val His Pro Ser Cys Lys Val Thr
    530                 535                 540

Ala Met Lys Cys Phe Leu Leu Glu Leu Gln Val Ile Ser Leu Glu Ser
545                 550                 555                 560

Gly Asp Ala Ser Ile His Asp Thr Val Glu Asn Leu Ile Ile Leu Ala
                565                 570                 575

Asn Asn Ser Leu Ser Ser Asn Gly Asn Val Thr Glu Ser Gly Cys Lys
            580                 585                 590

Glu Cys Glu Glu Leu Glu Glu Lys Asn Ile Lys Glu Phe Leu Gln Ser
        595                 600                 605

Phe Val His Ile Val Gln Met Phe Ile Asn Thr Ser
    610                 615                 620

<210> SEQ ID NO 194
<211> LENGTH: 1860
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs21 sequence"

<400> SEQUENCE: 194

| atccccccc | atgtgcaaaa | gagcgtgaac | aacgatatga | tcgtgaccga | caacaacggc | 60 |
| gccgtgaagt | ttccccagct | ctgcaagttc | tgcgatgtca | ggttcagcac | ctgcgataat | 120 |
| cagaagtcct | gcatgtccaa | ctgcagcatc | acctccatct | gcgagaagcc | caagaagtg | 180 |
| tgcgtggccg | tgtggcggaa | aaatgacgag | aacatcaccc | tggagaccgt | gtgtcacgac | 240 |
| cccaagctcc | cttatcacga | cttcattctg | gaggacgctg | cctcccccaa | atgcatcatg | 300 |
| aaggagaaga | agaagcccgg | agagaccttc | tttatgtgtt | cctgtagcag | cgacgagtgt | 360 |
| aacgacaaca | tcatcttcag | cgaagagtac | aacaccagca | accctgatgg | aggtggcgga | 420 |
| tccggaggtg | gaggttctgg | tggaggtggg | agtattcctc | cccacgtgca | gaagagcgtg | 480 |
| aataatgaca | tgatcgtgac | cgataacaat | ggcgccgtga | aatttcccca | gctgtgcaaa | 540 |
| ttctgcgatg | tgaggttttc | cacctgcgac | aaccagaagt | cctgtatgag | caactgctcc | 600 |
| atcacctcca | tctgtgagaa | gcctcaggag | gtgtgcgtgg | ctgtctggcg | gaagaatgac | 660 |
| gagaatatca | ccctggaaac | cgtctgccac | gatcccaagc | tgccctacca | cgatttcatc | 720 |
| ctggaagacg | ccgccagccc | taagtgcatc | atgaaagaga | aaagaagcc | tggcgagacc | 780 |
| tttttcatgt | gctcctgcag | cagcgacgaa | tgcaacgaca | tatcatctt | agcgaggaa | 840 |
| tacaatacca | gcaaccccga | cagcggcaca | accaacacag | tcgctgccta | aacctcact | 900 |
| tggaagagca | ccaacttcaa | aaccatcctc | gaatgggaac | ccaaacccgt | taaccaagtt | 960 |
| tacaccgtgc | agatcagcac | caagtccggc | gactggaagt | ccaaatgttt | ctataccacc | 1020 |
| gacaccgagt | gcgatctcac | cgatgagatc | gtgaaagatg | tgaaacagac | ctacctcgcc | 1080 |
| cgggtgttta | gctaccccgc | cggcaatgtg | gagagcactg | gttccgctgg | cgagcctta | 1140 |
| tacgagaaca | gccccgaatt | taccccttac | ctcgagacca | atttaggaca | gcccaccatc | 1200 |
| caaagctttg | agcaagttgg | cacaaaggtg | aatgtgacag | tggaggacga | gcggacttta | 1260 |
| gtgcggcgga | acaacaccctt | tctcagcctc | cgggatgtgt | tcggcaaaga | tttaatctac | 1320 |

```
acactgtatt actggaagtc ctcttcctcc ggcaagaaga cagctaaaac caacacaaac    1380
gagtttttaa tcgacgtgga taaaggcgaa aactactgtt tcagcgtgca agctgtgatc    1440
ccctcccgga ccgtgaatag gaaaagcacc gatagccccg ttgagtgcat gggccaagaa    1500
aagggcgagt tccgggagaa ctgggtgaac gtcatcagcg atttaaagaa gatcgaagat    1560
ttaattcagt ccatgcatat cgacgccact ttatacacag aatccgacgt gcacccctct    1620
tgtaaggtga ccgccatgaa atgtttttta ctggagctgc aagttatctc tttagagagc    1680
ggagacgcta gcatccacga caccgtggag aatttaatca ttttagccaa taactcttta    1740
tccagcaacg gcaacgtgac agagtccggc tgcaaggagt gcgaagagct ggaggagaag    1800
aacatcaagg agtttctgca atcctttgtg cacattgtcc agatgttcat caatacctcc    1860
```

<210> SEQ ID NO 195
<211> LENGTH: 638
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs21 sequence"

<400> SEQUENCE: 195

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
                20                  25                  30

Val Thr Asp Asn Asn Gly Ala Val Lys Phe Pro Gln Leu Cys Lys Phe
            35                  40                  45

Cys Asp Val Arg Phe Ser Thr Cys Asp Asn Gln Lys Ser Cys Met Ser
        50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
                100                 105                 110

Ser Pro Lys Cys Ile Met Lys Glu Lys Lys Pro Gly Glu Thr Phe
            115                 120                 125

Phe Met Cys Ser Cys Ser Ser Asp Glu Cys Asn Asp Asn Ile Ile Phe
        130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
                180                 185                 190

Phe Pro Gln Leu Cys Lys Phe Cys Asp Val Arg Phe Ser Thr Cys Asp
            195                 200                 205

Asn Gln Lys Ser Cys Met Ser Asn Cys Ser Ile Thr Ser Ile Cys Glu
        210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
```

```
                260                 265                 270
Lys Lys Pro Gly Glu Thr Phe Phe Met Cys Ser Cys Ser Ser Asp Glu
            275                 280                 285

Cys Asn Asp Asn Ile Ile Phe Ser Glu Glu Tyr Asn Thr Ser Asn Pro
            290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
                325                 330                 335

Gln Val Tyr Thr Val Gln Ile Ser Thr Lys Ser Gly Asp Trp Lys Ser
            340                 345                 350

Lys Cys Phe Tyr Thr Thr Asp Thr Glu Cys Asp Leu Thr Asp Glu Ile
            355                 360                 365

Val Lys Asp Val Lys Gln Thr Tyr Leu Ala Arg Val Phe Ser Tyr Pro
370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415

Thr Ile Gln Ser Phe Glu Gln Val Gly Thr Lys Val Asn Val Thr Val
            420                 425                 430

Glu Asp Glu Arg Thr Leu Val Arg Arg Asn Asn Thr Phe Leu Ser Leu
            435                 440                 445

Arg Asp Val Phe Gly Lys Asp Leu Ile Tyr Thr Leu Tyr Tyr Trp Lys
450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                485                 490                 495

Val Ile Pro Ser Arg Thr Val Asn Arg Lys Ser Thr Asp Ser Pro Val
            500                 505                 510

Glu Cys Met Gly Gln Glu Lys Gly Glu Phe Arg Glu Asn Trp Val Asn
            515                 520                 525

Val Ile Ser Asp Leu Lys Lys Ile Glu Asp Leu Ile Gln Ser Met His
            530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
            595                 600                 605

Cys Lys Glu Cys Glu Glu Leu Glu Glu Lys Asn Ile Lys Glu Phe Leu
            610                 615                 620

Gln Ser Phe Val His Ile Val Gln Met Phe Ile Asn Thr Ser
625                 630                 635

<210> SEQ ID NO 196
<211> LENGTH: 1914
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic TGFRt15-TGFRs21 sequence"

<400> SEQUENCE: 196

| | | | | | |
|---|---|---|---|---|---|
| atgaagtggg | tgaccttcat | cagcctgctg | ttcctgttct | ccagcgccta | ctccatcccc | 60 |
| ccccatgtgc | aaaagagcgt | gaacaacgat | atgatcgtga | ccgacaacaa | cggcgccgtg | 120 |
| aagtttcccc | agctctgcaa | gttctgcgat | gtcaggttca | gcacctgcga | taatcagaag | 180 |
| tcctgcatgt | ccaactgcag | catcacctcc | atctgcgaga | agcccaaga | agtgtgcgtg | 240 |
| gccgtgtggc | ggaaaaatga | cgagaacatc | accctggaga | ccgtgtgtca | cgaccccaag | 300 |
| ctcccttatc | acgacttcat | tctggaggac | gctgcctccc | ccaaatgcat | catgaaggag | 360 |
| aagaagaagc | ccggagagac | cttctttatg | tgttcctgta | gcagcgacga | gtgtaacgac | 420 |
| aacatcatct | tcagcgaaga | gtacaacacc | agcaaccctg | atggaggtgg | cggatccgga | 480 |
| ggtggaggtt | ctggtggagg | tgggagtatt | cctccccacg | tgcagaagag | cgtgaataat | 540 |
| gacatgatcg | tgaccgataa | caatggcgcc | gtgaaatttc | cccagctgtg | caaattctgc | 600 |
| gatgtgaggt | tttccacctg | cgacaaccag | aagtcctgta | tgagcaactg | ctccatcacc | 660 |
| tccatctgtg | agaagcctca | ggaggtgtgc | gtggctgtct | ggcggaagaa | tgacgagaat | 720 |
| atcaccctgg | aaaccgtctg | ccacgatccc | aagctgccct | accacgattt | catcctggaa | 780 |
| gacgccgcca | gccctaagtg | catcatgaaa | gagaaaaaga | agcctggcga | gacctttttc | 840 |
| atgtgctcct | gcagcagcga | cgaatgcaac | gacaatatca | tctttagcga | ggaatacaat | 900 |
| accagcaacc | ccgacagcgg | cacaaccaac | acagtcgctg | cctataacct | cacttggaag | 960 |
| agcaccaact | tcaaaaccat | cctcgaatgg | gaacccaaac | ccgttaacca | agtttacacc | 1020 |
| gtgcagatca | gcaccaagtc | cggcgactgg | aagtccaaat | gtttctatac | caccgacacc | 1080 |
| gagtgcgatc | tcaccgatga | gatcgtgaaa | gatgtgaaac | agacctacct | cgcccgggtg | 1140 |
| tttagctacc | ccgccggcaa | tgtggagagc | actggttccg | ctggcgagcc | tttatacgag | 1200 |
| aacagccccg | aatttacccc | ttacctcgag | accaatttag | gacagcccac | catccaaagc | 1260 |
| tttgagcaag | ttggcacaaa | ggtgaatgtg | acagtggagg | acgagcggac | tttagtgcgg | 1320 |
| cggaacaaca | ccttttctcag | cctccgggat | gtgttcggca | agatttaat | ctacacactg | 1380 |
| tattactgga | agtcctcttc | ctccggcaag | aagacagcta | aaaccaacac | aaacgagttt | 1440 |
| ttaatcgacg | tggataaagg | cgaaaactac | tgtttcagcg | tgcaagctgt | gatcccctcc | 1500 |
| cggaccgtga | ataggaaaag | caccgatagc | cccgttgagt | gcatgggcca | agaaaagggc | 1560 |
| gagttccggg | agaactgggt | gaacgtcatc | agcgatttaa | agaagatcga | agatttaatt | 1620 |
| cagtccatgc | atatcgacgc | cactttatac | acagaatccg | acgtgcaccc | ctcttgtaag | 1680 |
| gtgaccgcca | tgaatgtttt | tttactggag | ctgcaagtta | tctctttaga | gagcggagac | 1740 |
| gctagcatcc | acgacaccgt | ggagaattta | atcattttag | ccaataactc | tttatccagc | 1800 |
| aacggcaacg | tgacagagtc | cggctgcaag | gagtgcgaag | agctggagga | gaagaacatc | 1860 |
| aaggagtttc | tgcaatcctt | tgtgcacatt | gtccagatgt | tcatcaatac | ctcc | 1914 |

<210> SEQ ID NO 197
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic TGFRt15-TGFRs21 sequence"

<400> SEQUENCE: 197

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
            165                 170                 175

Gln Leu Cys Lys Phe Cys Asp Val Arg Phe Ser Thr Cys Asp Asn Gln
        180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
            245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ile
        275                 280                 285

Thr Cys Pro Pro Pro Met Ser Val Glu His Ala Asp Ile Trp Val Lys
        290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
                325                 330                 335

Ala Thr Asn Val Ala His Trp Thr Thr Pro Ser Leu Lys Cys Ile Arg
            340                 345                 350

Gln Gly Gln Asp Arg His Met Ile Arg Met Arg Gln Leu Ile Asp Ile
        355                 360                 365

Val Asp Gln Leu Lys Asn Tyr Val Asn Asp Leu Val Pro Glu Phe Leu
    370                 375                 380

Pro Ala Pro Glu Asp Val Glu Thr Asn Cys Glu Trp Ser Ala Phe Ser
385                 390                 395                 400

Cys Phe Gln Lys Ala Gln Leu Lys Ser Ala Asn Thr Gly Asn Asn Glu
                405                 410                 415
```

```
Arg Ile Ile Asn Val Ser Ile Lys Lys Leu Lys Arg Lys Pro Pro Ser
                420                 425                 430

Thr Asn Ala Gly Arg Arg Gln Lys His Arg Leu Thr Cys Pro Ser Cys
        435                 440                 445

Asp Ser Tyr Glu Lys Lys Pro Pro Lys Glu Phe Leu Glu Arg Phe Lys
    450                 455                 460

Ser Leu Leu Gln Lys Met Ile His Gln His Leu Ser Ser Arg Thr His
465                 470                 475                 480

Gly Ser Glu Asp Ser
            485

<210> SEQ ID NO 198
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs21 sequence"

<400> SEQUENCE: 198 atccccccc  atgtgcaaaa  gagcgtgaac  aacgatatga  tcgtgaccga  caacaacggc      60
gccgtgaagt  ttccccagct  ctgcaagttc  tgcgatgtca  ggttcagcac  ctgcgataat    120
cagaagtcct  gcatgtccaa  ctgcagcatc  acctccatct  gcgagaagcc  caagaagtg    180 tgcgtggccg  tgtggcggaa  aaatgacgag  aacatcaccc  tggagaccgt  gtgtcacgac    240
cccaagctcc  cttatcacga  cttcattctg  gaggacgctg  cctcccccaa  atgcatcatg    300
aaggagaaga  agaagcccgg  agagaccttc  tttatgtgtt  cctgtagcag  cgacgagtgt    360
aacgacaaca  tcatcttcag  cgaagagtac  aacaccagca  accctgatgg  aggtggcgga    420
tccggaggtg  gaggttctgg  tggaggtggg  agtattcctc  ccacgtgca   gaagagcgtg    480 aataatgaca  tgatcgtgac  cgataacaat  ggcgccgtga  aatttcccca  gctgtgcaaa    540
ttctgcgatg  tgaggttttc  cacctgcgac  aaccagaagt  cctgtatgag  caactgctcc    600
atcacctcca  tctgtgagaa  gcctcaggag  gtgtgcgtgg  ctgtctggcg  gaagaatgac    660
gagaatatca  ccctggaaac  cgtctgccac  gatcccaagc  tgccctacca  cgatttcatc    720
ctggaagacg  ccgccagccc  taagtgcatc  atgaaagaga  aaaagaagcc  tggcgagacc    780
tttttcatgt  gctcctgcag  cagcgacgaa  tgcaacgaca  atatcatctt  tagcgaggaa    840
tacaatacca  gcaaccccga  cattacatgc  ccccctccca  tgagcgtgga  gcacgccgac    900
atctgggtga  gagctatag   cctctacagc  cgggagaggt  atatctgtaa  cagcggcttc    960
aagaggaagg  ccggcaccag  cagcctcacc  gagtgcgtgc  tgaataaggc  taccaacgtg   1020
gctcactgga  caaacccctc  tttaaagtgc  atccggcagg  ccaggacag   gcacatgatc   1080 cggatgaggc  agctcatcga  catcgtcgac  cagctgaaga  actacgtgaa  cgacctggtg   1140
cccgagtttc  tgcctgcccc  cgaggacgtg  gagaccaact  gcgagtggtc  cgccttctcc   1200
tgctttcaga  aggcccagct  gaagtccgcc  aacaccggca  caacgagcg   gatcatcaac   1260 gtgagcatca  agaagctgaa  gcggaagcct  ccctccacaa  cgccggcag   gaggcagaag   1320 cacaggctga  cctgccccag  ctgtgactcc  tacgagaaga  gccccccaa   ggagttcctg   1380 gagaggttca  agtccctgct  gcagaagatg  atccatcagc  acctgtcctc  caggacccac   1440
ggctccgagg  actcc                                                        1455

<210> SEQ ID NO 199
```

<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-TGFRs21 sequence"

<400> SEQUENCE: 199

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365
```

Ile Arg Gln Gly Gln Asp Arg His Met Ile Arg Met Arg Gln Leu Ile
370             375                 380

Asp Ile Val Asp Gln Leu Lys Asn Tyr Val Asn Asp Leu Val Pro Glu
385                 390                 395                 400

Phe Leu Pro Ala Pro Glu Asp Val Glu Thr Asn Cys Glu Trp Ser Ala
                405                 410                 415

Phe Ser Cys Phe Gln Lys Ala Gln Leu Lys Ser Ala Asn Thr Gly Asn
                420                 425                 430

Asn Glu Arg Ile Ile Asn Val Ser Ile Lys Lys Leu Lys Arg Lys Pro
                435                 440                 445

Pro Ser Thr Asn Ala Gly Arg Arg Gln Lys His Arg Leu Thr Cys Pro
    450                 455                 460

Ser Cys Asp Ser Tyr Glu Lys Lys Pro Pro Lys Glu Phe Leu Glu Arg
465                 470                 475                 480

Phe Lys Ser Leu Leu Gln Lys Met Ile His Gln His Leu Ser Ser Arg
                485                 490                 495

Thr His Gly Ser Glu Asp Ser
            500

<210> SEQ ID NO 200
<211> LENGTH: 1509
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs21 sequence"

<400> SEQUENCE: 200
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agccccaaga agtgtgcgtg     240
gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaaccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg ctccatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gccctaagtg catcatgaaa gagaaaaaga gcctggcga accttttttc     840 atgtgctcct gcagcagcga cgaatgcaac gacaatatca tctttagcga ggaatacaat     900
accagcaacc ccgacattac atgcccccct cccatgagcg tggagcacgc cgacatctgg     960
gtgaagagct atagcctcta cagccgggag aggtatatct gtaacagcgg cttcaagagg    1020
aaggccggca ccagcagcct caccgagtgc gtgctgaata ggctaccaa cgtggctcac    1080 tggacaacac cctctttaaa gtgcatccgg cagggccagg acaggcacat gatccggatg    1140
aggcagctca tcgacatcgt cgaccagctg aagaactacg tgaacgacct ggtgcccgag    1200

-continued

```
tttctgcctg cccccgagga cgtggagacc aactgcgagt ggtccgcctt ctcctgcttt    1260
cagaaggccc agctgaagtc cgccaacacc ggcaacaacg agcggatcat caacgtgagc    1320
atcaagaagc tgaagcggaa gcctccctcc acaaacgccg gcaggaggca gaagcacagg    1380
ctgacctgcc ccagctgtga ctcctacgag aagaagcccc ccaaggagtt cctggagagg    1440
ttcaagtccc tgctgcagaa gatgatccat cagcacctgt cctccaggac ccacggctcc    1500
gaggactcc                                                            1509

<210> SEQ ID NO 201
<211> LENGTH: 620
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs16 sequence"

<400> SEQUENCE: 201

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ser
        275                 280                 285

Gly Thr Thr Asn Thr Val Ala Ala Tyr Asn Leu Thr Trp Lys Ser Thr
```

```
                    290                 295                 300
Asn Phe Lys Thr Ile Leu Glu Trp Glu Pro Lys Pro Val Asn Gln Val
305                 310                 315                 320

Tyr Thr Val Gln Ile Ser Thr Lys Ser Gly Asp Trp Lys Ser Lys Cys
                325                 330                 335

Phe Tyr Thr Thr Asp Thr Glu Cys Asp Leu Thr Asp Glu Ile Val Lys
            340                 345                 350

Asp Val Lys Gln Thr Tyr Leu Ala Arg Val Phe Ser Tyr Pro Ala Gly
        355                 360                 365

Asn Val Glu Ser Thr Gly Ser Ala Gly Glu Pro Leu Tyr Glu Asn Ser
370                 375                 380

Pro Glu Phe Thr Pro Tyr Leu Glu Thr Asn Leu Gly Gln Pro Thr Ile
385                 390                 395                 400

Gln Ser Phe Glu Gln Val Gly Thr Lys Val Asn Val Thr Val Glu Asp
                405                 410                 415

Glu Arg Thr Leu Val Arg Arg Asn Asn Thr Phe Leu Ser Leu Arg Asp
            420                 425                 430

Val Phe Gly Lys Asp Leu Ile Tyr Thr Leu Tyr Tyr Trp Lys Ser Ser
        435                 440                 445

Ser Ser Gly Lys Lys Thr Ala Lys Thr Asn Thr Asn Glu Phe Leu Ile
450                 455                 460

Asp Val Asp Lys Gly Glu Asn Tyr Cys Phe Ser Val Gln Ala Val Ile
465                 470                 475                 480

Pro Ser Arg Thr Val Asn Arg Lys Ser Thr Asp Ser Pro Val Glu Cys
                485                 490                 495

Met Gly Gln Glu Lys Gly Glu Phe Arg Glu Asn Trp Val Asn Val Ile
            500                 505                 510

Ser Asp Leu Lys Lys Ile Glu Asp Leu Ile Gln Ser Met His Ile Asp
        515                 520                 525

Ala Thr Leu Tyr Thr Glu Ser Asp Val His Pro Ser Cys Lys Val Thr
530                 535                 540

Ala Met Lys Cys Phe Leu Leu Glu Leu Gln Val Ile Ser Leu Glu Ser
545                 550                 555                 560

Gly Asp Ala Ser Ile His Asp Thr Val Glu Asn Leu Ile Ile Leu Ala
                565                 570                 575

Asn Asn Ser Leu Ser Ser Asn Gly Asn Val Thr Glu Ser Gly Cys Lys
            580                 585                 590

Glu Cys Glu Glu Leu Glu Glu Lys Asn Ile Lys Glu Phe Leu Gln Ser
        595                 600                 605

Phe Val His Ile Val Gln Met Phe Ile Asn Thr Ser
610                 615                 620

<210> SEQ ID NO 202
<211> LENGTH: 1860
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs16 sequence"

<400> SEQUENCE: 202 atccccccc  atgtgcaaaa gagcgtgaac aacgatatga tcgtgaccga caacaacggc    60
gccgtgaagt tccccagct  ctgcaagttc tgcgatgtca ggttcagcac ctgcgataat   120
cagaagtcct gcatgtccaa ctgcagcatc acctccatct gcgagaagcc ccaagaagtg   180
```

```
tgcgtggccg tgtggcggaa aaatgacgag aacatcaccc tggagaccgt gtgtcacgac      240
cccaagctcc cttatcacga cttcattctg gaggacgctg cctcccccaa atgcatcatg      300
aaggagaaga agaagcccgg agagaccttc tttatgtgtt cctgtagcag cgacgagtgt      360
aacgacaaca tcatcttcag cgaagagtac aacaccagca accctgatgg aggtggcgga      420
tccggaggtg gaggttctgg tggaggtggg agtattcctc ccacgtgca gaagagcgtg       480 aataatgaca tgatcgtgac cgataacaat ggcgccgtga aatttcccca gctgtgcaaa      540
ttctgcgatg tgaggttttc cacctgcgac aaccagaagt cctgtatgag caactgctcc      600
atcacctcca tctgtgagaa gcctcaggag gtgtgcgtgg ctgtctggcg aagaatgac       660 gagaatatca ccctggaaac cgtctgccac gatcccaagc tgccctacca cgatttcatc      720
ctggaagacg ccgccagccc taagtgcatc atgaaagaga aaagaagcc tggcgagacc       780 ttttcatgt gctcctgcag cagcgacgaa tgcaacgaca atatcatctt tagcgaggaa       840
tacaatacca gcaaccccga cagcggcaca accaacacag tcgctgccta aacctcact      900 tggaagagca ccaacttcaa aaccatcctc gaatgggaac ccaaacccgt taaccaagtt      960
tacaccgtgc agatcagcac caagtccggc gactggaagt ccaaatgttt ctataccacc      1020
gacaccgagt gcgatctcac cgatgagatc gtgaaagatg tgaaacagac ctacctcgcc      1080
cgggtgttta gctaccccgc cggcaatgtg gagagcactg gttccgctgg cgagccttta      1140
tacgagaaca gccccgaatt taccccttac ctcgagacca atttaggaca gcccaccatc      1200
caaagctttg agcaagttgg cacaaaggtg aatgtgacag tggaggacga gcggacttta      1260
gtgcggcgga acaacaccctt tctcagcctc cgggatgtgt tcggcaaaga tttaatctac      1320
acactgtatt actggaagtc ctcttcctcc ggcaagaaga cagctaaaac caacacaaac      1380
gagtttttaa tcgacgtgga taaaggcgaa aactactgtt tcagcgtgca agctgtgatc      1440
ccctcccgga ccgtgaatag gaaaagcacc gatagcccg ttgagtgcat gggccaagaa       1500
aagggcgagt tccgggagaa ctgggtgaac gtcatcagcg atttaaagaa gatcgaagat      1560
ttaattcagt ccatgcatat cgacgccact ttatacacag aatccgacgt gcacccctct      1620
tgtaaggtga ccgccatgaa atgttttta ctggagctgc aagttatctc tttagagagc       1680
ggagacgcta gcatccacga caccgtggag aatttaatca ttttagccaa taactcttta      1740
tccagcaacg gcaacgtgac agagtccggc tgcaaggagt cgcaagagct ggaggagaag      1800
aacatcaagg agtttctgca atcctttgtg cacattgtcc agatgttcat caataccctcc     1860
```

<210> SEQ ID NO 203
<211> LENGTH: 638
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs16 sequence"

<400> SEQUENCE: 203

Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser

-continued

```
                50                  55                  60
Asn Cys Ser Ile Thr Ser Ile Cys Glu Lys Pro Gln Glu Val Cys Val
 65                  70                  75                  80

Ala Val Trp Arg Lys Asn Asp Glu Asn Ile Thr Leu Glu Thr Val Cys
                 85                  90                  95

His Asp Pro Lys Leu Pro Tyr His Asp Phe Ile Leu Glu Asp Ala Ala
                100                 105                 110

Ser Pro Lys Cys Ile Met Lys Glu Lys Lys Pro Gly Glu Thr Phe
                115                 120                 125

Phe Met Cys Ser Cys Ser Ser Asp Glu Cys Asn Asp Asn Ile Ile Phe
                130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
                180                 185                 190

Phe Pro Gln Leu Cys Lys Phe Cys Asp Val Arg Phe Ser Thr Cys Asp
                195                 200                 205

Asn Gln Lys Ser Cys Met Ser Asn Cys Ser Ile Thr Ser Ile Cys Glu
                210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
                260                 265                 270

Lys Lys Pro Gly Glu Thr Phe Phe Met Cys Ser Cys Ser Ser Asp Glu
                275                 280                 285

Cys Asn Asp Asn Ile Ile Phe Ser Glu Glu Tyr Asn Thr Ser Asn Pro
                290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
                325                 330                 335

Gln Val Tyr Thr Val Gln Ile Ser Thr Lys Ser Gly Asp Trp Lys Ser
                340                 345                 350

Lys Cys Phe Tyr Thr Thr Asp Thr Glu Cys Asp Leu Thr Asp Glu Ile
                355                 360                 365

Val Lys Asp Val Lys Gln Thr Tyr Leu Ala Arg Val Phe Ser Tyr Pro
                370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415

Thr Ile Gln Ser Phe Glu Gln Val Gly Thr Lys Val Asn Val Thr Val
                420                 425                 430

Glu Asp Glu Arg Thr Leu Val Arg Arg Asn Asn Thr Phe Leu Ser Leu
                435                 440                 445

Arg Asp Val Phe Gly Lys Asp Leu Ile Tyr Thr Leu Tyr Tyr Trp Lys
                450                 455                 460

Ser Ser Ser Ser Gly Lys Lys Thr Ala Lys Thr Asn Thr Asn Glu Phe
465                 470                 475                 480
```

Leu Ile Asp Val Asp Lys Gly Glu Asn Tyr Cys Phe Ser Val Gln Ala
            485                 490                 495

Val Ile Pro Ser Arg Thr Val Asn Arg Lys Ser Thr Asp Ser Pro Val
            500                 505                 510

Glu Cys Met Gly Gln Glu Lys Gly Glu Phe Arg Glu Asn Trp Val Asn
            515                 520                 525

Val Ile Ser Asp Leu Lys Lys Ile Glu Asp Leu Ile Gln Ser Met His
            530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
                580                 585                 590

Leu Ala Asn Asn Ser Leu Ser Ser Asn Gly Asn Val Thr Glu Ser Gly
                595                 600                 605

Cys Lys Glu Cys Glu Glu Leu Glu Glu Lys Asn Ile Lys Glu Phe Leu
610                 615                 620

Gln Ser Phe Val His Ile Val Gln Met Phe Ile Asn Thr Ser
625                 630                 635

<210> SEQ ID NO 204
<211> LENGTH: 1914
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs16 sequence"

<400> SEQUENCE: 204
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agcccaaga agtgtgcgtg     240 gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc cggagagac cttctttatg tgttcctgta gcagcgacga gtgtaacgac     420
aacatcatct tcagcgaaga gtacaacacc agcaaccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg ctccatcacc     660
tccatctgtg agaagcctca ggaggtgtgc gtggctgtct ggcggaagaa tgacgagaat     720
atcaccctgg aaaccgtctg ccacgatccc aagctgccct accacgatt catcctggaa     780 gacgccgcca gccctaagtg catcatgaaa gagaaaaaga agcctggcga gacctttttc     840
atgtgctcct gcagcagcga cgaatgcaac gacaatatca tctttagcga ggaatacaat     900
accagcaacc ccgacagcgg cacaaccaac acagtcgctg cctataacct cacttggaag     960
agcaccaact tcaaaaccat cctcgaatgg gaacccaaac ccgttaacca agtttacacc    1020
gtgcagatca gcaccaagtc cggcgactgg aagtccaaat gtttctatac caccgacacc    1080

-continued

```
gagtgcgatc tcaccgatga gatcgtgaaa gatgtgaaac agacctacct cgcccgggtg  1140
tttagctacc ccgccggcaa tgtggagagc actggttccg ctggcgagcc tttatacgag  1200
aacagccccg aatttacccc ttacctcgag accaatttag gacagcccac catccaaagc  1260
tttgagcaag ttggcacaaa ggtgaatgtg acagtggagg acgagcggac tttagtgcgg  1320
cggaacaaca cctttctcag cctccgggat gtgttcggca agatttaat ctacacactg  1380 tattactgga agtcctcttc ctccggcaag aagacagcta aaccaacac aaacgagttt  1440 ttaatcgacg tggataaagg cgaaaactac tgtttcagcg tgcaagctgt gatccctcc  1500 cggaccgtga ataggaaaag caccgatagc cccgttgagt gcatgggcca agaaaagggc  1560
gagttccggg agaactgggt gaacgtcatc agcgatttaa agaagatcga agatttaatt  1620
cagtccatgc atatcgacgc cactttatac acagaatccg acgtgcaccc ctcttgtaag  1680
gtgaccgcca tgaaatgttt tttactggag ctgcaagtta tctctttaga gagcggagac  1740
gctagcatcc acgacaccgt ggagaattta atcattttag ccaataactc tttatccagc  1800
aacggcaacg tgacagagtc cggctgcaag gagtgcgaag agctggagga gaagaacatc  1860
aaggagtttc tgcaatcctt tgtgcacatt gtccagatgt tcatcaatac ctcc          1914
```

<210> SEQ ID NO 205
<211> LENGTH: 592
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-TGFRs16 sequence"

<400> SEQUENCE: 205

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205
```

| | | | | | | | | | | | |
|---|---|---|---|---|---|---|---|---|---|---|---|
|Gln|Glu|Val|Cys|Val|Ala|Val|Trp|Arg|Lys|Asn|Asp|Glu|Asn|Ile|Thr|
|210| | | | |215| | | | |220| | | | | |

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Tyr Asn Thr Ser Asn Pro Asp Ile
        275                 280                 285

Thr Cys Pro Pro Met Ser Val Glu His Ala Asp Ile Trp Val Lys
290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
                325                 330                 335

Ala Thr Asn Val Ala His Trp Thr Thr Pro Ser Leu Lys Cys Ile Arg
            340                 345                 350

Ser Glu Leu Thr Gln Asp Pro Ala Val Ser Val Ala Leu Gly Gln Thr
        355                 360                 365

Val Arg Ile Thr Cys Gln Gly Asp Ser Leu Arg Ser Tyr Tyr Ala Ser
370                 375                 380

Trp Tyr Gln Gln Lys Pro Gly Gln Ala Pro Val Leu Val Ile Tyr Gly
385                 390                 395                 400

Lys Asn Asn Arg Pro Ser Gly Ile Pro Asp Arg Phe Ser Gly Ser Ser
                405                 410                 415

Ser Gly Asn Thr Ala Ser Leu Thr Ile Thr Gly Ala Gln Ala Glu Asp
            420                 425                 430

Glu Ala Asp Tyr Tyr Cys Asn Ser Arg Asp Ser Ser Gly Asn His Val
        435                 440                 445

Val Phe Gly Gly Gly Thr Lys Leu Thr Val Gly His Gly Gly Gly Gly
450                 455                 460

Ser Gly Gly Gly Gly Ser Gly Gly Gly Ser Glu Val Gln Leu Val
465                 470                 475                 480

Glu Ser Gly Gly Gly Val Val Arg Pro Gly Gly Ser Leu Arg Leu Ser
                485                 490                 495

Cys Ala Ala Ser Gly Phe Thr Phe Asp Asp Tyr Gly Met Ser Trp Val
            500                 505                 510

Arg Gln Ala Pro Gly Lys Gly Leu Glu Trp Val Ser Gly Ile Asn Trp
        515                 520                 525

Asn Gly Gly Ser Thr Gly Tyr Ala Asp Ser Val Lys Gly Arg Phe Thr
530                 535                 540

Ile Ser Arg Asp Asn Ala Lys Asn Ser Leu Tyr Leu Gln Met Asn Ser
545                 550                 555                 560

Leu Arg Ala Glu Asp Thr Ala Val Tyr Tyr Cys Ala Arg Gly Arg Ser
                565                 570                 575

Leu Leu Phe Asp Tyr Trp Gly Gln Gly Thr Leu Val Thr Val Ser Arg
            580                 585                 590

<210> SEQ ID NO 206
<211> LENGTH: 1776
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic TGFRt15-TGFRs16 sequence"

<400> SEQUENCE: 206

```
atccccccccc atgtgcaaaa gagcgtgaac aacgatatga tcgtgaccga caacaacggc    60
gccgtgaagt tcccccagct ctgcaagttc tgcgatgtca ggttcagcac ctgcgataat   120
cagaagtcct gcatgtccaa ctgcagcatc acctccatct gcgagaagcc caagaagtg    180
tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga agaagcccgg agagaccttc tttatgtgtt cctgtagcag cgacgagtgt   360
aacgacaaca tcatcttcag cgaagagtac aacaccagca accctgatgg aggtggcgga   420
tccggaggtg gaggttctgg tggaggtggg agtattcctc cccacgtgca gaagagcgtg   480
aataatgaca tgatcgtgac cgataacaat ggcgccgtga atttccccca gctgtgcaaa   540
ttctgcgatg tgaggttttc cacctgcgac aaccagaagt cctgtatgag caactgctcc   600
atcacctcca tctgtgagaa gcctcaggag gtgtgcgtgg ctgtctggcg gaagaatgac   660
gagaatatca ccctggaaac cgtctgccac gatcccaagc tgccctacca cgatttcatc   720
ctggaagacg ccgccagccc taagtgcatc atgaaagaga aaaagaagcc tggcgagacc   780
tttttcatgt gctcctgcag cagcgacgaa tgcaacgaca tatcatcatctt agcgaggaa   840
tacaatacca gcaaccccga cattacatgc ccccctccca tgagcgtgga gcacgccgac   900
atctgggtga gagctatag cctctacagc cgggagaggt atatctgtaa cagcggcttc   960
aagaggaagg ccggcaccag cagcctcacc gagtgcgtgc tgaataaggc taccaacgtg  1020
gctcactgga caacaccctc tttaaagtgc atccggtccg agctgaccca ggaccctgct  1080
gtgtccgtgg ctctgggcca gaccgtgagg atcacctgcc agggcgactc cctgaggtcc  1140
tactacgcct cctggtacca gcagaagccc ggccaggctc ctgtgctggt gatctacggc  1200
aagaacaaca ggccctccgg catccctgac aggttctccg gatcctcctc cggcaacacc  1260
gcctccctga ccatcacagg cgctcaggcc gaggacgagg ctgactacta ctgcaactcc  1320
agggactcct ccggcaacca tgtggtgttc ggcgccggca ccaagctgac cgtgggccat  1380
ggcggcggcg gctccggagg cggcggcagc ggcggaggag gatccgaggt gcagctggtg  1440
gagtccggag gaggagtggt gaggcctgga ggctccctga ggctgagctg tgctgcctcc  1500
ggcttcacct tcgacgacta cggcatgtcc tgggtgaggc aggctcctgg aaagggcctg  1560
gagtgggtgt ccggcatcaa ctggaacggc ggatccaccg gctacgccga ttccgtgaag  1620
ggcaggttca ccatcagcag ggacaacgcc aagaactccc tgtacctgca gatgaactcc  1680
ctgaggggccg aggacaccgc cgtgtactac tgcgccaggg gcaggtccct gctgttcgac  1740
tactggggac agggcaccct ggtgaccgtg tccagg                              1776
```

<210> SEQ ID NO 207
<211> LENGTH: 610
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic TGFRt15-TGFRs16 sequence"

<400> SEQUENCE: 207

```
Met Lys Trp Val Thr Phe Ile Ser Leu Leu Phe Leu Phe Ser Ser Ala
1               5                   10                  15
```

```
Tyr Ser Ile Pro Pro His Val Gln Lys Ser Val Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
50                      55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
                100                 105                 110

Ser Pro Lys Cys Ile Met Lys Glu Lys Lys Pro Gly Glu Thr Phe
            115                 120                 125

Phe Met Cys Ser Cys Ser Ser Asp Glu Cys Asn Asp Asn Ile Ile Phe
130                     135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
            195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
                260                 265                 270

Lys Lys Pro Gly Glu Thr Phe Phe Met Cys Ser Cys Ser Ser Asp Glu
            275                 280                 285

Cys Asn Asp Asn Ile Ile Phe Ser Glu Glu Tyr Asn Thr Ser Asn Pro
290                 295                 300

Asp Ile Thr Cys Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
            355                 360                 365

Ile Arg Ser Glu Leu Thr Gln Asp Pro Ala Val Ser Val Ala Leu Gly
            370                 375                 380

Gln Thr Val Arg Ile Thr Cys Gln Gly Asp Ser Leu Arg Ser Tyr Tyr
385                 390                 395                 400

Ala Ser Trp Tyr Gln Gln Lys Pro Gly Gln Ala Pro Val Leu Val Ile
                405                 410                 415

Tyr Gly Lys Asn Asn Arg Pro Ser Gly Ile Pro Asp Arg Phe Ser Gly
                420                 425                 430
```

```
Ser Ser Ser Gly Asn Thr Ala Ser Leu Thr Ile Thr Gly Ala Gln Ala
            435                 440                 445

Glu Asp Glu Ala Asp Tyr Tyr Cys Asn Ser Arg Asp Ser Ser Gly Asn
450                 455                 460

His Val Val Phe Gly Gly Gly Thr Lys Leu Thr Val Gly His Gly Gly
465                 470                 475                 480

Gly Gly Ser Gly Gly Gly Ser Gly Gly Gly Ser Glu Val Gln
            485                 490                 495

Leu Val Glu Ser Gly Gly Gly Val Val Arg Pro Gly Gly Ser Leu Arg
            500                 505                 510

Leu Ser Cys Ala Ala Ser Gly Phe Thr Phe Asp Asp Tyr Gly Met Ser
            515                 520                 525

Trp Val Arg Gln Ala Pro Gly Lys Gly Leu Glu Trp Val Ser Gly Ile
            530                 535                 540

Asn Trp Asn Gly Gly Ser Thr Gly Tyr Ala Asp Ser Val Lys Gly Arg
545                 550                 555                 560

Phe Thr Ile Ser Arg Asp Asn Ala Lys Asn Ser Leu Tyr Leu Gln Met
                565                 570                 575

Asn Ser Leu Arg Ala Glu Asp Thr Ala Val Tyr Tyr Cys Ala Arg Gly
            580                 585                 590

Arg Ser Leu Leu Phe Asp Tyr Trp Gly Gln Gly Thr Leu Val Thr Val
            595                 600                 605

Ser Arg
    610

<210> SEQ ID NO 208
<211> LENGTH: 1830
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs16 sequence"

<400> SEQUENCE: 208
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agccccaaga gtgtgcgtg      240 gccgtgtggc ggaaaaatga cgagaacatc accctggaga ccgtgtgtca cgaccccaag     300
ctcccttatc acgacttcat tctggaggac gctgcctccc caaatgcat catgaaggag      360 aagaagaagc ccggagagac cttctttatg tgttcctgta gcagcgacga gtgtaacgac     420
aacatcatct cagcgaaga gtacaacacc agcaaccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg ctccatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gcctaagtg catcatgaaa gagaaaaaga gcctggcga gaccttttc      840 atgtgctcct gcagcagcga cgaatgcaac gacaatatca tctttagcga ggaatacaat     900
accagcaacc ccgacattac atgccccct cccatgagcg tggagcacgc cgacatctgg     960
```

```
gtgaagagct atagcctcta cagccgggag aggtatatct gtaacagcgg cttcaagagg    1020
aaggccggca ccagcagcct caccgagtgc gtgctgaata aggctaccaa cgtggctcac    1080
tggacaacac cctctttaaa gtgcatccgg tccgagctga cccaggaccc tgctgtgtcc    1140
gtggctctgg ccagaccgt gaggatcacc tgccagggcg actccctgag gtcctactac    1200
gcctcctggt accagcagaa gcccggccag gctcctgtgc tggtgatcta cggcaagaac    1260
aacaggccct ccggcatccc tgacaggttc tccggatcct cctccggcaa caccgcctcc    1320
ctgaccatca caggcgctca ggccgaggac gaggctgact actactgcaa ctccagggac    1380
tcctccggca accatgtggt gttcggcggc ggcaccaagc tgaccgtggg ccatggcggc    1440
ggcggctccg gaggcggcgg cagcggcgga ggaggatccg aggtgcagct ggtggagtcc    1500
ggaggaggag tggtgaggcc tggaggctcc ctgaggctga gctgtgctgc ctccggcttc    1560
accttcgacg actacggcat gtcctgggtg aggcaggctc ctggaaaggg cctggagtgg    1620
gtgtccggca tcaactggaa cggcggatcc accggctacg ccgattccgt gaagggcagg    1680
ttcaccatca gcagggacaa cgccaagaac tccctgtacc tgcagatgaa ctccctgagg    1740
gccgaggaca ccgccgtgta ctactgcgcc aggggcaggt ccctgctgtt cgactactgg    1800
ggacagggca ccctggtgac cgtgtccagg                                     1830
```

<210> SEQ ID NO 209
<211> LENGTH: 620
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-TGFRs137 sequence"

<400> SEQUENCE: 209

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190
```

```
Lys Ser Cys Met Ser Asn Cys Ser Ile Thr Ser Ile Cys Glu Lys Pro
            195                 200                 205

Gln Glu Val Cys Val Ala Val Trp Arg Lys Asn Asp Glu Asn Ile Thr
210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ser
            275                 280                 285

Gly Thr Thr Asn Thr Val Ala Ala Tyr Asn Leu Thr Trp Lys Ser Thr
            290                 295                 300

Asn Phe Lys Thr Ile Leu Glu Trp Glu Pro Lys Pro Val Asn Gln Val
305                 310                 315                 320

Tyr Thr Val Gln Ile Ser Thr Lys Ser Gly Asp Trp Lys Ser Lys Cys
                325                 330                 335

Phe Tyr Thr Thr Asp Thr Glu Cys Asp Leu Thr Asp Glu Ile Val Lys
                340                 345                 350

Asp Val Lys Gln Thr Tyr Leu Ala Arg Val Phe Ser Tyr Pro Ala Gly
            355                 360                 365

Asn Val Glu Ser Thr Gly Ser Ala Gly Glu Pro Leu Tyr Glu Asn Ser
            370                 375                 380

Pro Glu Phe Thr Pro Tyr Leu Glu Thr Asn Leu Gly Gln Pro Thr Ile
385                 390                 395                 400

Gln Ser Phe Glu Gln Val Gly Thr Lys Val Asn Val Thr Val Glu Asp
                405                 410                 415

Glu Arg Thr Leu Val Arg Arg Asn Asn Thr Phe Leu Ser Leu Arg Asp
                420                 425                 430

Val Phe Gly Lys Asp Leu Ile Tyr Thr Leu Tyr Tyr Trp Lys Ser Ser
            435                 440                 445

Ser Ser Gly Lys Lys Thr Ala Lys Thr Asn Thr Asn Glu Phe Leu Ile
450                 455                 460

Asp Val Asp Lys Gly Glu Asn Tyr Cys Phe Ser Val Gln Ala Val Ile
465                 470                 475                 480

Pro Ser Arg Thr Val Asn Arg Lys Ser Thr Asp Ser Pro Val Glu Cys
                485                 490                 495

Met Gly Gln Glu Lys Gly Glu Phe Arg Glu Asn Trp Val Asn Val Ile
            500                 505                 510

Ser Asp Leu Lys Lys Ile Glu Asp Leu Ile Gln Ser Met His Ile Asp
            515                 520                 525

Ala Thr Leu Tyr Thr Glu Ser Asp Val His Pro Ser Cys Lys Val Thr
            530                 535                 540

Ala Met Lys Cys Phe Leu Leu Glu Leu Gln Val Ile Ser Leu Glu Ser
545                 550                 555                 560

Gly Asp Ala Ser Ile His Asp Thr Val Glu Asn Leu Ile Ile Leu Ala
                565                 570                 575

Asn Asn Ser Leu Ser Ser Asn Gly Asn Val Thr Glu Ser Gly Cys Lys
            580                 585                 590

Glu Cys Glu Glu Leu Glu Glu Lys Asn Ile Lys Glu Phe Leu Gln Ser
            595                 600                 605

Phe Val His Ile Val Gln Met Phe Ile Asn Thr Ser
```

<210> SEQ ID NO 210
<211> LENGTH: 1860
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic TGFRt15-TGFRs137 sequence"

<400> SEQUENCE: 210

```
atccccccc  atgtgcaaaa  gagcgtgaac  aacgatatga  tcgtgaccga  caacaacggc      60
gccgtgaagt  ttccccagct  ctgcaagttc  tgcgatgtca  ggttcagcac  ctgcgataat     120
cagaagtcct  gcatgtccaa  ctgcagcatc  acctccatct  gcgagaagcc  ccaagaagtg     180
tgcgtggccg  tgtggcggaa  aaatgacgag  aacatcaccc  tggagaccgt  gtgtcacgac     240
cccaagctcc  cttatcacga  cttcattctg  gaggacgctg  cctcccccaa  atgcatcatg     300
aaggagaaga  agaagcccgg  agagaccttc  tttatgtgtt  cctgtagcag  cgacgagtgt     360
aacgacaaca  tcatcttcag  cgaagagtac  aaccaccagca  accctgatgg  aggtggcgga     420
tccggaggtg  gaggttctgg  tggaggtggg  agtattcctc  cccacgtgca  gaagagcgtg     480
aataatgaca  tgatcgtgac  cgataacaat  ggcgccgtga  atttcccca   gctgtgcaaa     540
ttctgcgatg  tgagggtttt  cacctgcgac  aaccagaagt  cctgtatgag  caactgctcc     600
atcacctcca  tctgtgagaa  gcctcaggag  gtgtgcgtgg  ctgtctggcg  gaagaatgac     660
gagaatatca  ccctggaaac  cgtctgccac  gatcccaagc  tgccctacca  cgatttcatc     720
ctggaagacg  ccgccagccc  taagtgcatc  atgaaagaga  aaaagaagcc  tggcgagacc     780
tttttcatgt  gctcctgcag  cagcgacgaa  tgcaacgaca  tatcatctt   tagcgaggaa     840
tacaatacca  gcaaccccga  cagcggcaca  accaacacag  tcgctgccta  taacctcact     900
tggaagagca  ccaacttcaa  aaccatcctc  gaatgggaac  ccaaaccgt   taaccaagtt     960
tacaccgtgc  agatcagcac  caagtccggc  gactggaagt  ccaaatgttt  ctataccacc    1020
gacaccgagt  cgatctcac   cgatgagatc  gtgaaagatg  tgaaacagac  ctacctcgcc    1080
cggggtgttta  gctaccccgc  cggcaatgtg  gagagcactg  gttccgctgg  cgagccttta   1140
tacgagaaca  gccccgaatt  taccccttac  ctcgagacca  atttaggaca  gcccaccatc    1200
caaagctttg  agcaagttgg  cacaaaggtg  aatgtgacag  tggaggacga  gcggacttta    1260
gtgcggcgga  acaacacctt  tctcagcctc  cgggatgtgt  tcggcaaaga  tttaatctac    1320
acactgtatt  actggaagtc  ctcttcctcc  ggcaagaaga  cagctaaaac  caacacaaac    1380
gagttttaa   tcgacgtgga  taaaggcgaa  aactactgtt  tcagcgtgca  agctgtgatc    1440
ccctcccgga  ccgtgaatag  gaaaagcacc  gatagccccg  ttgagtgcat  gggccaagaa    1500
aagggcgagt  tccgggagaa  ctgggtgaac  gtcatcagcg  atttaaagaa  gatcgaagat    1560
ttaattcagt  ccatgcatat  cgacgccact  ttatacacag  aatccgacgt  gcaccctct    1620
tgtaaggtga  ccgccatgaa  atgttttta   ctggagctgc  aagttatctc  tttagagagc    1680
ggagacgcta  gcatccacga  caccgtggag  aatttaatca  ttttagccaa  taactcttta    1740
tccagcaacg  gcaacgtgac  agagtccggc  tgcaaggagt  gcgaagagct  ggaggagaag    1800
aacatcaagg  agtttctgca  atcctttgtg  cacattgtcc  agatgttcat  caataccctcc   1860
```

<210> SEQ ID NO 211
<211> LENGTH: 638

<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-TGFRs137 sequence"

<400> SEQUENCE: 211

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
                325                 330                 335

Gln Val Tyr Thr Val Gln Ile Ser Thr Lys Ser Gly Asp Trp Lys Ser
            340                 345                 350

Lys Cys Phe Tyr Thr Thr Asp Thr Glu Cys Asp Leu Thr Asp Glu Ile
        355                 360                 365

Val Lys Asp Val Lys Gln Thr Tyr Leu Ala Arg Val Phe Ser Tyr Pro
```

```
        370                 375                 380
Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
            405                 410                 415

Thr Ile Gln Ser Phe Glu Gln Val Gly Thr Lys Val Asn Val Thr Val
                420                 425                 430

Glu Asp Glu Arg Thr Leu Val Arg Arg Asn Asn Thr Phe Leu Ser Leu
            435                 440                 445

Arg Asp Val Phe Gly Lys Asp Leu Ile Tyr Thr Leu Tyr Tyr Trp Lys
        450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                485                 490                 495

Val Ile Pro Ser Arg Thr Val Asn Arg Lys Ser Thr Asp Ser Pro Val
            500                 505                 510

Glu Cys Met Gly Gln Glu Lys Gly Glu Phe Arg Glu Asn Trp Val Asn
        515                 520                 525

Val Ile Ser Asp Leu Lys Lys Ile Glu Asp Leu Ile Gln Ser Met His
530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
        595                 600                 605

Cys Lys Glu Cys Glu Glu Leu Glu Glu Lys Asn Ile Lys Glu Phe Leu
610                 615                 620

Gln Ser Phe Val His Ile Val Gln Met Phe Ile Asn Thr Ser
625                 630                 635

<210> SEQ ID NO 212
<211> LENGTH: 1914
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs137 sequence"

<400> SEQUENCE: 212
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag    180
tcctgcatgt ccaactgcag catcacctcc atctgcgaga agccccaaga agtgtgcgtg    240
gccgtgtggc ggaaaaatga cgagaacatc accctggaga ccgtgtgtca cgaccccaag    300
ctcccttatc acgacttcat tctggaggac gctgcctccc ccaaatgcat catgaaggag    360
aagaagaagc ccggagagac cttctttatg tgttcctgta gcagcgacga gtgtaacgac    420
aacatcatct tcagcgaaga gtacaacacc agcaacctg atggaggtgg cggatccgga    480
ggtggaggtt ctggtggagg tgggagtatt cctccccacg tgcagaagag cgtgaataat    540
```

```
gacatgatcg tgaccgataa caatggcgcc gtgaaatttc cccagctgtg caaattctgc      600
gatgtgaggt tttccacctg cgacaaccag aagtcctgta tgagcaactg ctccatcacc      660
tccatctgtg agaagcctca ggaggtgtgc gtggctgtct ggcggaagaa tgacgagaat      720
atcaccctgg aaaccgtctg ccacgatccc aagctgccct accacgattt catcctggaa      780
gacgccgcca gccctaagtg catcatgaaa gagaaaaaga agcctggcga gacctttttc      840
atgtgctcct gcagcagcga cgaatgcaac gacaatatca tctttagcga ggaatacaat      900
accagcaacc ccgacagcgg cacaaccaac acagtcgctg cctataaccc tcacttggaag     960 agcaccaact tcaaaaccat cctcgaatgg gaacccaaac ccgttaacca gtttacacc      1020 gtgcagatca gcaccaagtc cggcgactgg aagtccaaat gtttctatac caccgacacc     1080
gagtgcgatc tcaccgatga gatcgtgaaa gatgtgaaac agacctacct cgcccgggtg     1140
tttagctacc ccgccggcaa tgtggagagc actggttccg ctggcgagcc tttatacgag     1200
aacagccccg aatttacccc ttacctcgag accaatttag acagcccac catccaaagc      1260 tttgagcaag ttggcacaaa ggtgaatgtg acagtggagg acgagcggac tttagtgcgg     1320
cggaacaaca ccttttctcag cctccgggat gtgttcggca agatttaat ctacacactg      1380 tattactgga agtcctcttc ctccggcaag aagacagcta aaaccaacac aaacgagttt     1440
ttaatcgacg tggataaagg cgaaaaactac tgtttcagcg tgcaagctgt gatcccctcc     1500
cggaccgtga ataggaaaag caccgatagc cccgttgagt gcatgggcca agaaaagggc     1560
gagttccggg agaactgggt gaacgtcatc agcgatttaa agaagatcga agatttaatt     1620
cagtccatgc atatcgacgc cactttatac acagaatccg acgtgcaccc ctcttgtaag     1680
gtgaccgcca tgaaatgttt tttactggag ctgcaagtta tctctttaga gagcggagac     1740
gctagcatcc acgacaccgt ggagaattta atcattttag ccaataactc tttatccagc     1800
aacggcaacg tgacagagtc cggctgcaag gagtgcgaag agctggagga aagaacatc      1860 aaggagtttc tgcaatcctt tgtgcacatt gtccagatgt tcatcaatac ctcc           1914
```

<210> SEQ ID NO 213
<211> LENGTH: 551
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-TGFRs137 sequence"

<400> SEQUENCE: 213

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110
```

-continued

Cys Ser Cys Ser Ser Asp Glu Cys Asn Asp Asn Ile Ile Phe Ser Glu
            115                 120                 125

Glu Tyr Asn Thr Ser Asn Pro Asp Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
            195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ile
        275                 280                 285

Thr Cys Pro Pro Pro Met Ser Val Glu His Ala Asp Ile Trp Val Lys
        290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
                325                 330                 335

Ala Thr Asn Val Ala His Trp Thr Thr Pro Ser Leu Lys Cys Ile Arg
            340                 345                 350

Gly Gly Gly Gly Ser Gly Gly Gly Ser Gly Gly Gly Gly Ser Arg
            355                 360                 365

Glu Gly Pro Glu Leu Ser Pro Asp Asp Pro Ala Gly Leu Leu Asp Leu
    370                 375                 380

Arg Gln Gly Met Phe Ala Gln Leu Val Ala Gln Asn Val Leu Leu Ile
385                 390                 395                 400

Asp Gly Pro Leu Ser Trp Tyr Ser Asp Pro Gly Leu Ala Gly Val Ser
                405                 410                 415

Leu Thr Gly Gly Leu Ser Tyr Lys Glu Asp Thr Lys Glu Leu Val Val
            420                 425                 430

Ala Lys Ala Gly Val Tyr Tyr Val Phe Phe Gln Leu Glu Leu Arg Arg
            435                 440                 445

Val Val Ala Gly Glu Gly Ser Gly Ser Val Ser Leu Ala Leu His Leu
    450                 455                 460

Gln Pro Leu Arg Ser Ala Ala Gly Ala Ala Ala Leu Ala Leu Thr Val
465                 470                 475                 480

Asp Leu Pro Pro Ala Ser Ser Glu Ala Arg Asn Ser Ala Phe Gly Phe
                485                 490                 495

Gln Gly Arg Leu Leu His Leu Ser Ala Gly Gln Arg Leu Gly Val His
            500                 505                 510

Leu His Thr Glu Ala Arg Ala Arg His Ala Trp Gln Leu Thr Gln Gly
            515                 520                 525

Ala Thr Val Leu Gly Leu Phe Arg Val Thr Pro Glu Ile Pro Ala Gly
    530                 535                 540

Leu Pro Ser Pro Arg Ser Glu
545                 550

<210> SEQ ID NO 214
<211> LENGTH: 1653
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs137 sequence"

<400> SEQUENCE: 214

```
atccccccccc atgtgcaaaa gagcgtgaac aacgatatga tcgtgaccga caacaacggc      60
gccgtgaagt ttccccagct ctgcaagttc tgcgatgtca ggttcagcac ctgcgataat     120
cagaagtcct gcatgtccaa ctgcagcatc acctccatct gcgagaagcc ccaagaagtg     180
tgcgtggccg tgtggcggaa aaatgacgag aacatcaccc tggagaccgt gtgtcacgac     240
cccaagctcc cttatcacga cttcattctg gaggacgctg cctcccccaa atgcatcatg     300
aaggagaaga gaagcccgg agagaccttc tttatgtgtt cctgtagcag cgacgagtgt     360
aacgacaaca tcatcttcag cgaagagtac aacaccagca accctgatgg aggtggcgga     420
tccggaggtg gaggttctgg tggaggtggg agtattcctc ccacgtgca gaagagcgtg      480
aataatgaca tgatcgtgac cgataacaat ggcgccgtga atttcccca gctgtgcaaa      540
ttctgcgatg tgaggttttc cacctgcgac aaccagaagt cctgtatgag caactgctcc     600
atcacctcca tctgtgagaa gcctcaggag gtgtgcgtgg ctgtctggcg gaagaatgac     660
gagaatatca ccctggaaac cgtctgccac gatcccaagc tgccctacca cgatttcatc     720
ctggaagacg ccgccagccc taagtgcatc atgaaagaga aaagaagcc tggcgagacc      780
tttttcatgt gctcctgcag cagcgacgaa tgcaacgaca tatcatctt tagcgaggaa      840
tacaatacca gcaaccccga cattacatgc cccctccca tgagcgtgga gcacgccgac     900
atctgggtga gagctatag cctctacagc cgggagaggg atatctgtaa cagcggcttc     960
aagaggaagg ccggcaccag cagcctcacc gagtgcgtgc tgaataaggc taccaacgtg    1020
gctcactgga caacccctc tttaaagtgc atccggggcg gtggaggatc cggaggaggt    1080
ggctccggcg gcggaggatc tcgcgagggt cccgagcttt cgcccgacga tcccgccggc    1140
ctcttggacc tgcggcaggg catgtttgcg cagctggtgg cccaaaatgt tctgctgatc    1200
gatgggcccc tgagctggta cagtgaccca ggcctggcag gcgtgtccct gacgggggc     1260
ctgagctaca agaggacac gaaggagctg gtggtggcca aggctggagt ctactatgtc    1320
ttctttcaac tagagctgcg gcgcgtggtg gccggcgagg gctcaggctc cgtttcactt    1380
gcgctgcacc tgcagccact gcgctctgct gctggggccg ccgccctggc tttgaccgtg    1440
gacctgccac ccgcctcctc cgaggctcgg aactcggcct tcggtttcca gggccgcttg    1500
ctgcacctga gtgccggcca gcgcctgggc gtccatcttc acactgaggc cagggcacgc    1560
catgcctggc agcttaccca gggcgccaca gtcttgggac tcttccgggt gaccccgaa     1620
atcccagccg gactcccttc accgaggtcg gaa                                 1653
```

<210> SEQ ID NO 215
<211> LENGTH: 569
<212> TYPE: PRT
<213> ORGANISM: Artificial Sequence
<220> FEATURE:
<221> NAME/KEY: source
<223> OTHER INFORMATION: /note="Description of Artificial Sequence: Synthetic TGFRt15-TGFRs137 sequence"

<400> SEQUENCE: 215

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
            85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
            115                 120                 125

Phe Met Cys Ser Cys Ser Ser Asp Glu Cys Asn Asp Asn Ile Ile Phe
130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
            165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
            195                 200                 205

Asn Gln Lys Ser Cys Met Ser Asn Cys Ser Ile Thr Ser Ile Cys Glu
            210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
            245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
            275                 280                 285

Cys Asn Asp Asn Ile Ile Phe Ser Glu Glu Tyr Asn Thr Ser Asn Pro
290                 295                 300

Asp Ile Thr Cys Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
            325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
            355                 360                 365

Ile Arg Gly Gly Gly Gly Ser Gly Gly Gly Ser Gly Gly Gly Gly
            370                 375                 380
```

```
Ser Arg Glu Gly Pro Glu Leu Ser Pro Asp Asp Pro Ala Gly Leu Leu
385                 390                 395                 400

Asp Leu Arg Gln Gly Met Phe Ala Gln Leu Val Ala Gln Asn Val Leu
            405                 410                 415

Leu Ile Asp Gly Pro Leu Ser Trp Tyr Ser Asp Pro Gly Leu Ala Gly
            420                 425                 430

Val Ser Leu Thr Gly Gly Leu Ser Tyr Lys Glu Asp Thr Lys Glu Leu
            435                 440                 445

Val Val Ala Lys Ala Gly Val Tyr Tyr Val Phe Phe Gln Leu Glu Leu
            450                 455                 460

Arg Arg Val Val Ala Gly Glu Gly Ser Gly Ser Val Ser Leu Ala Leu
465                 470                 475                 480

His Leu Gln Pro Leu Arg Ser Ala Ala Gly Ala Ala Leu Ala Leu
            485                 490                 495

Thr Val Asp Leu Pro Pro Ala Ser Ser Glu Ala Arg Asn Ser Ala Phe
            500                 505                 510

Gly Phe Gln Gly Arg Leu Leu His Leu Ser Ala Gly Gln Arg Leu Gly
            515                 520                 525

Val His Leu His Thr Glu Ala Arg Ala Arg His Ala Trp Gln Leu Thr
            530                 535                 540

Gln Gly Ala Thr Val Leu Gly Leu Phe Arg Val Thr Pro Glu Ile Pro
545                 550                 555                 560

Ala Gly Leu Pro Ser Pro Arg Ser Glu
            565

<210> SEQ ID NO 216
<211> LENGTH: 1707
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic TGFRt15-TGFRs137 sequence"

<400> SEQUENCE: 216
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag    180
tcctgcatgt ccaactgcag catcacctcc atctgcgaga agccccaaga agtgtgcgtg    240
gccgtgtggc ggaaaaatga cgagaacatc accctggaga ccgtgtgtca cgaccccaag    300 ctccccttatc acgacttcat tctggaggac gctgcctccc ccaaatgcat catgaaggag    360
aagaagaagc ccgagagac cttctttatg tgttcctgta gcagcgacga gtgtaacgac    420
aacatcatct cagcgaaga gtacaacacc agcaaccctg atggaggtgg cggatccgga    480
ggtggaggtt ctggtggagg tgggagtatt cctccccacg tgcagaagag cgtgaataat    540
gacatgatcg tgaccgataa caatggcgcc gtgaaatttc cccagctgtg caaattctgc    600
gatgtgaggt tttccacctg cgacaaccag aagtcctgta tgagcaactg ctccatcacc    660
tccatctgtg agaagcctca ggaggtgtgc gtggctgtct ggcggaagaa tgacgagaat    720 atcacccctgg aaaccgtctg ccacgatccc aagctgccct accacgattt catcctggaa    780
gacgccgcca gccctaagtg catcatgaaa gagaaaaaga gcctggcga gacctttttc    840 atgtgctcct gcagcagcga cgaatgcaac gacaatatca tctttagcga ggaatacaat    900
accagcaacc ccgacattac atgccccccct cccatgagcg tggagcacgc cgacatctgg    960
```

```
gtgaagagct atagcctcta cagccgggag aggtatatct gtaacagcgg cttcaagagg      1020
aaggccggca ccagcagcct caccgagtgc gtgctgaata aggctaccaa cgtggctcac      1080
tggacaacac cctcttttaaa gtgcatccgg ggcggtggag gatccggagg aggtggctcc     1140
ggcggcggag gatctcgcga gggtcccgag ctttcgcccg acgatcccgc cggcctcttg      1200
gacctgcggc agggcatgtt tgcgcagctg gtggcccaaa atgttctgct gatcgatggg      1260
cccctgagct ggtacagtga cccaggcctg gcaggcgtgt ccctgacggg gggcctgagc      1320
tacaaagagg acacgaagga gctggtggtg gccaaggctg gagtctacta tgtcttcttt      1380
caactagagc tgcggcgcgt ggtggccggc gagggctcag gctccgtttc acttgcgctg      1440
cacctgcagc cactgcgctc tgctgctggg gccgccgccc tggctttgac cgtggacctg      1500
ccacccgcct cctccgaggc tcggaactcg gccttcggtt tccagggccg cttgctgcac      1560
ctgagtgccg gccagcgcct gggcgtccat cttcacactg aggccagggc acgccatgcc      1620
tggcagctta cccagggcgc cacagtcttg ggactcttcc gggtgacccc cgaaatccca      1680
gccggactcc cttcaccgag gtcggaa                                          1707
```

<210> SEQ ID NO 217
<211> LENGTH: 720
<212> TYPE: DNA
<213> ORGANISM: Artificial Sequence
<220> FEATURE:
<221> NAME/KEY: source
<223> OTHER INFORMATION: /note="Description of Artificial Sequence: Synthetic IL-18/IL-15RalphaSu sequence"

<400> SEQUENCE: 217

```
atgaagtggg tcacatttat ctctttactg ttcctcttct ccagcgccta cagctacttc       60
ggcaaactgg aatccaagct gagcgtgatc cggaatttaa acgaccaagt tctgtttatc      120
gatcaaggta accggcctct gttcgaggac atgaccgact ccgattgccg ggacaatgcc      180
ccccggacca tcttcattat ctccatgtac aaggacagcc agccccgggg catggctgtg      240
acaattagcg tgaagtgtga aaaaatcagc actttatctt gtgagaacaa gatcatctcc      300
tttaaggaaa tgaacccccc cgataacatc aaggacacca gtccgatat catcttcttc       360 cagcggtccg tgcccggtca cgataacaag atgcagttcg aatcctcctc ctacgagggc      420
tactttttag cttgtgaaaa ggagagggat ttattcaagc tgatcctcaa gaaggaggac      480
gagctgggcg atcgttccat catgttcacc gtccaaaacg aggatattac atgccccct      540 cccatgagcg tggagcacgc cgacatctgg gtgaagagct atagcctcta cagccgggag      600
aggtatatct gtaacagcgg cttcaagagg aaggccggca ccagcagcct caccgagtgc      660
gtgctgaata aggctaccaa cgtggctcac tggacaacac cctcttttaaa gtgcatccgg    720
```

<210> SEQ ID NO 218
<211> LENGTH: 2607
<212> TYPE: DNA
<213> ORGANISM: Artificial Sequence
<220> FEATURE:
<221> NAME/KEY: source
<223> OTHER INFORMATION: /note="Description of Artificial Sequence: Synthetic IL-12/TF/IL-15 sequence"

<400> SEQUENCE: 218

```
atgaaatggg tgacctttat ttctttactg ttcctcttta gcagcgccta ctccatttgg       60
gaactgaaga aggacgtcta cgtggtcgaa ctggactggt atcccgatgc tcccggcgaa      120
```

```
atggtggtgc tcacttgtga cacccccgaa gaagacggca tcacttggac cctcgatcag    180
agcagcgagg tgctgggctc cggaaagacc ctcacaatcc aagttaagga gttcggagac    240
gctggccaat acacatgcca caagggaggc gaggtgctca gccattcctt attattatta    300
cacaagaagg aagacggaat ctggtccacc gacattttaa aagatcagaa ggagcccaag    360
aataagacct ttttaaggtg tgaggccaaa aactacagcg gtcgtttcac ttgttggtgg    420
ctgaccacca tttccaccga tttaaccttc tccgtgaaaa gcagccgggg aagctccgac    480
cctcaaggtg tgacatgtgg agccgctacc ctcagcgctg agagggttcg tggcgataac    540
aaggaatacg agtacagcgt ggagtgccaa gaagatagcg cttgtcccgc tgccgaagaa    600
tctttaccca ttgaggtgat ggtggacgcc gtgcacaaac tcaagtacga gaactacacc    660
tcctccttct ttatccggga catcattaag cccgatcctc ctaagaattt acagctgaag    720
cctctcaaaa atagccggca agttgaggtc tcttgggaat atcccgacac ttggagcaca    780
ccccacagct acttctcttt aaccttttgt gtgcaagttc aaggtaaaag caagcgggag    840
aagaaagacc gggtgtttac cgacaaaacc agcgccaccg tcatctgtcg gaagaacgcc    900
tccatcagcg tgagggctca agatcgttat tactccagca gctggtccga gtgggccagc    960
gtgccttgtt ccggcggtgg aggatccgga ggaggtggct ccggcggcgg aggatctcgt    1020
aacctccccg tggctacccc cgatcccgga atgttcccct gtttacacca cagccagaat    1080
ttactgaggg ccgtgagcaa catgctgcag aaagctaggc agactttaga attttaccct    1140
tgcaccagcg aggagatcga ccatgaagat atcaccaagg acaagacatc caccgtggag    1200
gcttgtttac ctctggagct gacaaagaac gagtcttgtc tcaactctcg tgaaaccagc    1260
ttcatcacaa atggctcttg tttagcttcc cggaagacct cctttatgat ggctttatgc    1320
ctcagctcca tctacgagga tttaaagatg taccaagtgg agttcaagac catgaacgcc    1380
aagctgctca tggaccctaa acggcagatc ttttttagacc agaacatgct ggctgtgatt    1440
gatgagctga tgcaagcttt aaacttcaac tccgagaccc tccctcagaa gtcctccctc    1500
gaggagcccg attttacaa gacaaagatc aaactgtgca ttttactcca cgcctttagg    1560
atccgggccc tgaccattga cccgggtcatg agctatttaa acgccagcag cggcacaacc    1620
aacacagtcg ctgcctataa cctcacttgg aagagcacca acttcaaaac catcctcgaa    1680
tgggaaccca acccgttaa ccaagtttac accgtgcaga tcagcaccaa gtccggcgac    1740
tggaagtcca atgtttcta taccaccgac accgagtgcg atctcaccga tgagatcgtg    1800
aaagatgtga acagaccta cctcgcccgg gtgtttagct accccgccgg caatgtggag    1860
agcactggtt ccgctggcga gcctttatac gagaacagcc ccgaatttac cccttacctc    1920
gagaccaatt taggacagcc caccatccaa agctttgagc aagttggcac aaaggtgaat    1980
gtgacagtgg aggacgagcg gactttagtg cggcggaaca cacctttct cagcctccgg    2040 gatgtgttcg gcaaagattt aatctacaca ctgtattact ggaagtcctc ttcctccggc    2100
aagaagacag ctaaaaccaa cacaaacgag ttttaatcg acgtggataa aggcgaaaac    2160
tactgtttca gcgtgcaagc tgtgatcccc tcccggaccg tgaataggaa aagcaccgat    2220
agccccgttg agtgcatggg ccaagaaag ggcgagttcc gggagaactg ggtgaacgtc    2280
atcagcgatt taagaagat cgaagattta attcagtcca tgcatatcga cgccacttta    2340
tacacagaat ccgacgtgca ccctctcttgt aaggtgaccg ccatgaaatg ttttttactg    2400
gagctgcaag ttatctcttt agagagcgga gacgctagca tccacgacac cgtggagaat    2460
ttaatcattt tagccaataa ctctttatcc agcaacggca acgtgacaga gtccggctgc    2520
```

```
aaggagtgcg aagagctgga ggagaagaac atcaaggagt ttctgcaatc ctttgtgcac    2580
attgtccaga tgttcatcaa tacctcc                                         2607
```

<210> SEQ ID NO 219
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic IL-18/IL-15RalphaSu sequence"

<400> SEQUENCE: 219

Met Lys Trp Val Thr Phe Ile Ser Leu Leu Phe Leu Phe Ser Ser Ala
1               5                   10                  15

Tyr Ser Tyr Phe Gly Lys Leu Glu Ser Lys Leu Ser Val Ile Arg Asn
            20                  25                  30

Leu Asn Asp Gln Val Leu Phe Ile Asp Gln Gly Asn Arg Pro Leu Phe
        35                  40                  45

Glu Asp Met Thr Asp Ser Asp Cys Arg Asp Asn Ala Pro Arg Thr Ile
    50                  55                  60

Phe Ile Ile Ser Met Tyr Lys Asp Ser Gln Pro Arg Gly Met Ala Val
65                  70                  75                  80

Thr Ile Ser Val Lys Cys Glu Lys Ile Ser Thr Leu Ser Cys Glu Asn
                85                  90                  95

Lys Ile Ile Ser Phe Lys Glu Met Asn Pro Pro Asp Asn Ile Lys Asp
            100                 105                 110

Thr Lys Ser Asp Ile Ile Phe Phe Gln Arg Ser Val Pro Gly His Asp
        115                 120                 125

Asn Lys Met Gln Phe Glu Ser Ser Ser Tyr Glu Gly Tyr Phe Leu Ala
    130                 135                 140

Cys Glu Lys Glu Arg Asp Leu Phe Lys Leu Ile Leu Lys Lys Glu Asp
145                 150                 155                 160

Glu Leu Gly Asp Arg Ser Ile Met Phe Thr Val Gln Asn Glu Asp Ile
                165                 170                 175

Thr Cys Pro Pro Pro Met Ser Val Glu His Ala Asp Ile Trp Val Lys
            180                 185                 190

Ser Tyr Ser Leu Tyr Ser Arg Glu Arg Tyr Ile Cys Asn Ser Gly Phe
        195                 200                 205

Lys Arg Lys Ala Gly Thr Ser Ser Leu Thr Glu Cys Val Leu Asn Lys
    210                 215                 220

Ala Thr Asn Val Ala His Trp Thr Thr Pro Ser Leu Lys Cys Ile Arg
225                 230                 235                 240

<210> SEQ ID NO 220
<211> LENGTH: 869
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic IL-12/TF/IL-15 sequence"

<400> SEQUENCE: 220

Met Lys Trp Val Thr Phe Ile Ser Leu Leu Phe Leu Phe Ser Ser Ala
1               5                   10                  15

Tyr Ser Ile Trp Glu Leu Lys Lys Asp Val Tyr Val Val Glu Leu Asp
            20                  25                  30

```
Trp Tyr Pro Asp Ala Pro Gly Glu Met Val Val Leu Thr Cys Asp Thr
         35                  40                  45

Pro Glu Glu Asp Gly Ile Thr Trp Thr Leu Asp Gln Ser Ser Glu Val
 50                  55                  60

Leu Gly Ser Gly Lys Thr Leu Thr Ile Gln Val Lys Glu Phe Gly Asp
 65                  70                  75                  80

Ala Gly Gln Tyr Thr Cys His Lys Gly Gly Glu Val Leu Ser His Ser
             85                  90                  95

Leu Leu Leu Leu His Lys Lys Glu Asp Gly Ile Trp Ser Thr Asp Ile
            100                 105                 110

Leu Lys Asp Gln Lys Glu Pro Lys Asn Lys Thr Phe Leu Arg Cys Glu
            115                 120                 125

Ala Lys Asn Tyr Ser Gly Arg Phe Thr Cys Trp Trp Leu Thr Thr Ile
        130                 135                 140

Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175

Arg Gly Asp Asn Lys Glu Tyr Glu Tyr Ser Val Glu Cys Gln Glu Asp
            180                 185                 190

Ser Ala Cys Pro Ala Ala Glu Glu Ser Leu Pro Ile Glu Val Met Val
        195                 200                 205

Asp Ala Val His Lys Leu Lys Tyr Glu Asn Tyr Thr Ser Ser Phe Phe
210                 215                 220

Ile Arg Asp Ile Ile Lys Pro Asp Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
        275                 280                 285

Lys Thr Ser Ala Thr Val Ile Cys Arg Lys Asn Ala Ser Ile Ser Val
290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Ser Gly Gly Gly Ser Gly Gly
                325                 330                 335

Gly Gly Ser Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
        355                 360                 365

Leu Gln Lys Ala Arg Gln Thr Leu Glu Phe Tyr Pro Cys Thr Ser Glu
370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
        435                 440                 445
```

-continued

```
Lys Met Tyr Gln Val Glu Phe Lys Thr Met Asn Ala Lys Leu Leu Met
450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
                500                 505                 510

Cys Ile Leu Leu His Ala Phe Arg Ile Arg Ala Val Thr Ile Asp Arg
                515                 520                 525

Val Met Ser Tyr Leu Asn Ala Ser Ser Gly Thr Thr Asn Thr Val Ala
530                 535                 540

Ala Tyr Asn Leu Thr Trp Lys Ser Thr Asn Phe Lys Thr Ile Leu Glu
545                 550                 555                 560

Trp Glu Pro Lys Pro Val Asn Gln Val Tyr Thr Val Gln Ile Ser Thr
                565                 570                 575

Lys Ser Gly Asp Trp Lys Ser Lys Cys Phe Tyr Thr Thr Asp Thr Glu
                580                 585                 590

Cys Asp Leu Thr Asp Glu Ile Val Lys Asp Val Lys Gln Thr Tyr Leu
                595                 600                 605

Ala Arg Val Phe Ser Tyr Pro Ala Gly Asn Val Glu Ser Thr Gly Ser
610                 615                 620

Ala Gly Glu Pro Leu Tyr Glu Asn Ser Pro Glu Phe Thr Pro Tyr Leu
625                 630                 635                 640

Glu Thr Asn Leu Gly Gln Pro Thr Ile Gln Ser Phe Glu Gln Val Gly
                645                 650                 655

Thr Lys Val Asn Val Thr Val Glu Asp Glu Arg Thr Leu Val Arg Arg
                660                 665                 670

Asn Asn Thr Phe Leu Ser Leu Arg Asp Val Phe Gly Lys Asp Leu Ile
675                 680                 685

Tyr Thr Leu Tyr Tyr Trp Lys Ser Ser Ser Gly Lys Lys Thr Ala
690                 695                 700

Lys Thr Asn Thr Asn Glu Phe Leu Ile Asp Val Asp Lys Gly Glu Asn
705                 710                 715                 720

Tyr Cys Phe Ser Val Gln Ala Val Ile Pro Ser Arg Thr Val Asn Arg
                725                 730                 735

Lys Ser Thr Asp Ser Pro Val Glu Cys Met Gly Gln Glu Lys Gly Glu
                740                 745                 750

Phe Arg Glu Asn Trp Val Asn Val Ile Ser Asp Leu Lys Lys Ile Glu
                755                 760                 765

Asp Leu Ile Gln Ser Met His Ile Asp Ala Thr Leu Tyr Thr Glu Ser
770                 775                 780

Asp Val His Pro Ser Cys Lys Val Thr Ala Met Lys Cys Phe Leu Leu
785                 790                 795                 800

Glu Leu Gln Val Ile Ser Leu Glu Ser Gly Asp Ala Ser Ile His Asp
                805                 810                 815

Thr Val Glu Asn Leu Ile Ile Leu Ala Asn Asn Ser Leu Ser Ser Asn
                820                 825                 830

Gly Asn Val Thr Glu Ser Gly Cys Lys Glu Cys Glu Glu Leu Glu Glu
                835                 840                 845

Lys Asn Ile Lys Glu Phe Leu Gln Ser Phe Val His Ile Val Gln Met
850                 855                 860

Phe Ile Asn Thr Ser
```

865

<210> SEQ ID NO 221
<211> LENGTH: 1452
<212> TYPE: DNA
<213> ORGANISM: Artificial Sequence
<220> FEATURE:
<221> NAME/KEY: source
<223> OTHER INFORMATION: /note="Description of Artificial Sequence: Synthetic IL-21/TF mutant/IL-15 sequence"

<400> SEQUENCE: 221

```
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
tacgtgaacg acctggtgcc cgagtttctg cctgccccg aggacgtgga gaccaactgc     180
gagtggtccg ccttctcctg ctttcagaag gcccagctga agtccgccaa caccggcaac     240
aacgagcgga tcatcaacgt gagcatcaag aagctgaagc ggaagcctcc ctccacaaac     300
gccggcagga ggcagaagca caggctgacc tgccccagct gtgactccta cgagaagaag     360
ccccccaagg agttcctgga gaggttcaag tccctgctgc agaagatgat ccatcagcac     420
ctgtcctcca ggacccacgg ctccgaggac tcctccggca ccaccaatac cgtggccgct     480
tataacctca catggaagag caccaacttc gcgacagctc tggaatggga cccaagccc      540
gtcaatcaag tttacaccgt gcagatctcc accaaatccg gagactggaa gagcaagtgc     600
ttctacacaa cagacaccga gtgtgcttta accgacgaaa tcgtcaagga cgtcaagcaa     660
acctatctgg ctcgggtctt ttcctacccc gctggcaatg tcgagtccac cggctccgct     720
ggcgagcctc tctacgagaa ttcccccgaa ttcaccccct atttagagac caatttaggc     780
cagcctacca tccagagctt cgagcaagtt ggcaccaagg tgaacgtcac cgtcgaggat     840
gaaaggactt tagtggcgcg aataacaca gctttatccc tccgggatgt gttcggcaaa      900
gacctcatct acacactgta ctattggaag tccagctcct ccggcaaaaa gaccgctaag     960
accaacacca acgagttttt aattgacgtg gacaaaggcg agaactactg cttcagcgtg    1020
caagccgtga tcccttctcg taccgtcaac cggaagagca cagattcccc cgttgagtgc    1080
atgggccaag aaaagggcga gttccgggag aactgggtga cgtcatcag cgatttaaag    1140
aagatcgaag atttaattca gtccatgcat atcgacgcca ctttatacac agaatccgac    1200
gtgcaccct cttgtaaggt gaccgccatg aaatgttttt tactggagct gcaagttatc    1260
tctttagaga gcggagacgc tagcatccac gacaccgtgg agaattaat catttttagcc    1320
aataactctt tatccagcaa cggcaacgtg acagagtccg gctgcaagga gtgcgaagag    1380
ctggaggaga agaacatcaa ggagtttctg caatcctttg tgcacattgt ccagatgttc    1440
atcaatacct cc                                                        1452
```

<210> SEQ ID NO 222
<211> LENGTH: 483
<212> TYPE: PRT
<213> ORGANISM: Artificial Sequence
<220> FEATURE:
<221> NAME/KEY: source
<223> OTHER INFORMATION: /note="Description of Artificial Sequence: Synthetic IL-21/TF mutant/IL-15 sequence"

<400> SEQUENCE: 222

Lys Trp Val Thr Phe Ile Ser Leu Leu Phe Leu Phe Ser Ser Ala Tyr
1               5                   10                  15

-continued

Ser Gln Gly Gln Asp Arg His Met Ile Arg Met Arg Gln Leu Ile Asp
            20                  25                  30

Ile Val Asp Gln Leu Lys Asn Tyr Val Asn Asp Leu Val Pro Glu Phe
        35                  40                  45

Leu Pro Ala Pro Glu Asp Val Glu Thr Asn Cys Glu Trp Ser Ala Phe
    50                  55                  60

Ser Cys Phe Gln Lys Ala Gln Leu Lys Ser Ala Asn Thr Gly Asn Asn
65                  70                  75                  80

Glu Arg Ile Ile Asn Val Ser Ile Lys Lys Leu Lys Arg Lys Pro Pro
                85                  90                  95

Ser Thr Asn Ala Gly Arg Arg Gln Lys His Arg Leu Thr Cys Pro Ser
            100                 105                 110

Cys Asp Ser Tyr Glu Lys Lys Pro Pro Lys Glu Phe Leu Glu Arg Phe
        115                 120                 125

Lys Ser Leu Leu Gln Lys Met Ile His Gln His Leu Ser Ser Arg Thr
    130                 135                 140

His Gly Ser Glu Asp Ser Ser Gly Thr Thr Asn Thr Val Ala Ala Tyr
145                 150                 155                 160

Asn Leu Thr Trp Lys Ser Thr Asn Phe Ala Thr Ala Leu Glu Trp Glu
                165                 170                 175

Pro Lys Pro Val Asn Gln Val Tyr Thr Val Gln Ile Ser Thr Lys Ser
            180                 185                 190

Gly Asp Trp Lys Ser Lys Cys Phe Tyr Thr Thr Asp Thr Glu Cys Ala
        195                 200                 205

Leu Thr Asp Glu Ile Val Lys Asp Val Lys Gln Thr Tyr Leu Ala Arg
    210                 215                 220

Val Phe Ser Tyr Pro Ala Gly Asn Val Glu Ser Thr Gly Ser Ala Gly
225                 230                 235                 240

Glu Pro Leu Tyr Glu Asn Ser Pro Glu Phe Thr Pro Tyr Leu Glu Thr
                245                 250                 255

Asn Leu Gly Gln Pro Thr Ile Gln Ser Phe Glu Gln Val Gly Thr Lys
            260                 265                 270

Val Asn Val Thr Val Glu Asp Glu Arg Thr Leu Val Ala Arg Asn Asn
        275                 280                 285

Thr Ala Leu Ser Leu Arg Asp Val Phe Gly Lys Asp Leu Ile Tyr Thr
    290                 295                 300

Leu Tyr Tyr Trp Lys Ser Ser Ser Gly Lys Lys Thr Ala Lys Thr
305                 310                 315                 320

Asn Thr Asn Glu Phe Leu Ile Asp Val Asp Lys Gly Glu Asn Tyr Cys
                325                 330                 335

Phe Ser Val Gln Ala Val Ile Pro Ser Arg Thr Val Asn Arg Lys Ser
            340                 345                 350

Thr Asp Ser Pro Val Glu Cys Met Gly Gln Glu Lys Gly Glu Phe Arg
        355                 360                 365

Glu Asn Trp Val Asn Val Ile Ser Asp Leu Lys Lys Ile Glu Asp Leu
    370                 375                 380

Ile Gln Ser Met His Ile Asp Ala Thr Leu Tyr Thr Glu Ser Asp Val
385                 390                 395                 400

His Pro Ser Cys Lys Val Thr Ala Met Lys Cys Phe Leu Leu Glu Leu
                405                 410                 415

Gln Val Ile Ser Leu Glu Ser Gly Asp Ala Ser Ile His Asp Thr Val
            420                 425                 430

Glu Asn Leu Ile Ile Leu Ala Asn Asn Ser Leu Ser Ser Asn Gly Asn

```
            435                 440                 445
Val Thr Glu Ser Gly Cys Lys Glu Cys Glu Glu Leu Glu Glu Lys Asn
    450                 455                 460

Ile Lys Glu Phe Leu Gln Ser Phe Val His Ile Val Gln Met Phe Ile
465                 470                 475                 480

Asn Thr Ser

<210> SEQ ID NO 223
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Signal sequence"

<400> SEQUENCE: 223

Met Gly Val Lys Val Leu Phe Ala Leu Ile Cys Ile Ala Val Ala Glu
1               5                   10                  15

Ala

<210> SEQ ID NO 224
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic Linker sequence"

<400> SEQUENCE: 224

Gly Gly Gly Ser Gly Gly Gly Ser
1               5

<210> SEQ ID NO 225
<211> LENGTH: 1245
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic 21s137L sequence"

<400> SEQUENCE: 225
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
tacgtgaacg acctggtgcc cgagtttctg cctgcccccg aggacgtgga gaccaactgc     180
gagtggtccg ccttctcctg ctttcagaag gcccagctga gtccgccaa caccggcaac      240 aacgagcgga tcatcaacgt gagcatcaag aagctgaagc ggaagcctcc ctccacaaac     300
gccggcagga ggcagaagca caggctgacc tgccccagct gtgactccta cgagaagaag     360
ccccccaagg agttcctgga gaggttcaag tccctgctgc agaagatgat ccatcagcac     420
ctgtcctcca ggacccacgg ctccgaggac tccattacat gccccccctcc catgagcgtg     480 gagcacgccg acatctgggt gaagagctat agcctctaca gccgggagag gtatatctgt     540
aacagcggct tcaagaggaa ggccggcacc agcagcctca ccgagtgcgt gctgaataag     600
gctaccaacg tggctcactg gacaacaccc tctttaaagt gcatccgggg cggtggagga     660
tccggaggag gtggctccgg cggcggagga tctcgcgagg gtcccgagct ttcgcccgac     720
gatcccgccg gcctcttgga cctgcggcag ggcatgtttg cgcagctggt ggcccaaaat     780
```

```
gttctgctga tcgatgggcc cctgagctgg tacagtgacc caggcctggc aggcgtgtcc      840
ctgacggggg gcctgagcta caaagaggac acgaaggagc tggtggtggc caaggctgga      900
gtctactatg tcttctttca actagagctg cggcgcgtgg tggccggcga gggctcaggc      960
tccgtttcac ttgcgctgca cctgcagcca ctgcgctctg ctgctgggc cgccgccctg      1020 gctttgaccg tggacctgcc acccgcctcc tccgaggctc ggaactcggc cttcggtttc      1080
cagggccgct tgctgcacct gagtgccggc cagcgcctgg cgtccatct tcacactgag      1140 gccagggcac gccatgcctg gcagcttacc cagggcgcca cagtcttggg actcttccgg      1200
gtgacccccg aaatcccagc cggactccct tcaccgaggt cggaa                     1245
```

<210> SEQ ID NO 226
<211> LENGTH: 415
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 21s137L sequence"

<400> SEQUENCE: 226

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr
        195                 200                 205

Thr Pro Ser Leu Lys Cys Ile Arg Gly Gly Gly Ser Gly Gly
    210                 215                 220

Gly Ser Gly Gly Gly Ser Arg Glu Gly Pro Glu Leu Ser Pro Asp
225                 230                 235                 240

Asp Pro Ala Gly Leu Leu Asp Leu Arg Gln Gly Met Phe Ala Gln Leu
                245                 250                 255

Val Ala Gln Asn Val Leu Leu Ile Asp Gly Pro Leu Ser Trp Tyr Ser
            260                 265                 270
```

-continued

```
Asp Pro Gly Leu Ala Gly Val Ser Leu Thr Gly Gly Leu Ser Tyr Lys
        275                 280                 285

Glu Asp Thr Lys Glu Leu Val Val Ala Lys Ala Gly Val Tyr Tyr Val
    290                 295                 300

Phe Phe Gln Leu Glu Leu Arg Arg Val Val Ala Gly Glu Gly Ser Gly
305                 310                 315                 320

Ser Val Ser Leu Ala Leu His Leu Gln Pro Leu Arg Ser Ala Ala Gly
                325                 330                 335

Ala Ala Ala Leu Ala Leu Thr Val Asp Leu Pro Pro Ala Ser Ser Glu
                340                 345                 350

Ala Arg Asn Ser Ala Phe Gly Phe Gln Gly Arg Leu Leu His Leu Ser
                355                 360                 365

Ala Gly Gln Arg Leu Gly Val His Leu His Thr Glu Ala Arg Ala Arg
        370                 375                 380

His Ala Trp Gln Leu Thr Gln Gly Ala Thr Val Leu Gly Leu Phe Arg
385                 390                 395                 400

Val Thr Pro Glu Ile Pro Ala Gly Leu Pro Ser Pro Arg Ser Glu
                405                 410                 415
```